United States Patent
Konteatis et al.

(10) Patent No.: US 11,524,960 B2
(45) Date of Patent: Dec. 13, 2022

(54) HETEROBICYCLIC INHIBITORS OF MAT2A AND METHODS OF USE FOR TREATING CANCER

(71) Applicant: AGIOS PHARMACEUTICALS, INC., Cambridge, MA (US)

(72) Inventors: Zenon D. Konteatis, Chatham, NJ (US); Mingzong Li, Medford, MA (US); Peng Liu, Cambridge, MA (US); Matthew Medeiros, Cambridge, MA (US); Samuel K. Reznik, Cambridge, MA (US); Zhihua Sui, Cambridge, MA (US); Jeremy M. Travins, Southborough, MA (US); Janeta Popovici-Muller, Windham, NH (US); Shubao Zhou, Shanghai (CN); Guangning Ma, Shanghai (CN)

(73) Assignee: SERVIER PHARMACEUTICALS LLC, Boston, MA (US)

(*) Notice: Subject to any disclaimer, the term of this patent is extended or adjusted under 35 U.S.C. 154(b) by 27 days.

(21) Appl. No.: 17/040,614

(22) PCT Filed: Mar. 28, 2019

(86) PCT No.: PCT/US2019/024645
§ 371 (c)(1),
(2) Date: Sep. 23, 2020

(87) PCT Pub. No.: WO2019/191470
PCT Pub. Date: Oct. 3, 2019

(65) Prior Publication Data
US 2021/0115045 A1 Apr. 22, 2021

(30) Foreign Application Priority Data
Mar. 30, 2018 (WO) ................ PCT/CN2018/081328

(51) Int. Cl.
| | |
|---|---|
| *C07D 471/20* | (2006.01) |
| *A61K 31/519* | (2006.01) |
| *A61P 35/00* | (2006.01) |
| *C07D 471/04* | (2006.01) |
| *C07D 471/10* | (2006.01) |
| *C07D 519/00* | (2006.01) |

(52) U.S. Cl.
CPC ............ *C07D 471/20* (2013.01); *A61P 35/00* (2018.01); *C07D 471/04* (2013.01); *C07D 471/10* (2013.01); *C07D 519/00* (2013.01)

(58) Field of Classification Search
CPC .. C07D 471/04; C07D 471/20; A61K 31/519; A61K 31/4375; A61P 35/00
USPC ............ 544/279, 230, 234, 350; 514/264.11, 514/257, 300
See application file for complete search history.

(56) References Cited

U.S. PATENT DOCUMENTS

| | | | |
|---|---|---|---|
| 9,890,156 B2 * | 2/2018 | Lu | ........................ C07D 471/04 |
| 2004/0038959 A1 | 2/2004 | Bunker et al. | |

FOREIGN PATENT DOCUMENTS

| | | |
|---|---|---|
| WO | 99/64400 A1 | 12/1999 |
| WO | 99/67634 A1 | 12/1999 |
| WO | 2016/064960 A1 | 4/2016 |
| WO | 2018/039972 A1 | 3/2018 |
| WO | 2018/045071 A1 | 3/2018 |

OTHER PUBLICATIONS

Cai et al., Cancer Res., 1998, 58, 1444-1450.
Cairns etal., 1995, Nat. Gen., 11, 210-212.
Chen et al., Gastroenterology, 2007, 133, 207-218.
Garcia-Castellano et al., Clin. Cancer Res., 2002, 8(3), 782-787.
Jani etal, Cell. Res., 2009, 19, 358-369.
Li et al., J. Cancer, 2016, 7(10), 1317-1327.
(Continued)

*Primary Examiner* — Charanjit Aulakh
(74) *Attorney, Agent, or Firm* — BakerHostetler

(57) ABSTRACT

The present disclosure provides for compounds according to Formula I or Formula II and their pharmaceutically acceptable salts, stereoisomers, and/or tautomers thereof. Also provided are pharmaceutical compositions and the compounds of formulae I and II for use in methods of treating cancers, via inhibition of MAT2A, including some cancers in which the gene encoding methylthioadenosine phosphorylase (MTAP) is deleted and/or not fully functioning.

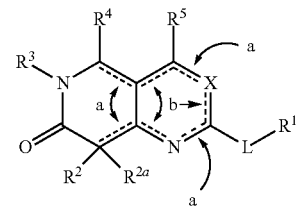

(I)

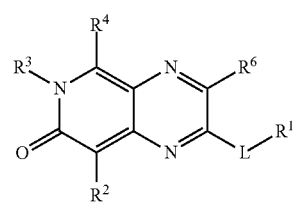

(II)

44 Claims, No Drawings

(56) References Cited

OTHER PUBLICATIONS

Liu et al. Hepatol. Res., 2007, 37, 376-388.
Lu et al., Chemistry & Biology, 2015, 22, 755-763.
Marjon et al., Cell Reports, 2016, 15(3), 574-587.
Pomerantz et al., 1998, Cell, 92, 713-723.
Batova et al., "Frequent deletion in the methylthioadenosine phosphorylase gene in T-cell acute lymphoblastic Teukemia: strategies for enzyme-targeted therapy," Blood, vol. 88, 1996, pp. 3083-3090.
Bertino et al., "Lack of expression of MTAP in uncommon T-cell lymphomas," Clin. Lymphoma Myeloma Leuk, vol. 12, 2012, pp. 306-309.
Brat et al., "Molecular genetic alterations in radiation-induced astrocytomas," Am. J. Pathol, vol. 154, 1999, pp. 1431-1438.
Chen et al., "Genome-wide profiling of oral squamous cell carcinoma," J. Pathol, vol. 204, 2004, pp. 326-332.
Collins et al., "Next generation sequencing of prostate cancer from a patient identifies a deficiency of methylthioadenosine phosphorylase, an exploitable tumor target," Mol. Cancer Ther, vol. 11, 2012, pp. 775-783.
Crespo et al., "Amplified and homozygously deleted genes in glioblastoma: impact on gene expression levels," PLOS One, vol. 7, 2012, e46088, pp. 11.
Curtis et al., "The genomic and transcriptomic architecture of 2,000 breast tumours reveals novel subgroups," Nature, vol. 486, 2012, pp. 346-352.
Dreyling et al., "Codeletion of CDKN2 and MTAP genes in a subset of non-Hodgkin's lymphoma may be associated with histologic transformation from low-grade to diffuse large-cell lymphoma," Genes Chromosomes Cancer, vol. 22, 1998, pp. 72-80.
Frau et al., "Pleiotropic effects of methionine adenosyltransferases deregulation as determinants of liver cancer progression and prognosis," J. Hepatol, vol. 59, Issue 4, 2013, pp. 830-841.
Hori et al., "The methylthioadenosine phosphorylase gene is frequently co-deleted with the p16INK4a gene in acute type adult T-cell leukemia," Int. J. Cancer, vol. 75, 1998, pp. 51-56.
Huang et al., "Homozygous deletion of MTAP gene as a poor prognosticator in gastrointestinal stromal tumors," Clin. Cancer Res, vol. 15, 2009, pp. 6963-6972.
Hustinx et al., "Homozygous deletion of the MTAP gene in invasive adenocarcinoma of the pancreas and in periampullary cancer: a potential new target for therapy," Cancer Biol. Ther, vol. 4, 2005, pp. 83-86.
Illei et al., "Homozygous deletion of CDKN2A and codeletion of the methylthioadenosine phosphorylase gene in the majority of pleural mesotheliomas," Clin. Cancer Res, vol. 9, 2003, pp. 2108-2113.
Karikari et al., "Homozygous deletions of methylthioadenosine phosphorylase in human biliary tract cancers," Mol. Cancer Ther, vol. 4, 2005, pp. 1860-1866.
Kim et al., "Downregulation of methylthioadenosin phosphorylase by homozygous deletion in gastric carcinoma," Genes Chromosomes Cancer, vol. 50, 2011, pp. 421-433.
Kryukov et al., "MTAP deletion confers enhanced dependency on the arginine methyltransferase PRMT5 in human cancer cells," Science, vol. 351, Issue 6278, 2016, pp. 1214-1218.
Liu et al., "Hypoxia induces genomic DNA demethylation through the activation of HIF-1a and transcriptional upregulation of MAT2A in hepatoma cells," Mol. Cancer Ther, vol. 10, Issue 6, 2011, pp. 1113-1123.
Meyer et al., "A seven-marker signature and clinical outcome in malignant melanoma: a largescale tissue-microarray study with two independent patient cohorts," PLOS One, vol. 7, 2012, e38222, pp. 14.
Powel et al., "Concordant loss of MTAP and p16/CDKN2A expression in gastroesophageal carcinogenesis evidence of homozygous deletion in esophageal noninvasive precursor lesions and therapeutic implications," Am. J. Surg. Pathol, vol. 29, 2005, pp. 1497-1504.
Ramani et al., "Leptin's mitogenic effect in human liver cancer cells requires induction of both methionine adenosyltransferase 2A and 2B," Hepatology, vol. 47, Issue 2, 2008, pp. 521-531.
Rodriguez et al., "Transcription of the MAT2A gene, coding for methionine adenosyltransferase, is up-regulated by E2F and Sp1 at a chromatin level during proliferation of liver cells," Int. J. Biochem. Cell Biol, vol. 39, Issue 4, 2007, pp. 842-850.
Schmid et al., "Homozygous deletions of methylthioadenosine phosphorylase (MTAP) are more frequent than p16INK4A (CDKN2) homozygous deletions in primary non-small cell lung cancers (NSCLC)," Oncogene, vol. 17, 1998, pp. 2669-2675.
Stadler et al., "The 9p21 region in bladder cancer cell lines: large homozygous deletion inactivate the CDKN2, CDKN2B and MTAP genes," Urol. Res, vol. 24, 1996, pp. 239-244.
Subhi et al., "Loss of methylthioadenosine phosphorylase and elevated ornithine decarboxylase is common in pancreatic cancer," Clin. Cancer Res, vol. 10, 2004, pp. 7290-7296.
Suzuki et al., "Genetic analysis of human glioblastomas using a genomic microarray system," Brain Tumor Pathol, vol. 21, 2004, pp. 27-34.
Tang et al., "Specific Targeting of MTAP-Deleted Tumors with a Combination of 2'-Fluoroadenine and 5'-Methylthioadenosine," Cancer Res, vol. 78, Issue 15, 2018, pp. 4386-4395.
Tomasi et al., "Methionine adenosyltransferase a2 sumoylation positively regulate Bcl-2 expression in human colon and liver cancer cells," Oncotarget, vol. 6, Issue 35, 2015, pp. 37706-37723.
Tomasi et al., "Polyamine and methionine adenosyltransferase 2A crosstalk in human colon and liver cancer," Exp. Cell Res, vol. 319, Issue12, 2013, pp. 1902-1911.
Usvasalo et al., "Focal 9p instability in hematologic neoplasias revealed by comparative genomic hybridization and single-nucleotide polymorphism microarray analyses," Genes Chromosomes Cancer, vol. 49, 2010, pp. 309-318.
Wang et al., "Expression of methionine adenosyltransferase 2A in renal cell carcinomas and potential mechanism for kidney carcinogenesis," BMC Cancer, vol. 14, 2014, 196, pp. 9.
Watanabe et al., "Immunohistochemical diagnosis of methylthioadenosine phosphorylase (MTAP) deficiency in non-small cell lung carcinoma," Lung Cancer, vol. 63, 2009, pp. 39-44.
Wong et al., "MTAP gene deletion in endometrial cancer," Gynecol. Obstet. Invest, vol. 45, 1998, pp. 272-276.
Yang et al., "Insulin-like growth factor 1 activates methionine adenosyltransferase 2A transcription by multiple pathways in human colon cancer cells," Biochem. J, vol. 436, Issue 2, 2011, pp. 507-516.
Zhang et al., "Characterizing and optimizing human anticancer drug targets based on topological properties in the context of biological pathways," J. Biomed. Inform, vol. 54, 2015, pp. 132-140.
Zhang et al., "Codeletion of the genes for p16INK4, methylthioadenosine phosphorylase, interferon-a1, interferon-β1, and other 9p21 markers in human malignant cell lines," Cancer Genet. Cytogenet, vol. 86, Issue 1, 1996, pp. 22-81.
Zimling et al., "The diagnostic value of immunohistochemically detected methylthioadenosine phosphorylase deficiency in malignant pleural mesotheliomas," Histopathology, vol. 60, 2012, pp. E96-E105.

* cited by examiner

HETEROBICYCLIC INHIBITORS OF MAT2A AND METHODS OF USE FOR TREATING CANCER

BACKGROUND

Methionine adenosyltransferase (MAT), which is also known as S-adenosylmethionine synthetase, is a cellular enzyme that catalyzes the synthesis of S-adenosyl methionine (SAM or AdoMet) from methionine and ATP; the catalysis is considered to be rate-limiting step of the methionine cycle. SAM is the propylamino donor in polyamine biosynthesis, the principal methyl donor for DNA methylation, and is involved in gene transcription and cellular proliferation as well as the production of secondary metabolites.

Two genes designated as MAT1A and MAT2A encode two distinct catalytic MAT isoforms, respectively. A third gene, MAT2B, encodes a MAT2A regulatory subunit. MAT1A is specifically expressed in the adult liver, whereas MAT2A is widely distributed. Because MAT isoforms differ in catalytic kinetics and regulatory properties, MAT1A-expressing cells have considerably higher SAM levels than do MAT2A-expressing cells. It has been found that hypomethylation of the MAT2A promoter and histone acetylation causes upregulation of MAT2A expression.

In hepatocellular carcinoma (HCC), the downregulation of MAT1A and the up-regulation of MAT2A occur, which is known as the MAT1A:MAT2A switch. The switch, accompanied with up-regulation of MAT2B, results in lower SAM contents, which provide a growth advantage to hepatoma cells. Because MAT2A plays a crucial role in facilitating the growth of hepatoma cells, it is a target for antineoplastic therapy. Recent studies have shown that silencing by using small interfering RNA substantially suppresses growth and induces apoptosis in hepatoma cells. See, e.g., T. Li et al., *J. Cancer* 7(10) (2016) 1317-1327.

Some cancer cell lines that are MTAP deficient are particularly sensitive to inhibition of MAT2A. Marjon et al. (Cell Reports 15(3) (2016) 574-587). MTAP (methylthioadenosine phosphorylase) is an enzyme widely expressed in normal tissues that catalyzes the conversion of methylthioadenosine (MTA) into adenine and 5-methylthioribose-1-phosphate. The adenine is salvaged to generate adenosine monophosphate, and the 5-methylthioribose-1-phosphate is converted to methionine and formate. Because of this salvage pathway, MTA can serve as an alternative purine source when de novo purine synthesis is blocked, e.g., with antimetabolites, such as L-alanosine.

MAT2A is dysregulated in additional cancers that lack MTAP-deletion, including hepatocellular carcinoma and leukemia. J. Cai et al., *Cancer Res.* 58 (1998) 1444-1450; T. S. Jani et al., *Cell. Res.* 19 (2009) 358-369. Silencing of MAT2A expression via RNA-interference results in antiproliferative effects in several cancer models. H. Chen et al., *Gastroenterology* 133 (2007) 207-218; Q. Liu et al. *Hepatol. Res.* 37 (2007) 376-388.

Many human and murine malignant cells lack MTAP activity. MTAP deficiency is found not only in tissue culture cells but the deficiency is also present in primary leukemias, gliomas, melanomas, pancreatic cancers, non-small cell lung cancers (NSCLC), bladder cancers, astrocytomas, osteosarcomas, head and neck cancers, myxoid chondrosarcomas, ovarian cancers, endometrial cancers, breast cancers, soft tissue sarcomas, non-Hodgkin lymphoma, and mesotheliomas. The gene encoding for human MTAP maps to region 9p21 on human chromosome 9p. This region also contains the tumor suppressor genes p16INK4A (also known as CDKN2A) and p15INK4B. These genes code for p16 and p15, which are inhibitors of the cyclin D-dependent kinases cdk4 and cdk6, respectively.

The p16INK4A transcript can alternatively be alternative reading frame (ARF) spliced into a transcript encoding p14ARF. p14ARF binds to MDM2 and prevents degradation of p53 (Pomerantz et al. (1998) Cell 92:713-723). The 9p21 chromosomal region is of interest because it is frequently homozygously deleted in a variety of cancers, including leukemias, NSLC, pancreatic cancers, gliomas, melanomas, and mesothelioma. The deletions often inactivate more than one gene. For example, Cairns et al. ((1995) *Nat. Gen.* 11:210-212) reported that after studying more than 500 primary tumors, almost all the deletions identified in such tumors involved a 170 kb region containing MTAP, p14ARF and P16INK4A. Carson et al. (WO 99/67634) reported that a correlation exists between the stage of tumor development and loss of homozygosity of the gene encoding MTAP and the gene encoding p16. For example, deletion of the MTAP gene, but not p16INK4A was reported to be indicative of a cancer at an early stage of development, whereas deletion of the genes encoding for p16 and MTAP was reported to be indicative of a cancer at a more advanced stage of tumor development. In some osteosarcoma patients, the MTAP gene was present at diagnosis but was deleted at a later time point (Garcia-Castellano et al., *Clin. Cancer Res.* 8(3) 2002 782-787).

SUMMARY

The present disclosure provides compounds that inhibit MAT2A. The compounds and their pharmaceutical compositions are useful in methods for treating various cancers, including those that are refractory to standard treatments, such as surgery, radiation therapy, chemotherapy, and hormonal therapy.

Thus, in accordance with some embodiments, the present disclosure provides compounds according to Formula I or pharmaceutically acceptable salts thereof:

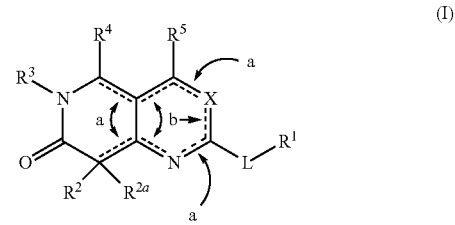

In Formula I, X is N or $CR^6$; L is O, S, NR, or a bond; and R is H or $C_1$-$C_6$-alkyl.

$R^1$ is selected from the group consisting of $C_1$-$C_6$-alkyl, $C_3$-$C_6$-carbocyclyl, —($C_1$-$C_6$-alkyl)($C_3$-$C_6$-carbocyclyl), and —($C_1$-$C_6$-alkyl)($C_3$-$C_6$-cycloalkenyl), wherein any alkyl in $R^1$ is straight or branched, and $R^1$ is optionally substituted by 1-6 halo.

Alternatively, when L is N, then R and $R^1$ in combination with L represent a 3- to 6-membered heterocycloalkyl (wherein 1-4 ring members are independently selected from N, O, and S) that is optionally substituted by one or more $R^4$.

$R^2$ and $R^3$ are independently selected from the group consisting of $C_6$-$C_{10}$-aryl, 5- to 10-membered heteroaryl (wherein 1-4 heteroaryl members are independently selected from N, O, and S), and 3- to 14-membered heterocycloalkyl (wherein 1-4 heterocycloalkyl members are independently selected from N, O, and S). $R^2$ and $R^3$ are independently and optionally substituted by one or more substituents that are selected from the group consisting of $R^A$, $OR^A$, halo, —N=N—$R^A$, $N^AR^B$, —($C_1$-$C_6$-alkyl)$NR^AR^B$, —C(O)$OR^A$, —C(O)$NR^AR^B$, —OC(O)$R^A$, and —CN.

$R^{2a}$ is absent or present and, if present, it is taken together with $R^2$ and the carbon atom to which they are attached to form a spiro-fused 5- to 6-membered carbocyclyl or heterocycloalkyl (wherein 1-4 ring members are independently selected from $NR^A$, O, and S), wherein the spiro-fused 5- to 6-membered carbocyclyl or heterocycloalkyl is optionally substituted by one or more $R^A$, and each bond, ═══(a) represents a single bond and each bond ═══(b) represents a double bond.

When $R^{2a}$ is absent, then each bond ═══(a) represents a double bond and each bond ═══(b) represents a single bond.

$R^4$, $R^5$, and $R^6$ are independently selected from the group consisting of $R^A$, $OR^A$, halo, $NR^AR^B$, —($C_1$-$C_6$-alkyl) $NR^AR^B$, —C(O)$OR^A$, —C(O)$NR^AR^B$ and —OC(O)$R^A$;

$R^A$ and $R^B$ are independently selected from the group consisting of H, —CN, hydroxy, oxo, $C_1$-$C_6$-alkyl, $C_1$-$C_6$-alkoxy, $C_2$-$C_6$-alkenyl, $C_2$-$C_6$-alkynyl, $NH_2$, —S(O)$_{0-2}$—($C_1$-$C_6$-alkyl), —S(O)$_{0-2}$—($C_6$-$C_{10}$-aryl), —C(O)($C_1$-$C_6$-alkyl), —C(O)($C_3$-$C_{14}$-carbocyclyl), —$C_3$-$C_{14}$-carbocyclyl, —($C_1$-$C_6$-alkyl)($C_3$-$C_{14}$-carbocyclyl), $C_6$-$C_{10}$-aryl, 3- to 14-membered heterocycloalkyl, and —($C_1$-$C_6$-alkyl)-(3- to 14-membered heterocycloalkyl) (wherein 1-4 heterocycloalkyl members are independently selected from N, O, and S), and 5- to 10-membered heteroaryl (wherein 1-4 heteroaryl members are independently selected from N, O, and S).

Each alkyl, alkoxy, alkenyl, alkynyl, aryl, carbocyclyl, heterocycloalkyl, and heteroaryl moiety of $R^A$ and $R^B$ is optionally substituted with one or more substituents selected from the group consisting of hydroxy, halo, —$NR'_2$ (wherein each R is independently selected from the group consisting of $C_1$-$C_6$-alkyl, $C_2$-$C_6$-alkenyl, $C_2$-$C_6$-alkynyl, $C_6$-$C_{10}$-aryl, 3- to 14-membered heterocycloalkyl and —($C_1$-$C_6$-alkyl)-(3- to 14-membered heterocycloalkyl) (wherein 1-4 ring members are independently selected from N, O, and S), and 5- to 10-membered heteroaryl (wherein 1-4 ring members are independently selected from N, O, and S), —NHC(O)(O$C_1$-$C_6$-alkyl), —$NO_2$, —CN, oxo, —C(O)OH, —C(O)O($C_1$-$C_6$-alkyl), —$C_1$-$C_6$-alkyl($C_1$-$C_6$-alkoxy), —C(O)$NH_2$, $C_1$-$C_6$-alkyl, —C(O)$C_1$-$C_6$-alkyl, —O$C_1$-$C_6$-alkyl, —Si($C_1$-$C_6$-alkyl)$_3$, —S(O)$_{0-2}$—($C_1$-$C_6$-alkyl), $C_6$-$C_{10}$-aryl, —($C_1$-$C_6$-alkyl)($C_6$-$C_{10}$-aryl), 3- to 14-membered heterocycloalkyl, and —($C_1$-$C_6$-alkyl)-(3- to 14-membered heterocycloalkyl) (wherein 1-4 ring members are independently selected from N, O, and S), and —O($C_6$-$C_{14}$-aryl), wherein each alkyl, aryl, and heterocycloalkyl in $R^A$ and $R^B$ is optionally substituted with one or more substituents selected from the group consisting of hydroxy, —O$C_1$-$C_6$-alkyl, halo, —$NH_2$, —($C_1$-$C_6$-alkyl)$NH_2$, —C(O)OH, CN, and oxo.

The present disclosure also provides, in accordance with additional embodiments, compounds according to Formula II or pharmaceutically acceptable salts thereof:

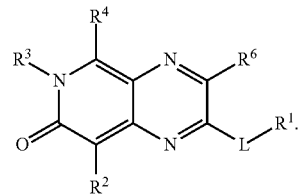

(II)

In Formula II, L is O, S, NR, or a bond; and R is H or $C_1$-$C_6$-alkyl.

$R^1$ is selected from the group consisting of $C_1$-$C_6$-alkyl, $C_2$-$C_6$-alkenyl, $C_3$-$C_6$-carbocyclyl, —($C_1$-$C_6$-alkyl)($C_3$-$C_6$-carbocyclyl), and —($C_1$-$C_6$-alkyl)($C_3$-$C_6$-cycloalkenyl) wherein any alkyl in $R^1$ is straight or branched, and $R^1$ is optionally substituted by 1-6 halo.

Alternatively, in some embodiments when L is NR, then R and $R^1$ in combination with L represent a 3- to 6-membered heterocycloalkyl (wherein 1-4 ring members are independently selected from N, O, and S) optionally substituted by one or more $R^A$.

$R^2$ and $R^3$ are independently selected from the group consisting of $C_6$-$C_{10}$-aryl, 5- to 10-membered heteroaryl (wherein 1-4 heteroaryl members are independently selected from N, O, and S), and 3- to 14-membered heterocycloalkyl (wherein 1-4 heterocycloalkyl members are independently selected from N, O, and S), wherein $R^2$ and $R^3$ are independently and optionally substituted by one or more substituents that are selected from the group consisting of $R^A$, $OR^A$, halo, —N=N—$R^A$, $NR^AR^B$, —($C_1$-$C_6$-alkyl)$NR^AR^B$, —C(O)$OR^A$, —C(O)$NR^AR^B$, —OC(O)$R^A$, and —CN.

$R^4$ and $R^6$ are independently selected from the group consisting of $R^A$, $OR^A$, halo, $NR^AR^B$, —($C_1$-$C_6$-alkyl) $NR^AR^B$, —C(O)$OR^A$, —C(O)$NR^AR^B$ and —OC(O)$R^A$.

$R^A$ and $R^B$ are independently selected from the group consisting of H, —CN, -hydroxy, oxo, $C_1$-$C_6$-alkyl, $C_1$-$C_6$-alkoxy, $C_2$-$C_6$-alkenyl, $C_2$-$C_6$-alkynyl, $NH_2$, —S(O)$_{0-2}$—($C_1$-$C_6$-alkyl), —S(O)$_{0-2}$—($C_6$-$C_{10}$-aryl), —C(O)($C_1$-$C_6$-alkyl), —C(O)($C_3$-$C_{14}$-carbocyclyl), —$C_3$-$C_{14}$-carbocyclyl, —($C_1$-$C_6$-alkyl)($C_3$-$C_{14}$-carbocyclyl), $C_6$-$C_{10}$-aryl, 3- to 14-membered heterocycloalkyl and —($C_1$-$C_6$-alkyl)-(3- to 14-membered heterocycloalkyl) (wherein 1-4 heterocycloalkyl members are independently selected from N, O, and S), and 5- to 10-membered heteroaryl (wherein 1-4 heteroaryl members are independently selected from N, O, and S);

In $R^A$ and $R^B$, each alkyl, alkoxy, alkenyl, alkynyl, aryl, carbocyclyl, heterocycloalkyl, and heteroaryl moiety of $R^A$ and $R^B$ is optionally substituted with one or more substituents selected from the group consisting of hydroxy, halo, —$NR'_2$ (wherein each R' is independently selected from the group consisting of $C_1$-$C_6$-alkyl, $C_2$-$C_6$-alkenyl, $C_2$-$C_6$-alkynyl, $C_6$-$C_{10}$-aryl, 3- to 14-membered heterocycloalkyl and —($C_1$-$C_6$-alkyl)-(3- to 14-membered heterocycloalkyl) (wherein 1-4 ring members are independently selected from N, O, and S), and 5- to 10-membered heteroaryl (wherein 1-4 heteroaryl members are independently selected from N, O, and S), —NHC(O)(O$C_1$-$C_6$-alkyl), —$NO_2$, —CN, oxo, —C(O)OH, —C(O)O($C_1$-$C_6$-alkyl), —$C_1$-$C_6$-alkyl($C_1$-$C_6$-alkoxy), —C(O)$NH_2$, $C_1$-$C_6$-alkyl, —C(O)$C_1$-$C_6$-alkyl, —O$C_1$-$C_6$-alkyl, —Si($C_1$-$C_6$-alkyl)$_3$, —S(O)$_{0-2}$—($C_1$-$C_6$-alkyl), $C_6$-$C_{10}$-aryl, —($C_1$-$C_6$-alkyl)($C_6$-$C_{10}$-aryl), 3- to 14-membered heterocycloalkyl, and —($C_1$-$C_6$-alkyl)-(3- to 14-membered heterocycle) (wherein 1-4 heterocycle members are independently selected from N, O, and S), and —O($C_1$-$C_{14}$-aryl), and wherein each alkyl, alkenyl, aryl, and heterocycloalkyl in $R^A$ and $R^B$ is optionally substituted with one or more substituents selected from the group consisting of hydroxy, —OC$_1$-C$_6$-alkyl, halo, —NH$_2$, —(C$_1$-C$_6$-alkyl)NH$_2$, —C(O)OH, CN, and oxo.

In another embodiment, the present disclosure provides a pharmaceutical composition comprising a compound of Formula I or Formula II or a pharmaceutically acceptable salt thereof, and a pharmaceutically acceptable carrier.

In yet another embodiment, the present disclosure provides a method for inhibiting the synthesis of SAM in a cell, comprising contacting the cell with an effective amount of a compound of Formula I or Formula II or a pharmaceutically acceptable salt thereof.

In yet another embodiment, the present disclosure provides a method for inhibiting the synthesis of SAM in a subject, comprising administering to the subject an effective amount of a compound of Formula I or Formula II or a pharmaceutically acceptable salt thereof.

Yet another embodiment is a method of treating a cancer in a subject suffering therefrom, comprising administering to the subject an effective amount of a compound of Formula I or Formula II or a pharmaceutically acceptable salt thereof. In some embodiments, the cancer is an MTAP-deleted cancer.

Also provided in an embodiment is a method for treating a cancer in a subject suffering therefrom, wherein the cancer is characterized by a reduction or absence of MTAP gene expression, or reduced or absent function of MTAP protein, as compared to cancers where the MTAP gene or protein is present and/or fully functioning, or as compared to cancers with wild type MTAP gene, comprising administering to the subject a therapeutically effective amount of a compound of Formula I or Formula II or a pharmaceutically acceptable salt thereof.

In another embodiment, optionally in combination with any other embodiment described herein, the present disclosure provides a compound of Formula I or Formula III or a pharmaceutically acceptable salt thereof, for use in inhibiting the synthesis of SAM in a cell. Alternatively, in accordance with some embodiments, optionally in combination with any other embodiment described herein, the compound is useful for inhibiting the synthesis of SAM in a subject. Another embodiment, optionally in combination with any other embodiment described herein, provides the use of a compound of Formula I or Formula II or a pharmaceutically acceptable salt thereof in the manufacture of a medicament for inhibiting the synthesis of SAM in a subject.

Yet another embodiment, optionally in combination with any other embodiment described herein, provides a compound of Formula I or Formula II or a pharmaceutically acceptable salt thereof, for use in treating a cancer in a subject suffering therefrom. An embodiment, optionally in combination with any other embodiment described herein, is the use of a compound of Formula I or Formula II or a pharmaceutically acceptable salt thereof in the manufacture of a medicament for treating a cancer in a subject suffering therefrom. In some embodiments, the cancer is an MTAP-deleted cancer, or is characterized by a reduction or absence of MTAP gene expression, or reduced function of MTAP protein, as compared to cancers with fully functional MTAP gene expression or function, or to cancers with fully functional MTAP protein function.

DETAILED DESCRIPTION

The compounds described herein are inhibitors of MAT2A. The present disclosure thus relates not only to such compounds having a structure according to Formula I or Formula II, but also to their pharmaceutical compositions. The compounds and compositions disclosed herein are useful in treating cancers. Some cancers include various MTAP-deleted cancers, i.e., those cancers characterized by the absence or deletion of the MTAP gene.

Definitions

"Alkyl" refers to straight, branched chain, or cyclic hydrocarbyl groups, e.g., "cycloalkyl," including from 1 to about 20 carbon atoms. For instance, an alkyl can have from 1 to 10 carbon atoms or 1 to 6 carbon atoms. Exemplary alkyl includes straight chain alkyl groups such as methyl, ethyl, propyl, butyl, pentyl, hexyl, heptyl, octyl, nonyl, decyl, undecyl, dodecyl, and the like, and also includes branched chain isomers of straight chain alkyl groups, for example without limitation, —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, and the like. Thus, alkyl groups include primary alkyl groups, secondary alkyl groups, and tertiary alkyl groups. An alkyl group can be unsubstituted or optionally substituted with one or more substituents as described herein below.

The phrase "substituted alkyl" refers to alkyl substituted at one or more positions, for example, 1, 2, 3, 4, 5, or even 6 positions, which substituents are attached at any available atom to produce a stable compound, with substitution as described herein. "Optionally substituted alkyl" refers to alkyl or substituted alkyl.

Each of the terms "halogen," "halide," and "halo" refers to —F, —Cl, —Br, or —I.

The term "alkenyl" refers to straight, branched chain, or cyclic hydrocarbyl groups, e.g., "cycloalkenyl," including from 2 to about 20 carbon atoms having 1-3, 1-2, or at least one carbon to carbon double bond. The term "cycloalkenyl" refers specifically to cyclic alkenyl, such as C$_3$-C$_6$-cycloalkenyl. An alkenyl group can be unsubstituted or optionally substituted with one or more substituents as described herein below.

"Substituted alkenyl" refers to alkenyl substituted at 1 or more, e.g., 1, 2, 3, 4, 5, or even 6 positions, which substituents are attached at any available atom to produce a stable compound, with substitution as described herein. "Optionally substituted alkenyl" refers to alkenyl or substituted alkenyl.

"Alkyne or "alkynyl" refers to a straight or branched chain unsaturated hydrocarbon having the indicated number of carbon atoms and at least one triple bond. Examples of a (C$_2$-C$_8$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

"Substituted alkynyl" refers to an alkynyl substituted at 1 or more, e.g., 1, 2, 3, 4, 5, or even 6 positions, which substituents are attached at any available atom to produce a stable compound, with substitution as described herein. "Optionally substituted alkynyl" refers to alkynyl or substituted alkynyl.

The term "alkoxy" refers to an —O-alkyl group having the indicated number of carbon atoms. For example, a (C$_1$-C$_6$)alkoxy group includes —O-methyl, —O-ethyl, —O- propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "carbocyclyl" refers to a monocyclic, bicyclic, tricyclic, or polycyclic, 3- to 14-membered ring system, which is either saturated, such as "cycloalkyl," or unsaturated, such as "cycloalkenyl." The carbocyclyl may be attached via any atom. Carbocyclyl, for instance, also contemplates fused rings wherein, for instance, a carbocyclyl is fused to an aryl or heteroaryl ring as defined herein. Representative examples of carbocyclyl include, but are not limited to cyclopropyl, cyclobutyl, cyclopentyl, cyclohexyl, cyclopropenyl, cyclobutenyl, cyclopentenyl, cyclohexenyl, phenyl, naphthyl, anthracyl, benzofuranyl, and benzothiophenyl. A carbocyclyl group can be unsubstituted or optionally substituted with one or more substituents as described herein below.

"Substituted carbocyclyl" refers to carbocyclyl substituted at 1 or more, e.g., 1, 2, 3, 4, 5, or even 6 positions, which substituents are attached at any available atom to produce a stable compound, with substitution as described herein. "Optionally substituted carbocyclyl" refers to carbocyclyl or substituted carbocyclyl.

"Aryl" when used alone or as part of another term means a carbocyclic aromatic group whether or not fused having the number of carbon atoms designated or if no number is designated, up to 14 carbon atoms, such as a $C_6$-$C_{14}$-aryl. Particular aryl groups are phenyl, naphthyl, biphenyl, phenanthrenyl, naphthacenyl, and the like (see e.g. *Lang's Handbook of Chemistry* (Dean, J. A., ed) 13th ed. Table 7-2 [1985]). A particular aryl is phenyl. "Aryl" also includes aromatic ring systems that are optionally fused with a carbocyclyl ring, as herein defined. An aryl group can be unsubstituted or optionally substituted with one or more substituents as described herein below.

A "substituted aryl" is an aryl that is independently substituted with one or more substituents attached at any available atom to produce a stable compound, wherein the substituents are as described herein. "Optionally substituted aryl" refers to aryl or substituted aryl.

The term "heteroatom" refers to N, O, and S. Disclosed compounds that contain N or S atoms can be optionally oxidized to the corresponding N-oxide, sulfoxide, or sulfone compounds.

"Heteroaryl," alone or in combination with any other moiety described herein, refers to a monocyclic aromatic ring structure containing 5 to 10, such as 5 or 6 ring atoms, or a bicyclic aromatic group having 8 to 10 atoms, containing one or more, such as 1-4, 1-3, or 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or heteroatom is the point of attachment of the heteroaryl ring structure such that a stable compound is produced. Examples of heteroaryl groups include, but are not limited to, pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl. A heteroaryl group can be unsubstituted or optionally substituted with one or more substituents as described herein below.

A "substituted heteroaryl" is a heteroaryl that is independently substituted, unless indicated otherwise, with one or more, e.g., 1, 2, 3, 4 or 5, also 1, 2, or 3 substituents, also 1 substituent, attached at any available atom to produce a stable compound, wherein the substituents are as described herein. "Optionally substituted heteroaryl" refers to heteroaryl or substituted heteroaryl.

"Heterocycloalkyl" means a saturated or unsaturated non-aromatic monocyclic, bicyclic, tricyclic or polycyclic ring system that has from 3 to 14, such as 3 to 6, atoms in which from 1 to 3 carbon atoms in the ring are replaced by heteroatoms of O, S or N. A heterocycloalkyl is optionally fused with aryl or heteroaryl of 5-6 ring members, and includes oxidized S or N, such as sulfinyl, sulfonyl and N-oxide of a tertiary ring nitrogen. The point of attachment of the heterocycloalkyl ring is at a carbon or heteroatom such that a stable ring is retained. Examples of heterocycloalkyl groups include without limitation morpholino, tetrahydrofuranyl, dihydropyridinyl, piperidinyl, pyrrolidinyl, piperazinyl, dihydrobenzofuryl, and dihydroindolyl. A hetercycloalkyl group can be unsubstituted or optionally substituted with one or more substituents as described herein below.

"Optionally substituted heterocycloalkyl" denotes a heterocycloalkyl that is substituted with 1 to 3 substituents, e.g., 1, 2 or 3 substituents, attached at any available atom to produce a stable compound, wherein the substituents are as described herein.

The term "nitrile" or "cyano" can be used interchangeably and refer to a —CN group which is bound to a carbon atom of a heteroaryl ring, aryl ring and a heterocycloalkyl ring.

The term "oxo" refers to a =O atom attached to a saturated or unsaturated moiety. The =O atom can be attached to a carbon, sulfur, or nitrogen atom that is part of a cyclic or acyclic moiety.

A "hydroxyl" or "hydroxy" refers to an —OH group.

The substituent —$CO_2H$ may be replaced with bioisosteric replacements such as:

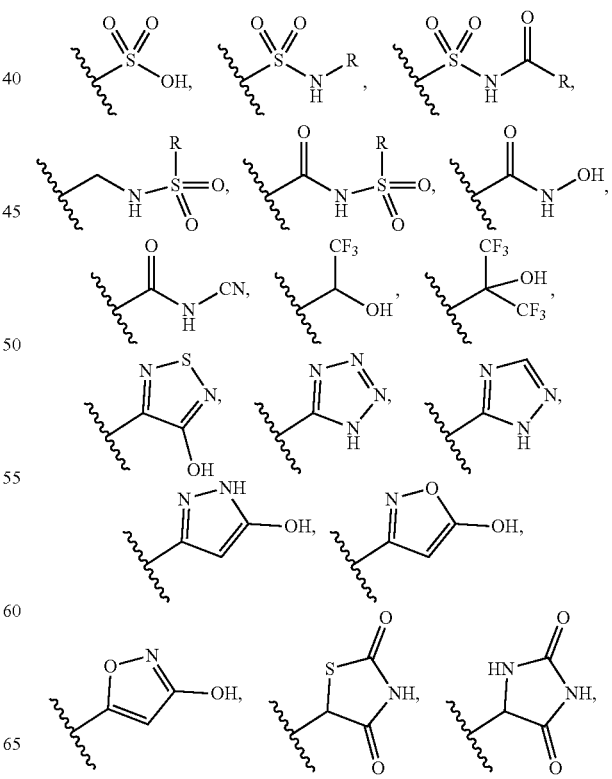

-continued

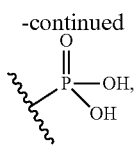

and the like, wherein R has the same definition as $R^A$ as defined herein. See, e.g., THE PRACTICE OF MEDICINAL CHEMISTRY (Academic Press: New York, 1996), at page 203.

Compounds described herein can exist in various isomeric forms, including configurational, geometric, and conformational isomers, including, for example, cis- or trans-conformations. The compounds may also exist in one or more tautomeric forms, including both single tautomers and mixtures of tautomers. The term "isomer" is intended to encompass all isomeric forms of a compound of this disclosure, including tautomeric forms of the compound. The compounds of the present disclosure may also exist in open-chain or cyclized forms. In some cases, one or more of the cyclized forms may result from the loss of water. The specific composition of the open-chain and cyclized forms may be dependent on how the compound is isolated, stored or administered. For example, the compound may exist primarily in an open-chained form under acidic conditions but cyclize under neutral conditions. All forms are included in the present disclosure.

Some compounds described herein can have asymmetric centers and therefore exist in different enantiomeric and diastereomeric forms. A compound of the present disclosure can be in the form of an optical isomer or a diastereomer. Accordingly, the disclosure encompasses compounds and their uses as described herein in the form of their optical isomers, diastereoisomers and mixtures thereof, including a racemic mixture. Optical isomers of the compounds of the disclosure can be obtained by known techniques such as asymmetric synthesis, chiral chromatography, simulated moving bed technology or via chemical separation of stereoisomers through the employment of optically active resolving agents.

Unless otherwise indicated, the term "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound. The stereoisomer as described above can be viewed as composition comprising two stereoisomers that are present in their respective weight percentages described herein.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

As used herein, and unless expressly and specifically stated to the contrary, the term "compound" is inclusive in that it encompasses a compound or a pharmaceutically acceptable salt, stereoisomer, and/or tautomer thereof. Thus, for instance, a compound of Formula I or Formula II includes a pharmaceutically acceptable salt of the compound. Similarly, a compound of Formula I or Formula II includes a pharmaceutically acceptable salt of a tautomer of the compound.

In this description, a "pharmaceutically acceptable salt" is a pharmaceutically acceptable, organic or inorganic acid or base salt of a compound of the present disclosure. Representative pharmaceutically acceptable salts include, e.g., alkali metal salts, alkali earth salts, ammonium salts, water-soluble and water-insoluble salts, such as the acetate, amsonate (4,4-diaminostilbene-2, 2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient or subject with such a disease.

The terms "prevent," "preventing," and "prevention" refer to the prevention of the onset, recurrence, or spread of the disease in a patient or subject resulting from the administration of a prophylactic or therapeutic agent.

The term "effective amount" refers to an amount of a compound of the present disclosure or other active ingredient sufficient to provide a therapeutic or prophylactic benefit in the treatment or prevention of a disease or to delay or minimize symptoms associated with a disease. Further, a therapeutically effective amount with respect to a compound of the present disclosure means that amount of therapeutic agent alone, or in combination with other therapies, that provides a therapeutic benefit in the treatment or prevention of a disease. Used in connection with a compound of the present disclosure, the term can encompass an amount that improves overall therapy, reduces or avoids symptoms or causes of disease, or enhances the therapeutic efficacy of or is synergistic with another therapeutic agent.

A "patient" or "subject" includes an animal, such as a human, cow, horse, sheep, lamb, pig, chicken, turkey, quail, cat, dog, mouse, rat, rabbit or guinea pig. In accordance with some embodiments, the animal is a mammal such as a non-primate and a primate (e.g., monkey and human). In the present disclosure, the terms "patient" and "subject" are used interchangeably. In one embodiment, a patient or subject is a human, and in other embodiments a patient or subject is a human infant, child, adolescent or adult.

"Inhibitor" means a compound which prevents or reduces the amount of synthesis of SAM. In an embodiment, an inhibitor binds to MAT2A.

Compounds

As described generally above, the present disclosure provides compounds according to Formula I and pharmaceutically acceptable salts

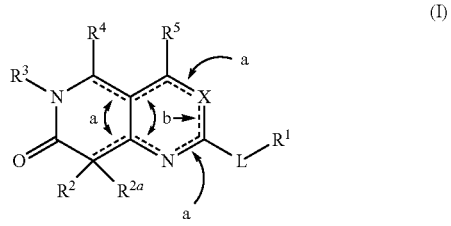

(I)

In Formula I, X is N or $CR^6$; L is O, S, NR, or a bond; and R is H or $C_1$-$C_6$-alkyl.

$R^1$ is selected from the group consisting of $C_1$-$C_6$-alkyl, $C_2$-$C_6$-alkenyl, $C_3$-$C_6$-carbocyclyl, —($C_1$-$C_6$-alkyl)($C_3$-$C_6$-carbocyclyl), and —($C_1$-$C_6$-alkyl)($C_3$-$C_6$-cycloalkenyl) wherein any alkyl in $R^1$ is straight or branched, and $R^1$ is optionally substituted by 1-6 halo.

In an embodiment when L is N, then R and $R^1$ in combination with L represent a 3- to 6-membered heterocycloalkyl (wherein 1-4 heterocycloalkyl members are independently selected from N, O, and S) that is optionally substituted by one or more $R^4$.

$R^2$ and $R^3$ are independently selected from the group consisting of $C_6$-$C_{10}$-aryl, 5- to 10-membered heteroaryl (wherein 1-4 heteroaryl members are independently selected from N, O, and S), and 3- to 14-membered heterocycloalkyl (wherein 1-4 heterocycloalkyl members are independently selected from N, O, and S), wherein $R^2$ and $R^3$ are independently and optionally substituted by one or more substituents that are selected from the group consisting of $R^A$, $OR^A$, halo, —N═N—$R^A$, $N^AR^B$, —($C_1$-$C_6$-alkyl)$NR^AR^B$, —C(O)$OR^A$, —C(O)$NR^AR^B$, —OC(O)$R^A$, and —CN.

$R^{2a}$ is absent or present and, if present, it is taken together with $R^2$ and the carbon atom to which they are attached to form a spiro-fused 5- to 6-membered carbocyclyl or heterocycloalkyl (wherein 1-4 heterocycloalkyl members are independently selected from N, O, and S); and each bond ═══(a) represents a single bond and each bond ═══(b) represents a double bond, wherein the spiro-fused 5- to 6-membered carbocyclyl or heterocycloalkyl is optionally substituted by one or more $R^4$.

If $R^{2a}$ is absent, then each bond ═══(a) represents a double bond and each bond ═══(b) represents a single bond.

$R^4$, $R^5$, and $R^6$ are independently selected from the group consisting of $R^A$, $OR^A$, halo, $NR^AR^B$, —($C_1$-$C_6$-alkyl) $NR^AR^B$, —C(O)$OR^A$, —C(O)$NR^AR^B$ and —OC(O)$R^A$.

$R^A$ and $R^B$ are independently selected from the group consisting of H, —CN, hydroxy, oxo, $C_1$-$C_6$-alkyl, $C_1$-$C_6$-alkoxy, $C_2$-$C_6$-alkenyl, $C_2$-$C_6$-alkynyl, $NH_2$, —S(O)$_{0-2}$—($C_1$-$C_6$-alkyl), —S(O)$_{0-2}$—($C_6$-$C_{10}$-aryl), —C(O)($C_1$-$C_6$-alkyl), —C(O)($C_3$-$C_{14}$-carbocyclyl), —$C_3$-$C_{14}$-carbocyclyl, —($C_1$-$C_6$-alkyl)($C_3$-$C_{14}$-carbocyclyl), $C_6$-$C_{10}$-aryl, 3- to 14-membered heterocycloalkyl, and —($C_1$-$C_6$-alkyl)-(3- to 14-membered heterocycloalkyl) (wherein 1-4 heterocycloalkyl members are independently selected from N, O, and S), and 5- to 10-membered heteroaryl (wherein 1-4 heteroaryl members are independently selected from N, O, and S); wherein each alkyl, alkoxy, alkenyl, alkynyl, aryl, carbocyclyl, heterocycloalkyl, and heteroaryl moiety of $R^A$ and $R^B$ is optionally substituted with one or more substituents selected from the group consisting of hydroxy, halo, —NR'$_2$ (wherein each R' is independently selected from the group consisting of $C_1$-$C_6$-alkyl, $C_2$-$C_6$-alkenyl, $C_2$-$C_6$-alkynyl, $C_6$-$C_{10}$-aryl, 3- to 14-membered heterocycloalkyl and —($C_1$-$C_6$-alkyl)-(3- to 14-membered heterocycloalkyl) (wherein 1-4 heterocycloalkyl members are independently selected from N, O, and S), and 5- to 10-membered heteroaryl (wherein 1-4 heteroaryl members are independently selected from N, O, and S), —NHC(O)(O$C_1$-$C_6$-alkyl), —$NO_2$, —CN, oxo, —C(O)OH, —C(O)O($C_1$-$C_6$-alkyl), —$C_1$-$C_6$-alkyl($C_1$-$C_6$-alkoxy), —C(O)$NH_2$, $C_1$-$C_6$-alkyl, —C(O)$C_1$-$C_6$-alkyl, —O$C_1$-$C_6$-alkyl, —Si($C_1$-$C_6$-alkyl)$_3$, —S(O)$_{0-2}$—($C_1$-$C_6$-alkyl), $C_6$-$C_{10}$-aryl, —($C_1$-$C_6$-alkyl) ($C_6$-$C_{10}$-aryl), 3- to 14-membered heterocycloalkyl, and —($C_1$-$C_6$-alkyl)-(3- to 14-membered heterocycloalkyl) (wherein 1-4 ring members are independently selected from N, O, and S), and —O($C_6$-$C_{14}$-aryl), and wherein each alkyl, alkenyl, aryl, and heterocycloalkyl in $R^A$ and $R^B$ is optionally substituted with one or more substituents selected from the group consisting of hydroxy, —O$C_1$-$C_6$-alkyl, halo, —$NH_2$, —($C_1$-$C_6$-alkyl)$NH_2$, —C(O)OH, CN, and oxo.

According to various embodiments, when $R^{2a}$ is absent, each bond ═══(a) represents a double bond and each bond ═══(b) represents a single bond. In one embodiment, X is N. In another embodiment, X is $CR^6$.

In accordance with various embodiments, compounds of Formula (I) have a structure according to Formula (IA):

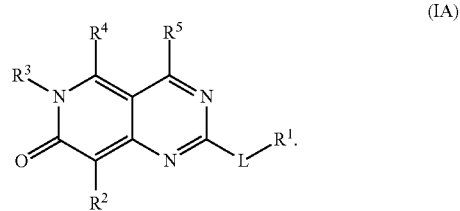

(IA)

Alternatively, compounds of Formula (I) have a structure according to Formula (IB):

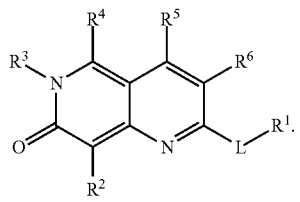
(IB)

The present disclosure also provides compounds according to Formula II and pharmaceutically acceptable salts thereof:

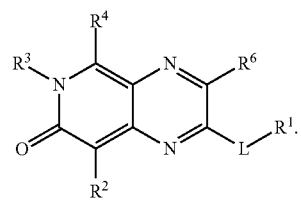
(II)

In Formula II, L is O, S, NR, or a bond; and R is H or $C_1$-$C_6$-alkyl.

$R^1$ is selected from the group consisting of $C_1$-$C_6$-alkyl, $C_2$-$C_6$-alkenyl, $C_3$-$C_6$-carbocyclyl, —($C_1$-$C_6$-alkyl)($C_3$-$C_6$-carbocyclyl), and —($C_1$-$C_6$-alkyl)($C_3$-$C_6$-cycloalkenyl) wherein any alkyl in $R^1$ is straight or branched, and $R^1$ is optionally substituted by 1-6 halo.

Alternatively, in some embodiments when L is NR, then R and $R^1$ in combination with L represent a 3- to 6-membered heterocycloalkyl (wherein 1-4 ring members are independently selected from N, O, and S) optionally substituted by one or more $R^A$.

$R^2$ and $R^3$ are independently selected from the group consisting of $C_6$-$C_{10}$-aryl, 5- to 10-membered heteroaryl (wherein 1-4 heteroaryl members are independently selected from N, O, and S), and 3- to 14-membered heterocycloalkyl (wherein 1-4 heterocycloalkyl members are independently selected from N, O, and S), wherein $R^2$ and $R^3$ are independently and optionally substituted by one or more substituents that are selected from the group consisting of $R^A$, $OR^A$, halo, —N=N—$R^A$, $NR^AR^B$, —($C_1$-$C_6$-alkyl)$NR^AR^B$, —C(O)$OR^A$, —C(O)$NR^AR^B$, —OC(O)$R^A$, and —CN.

$R^4$ and $R^6$ are independently selected from the group consisting of $R^A$, $OR^A$, halo, $NR^AR^B$, —($C_1$-$C_6$-alkyl)$NR^AR^B$, —C(O)$OR^A$, —C(O)$NR^AR^B$ and —OC(O)$R^A$.

$R^A$ and $R^B$ are independently selected from the group consisting of H, —CN, -hydroxy, oxo, $C_1$-$C_6$-alkyl, $C_1$-$C_6$-alkoxy, $C_2$-$C_6$-alkenyl, $C_2$-$C_6$-alkynyl, $NH_2$, —$S(O)_{0-2}$—($C_1$-$C_6$-alkyl), —$S(O)_{0-2}$—($C_6$-$C_{10}$-aryl), —C(O)($C_1$-$C_6$-alkyl), —C(O)($C_3$-$C_{14}$-carbocyclyl), —$C_3$-$C_{14}$-carbocyclyl, —($C_1$-$C_6$-alkyl)($C_3$-$C_{14}$-carbocyclyl), $C_6$-$C_{10}$-aryl, 3- to 14-membered heterocycloalkyl and —($C_1$-$C_6$-alkyl)-(3- to 14-membered heterocycloalkyl) (wherein 1-4 heterocycloalkyl members are independently selected from N, O, and S), and 5- to 10-membered heteroaryl (wherein 1-4 heteroaryl members are independently selected from N, O, and S);

In $R^A$ and $R^B$, each alkyl, alkoxy, alkenyl, alkynyl, aryl, carbocyclyl, heterocycloalkyl, and heteroaryl moiety of $R^A$ and $R^B$ is optionally substituted with one or more substituents selected from the group consisting of hydroxy, halo, —$NR'_2$ (wherein each R' is independently selected from the group consisting of $C_1$-$C_6$-alkyl, $C_2$-$C_6$-alkenyl, $C_2$-$C_6$-alkynyl, $C_6$-$C_{10}$-aryl, 3- to 14-membered heterocycloalkyl and —($C_1$-$C_6$-alkyl)-(3- to 14-membered heterocycloalkyl) (wherein 1-4 ring members are independently selected from N, O, and S), and 5- to 10-membered heteroaryl (wherein 1-4 heteroaryl members are independently selected from N, O, and S), —NHC(O)(O$C_1$-$C_6$-alkyl), —$NO_2$, —CN, oxo, —C(O)OH, —C(O)O($C_1$-$C_6$-alkyl), —$C_1$-$C_6$-alkyl($C_1$-$C_6$-alkoxy), —C(O)$NH_2$, $C_1$-$C_6$-alkyl, —C(O)$C_1$-$C_6$-alkyl, —O$C_1$-$C_6$-alkyl, —Si($C_1$-$C_6$-alkyl)$_3$, —$S(O)_{0-2}$—($C_1$-$C_6$-alkyl), $C_6$-$C_{10}$-aryl, —($C_1$-$C_6$-alkyl)($C_1$-$C_{10}$-aryl), 3- to 14-membered heterocycloalkyl, and —($C_1$-$C_6$-alkyl)-(3- to 14-membered heterocycle) (wherein 1-4 heterocycle members are independently selected from N, O, and S), and —O($C_6$-$C_{14}$-aryl), and wherein each alkyl, alkenyl, aryl, and heterocycloalkyl in $R^A$ and $R^B$ is optionally substituted with one or more substituents selected from the group consisting of hydroxy, —O$C_1$-$C_6$-alkyl, halo, —$NH_2$, —($C_1$-$C_6$-alkyl)$NH_2$, —C(O)OH, CN, and oxo.

In various embodiments, a compound of Formula (I), (II), (IA), or (IB) has substituents $R^4$, $R^5$, and $R^6$ (if present) that are independently selected from the group consisting of H, $C_1$-$C_6$-alkyl, and $C_1$-$C_6$-alkoxy.

Optionally in combination with any other embodiment, another embodiment provides each of $R^4$, $R^5$, and $R^6$ (if present) as H. Alternatively, according to various embodiments, one of $R^4$, $R^5$, and $R^6$ is H. For instance, $R^4$ is H. Another embodiment provides $R^5$ as H. In still another embodiment, $R^6$ is H. In additional embodiments, any two of $R^4$, $R^5$, and $R^6$ are H. For example, $R^4$ and $R^5$ are H; $R^4$ and $R^6$ are H; or $R^5$ and $R^6$ are H.

In some compounds, according to another embodiment, $R^2$ is $C_6$-$C_{10}$-aryl or 5- to 10-membered heteroaryl. For instance, $R^2$ is $C_6$-$C_{10}$-aryl, such as phenyl.

In other compounds, according to another embodiment, $R^2$ is 5- to 10-membered heteroaryl that contains N as the only ring member heteroatom. Thus, for example, $R^2$ is pyridyl.

According to various embodiments, $R^3$ is 3- to 14-membered heterocycloalkyl or 5- to 10-membered heteroaryl. Examples include compounds wherein $R^3$ is a $C_3$-$C_{10}$-heteroaryl containing only 2 ring members as heteroatoms independently selected from N, O, and S. Illustrative heteroaryl groups thus include benzothiazolyl, benzoisothiazolyl, benzoxazolyl, pyridinyl, pyridinonyl, benzimidazolyl, benzotriazolyl, indazolyl, quinoxalinyl, quinolinyl, quinazolinyl, imidazopyridinyl, pyrazolopyridinyl, cinnolinyl, isoxazolyl, pyrazolyl, benzofuranyl, dihydrobenzofuranyl, and tetrahydrobenzodioxinyl.

Other embodiments, optionally in combination with any other embodiment described herein, provide a compound wherein L is O or NR. In these embodiments, $R^1$ can be $C_1$-$C_6$-alkyl or $C_3$-$C_6$-carbocyclyl. For example, $R^1$ is $C_1$-$C_3$-alkyl that is optionally substituted by 1-3 F.

In various embodiments, optionally in combination with any other embodiment, $R^3$ is $C_6$-$C_{10}$-aryl.

Still further embodiments provide a compound of Formula I or Formula II wherein L is O or NR. Optionally in combination with this embodiment are embodiments wherein $R^1$ is $C_1$-$C_6$-alkyl or $C_3$-$C_6$-carbocyclyl. In other embodiments, $R^1$ is $C_1$-$C_3$-alkyl that is optionally substituted by 1-3 F.

Some compounds, in accordance with various embodiments, are those wherein L is O or NR and R is H; $R^1$ is $C_1$-$C_3$-alkyl that is optionally substituted by 1-3 F; $R^2$ is 3- to 14-membered heterocycloalkyl or 5- to 10-membered heteroaryl (wherein 1 ring member is N) or $C_6$-$C_{10}$-aryl; $R^3$ is 5- to 10-membered heteroaryl wherein 1 to 3 ring members are independently selected from N, O, and S; and each of $R^4$, $R^5$, and $R^6$ (if present) is H.

In various embodiments, optionally in combination with any other embodiment, L is NR. For example, in some embodiments, L is NH.

In other embodiments of the present disclosure, constituting a subgenus of Formula I, $R^{2a}$ is present. In these embodiments, each bond === (a) represents a single bond and each bond === (b) represents a double bond. In addition, $R^{2a}$ is present and is taken together with $R^2$ and the carbon atom to which these moieties are attached to form a spiro-fused 5- to 6-membered carbocyclyl or heterocycloalkyl (wherein 1-4 ring members are independently selected from N, O, and S), wherein the spiro-fused 5- to 6-membered carbocyclyl or heterocycloalkyl is optionally substituted by one or more $R^4$.

Examples of such spiro-fused compounds include those wherein $R^{2a}$, $R^2$, and the carbon atom to which $R^2$ and $R^{2a}$ are attached are taken to together to forma spiro-fused 5-membered heterocycloalkyl, wherein 1 ring member is N. Alternatively, $R^{2a}$, $R^2$, and the carbon atom to which $R^2$ and $R^{2a}$ are attached are taken together to form a spiro-fused 6-membered heterocycloalkyl, wherein 1 ring member is N. In still other embodiments, $R^{2a}$, $R^2$, and the carbon atom to which $R^2$ and $R^{2a}$ are attached are taken together to form a spiro-fused 6-membered carbocyclyl.

In this subgenus of Formula I, for instance, each of $R^4$ and $R^5$ is independently selected from the group consisting of H, $C_1$-$C_6$-alkyl, and $C_1$-$C_6$-alkoxy. Optionally, in addition, X is N. Further, in accordance with some embodiments, each of $R^4$ and $R^5$ is H. Alternatively, or in addition, $R^3$ is 5- to 10-membered heteroaryl having only 2 ring heteroatoms independently selected from N, O, and S. In other embodiments, $R^3$ is $C_6$-$C_{10}$-aryl.

In various embodiments, the present disclosure provides specific, illustrative examples of spiro-fused compounds of Formula I as set forth in Table 1 below:

TABLE 1

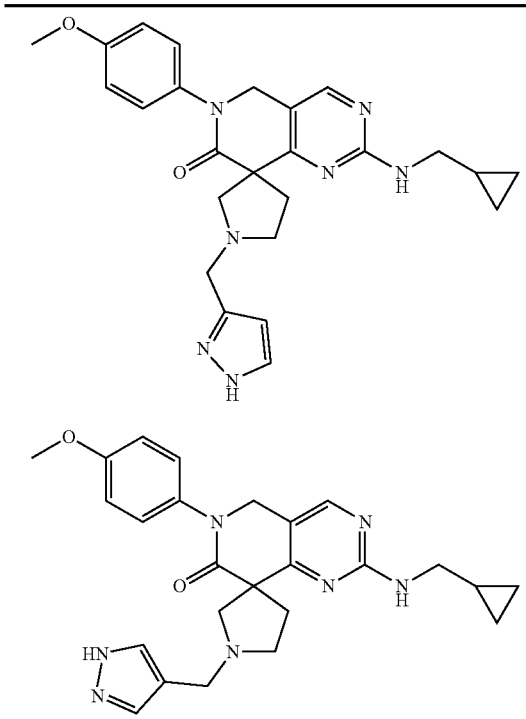

TABLE 1-continued

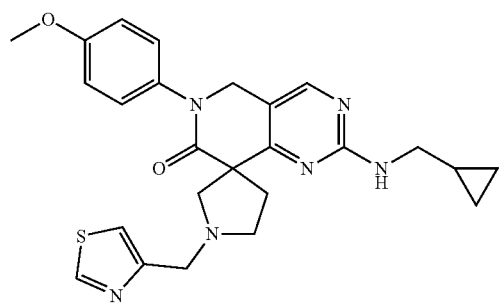 [SMILES: COc1ccc(N2Cc3cnc(NCC4CC4)nc3C3(CCN(Cc4cscn4)C3)C2=O)cc1]

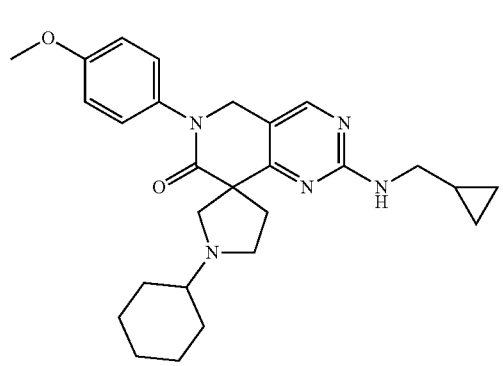 [SMILES: COc1ccc(N2Cc3cnc(NCC4CC4)nc3C3(CCN(C4CCCCC4)C3)C2=O)cc1]

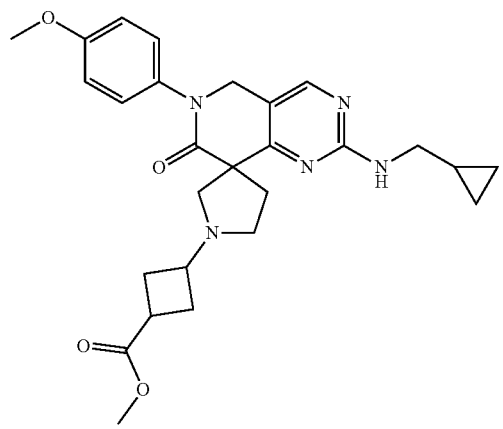 [SMILES: COC(=O)C1CC(N2CCC3(C2)C(=O)N(c2ccc(OC)cc2)Cc2cnc(NCC4CC4)nc23)C1]

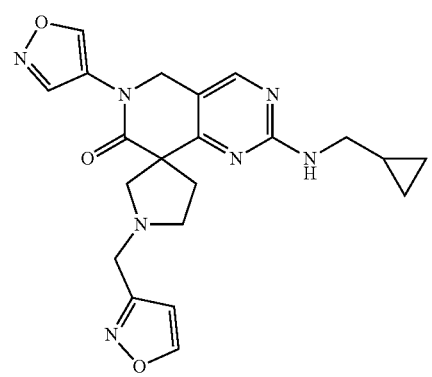 [SMILES: O=C1N(c2cnoc2)Cc2cnc(NCC3CC3)nc2C12CCN(Cc1ccon1)C2]

TABLE 1-continued
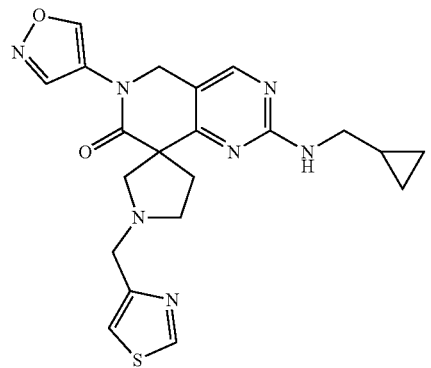 [SMILES: O=C1N(c2cnoc2)Cc2cnc(NCC3CC3)nc2C12CCN(Cc1cscn1)C2] 107
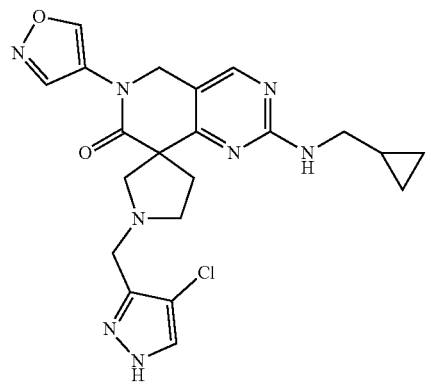 [SMILES: O=C1N(c2cnoc2)Cc2cnc(NCC3CC3)nc2C12CCN(Cc1n[nH]cc1Cl)C2] 108
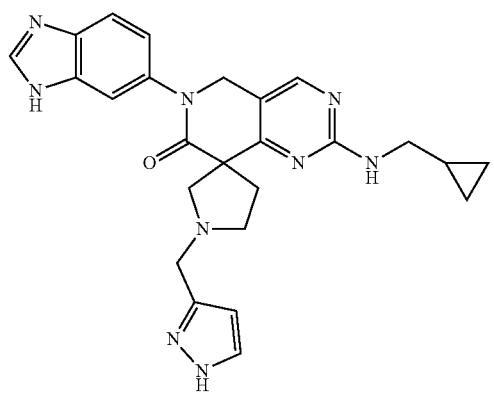 [SMILES: O=C1N(c2ccc3nc[nH]c3c2)Cc2cnc(NCC3CC3)nc2C12CCN(Cc1cc[nH]n1)C2] 109
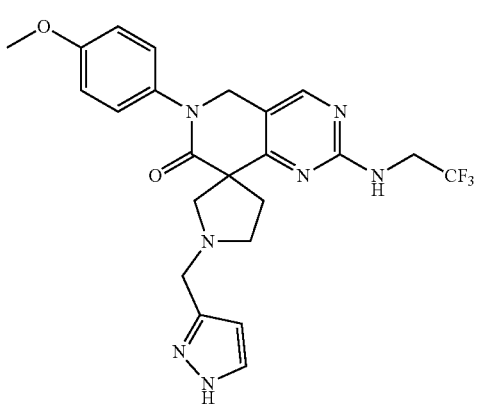 [SMILES: COc1ccc(N2Cc3cnc(NCC(F)(F)F)nc3C3(CCN(Cc4cc[nH]n4)C3)C2=O)cc1] 110
TABLE 1-continued
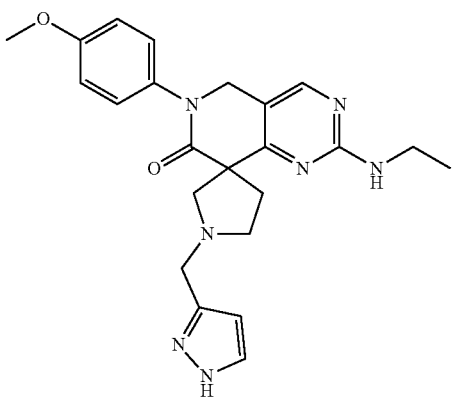 [SMILES: CCNc1ncc2c(n1)C1(CCN(Cc3cc[nH]n3)C1)C(=O)N(c1ccc(OC)cc1)C2] 111
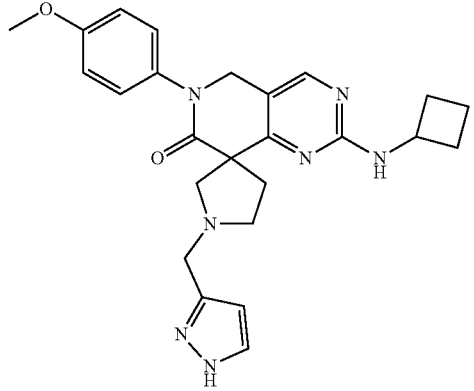 [SMILES: COc1ccc(N2Cc3cnc(NC4CCC4)nc3C3(CCN(Cc4cc[nH]n4)C3)C2=O)cc1] 112
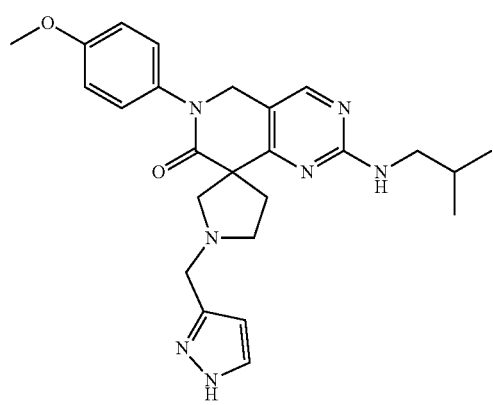 [SMILES: COc1ccc(N2Cc3cnc(NCC(C)C)nc3C3(CCN(Cc4cc[nH]n4)C3)C2=O)cc1] 113
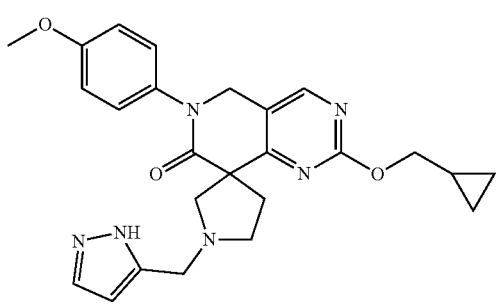 [SMILES: COc1ccc(N2Cc3cnc(OCC4CC4)nc3C3(CCN(Cc4ccn[nH]4)C3)C2=O)cc1] 114

TABLE 1-continued
115
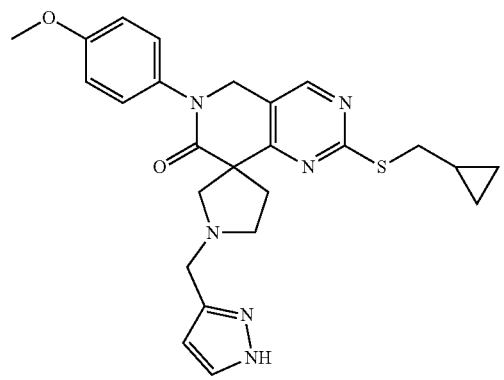 [SMILES: COc1ccc(N2Cc3cnc(SCC4CC4)nc3C3(CCN(Cc4cc[nH]n4)C3)C2=O)cc1]
116
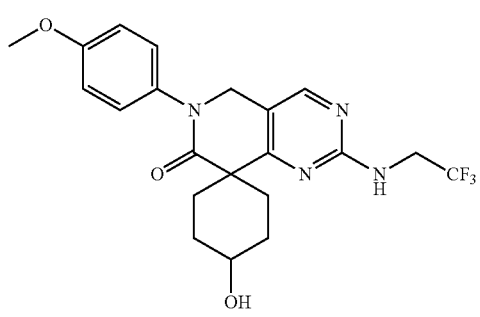 [SMILES: COc1ccc(N2Cc3cnc(NCC(F)(F)F)nc3C3(CCC(O)CC3)C2=O)cc1]
117
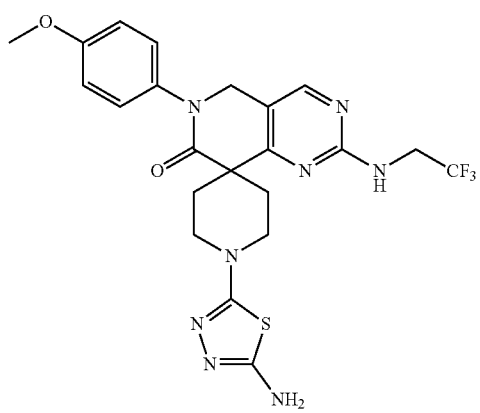 [SMILES: COc1ccc(N2Cc3cnc(NCC(F)(F)F)nc3C3(CCN(c4nnc(N)s4)CC3)C2=O)cc1]
118
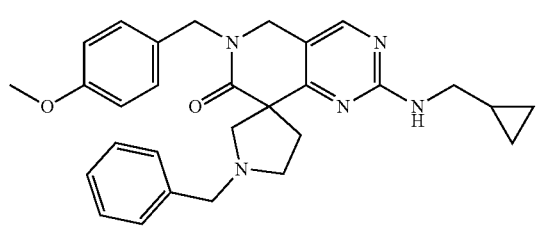 [SMILES: COc1ccc(CN2Cc3cnc(NCC4CC4)nc3C3(CCN(Cc4ccccc4)C3)C2=O)cc1]
TABLE 1-continued
119
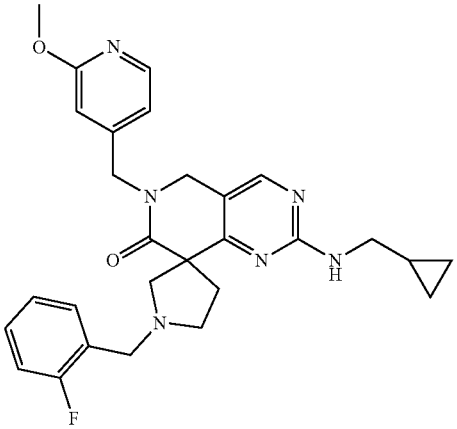 [SMILES: COc1cc(CN2Cc3cnc(NCC4CC4)nc3C3(CCN(Cc4ccccc4F)C3)C2=O)ccn1]
120
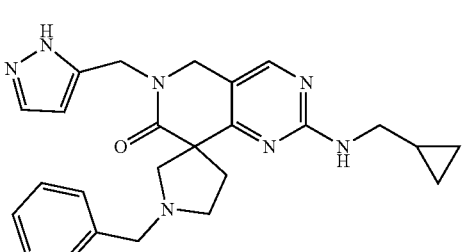
121
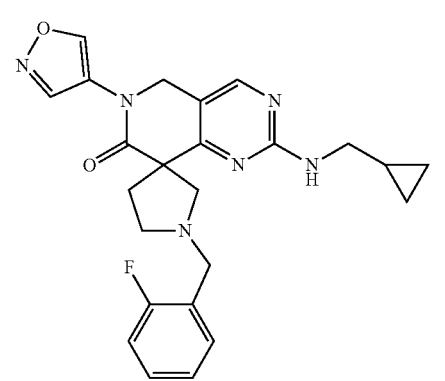 [SMILES: O=C1N(c2cnoc2)Cc2cnc(NCC3CC3)nc2C12CCN(Cc1ccccc1F)C2]
122
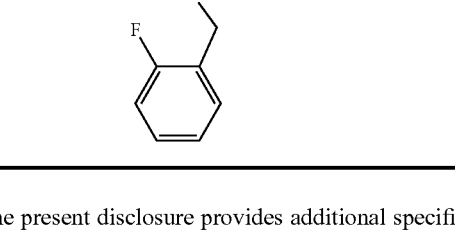
The present disclosure provides additional specific, illustrative examples of compounds of Formula I as set forth in Table 2 below.

TABLE 2
123
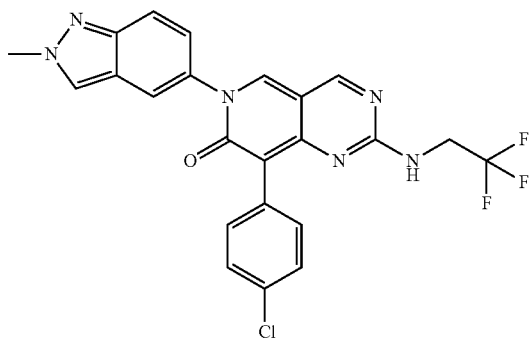 [SMILES: Cn1cc2cc(-n3cc4cnc(NCC(F)(F)F)nc4c(-c4ccc(Cl)cc4)c3=O)ccc2n1]
124
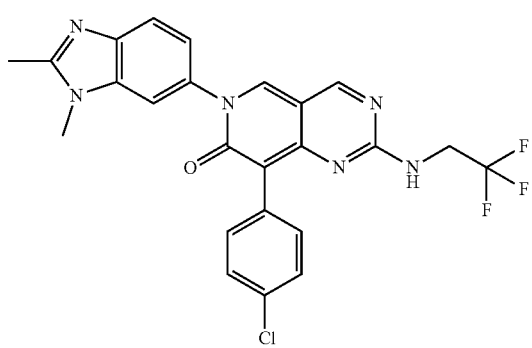 [SMILES: Cc1nc2ccc(-n3cc4cnc(NCC(F)(F)F)nc4c(-c4ccc(Cl)cc4)c3=O)cc2n1C]
125
TABLE 2-continued
127
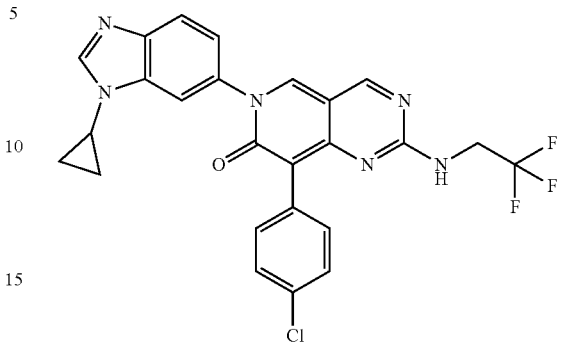
128
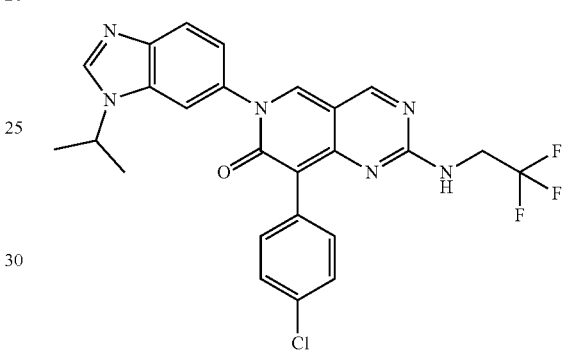
129
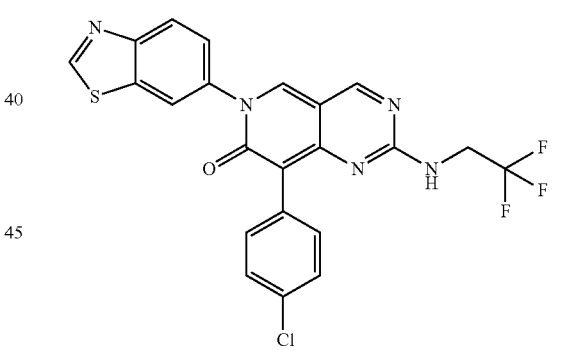
126
130
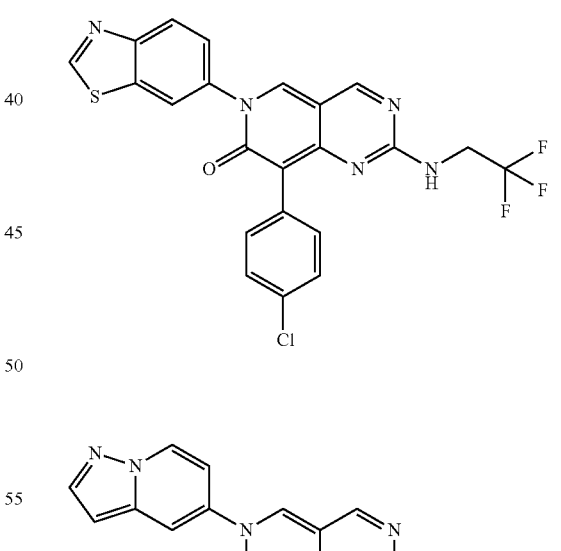

TABLE 2-continued
131
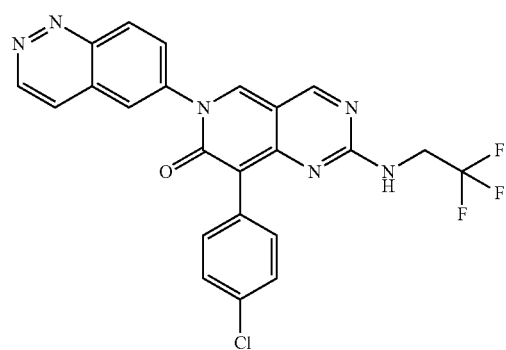 [SMILES: O=c1c(-c2ccc(Cl)cc2)c2nc(NCC(F)(F)F)ncc2cn1-c1ccc2nnccc2c1]
132
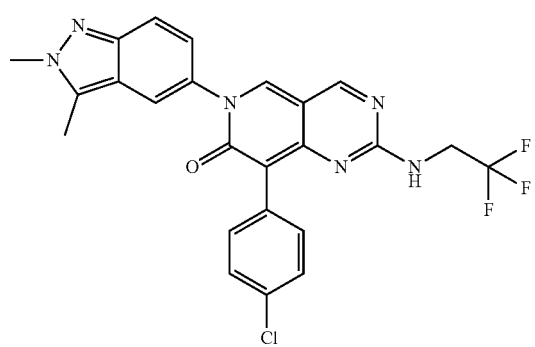 [SMILES: Cc1c2cc(-n3cc4cnc(NCC(F)(F)F)nc4c(-c4ccc(Cl)cc4)c3=O)ccc2nn1C]
133
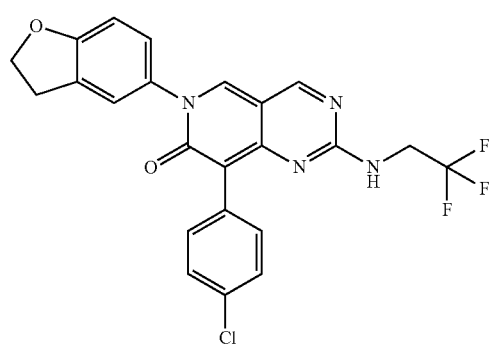 [SMILES: O=c1c(-c2ccc(Cl)cc2)c2nc(NCC(F)(F)F)ncc2cn1-c1ccc2c(c1)CCO2]
134
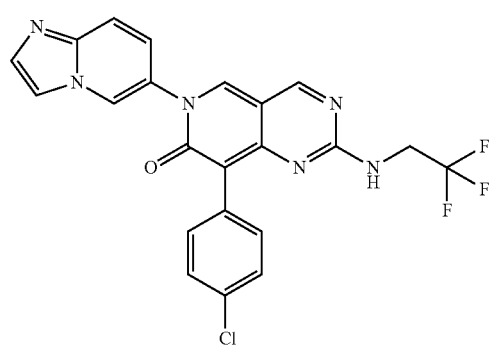 [SMILES: O=c1c(-c2ccc(Cl)cc2)c2nc(NCC(F)(F)F)ncc2cn1-c1ccc2nccn2c1]
TABLE 2-continued
135
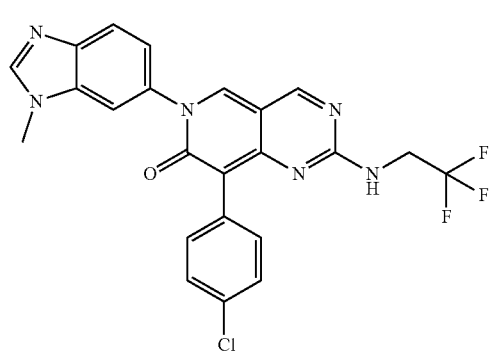
136
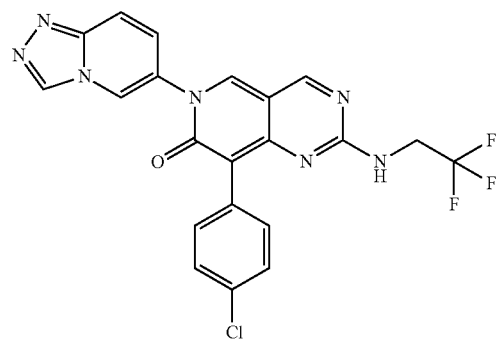 [SMILES: O=c1c(-c2ccc(Cl)cc2)c2nc(NCC(F)(F)F)ncc2cn1-c1ccc2nncn2c1]
137
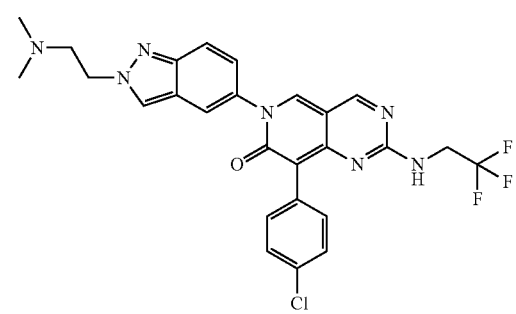 [SMILES: CN(C)CCn1cc2cc(-n3cc4cnc(NCC(F)(F)F)nc4c(-c4ccc(Cl)cc4)c3=O)ccc2n1]
138
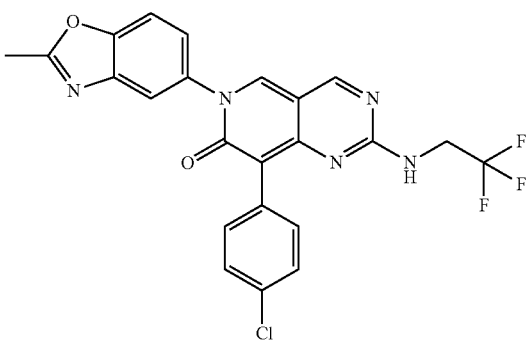 [SMILES: Cc1nc2cc(-n3cc4cnc(NCC(F)(F)F)nc4c(-c4ccc(Cl)cc4)c3=O)ccc2o1]

TABLE 2-continued
139
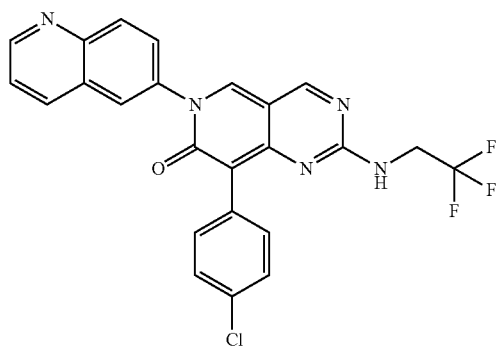 [SMILES: O=c1c(-c2ccc(Cl)cc2)c2nc(NCC(F)(F)F)ncc2cn1-c1ccc2ncccc2c1]
140
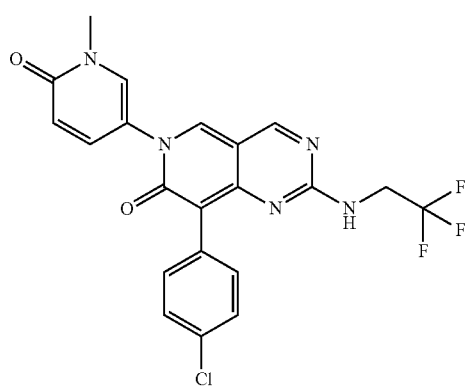 [SMILES: Cn1cc(-n2cc3cnc(NCC(F)(F)F)nc3c(-c3ccc(Cl)cc3)c2=O)ccc1=O]
141
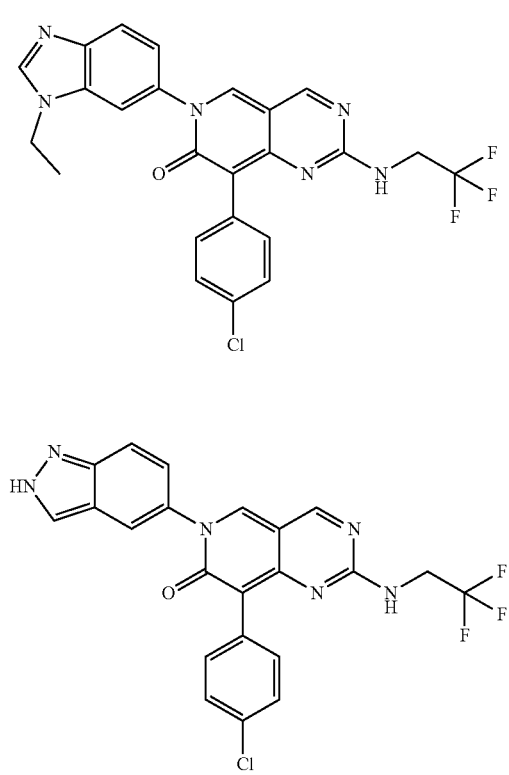
TABLE 2-continued
143
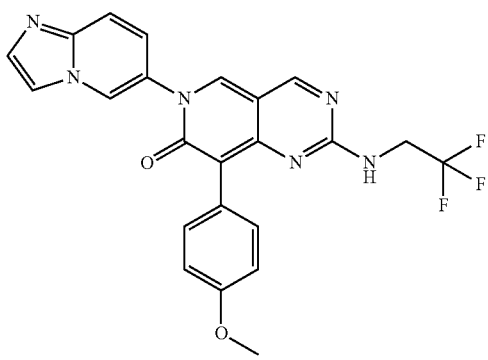 [SMILES: COc1ccc(-c2c(=O)n(-c3ccc4nccn4c3)cc3cnc(NCC(F)(F)F)nc23)cc1]
144
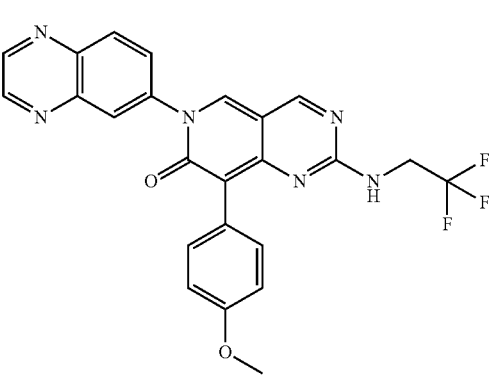 [SMILES: COc1ccc(-c2c(=O)n(-c3ccc4nccnc4c3)cc3cnc(NCC(F)(F)F)nc23)cc1]
145
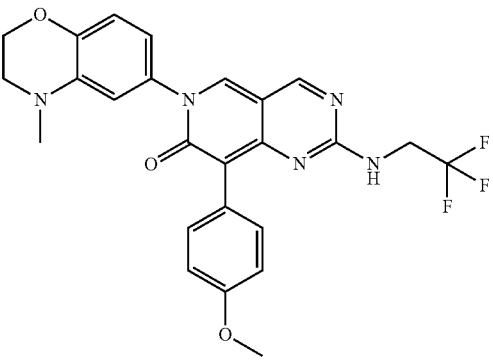 [SMILES: COc1ccc(-c2c(=O)n(-c3ccc4c(c3)N(C)CCO4)cc3cnc(NCC(F)(F)F)nc23)cc1]
146
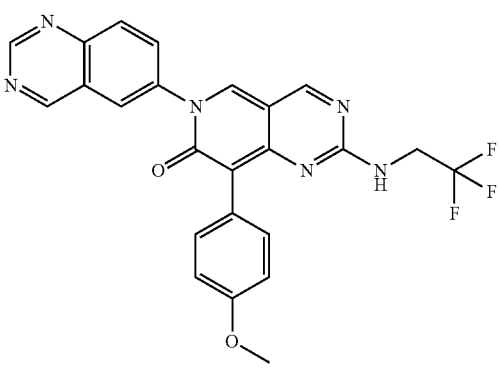
142

TABLE 2-continued
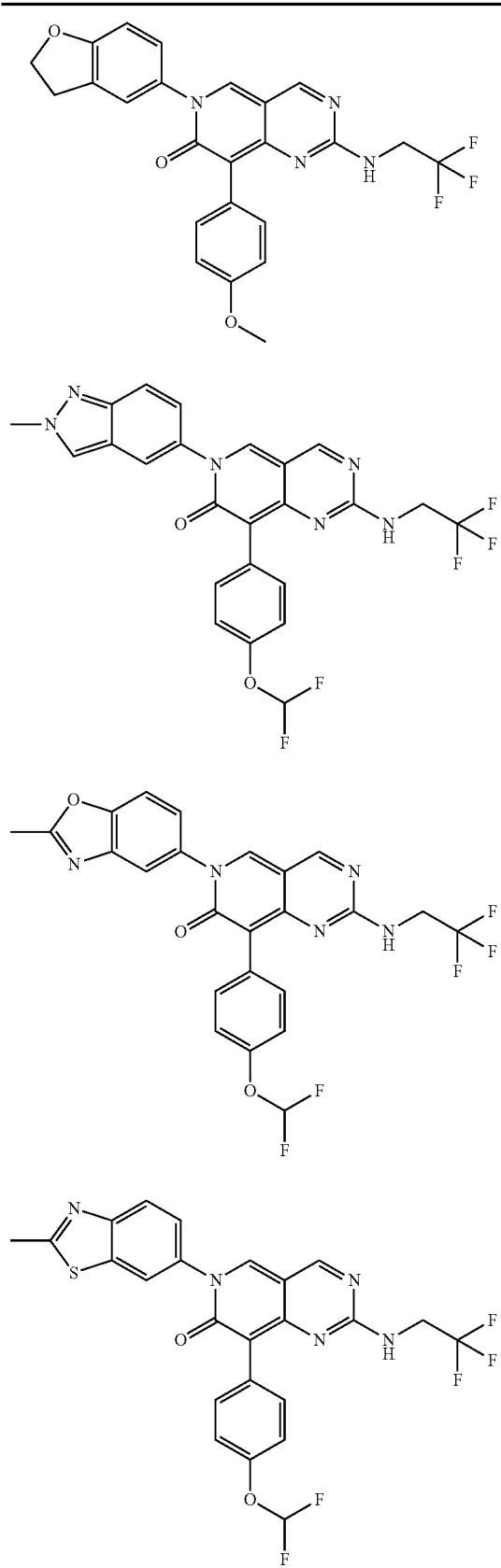
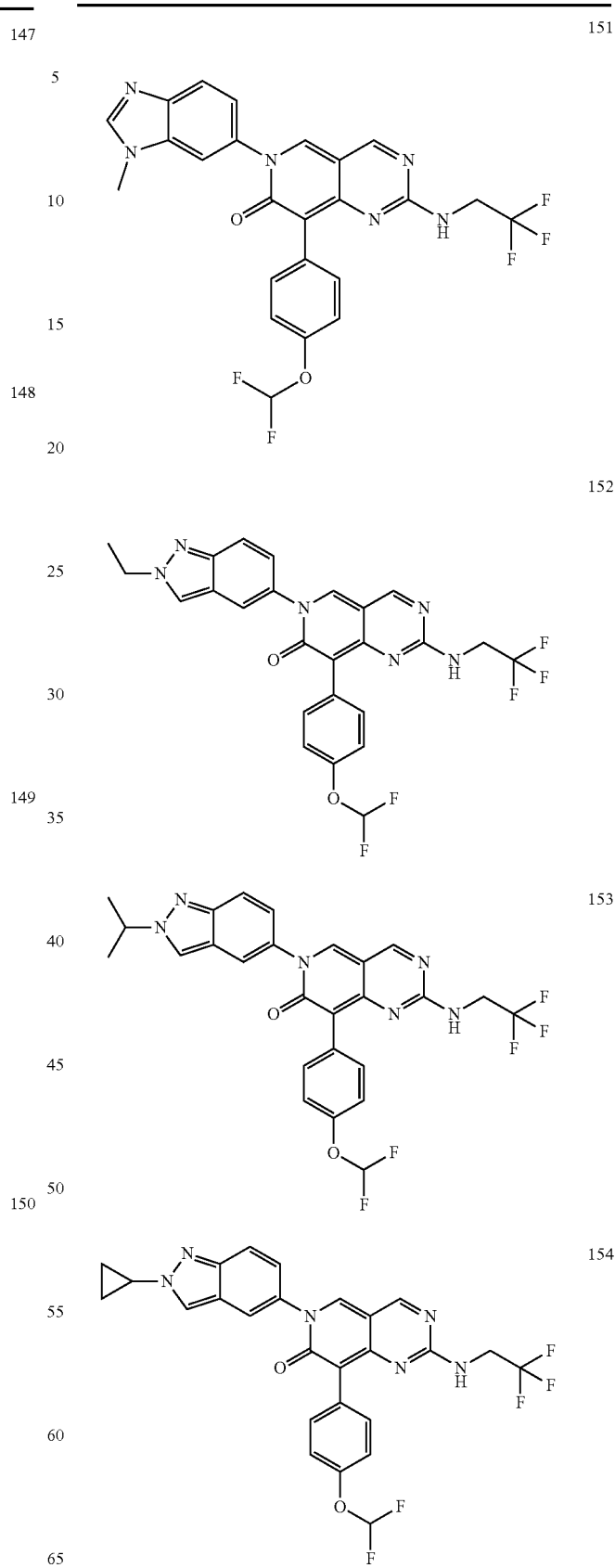

TABLE 2-continued
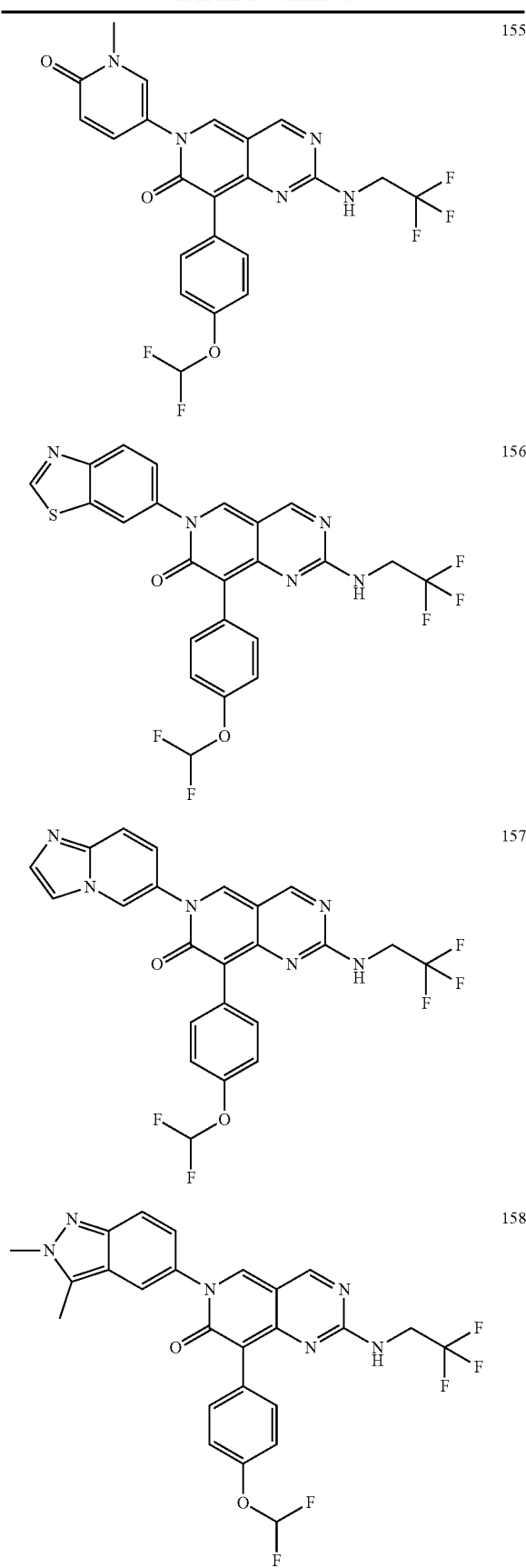
TABLE 2-continued
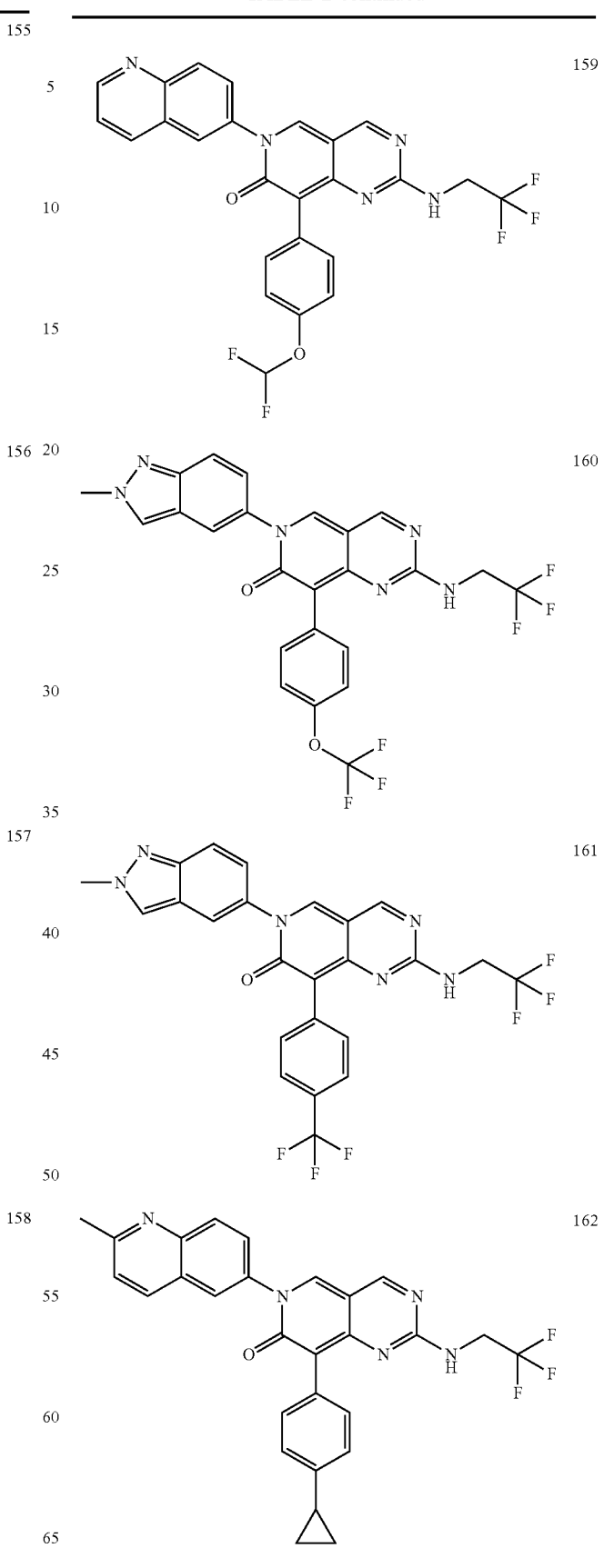

TABLE 2-continued
163
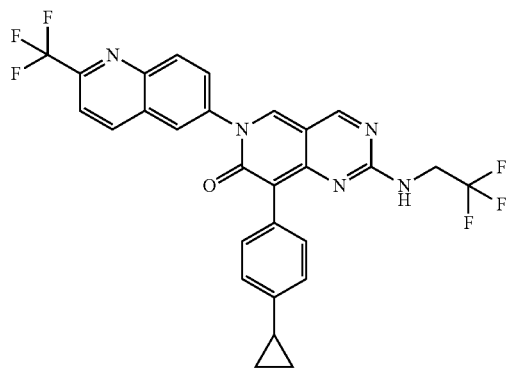 [SMILES: O=c1c(-c2ccc(C3CC3)cc2)c2nc(NCC(F)(F)F)ncc2cn1-c1ccc2nc(C(F)(F)F)ccc2c1]
164
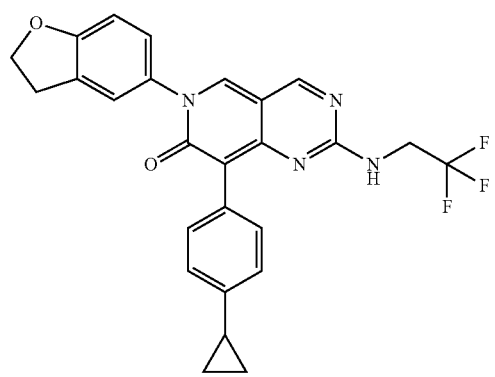 [SMILES: O=c1c(-c2ccc(C3CC3)cc2)c2nc(NCC(F)(F)F)ncc2cn1-c1ccc2c(c1)CCO2]
165
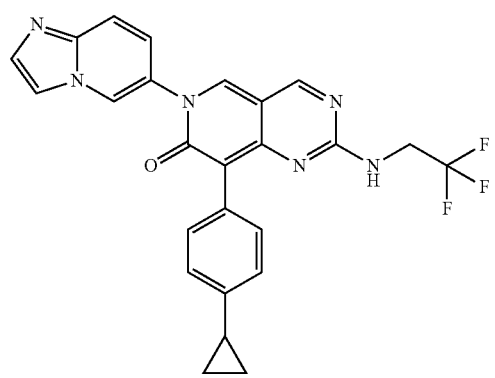 [SMILES: O=c1c(-c2ccc(C3CC3)cc2)c2nc(NCC(F)(F)F)ncc2cn1-c1ccc2nccn2c1]
166
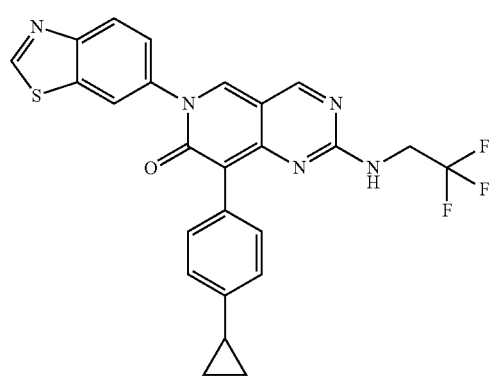 [SMILES: O=c1c(-c2ccc(C3CC3)cc2)c2nc(NCC(F)(F)F)ncc2cn1-c1ccc2ncsc2c1]
TABLE 2-continued
167
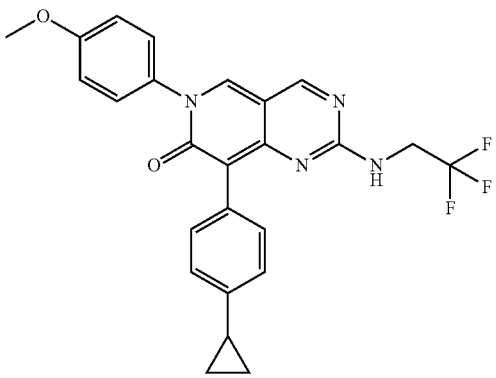
168
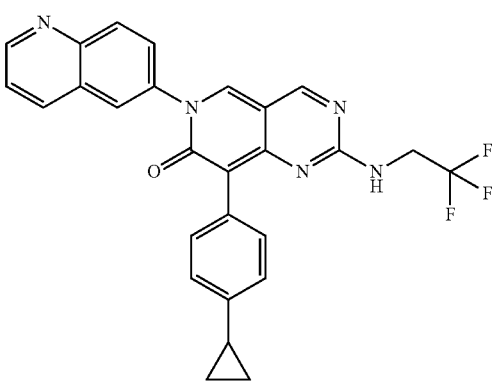 [SMILES: O=c1c(-c2ccc(C3CC3)cc2)c2nc(NCC(F)(F)F)ncc2cn1-c1ccc2ncccc2c1]
169

170
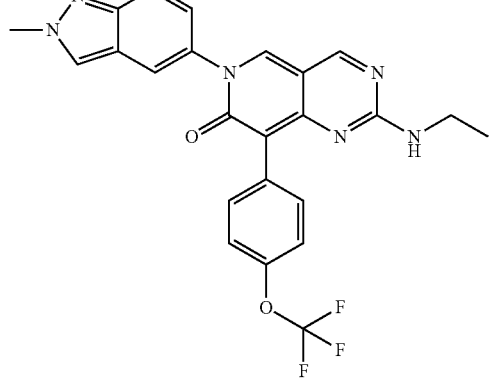

TABLE 2-continued
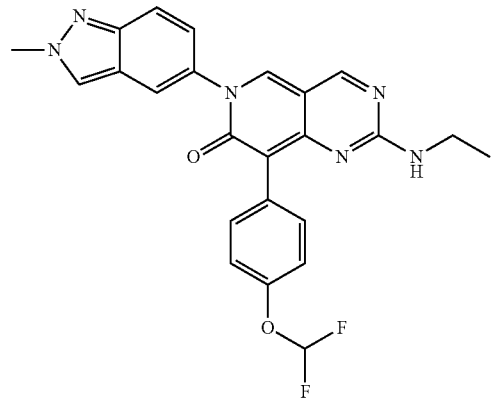 [SMILES: CCNc1ncc2cn(-c3ccc4nn(C)cc4c3)c(=O)c(-c3ccc(OC(F)F)cc3)c2n1]
171
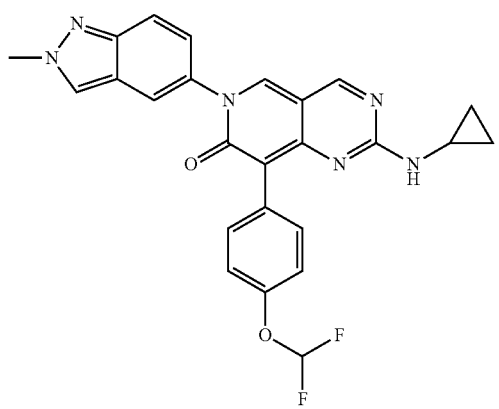 [SMILES: Cn1cc2cc(-n3cc4cnc(NC5CC5)nc4c(-c4ccc(OC(F)F)cc4)c3=O)ccc2n1]
172
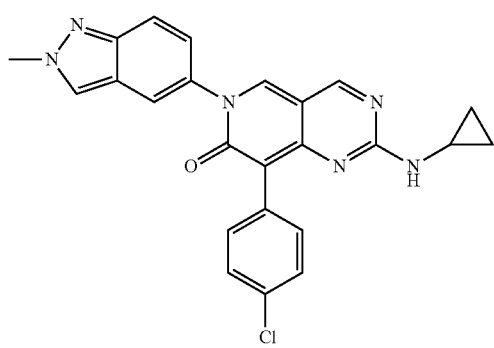 [SMILES: Cn1cc2cc(-n3cc4cnc(NC5CC5)nc4c(-c4ccc(Cl)cc4)c3=O)ccc2n1]
173
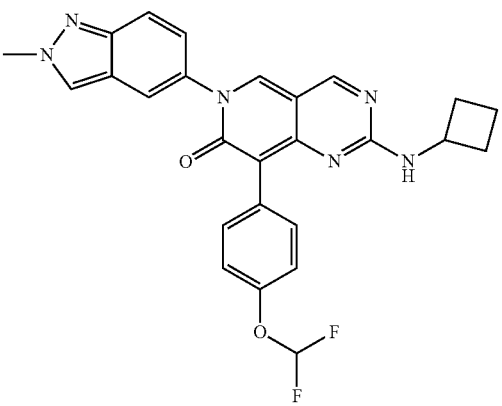 [SMILES: Cn1cc2cc(-n3cc4cnc(NC5CCC5)nc4c(-c4ccc(OC(F)F)cc4)c3=O)ccc2n1]
174
TABLE 2-continued
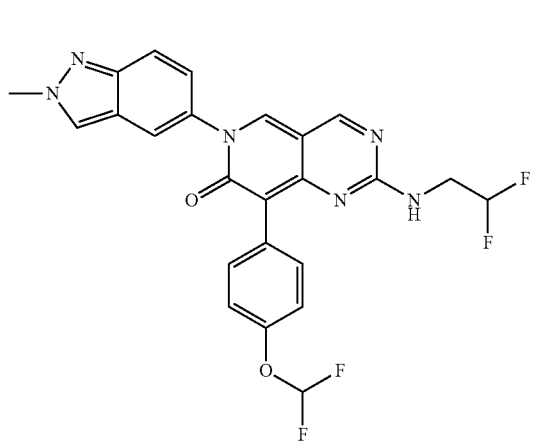 [SMILES: Cn1cc2cc(-n3cc4cnc(NCC(F)F)nc4c(-c4ccc(OC(F)F)cc4)c3=O)ccc2n1]
175
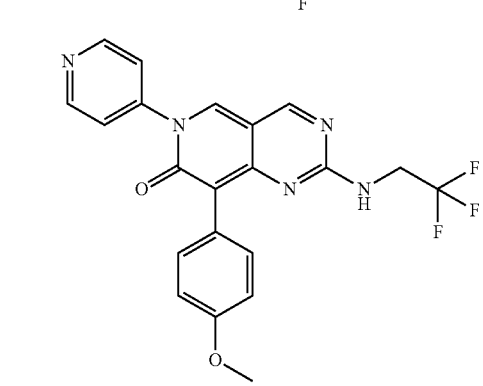
176
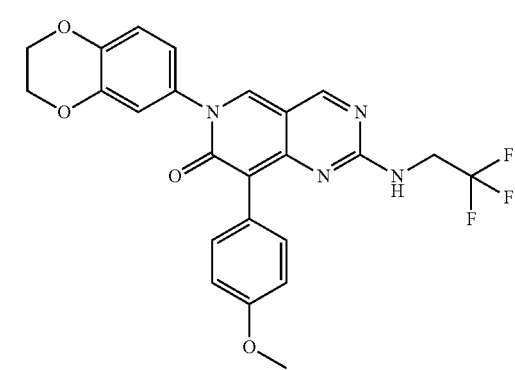 [SMILES: COc1ccc(-c2c(=O)n(-c3ccc4c(c3)OCCO4)cc3cnc(NCC(F)(F)F)nc23)cc1]
177
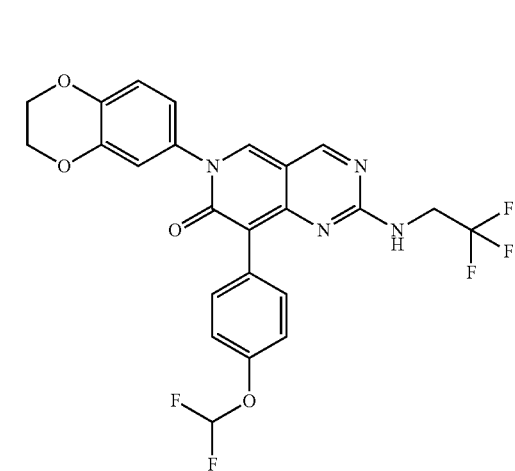 [SMILES: O=c1c(-c2ccc(OC(F)F)cc2)c2nc(NCC(F)(F)F)ncc2cn1-c1ccc2c(c1)OCCO2]
178

TABLE 2-continued
179 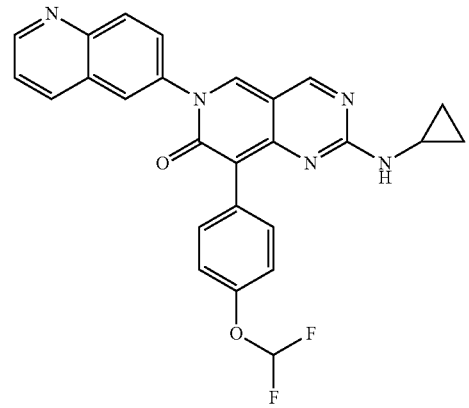 [SMILES: O=c1c(-c2ccc(OC(F)F)cc2)c2nc(NC3CC3)ncc2cn1-c1ccc2ncccc2c1]
180 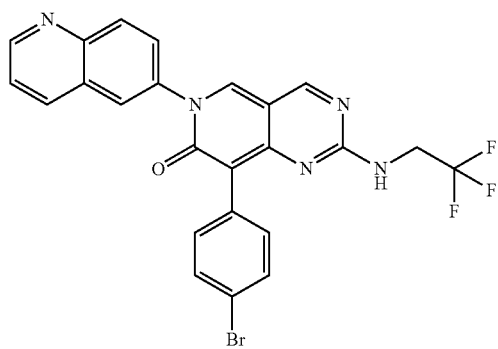
181 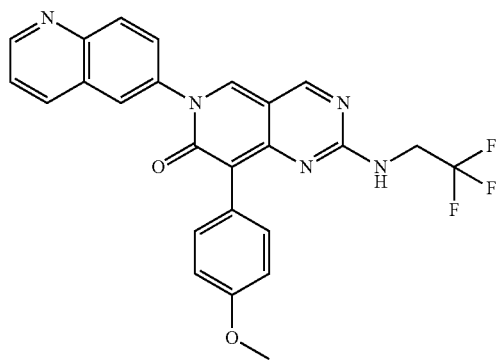 [SMILES: COc1ccc(-c2c(=O)n(-c3ccc4ncccc4c3)cc3cnc(NCC(F)(F)F)nc23)cc1]
182 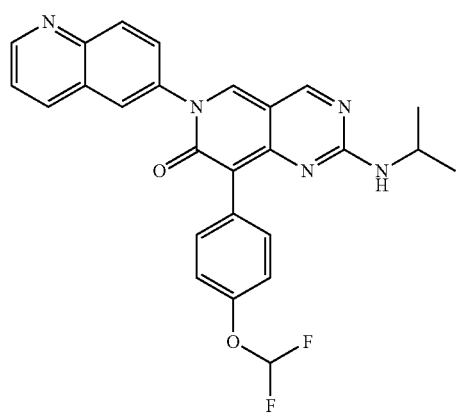 [SMILES: CC(C)Nc1ncc2cn(-c3ccc4ncccc4c3)c(=O)c(-c3ccc(OC(F)F)cc3)c2n1]
183 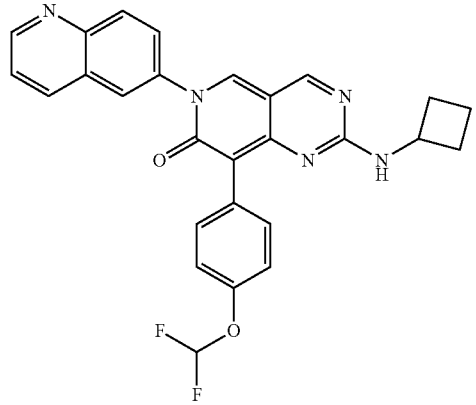 [SMILES: O=c1c(-c2ccc(OC(F)F)cc2)c2nc(NC3CCC3)ncc2cn1-c1ccc2ncccc2c1]
184 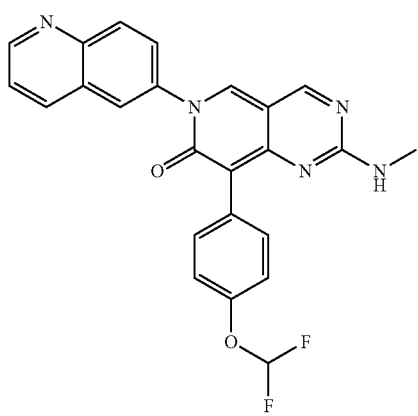 [SMILES: CNc1ncc2cn(-c3ccc4ncccc4c3)c(=O)c(-c3ccc(OC(F)F)cc3)c2n1]
185 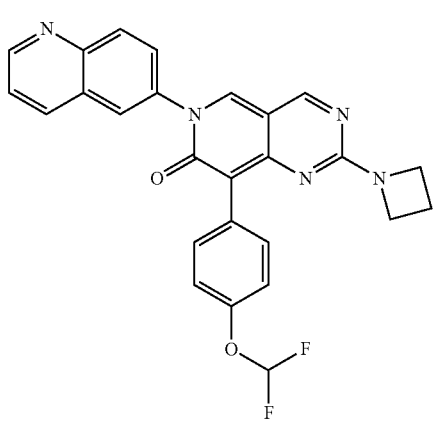 [SMILES: O=c1c(-c2ccc(OC(F)F)cc2)c2nc(N3CCC3)ncc2cn1-c1ccc2ncccc2c1]
186 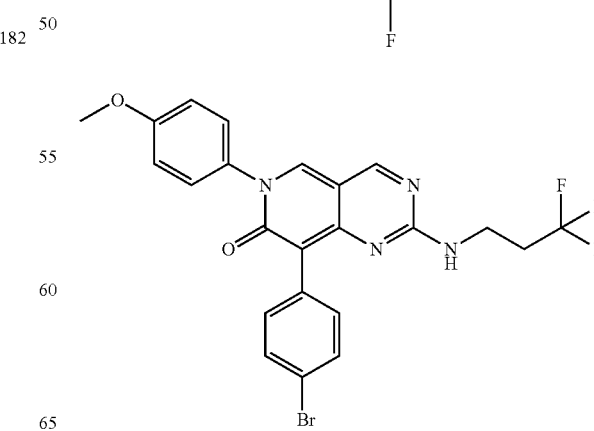

TABLE 2-continued
187
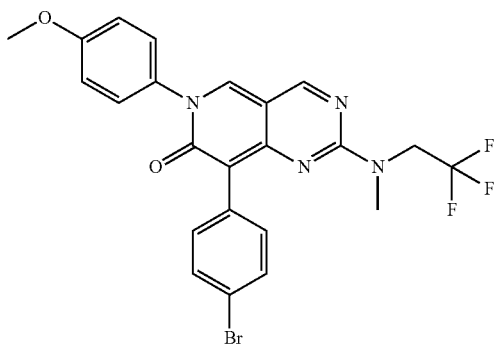
188
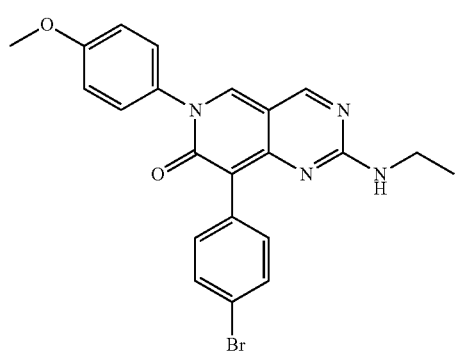 [SMILES: CCNc1ncc2cn(-c3ccc(OC)cc3)c(=O)c(-c3ccc(Br)cc3)c2n1]
189
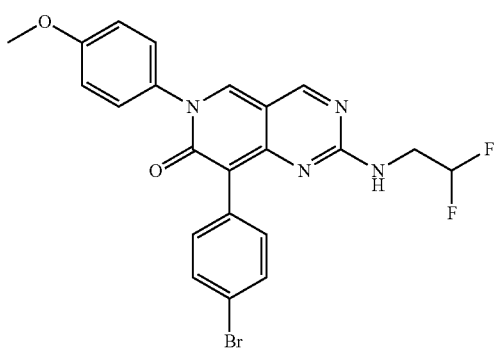 [SMILES: COc1ccc(-n2cc3cnc(NCC(F)F)nc3c(-c3ccc(Br)cc3)c2=O)cc1]
190
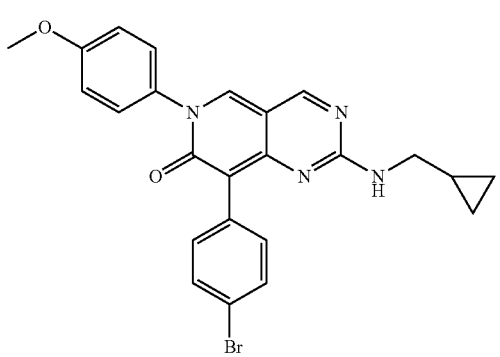 [SMILES: COc1ccc(-n2cc3cnc(NCC4CC4)nc3c(-c3ccc(Br)cc3)c2=O)cc1]
TABLE 2-continued
191
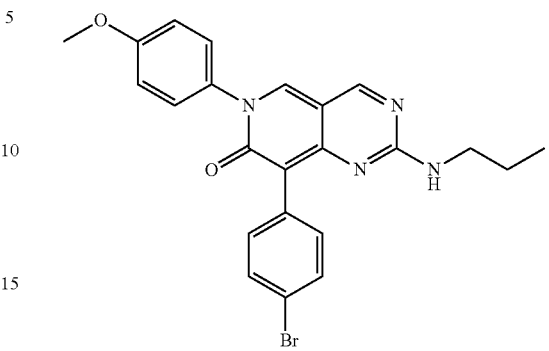
192
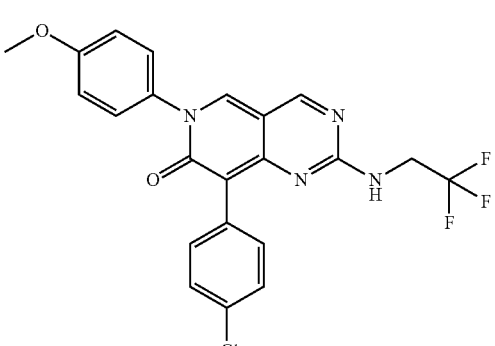
193
194
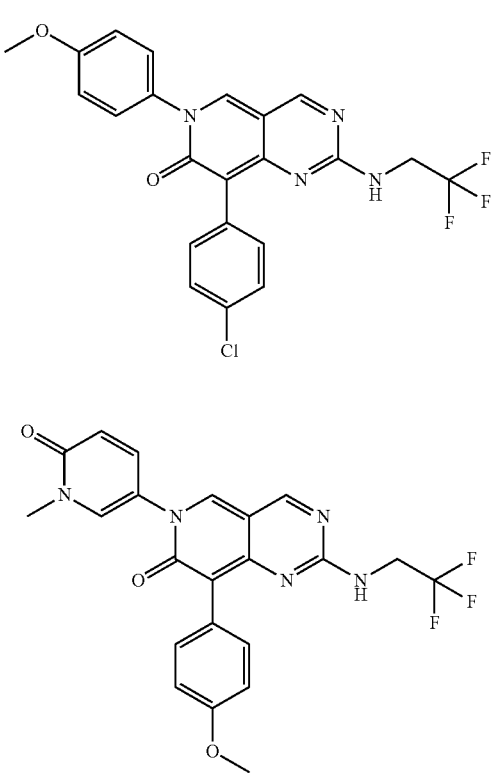

TABLE 2-continued
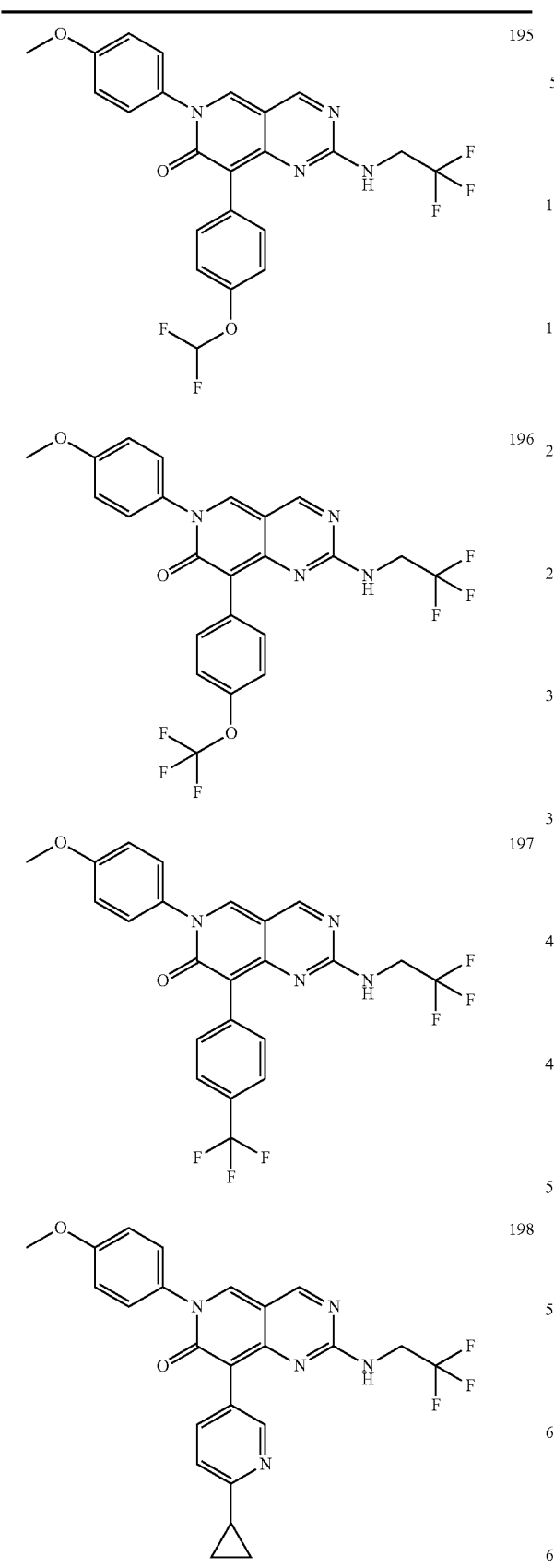
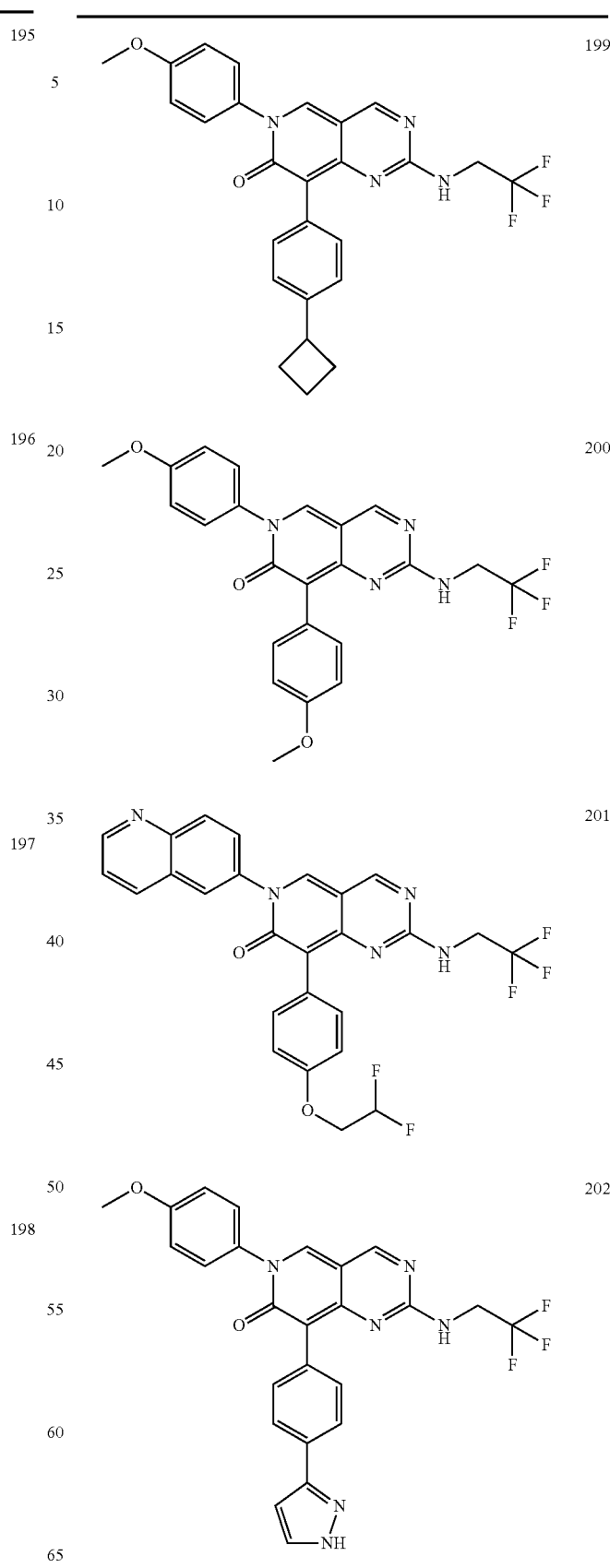

TABLE 2-continued
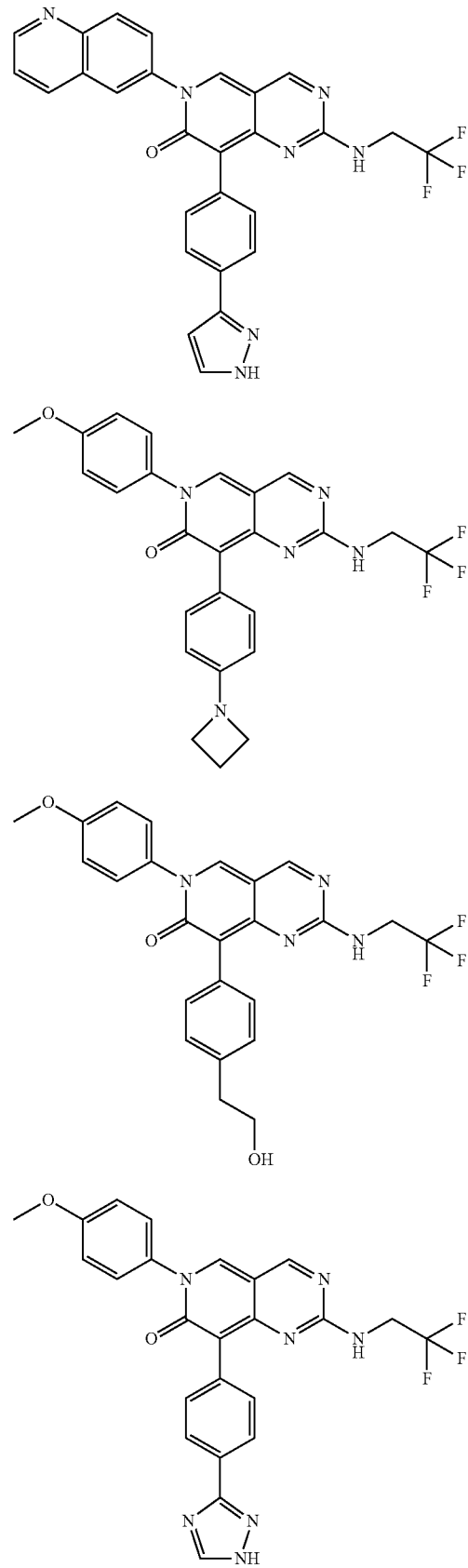
TABLE 2-continued
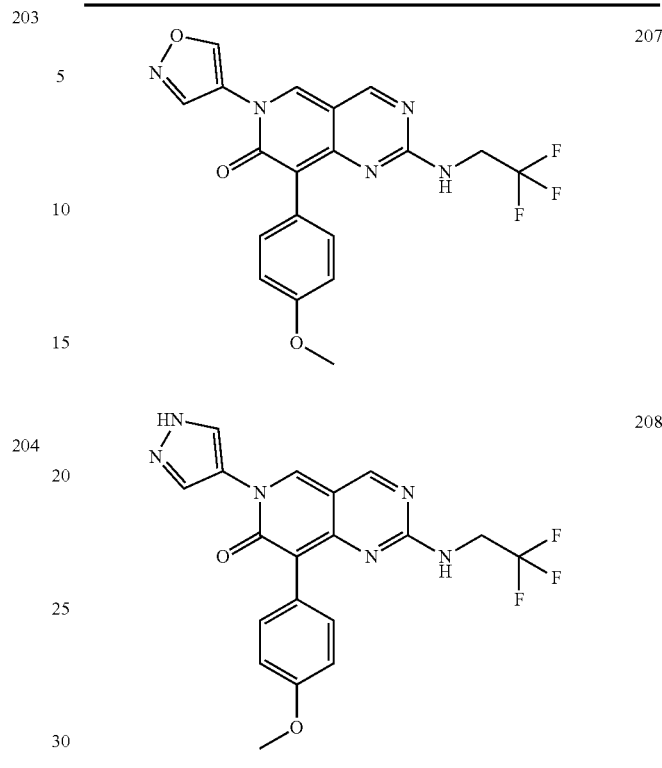
In still additional embodiments, the present disclosure provides the following specific, illustrative compounds as shown in Table 3.
TABLE 3
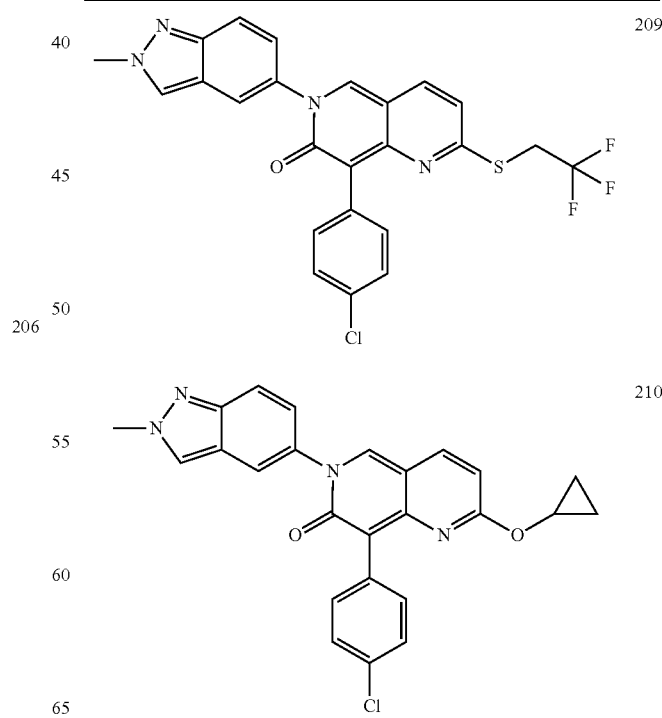

TABLE 3-continued
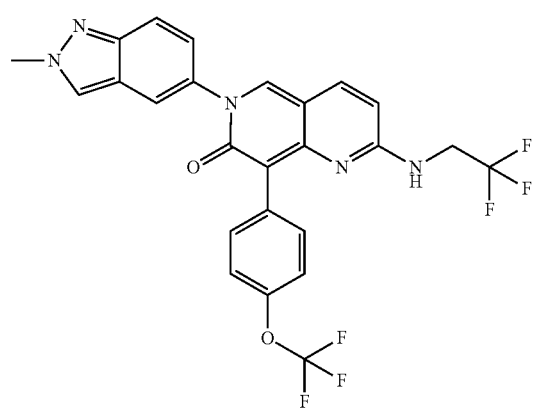 [SMILES: Cn1cc2cc(-n3cc4ccc(NCC(F)(F)F)nc4c(-c4ccc(OC(F)(F)F)cc4)c3=O)ccc2n1]
211
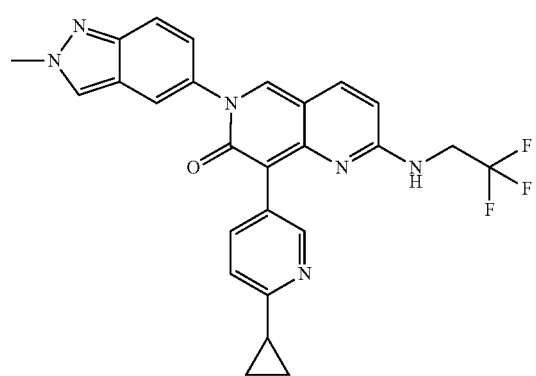 [SMILES: Cn1cc2cc(-n3cc4ccc(NCC(F)(F)F)nc4c(-c4ccc(C5CC5)nc4)c3=O)ccc2n1]
212
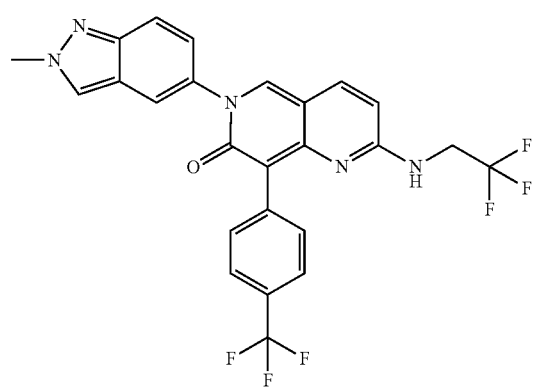 [SMILES: Cn1cc2cc(-n3cc4ccc(NCC(F)(F)F)nc4c(-c4ccc(C(F)(F)F)cc4)c3=O)ccc2n1]
213
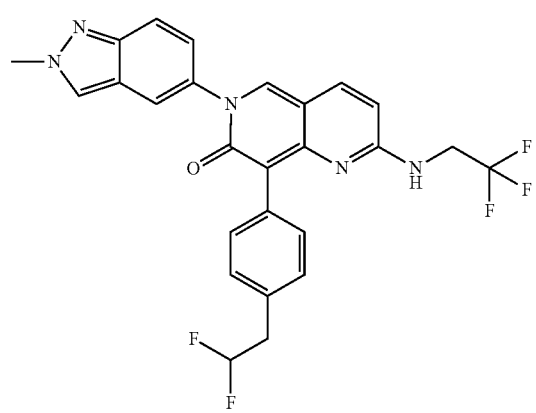 [SMILES: Cn1cc2cc(-n3cc4ccc(NCC(F)(F)F)nc4c(-c4ccc(CC(F)F)cc4)c3=O)ccc2n1]
214
TABLE 3-continued
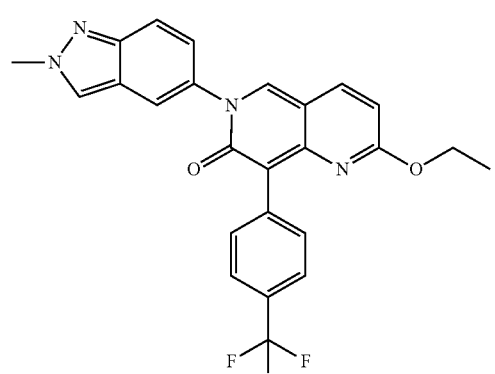
215
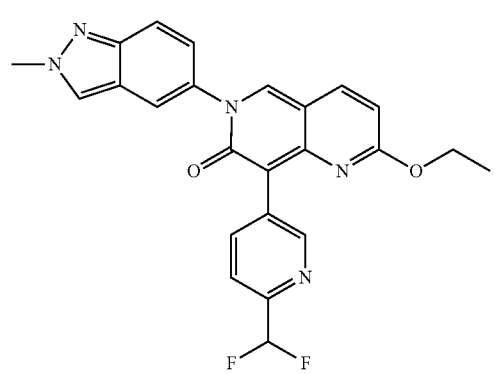 [SMILES: CCOc1ccc2cn(-c3ccc4nn(C)cc4c3)c(=O)c(-c3ccc(C(F)F)nc3)c2n1]
216
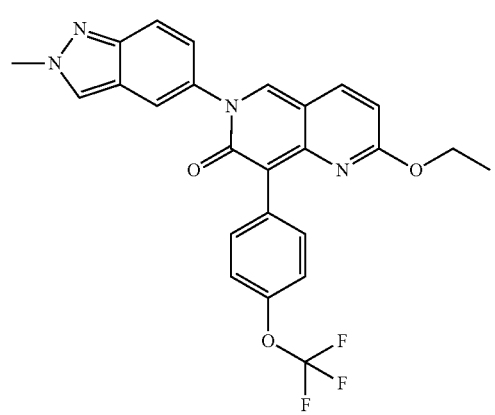 [SMILES: CCOc1ccc2cn(-c3ccc4nn(C)cc4c3)c(=O)c(-c3ccc(OC(F)(F)F)cc3)c2n1]
217
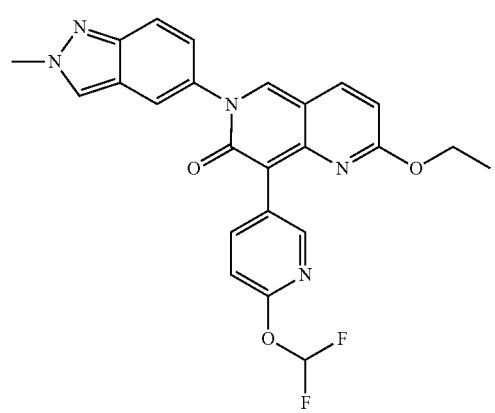
218

TABLE 3-continued
| | |
|---|---|
| 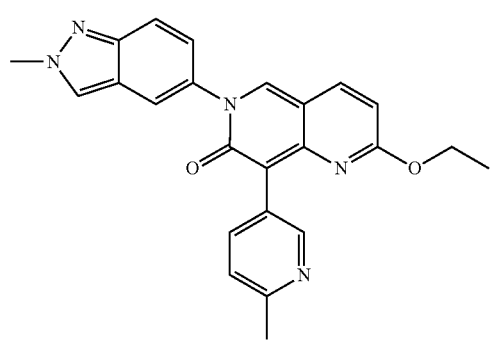 [SMILES: CCOc1ccc2cn(-c3ccc4nn(C)cc4c3)c(=O)c(-c3ccc(C)nc3)c2n1] 219 | 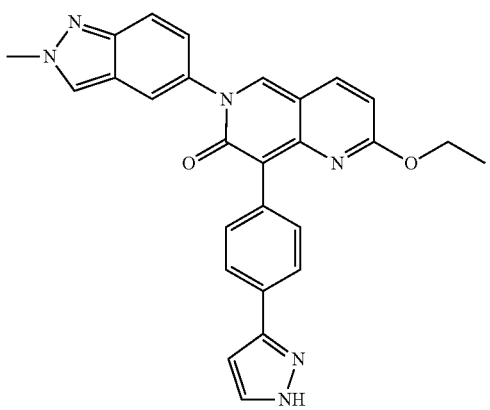 223 |
| 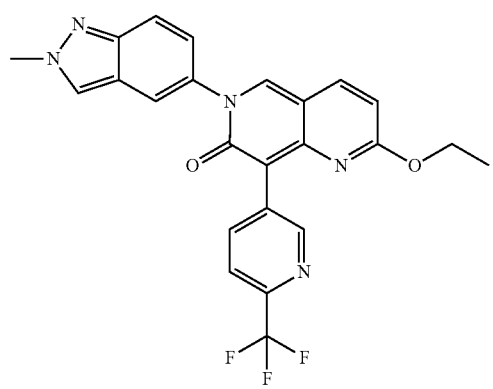 [SMILES: CCOc1ccc2cn(-c3ccc4nn(C)cc4c3)c(=O)c(-c3ccc(C(F)(F)F)nc3)c2n1] 220 | 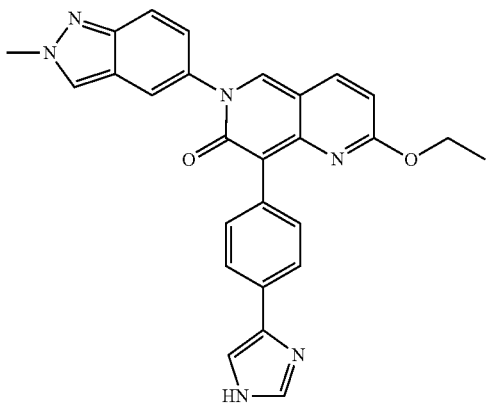 224 |
| 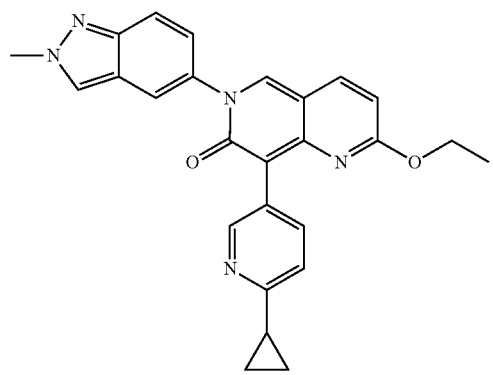 [SMILES: CCOc1ccc2cn(-c3ccc4nn(C)cc4c3)c(=O)c(-c3ccc(C4CC4)nc3)c2n1] 221 | 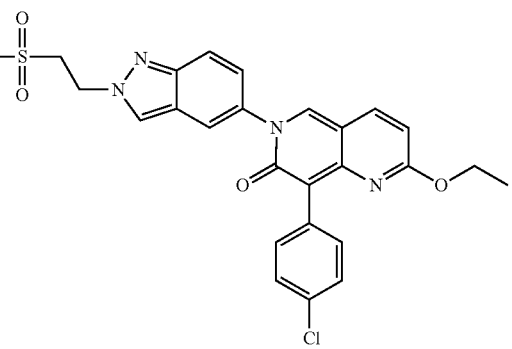 225 |
| 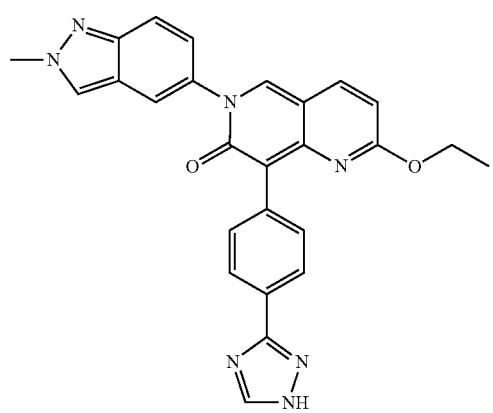 [SMILES: CCOc1ccc2cn(-c3ccc4nn(C)cc4c3)c(=O)c(-c3ccc(-c4nc[nH]n4)cc3)c2n1] 222 | 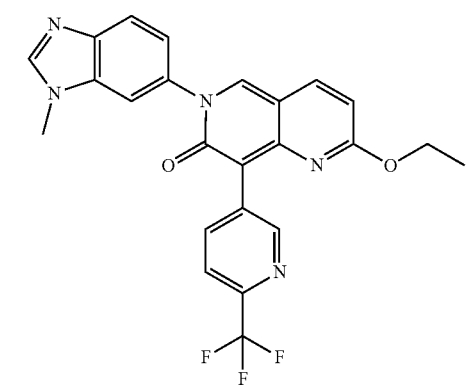 [SMILES: CCOc1ccc2cn(-c3ccc4ncn(C)c4c3)c(=O)c(-c3ccc(C(F)(F)F)nc3)c2n1] 226 |

TABLE 3-continued
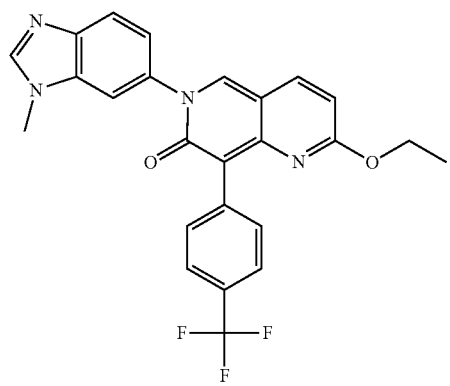 [SMILES: CCOc1ccc2cn(-c3ccc4ncn(C)c4c3)c(=O)c(-c3ccc(C(F)(F)F)cc3)c2n1]
227
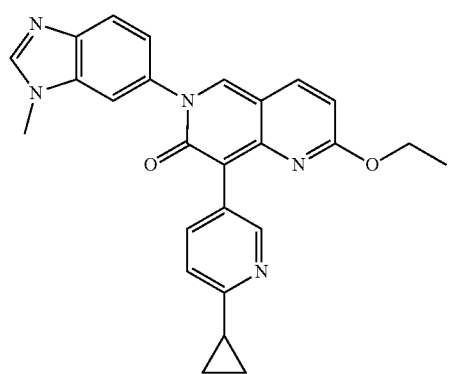 [SMILES: CCOc1ccc2cn(-c3ccc4ncn(C)c4c3)c(=O)c(-c3ccc(C4CC4)nc3)c2n1]
228
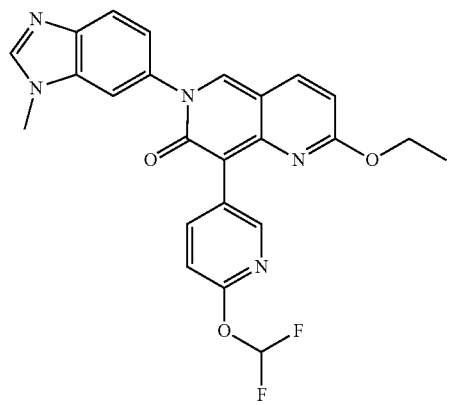 [SMILES: CCOc1ccc2cn(-c3ccc4ncn(C)c4c3)c(=O)c(-c3ccc(OC(F)F)nc3)c2n1]
229
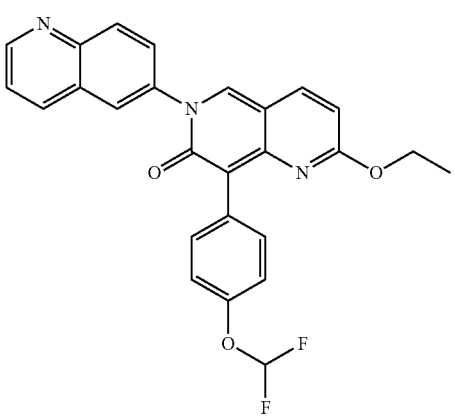 [SMILES: CCOc1ccc2cn(-c3ccc4ncccc4c3)c(=O)c(-c3ccc(OC(F)F)cc3)c2n1]
230
TABLE 3-continued
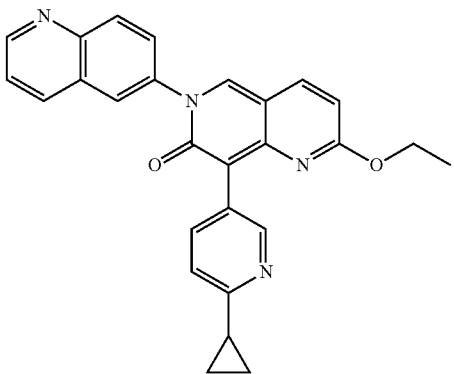 [SMILES: CCOc1ccc2cn(-c3ccc4ncccc4c3)c(=O)c(-c3ccc(C4CC4)nc3)c2n1]
231
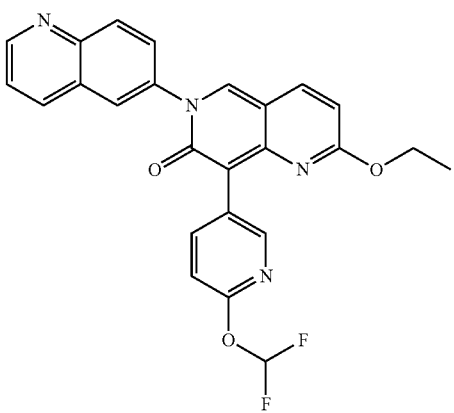 [SMILES: CCOc1ccc2cn(-c3ccc4ncccc4c3)c(=O)c(-c3ccc(OC(F)F)nc3)c2n1]
232
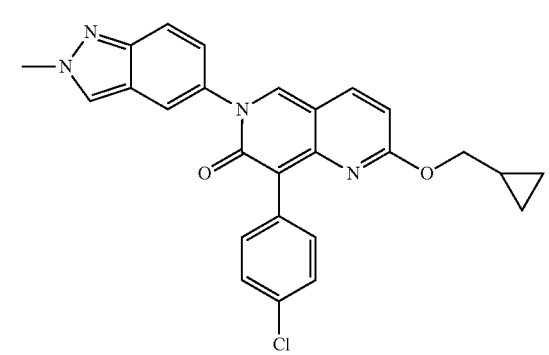 [SMILES: Cn1cc2cc(-n3cc4ccc(OCC5CC5)nc4c(-c4ccc(Cl)cc4)c3=O)ccc2n1]
233
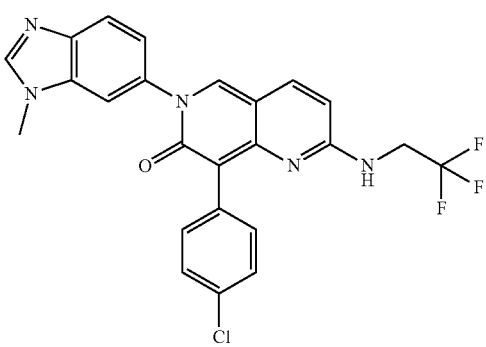 [SMILES: Cn1cnc2ccc(-n3cc4ccc(NCC(F)(F)F)nc4c(-c4ccc(Cl)cc4)c3=O)cc21]
234

US 11,524,960 B2
49
TABLE 3-continued
235
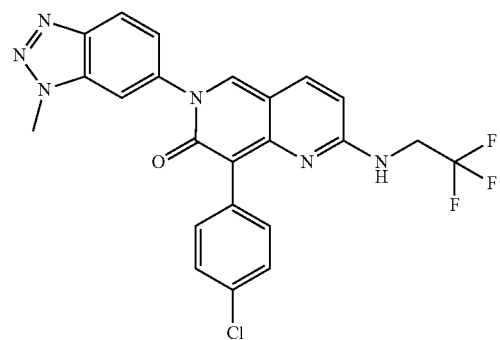 [SMILES: Cn1nnc2ccc(-n3cc4ccc(NCC(F)(F)F)nc4c(-c4ccc(Cl)cc4)c3=O)cc21]
236
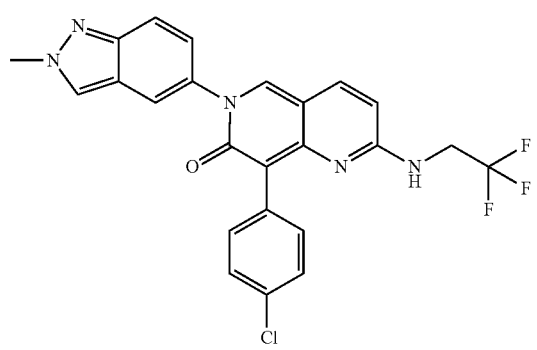 [SMILES: Cn1cc2cc(-n3cc4ccc(NCC(F)(F)F)nc4c(-c4ccc(Cl)cc4)c3=O)ccc2n1]
237
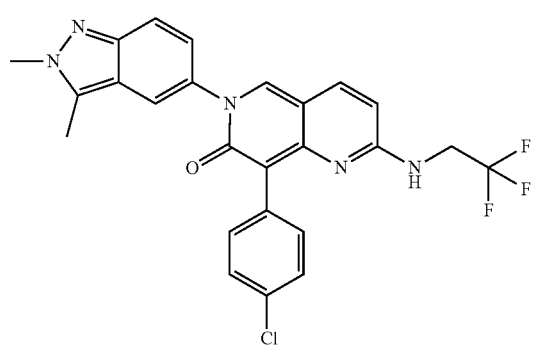 [SMILES: Cc1c2cc(-n3cc4ccc(NCC(F)(F)F)nc4c(-c4ccc(Cl)cc4)c3=O)ccc2nn1C]
238
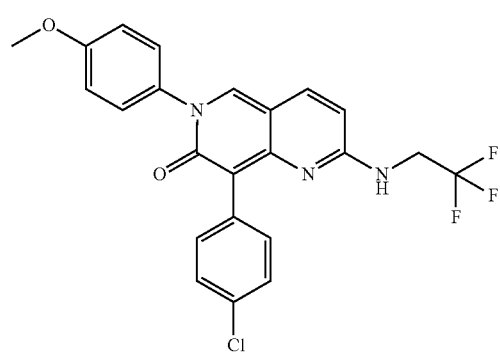 [SMILES: COc1ccc(-n2cc3ccc(NCC(F)(F)F)nc3c(-c3ccc(Cl)cc3)c2=O)cc1]
50
TABLE 3-continued
239
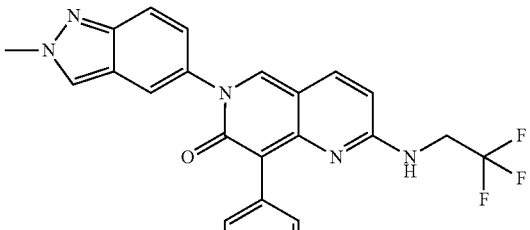
240
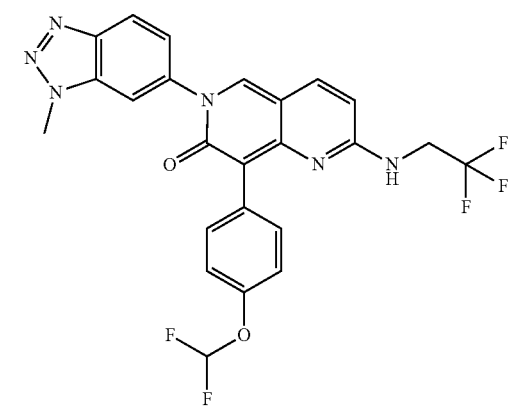 [SMILES: Cn1nnc2ccc(-n3cc4ccc(NCC(F)(F)F)nc4c(-c4ccc(OC(F)F)cc4)c3=O)cc21]
241
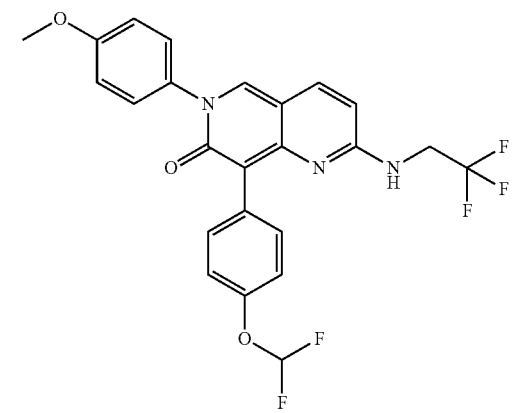 [SMILES: COc1ccc(-n2cc3ccc(NCC(F)(F)F)nc3c(-c3ccc(OC(F)F)cc3)c2=O)cc1]
242
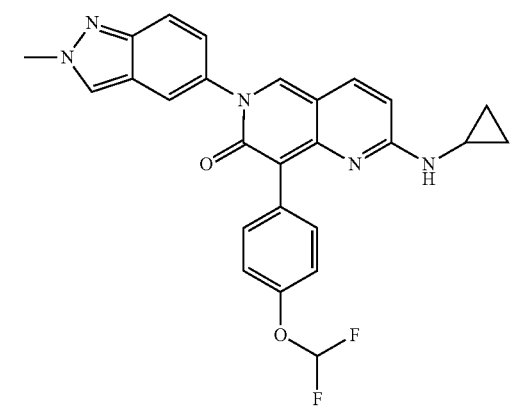

TABLE 3-continued

243

244

245

246

247

248

249

250

TABLE 3-continued
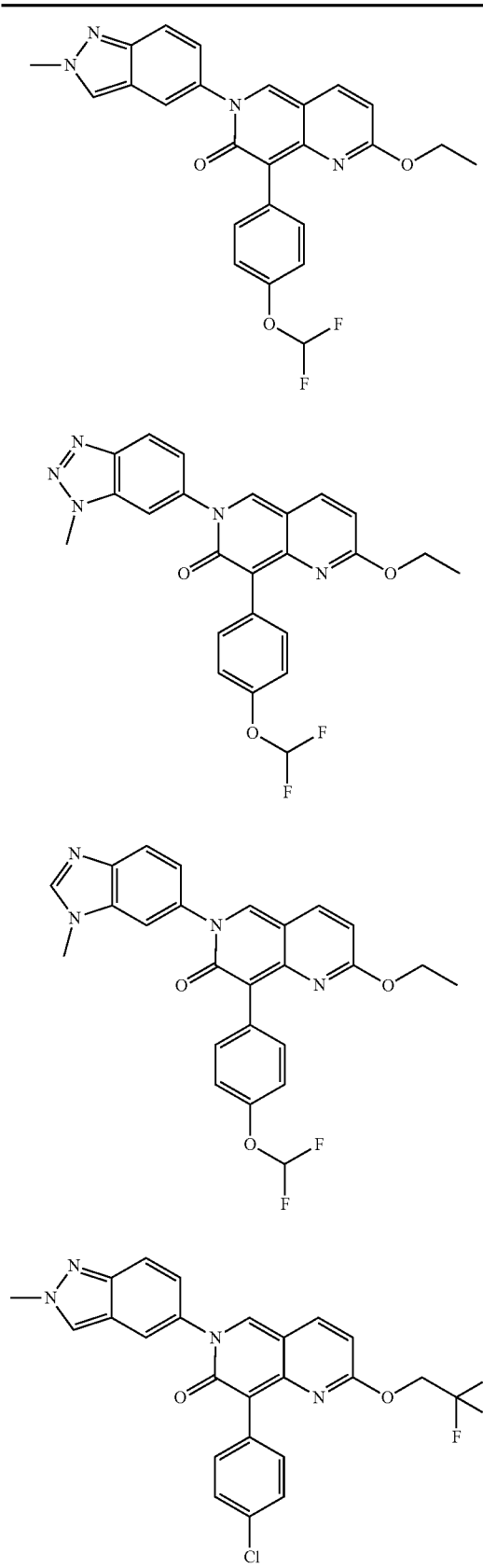
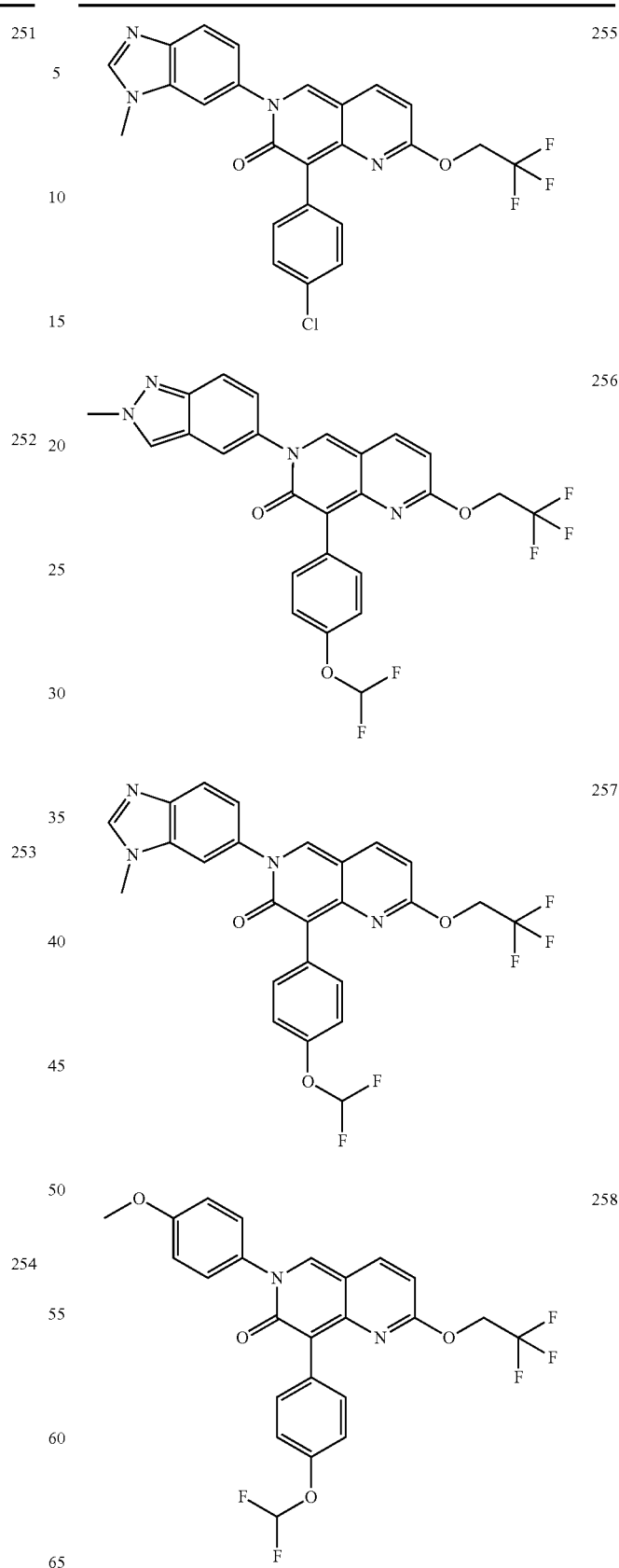

TABLE 3-continued
259
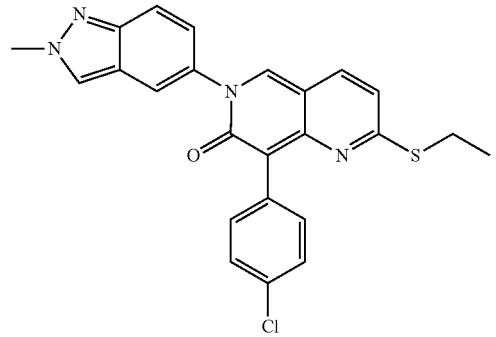 [SMILES: CCOc1ccc2cn(-c3ccc4nn(C)cc4c3)c(=O)c(-c3ccc(Cl)cc3)c2n1]
260
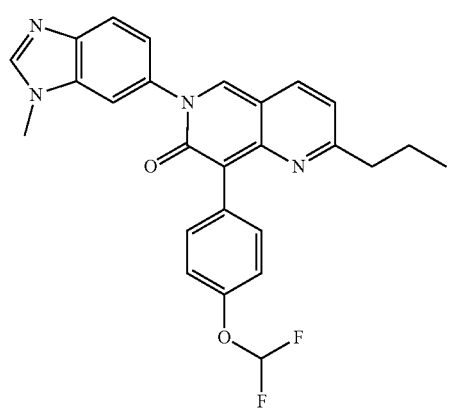 [SMILES: CCCc1ccc2cn(-c3ccc4ncn(C)c4c3)c(=O)c(-c3ccc(OC(F)F)cc3)c2n1]
261
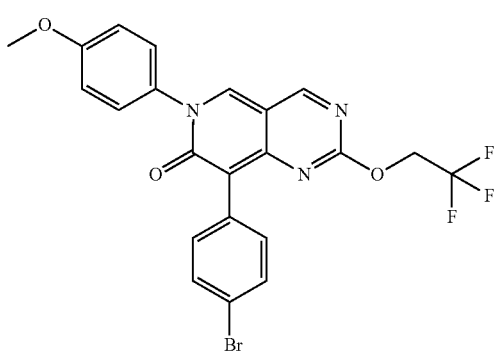 [SMILES: COc1ccc(-n2cc3cnc(OCC(F)(F)F)nc3c(-c3ccc(Br)cc3)c2=O)cc1]
262
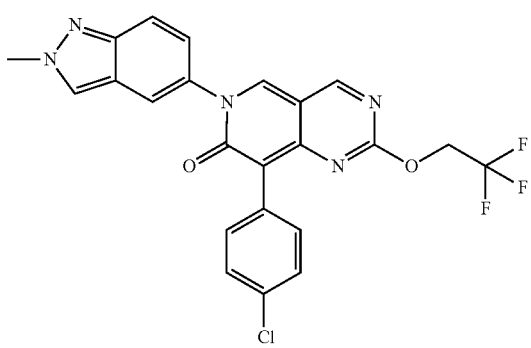 [SMILES: Cn1cc2cc(-n3cc4cnc(OCC(F)(F)F)nc4c(-c4ccc(Cl)cc4)c3=O)ccc2n1]
TABLE 3-continued
263
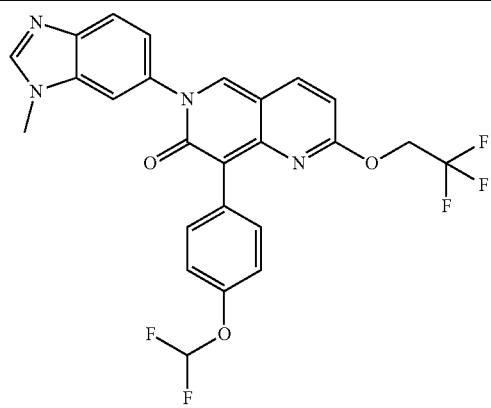
264
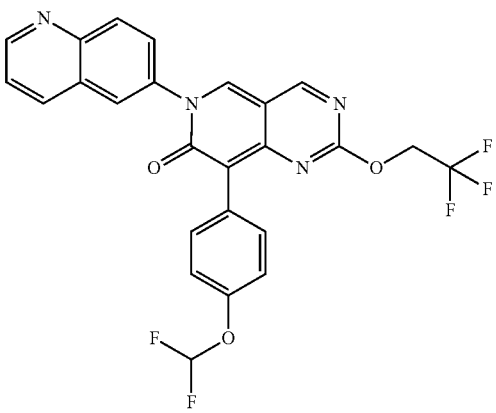
265
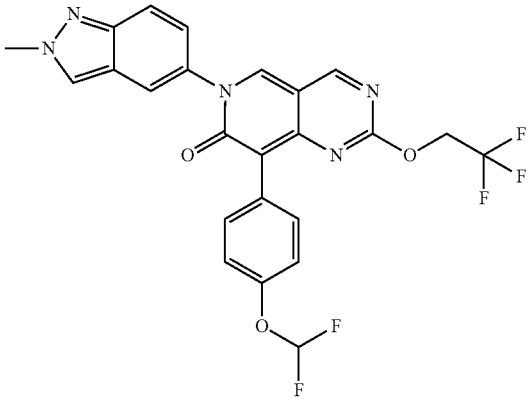 [SMILES: Cn1cc2cc(-n3cc4cnc(OCC(F)(F)F)nc4c(-c4ccc(OC(F)F)cc4)c3=O)ccc2n1]
266
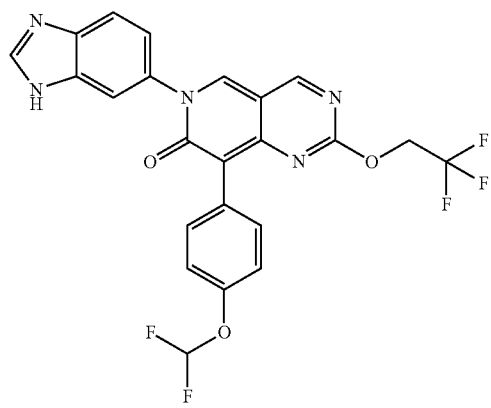 [SMILES: O=c1c(-c2ccc(OC(F)F)cc2)c2nc(OCC(F)(F)F)ncc2cn1-c1ccc2nc[nH]c2c1]

TABLE 3-continued
267 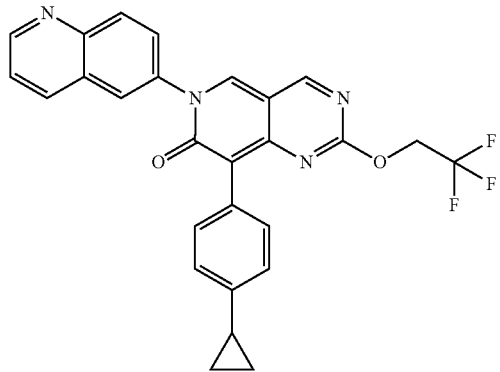 [SMILES: O=c1c(-c2ccc(C3CC3)cc2)c2nc(OCC(F)(F)F)ncc2cn1-c1ccc2ncccc2c1]
268 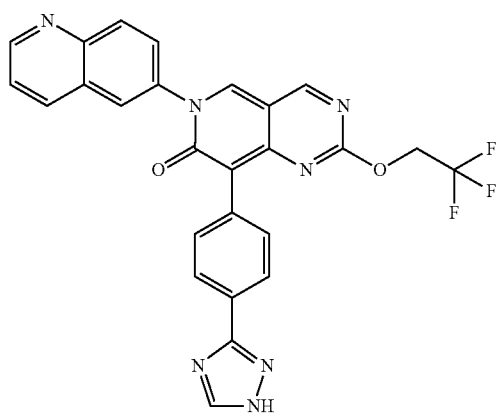 [SMILES: O=c1c(-c2ccc(-c3nc[nH]n3)cc2)c2nc(OCC(F)(F)F)ncc2cn1-c1ccc2ncccc2c1]
269 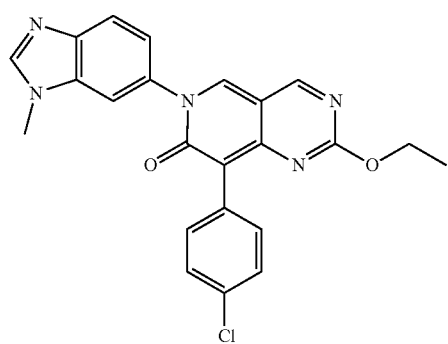
270 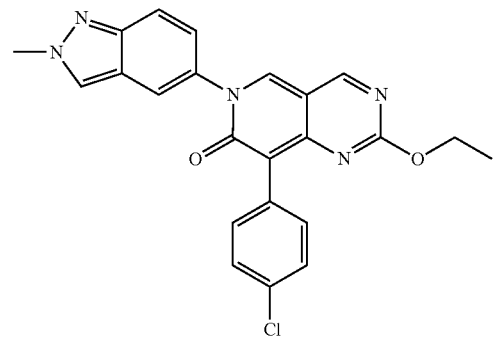
TABLE 3-continued
271 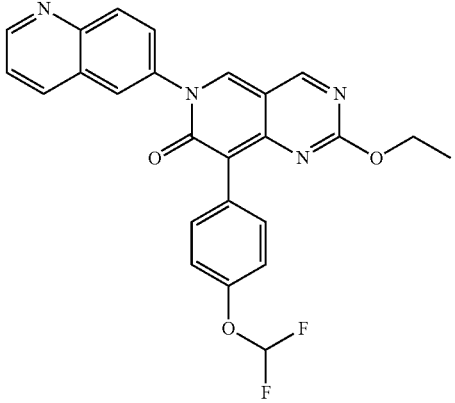 [SMILES: CCOc1ncc2cn(-c3ccc4ncccc4c3)c(=O)c(-c3ccc(OC(F)F)cc3)c2n1]
272 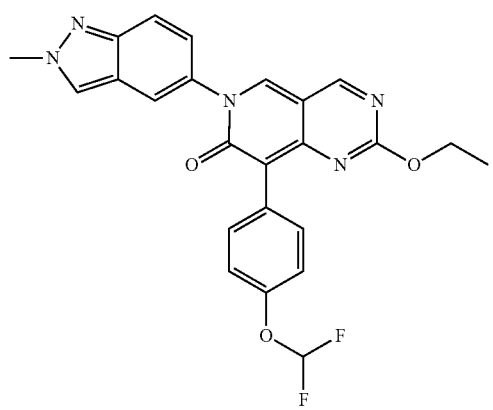 [SMILES: CCOc1ncc2cn(-c3ccc4nn(C)cc4c3)c(=O)c(-c3ccc(OC(F)F)cc3)c2n1]
273 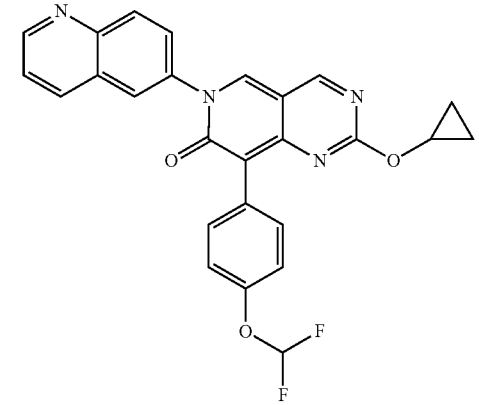 [SMILES: O=c1c(-c2ccc(OC(F)F)cc2)c2nc(OC3CC3)ncc2cn1-c1ccc2ncccc2c1]
274 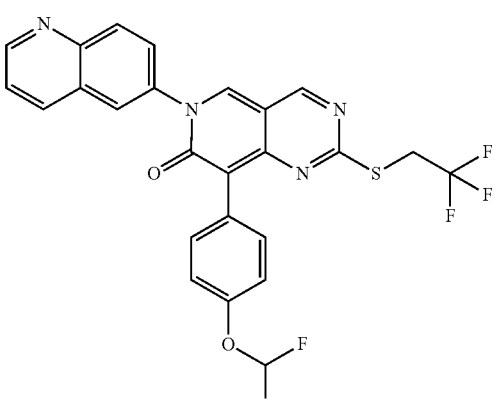

In still additional embodiments, the present disclosure provides the following specific, illustrative compounds of Formula I as set forth in Table 1-A below.
TABLE 1-A
101-A
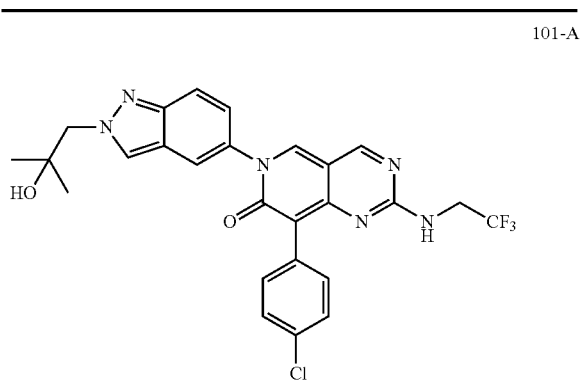
102-A
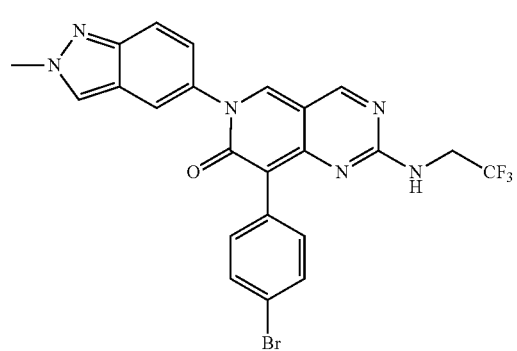
103-A
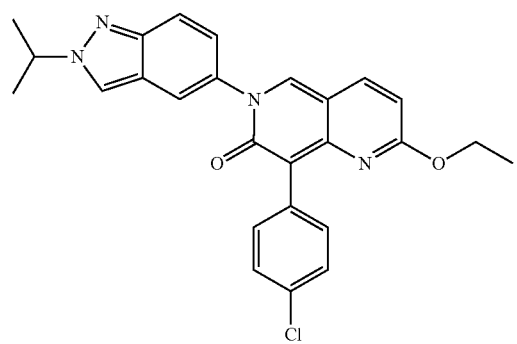 [SMILES: CCOc1ccc2cn(-c3ccc4nn(C(C)C)cc4c3)c(=O)c(-c3ccc(Cl)cc3)c2n1]
TABLE 1-A-continued
105-A
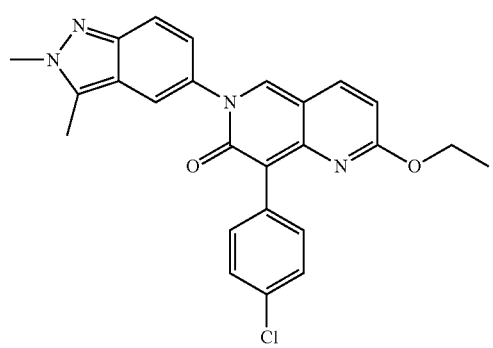 [SMILES: CCOc1ccc2cn(-c3ccc4nn(C)c(C)c4c3)c(=O)c(-c3ccc(Cl)cc3)c2n1]
106-A
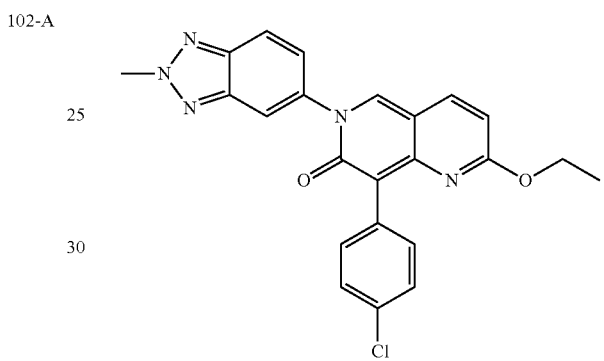
107-A
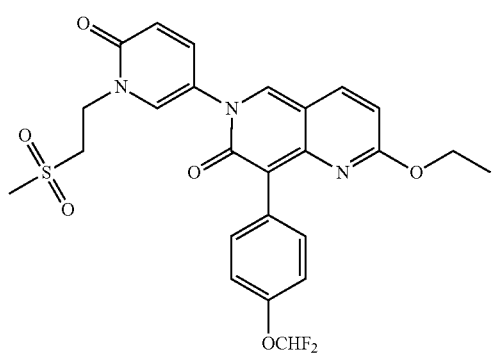 [SMILES: CCOc1ccc2cn(-c3ccc(=O)n(CCS(C)(=O)=O)c3)c(=O)c(-c3ccc(OC(F)F)cc3)c2n1]
108-A
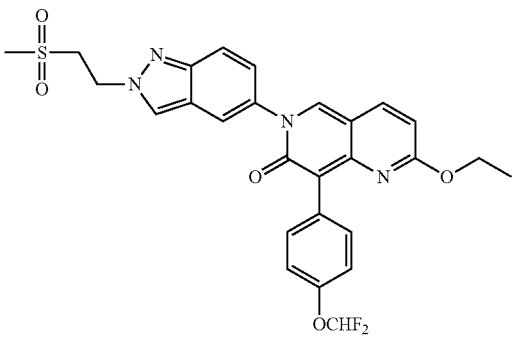 [SMILES: CCOc1ccc2cn(-c3ccc4nn(CCS(C)(=O)=O)cc4c3)c(=O)c(-c3ccc(OC(F)F)cc3)c2n1]
104-A TABLE 1-A-continued
109-A
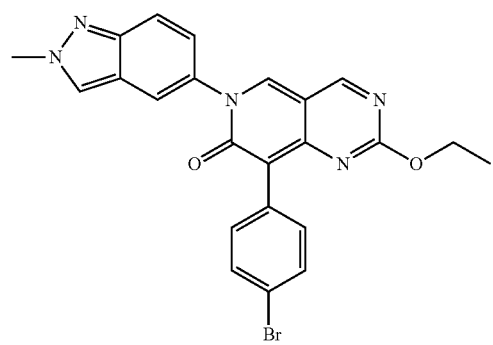 [SMILES: CCOc1ncc2cn(-c3ccc4nn(C)cc4c3)c(=O)c(-c3ccc(Br)cc3)c2n1]
110-A
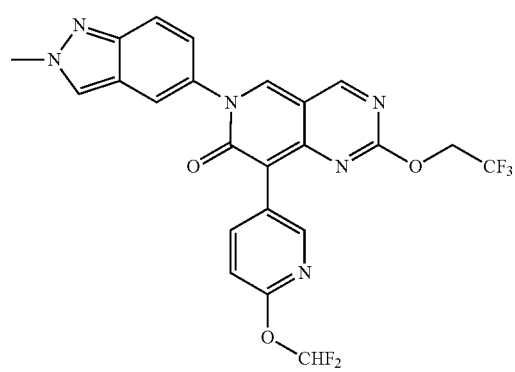 [SMILES: Cn1cc2cc(-n3cc4cnc(OCC(F)(F)F)nc4c(-c4ccc(OC(F)F)nc4)c3=O)ccc2n1]
111-A
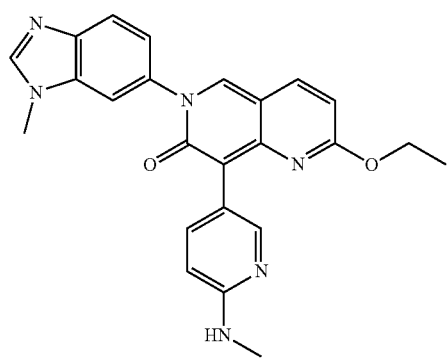 [SMILES: CCOc1ccc2cn(-c3ccc4ncn(C)c4c3)c(=O)c(-c3ccc(NC)nc3)c2n1]
112-A
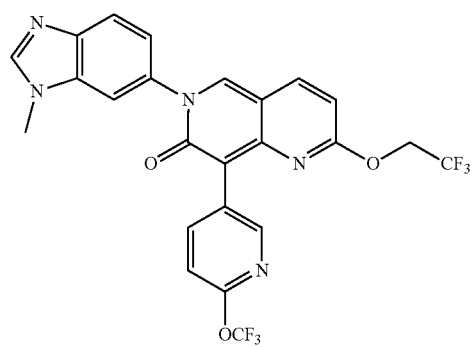 [SMILES: Cn1cnc2ccc(-n3cc4ccc(OCC(F)(F)F)nc4c(-c4ccc(OC(F)(F)F)nc4)c3=O)cc21]
TABLE 1-A-continued
113-A
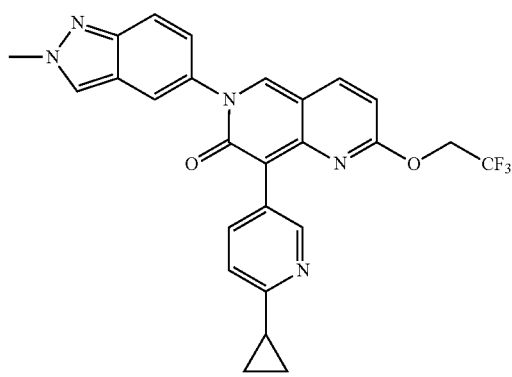 [SMILES: Cn1cc2cc(-n3cc4ccc(OCC(F)(F)F)nc4c(-c4ccc(C5CC5)nc4)c3=O)ccc2n1]
114-A
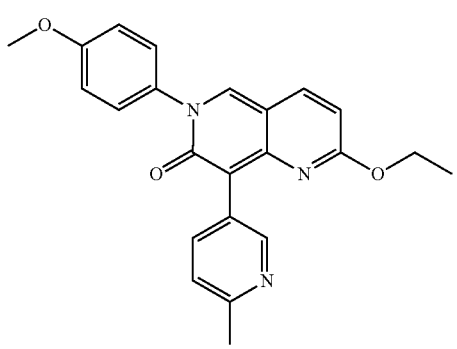 [SMILES: CCOc1ccc2cn(-c3ccc(OC)cc3)c(=O)c(-c3ccc(C)nc3)c2n1]
115-A
116-A
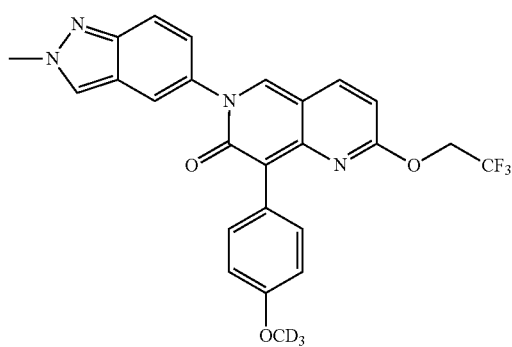

TABLE 1-A-continued
117-A
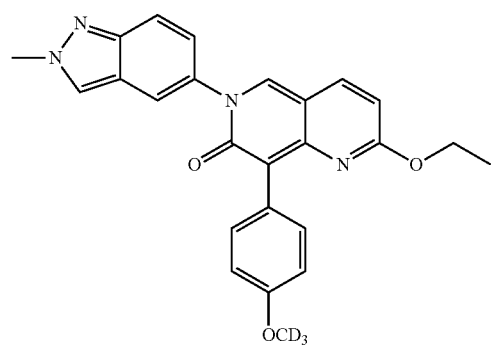
118-A
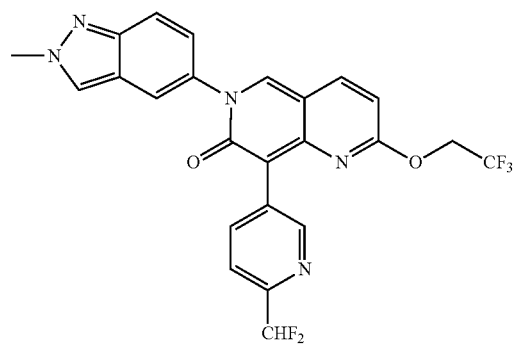
119-A
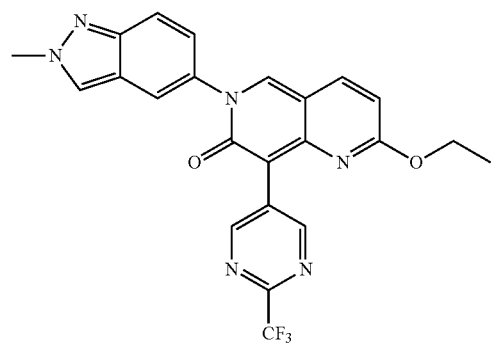 [SMILES: CCOc1ccc2cn(-c3ccc4nn(C)cc4c3)c(=O)c(-c3cnc(C(F)(F)F)nc3)c2n1]
120-A
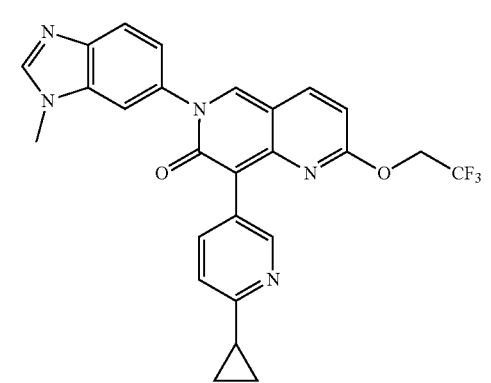 [SMILES: Cn1cnc2ccc(-n3cc4ccc(OCC(F)(F)F)nc4c(-c4ccc(C5CC5)nc4)c3=O)cc21]
TABLE 1-A-continued
121-A
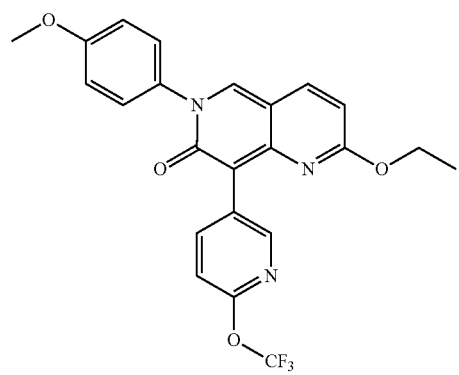 [SMILES: CCOc1ccc2cn(-c3ccc(OC)cc3)c(=O)c(-c3ccc(OC(F)(F)F)nc3)c2n1]
122-A
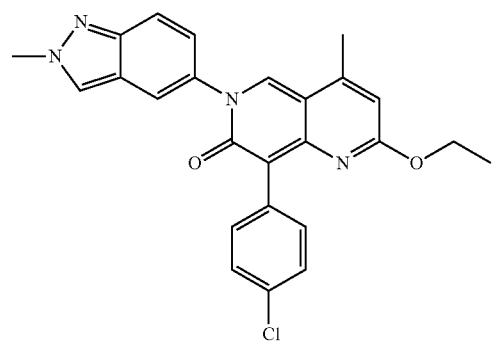 [SMILES: CCOc1cc(C)c2cn(-c3ccc4nn(C)cc4c3)c(=O)c(-c3ccc(Cl)cc3)c2n1]
123-A
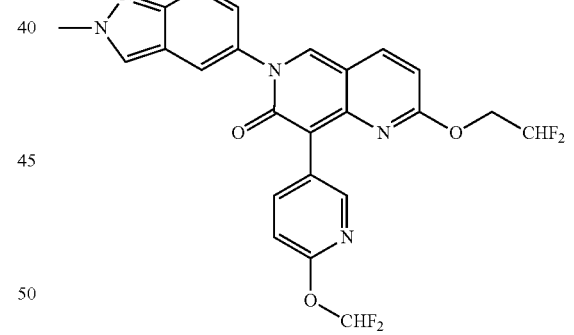
124-A
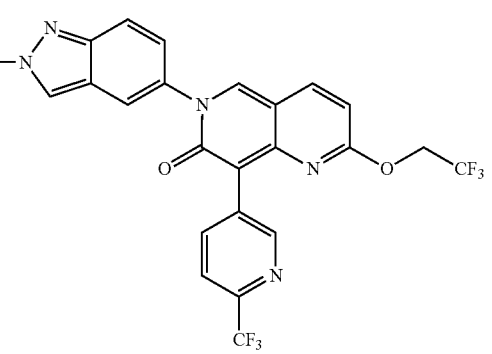

TABLE 1-A-continued
125-A
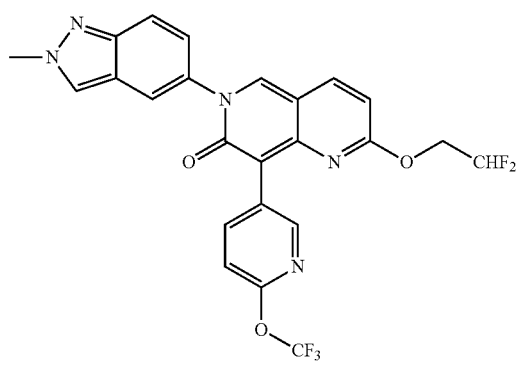
126-A
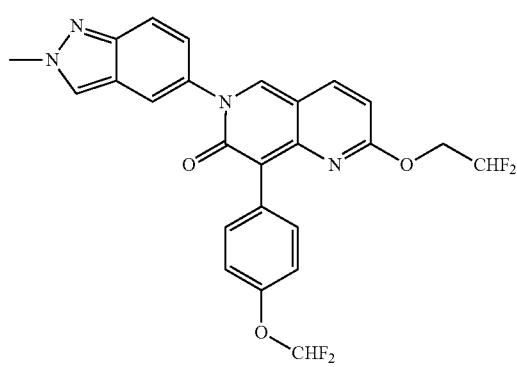
127-A
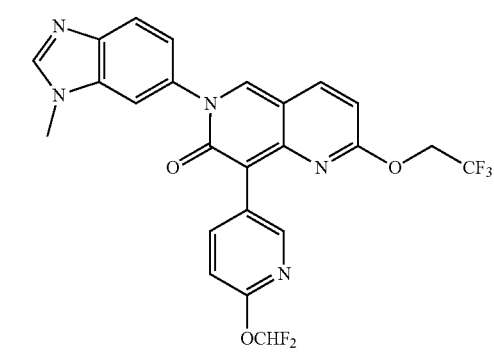 [SMILES: Cn1cnc2ccc(-n3cc4ccc(OCC(F)(F)F)nc4c(-c4ccc(OC(F)F)nc4)c3=O)cc21]
128-A
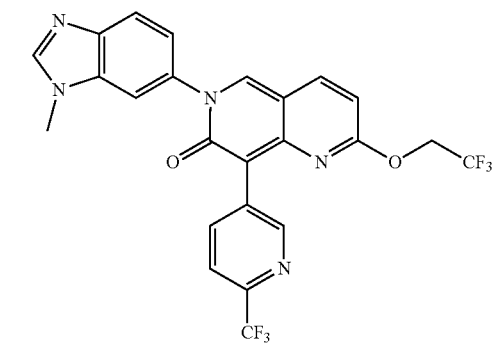
129-A
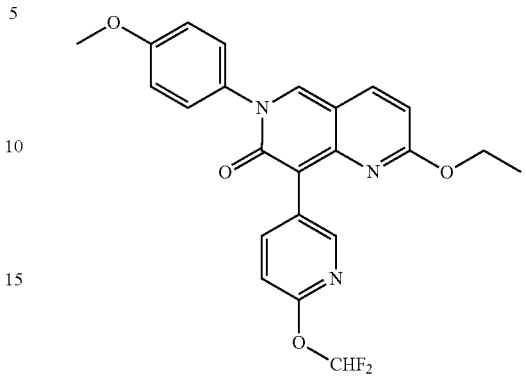
130-A
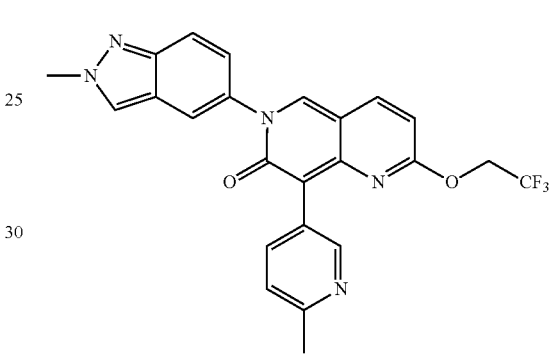
131-A
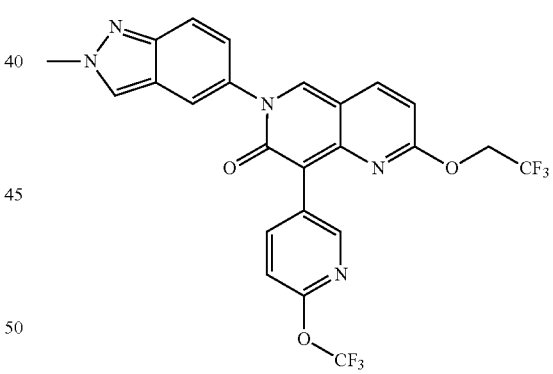
132-A
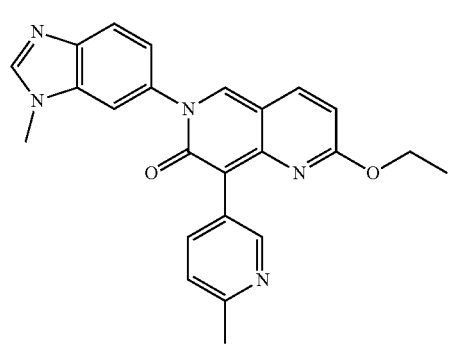 [SMILES: CCOc1ccc2cn(-c3ccc4ncn(C)c4c3)c(=O)c(-c3ccc(C)nc3)c2n1]

TABLE 1-A-continued
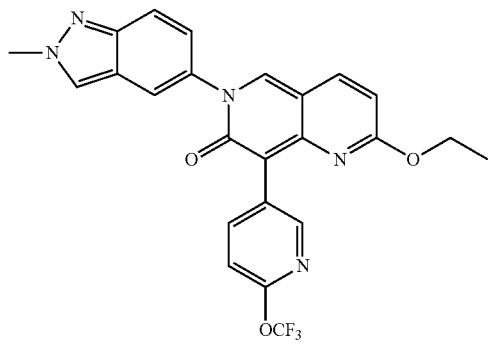 [SMILES: CCOc1ccc2cn(-c3ccc4nn(C)cc4c3)c(=O)c(-c3ccc(OC(F)(F)F)nc3)c2n1]
133-A
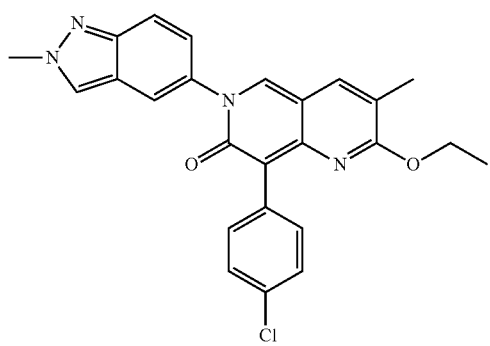 [SMILES: CCOc1nc2c(-c3ccc(Cl)cc3)c(=O)n(-c3ccc4nn(C)cc4c3)cc2cc1C]
134-A
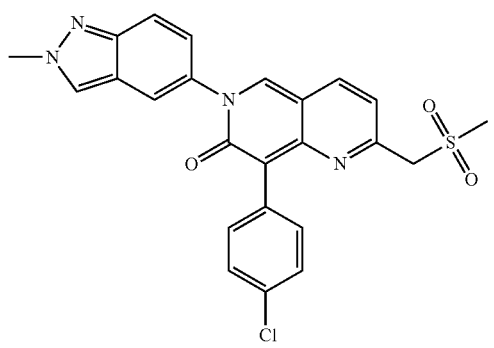
135-A
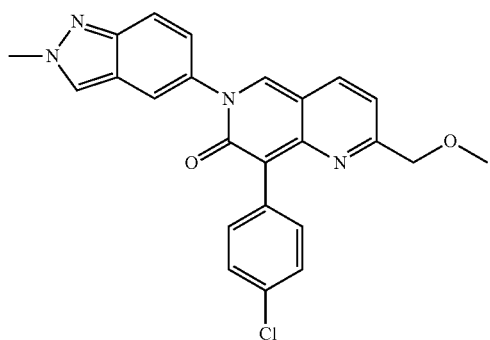
136-A
TABLE 1-A-continued
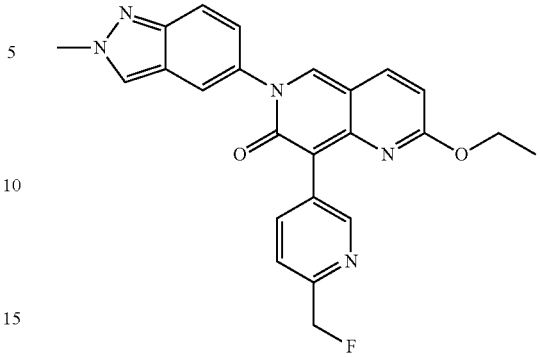
137-A
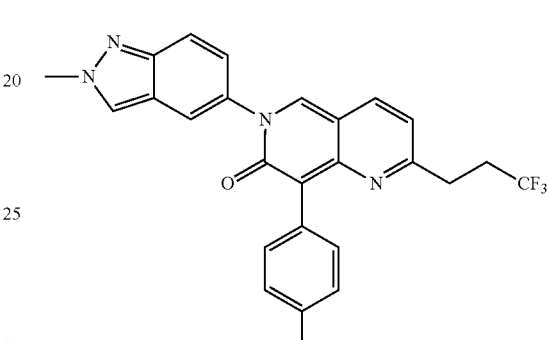
138-A
In various embodiments, the present disclosure provides specific, illustrative examples of compounds of Formula II, as set forth in Table 2-A below:
TABLE 2-A
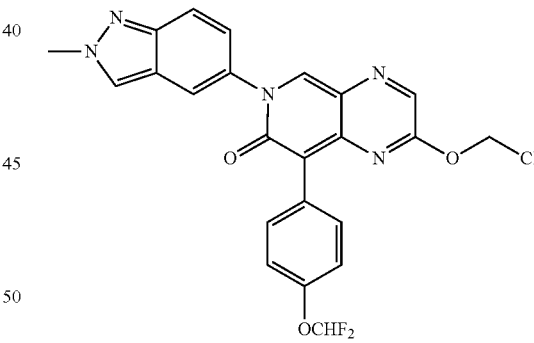
139-A
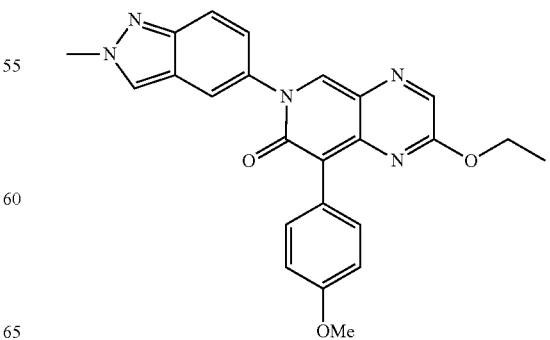
140-A TABLE 2-A-continued
141-A
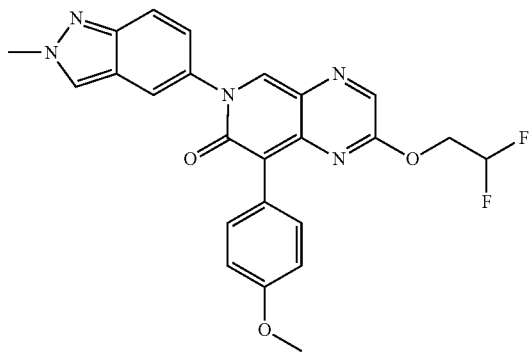 [SMILES: COc1ccc(-c2c(=O)n(-c3ccc4nn(C)cc4c3)cc3ncc(OCC(F)F)nc23)cc1]
142-A
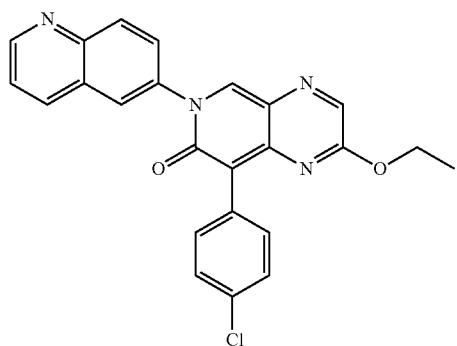 [SMILES: CCOc1cnc2cn(-c3ccc4ncccc4c3)c(=O)c(-c3ccc(Cl)cc3)c2n1]
143-A
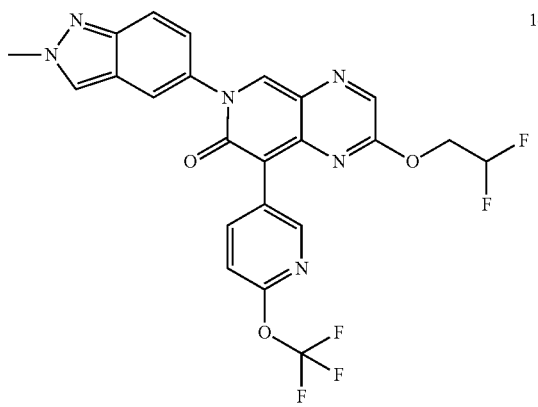
144-A
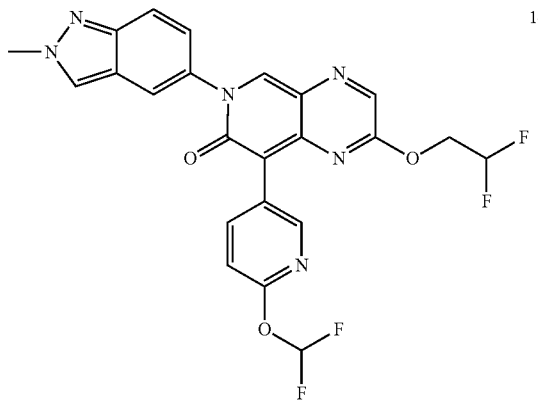
TABLE 2-A-continued
145-A
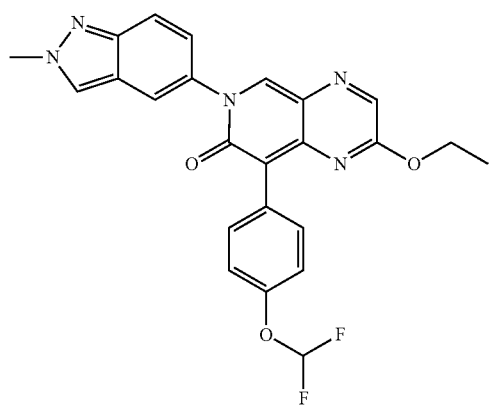 [SMILES: CCOc1cnc2cn(-c3ccc4nn(C)cc4c3)c(=O)c(-c3ccc(OC(F)F)cc3)c2n1]
146-A
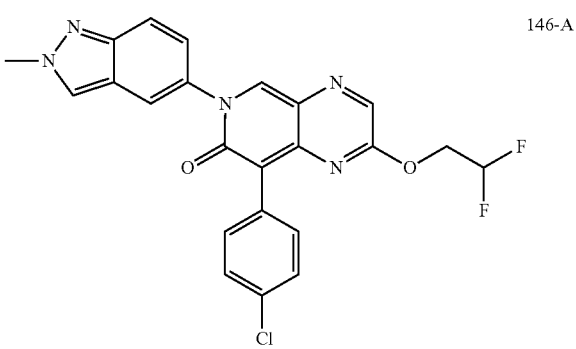
147-A
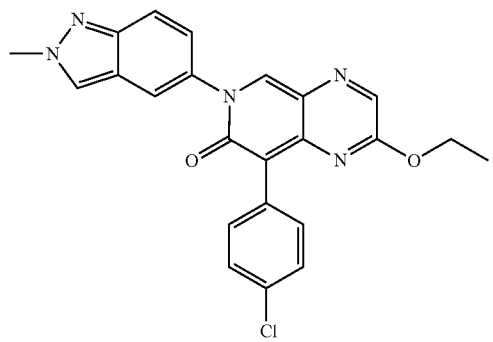 [SMILES: CCOc1cnc2cn(-c3ccc4nn(C)cc4c3)c(=O)c(-c3ccc(Cl)cc3)c2n1]
148-A
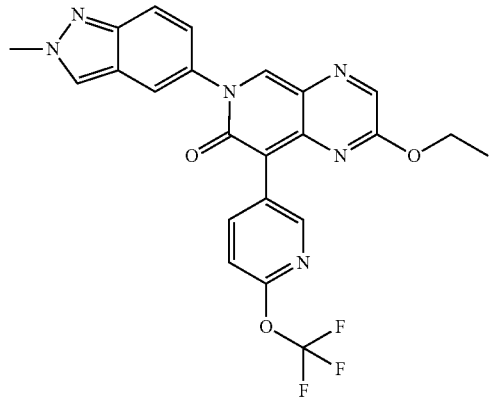 [SMILES: CCOc1cnc2cn(-c3ccc4nn(C)cc4c3)c(=O)c(-c3ccc(OC(F)(F)F)nc3)c2n1]

TABLE 2-A-continued

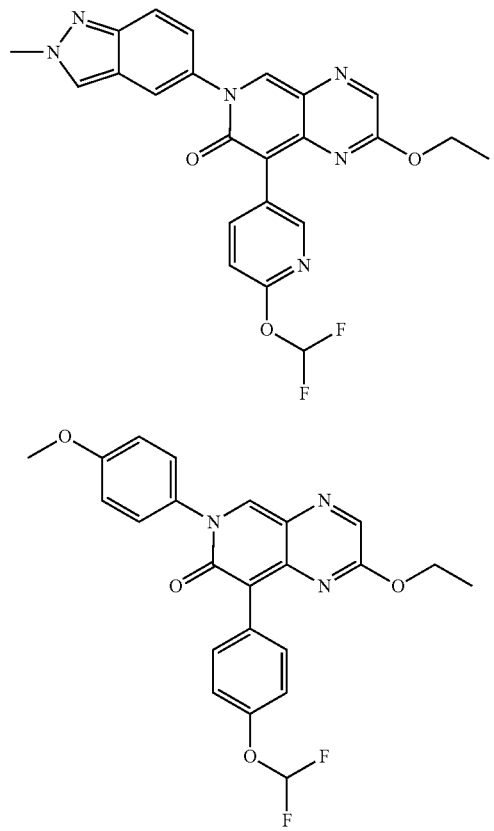

149-A

150-A

Pharmaceutical Compositions

The present disclosure also provides a pharmaceutical composition comprising a therapeutically effective amount of one or more compounds according to Formula I or Formula II or a pharmaceutically acceptable salt, stereoisomer, or tautomer thereof, in admixture with a pharmaceutically acceptable carrier. In some embodiments, the composition further contains, in accordance with accepted practices of pharmaceutical compounding, one or more additional therapeutic agents, pharmaceutically acceptable excipients, diluents, adjuvants, stabilizers, emulsifiers, preservatives, colorants, buffers, flavor imparting agents.

In one embodiment, the pharmaceutical composition comprises a compound selected from those provided in Tables 1-3, 1-A, and 2-A, or a pharmaceutically acceptable salt, stereoisomer, or tautomer thereof, and a pharmaceutically acceptable carrier.

The pharmaceutical composition of the present disclosure is formulated, dosed, and administered in a fashion consistent with good medical practice. Factors for consideration in this context include the particular disorder being treated, the particular subject being treated, the clinical condition of the subject, the cause of the disorder, the site of delivery of the agent, the method of administration, the scheduling of administration, and other factors known to medical practitioners.

The "therapeutically effective amount" of a compound (or a pharmaceutically acceptable salt, stereoisomer, or tautomer thereof) that is administered is governed by such considerations, and is the minimum amount necessary to exert a cytotoxic effect on a cancer, or to inhibit MAT2A activity, or both. Such amount may be below the amount that is toxic to normal cells, or the subject as a whole. Generally, in some embodiments a therapeutically effective amount of a compound (or a pharmaceutically acceptable salt, stereoisomer, or tautomer thereof) of the present disclosure that is administered is in the range of about 0.01 to about 200 mg/kg or about 0.1 to about 20 mg/kg of patient body weight per day, with the typical range being about 0.3 to about 15 mg/kg/day. Oral unit dosage forms, such as tablets and capsules, may contain from about 0.1 mg to about 1000 mg of a compound (or a pharmaceutically acceptable salt, stereoisomer, or tautomer thereof) of the present disclosure. In another embodiment, such dosage forms contain from about 50 mg to about 500 mg of a compound (or a pharmaceutically acceptable salt, stereoisomer, or tautomer thereof) of the present disclosure. In yet another embodiment, such dosage forms contain from about 25 mg to about 200 mg of a compound (or a pharmaceutically acceptable salt, stereoisomer, or tautomer thereof) of the present disclosure. In still another embodiment, such dosage forms contain from about 10 mg to about 100 mg of a compound (or a pharmaceutically acceptable salt, stereoisomer, or tautomer thereof) of the present disclosure. In a further embodiment, such dosage forms contain from about 5 mg to about 50 mg of a compound (or a pharmaceutically acceptable salt, stereoisomer, or tautomer thereof) of the present disclosure. In still other embodiments, such dosage forms contain from about 0.1 mg to about 10 mg of a compound (or a pharmaceutically acceptable salt, stereoisomer, or tautomer thereof) of the present disclosure. In any of the foregoing embodiments the dosage form can be administered once a day or twice a day.

The compositions of the present disclosure can be administered orally, topically, parenterally, by inhalation or spray or rectally in dosage unit formulations. The term parenteral as used herein includes subcutaneous injections, intravenous, intramuscular, intrasternal injection or infusion techniques.

Suitable oral compositions in accordance with the present disclosure include without limitation tablets, troches, lozenges, aqueous or oily suspensions, dispersible powders or granules, emulsion, hard or soft capsules, syrups or elixirs.

Encompassed within the scope of the present disclosure are pharmaceutical compositions suitable for single unit dosages that comprise a compound of the disclosure or its pharmaceutically acceptable stereoisomer, salt, or tautomer and a pharmaceutically acceptable carrier.

Compositions suitable for oral use may be prepared according to any method known to the art for the manufacture of pharmaceutical compositions. For instance, liquid formulations of the compounds of the present disclosure contain one or more agents selected from the group consisting of sweetening agents, flavoring agents, coloring agents and preserving agents.

For tablet compositions, a compound of the present disclosure in admixture with non-toxic pharmaceutically acceptable excipients is used for the manufacture of tablets. Examples of such excipients include without limitation inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

For aqueous suspensions, a compound of the present disclosure is admixed with excipients suitable for maintaining a stable suspension. Examples of such excipients include without limitation are sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending a compound of the present disclosure in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water may be formulated by providing a compound of the present disclosure in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the present disclosure may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensaturatedion products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable, an aqueous suspension or an oleaginous suspension. This suspension may be formulated according to techniques known in the art using one of more suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general Formula I or Formula II may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compositions for parenteral administrations are administered in a sterile medium. Depending on the vehicle used and concentration the concentration of the drug in the formulation, the parenteral formulation can either be a suspension or a solution containing dissolved drug. Adjuvants such as local anesthetics, preservatives and buffering agents can also be added to parenteral compositions.

Methods of Use

The MAT2A enzyme catalyzes the synthesis of S-adenosyl methionine (SAM) from methionine and ATP in cells. Accordingly, in another embodiment of the present disclosure there is provided a method of inhibiting in a cell the synthesis of SAM comprising introducing into the cell an effective amount of a compound of Formula I or Formula II or a pharmaceutically acceptable salt, stereoisomer, or tautomer thereof. In some embodiments, a Formula I or Formula II compound is used to identify other compounds that are inhibitors of MAT2A, for example, in a competition assay for binding to MAT2A or for the inhibition of SAM production. Binding to MAT2A or the inhibition of SAM production by a test compound having a detectable label can be measured with and without the presence of an unlabeled compound of the present disclosure.

The present disclosure also provides a method for treating a cancer in a subject suffering therefrom, comprising administering to the subject an effective amount of a compound of Formula I or Formula II or a pharmaceutically acceptable salt thereof. In one embodiment, optionally in combination with any other embodiment disclosed herein, the subject is a mammal, such as a human.

The present disclosure additionally provides a method for treating a cancer in a subject suffering therefrom, comprising administering to the subject an effective amount of a MAT2A inhibitor. In some embodiments, the MAT2A inhibitor is a compound of Formula I or Formula II or a pharmaceutically acceptable salt thereof. In an embodiment, optionally in combination with any other embodiment disclosed herein, the subject is a mammal, such as a human.

In an embodiment, the cancer is an MTAP-deleted cancer. Alternatively, or in combination, other embodiments provide the cancer as one selected from the group consisting of mesothelioma, neuroblastoma, intestine carcinoma such as rectum carcinoma, colon carcinoma, familiary adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroidea carcinoma, papillary thyroidea carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, bladder carcinoma, testis carcinoma, breast carcinoma, urinary carcinoma, melanoma, brain tumors, head and neck cancer, lymphoma, acute lymphatic leukemia (ALL), chronic lymphatic leukemia (CLL), acute myeloid leukemia (AML), chronic myeloid leukemia (CML), hepatocellular carcinoma, gall bladder carcinoma, bronchial carcinoma, small cell lung carcinoma (SCLC), non-small cell lung carcinoma (NSCLC), multiple myeloma (MM), basalioma, teratoma, retinoblastoma, choroidea melanoma, seminoma, rhabdomyo sarcoma, osteosarcoma, chondrosarcoma, myosarcoma, liposarcoma, fibrosarcoma, Ewing sarcoma, and plasmocytoma.

In other embodiments, the cancer is selected from lung cancer, non-small cell lung cancer, bronchioloalviolar cell lung cancer, bone cancer, pancreatic cancer, skin cancer, head and neck cancer, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, chronic or acute leukemia, lymphocytic lymphoma, neoplasms of the central nervous system (CNS), spinal axis tumors, brain stem glioma, glioblastoma multiforme, astrocytomas, schwannomas, ependymomas, medulloblastomas, meningiomas, squamous cell carcinomas, pituitary adenomas, including resistant and/or refractory versions of any of the above cancers, and a combination of one or more of the above cancers.

In some embodiments, the cancer is selected from the group consisting of B-cell acute lymphocytic leukemia (B-ALL), mesothelioma, lymphoma, pancreatic carcinoma, lung cancer, gastric cancer, esophageal cancer, bladder carcinoma, brain cancer, head and neck cancer, melanoma and breast cancer.

In other embodiments the lung cancer is non-small cell lung cancer, small cell lung cancer, adenocarcinoma of the lung, and squamous cell carcinoma of the lung.

In other embodiments the breast cancer is triple negative breast cancer (TNBC).

In other embodiments, the brain cancer is a brain tumor selected from the group consisting of glioma, glioblastoma, astrocytoma, meningioma, medulloblastoma, peripheral neuroectodermal tumors, and craniopharyngioma.

In still other embodiments, the cancer is a lymphoma selected from the group consisting of mantle cell lymphoma, Hodgkin lymphoma, non-Hodgkin lymphoma, Burkitt lymphoma, diffuse large B-cell lymphoma (DLBCL), and adult T-cell leukemia/lymphoma (ATLL). As used herein, the expression adult T-cell leukemia/lymphoma refers to a rare and often aggressive T-cell lymphoma that can be found in the blood (leukemia), lymph nodes (lymphoma), skin, or multiple areas of the body.

As described generally above, methylthioadenosine phosphorylase (MTAP) is an enzyme found in all normal tissues that catalyzes the conversion of methylthioadenosine (MTA) into adenine and 5-methylthioribose-1-phosphate. The adenine is salvaged to generate adenosine monophosphate, and the 5-methylthioribose-1-phosphate is converted to methionine and formate. Because of this salvage pathway, MTA can serve as an alternative purine source when de novo purine synthesis is blocked, e.g., with antimetabolites, such as L-alanosine. Many human and murine malignant cells lack MTAP activity. MTAP deficiency is not only found in tissue culture cells but the deficiency is also present in primary leukemias, gliomas, melanomas, pancreatic cancers, non-small cell lung cancers (NSCLC), bladder cancers, astrocytomas, osteosarcomas, head and neck cancers, myxoid chondrosarcomas, ovarian cancers, endometrial cancers, breast cancers, soft tissue sarcomas, non-Hodgkin lymphomas, and mesotheliomas. For example, proliferation of cancer cells that are MTAP null, i.e., MTAP-deleted, is inhibited by knocking down MAT2A expression with shRNA which was confirmed using small molecule inhibitors of MAT2A. K. Marjon et al., *Cell Reports* 15 (2016) 574-587, incorporated herein by reference. An MTAP null or MTAP-deleted cancer is a cancer in which the MTAP gene has been deleted or lost or otherwise deactivated or a cancer in which the MTAP protein has a reduced or impaired function.

Accordingly, in an embodiment of the present disclosure there is provided a method for treating a cancer in a subject wherein the cancer is characterized by a reduction or absence of MTAP expression or absence of the MTAP gene or reduced function of MTAP protein as compared to cancers where the MTAP gene and/or protein is present and fully functioning, or as compared to cancers with the wild type MTAP gene. The method comprises administering to the subject a therapeutically effective amount of a compound of Formula I or Formula II or a pharmaceutically acceptable salt thereof.

In another embodiment, there is provided a method of treating an MTAP deleted cancer in a subject comprising administering to the subject an effective amount of a compound of Formula I or Formula II or a pharmaceutically acceptable salt thereof. In an embodiment, the MTAP deleted cancer is selected from leukemia, glioma, melanoma, pancreatic cancer, non-small cell lung cancer (NSCLC), bladder cancer, astrocytoma, osteosarcoma, head and neck cancer, myxoid chondrosarcoma, ovarian cancer, endometrial cancer, breast cancer, soft tissue sarcoma, lymphoma, and mesothelioma.

In an embodiment, the MTAP deleted cancer is pancreatic cancer. In another embodiment, the MTAP deleted cancer is selected from bladder cancer, melanoma, brain cancer, lung cancer, pancreatic cancer, breast cancer, liver cancer, esophageal cancer, gastric cancer, colon cancer, head and neck cancer, kidney cancer, colon cancer, diffuse large B cell lymphoma (DLBCL), acute lymphoblastic leukemia (ALL), mantle cell lymphoma (MCL), glioblastoma multiforme (GBM), and non-small cell lung cancer (NSCLC).

Genomic analysis of MTAP null cell lines revealed that cell lines incorporating a KRAS mutation or a p53 mutation were sensitive to MAT2A inhibition. Accordingly, an embodiment of the present disclosure provides a method for treating a cancer in a subject wherein the cancer is characterized by reduction or absence of MTAP expression or absence of the MTAP gene or reduced function of MTAP protein, the method comprising administering to the subject a therapeutically effective amount of a compound of Formula I, wherein said cancer is further characterized by the presence of mutant KRAS or mutant p53. In an embodiment, there is provided a method of treating an MTAP null cancer having a mutant KRAS or mutant p53 in a subject, comprising administering to the subject an effective amount of a compound of Formula I or a pharmaceutically acceptable salt thereof. For example, the cancer is MTAP null and KRAS mutant, MTAP null and p53 mutant, or each of MTAP null, KRAS mutant and p53 mutant.

The term "mutant KRAS" or "KRAS mutation" refers to a KRAS protein incorporating an activating mutation that alters its normal function and the gene encoding such a protein. For example, a mutant KRAS protein may incorporate a single amino acid substitution at position 12 or 13. In a particular embodiment, the KRAS mutant incorporates a G12X or G13X substitution, wherein X represents any amino acid change at the indicated position. In a particular embodiment, the substitution is G12V, G12R, G12C or G13D. In another embodiment, the substitution is G13D. By "mutant p53" or "p53 mutation" is meant p53 protein (or gene encoding said protein) incorporating a mutation that inhibits or eliminates its tumor suppressor function. In an embodiment, said p53 mutation is, Y126_splice, K132Q, M133K, R174fs, R175H, R196*, C238S, C242Y, G245S, R248W, R248Q, I255T, D259V, S261_splice, R267P, R273C, R282W, A159V or R280K. In an embodiment, the foregoing cancer is non-small cell lung cancer (NSCLC), pancreatic cancer, head and neck cancer, gastric cancer, breast cancer, colon cancer or ovarian cancer.

In another embodiment, the compounds disclosed herein are useful as ligands for degradation of disease-associated proteins. An example of this approach is PROTACs (PROteolysis TArgeting Chimeras). PROTACs are bifunctional molecules that comprise both a ligand moiety selected from one of the compounds disclosed herein, which is capable of binding the target protein, and a peptide portion (referred to as the degron) that is recognized and polyubiquitinated by E3 ligase. Thus, the PROTAC non-covalently binds to a target protein, and recruits E3 ligase via the degron peptide, which results in polyubiquination and degradation of the bound target. A number of publications describe the preclinical use of PROTACs in a variety of therapeutic areas including oncology. See, e.g., Lu et al. *Chemistry & Biology* 22 (2015) 755-763.

EXAMPLES

The present disclosure will be more fully understood by reference to the following examples. The examples provided herein are illustrative and should not, however, be construed as limiting the scope of the present disclosure.

Abbreviations and Terms List anhy. anhydrous
aq. aqueous
min minute(s)
mL milliliter
mmol millimole(s)
mol mole(s)
MS mass spectrometry
NMR nuclear magnetic resonance
TLC thin layer chromatography
HPLC high-performance liquid chromatography
RT(r.t.) room temperature
Spectrum
Hz hertz
δ chemical shift
J coupling constant
s singlet
d doublet
t triplet
q quartet
m multiplet
br broad
qd quartet of doublets
dquin doublet of quintets
dd doublet of doublets
dt doublet of triplets
Solvents and Reagents:
$CHCl_3$ chloroform
DCM dichloromethane
DMF dimethylformamide
$Et_2O$ diethyl ether
EtOH ethyl alcohol
EtOAc ethyl acetate
EA ethyl acetate
MeOH methyl alcohol
MeCN acetonitrile
PE petroleum ether
THF tetrahydrofuran
AcOH acetic acid
HCl hydrochloric acid
$H_2SO_4$ sulfuric acid
$NH_4Cl$ ammonium chloride
KOH potassium hydroxide
NaOH sodium hydroxide
$K_2CO_3$ potassium carbonate
$Na_2CO_3$ sodium carbonate
TFA trifluoroacetic acid
$Na_2SO_4$ sodium sulfate
$NaBH_4$ sodium borohydride
$NaHCO_3$ sodium bicarbonate
LiHMDS lithium hexamethyldisilylamide
NaHMDS sodium hexamethyldisilylamide
LAH lithium aluminum hydride
$NaBH_4$ sodium borohydride
LDA lithium diisopropylamide
$Et_3N$ triethylamine
DMAP 4-(dimethylamino)pyridine
DIPEA N,N-diisopropylethylamine
$NH_4OH$ ammonium hydroxide
EDCI 1-ethyl-3-(3-dimethylaminopropyl)carbodiimide
HOBt 1-hydroxybenzotriazole
HATU O-(7-azabenzotriazol-1-yl)-N,N,N',N'-tetramethyluronium
Xphos 2-Dicyclohexylphosphino-2',4',6'-triisopropylbiphenyl
BINAP 2,2'-bis(diphenylphosphanyl)-1,1'-binaphthyl
General Experimental In the following examples, the reagents and solvents were purchased from commercial sources (such as Alfa, Acros, Sigma Aldrich, TCI and Shanghai Chemical Reagent Company), and used without further purification unless otherwise specified. Flash chromatography was performed on an Ez Purifier III using column with silica gel particles of 200-300 mesh. Analytical and preparative thin layer chromatography (TLC) plates were HSGF 254 (0.15-0.2 mm thickness, Shanghai Anbang Company, China). Nuclear magnetic resonance (NMR) spectra were obtained on a Brucker AMX-400 NMR (Brucker, Switzerland). Chemical shifts were reported in parts per million (ppm, δ) downfield from tetramethylsilane. Mass spectra were given with electrospray ionization (ESI) from a Waters LCT TOF Mass Spectrometer (Waters, USA). HPLC chromatographs were record on an Agilent 1200 Liquid Chromatography (Agilent, USA, column: Ultimate 4.6 mm×50 mm, 5 μm, mobile phase A: 0.1% formic acid in water; mobile phase B: acetonitrile). Microwave reactions were run on an Initiator 2.5 Microwave Synthesizer (Biotage, Sweden).

General Procedure I

General procedure I

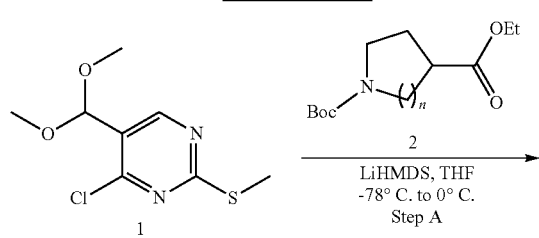

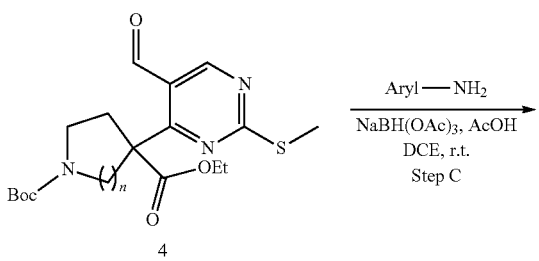

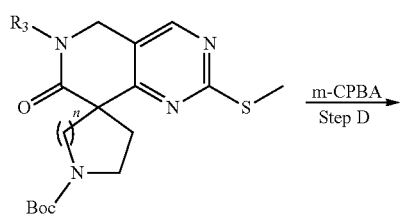

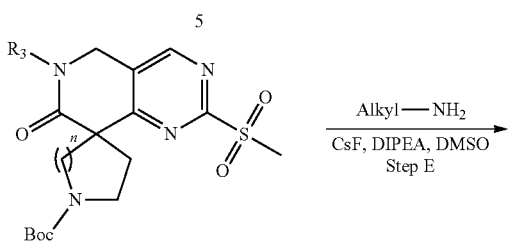

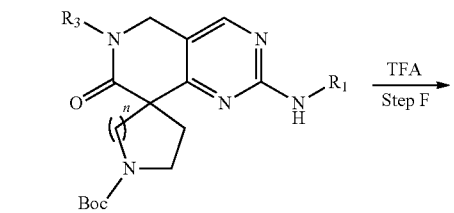

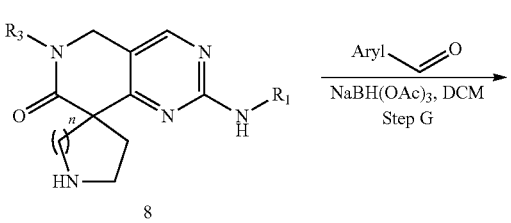

Alternative Route

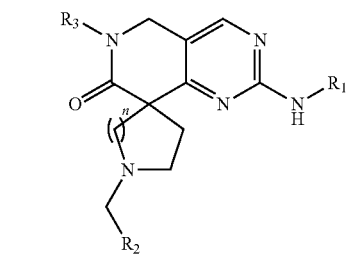

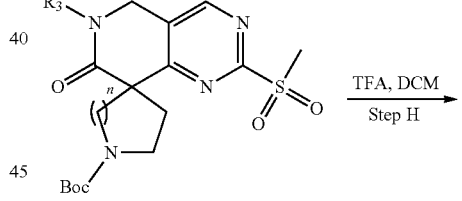

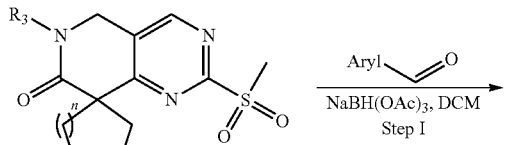

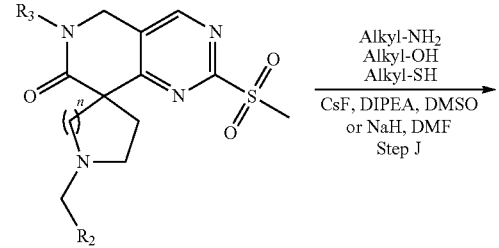

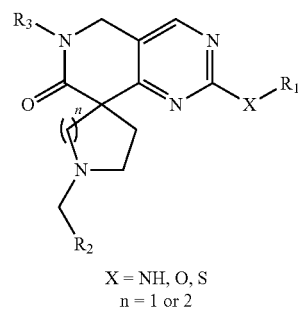
X = NH, O, S
n = 1 or 2
Preparation of Example 101 via General Procedure I
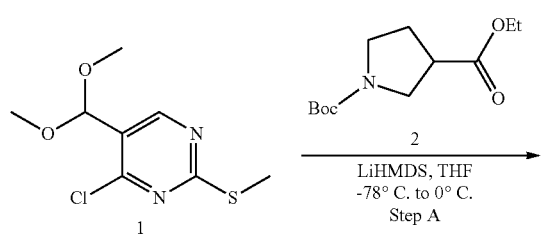
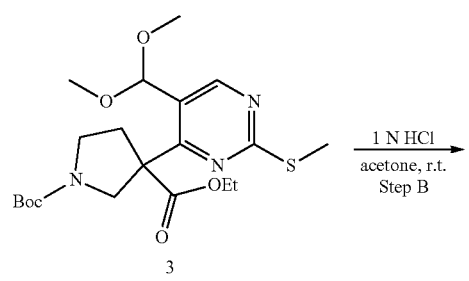
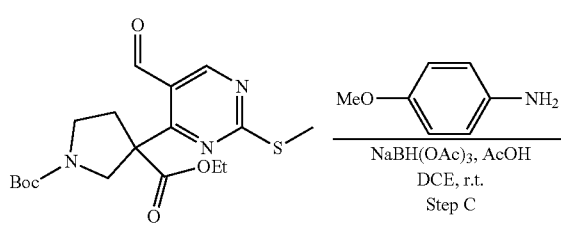
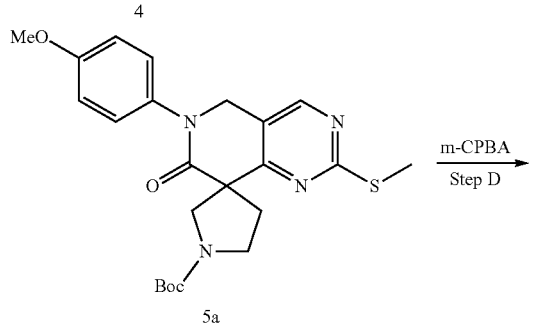
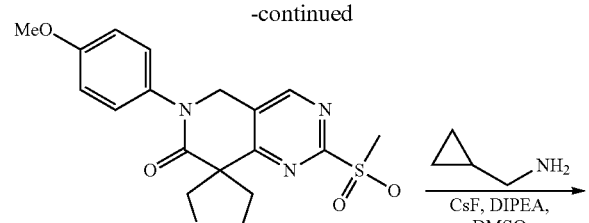
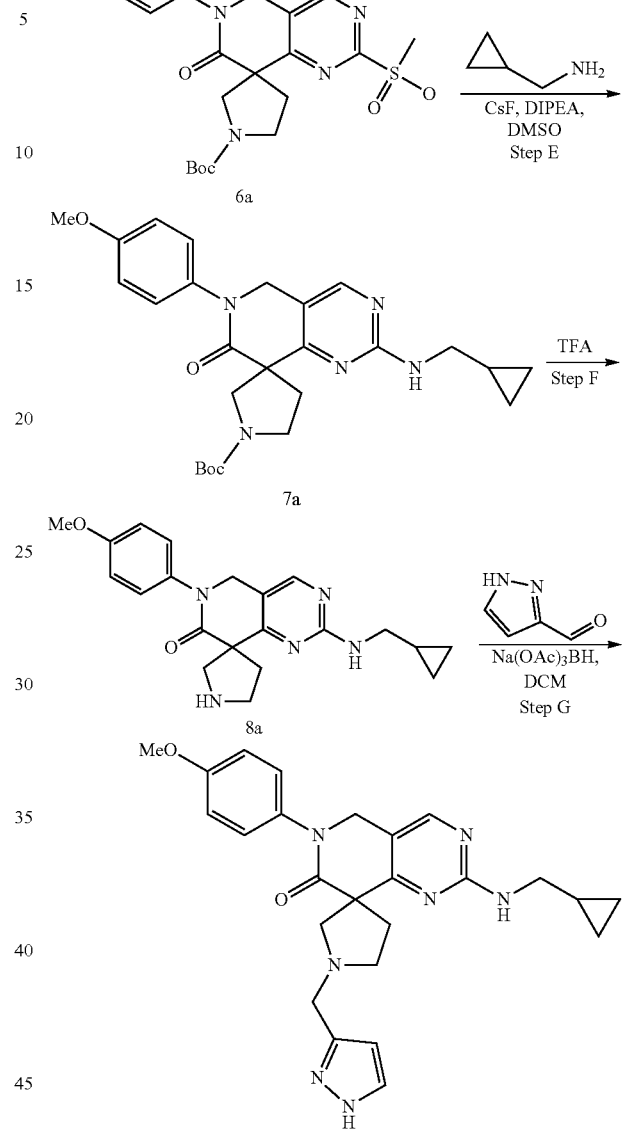
Step A: 1-tert-butyl 3-ethyl 3-(5-(dimethoxymethyl)-2-(methylthio)pyrimidin-4-yl)pyrrolidine-1,3-dicarboxylate
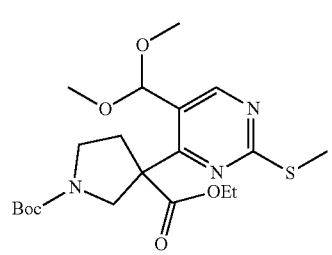 [SMILES: CCOC(=O)C1(c2nc(SC)ncc2C(OC)OC)CCN(C(=O)OC(C)(C)C)C1]
To a solution of 1-tert-butyl 3-ethyl pyrrolidine-1,3-dicarboxylate (4.8 g, 19.8 mmol, 1.5 equiv.) in THF (30 mL) was added LiHMDS (1 Min THF, 26.4 mL, 26.4 mmol, 2.0 equiv.) at −78° C. over 1 h via the addition funnel. The mixture was stirred at −78° C. for 4 h. Then a solution of 4-chloro-5-(dimethoxymethyl)-2-(methylthio)pyrimidine (3.1 g, 13.2 mmol, 1.0 equiv.) in THF (10 mL) was added. The reaction mixture was allowed to warm to room temperature and stirred for an additional 3 h. Then the reaction mixture was quenched with NH$_4$Cl (sat. aq.) (50 mL) and extracted with EtOAc (50 mL×3).

The organic layers were combined, dried over Na$_2$SO$_4$, filtered, concentrated, and the resulting residue was purified by flash column chromatography on silica gel (PE/EtOAc=20/1 to 4/1) to afford 1-tert-butyl 3-ethyl3-(5-(dimethoxymethyl)-2-(methylthio)pyrimidin-4-yl)pyrrolidine-1,3-dicarboxylate (3.2 g, 55% yield) as a yellow oil. LC-MS: m/z 442 [M+H]$^+$.

Step B: 1-tert-butyl 3-ethyl 3-(5-formyl-2-(methylthio)pyrimidin-4-yl)pyrrolidine-1,3-dicarboxylate

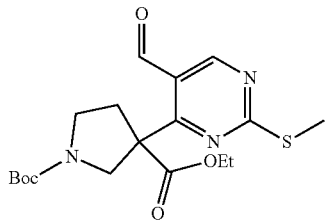 [SMILES: CCOC(=O)C1(c2nc(SC)ncc2C=O)CCN(C(=O)OC(C)(C)C)C1]

To a solution of 1-tert-butyl 3-ethyl 3-(5-(dimethoxymethyl)-2-(methylthio)pyrimidin-4-yl)pyrrolidine-1,3-dicarboxylate (3.1 g, 7.0 mmol, 1.0 equiv.) in acetone (30 mL) was added dilute HCl solution (1N, aq) (56.0 mL, 56.0 mmol, 8.0 equiv.). The resulting mixture was stirred at room temperature for 6 h. The reaction was quenched by adding ice water (50 mL) and extracted with EtOAc (30 mL×3). The organic layers were combined, dried over Na$_2$SO$_4$, filtered, concentrated, and the crude residue was used directly without further purification (2.8 g, crude) as a colorless oil. LC-MS: m/z 396 [M+H]+

Step C: tert-butyl 6-(4-methoxyphenyl)-2-(methylthio)-7-oxo-6,7-dihydro-5H-spiro[pyrido[4,3-d]pyrimidine-8,3'-pyrrolidine]-1'-carboxylate

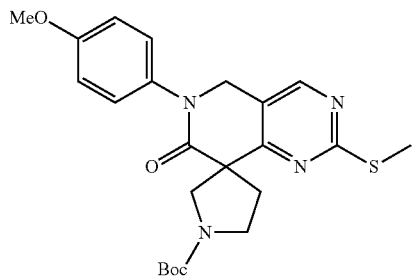 [SMILES: COc1ccc(N2Cc3cnc(SC)nc3C3(CCN(C(=O)OC(C)(C)C)C3)C2=O)cc1]

To a solution of 1-tert-butyl 3-ethyl 3-(5-(dimethoxymethyl)-2-(methylthio)pyrimidin-4-yl)pyrrolidine-1,3-dicarboxylate (2.8 g, 7.0 mmol, 1.0 equiv.) and 4-methoxyaniline (1.9 g, 15.4 mmol, 2.2 equiv.) in DCE (18.0 ml) was added AcOH (1.4 mL, 24.5 mmol, 3.5 equiv.). The resulting solution was stirred at room temperature for 1 h. At this point, NaBH(AcO)$_3$ (3.7 g, 17.5 mmol, 2.5 equiv.) was added in portions over the course of 0.5 h and the resulting mixture was stirred at room temperature overnight. The reaction mixture was quenched with ice water and extracted with EtOAc (30 mL×3). All the organic layers were combined, dried over Na$_2$SO$_4$, filtered, concentrated under reduce pressure, and the residue was purified by flash column chromatography on silica gel (PE/EtOAc=10/1 to 1/1) to give tert-butyl 6-(4-methoxyphenyl)-2-(methylthio)-7-oxo-6,7-dihydro-5H-spiro[pyrido[4,3-d]pyrimidine-8,3'-pyrrolidine]-1'-carboxylate (2.5 g, 79% yield) as a light brown solid. LC-MS: m/z 457 [M+H]$^+$.

Step D: tert-butyl 6-(4-methoxyphenyl)-2-(methylsulfonyl)-7-oxo-6,7-dihydro-5H-spiro[pyrido[4,3-d]pyrimidine-8,3'-pyrrolidine]-1'-carboxylate

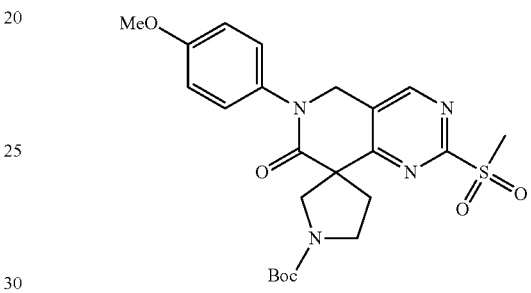

To a solution of tert-butyl 6-(4-methoxyphenyl)-2-(methylthio)-7-oxo-6,7-dihydro-5H-spiro[pyrido[4,3-d]pyrimidine-8,3'-pyrrolidine]-1'-carboxylate (500 mg, 1.1 mmol, 1.0 equiv.) in DCM (10.0 mL) was added m-CPBA (565 mg, 3.3 mmol, 3.0 equiv.) in small portions during 0.5 h. The resulting mixture was stirred at room temperature for an additional 2 h, before being quenched with ice water (20.0 mL) and extracted with DCM (20 mL×3). The organic layers were combined, washed with brine (30 mL), dried over Na$_2$SO$_4$, filtered, concentrated under reduce pressure, and the residue was purified by flash column chromatography on silica gel (PE/EtOAc=2/1 to 1/1) to afford tert-butyl 6-(4-methoxyphenyl)-2-(methylsulfonyl)-7-oxo-6,7-dihydro-5H-spiro[pyrido[4,3-d]pyrimidine-8,3'-pyrrolidine]-1'-carboxylate (500 mg, 94% yield) as a white solid. LCMS: m/z 489 [M+H]$^+$.

Step E: tert-butyl 2-((cyclopropylmethyl)amino)-6-(4-methoxyphenyl)-7-oxo-6,7-dihydro-5H-spiro[pyrido[4,3-d]pyrimidine-8,3'-pyrrolidine]-1'-carboxylate

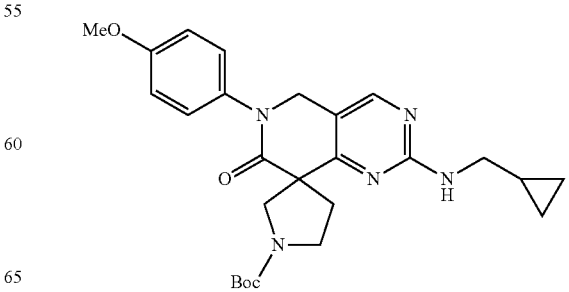

To a solution of tert-butyl 6-(4-methoxyphenyl)-2-(methylsulfonyl)-7-oxo-6,7-dihydro-5H-spiro[pyrido[4,3-d]pyrimidine-8,3'-pyrrolidine]-1'-carboxylate (1.2 g, 2.5 mmol, 1.0 equiv.) in DMSO (15.0 mL) was added CsF (380 mg, 2.5 mmol, 1.0 equiv.), DIPEA (967 mg, 7.5 mmol, 3.0 equiv.) and cyclopropylmethanamine (532 mg, 7.5 mmol, 3.0 equiv.) at room temperature. The resulting mixture was stirred at 80° C. overnight, then water (10 mL) was added. The reaction mixture was extracted with DCM (20 mL×3), the organic layers were combined, washed with brine (30 mL), dried over $Na_2SO_4$, filtered and concentrated under reduce pressure. The resulting residue was purified by flash column chromatography on silica gel to give tert-butyl 2-((cyclopropylmethyl)amino)-6-(4-methoxyphenyl)-7-oxo-6,7-dihydro-5H-spiro[pyrido[4,3-d]pyrimidine-8,3'-pyrrolidine]-1'-carboxylate (850 mg, 71% yield) as a white solid. LCMS: m/z 480 $[M+H]^+$.

Step F: 2-((cyclopropylmethyl)amino)-6-(4-methoxyphenyl)-5H-spiro[pyrido[4,3-d]pyrimidine-8,3'-pyrrolidin]-7(6H)-one

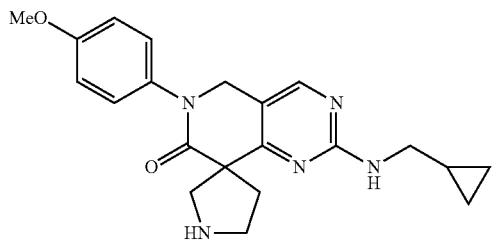

8a

To a solution of tert-butyl 2-((cyclopropylmethyl)amino)-6-(4-methoxyphenyl)-7-oxo-6,7-dihydro-5H-spiro[pyrido [4,3-d]pyrimidine-8,3'-pyrrolidine]-1'-carboxylate (850 mg, 1.8 mmol, 1.0 equiv.) in DCM (10 mL) was added TFA (3 mL) at room temperature. The resulting mixture was stirred for 1 h, then the reaction was quenched with $NaHCO_3$(sat. aq. 20 mL). The resulting mixture was extracted with DCM (20 mL×3), the organic layers were combined, washed with brine (30.0 mL), dried over $Na_2SO_4$ and concentrated. The crude 2-((cyclopropylmethyl)amino)-6-(4-methoxyphenyl)-5H-spiro[pyrido[4,3-d]pyrimidine-8,3'-pyrrolidin]-7(6H)-one (500 mg, crude) was used without further purification as a white solid. LCMS: m/z 380 [M+H]+.

Step G: 1'-((1H-pyrazol-3-yl)methyl)-2-((cyclopropylmethyl)amino)-6-(4-methoxyphenyl)-5H-spiro[pyrido[4,3-d]pyrimidine-8,3'-pyrrolidin]-7(6H)-one (Example 101)

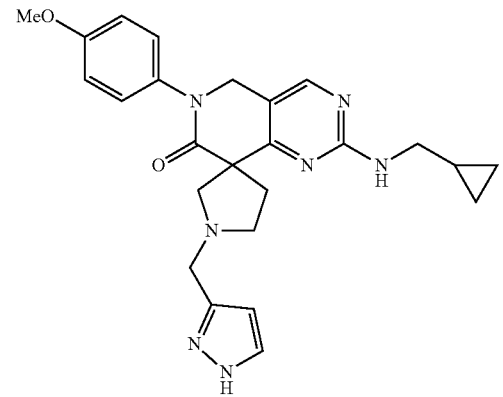 [SMILES: COc1ccc(N2Cc3cnc(NCC4CC4)nc3C3(CCN(Cc4cc[nH]n4)C3)C2=O)cc1]

To a solution of 6-(4-methoxyphenyl)-2-(methylsulfonyl)-5H-spiro[pyrido[4,3-d]pyrimidine-8,3'-pyrrolidin]-7(6H)-one (56.0 mg, 0.15 mmol, 1.0 equiv.) in DCE (3 mL) was added 1H-pyrazole-3-carbaldehyde (28.0 mg, 0.29 mmol, 2.0 equiv.) and AcOH (60.0 μL, catalytic amount) at room temperature. The resulting mixture was stirred for 1 h, after which $NaBH_3CN$ (10.0 mg, 0.158 mmol, 1.1 equiv.) was added. The reaction mixture was stirred for an additional 0.5 h before being quenched with ice water (2.0 mL) and extracted with DCM (5 mL×3). The organic layers were combined and washed with brine (10 mL), dried over $Na_2SO_4$ and concentrated under reduce pressure. The resulting residue was purified by RP-prep-HPLC to afford 1'-((H-pyrazol-3-yl)methyl)-2-((cyclopropylmethyl)amino)-6-(4-methoxyphenyl)-5H-spiro[pyrido[4,3-d]pyrimidine-8,3'-pyrrolidin]-7(6H)-one (Example 101).

$^1$H NMR (400 MHz, $CDCl_3$) δ: 8.47 (br s, 1H), 8.13 (s, 1H), 7.54 (s, 1H), 7.18 (d, J=8.6 Hz, 2H), 6.99 (d, J=8.6 Hz, 2H), 6.34 (s, 1H), 4.79 (d, J=15.4 Hz, 1H), 4.52 (d, J=15.4 Hz, 1H), 4.38 (d, J=13.2 Hz, 1H), 4.31 (d, J=13.2 Hz, 1H), 4.11 (d, J=10.8 Hz, 1H), 3.83 (s, 3H), 3.67 (d, J=10.8 Hz, 1H), 3.65-3.47 (m, 1H), 3.35-3.28 (m, H), 3.26-3.16 (m, 1H), 2.61-2.51 (m, 1H), 2.48-2.37 (m, 1H), 1.15-1.04 (m, 1H), 0.60-0.50 (m, 2H), 0.32-0.23 (m, 2H) [one NH not observed underneath $CDCl_3$]. LCMS: m/z 460 $[M+H]^+$.

Example 102: 1'-((1H-pyrazol-4-yl)methyl)-2-((cyclopropylmethyl)amino)-6-(4-methoxyphenyl)-5H-spiro[pyrido[4,3-d]pyrimidine-8,3'-pyrrolidin]-7(6H)-one

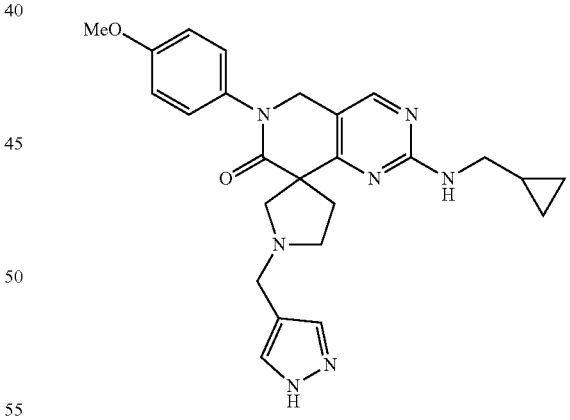

The title compound was synthesized from intermediate 8a with 1H-pyrazole-4-carbaldehyde via general procedure I: ($NaBH_3CN$, HOAc, DCE).

$^1$H NMR (400 MHz, $CDCl_3$)($HCO_2H$ salt) δ: 8.61 (s, 1H), 8.12 (s, 1H), 7.75 (s, 2H), 7.19 (d, J=8.8 Hz, 2H), 6.97 (d, J=8.8 Hz, 2H), 4.81 (d, J=15.2 Hz, 1H), 4.51 (d, J=15.2 Hz, 1H), 4.44-4.30 (m, 2H), 4.22 (d, J=13.2 Hz, 1H), 3.83 (s, 3H), 3.68 (d, J=11.6 Hz, 1H), 3.38-3.18 (m, 5H), 2.60-2.37 (m, 2H), 1.17-1.04 (m, 1H), 0.57-0.48 (m, 2H), 0.29-0.22 (m, 2H). LC-MS: m/z 460 $[M+H]^+$.

Example 103: 2-((cyclopropylmethyl)amino)-6-(4-methoxyphenyl)-1'-(thiazol-4-ylmethyl)-5H-spiro[pyrido[4,3-d]pyrimidine-8,3'-pyrrolidin]-7(6H)-one

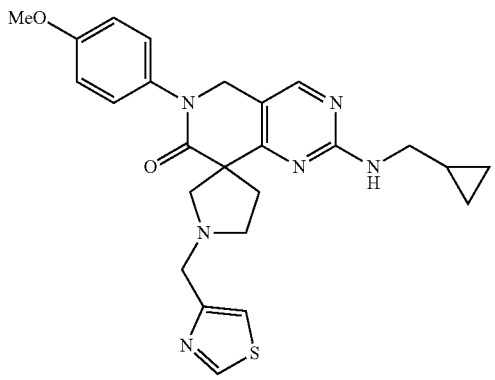 [SMILES: COc1ccc(N2Cc3cnc(NCC4CC4)nc3C3(CCN(Cc4cscn4)C3)C2=O)cc1]

The title compound was synthesized from intermediate 8a with thiazole-4-carbaldehyde via general procedure I: (NaBH$_3$CN, HOAc, DCE).

$^1$H NMR (400 MHz, CDCl$_3$) δ: 8.76 (d, J=2.0 Hz, 1H), 8.07 (s, 1H), 7.33 (d, J=2.0 Hz, 1H), 7.18 (d, J=8.8 Hz, 2H), 6.93 (d, J=8.8 Hz, 2H), 5.53 (br s, 1H), 4.65 (d, J=15.2 Hz, 1H), 4.57 (d, J=15.2 Hz, 1H), 4.06 (d, J=14.0 Hz, 1H), 4.01 (d, J=14.0 Hz, 1H), 3.81 (s, 3H), 3.51 (d, J=9.6 Hz, 1H), 3.43 (d, J=9.6 Hz, 1H), 3.29 (m, 2H), 3.13-3.05 (m, 1H), 3.02-2.92 (m, 1H), 2.55-2.49 (m, 1H), 2.46-2.39 (m, 1H), 1.17-1.07 (m, 1H), 0.59-0.49 (m, 2H), 0.30-0.23 (m, 2H). LC-MS: m/z 477 [M+H]$^+$.

Example 104: 1'-cyclohexyl-2-((cyclopropylmethyl)amino)-6-(4-methoxyphenyl)-5H-spiro[pyrido[4,3-d]pyrimidine-8,3'-pyrrolidin]-7(6H)-one

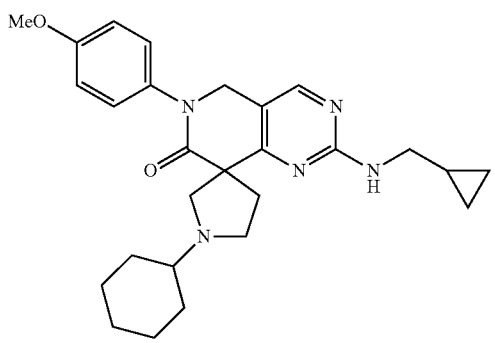 [SMILES: COc1ccc(N2Cc3cnc(NCC4CC4)nc3C3(CCN(C4CCCCC4)C3)C2=O)cc1]

The title compound was synthesized from intermediate 8a with cyclohexanone via General Procedure I: (NaBH$_3$CN, HOAc, DCE).

$^1$H NMR (400 MHz, CDCl$_3$) δ: 8.09 (s, 1H), 7.18 (d, J=8.8 Hz, 2H), 6.94 (d, J=8.8 Hz, 2H), 5.54 (br s, 1H), 4.70 (d, J=15.2 Hz, 1H), 4.55 (d, J=15.2 Hz, 1H), 3.82 (s, 3H), 3.47 (d, J=10.4 Hz, 1H), 3.36-3.29 (m, 3H), 2.98-2.92 (m, 1H), 2.58-2.38 (m, 4H), 1.77 (m, 2H), 1.63-1.56 (m, 1H), 1.47-1.34 (m, 2H), 1.30-1.04 (m, 6H), 0.60-0.50 (m, 2H), 0.30-0.24 (m, 2H). LC-MS: m/z 462 [M+H]$^+$.

Example 105: methyl 3-(2-((cyclopropylmethyl)amino)-6-(4-methoxyphenyl)-7-oxo-6,7-dihydro-5H-spiro[pyrido[4,3-d]pyrimidine-8,3'-pyrrolidin]-1'-yl)cyclobutanecarboxylate

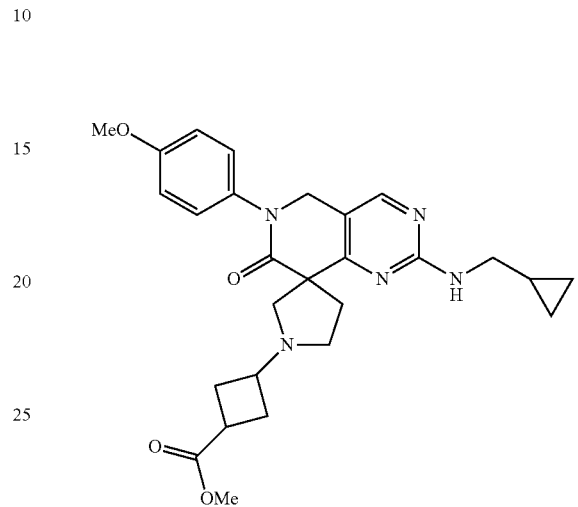

The title compound was synthesized from intermediate 8a with methyl 3-oxocyclobutanecarboxylate via general procedure I: (NaBH$_3$CN, HOAc, DCE).

$^1$H NMR (400 MHz, CDCl$_3$) δ: 8.08 (s, 1H), 7.18 (d, J=8.8 Hz, 2H), 6.94 (d, J=8.8 Hz, 2H), 5.45 (br s, 1H), 4.65 (d, J=15.2 Hz, 1H), 4.59 (d, J=15.2 Hz, 1H), 3.82 (s, 3H), 3.67 (s, 3H), 3.41 (d, J=9.6 Hz, 1H), 3.34-3.28 (m, 2H), 3.26-3.15 (m, 2H), 3.00-2.92 (m, 1H), 2.85-2.72 (m, 2H), 2.57-2.48 (m, 1H), 2.47-2.39 (m, 1H), 2.37-2.26 (m, 4H), 1.16-1.04 (m, 1H), 0.58-0.50 (m, 2H), 0.32-0.24 (m, 2H). LC-MS: m/z 492 [M+H]$^+$.

Preparation of 2-((cyclopropylmethyl)amino)-6-(isoxazol-4-yl)-5H-spiro[pyrido[4,3-d]pyrimidine-8,3'-pyrrolidin]-7(6H)-one 8b 8b

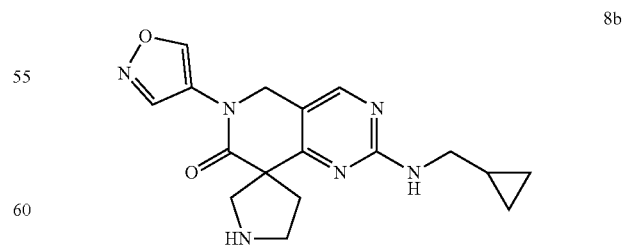

2-((cyclopropylmethyl)amino)-6-(isoxazol-4-yl)-5H-spiro[pyrido[4,3-d]pyrimidine-8,3'-pyrrolidin]-7(6H)-one 8b was synthesized from isoxazol-4-amine via general procedure I (Step C-F). LC-MS: m/z 341 [M+H]$^+$.

Example 106: Preparation of 2-((cyclopropylmethyl)amino)-1'-(isoxazol-3-ylmethyl)-6-(isoxazol-4-yl)-5H-spiro[pyrido[4,3-d]pyrimidine-8,3'-pyrrolidin]-7(6H)-one

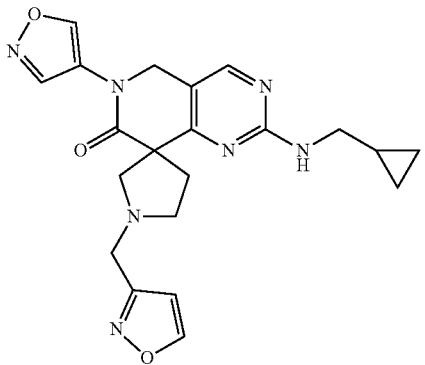 [SMILES: O=C1N(c2cnoc2)Cc2cnc(NCC3CC3)nc2C12CCN(Cc1ccon1)C2]

The title compound was synthesized from intermediate 8b with isoxazole-3-carbaldehyde via General Procedure I: (NaBH$_3$CN, HOAc, DCE).

$^1$H NMR (400 MHz, CDCl$_3$) δ: 9.29 (s, 1H), 9.00 (s, 1H), 8.82 (s, 1H), 8.20 (s, 1H), 7.37 (t, J=5.6 Hz, 1H), 6.52 (s, 1H), 4.79 (s, 2H), 3.77 (s, 2H), 3.17-3.05 (m, 4H), 2.87-2.74 (m, 2H), 2.53-2.35 (m, 2H), 1.13-1.01 (m, 1H), 0.43-0.33 (m, 2H), 0.25-0.16 (m, 2H). LC-MS: m/z 422 [M+H]$^+$.

Example 107: 2-((cyclopropylmethyl)amino)-6-(isoxazol-4-yl)-1'-(thiazol-4-ylmethyl)-5H-spiro[pyrido[4,3-d]pyrimidine-8,3'-pyrrolidin]-7(6H)-one

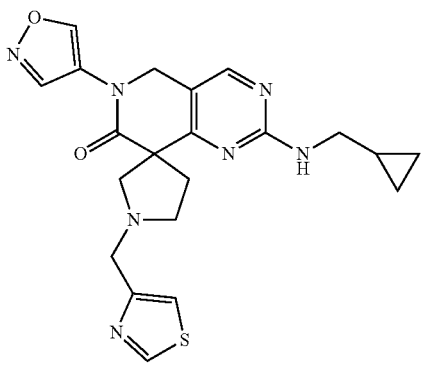 [SMILES: O=C1N(c2cnoc2)Cc2cnc(NCC3CC3)nc2C12CCN(Cc1cscn1)C2]

The title compound was synthesized from intermediate 8b with thiazole-4-carbaldehyde via General Procedure I: (NaBH$_3$CN, HOAc, DCE).

$^1$H NMR (400 MHz, MeOD-d$_4$) δ: 9.14 (s, 1H), 8.95 (d, J=2.0 Hz, 1H), 8.88 (s, 1H), 8.19 (s, 1H), 7.53 (d, J=2.0 Hz, 1H), 4.80 (d, J=1.6 Hz, 2H), 4.59 (br, s, 1H), 4.03 (s, 2H), 3.45 (d, J=10.0 Hz, 1H), 3.41 (d, J=10.0 Hz, 1H), 3.27 (d, J=4.0 Hz, 1H), 3.26 (d, J=4.0 Hz, 1H), 3.03 (t, J=6.4 Hz, 2H), 2.60-2.43 (m, 2H), 1.18-1.05 (m, 1H), 0.54-0.45 (m, 2H), 0.29-0.22 (m, 2H). LC-MS: m/z 438 [M+H]$^+$.

Example 108: 1'-((4-chloro-1H-pyrazol-3-yl)methyl)-2-((cyclopropylmethyl)amino)-6-(isoxazol-4-yl)-5H-spiro[pyrido[4,3-d]pyrimidine-8,3'-pyrrolidin]-7(6H)-one

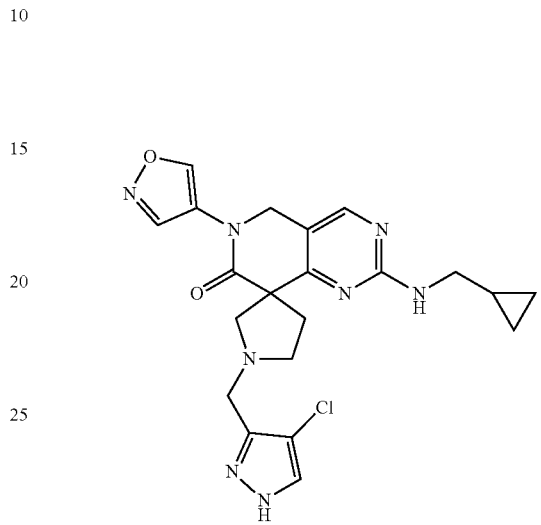

The title compound was synthesized from intermediate 8b with 4-chloro-1H-pyrazole-3-carbaldehyde via General Procedure I: (NaBH$_3$CN, HOAc, DCE).

$^1$H NMR (400 MHz, MeOD-d$_4$) δ:: 9.19 (s, 1H), 8.92 (s, 1H), 8.27 (s, 1H), 7.76 (br s, 1H), 4.86 (s, 2H), 4.44-4.16 (m, 2H), 4.05-3.75 (m, 2H), 3.52-3.30 (m, 2H), 3.28 (dd, J=6.8 Hz, 2.4 Hz, 2H), 2.67-2.57 (m, 1H), 2.51-2.41 (m, 1H), 1.19-1.07 (m, 1H), 0.56-0.50 (m, 2H), 0.30-0.25 (m, 2H). LC-MS: m/z 455 [M+H]$^+$.

Preparation of 6-(1H-benzo[d]imidazol-6-yl)-2-((cyclopropylmethyl)amino)-5H-spiro[pyrido[4,3-d]pyrimidine-8,3'-pyrrolidin]-7(6H)-one 8c

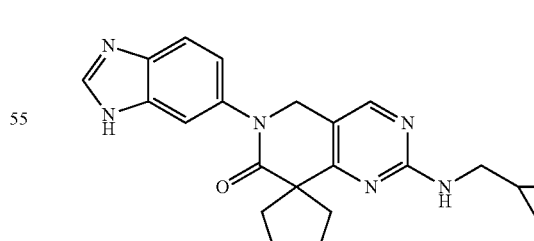

8c 6-(1H-benzo[d]imidazol-6-yl)-2-((cyclopropylmethyl)amino)-5H-spiro[pyrido[4,3-d]pyrimidine-8,3'-pyrrolidin]-7(6H)-one 8c was synthesized from 1H-benzo[d]imidazol-6-amine via general procedure I (Step C-F). LC-MS: m/z 390 [M+H]$^+$

Example 109: Preparation of 1'-((H-pyrazol-3-yl)methyl)-6-(1H-benzo[d]imidazol-6-yl)-2-((cyclopropylmethyl)amino)-5H-spiro[pyrido[4,3-d]pyrimidine-8,3'-pyrrolidin]-7(6H)-one

Example 110: Preparation of 1'-((1H-pyrazol-3-yl)methyl)-6-(4-methoxyphenyl)-2-((2,2,2-trifluoroethyl)amino)-5H-spiro[pyrido[4,3-d]pyrimidine-8,3'-pyrrolidin]-7(6H-one

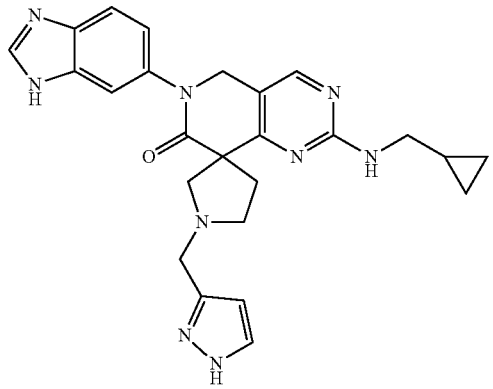 [SMILES: O=C1N(c2ccc3nc[nH]c3c2)Cc2cnc(NCC3CC3)nc2C12CCN(Cc1cc[nH]n1)C2]

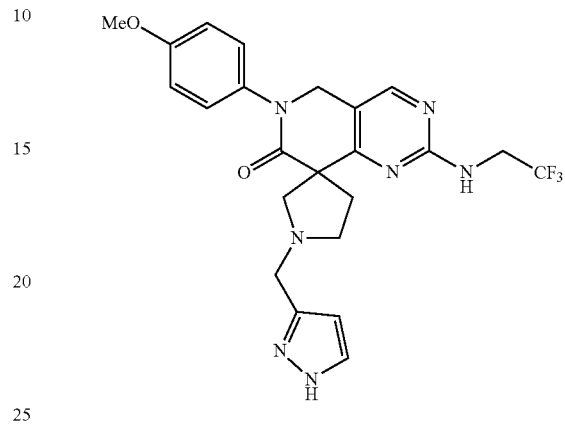

The title compound was synthesized from intermediate 8c with 1H-pyrazole-3-carbaldehyde via General Procedure I: (NaBH₃CN, HOAc, DCE).

¹H NMR (400 MHz, DMSO-d₆) δ: 12.55 (br s, 2H), 8.26 (s, 1H), 8.21 (s, 1H), 7.69-7.42 (m, 3H), 7.31 (t, J=5.6 Hz, 1H), 7.12 (d, J=8.0 Hz, 1H), 6.17 (s, 1H), 4.77 (d, J=15.6 Hz, 1H), 4.69 (d, J=15.2 Hz, 1H), 3.85-3.67 (m, 2H), 3.29-3.09 (m, 4H), 2.69-2.71 (m, 2H), 2.61-2.53 (m, 2H), 1.17-1.03 (m, 1H), 0.46-0.36 (m, 2H), 0.27-0.17 (m, 2H). LC-MS: m/z 470 [M+H]⁺.

The title compound was synthesized from intermediate 8d with 1H-pyrazole-3-carbaldehyde via General Procedure I: (NaBH₃CN, HOAc, DCE).

¹H NMR (400 MHz, CDCl₃) δ: 8.17 (s, 1H), 7.52 (d, J=1.2 Hz, 1H), 7.18 (d, J=8.8 Hz, 2H), 6.94 (d, J=8.8 Hz, 2H), 6.19 (s, 1H), 4.73 (d, J=15.6 Hz, 1H), 4.58 (d, J=15.6 Hz, 1H), 4.31-4.13 (m, 2H), 3.99 (d, J=14.0 Hz, 1H), 3.89 (d, J=14.0 Hz, 1H), 3.82 (s, 3H), 3.53-3.34 (m, 2H), 3.16-3.05 (m, 1H), 3.04-2.94 (m, 1H), 2.68-2.55 (m, 1H), 2.48-2.35 (m, 1H) 2NH protons not shown. LC-MS: m/z 488 [M+H]⁺.

Preparation of 6-(4-methoxyphenyl)-2-((2,2,2-trifluoroethyl)amino)-5H-spiro[pyrido[4,3-d]pyrimidine-8,3'-pyrrolidin]-7(6H)-one 8d

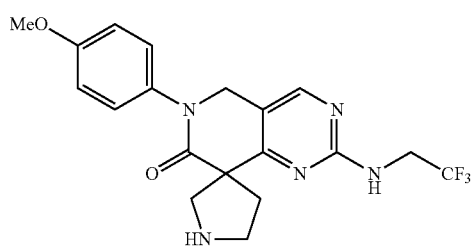

8d 6-(4-methoxyphenyl)-2-((2,2,2-trifluoroethyl)amino)-5H-spiro[pyrido[4,3-d]pyrimidine-8,3'-pyrrolidin]-7(6H)-one 8d was synthesized from 2,2,2-trifluoroethanamine via general procedure I (Step E, F). LC-MS: m/z 408 [M+H]⁺

Preparation of Example 111

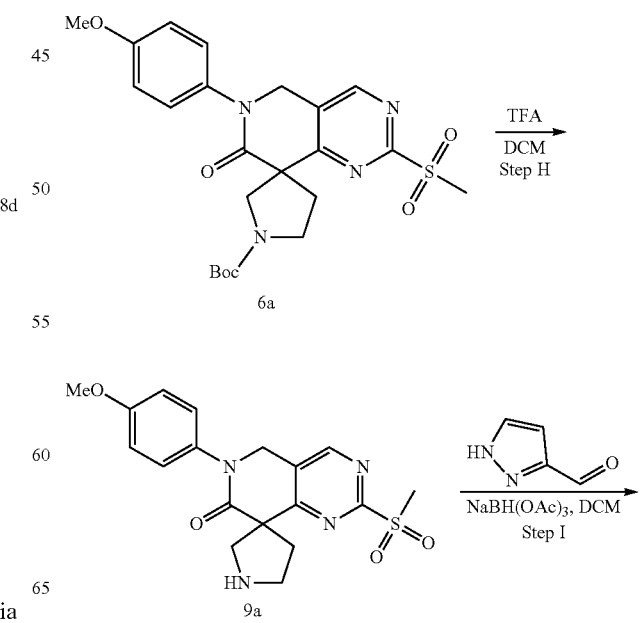

93

-continued

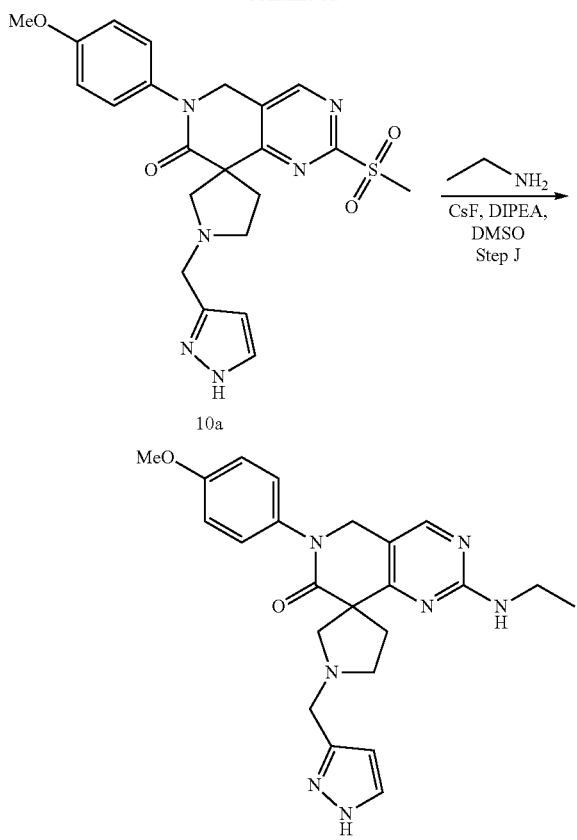

10a

Step H: 6-(4-methoxyphenyl)-2-(methylsulfonyl)-5H-spiro[pyrido[4,3-d]pyrimidine-8,3'-pyrrolidin]-7(6H)-one

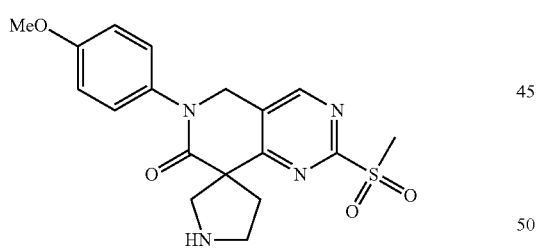

To a solution of tert-butyl 6-(4-methoxyphenyl)-2-(methylsulfonyl)-7-oxo-6,7-dihydro-5H-spiro[pyrido[4,3-d]pyrimidine-8,3'-pyrrolidine]-1'-carboxylate (500 mg, 1.0 mmol, 1.0 equiv) in DCM (5 mL) was added trifluoroacetic acid (1.5 mL) at room temperature. The resulting mixture was stirred for 1 h, then the reaction mixture was quenched with cold NaHCO₃ (50 mL, sat. aq.) and extracted with DCM (50 mL×2). The organic layers were combined and washed with brine (30 mL), dried over Na₂SO₄ and concentrated under reduced pressure. The residue was purified by flash column chromatography (PE/EA=3/1-1/1) to afford 6-(4-methoxyphenyl)-2-(methylsulfonyl)-5H-spiro[pyrido[4,3-d]pyrimidine-8,3'-pyrrolidin]-7(6H)-one (340 mg, 85% yield) as a white solid. LC-MS: m/z 389 [M+H]⁺.

94

Step I: 1'-((1H-pyrazol-3-yl)methyl)-6-(4-methoxyphenyl)-2-(methylsulfonyl)-5H-spiro[pyrido[4,3-d]pyrimidine-8,3'-pyrrolidin]-7(6H)-one 10a To a solution of 6-(4-methoxyphenyl)-2-(methylsulfonyl)-5H-spiro[pyrido[4,3-d]pyrimidine-8,3'-pyrrolidin]-7(6H)-one (100 mg, 0.26 mmol, 1.0 equiv.) in DCM (5 mL) was added 1H-pyrazole-3-carbaldehyde (50 mg, 0.52 mmol, 2.0 equiv.) and AcOH (60.0 μL, catalytic amount) at room temperature. The resulting mixture was stirred for 1 h, and then NaBH₃CN (16.0 mg, 0.25 mmol, 1.0 equiv) was added. After 0.5 h, the reaction mixture was quenched with ice water (10 mL) and extracted with DCM (10 mL×3). All the organic layers were combined and washed with brine (30 mL), dried over Na₂SO₄ and concentrated under reduced pressure. The residue was purified by RP-prep-HPLC to afford 1'-((1H-pyrazol-3-yl)methyl)-6-(4-methoxyphenyl)-2-(methylsulfonyl)-5H-spiro[pyrido[4,3-d]pyrimidine-8,3'-pyrrolidin]-7(6H)-one (60.0 mg, 49% yield) as a white solid. LC-MS: m/z 469 [M+H]₋.

Step J: 1'-((1H-pyrazol-3-yl)methyl)-2-(ethylamino)-6-(4-methoxyphenyl)-5H-spiro[pyrido[4,3-d]pyrimidine-8,3'-pyrrolidin]-7(6H)-one (Example 111)

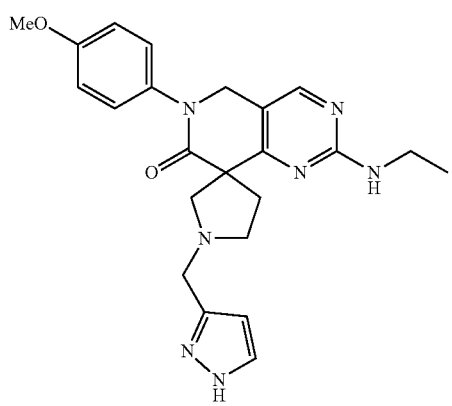 [SMILES: CCNc1ncc2c(n1)C1(CCN(Cc3cc[nH]n3)C1)C(=O)N(c1ccc(OC)cc1)C2]

To a solution of 1'-((1H-pyrazol-3-yl)methyl)-6-(4-methoxyphenyl)-2-(methylsulfonyl)-5H-spiro[pyrido[4,3-d]pyrimidine-8,3'-pyrrolidin]-7(6H)-one (60.0 mg, 0.13 mmol, 1.0 equiv.) in DMSO (1 mL) was added CsF (20.0 mg, 0.13 mmol, 1.0 equiv.), DIPEA (50.0 mg, 0.39 mmol, 3.0 equiv.) and ethanamine hydrochloride (30.0 mg, 0.37 mmol, 3.0 equiv.) at room temperature. The resulting mixture was stirred at 80° C. overnight. Then the reaction mixture was quenched with ice water (10 mL) and extracted with DCM (10 mL×3). All the organic layers were combined and washed with brine (30 mL), dried over $Na_2SO_4$ and concentrated under reduced pressure. The residue was purified by RP-prep-HPLC to afford 1'-((1H-pyrazol-3-yl)methyl)-N-ethyl-6-(4-methoxyphenyl)-6,7-dihydro-5H-spiro[pyrido[4,3-d]pyrimidine-8,3'-pyrrolidin]-2-amine (Example 111).

$^1$H NMR (400 MHz, DMSO-$d_6$) (HCOOH salt) δ: 8.26 (br s, 1H), 8.19 (s, 1H), 7.51 (d, J=1.2 Hz, 1H), 7.23 (d, J=8.8 Hz, 2H), 7.18 (t, J=6.0 Hz, 1H), 6.97 (d, J=8.8 Hz, 2H), 6.14 (d, J=1.6 Hz, 1H), 4.68 (d, J=15.4 Hz, 1H), 4.58 (d, J=15.4 Hz, 1H), 3.77 (s, 3H), 3.67 (s, 2H), 3.36-3.16 (m, 2H), 3.13-3.10 (m, 2H), 2.86-2.65 (m, 3H), 2.52-2.41 (m, 2H), 1.13 (t, J=7.2 Hz, 3H). LC-MS: m/z 434 [M+H]$^+$.

Example 112: 1'-((1H-pyrazol-3-yl)methyl)-2-(cyclobutylamino)-6-(4-methoxyphenyl)-5H-spiro[pyrido[4,3-d]pyrimidine-8,3'-pyrrolidin]-7(6H)-one

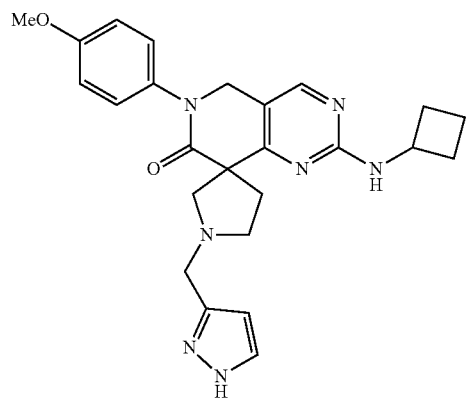 [SMILES: COc1ccc(N2Cc3cnc(NC4CCC4)nc3C3(CCN(Cc4cc[nH]n4)C3)C2=O)cc1]

The title compound was synthesized from intermediate 10a with cyclobutanamine via general procedure I: (CsF, DIPEA, DMSO).

$^1$H NMR (400 MHz, CDCl$_3$) δ: 8.11 (s, 1H), 7.53 (d, J=2.0 Hz, 1H), 7.17 (d, J=8.8 Hz, 2H), 6.94 (d, J=8.8 Hz, 2H), 6.22 (s, 1H), 4.70 (d, J=15.2 Hz, 1H), 4.53 (d, J=15.2 Hz, 1H), 4.49 (d, J=8.0 Hz, 1H), 4.45 (d, J=8.0 Hz, 1H), 4.09-4.04 (m, 1H), 3.96 (d, J=9.6 Hz, 1H), 3.82 (s, 3H), 3.57-3.48 (m, 1H), 3.43 (d, J=9.6 Hz, 1H), 3.23-3.12 (m, 1H), 3.07-2.96 (m, 1H), 2.62-2.52 (m, 1H), 2.48-2.36 (m, 3H), 2.06-1.93 (m, 2H), 1.86-1.70 (m, 2H). LC-MS: m/z 460 [M+H]$^+$.

Example 113: 1'-((1H-pyrazol-3-yl)methyl)-2-(isobutylamino)-6-(4-methoxyphenyl)-5H-spiro[pyrido[4,3-d]pyrimidine-8,3'-pyrrolidin]-7(6H)-one

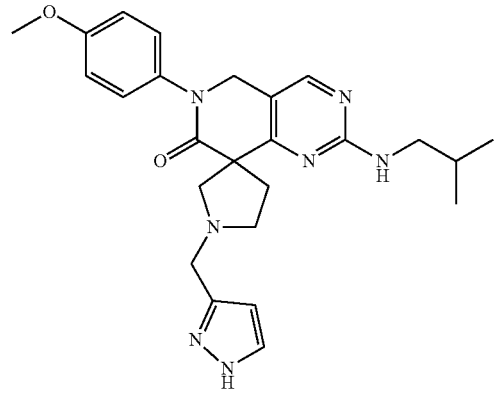 [SMILES: COc1ccc(N2Cc3cnc(NCC(C)C)nc3C3(CCN(Cc4cc[nH]n4)C3)C2=O)cc1]

The title compound was synthesized from intermediate 10a with 2-methylpropan-1-amine via general procedure I: (CsF, DIPEA, DMSO).

$^1$H NMR (400 MHz, DMSO-$d_6$) δ: 12.79-12.41 (br s, 1H), 8.18 (s, 1H), 7.69-7.35 (m, 1H), 7.29 (br s, 1H), 7.24 (d, J=8.8 Hz, 2H), 6.97 (d, J=8.8 Hz, 2H), 6.12 (s, 1H), 4.68 (d, J=15.2 Hz, 1H), 4.58 (d, J=15.2 Hz, 1H), 3.77 (s, 3H), 3.65 (s, 2H), 3.21-3.03 (m, 4H), 2.85-2.65 (m, 2H), 2.49-2.40 (m, 2H), 1.99-1.81 (m, 1H), 0.88 (dd, J=6.8 Hz, 1.2 Hz, 6H). LC-MS: m/z 462 [M+H]$^+$.

Example 114: 1'-((1H-pyrazol-3-yl)methyl)-2-(cyclopropylmethoxy)-6-(4-methoxyphenyl)-5H-spiro[pyrido[4,3-d]pyrimidine-8,3'-pyrrolidin]-7(6H)-one

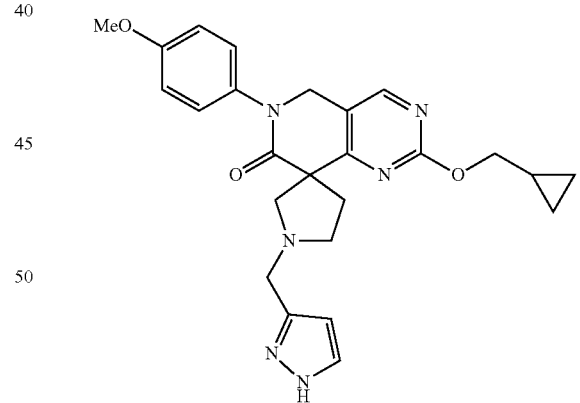

The title compound was synthesized from intermediate 10a with cyclopropylmethanol via general procedure I: (Step J: alternative condition: NaH, DMF).

To a solution of cyclopropylmethanol (50 mg, 0.7 mmol, 4.0 equiv) in anhydrous DMF (2 mL) was added NaH (60% in mineral oil, 57 mg, 1.4 mmol, 8.0 equiv) at 0° C. The resulting mixture was stirred at 0° C. for 1 h. Then a solution of 10a (82 mg, 0.18 mmol, 1.0 equiv) was added. The resulting mixture was stirred at room temperature for 1 h. Then the reaction was quenched with ice NH$_4$Cl (Sat. aq., 10 mL) and extracted with DCM (10 mL×3). The combined extracts were washed with brine (20 mL), dried over anhydrous Na$_2$SO$_4$ and concentrated. The residue was purified by RP-prep-HPLC to afford 1'-((1H-pyrazol-3-yl)methyl)-2-(cyclopropylmethoxy)-6-(4-methoxyphenyl)-5H-spiro[pyrido[4,3-d]pyrimidine-8,3'-pyrrolidin]-7(6H)-one.

$^1$H NMR (400 MHz, DMSO-d$_6$) δ: 12.82-12.41 (m, 1H), 8.50 (s, 1H), 7.68-7.31 (m, 1H), 7.26 (d, J=8.8 Hz, 2H), 6.98 (d, J=8.8 Hz, 2H), 6.13 (s, 1H), 4.84 (d, J=15.6 Hz, 1H), 4.74 (d, J=15.6 Hz, 1H), 4.24-4.11 (m, 2H), 3.77 (s, 3H), 3.65 (s, 2H), 3.20-3.05 (m, 2H), 2.90-2.81 (m, 1H), 2.76-2.66 (m, 1H), 2.98-2.53 (m, 2H), 1.37-124 (m, 1H), 0.61-0.52 (m, 2H), 0.39-0.33 (m, 2H). LC-MS: m/z 461 [M+H]$^+$.

Example 115: 1'-((1H-pyrazol-3-yl)methyl)-2-((cyclopropylmethyl)thio)-6-(4-methoxyphenyl)-5H-spiro[pyrido[4,3-d]pyrimidine-8,3'-pyrrolidin]-7(6H)-one

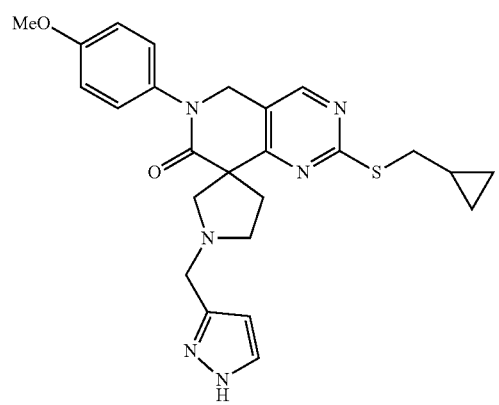 [SMILES: COc1ccc(N2Cc3cnc(OCC4CC4)nc3C3(CCN(Cc4cc[nH]n4)C3)C2=O)cc1]

The title compound was synthesized from intermediate 10a with cyclopropylmethanethiol via general procedure I: (Step J: alternative method, NaH, DMF, as prepared in Example 114).

$^1$H NMR (400 MHz, DMSO-d$_6$) δ: 12.56 (brs, 1H), 8.55 (s, 1H), 7.53 (br s, 1H), 7.26 (d, J=8.8 Hz, 2H), 6.98 (d, J=8.8 Hz, 2H), 6.12 (d, J=1.2 Hz, 1H), 4.86 (d, J=16.4 Hz, 1H), 4.76 (d, J=16.4 Hz, 1H), 3.78 (s, 3H), 3.65 (s, 2H), 3.20-3.12 (m, 3H), 3.03 (dd, J=13.6 Hz, 7.2 Hz, 1H), 2.94-2.84 (m, 1H), 2.79-2.68 (m, 1H), 2.59-2.43 (m, 2H), 1.27-1.17 (m, 1H), 0.58-0.46 (m, 2H), 0.35-0.26 (m, 2H). LC-MS: m/z 477 [M+H]$^+$.

Preparation of Example 116

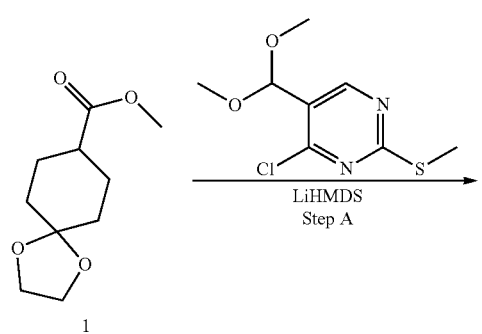

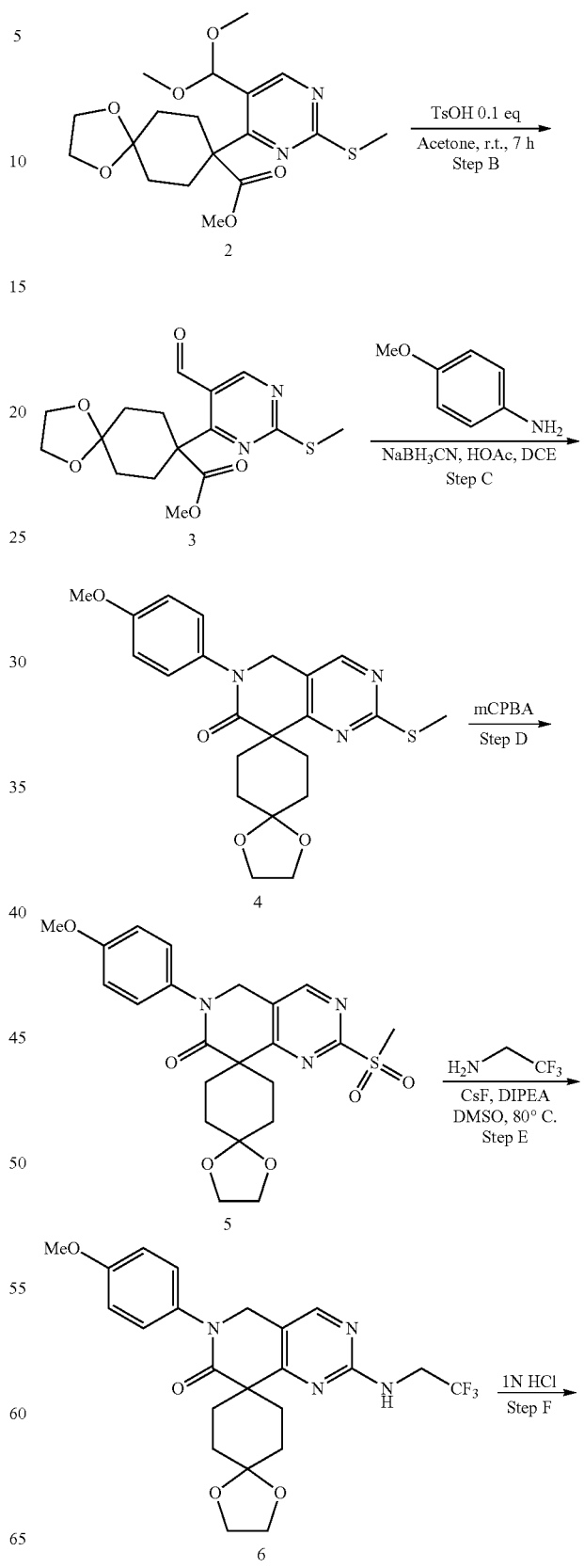

-continued

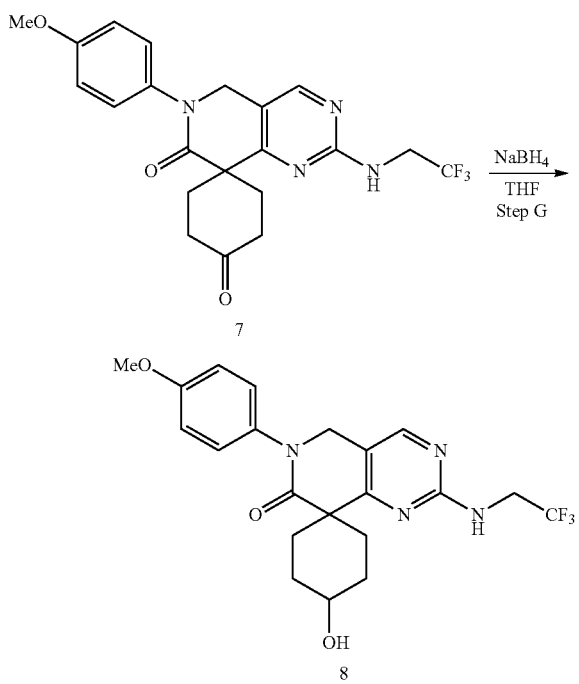

Step A: methyl 8-(5-(dimethoxymethyl)-2-(methylthio)pyrimidin-4-yl)-1,4-dioxaspiro[4.5]decane-8-carboxylate

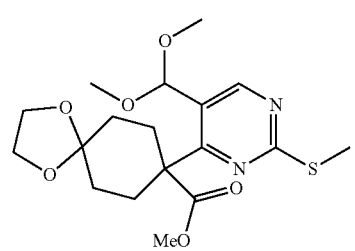 [SMILES: COC(=O)C1(c2nc(SC)ncc2C(OC)OC)CCC2(CC1)OCCO2]

To a solution of methyl 1,4-dioxaspiro[4.5]decane-8-carboxylate (3.9 g, 19.8 mmol, 1.5 equiv.) in THF (30 mL) was added LiHMDS (1 M in THF, 26.4 mL, 26.4 mmol, 2.0 equiv.) at −78° C. over 1 h via the addition funnel. The mixture was stirred at −78° C. for 4 h. Then a solution of 4-chloro-5-(dimethoxymethyl)-2-(methylthio)pyrimidine (3.1 g, 13.2 mmol, 1.0 equiv.) in THF (10 mL) was added. The reaction mixture was allowed to warm to room temperature and stirred for an additional 3 h. Then the reaction mixture was quenched with NH$_4$Cl (sat. aq., 50 mL) and extracted with EtOAc (50 mL×3). The organic layers were combined, dried over Na$_2$SO$_4$, filtered, concentrated, and the resulting residue was purified by flash column chromatography on silica gel (PE/EtOAc=20/1 to 4/1) to afford methyl 8-(5-(dimethoxymethyl)-2-(methylthio)pyrimidin-4-yl)-1,4-dioxaspiro[4.5]decane-8-carboxylate (2.9 g, 55% yield) as a yellow oil. LC-MS: m/z 399 [M+H]+.

Step B: methyl 8-(5-formyl-2-(methylthio)pyrimidin-4-yl)-1,4-dioxaspiro[4.5]decane-8-carboxylate

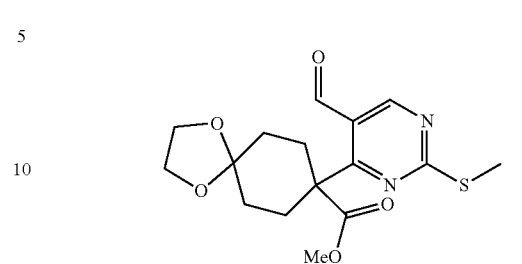

To a solution of methyl 8-(5-(dimethoxymethyl)-2-(methylthio)pyrimidin-4-yl)-1,4-dioxaspiro[4.5]decane-8-carboxylate (1.6 g, 4.1 mmol, 1.0 equiv.) in acetone (80 mL) was added p-TSA (68 mg, 0.4 mmol, 0.1 equiv.). The resulting mixture was stirred at room temperature for 4 h. The reaction mixture was quenched by adding ice water (50 mL) and extracted with EtOAc (30 mL×3). The organic layers were combined, dried over Na$_2$SO$_4$, filtered, concentrated, and the crude residue was used directly without further purification (1.5 g, crude) as a colorless oil. LC-MS: m/z 353 [M+H]+

Step C: 6-(4-methoxyphenyl)-8-(1',4'-dioxaspiro[4.5]decane)-2-(methylthio)-5,6-dihydropyrido[4,3-d]pyrimidin-7(8)-one

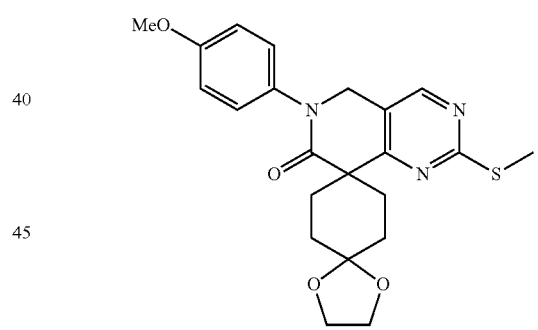

To a solution of methyl 8-(5-formyl-2-(methylthio)pyrimidin-4-yl)-1,4-dioxaspiro[4.5]decane-8-carboxylate (1.5 g, 4.3 mmol, 1.0 equiv.) and 4-methoxyaniline (1.2 g, 9.5 mmol, 2.2 equiv.) in DCE (18 ml) was added AcOH (0.9 mL, 15.1 mmol, 3.5 equiv.). The resulting solution was stirred at room temperature for 1 h. after which NaBH$_3$CN (0.7 g, 10.8 mmol, 2.5 equiv.) was added in several portions over the course of 0.5 h and the resulting mixture was stirred at room temperature overnight. The reaction mixture was quenched with ice water (10 mL) and extracted with EtOAc (30 mL×3). All the organic layers were combined, dried over Na$_2$SO$_4$, filtered, concentrated under reduce pressure, and the residue was purified by flash column chromatography on silica gel (PE/EtOAc=10/1 to 1/1) to give 6-(4-methoxyphenyl)-8-(1',4'-dioxaspiro[4.5]decane)-2-(methylthio)-5,6-dihydropyrido[4,3-d]pyrimidin-7(8H)-one (1.4 g, 79% yield) as a light brown solid. LC-MS: m/z 428 [M+H]+.

Step D: 6-(4-methoxyphenyl)-8-(1',4'-dioxaspiro[4.5]decane)-2-(methylsulfonyl)-5,6-dihydropyrido[4,3-d]pyrimidin-7(8H)-one

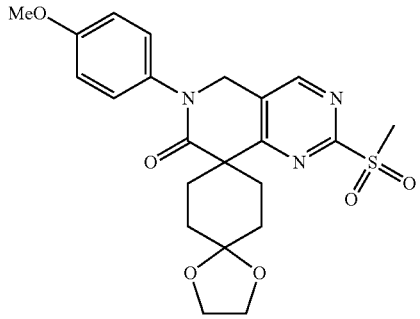 [SMILES: COc1ccc(N2Cc3cnc(S(C)(=O)=O)nc3C3(CCC4(CC3)OCCO4)C2=O)cc1]

To a solution of 6-(4-methoxyphenyl)-8-(1',4'-dioxaspiro[4.5]decane)-2-(methylthio)-5,6-dihydropyrido[4,3-d]pyrimidin-7(8H)-one (470 mg, 1.1 mmol, 1.0 equiv.) in DCM (10 mL) was added mCPBA (565 mg, 3.3 mmol, 3.0 equiv.) in several portions during in the course of 0.5 h. The resulting mixture was stirred at room temperature for an additional 2 h, before being quenched with ice water (20 mL) and extracted with DCM (20 mL×3). The organic layers were combined, washed with brine (30 mL), dried over $Na_2SO_4$, filtered, concentrated under reduce pressure, and the residue was purified by flash column chromatography on silica gel (PE/EtOAc=2/1 to 1/1) to afford 6-(4-methoxyphenyl)-8-(1',4'-dioxaspiro[4.5]decane)-2-(methylsulfonyl)-5,6-dihydropyrido[4,3-d]pyrimidin-7(8H)-one (475 mg, 94% yield) as a white solid. LCMS: m/z 460 [M+H]$^+$.

Step E: 8-(1',4'-dioxaspiro[4.5]decane)-6-(4-methoxyphenyl)-2-((2,2,2-trifluoroethyl)amino)-5,6-dihydropyrido[4,3-d]pyrimidin-7(8)-one

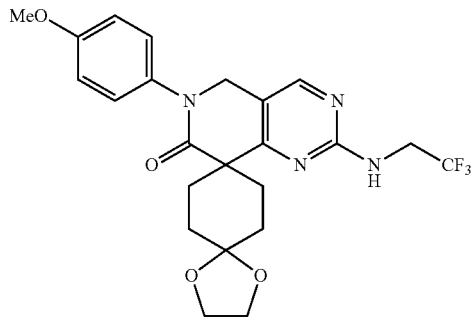 [SMILES: COc1ccc(N2Cc3cnc(NCC(F)(F)F)nc3C3(CCC4(CC3)OCCO4)C2=O)cc1]

To a solution of 6-(4-methoxyphenyl)-8-(1',4'-dioxaspiro[4.5]decane)-2-(methylsulfonyl)-5,6-dihydropyrido[4,3-d]pyrimidin-7(8H)-one (1.1 g, 2.5 mmol, 1.0 equiv.) in DMSO (15 mL) was added CsF (380 mg, 2.5 mmol, 1.0 equiv.), DIPEA (967 mg, 7.5 mmol, 3.0 equiv.) and 2,2,2-trifluoroethanamine (740 mg, 7.5 mmol, 3.0 equiv.) at room temperature. The resulting mixture was stirred at 80° C. overnight, then water (10 mL) was added. The reaction mixture was extracted with DCM (20 mL×3), the organic layers were combined, washed with brine (30 mL), dried over $Na_2SO_4$, filtered and concentrated under reduce pressure. The resulting residue was purified by flash column chromatography on silica gel to give 8-(1',4'-dioxaspiro[4.5]decane)-6-(4-methoxyphenyl)-2-((2,2,2-trifluoroethyl)amino)-5,6-dihydropyrido[4,3-d]pyrimidin-7(8H)-one (850 mg, 71% yield) as a white solid. LCMS: m/z 479 [M+H]$^+$.

Step F: 6'-(4-methoxyphenyl)-2'-((2,2,2-trifluoroethyl)amino)-5'H-spiro[cyclohexane-1,8'-pyrido[4,3-d]pyrimidine]-4,7'(6'H)-dione

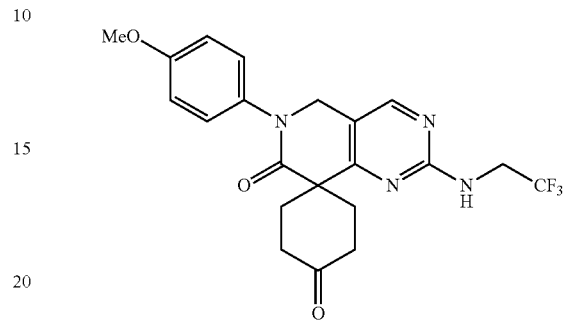

To a solution of 8-(1',4'-dioxaspiro[4.5]decane)-6-(4-methoxyphenyl)-2-((2,2,2-trifluoroethyl)amino)-5,6-dihydropyrido[4,3-d]pyrimidin-7(8H)-one (50.0 mg, 0.1 mmol, 1.0 equiv.) in acetone (2.0 mL) was added 1N HCl (aq.) (0.5 mL, 0.5 mmol, 5.0 equiv.). The resulting solution was stirred at 80° C. for 2 h. Then the reaction mixture was concentrated and purified by RP-prep-HPLC to afford the desired product (14 mg, 31% yield) as a white solid. LC-MS: m/z 435 [M+H]$^+$.

Step G: 4-hydroxy-6'-(4-methoxyphenyl)-2'-((2,2,2-trifluoroethyl)amino)-5'H-spiro[cyclohexane-1,8'-pyrido[4,3-d]pyrimidin]-7'(6'H)-one (Example 116)

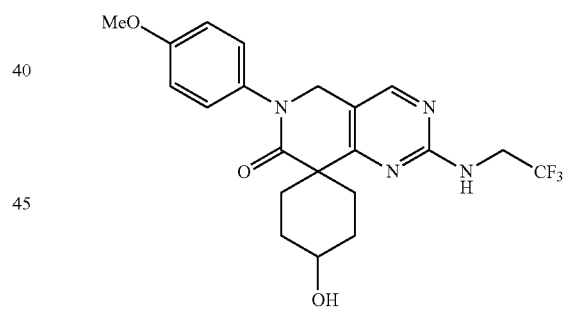

To a solution of 6'-(4-methoxyphenyl)-2'-((2,2,2-trifluoroethyl)amino)-5'H-spiro[cyclohexane-1,8'-pyrido[4,3-d]pyrimidine]-4,7'(6'H)-dione (10 mg, 0.023 mmol, 1.0 equiv) in THF (4 mL) was added $NaBH_4$ (3.8 mg, 0.10 mmol, 4.0 equiv) at −20° C. The mixture was stirred at −20° C. for 1 h. Then the reaction was quenched with $NH_4Cl$ (sat. aq., 5 mL) and extracted with EtOAc (5 mL×3). The organic layers were combined, washed with brine (30 mL), dried with $Na_2SO_4$, filtered and concentrated. The residue was purified by RP-prep-HPLC to afford 4-hydroxy-6'-(4-methoxyphenyl)-2'-((2,2,2-trifluoroethyl)amino)-5'H-spiro[cyclohexane-1,8'-pyrido[4,3-d]pyrimidin]-7'(6'H)-one (Example 116).
$^1$H NMR (400 MHz, CDCl$_3$) δ: 8.14 (s, 1H), 7.17 (d, J=8.4 Hz, 2H), 6.94 (d, J=8.4 Hz, 2H), 5.50-5.34 (m, 1H), 4.66 (s, 2H), 4.28-4.13 (m, 2H), 3.82 (s, 3H), 3.83-3.72 (m, 1H), 2.31-1.77 (m, 8H). LC-MS: m/z 437 [M+H]$^+$.

Preparation of Example 117

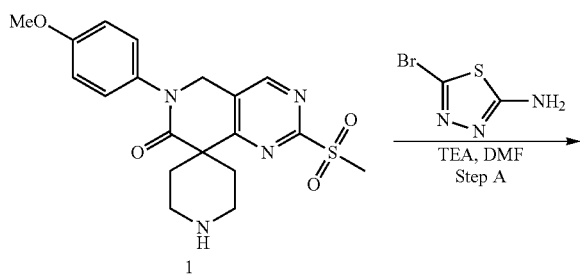

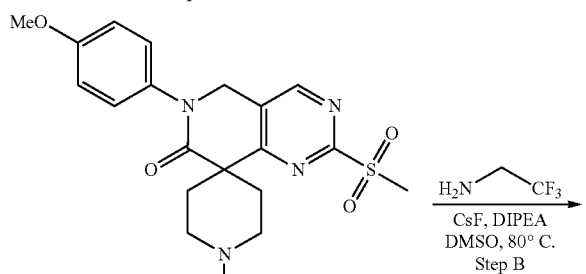

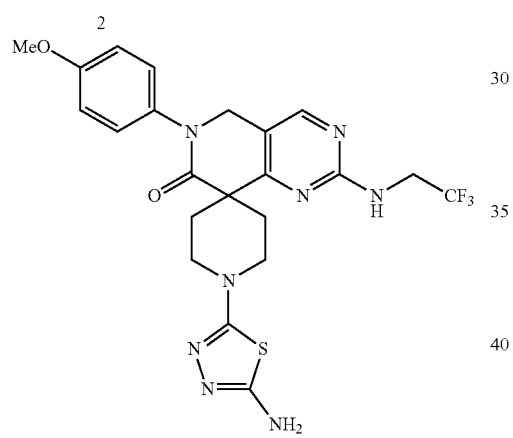

Step A: 1-(5-amino-1,3,4-thiadiazol-2-yl)-6'-(4-methoxyphenyl)-2'-(methylsulfonyl)-5'H-spiro[piperidine-4,8'-pyrido[4,3-d]pyrimidin]-7'(6'H)-one

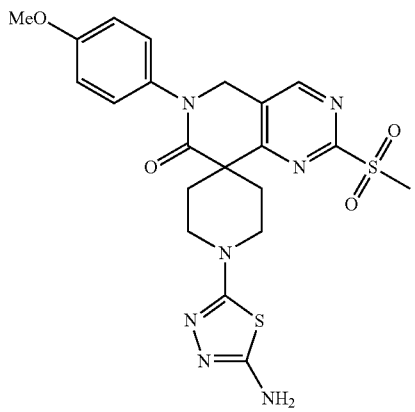 [SMILES: COc1ccc(N2Cc3cnc(S(C)(=O)=O)nc3C3(CCN(c4nnc(N)s4)CC3)C2=O)cc1]

A mixture of 6'-(4-methoxyphenyl)-2'-(methylsulfonyl)-5'H-spiro[piperidine-4,8'-pyrido[4,3-d]pyrimidin]-7'(6'H)-one (prepared in the procedure for General procedure I, Step A-D and H, (n=2) from 1-tert-butyl 4-ethyl piperidine-1,4-dicarboxylate. LC-MS: m/z 403 [M+H]$^+$) (150.0 mg, 0.37 mmol, 1.0 equiv), 5-bromo-1,3,4-thiadiazol-2-amine (80.0 mg, 0.45 mmol, 1.2 equiv), TEA (75.0 mg, 0.74 mmol, 2.0 equiv) and 3.0 mL of DMF was stirred at r.t. for 1 h. Then the reaction mixture was concentrated under reduced pressure, and then purified by flash column chromatography on silica gel to afford 1-(5-amino-1,3,4-thiadiazol-2-yl)-6'-(4-methoxyphenyl)-2'-(methylsulfonyl)-5'H-spiro[piperidine-4,8'-pyrido[4,3-d]pyrimidin]-7'(6'H)-one (100.0 mg, 54% yield). LC-MS: m/z 502 [M+H]$^+$.

Step B: 1-(5-amino-1,3,4-thiadiazol-2-yl)-6'-(4-methoxyphenyl)-2'-((2,2,2-trifluoroethyl)amino)-5'H-spiro[piperidine-4,8'-pyrido[4,3-d]pyrimidin]-7'(6'H)-one (Example 117)

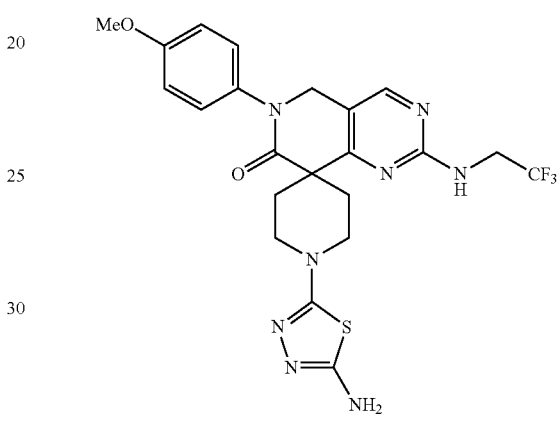

A mixture of 1-(5-amino-1,3,4-thiadiazol-2-yl)-6'-(4-methoxyphenyl)-2'-(methylsulfonyl)-5'H-spiro[piperidine-4,8'-pyrido[4,3-d]pyrimidin]-7'(6'H)-one (100.0 mg, 0.2 mmol, 1.0 equiv), CsF (30.0 mg, 0.2 mmol, 1.0 equiv), DIPEA (78.0 mg, 0.6 mmol, 3.0 equiv) and 2,2,2-trifluoro-ethanamine (60.0 mg, 0.6 mmol, 3.0 equiv) in 2.0 mL of DMSO was stirred at 80° C. for 3 h. Then water (10.0 mL) was added and the resulting mixture was extracted with DCM (20 mL×3). All the organic layers were combined and washed with brine (30 mL), dried over Na$_2$SO$_4$, filtered and concentrated under reduced pressure. The residue was purified by RP-prep-HPLC to afford 1-(5-amino-1,3,4-thiadiazol-2-yl)-6'-(4-methoxyphenyl)-2'-((2,2,2-trifluoroethyl)amino)-5'H-spiro[piperidine-4,8'-pyrido[4,3-d]pyrimidin]-7'(6'H)-one (Example 117).
$^1$H NMR (400 MHz, CDCl$_3$) δ:: 8.18 (s, 1H), 7.17 (d, J=9.2 Hz, 2H), 6.95 (d, J=9.2 Hz, 2H), 5.45 (t, J=6.4 Hz, 1H), 4.71-4.68 (br s, 2H), 4.69 (s, 2H), 4.23-4.10 (m, 2H), 3.82 (s, 3H), 3.81-3.71 (m, 4H), 2.35-2.29 (m, 2H), 2.25-2.17 (m, 2H). LC-MS: m/z 5

Preparation of Example 118

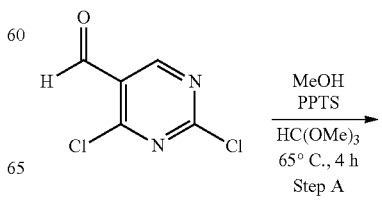

-continued

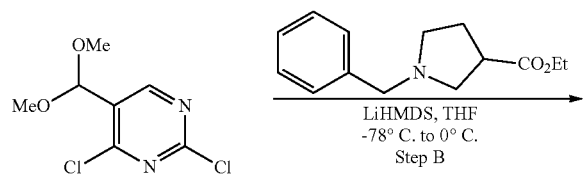

Step B

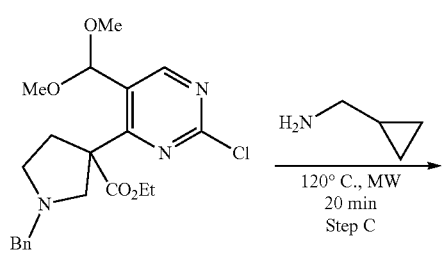

Step C

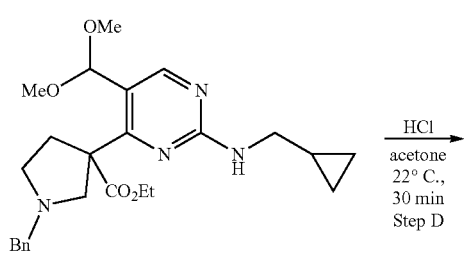

Step D

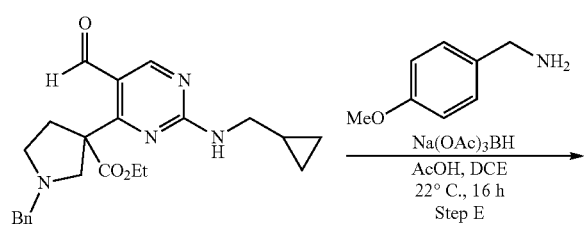

Step E

Step A:
2,4-dichloro-5-(dimethoxymethyl)pyrimidine

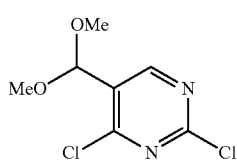 [SMILES: COC(OC)c1cnc(Cl)nc1Cl]

To a flask containing MeOH (24.0 mL), was added 2,4-dichloropyrimidine-5-carbaldehyde (1.5159 g, 1.0 equiv.), PPTS (215.0 mg, 0.1 equiv.) and trimethyl orthoformate (6.0 mL). The reaction mixture was stirred at 65° C. for 14 h, cooled to rt and concentrated. The resulting residue was purified via column chromatography to yield the title compound as an oil (1.4361 g, 75% yield). $^1$H NMR (400 MHz, Chloroform-d) δ 8.73 (s, 1H), 5.54 (s, 1H), 3.38 (s, 7H). LC-MS: m/z 223, 225 [M+H]$^+$.

Step B ethyl 1-benzyl-3-(2-chloro-5-(dimethoxymethyl)pyrimidin-4-yl)pyrrolidine-3-carboxylate

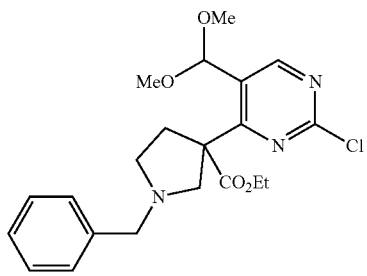 [SMILES: CCOC(=O)C1(c2nc(Cl)ncc2C(OC)OC)CCN(Cc2ccccc2)C1]

To a flask was added ethyl 1-benzylpyrrolidine-3-carboxylate (314.0 mg, 1.5 equiv.) and THF (10.0 mL). The mixture was cooled to −78° C. followed by the addition of LiHMDS (1.0 M in THF, 1.35 mL, 1.5 equiv.) and stirred at −78° C. for 30 min. To this mixture was added 2,4-dichloro-5-(dimethoxymethyl)pyrimidine (200.0 mg, 1.0 equiv.) at −78° C. The reaction was stirred at −78° C. for 30 min, warmed to 0° C. and stirred for 1 h before it was quenched with silica gel. The resulting mixture was concentrated and purified via column chromatography to yield the title compound (269.7 mg, 72% yield). LC-MS: m/z 420 [M+H]$^+$.

Step C: ethyl 1-benzyl-3-(2-((cyclopropylmethyl)amino)-5-(dimethoxymethyl)pyrimidin-4-yl)pyrrolidine-3-carboxylate

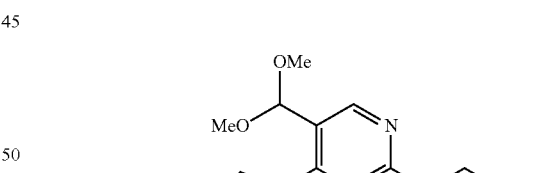

To a microwave reaction tube, was added ethyl 1-benzyl-3-(2-chloro-5-(dimethoxymethyl)pyrimidin-4-yl)pyrrolidine-3-carboxylate (269.7 mg, 1.0 equiv.) and cyclopropylmethanamine (2.5 mL). The reaction was stirred at 120° C. for 20 minutes using a Biotage microwave reactor and cooled to rt. The mixture was concentrated and purified via column chromatography to yield the title compound (201.8 mg, 69% yield). LC-MS: m/z 455 [M+H]$^+$.

Step D: ethyl 1-benzyl-3-(2-((cyclopropylmethyl)amino)-5-formylpyrimidin-4-yl)pyrrolidine-3-carboxylate

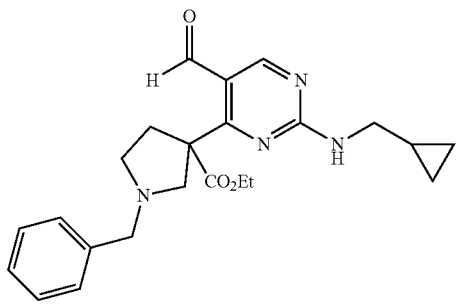 [SMILES: CCOC(=O)C1(c2nc(NCC3CC3)ncc2C=O)CCN(Cc2ccccc2)C1]

To a flask containing acetone, was added 1N HCl (0.4 mL) and ethyl 1-benzyl-3-(2-((cyclopropylmethyl)amino)-5-(dimethoxymethyl)pyrimidin-4-yl)pyrrolidine-3-carboxylate (201.8 mg, 1.0 equiv.). The reaction was stirred at 22° C. for 30 minutes and quenched with aq. NaHCO$_3$. The mixture was concentrated and purified via column chromatography to yield the title compound (165.7 mg, 91% yield). LC-MS: m/z 409 [M+H]$^+$.

Step E: 1'-benzyl-2-((cyclopropylmethyl)amino)-6-(4-methoxybenzyl)-5,6-dihydro-7H-spiro[pyrido[4,3-d]pyrimidine-8,3'-pyrrolidin]-7-one (Example 118)

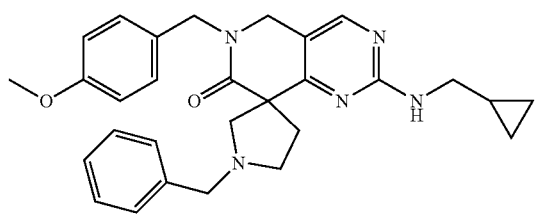 [SMILES: COc1ccc(CN2Cc3cnc(NCC4CC4)nc3C3(CCN(Cc4ccccc4)C3)C2=O)cc1]

To a flask was added ethyl 1-benzyl-3-(2-((cyclopropylmethyl)amino)-5-formylpyrimidin-4-yl)pyrrolidine-3-carboxylate (36.6 mg, 1.0 equiv.), (4-methoxyphenyl)methanamine (26 uL, 2.2 equiv.), sodium triacetoxyborohydride (28.5 mg, 1.5 equiv.), dichloroethane (DCE, 2.0 mL) and acetic acid (15 uL, 3.0 equiv.). The reaction was stirred at 22° C. for 16 h before it was quenched with aq. NaHCO$_3$. The mixture was concentrated and purified via column chromatography to yield the title compound (Example 118). $^1$H NMR (400 MHz, Chloroform-d)$^1$H NMR (400 MHz, Chloroform-d) δ 7.93 (s, 1H), 7.46-7.39 (m, 2H), 7.35-7.29 (m, 2H), 7.27 (d, J=7.1 Hz, 1H), 7.19-7.12 (m, 2H), 6.87-6.79 (m, 2H), 4.75-4.59 (m, 2H), 4.19-4.05 (m, 2H), 3.98 (s, 2H), 3.78 (s, 3H), 3.47 (d, J=10.2 Hz, 1H), 3.34 (d, J=10.2 Hz, 1H), 3.27 (t, J=6.3 Hz, 2H), 3.20 (s, 1H), 3.05 (dt, J=9.3, 7.1 Hz, 1H), 2.57-2.38 (m, 2H), 1.13-1.03 (m, 1H), 0.58-0.47 (m, 2H), 0.26 (dt, J=6.0, 4.5 Hz, 2H). m/z 484 [M+H]$^+$.

Preparation of Example 119, Example 120, Example 121 and Example 122 via General Procedure II

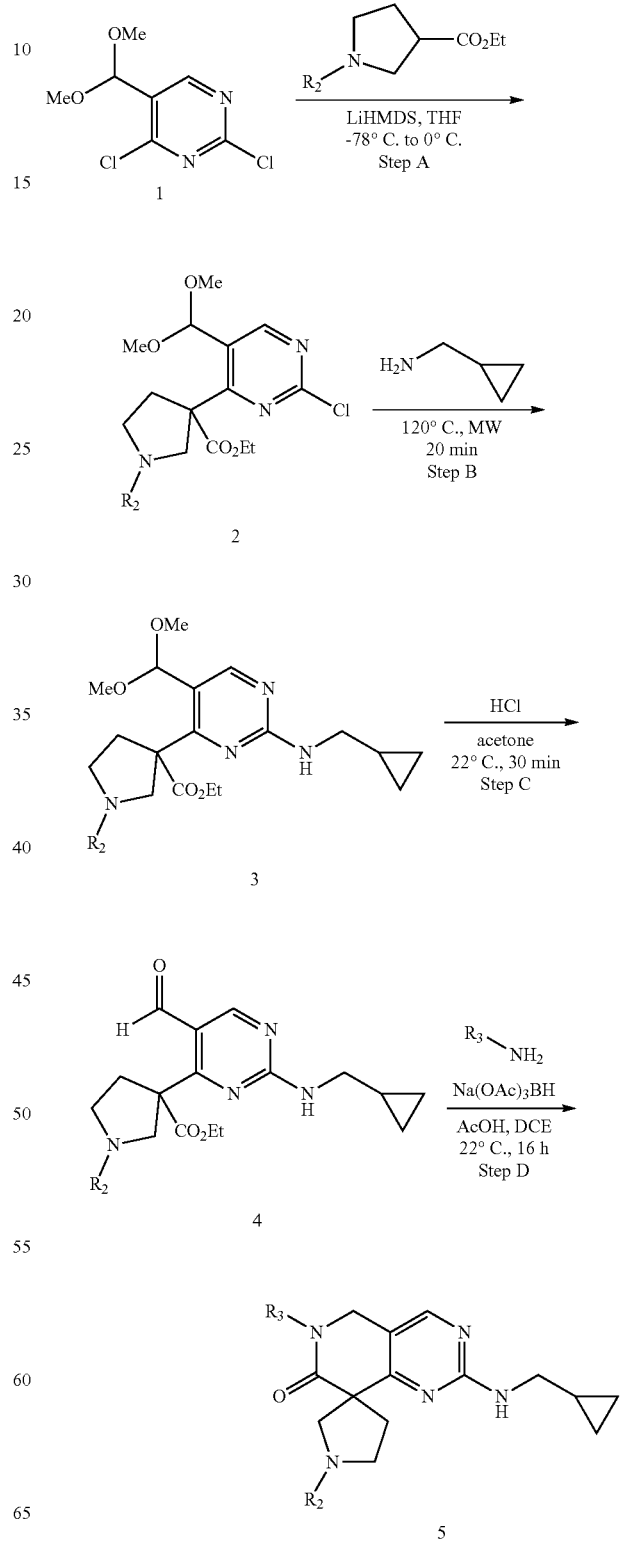

-continued

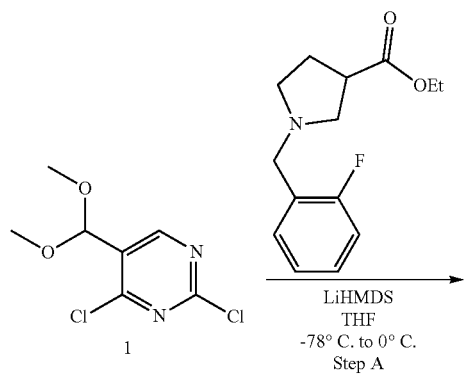

1

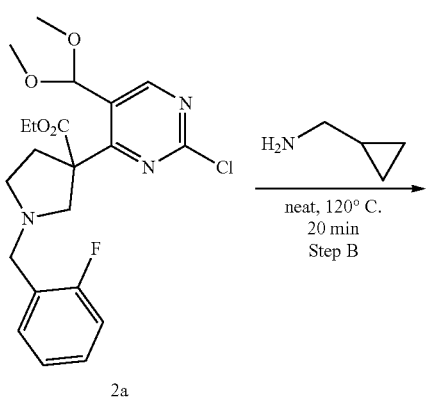

2a

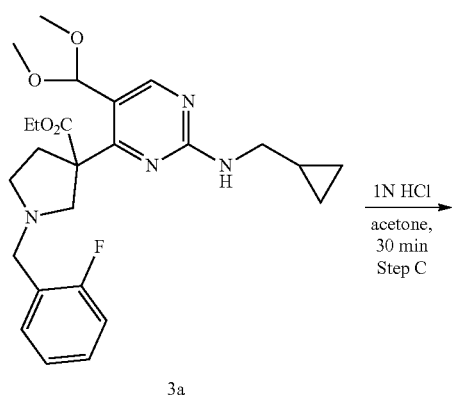

3a

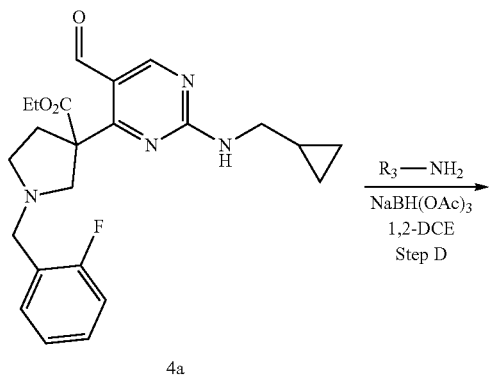

4a

-continued

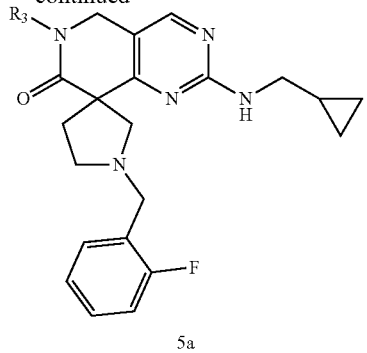

5a

Step A: ethyl 3-(2-chloro-5-(dimethoxymethyl)pyrimidin-4-yl)-1-(2-fluorobenzyl)pyrrolidine-3-carboxylate

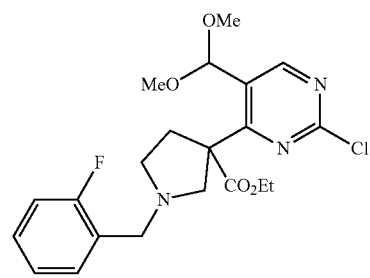 [SMILES: CCOC(=O)C1(c2nc(Cl)ncc2C(OC)OC)CCN(Cc2ccccc2F)C1]

To a flask was added ethyl 1-(2-fluorobenzyl)pyrrolidine-3-carboxylate (2.02 g, 1.5 equiv., as prepared for Example 118) and THF (15.0 mL). The mixture was cooled to −78° C. followed by the addition of LiHMDS (1.0 M in THF, 8.1 mL, 1.5 equiv.). The reaction was stirred at −78° C. for 40 minutes and 2,4-dichloro-5-(dimethoxymethyl)pyrimidine (1.1965 g, 1.0 equiv.) was added dropwise at −78° C. The reaction was stirred at −78° C. for 1 h, warmed to 0° C. and stirred for 45 minutes before it was quenched with silica gel. The resulting mixture was concentrated and purified via column chromatography to yield the title compound (1.30 g, 55% yield). LC-MS: m/z 438 [M+H]⁺.

Step B: ethyl 3-(2-(((cyclopropylmethyl)amino)-5-(dimethoxymethyl)pyrimidin-4-yl)-1-(2-fluorobenzyl)pyrrolidine-3-carboxylate

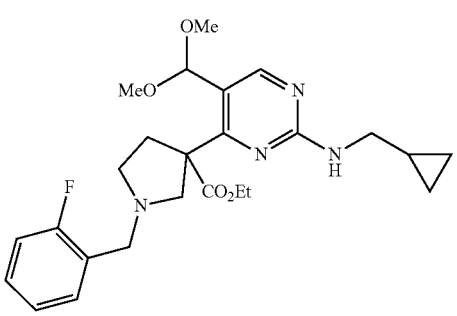 [SMILES: CCOC(=O)C1(c2nc(NCC3CC3)ncc2C(OC)OC)CCN(Cc2ccccc2F)C1]

To a microwave reaction tube, was added ethyl 3-(2-chloro-5-(dimethoxymethyl)pyrimidin-4-yl)-1-(2-fluorobenzyl)pyrrolidine-3-carboxylate (398.8 mg, 1.0 equiv.) and cyclopropylmethanamine (2.5 mL). The reaction was stirred at 120° C. for 20 minutes using a Biotage microwave reactor and cooled to rt. The mixture was concentrated and purified via column chromatography to yield the title compound (312.3 mg, 73% yield). LC-MS: m/z 473 [M+H]$^+$.

Step C: ethyl 3-(2-((cyclopropylmethyl)amino)-5-formylpyrimidin-4-yl)-1-(2-fluorobenzyl)pyrrolidine-3-carboxylate

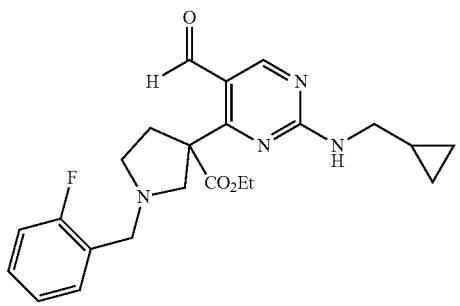 [SMILES: CCOC(=O)C1(c2nc(NCC3CC3)ncc2C=O)CCN(Cc2ccccc2F)C1]

To a flask containing acetone, was added ethyl 3-(2-((cyclopropylmethyl)amino)-5-(dimethoxymethyl)pyrimidin-4-yl)-1-(2-fluorobenzyl)pyrrolidine-3-carboxylate (312.3 mg, 1.0 equiv.) and 1N HCl (0.7 mL). The reaction was stirred at 22° C. for 15 minutes and quenched with aq. NaHCO$_3$. The mixture was concentrated and purified via column chromatography to yield the title compound (230.0 mg, 82% yield). LC-MS: m/z 427 [M+H]$^+$.

2-((cyclopropylmethyl)amino)-1'-(2-fluorobenzyl)-6-((2-methoxypyridin-4-yl)methyl)-5,6-dihydro-7H-spiro[pyrido[4,3-d]pyrimidine-8,3'-pyrrolidin]-7-one (Example 119)

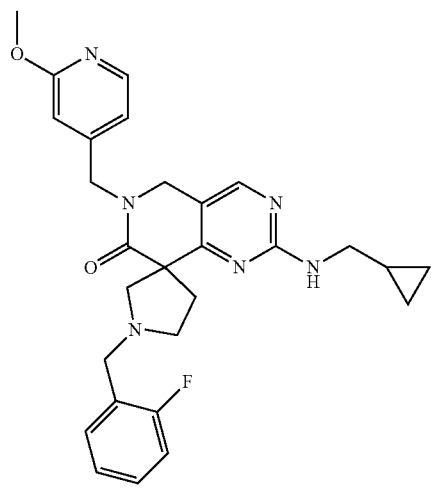 [SMILES: COc1cc(CN2Cc3cnc(NCC4CC4)nc3C3(CCN(Cc4ccccc4F)C3)C2=O)ccn1]

General procedure II (Step D): To a flask was added ethyl 3-(2-((cyclopropylmethyl)amino)-5-formylpyrimidin-4-yl)-1-(2-fluorobenzyl)pyrrolidine-3-carboxylate (30.0 mg, 1.0 equiv.), (6-methoxypyridin-3-yl)methanamine (21.4 mg, 2.2 equiv.), sodium triacetoxyborohydride (22.4 mg, 1.5 equiv.), dichloroethane (DCE, 2.0 mL) and acetic acid (14 uL, 3.0 equiv.). The reaction was stirred at 22° C. for 16 h before it was quenched with aq. NaHCO$_3$. The mixture was concentrated and purified via column chromatography to yield the title compound (Example 119). $^1$H NMR (400 MHz, Chloroform-d) δ 8.06 (d, J=2.4 Hz, 1H), 7.96 (s, 1H), 7.52 (dd, J=8.5, 2.5 Hz, 2H), 7.23 (s, 1H), 7.11 (t, J=7.4 Hz, 1H), 7.01 (t, J=9.1 Hz, 1H), 6.70 (d, J=8.5 Hz, 1H), 4.73-4.58 (m, 2H), 4.15 (s, 2H), 3.92 (d, J=0.8 Hz, 3H), 3.89 (s, 2H), 3.34-3.14 (m, 4H), 3.02 (s, 2H), 2.47 (ddt, J=25.8, 12.6, 6.4 Hz, 2H), 1.13-1.03 (m, 1H), 0.62-0.44 (m, 2H), 0.25 (d, J=5.0 Hz, 2H). LC-MS: m/z 503 [M+H]$^+$.

6-((1H-pyrazol-5-yl)methyl)-2-((cyclopropylmethyl)amino)-1'-(2-fluorobenzyl)-5,6-dihydro-7H-spiro[pyrido[4,3-d]pyrimidine-8,3'-pyrrolidin]-7-one (Example 120)

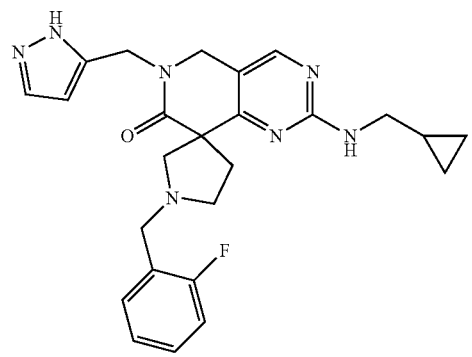 [SMILES: O=C1N(Cc2ccn[nH]2)Cc2cnc(NCC3CC3)nc2C12CCN(Cc1ccccc1F)C2]

General procedure II (Step D): To a flask was added ethyl 3-(2-((cyclopropylmethyl)amino)-5-formylpyrimidin-4-yl)-1-(2-fluorobenzyl)pyrrolidine-3-carboxylate (30.0 mg, 1.0 equiv.), (6-methoxypyridin-3-yl)methanamine (15.0 mg, 2.2 equiv.), sodium triacetoxyborohydride (22.4 mg, 1.5 equiv.), dichloroethane (DCE, 2.0 mL) and acetic acid (14 uL, 3.0 equiv.). The reaction was stirred at 22° C. for 16 h before it was quenched with aq. NaHCO$_3$. The mixture was concentrated and purified via column chromatography to yield the title compound (Example 120). $^1$H NMR (400 MHz, Chloroform-d) δ 7.99 (s, 1H), 7.50 (t, J=5.0 Hz, 2H), 7.21 (ddd, J=7.4, 5.5, 1.9 Hz, 1H), 7.11 (td, J=7.5, 1.3 Hz, 1H), 7.01 (ddd, J=9.7, 8.1, 1.3 Hz, 1H), 6.25 (d, J=2.1 Hz, 1H), 4.72 (s, 2H), 4.29 (s, 2H), 3.90 (s, 2H), 3.38-3.13 (m, 4H), 3.02 (d, J=7.0 Hz, 2H), 2.51 (dt, J=12.7, 6.5 Hz, 1H), 2.40 (dt, J=12.6, 6.6 Hz, 1H), 1.13-1.01 (m, 1H), 0.59-0.47 (m, 2H), 0.25 (dt, J=6.1, 4.5 Hz, 2H). LC-MS: m/z 462 [M+H]$^+$.

Example 121: 2-((cyclopropylmethyl)amino)-1'-(2-fluorobenzyl)-6-(isoxazol-4-yl)-5,6-dihydro-7H-spiro[pyrido[4,3-d]pyrimidine-8,3'-pyrrolidin]-7-one

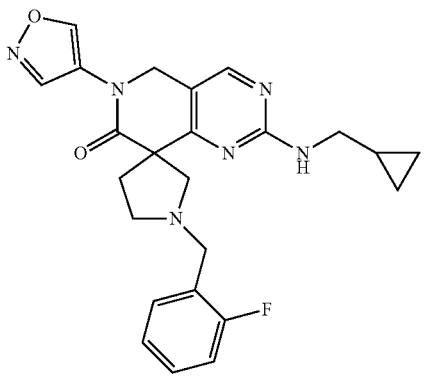 [SMILES: O=C1N(c2cnoc2)Cc2cnc(NCC3CC3)nc2C12CCN(Cc1ccccc1F)C2]

General procedure II (Step D): To a solution of ethyl 3-((2-cyclopropylmethylamino)-5-formylpyrimidin-4-yl)-1-(2-fluorobenzyl)pyrrolidine-3-carboxylate (60 mg, 0.14 mmol, 1 equiv.) in 1,2-dichloroethane (0.7 ml) was added isoxazol-4-amine hydrochloride (25.4 mg, 0.21 mmol, 1.5 equiv.). The mixture was stirred at 75° C. for 1 h. The reaction was cooled to 60° C. before adding sodium triacetoxyborohydride (60 mg, 0.28 mmol, 2 equiv.) and stirring for another 3 h. The crude reaction mixture was purified via column chromatography (CombiFlash, 100:0 to 80:20 dichloromethane:methanol) to provide the title compound (Example 121). $^1$H NMR (400 MHz, Chloroform-d) δ 9.01 (s, 1H), 8.66 (s, 1H), 8.15 (s, 1H), 7.50-7.44 (m, 1H), 7.21 (t, J=6.6 Hz, 1H), 7.10 (t, J=7.4 Hz, 1H), 7.01 (t, J=9.1 Hz, 1H), 5.35 (s, 1H), 4.66 (s, 2H), 3.86 (s, 2H), 3.28 (td, J=7.2, 6.4, 3.0 Hz, 3H), 3.20 (d, J=9.4 Hz, 1H), 2.99 (t, J=6.6 Hz, 2H), 2.56 (d, J=10.0 Hz, 2H), 1.09 (s, 1H), 0.60-0.51 (m, 2H), 0.27 (d, J=5.0 Hz, 2H). LC-MS: m/z 449 [M+H]$^+$.

Example 122: 2-((cyclopropylmethyl)amino)-1'-(2-fluorobenzyl)-6-(1H-pyrazol-4-yl)-5,6-dihydro-7H-spiro[pyrido[4,3-d]pyrimidine-8,3'-pyrrolidin]-7-one

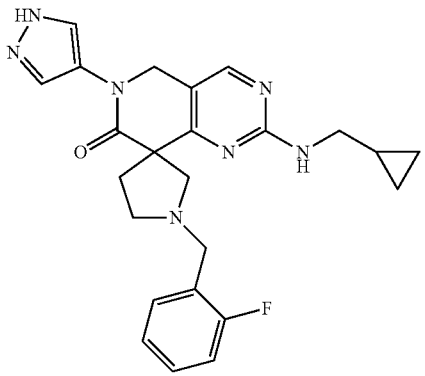 [SMILES: O=C1N(c2cn[nH]c2)Cc2cnc(NCC3CC3)nc2C12CCN(Cc1ccccc1F)C2]

General procedure II (Step D): To a mixture of ethyl 3-((2-cyclopropylmethylamino)-5-formylpyrimidin-4-yl)-1-(2-fluorobenzyl)pyrrolidine-3-carboxylate (60 mg, 0.14 mmol, 1 equiv.) and acetic acid (0.025 mL, 0.42 mmol, 3 equiv.) in 1,2-dichloroethane (0.7 ml) was added isoxazol-4-amine hydrochloride (25.4 mg, 0.21 mmol, 1.5 equiv.). The mixture was stirred at room temperature for 2 h. The sodium triacetoxyborohydride (60 mg, 0.28 mmol, 2 equiv.) was added and the mixture was stirred for 48 h at room temperature. The crude reaction mixture was purified via column chromatography (CombiFlash, 100:0 to 80:20 dichloromethane:methanol). The appropriate fractions were pooled and concentrated and the residue was washed with saturated NaHCO$_3$ solution and extracted with dichlormethane (2×5 mL). The organic extracts were combined, dried over Na$_2$SO$_4$ and concentrated to provide the title compound (Example 122). $^1$H NMR (400 MHz, Chloroform-d) δ 8.12 (s, 1H), 7.96 (s, 2H), 7.46 (t, J=7.4 Hz, 1H), 7.18 (d, J=7.0 Hz, 1H), 7.10-7.04 (m, 1H), 6.98 (dd, J=9.9, 8.2 Hz, 1H), 5.34 (s, 1H), 4.66 (s, 2H), 3.84 (d, J=2.5 Hz, 2H), 3.32-3.18 (m, 4H), 2.97 (d, J=5.5 Hz, 2H), 2.54 (d, J=19.0 Hz, 3H), 1.07 (ddt, J=10.4, 7.4, 3.7 Hz, 1H), 0.55-0.49 (m, 2H), 0.25 (q, J=5.1 Hz, 2H). LC-MS: m/z 448 [M+H]$^+$.

General Procedure III

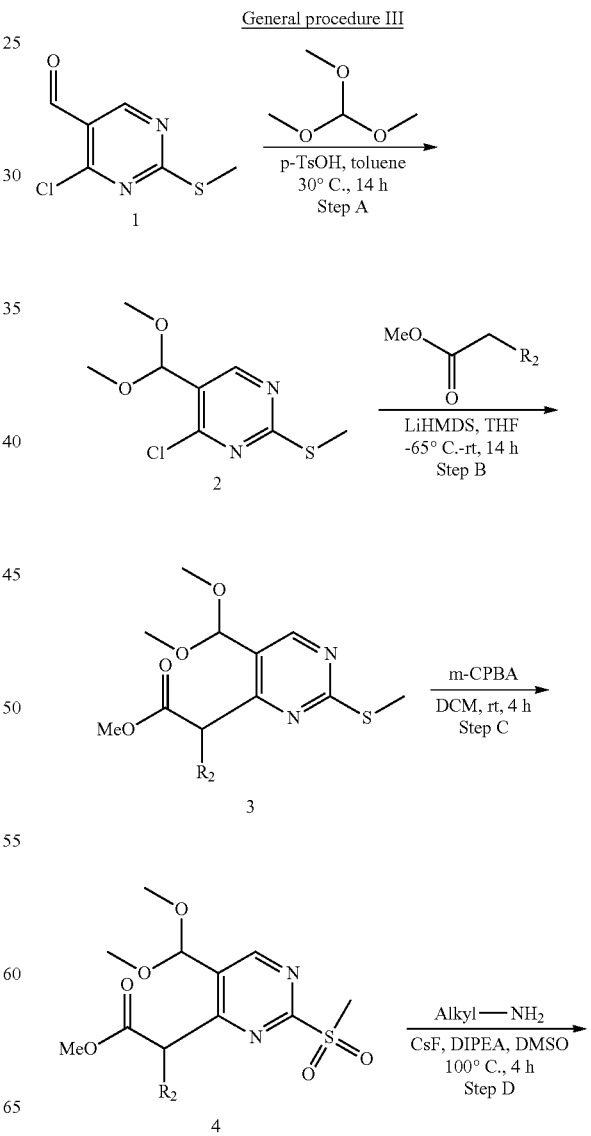

115
-continued

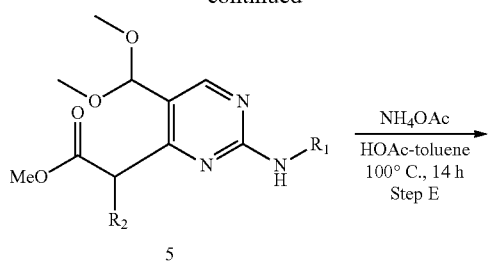

$\xrightarrow{\text{NH}_4\text{OAc}}$ HOAc-toluene 100° C., 14 h Step E

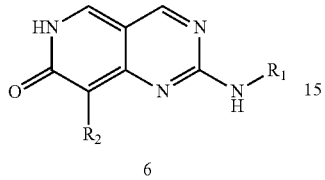

6

Method A: Ullmann coupling
CuI/Ligand, Cs$_2$CO$_3$ or CsF,
dioxane or acetonitrile, 100° C.

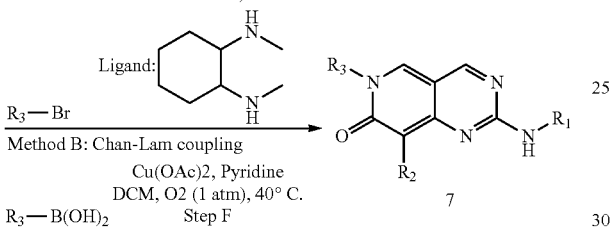

Ligand: (cyclohexane diamine)

R$_3$—Br
Method B: Chan-Lam coupling
Cu(OAc)2, Pyridine
DCM, O2 (1 atm), 40° C.
R$_3$—B(OH)$_2$ Step F Alternative Route

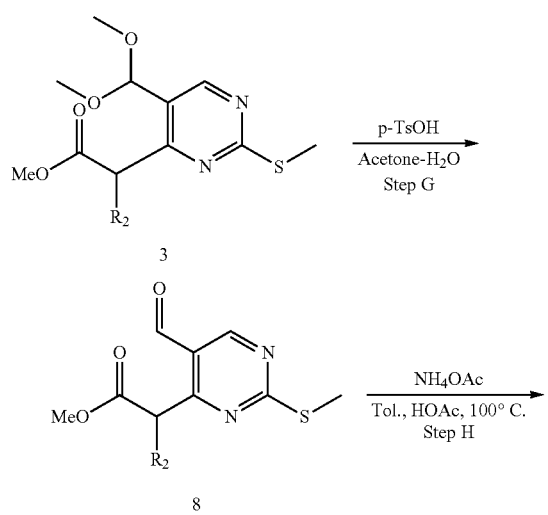

3

$\xrightarrow{\text{p-TsOH}}$ Acetone-H$_2$O Step G

8

$\xrightarrow{\text{NH}_4\text{OAc}}$ Tol., HOAc, 100° C. Step H

9

$\xrightarrow[\text{Cu(OAc)}_2]{\text{Aryl—B(OH)}_2 \text{ 2 eq}}$ pyridine 4 eq DCM, rt Step I

10

$\xrightarrow{\text{Alkyl—NH}_2}$ HOAc Step J

116
-continued

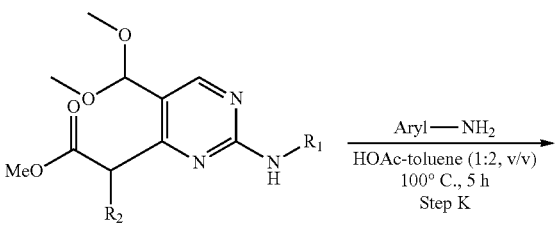

7

Alternative Route

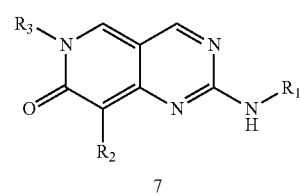

5

$\xrightarrow[\text{HOAc-toluene (1:2, v/v)}]{\text{Aryl—NH}_2}$ 100° C., 5 h Step K

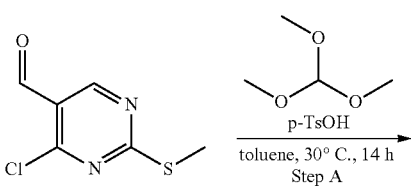

7

Preparation of Example 123 from General Procedure III

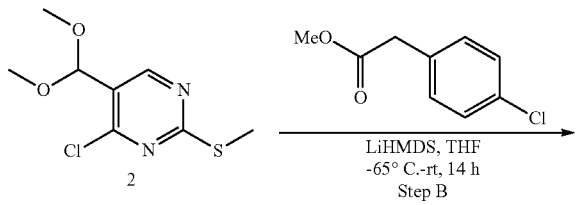

1

$\xrightarrow[\text{toluene, 30° C., 14 h}]{\text{p-TsOH}}$ Step A

2

$\xrightarrow[\text{LiHMDS, THF}]{}$ −65° C.-rt, 14 h Step B

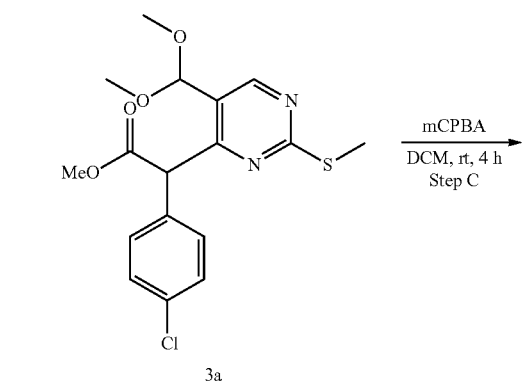

$\xrightarrow{\text{mCPBA}}$ DCM, rt, 4 h Step C

3a

118

Step A: 4-chloro-5-(dimethoxymethyl)-2-(methylthio)pyrimidine

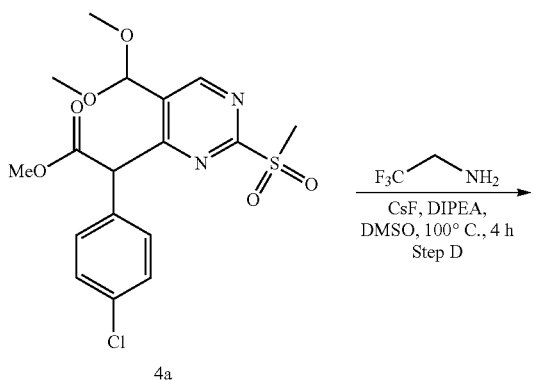

4-chloro-2-(methylthio)pyrimidine-5-carbaldehyde (15.0 g, 79.8 mmol, 1.0 equiv.) and p-TsOH.H₂O (90.0 mg, 0.473 mmol, 0.006 equiv.) were dissolved in toluene (75.0 mL). Triethyl orthoformate (42.3 g, 399.0 mmol, 5.0 equiv) was added to the solution at 0° C. The resulting solution was stirred at 30° C. for an additional 14 h. Then the mixture was concentrated directly. The residue was re-dissolved in DCM (50.0 mL) and purified by flash chromatography on silica gel eluting with (PE/EA=10/1) to afford the desired product (18 g, 96% yield) as a colorless oil. LC-MS (ESI): m/z 235 [M+H]⁺.

Step B: methyl 2-(4-chlorophenyl)-2-(5-(dimethoxymethyl)-2-(methylthio)pyrimidin-4-yl)acetate Methyl 2-(4-chlorophenyl)acetate (31.6 g, 170.9 mmol, 2.0 equiv.) was dissolved in anhydrous THF (200 mL), cooled to −65° C. under N₂ atmosphere. LiHMDS (1N, in THF, 256 mL, 256.0 mmol, 3.0 equiv.) was added drop wise to the solution at −65° C. After addition, the resulting mixture was stirred at −65° C. for 2 h, then a solution of 4-chloro-5-(dimethoxymethyl)-2-(methylthio)pyrimidine (20 g, 85.4 mmol, 1.0 equiv) in anhydrous THF (80 mL) was added drop-wisely via an addition funnel into the reaction mixture.

Following addition, the reaction mixture was slowly warmed to room temperature and stirred at room temperature for 14 h. At this point, the mixture was quenched with NH₄Cl (Sat. aq., 500 mL) and extracted with EA (500 mL×3). The organic layers were combined, washed with brine (500 mL), dried over anhydrous Na₂SO₄ and concentrated under reduced pressure. The residue was purified by flash chromatography on silica gel eluting with (PE/EA=10:1-5:1) to afford the desired product (30 g, 93% yield) as a yellow solid. LC-MS: m/z 383 [M+H]⁺.

Step C: methyl 2-(4-chlorophenyl)-2-(5-(dimethoxymethyl)-2-(methylsulfonyl)pyrimidin-4-yl)acetate

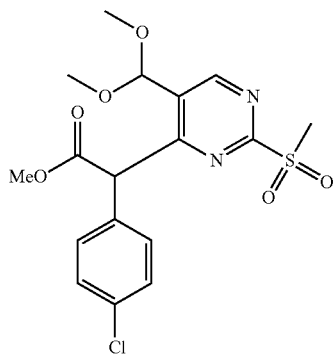 [SMILES: COC(=O)C(c1ccc(Cl)cc1)c1nc(S(C)(=O)=O)ncc1C(OC)OC]

To a solution of methyl 2-(4-chlorophenyl)-2-(5-(dimethoxymethyl)-2-(methylthio)pyrimidin-4-yl)acetate (30 g, 78.3 mmol, 1.0 equiv.) in DCM (500 mL) was added 3-Chloroperoxybenzoic acid (40.4 g, 235.1 mmol, 3.0 equiv.) in portions over 1 h. The mixture was stirred at room temperature for 4 h. The reaction mixture was diluted with DCM (1 L) and washed with $NaHCO_3$(Sat. aq., 1 L×3), dried over anhydrous $Na_2SO_4$, and concentrated under reduced pressure. The residue was purified by flash chromatography on silica gel eluting with (PE/EA=10:1-2:1) to afford the desired product (27 g, 83% yield) as a white solid. LC-MS: m/z 415 $[M+H]^+$.

Step D: methyl 2-(4-chlorophenyl)-2-(5-(dimethoxymethyl)-2-((2,2,2-trifluoroethyl)amino)pyrimidin-4-yl)acetate

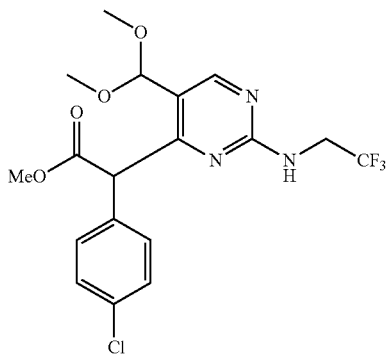 [SMILES: COC(=O)C(c1ccc(Cl)cc1)c1nc(NCC(F)(F)F)ncc1C(OC)OC]

A mixture of methyl 2-(4-chlorophenyl)-2-(5-(dimethoxymethyl)-2-((2,2,2-trifluoro-ethyl)amino)pyrimidin-4-yl)acetate (15 g, 36.1 mmol, 1.0 equiv.), CsF (5.5 g, 36.1 mmol, 1.0 equiv.), DIPEA (23.3 g, 180.5 mmol, 5.0 equiv.), and 2,2,2-trifluoroethanamine (35.8 g, 361.5 mmol, 10 equiv.) in DMSO (150 mL) was stirred at 100° C. overnight in a sealed tube. The reaction mixture was then concentrated to remove the excess 2,2,2-trifluoroethanamine. The resulting residue was poured into ice water (500 mL) and extracted with EA (500 mL×3). The organic layers were combined, washed with brine (500 mL), dried over anhydrous $Na_2SO_4$, and concentrated under reduced pressure. The residue was purified by flash chromatography on silica gel eluting with (PE/EA=5:1-3:1) to afford the desired product (10 g, 64% yield) as a yellow solid. LC-MS: m/z 434 $[M+H]^+$.

Step E: 8-(4-chlorophenyl)-2-((2,2,2-trifluoroethyl)amino)pyrido[4,3-d]pyrimidin-7(6H)-one

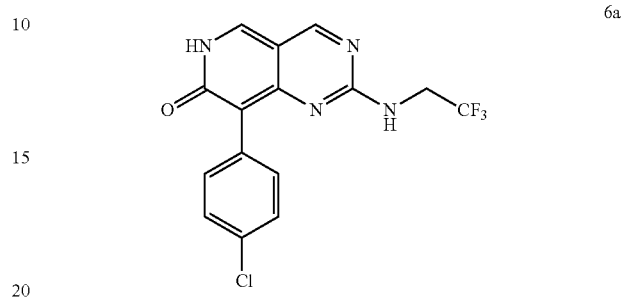

6a

A mixture of methyl 2-(4-chlorophenyl)-2-(5-(dimethoxymethyl)-2-((2,2,2-trifluoro-ethyl)amino)pyrimidin-4-yl)acetate (30 g, 69.1 mmol, 1.0 equiv.), $NH_4OAc$ (180 g, 779 mmol, 11.3 equiv.), AcOH (75 mL) and toluene (150 mL) was stirred at 100° C. for an additional 14 h. Then the mixture was concentrated under reduced pressure, and the residue was poured into ice water (500 mL). This mixture was filtered and the collected precipitate was washed with $NaHCO_3$(Sat, aq., 500 mL) followed by water (1 L). The obtained solid was dried in vacuo to afford the desired product (21 g, 85% yield) as a yellow solid. LC-MS: m/z 355 $[M+H]^+$.

Step F: (Method A: Ullmann coupling). 8-(4-chlorophenyl)-6-(2-methyl-2H-indazol-5-yl)-2-((2,2,2-trifluoroethyl)amino)pyrido[4,3-d]pyrimidin-7(6H)-one (Example 123)

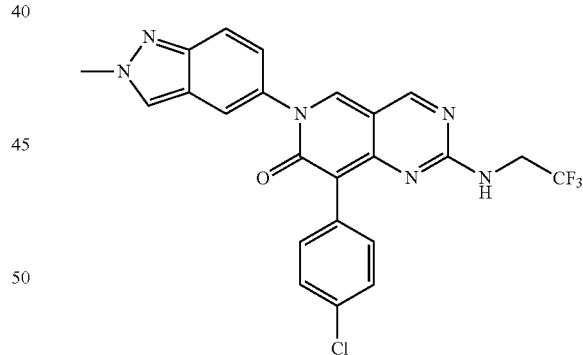

A mixture of 8-(4-chlorophenyl)-2-((2,2,2-trifluoroethyl)amino)pyrido[4,3-d]pyrimi-din-7(6H)-one (100 mg, 0.28 mmol, 1.0 equiv), 5-bromo-2-methyl-2H-indazole (119 mg, 0.56 mmol, 2.0 equiv.), CuI (5.4 mg, 0.028 mmol, 0.1 equiv.), $N^1,N^2$-dimethylcyclohexane-1,2-diamine (8.1 mg, 0.056 mmol, 0.2 equiv.), $Cs_2CO_3$ (276 mg, 0.847 mmol, 3.0 equiv.) and dioxane (2 mL) was stirred at 100° C. under $N_2$ atmosphere for 16 h. The crude mixture was concentrated under reduced pressure, and the resulting residue was purified by flash column chromatography on silica gel to yield 8-(4-chlorophenyl)-6-(2-methyl-2H-indazol-5-yl)-2-((2,2,2-trifluoroethyl)amino)pyrido[4,3-d]pyrimidin-7(6H)-one (Example 123).

$^1$H NMR (400 MHz, DMSO-d$_6$) δ 8.97 (s, 1H), 8.91 (s, 1H), 8.59 (t, J=6.4 Hz, 1H), 8.51 (s, 1H), 7.89 (d, J=1.6 Hz, 1H), 7.72-7.64 (m, 3H), 7.38-7.28 (m, 3H), 4.22 (s, 3H), 4.12-4.03 (m, 2H). LC-MS: m/z 485 [M+H]$^+$.

Example 124: 8-(4-chlorophenyl)-6-(1,2-dimethyl-1H-benzo[d]imidazol-6-yl)-2-((2,2,2-trifluoroethyl)amino)pyrido[4,3-d]pyrimidin-7(6H)-one

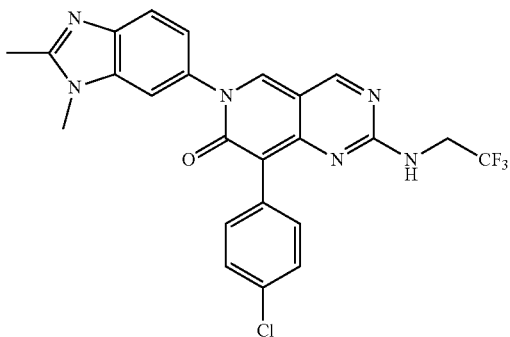 [SMILES: Cc1nc2ccc(-n3cc4cnc(NCC(F)(F)F)nc4c(-c4ccc(Cl)cc4)c3=O)cc2n1C]

The title compound was synthesized from intermediate 6a with 6-bromo-1,2-dimethyl-1H-benzo[d]imidazole via general procedure III method A (CuI, N$^1$,N$^2$-dimethylcyclohexane-1,2-diamine, Cs$_2$CO$_3$, 1,4-dioxane, 100° C.).

$^1$H NMR (400 MHz, DMSO-d$_6$) δ 8.98 (s, 1H), 8.89 (s, 1H), 8.59 (t, J=6.4 Hz, 1H), 7.74 (d, J=2.0 Hz, 1H), 7.67 (d, J=8.4 Hz, 2H), 7.63 (d, J=8.8 Hz, 1H), 7.35 (d, J=8.4 Hz, 2H), 7.26 (dd, J=8.4, 2.0 Hz, 1H), 4.15-4.01 (m, 2H), 3.75 (s, 3H), 2.57 (s, 3H). LC-MS: m/z 499 [M+H]$^+$.

Example 125: 6-(benzo[c]isothiazol-5-yl)-8-(4-chlorophenyl)-2-((2,2,2-trifluoroethyl)amino)pyrido[4,3-d]pyrimidin-7(6H)-one

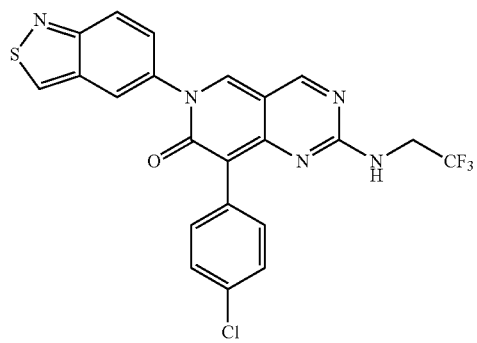 [SMILES: O=c1c(-c2ccc(Cl)cc2)c2nc(NCC(F)(F)F)ncc2cn1-c1ccc2nscc2c1]

The title compound was synthesized from intermediate 6a with 5-bromobenzo[c]isothiazole via general procedure III method A (CuI, N$^1$,N$^2$-dimethylcyclohexane-1,2-diamine, Cs$_2$CO$_3$, 1,4-dioxane, 100° C.).

$^1$H NMR (400 MHz, DMSO-d$_6$) δ 9.94 (s, 1H), 8.99 (s, 1H), 8.98 (s, 1H), 8.65 (t, J=6.4 Hz, 1H), 8.15 (d, J=1.2 Hz, 1H), 7.91 (d, J=9.2 Hz, 1H), 7.69 (d, J=8.4 Hz, 2H), 7.63 (dd, J=9.2, 2.0 Hz, 1H), 7.36 (d, J=8.4 Hz, 2H), 4.16-4.03 (m, 2H). LC-MS: m/z 488 [M+H]$^+$.

Example 126: 8-(4-chlorophenyl)-6-(2-methyl-2H-pyrazolo[3,4-b]pyridin-5-yl)-2-((2,2,2-trifluoroethyl)amino)pyrido[4,3-d]pyrimidin-7(6H)-one

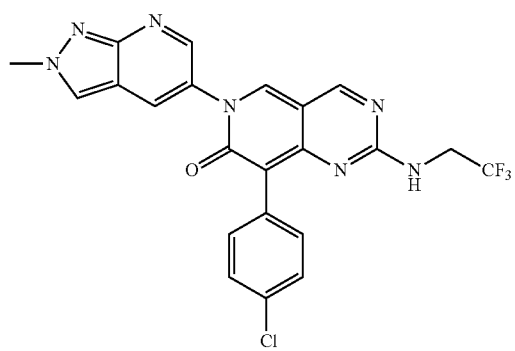 [SMILES: Cn1cc2cc(-n3cc4cnc(NCC(F)(F)F)nc4c(-c4ccc(Cl)cc4)c3=O)cnc2n1]

The title compound was synthesized from intermediate 6a with 5-bromo-2-methyl-2H-pyrazolo[3,4-b]pyridine via general procedure III method A (CuI, N$^1$,N-dimethylcyclohexane-1,2-diamine, Cs$_2$CO$_3$, 1,4-dioxane, 100° C.).

$^1$H NMR (400 MHz, DMSO-d$_6$) δ 8.98 (s, 1H), 8.97 (s, 1H), 8.67 (d, J=2.4 Hz, 1H), 8.65 (t, J=6.4 Hz, 1H), 8.60 (s, 1H), 8.45 (d, J=2.4 Hz, 1H), 7.68 (d, J=8.4 Hz, 2H), 7.36 (d, J=8.8 Hz, 2H), 4.26 (s, 3H), 4.15-4.03 (m, 2H). LC-MS: m/z 486 [M+H]$^+$.

Example 127: 8-(4-chlorophenyl)-6-(1-cyclopropyl-1H-benzo[d]imidazol-6-yl)-2-(2,2,2-trifluoroethylamino)pyrido[4,3-d]pyrimidin-7(6H)-one

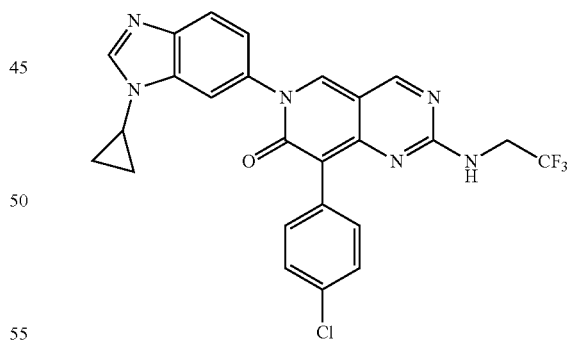

The title compound was synthesized from intermediate 6a with 6-bromo-1-cyclopropyl-1H-benzo[d]imidazole via general procedure III method A (CuI, N$^1$,N$^2$-dimethylcyclohexane-1,2-diamine, Cs$_2$CO$_3$, 1,4-dioxane, 100° C.).

$^1$H NMR (400 MHz, DMSO-d$_6$) δ 8.99 (s, 1H), 8.91 (s, 1H), 8.60 (t, J=6.8 Hz, 1H), 8.38 (s, 1H), 7.87 (d, J=1.6 Hz, 1H), 7.78 (d, J=8.8 Hz, 1H), 7.68 (d, J=8.4 Hz, 2H), 7.36 (d, J=8.4 Hz, 1H), 7.35 (d, J=8.8 Hz, 2H), 4.16-4.02 (m, 2H), 3.57-3.48 (m, 1H), 1.13-1.04 (m, 4H). LC-MS: m/z 511 [M+H]$^+$.

Example 128: 8-(4-chlorophenyl)-6-(1-isopropyl-1H-benzo[d]imidazol-6-yl)-2-(2,2,2-trifluoroethylamino)pyrido[4,3-d]pyrimidin-7(6H)-one

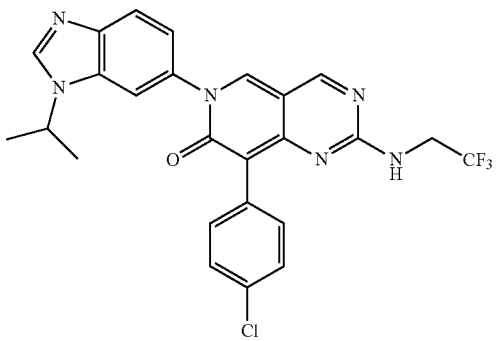 [SMILES: CC(C)n1cnc2ccc(-n3cc4cnc(NCC(F)(F)F)nc4c(-c4ccc(Cl)cc4)c3=O)cc21]

The title compound was synthesized from intermediate 6a with 6-bromo-1-isopropyl-1H-benzo[d]imidazole via general procedure III method A (CuI, $N^1,N^2$-dimethylcyclohexane-1,2-diamine, $Cs_2CO_3$, 1,4-dioxane, 100° C.).

$^1$H NMR (400 MHz, DMSO-$d_6$) δ 9.00 (s, 1H), 8.94 (s, 1H), 8.62 (t, J=6.4 Hz, 1H), 8.51 (s, 1H), 7.93 (d, J=1.6 Hz, 1H), 7.78 (d, J=8.4 Hz, 1H), 7.18 (d, J=8.4 Hz, 2H), 7.36 (d, J=8.4 Hz, 2H), 7.34 (dd, J=8.4, 1.6 Hz, 1H), 4.84-4.74 (m, 1H), 4.16-4.03 (m, 2H), 1.55 (d, J=6.8 Hz, 6H). LC-MS: m/z 513 [M+H]$^+$.

Example 129: 6-(benzo[d]thiazol-6-yl)-8-(4-chlorophenyl)-2-(2,2,2-trifluoroethylamino)pyrido[4,3-d]pyrimidin-7(6H)-one

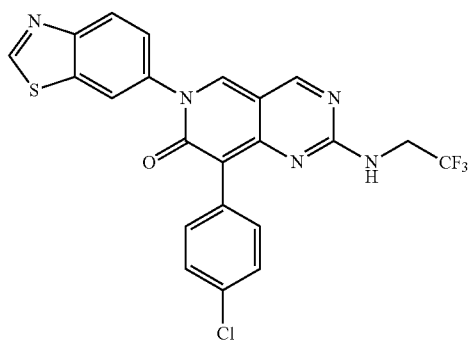 [SMILES: O=c1c(-c2ccc(Cl)cc2)c2nc(NCC(F)(F)F)ncc2cn1-c1ccc2ncsc2c1]

The title compound was synthesized from intermediate 6a with 6-bromobenzo[d]thiazole via general procedure III method A (CuI, $N^1,N^2$-dimethylcyclohexane-1,2-diamine, $Cs_2CO_3$, 1,4-dioxane, 100° C.). LC-MS: m/z 488 [M+H]$^+$.

Example 130: 8-(4-chlorophenyl)-6-(pyrazolo[1,5-a]pyridin-5-yl)-2-(2,2,2-trifluoroethylamino)pyrido[4,3-d]pyrimidin-7(6H)-one

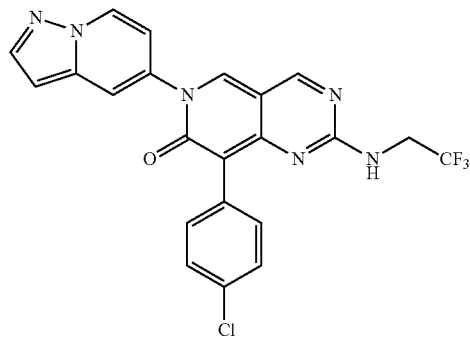 [SMILES: O=c1c(-c2ccc(Cl)cc2)c2nc(NCC(F)(F)F)ncc2cn1-c1ccn2nccc2c1]

The title compound was synthesized from intermediate 6a with 5-bromopyrazolo[1,5-a]pyridine via general procedure III method A (CuI, $N^1,N^2$-dimethylcyclohexane-1,2-diamine, $Cs_2CO_3$, 1,4-dioxane, 100° C.).

$^1$H NMR (400 MHz, DMSO-$d_6$) δ: 8.98 (s, 1H), 8.96 (s, 1H), 8.83 (d, J=7.6 Hz, 1H), 8.67 (t, J=6.4 Hz, 1H), 8.13 (d, J=2.0 Hz, 1H), 7.99 (s, 1H), 7.68 (d, J=8.4 Hz, 2H), 7.37 (d, J=8.4 Hz, 2H), 7.09 (dd, J=7.2 Hz, 2.0 Hz, 1H), 6.79 (d, J=1.2 Hz, 1H), 4.19-4.01 (m, 2H). LC-MS: m/z 471 [M+H]$^+$.

Example 131: 8-(4-chlorophenyl)-6-(cinnolin-6-yl)-2-(2,2,2-trifluoroethylamino)pyrido[4,3-d]pyrimidin-7(6)-one

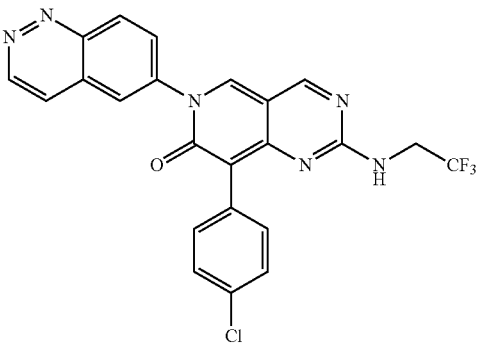 [SMILES: O=c1c(-c2ccc(Cl)cc2)c2nc(NCC(F)(F)F)ncc2cn1-c1ccc2nnccc2c1]

The title compound was synthesized from intermediate 6a with 6-bromocinnoline via general procedure III method A (CuI, $N^1,N^2$-dimethylcyclohexane-1,2-diamine, $Cs_2CO_3$, 1,4-dioxane, 100° C.).

$^1$H NMR (400 MHz, DMSO-$d_6$) δ: 9.51 (d, J=6.0 Hz, 1H), 9.05 (s, 1H), 9.02 (s, 1H), 8.73 (d, J=6.4 Hz, 1H), 8.63 (d, J=8.8 Hz, 1H), 8.37 (d, J=2.0 Hz, 1H), 8.36 (d, J=5.6 Hz, 1H), 8.16 (dd, J=9.2 Hz, 2.4 Hz, 1H), 7.71 (d, J=8.8 Hz, 2H), 7.39 (d, J=8.8 Hz, 2H), 4.18-4.03 (m, 2H). LC-MS: m/z 483 [M+H]$^+$.

Example 132: 8-(4-chlorophenyl)-6-(2,3-dimethyl-2H-indazol-5-yl)-2-(2,2,2-trifluoroethylamino)pyrido[4,3-d]pyrimidin-7(6)-one

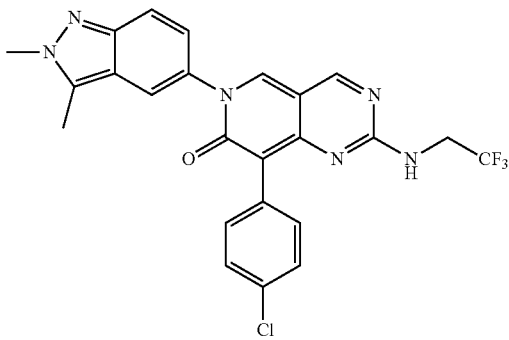 [SMILES: Cc1c2cc(-n3cc4cnc(NCC(F)(F)F)nc4c(-c4ccc(Cl)cc4)c3=O)ccc2nn1C]

The title compound was synthesized from intermediate 6a with 5-bromo-2,3-dimethyl-2H-indazole via general procedure III method A (CuI, $N^1,N^2$-dimethylcyclohexane-1,2-diamine, $Cs_2CO_3$, 1,4-dioxane, 100° C.).

$^1$H NMR (400 MHz, DMSO-d$_6$) δ 8.99 (s, 1H), 8.92 (s, 1H), 8.59 (t, J=6.4 Hz, 1H), 7.89 (d, J=1.2 Hz, 1H), 7.68 (d, J=8.4 Hz, 2H), 7.61 (d, J=8.8 Hz, 1H), 7.36 (d, J=8.8 Hz, 2H), 7.29 (dd, J=9.2 Hz, 2.0 Hz, 1H), 4.15-4.02 (m, 2H), 4.11 (s, 3H), 2.64 (s, 3H). LC-MS: m/z 499 [M+H]$^+$.

Example 133: 8-(4-chlorophenyl)-6-(2,3-dihydrobenzofuran-5-yl)-2-(2,2,2-trifluoroethylamino)pyrido[4,3-d]pyrimidin-7(6H)-one

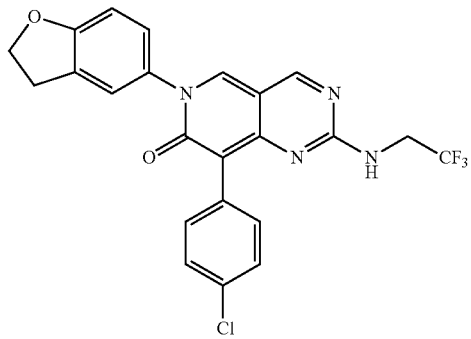 [SMILES: O=c1c(-c2ccc(Cl)cc2)c2nc(NCC(F)(F)F)ncc2cn1-c1ccc2c(c1)CCO2]

The title compound was synthesized from intermediate 6a with 5-bromo-2,3-dihydrobenzofuran via general procedure III method A (CuI, $N^1,N^2$-dimethylcyclohexane-1,2-diamine, $Cs_2CO_3$, 1,4-dioxane, 100° C.).

$^1$H NMR (400 MHz, DMSO-d$_6$) δ: 8.96 (s, 1H), 8.82 (s, 1H), 8.58 (t, J=6.4 Hz, 1H), 7.66 (d, J=8.4 Hz, 2H), 7.04 (s, 1H), 7.35 (d, J=8.4 Hz, 2H), 7.24 (d, J=8.4 Hz, 2H), 6.91 (d, J=8.4 Hz, 1H), 4.63 (d, J=8.8 Hz, 2H), 2.82 (d, J=8.8 Hz, 2H), 4.15-4.03 (m, 2H), 3.26 (t, J=8.8 Hz, 2H). LC-MS: m/z 473 [M+H]$^+$.

Example 134: 8-(4-chlorophenyl)-6-(imidazo[1,2-a]pyridin-6-yl)-2-(2,2,2-trifluoroethylamino)pyrido[4,3-d]pyrimidin-7(6H)-one

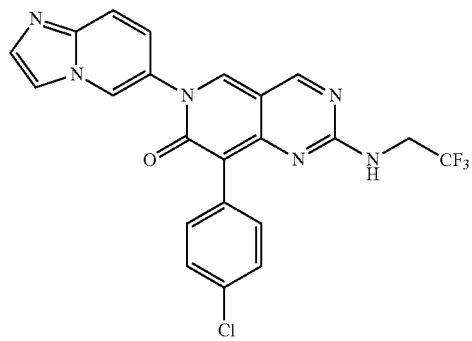 [SMILES: O=c1c(-c2ccc(Cl)cc2)c2nc(NCC(F)(F)F)ncc2cn1-c1ccc2nccn2c1]

The title compound was synthesize from intermediate 6a with 6-bromoimidazo[1,2-a]pyridine via general procedure III method A (CuI, $N^1,N^2$-dimethylcyclohexane-1,2-diamine, $Cs_2CO_3$, 1,4-dioxane, 100° C.).

$^1$H NMR (400 MHz, DMSO-d$_6$) δ 8.98 (s, 1H), 8.97 (s, 1H), 8.69 (t, J=6.4 Hz, 1H), 8.08 (s, 1H), 8.17 (d, J=9.2 Hz, 1H), 8.12 (s, 1H), 7.77-7.63 (m, 3H), 7.43 (dd, J=9.2 Hz, 1.6 Hz, 1H), 7.37 (d, J=8.8 Hz, 2H), 4.17-4.03 (m, 2H). LC-MS: m/z 471 [M+H]$^+$.

Example 135: 8-(4-chlorophenyl)-6-(1-methyl-1H-benzo[d]imidazol-6-yl)-2-(2,2,2-trifluoroethylamino)pyrido[4,3-d]pyrimidin-7(6H)-one

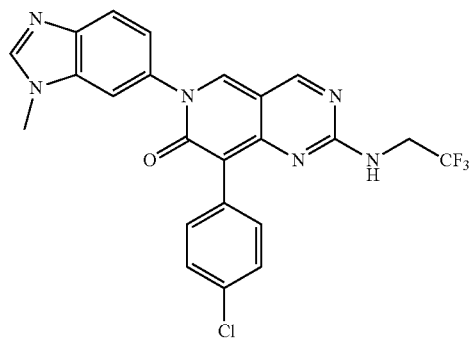 [SMILES: Cn1cnc2ccc(-n3cc4cnc(NCC(F)(F)F)nc4c(-c4ccc(Cl)cc4)c3=O)cc21]

The title compound was synthesized from intermediate 6a with 6-bromo-1-methyl-1H-benzo[d]imidazole via general procedure III method A (CuI, $N^1,N^2$-dimethylcyclohexane-1,2-diamine, $Cs_2CO_3$, 1,4-dioxane, 100° C.).

$^1$H NMR (400 MHz, DMSO-d$_6$) δ: 8.99 (s, 1H), 8.91 (s, 1H), 8.61 (t, J=6.4 Hz, 1H), 8.34 (s, 1H), 7.85 (d, J=2.0 Hz, 1H), 7.78 (d, J=8.4 Hz, 1H), 7.68 (d, J=8.8 Hz, 2H), 7.36 (d, J=8.8 Hz, 2H), 7.35 (dd, J=8.0 Hz, 2.0 Hz, 1H), 4.15-4.02 (m, 2H), 3.87 (s, 3H). LC-MS: m/z 485 [M+H]$^+$.

Example 136: 6-([1,2,4]triazolo[4,3-a]pyridin-6-yl)-8-(4-chlorophenyl)-2-((2,2,2-trifluoroethyl)amino)pyrido[4,3-d]pyrimidin-7(6H)-one

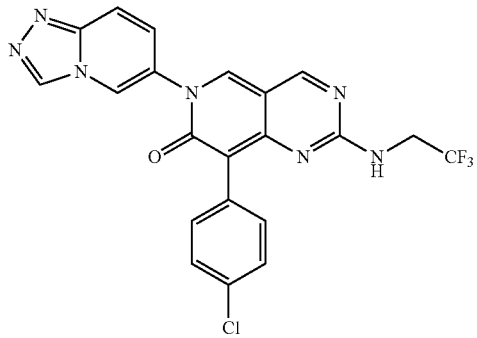 [SMILES: O=c1c(-c2ccc(Cl)cc2)c2nc(NCC(F)(F)F)ncc2cn1-c1ccc2nncn2c1]

The title compound was synthesized from intermediate 6a with 6-bromo-[1,2,4]triazolo[4,3-a]pyridine via general procedure III method A (CuI, N$^1$,N$^2$-dimethylcyclohexane-1,2-diamine, Cs$_2$CO$_3$, 1,4-dioxane, 100° C.).

$^1$H NMR (400 MHz, DMSO-d$_6$) δ: 9.41 (s, 1H), 9.00 (s, 1H), 8.98 (s, 1H), 8.95 (s, 1H), 8.72 (t, J=6.4 Hz, 1H), 7.92 (d, J=9.6 Hz, 1H), 7.68 (d, J=8.4 Hz, 2H), 7.58 (dd, J=9.6 Hz, 1.6 Hz, 1H), 7.37 (d, J=8.4 Hz, 2H), 4.17-4.03 (m, 2H). LC-MS: m/z 472 [M+H]$^+$.

Example 137: 8-(4-chlorophenyl)-6-(2-(2-(dimethylamino)ethyl)-2H-indazol-5-yl)-2-((2,2,2-trifluoroethyl)amino)pyrido[4,3-d]pyrimidin-7(6H)-one

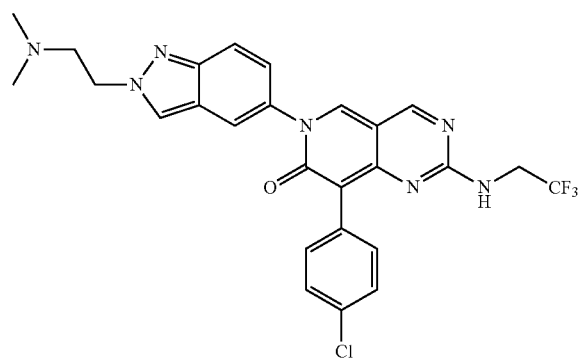 [SMILES: CN(C)CCn1cc2cc(-n3cc4cnc(NCC(F)(F)F)nc4c(-c4ccc(Cl)cc4)c3=O)ccc2n1]

The title compound was synthesized from intermediate 6a with 2-(5-bromo-2H-indazol-2-yl)-N,N-dimethylethanamine via general procedure III method A (CuI, N$^1$,N$^2$-dimethylcyclohexane-1,2-diamine, Cs$_2$CO$_3$, 1,4-dioxane, 100° C.).

$^1$H NMR (400 MHz, DMSO-d$_6$) δ 8.97 (s, 1H), 8.92 (s, 1H), 8.59 (t, J=6.4 Hz, 1H), 8.55 (s, 1H), 7.90 (d, J=1.2 Hz, 1H), 7.71 (d, J=9.2 Hz, 1H), 7.68 (d, J=8.8 Hz, 2H), 7.35 (d, J=8.8 Hz, 2H), 7.33 (dd, J=9.2 Hz, 2.0H, 1H), 4.56 (t, J=6.4 Hz, 2H), 4.14-4.03 (m, 2H), 2.81 (t, J=6.4 Hz, 1H), 2.18 (s, 6H). LC-MS: m/z 542 [M+H]$^+$.

Example 138: 8-(4-chlorophenyl)-6-(2-methylbenzo[d]oxazol-5-yl)-2-((2,2,2-trifluoroethyl)amino)pyrido[4,3-d]pyrimidin-7(6H)-one

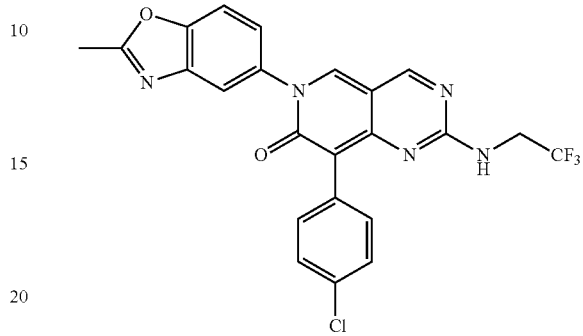

The title compound was synthesized from intermediate 6a with 5-bromo-2-methylbenzo[d]oxazole via general procedure III method A (CuI, N$^1$,N$^2$-dimethylcyclohexane-1,2-diamine, Cs$_2$CO$_3$, 1,4-dioxane, 100° C.).

$^1$H NMR (400 MHz, DMSO-d$_6$) δ 8.97 (s, 1H), 8.90 (s, 1H), 8.61 (t, J=6.4 Hz, 1H), 7.91 (s, 1H), 7.83 (d, J=8.8 Hz, 1H), 7.67 (d, J=8.4 Hz, 2H), 7.52 (d, J=8.4 Hz, 1H), 7.35 (d, J=8.4 Hz, 2H), 4.16-4.01 (m, 2H), 2.67 (s, 3H). LC-MS: m/z 486 [M+H]$^+$.

Example 139: 8-(4-chlorophenyl)-6-(quinolin-6-yl)-2-((2,2,2-trifluoroethyl)amino)pyrido[4,3-d]pyrimidin-7(6)-one

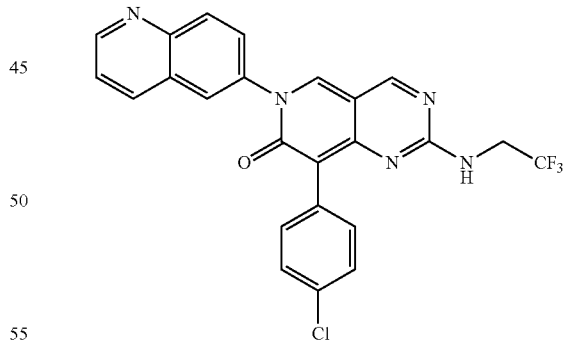

The title compound was synthesized from intermediate 6a with 6-bromoquinoline via general procedure III method A (CuI, N$^1$,N$^2$-dimethylcyclohexane-1,2-diamine, Cs$_2$CO$_3$, 1,4-dioxane, 100° C.).

$^1$H NMR (400 MHz, DMSO-d$_6$) δ 9.03 (d, J=4.0 Hz, 1.6 Hz, 1H), 9.02 (s, 1H), 9.00 (s, 1H), 8.67 (t, J=6.4 Hz, 1H), 8.48 (d, J=8.0 Hz, 1H), 8.24 (d, J=2.0 Hz, 1H), 8.17 (d, J=9.2 Hz, 1H), 7.94 (dd, J=9.2 Hz, 2.4 Hz, 1H), 7.70 (d, J=8.4 Hz, 2H), 7.66 (dd, J=8.4 Hz, 4.0 Hz, 1H), 7.38 (d, J=8.4 Hz, 2H), 4.17-4.03 (m, 2H). LC-MS: m/z 482 [M+H]$^+$.

Example 140: 8-(4-chlorophenyl)-6-(1-methyl-6-oxo-1,6-dihydropyridin-3-yl)-2-((2,2,2-trifluoroethyl)amino)pyrido[4,3-d]pyrimidin-7(6H)-one

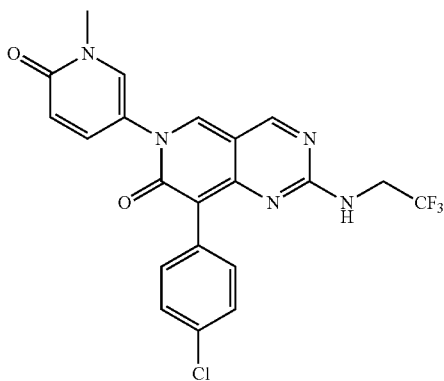 [SMILES: Cn1cc(-n2cc3cnc(NCC(F)(F)F)nc3c(-c3ccc(Cl)cc3)c2=O)ccc1=O]

The title compound was synthesized from intermediate 6a with 5-bromo-1-methylpyridin-2(H)-one via general procedure III method A (CuI, $N^1,N^2$-dimethylcyclohexane-1,2-diamine, $Cs_2CO_3$, 1,4-dioxane, 100° C.).

$^1$H NMR (400 MHz, DMSO-$d_6$) δ 8.95 (s, 1H), 8.86 (s, 1H), 8.65 (t, J=6.4 Hz, 1H), 8.14 (d, J=2.8 Hz, 1H), 7.65 (d, J=8.4 Hz, 2H), 7.63 (dd, J=9.6 Hz, 2.8 Hz, 1H), 7.35 (d, J=8.8 Hz, 2H), 6.48 (d, J=9.6 Hz, 1H), 4.14-4.00 (m, 2H), 3.48 (s, 3H). LC-MS: m/z 462 [M+H]$^+$.

Example 141: 8-(4-chlorophenyl)-6-(1-ethyl-1H-benzo[d]imidazol-6-yl)-2-((2,2,2-trifluoroethyl)amino)pyrido[4,3-d]pyrimidin-7(6H)-one

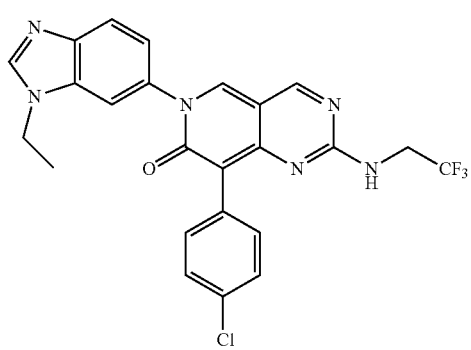 [SMILES: CCn1cnc2ccc(-n3cc4cnc(NCC(F)(F)F)nc4c(-c4ccc(Cl)cc4)c3=O)cc21]

The title compound was synthesized from intermediate 6a with 6-bromo-1-ethyl-1H-benzo[d]imidazole via general procedure III method A (CuI, $N^1,N^2$-dimethylcyclohexane-1,2-diamine, $Cs_2CO_3$, 1,4-dioxane, 100° C.).

$^1$H NMR (400 MHz, DMSO-$d_6$) δ 8.98 (s, 1H), 8.92 (s, 1H), 8.60 (t, J=6.4 Hz, 1H), 8.41 (s, 1H), 7.90 (d, J=1.6 Hz, 1H), 7.78 (d, J=8.4 Hz, 1H), 7.68 (d, J=8.4 Hz, 2H), 7.36 (d, J=8.4 Hz, 2H), 7.34 (dd, J=8.4 Hz, 2.0 Hz, 1H), 4.31 (q, J=7.2 Hz, 2H), 4.15-4.02 (m, 2H), 1.43 (t, J=7.2 Hz, 3H). LC-MS: m/z 499 [M+H]$^+$.

Example 142: 8-(4-chlorophenyl)-6-(2H-indazol-5-yl)-2-((2,2,2-trifluoroethyl)amino)pyrido[4,3-d]pyrimidin-7(6H)-one

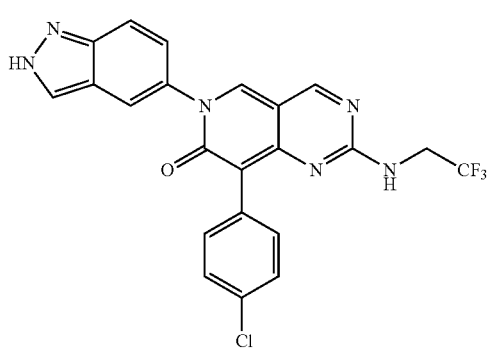 [SMILES: O=c1c(-c2ccc(Cl)cc2)c2nc(NCC(F)(F)F)ncc2cn1-c1ccc2n[nH]cc2c1]

The title compound was synthesized from intermediate 6a with 5-bromo-2-((2-(trimethylsilyl)ethoxy)methyl)-2H-indazole via general procedure III method A (CuI, $N^1,N^2$-dimethylcyclohexane-1,2-diamine, $Cs_2CO_3$, 1,4-dioxane, 100° C.), and then de-protection with TFA via general procedure I (Step F).

$^1$H NMR (400 MHz, DMSO-$d_6$) δ: 13.37 (s, 1H), 8.97 (s, 1H), 8.92 (s, 1H), 8.60 (t, J=6.4 Hz, 1H), 8.21 (s, 1H), 7.95 (d, J=1.6 Hz, 1H), 7.72-7.65 (m, 3H), 7.48 (dd, J=8.8 Hz, 2.0 Hz, 1H), 7.35 (d, J=8.8 Hz, 2H), 4.16-4.02 (m, 2H). LC-MS: m/z 471 [M+H]$^+$.

Preparation of 8-(4-methoxyphenyl)-2-((2,2,2-trifluoroethyl)amino)pyrido[4,3-d]pyrimidin-7(6H)-one 6b

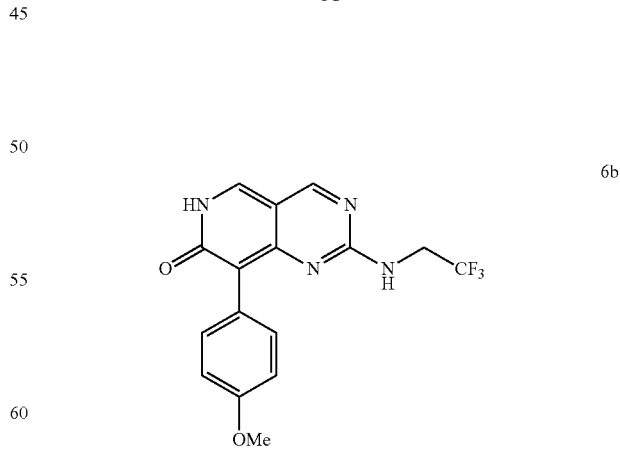

6b 8-(4-methoxyphenyl)-2-((2,2,2-trifluoroethyl)amino)pyrido[4,3-d]pyrimidin-7(6H)-one 6b was synthesized from methyl 2-(4-methoxyphenyl)acetate via general procedure III (Step B-E). LC-MS: m/z 351 [M+H]$^+$.

Example 143: 6-(imidazo[1,2-a]pyridin-6-yl)-8-(4-methoxyphenyl)-2-((2,2,2-trifluoroethyl)amino)pyrido[4,3-d]pyrimidin-7(6H)-one

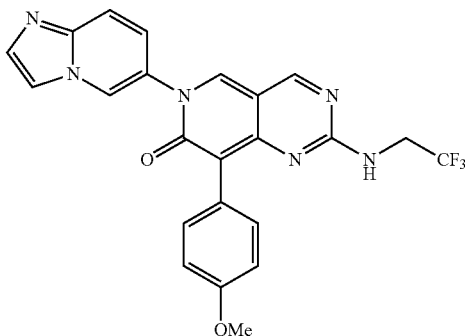 [SMILES: COc1ccc(-c2c(=O)n(-c3ccc4nccn4c3)cc3cnc(NCC(F)(F)F)nc23)cc1]

The title compound was synthesized from intermediate 6b with 6-bromoimidazo[1,2-a]pyridine via general procedure III method A (CuI, $N^1,N^2$-dimethylcyclohexane-1,2-diamine, CsF, 1,4-dioxane, 100° C.).

$^1$H NMR (400 MHz, CDCl$_3$) δ 8.75 (s, 1H), 8.45 (s, 1H), 8.16 (s, 1H), 7.78 (d, J=10.0 Hz, 1H), 7.76 (s, 1H), 7.71-7.65 (m, 3H), 7.25 (dd, J=10.0, 2.0 Hz, 1H), 6.96 (d, J=8.8 Hz, 2H), 5.81 (t, J=6.4 Hz, 1H), 4.21-4.07 (m, 2H), 3.86 (s, 3H). LC-MS: m/z 467 [M+H]$^+$.

Example 144: 8-(4-methoxyphenyl)-6-(quinoxalin-6-yl)-2-((2,2,2-trifluoroethyl)amino)pyrido[4,3-d]pyrimidin-7(6H)-one

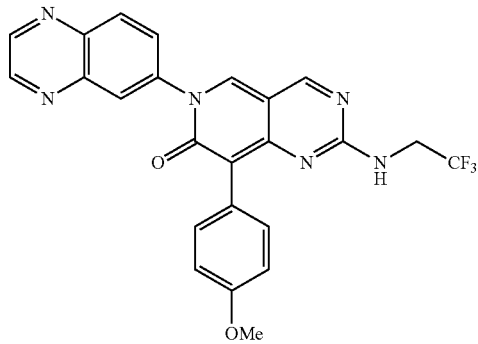 [SMILES: COc1ccc(-c2c(=O)n(-c3ccc4nccnc4c3)cc3cnc(NCC(F)(F)F)nc23)cc1]

The title compound was synthesized from intermediate 6b with 6-bromoquinoxaline via general procedure III method A (CuI, $N^1,N^2$-dimethylcyclohexane-1,2-diamine, CsF, 1,4-dioxane, 100° C.).

$^1$H NMR (400 MHz, DMSO-d$_6$) δ 8.88 (d, J=2.0 Hz, 1H), 8.86 (d, J=2.0 Hz, 1H), 8.70 (s, 1H), 8.19 (s, 1H), 8.18 (d, J=8.8 Hz, 1H), 8.11 (d, J=2.4 Hz, 1H), 7.91 (dd, J=8.8 Hz, 2.4 Hz, 1H), 7.66 (d, J=8.8 Hz, 2H), 6.89 (d, J=8.8 Hz, 2H), 5.71 (t, J=6.4 Hz, 1H), 4.14-4.03 (m, 2H), 3.79 (s, 3H). LC-MS: m/z 479 [M+H]$^+$.

Example 145: 8-(4-methoxyphenyl)-6-(4-methyl-3,4-dihydro-2H-benzo[b][1,4]oxazin-6-yl)-2-((2,2,2-trifluoroethyl)amino)pyrido[4,3-d]pyrimidin-7(6H)-one

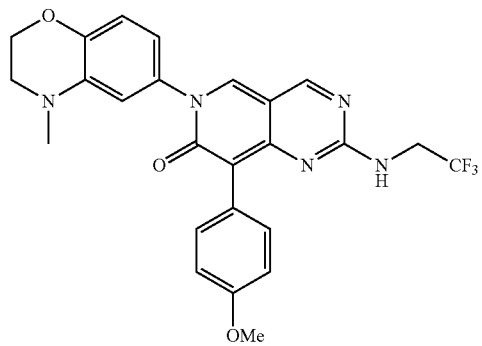

The title compound was synthesized from intermediate 6b with 6-bromo-4-methyl-3,4-dihydro-2H-benzo[b][1,4]oxazine via general procedure III method A (CuI, $N^1,N^2$-dimethylcyclohexane-1,2-diamine, CsF, 1,4-dioxane, 100° C.).

$^1$H NMR (400 MHz, DMSO-d$_6$) δ 8.69 (s, 1H), 8.13 (s, 1H), 7.72 (d, J=8.4 Hz, 2H), 6.94 (d, J=8.8 Hz, 2H), 6.84 (d, J=8.0 Hz, 1H), 6.69 (d, J=8.8 Hz, 1H), 6.61 (dd, J=8.0 Hz, 2.4 Hz, 1H), 5.72 (t, J=6.4 Hz, 1H), 4.32 (t, J=4.4 Hz, 2H), 4.18-4.06 (m, 2H), 3.84 (s, 3H), 3.31 (t, J=4.4 Hz, 2H), 2.88 (s, 3H). LC-MS: m/z 498 [M+H]$^+$.

Example 146: 8-(4-methoxyphenyl)-6-(quinazolin-6-yl)-2-((2,2,2-trifluoroethyl)amino)pyrido[4,3-d]pyrimidin-7(6H)-one

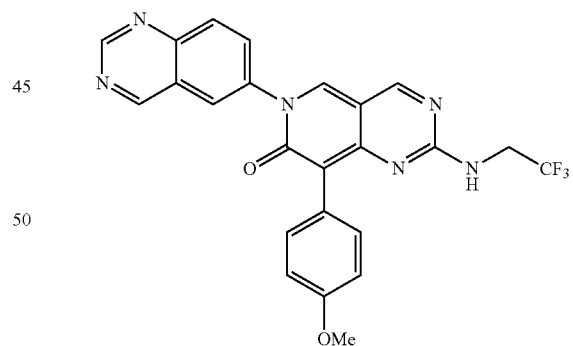

The title compound was synthesized from intermediate 6b with 6-bromoquinazoline via general procedure III method A (CuI, $N^1,N^2$-dimethylcyclohexane-1,2-diamine, CsF, 1,4-dioxane, 100° C.).

$^1$H NMR (400 MHz, DMSO-d$_6$) δ 9.73 (s, 1H), 9.43 (s, 1H), 9.00 (s, 1H), 8.97 (s, 1H), 8.61 (t, J=6.4 Hz, 1H), 8.44 (d, J=2.0 Hz, 1H), 8.23 (dd, J=8.8 Hz, 2.4 Hz, 1H), 8.18 (d, J=8.8 Hz, 1H), 7.62 (d, J=8.4 Hz, 2H), 6.89 (d, J=8.8 Hz, 2H), 4.18-4.04 (m, 2H), 3.78 (s, 3H). LC-MS: m/z 479 [M+H]$^+$.

Example 147: 6-(2,3-dihydrobenzofuran-5-yl)-8-(4-methoxyphenyl)-2-((2,2,2-trifluoroethyl)amino)pyrido[4,3-d]pyrimidin-7(6H)-one

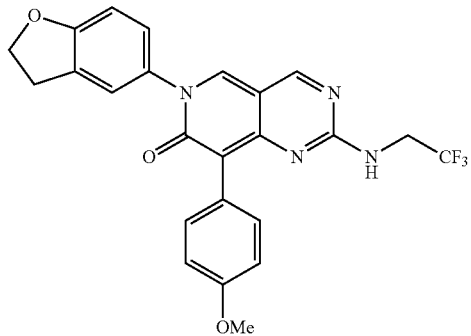 [SMILES: COc1ccc(-c2c(=O)n(-c3ccc4c(c3)CCO4)cc3cnc(NCC(F)(F)F)nc23)cc1]

The title compound was synthesized from intermediate 6b with 5-bromo-2,3-dihydrobenzofuran via general procedure III method A (CuI, $N^1,N^2$-dimethylcyclohexane-1,2-diamine, CsF, 1,4-dioxane, 100° C.).
$^1$H NMR (400 MHz, CDCl$_3$) δ 8.70 (s, 1H), 8.13 (s, 1H), 7.71 (d, J=8.8 Hz, 2H), 7.31 (s, 1H), 7.11 (dd, J=8.4 Hz, 2.0 Hz, 1H), 6.94 (d, J=8.8 Hz, 2H), 6.87 (d, J=8.4 Hz, 1H), 5.69 (t, J=5.6 Hz, 1H), 4.66 (t, J=8.8 Hz, 2H), 4.21-4.07 (m, 2H), 3.85 (s, 3H), 3.27 (t, J=8.8 Hz, 2H). LC-MS: m/z 469 [M+H]$^+$.

Preparation of 8-(4-(difluoromethoxy)phenyl)-2-((2,2,2-trifluoroethyl)amino)pyrido[4,3-d]pyrimidin-7(6H)-one 6c

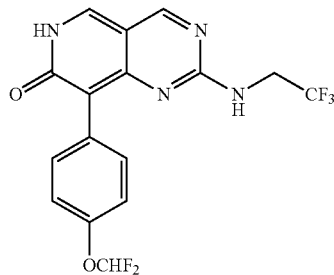

6c 8-(4-(difluoromethoxy)phenyl)-2-((2,2,2-trifluoroethyl)amino)pyrido[4,3-d]pyrimidin-7(6H)-one 6c was synthesized from methyl 2-(4-(difluoromethoxy)phenyl)acetate via general procedure III (Step B-E). LC-MS: m/z 387 [M+H]$^+$.

Example 148: 8-(4-(difluoromethoxy)phenyl)-6-(2-methyl-2H-indazol-5-yl)-2-((2,2,2-trifluoroethyl)amino)pyrido[4,3-d]pyrimidin-7(6H)-one

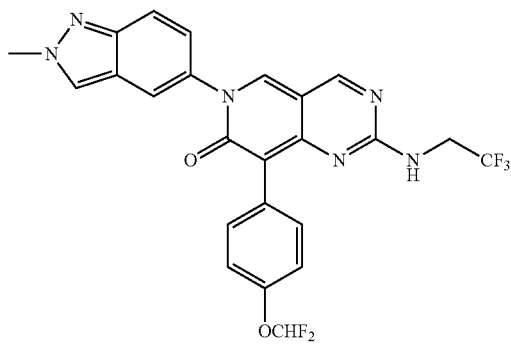 [SMILES: Cn1cc2cc(-n3cc4cnc(NCC(F)(F)F)nc4c(-c4ccc(OC(F)F)cc4)c3=O)ccc2n1]

The title compound was synthesized from intermediate 6c with 5-bromo-2-methyl-2H-indazole via general procedure III method A (CuI, $N^1,N^2$-dimethylcyclohexane-1,2-diamine, CsF, 1,4-dioxane, 100° C.).
$^1$H NMR (400 MHz, DMSO-d$_6$) δ: 8.97 (s, 1H), 8.90 (s, 1H), 8.57 (t, J=6.4 Hz, 1H), 8.51 (s, 1H), 7.90 (d, J=1.2 Hz, 1H), 7.72-7.69 (m, 3H), 7.34 (dd, J=9.2 Hz, 2.0 Hz, 1H), 7.26 (t, J$_{HF}$=74.4 Hz, 1H), 7.11 (d, J=8.8 Hz, 2H), 4.22 (s, 3H), 4.15-4.02 (m, 2H). LC-MS: m/z 517 [M+H]$^+$.

Example 149: 8-(4-(difluoromethoxy)phenyl)-6-(2-methylbenzo[d]oxazol-5-yl)-2-((2,2,2-trifluoroethyl)amino)pyrido[4,3-d]pyrimidin-7(6H)-one

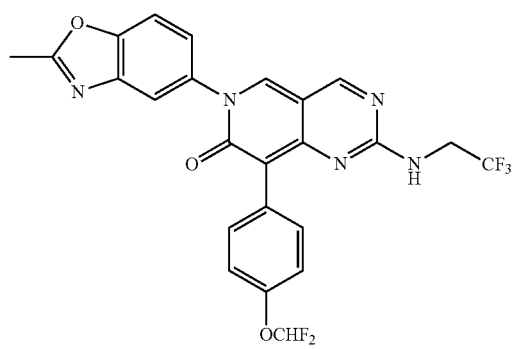 [SMILES: Cc1nc2cc(-n3cc4cnc(NCC(F)(F)F)nc4c(-c4ccc(OC(F)F)cc4)c3=O)ccc2o1]

The title compound was synthesized from intermediate 6c with 5-bromo-2-methylbenzo[d]oxazole via general procedure III method A (CuI, $N^1,N^2$-dimethylcyclohexane-1,2-diamine, CsF, 1,4-dioxane, 100° C.).
$^1$H NMR (400 MHz, DMSO-d$_6$) δ: 8.97 (s, 1H), 8.89 (s, 1H), 8.59 (t, J=6.0 Hz, 1H), 7.91 (d, J=2.0 Hz, 1H), 7.84 (d, J=8.4 Hz, 1H), 7.70 (d, J=8.8 Hz, 2H), 7.52 (dd, J=8.8 Hz, 2.0 Hz, 1H), 7.26 (t, J$_{HF}$=74.4 Hz, 1H), 7.11 (d, J=8.8 Hz, 2H), 4.15-4.01 (m, 2H), 2.67 (s, 3H). LC-MS: m/z 518 [M+H]$^+$.

Example 150: 8-(4-(difluoromethoxy)phenyl)-6-(2-methylbenzo[d]thiazol-6-yl)-2-((2,2,2-trifluoroethyl)amino)pyrido[4,3-d]pyrimidin-7(6H)-one

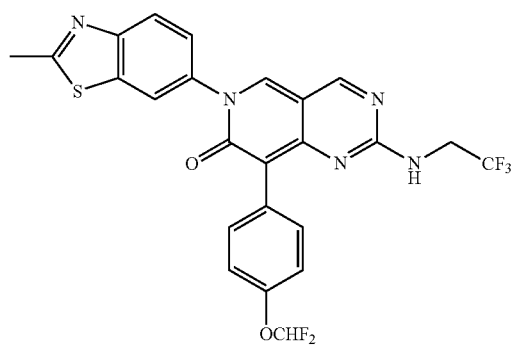 [SMILES: Cc1nc2ccc(-n3cc4cnc(NCC(F)(F)F)nc4c(-c4ccc(OC(F)F)cc4)c3=O)cc2s1]

The title compound was synthesized from intermediate 6c with 6-bromo-2-methylbenzo[d]thiazole via general procedure III method A (CuI, $N^1,N^2$-dimethylcyclohexane-1,2-diamine, CsF, 1,4-dioxane, 100° C.).
$^1$H NMR (400 MHz, DMSO-d$_6$) δ 8.98 (s, 1H), 8.94 (s, 1H), 8.63 (t, J=6.4 Hz, 1H), 8.29 (d, J=2.0 Hz, 1H), 8.07 (d, J=8.4 Hz, 1H), 7.71 (d, J=8.8 Hz, 2H), 7.65 (dd, J=8.8 Hz, 2.4 Hz, 1H), 7.27 (t, J$_{HF}$=74.4 Hz, 1H), 7.12 (d, J=8.8 Hz, 2H), 4.15-4.03 (m, 2H), 2.87 (s, 3H). LC-MS: m/z 534 [M+H]$^+$.

Example 151: 8-(4-(difluoromethoxy)phenyl)-6-(1-methyl-1H-benzo[d]imidazol-6-yl)-2-((2,2,2-trifluoroethyl)amino)pyrido[4,3-d]pyrimidin-7(6H)-one

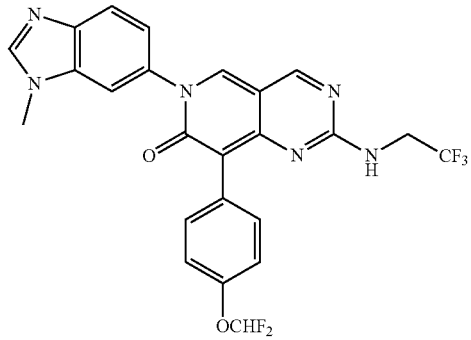 [SMILES: Cn1cnc2ccc(-n3cc4cnc(NCC(F)(F)F)nc4c(-c4ccc(OC(F)F)cc4)c3=O)cc21]

The title compound was synthesized from intermediate 6c with 6-bromo-1-methyl-1H-benzo[d]imidazole via general procedure III method A (CuI, N$^1$,N$^2$-dimethylcyclohexane-1,2-diamine, CsF, 1,4-dioxane, 100° C.).

$^1$H NMR (400 MHz, DMSO-d$_6$) δ: 8.98 (s, 1H), 8.70 (s, 1H), 8.59 (t, J=6.4 Hz, 1H), 8.35 (br s, 1H), 7.86 (d, J=1.2 Hz, 1H), 7.78 (d, J=8.4 Hz, 1H), 7.70 (d, J=8.8 Hz, 2H), 7.34 (d, J=8.4 Hz, 2.0 Hz, 1H), 7.28 (t, J$_{HF}$=74.4 Hz, 1H), 7.11 (d, J=8.8 Hz, 2H), 4.15-4.02 (m, 2H), 3.87 (s, 3H). LC-MS: m/z 517 [M+H]$^+$.

Example 152: 8-(4-(difluoromethoxy)phenyl)-6-(2-ethyl-2H-indazol-5-yl)-2-((2,2,2-trifluoroethyl)amino)pyrido[4,3-d]pyrimidin-7(6H)-one

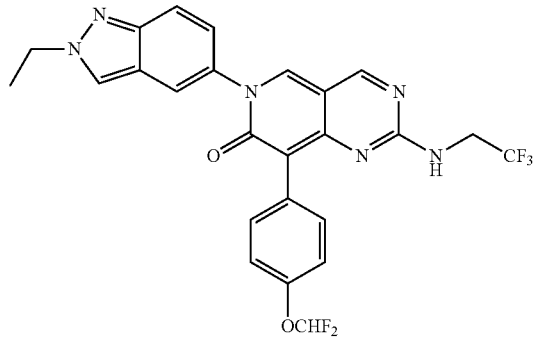 [SMILES: CCn1cc2cc(-n3cc4cnc(NCC(F)(F)F)nc4c(-c4ccc(OC(F)F)cc4)c3=O)ccc2n1]

The title compound was synthesized from intermediate 6c with 5-bromo-2-ethyl-2H-indazole via general procedure III method A (CuI, N$^1$,N$^2$-dimethylcyclohexane-1,2-diamine, CsF, 1,4-dioxane, 100° C.).

$^1$HNMR (400 MHz, DMSO-d$_6$) δ: 8.97 (s, 1H), 8.89 (s, 1H), 8.57 (t, J=6.4 Hz, 1H), 8.56 (s, 1H), 7.90 (d, J=1.2 Hz, 1H), 7.75-7.67 (m, 3H), 7.33 (dd, J=9.2 Hz, 2.0 Hz, 1H), 7.26 (t, J$_{HF}$=74.4 Hz, 1H), 7.11 (d, J=8.4 Hz, 2H), 4.51 (q, J=7.2 Hz, 2H), 4.17-4.02 (m, 2H), 1.54 (t, J=7.2 Hz, 3H). LC-MS: m/z 531 [M+H]$^+$.

Example 153: 8-(4-(difluoromethoxy)phenyl)-6-(2-isopropyl-2H-indazol-5-yl)-2-((2,2,2-trifluoroethyl)amino)pyrido[4,3-d]pyrimidin-7(6H)-one

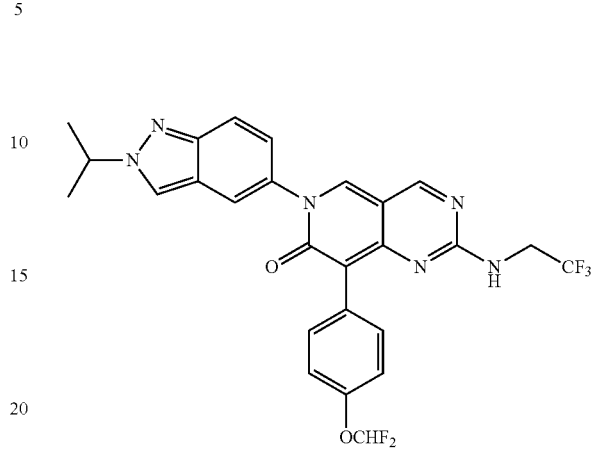

The title compound was synthesized from intermediate 6c with 5-bromo-2-isopropyl-2H-indazole via general procedure III method A (CuI, N$^1$,N$^2$-dimethylcyclohexane-1,2-diamine, CsF, 1,4-dioxane, 100° C.).

$^1$HNMR (400 MHz, DMSO-d$_6$) δ: 8.97 (s, 1H), 8.88 (s, 1H), 8.58 (s, 1H), 8.57 (t, J=6.4 Hz, 1H), 7.88 (d, J=1.6 Hz, 1H), 7.75-7.67 (m, 3H), 7.32 (dd, J=8.8 Hz, 2.0 Hz, 1H), 7.26 (t, J$_{HF}$=74.4 Hz, 1H), 7.11 (d, J=8.8 Hz, 2H), 4.89 (hept, J=6.8 Hz, 1H), 4.15-4.02 (m, 2H), 1.58 (d, J=6.8 Hz, 6H). LC-MS: m/z 545 [M+H]$^+$.

Example 154: 6-(2-cyclopropyl-2H-indazol-5-yl)-8-(4-(difluoromethoxy)phenyl)-2-((2,2,2-trifluoroethyl)amino)pyrido[4,3-d]pyrimidin-7(6H)-one

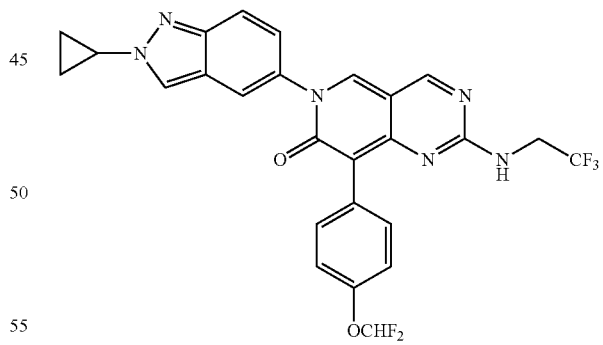

The title compound was synthesized from intermediate 6c with 5-bromo-2-cyclopropyl-2H-indazole via general procedure III method A (CuI, N$^1$,N$^2$-dimethylcyclohexane-1,2-diamine, CsF, 1,4-dioxane, 100° C.).

$^1$H NMR (400 MHz, DMSO-d$_6$) δ 8.98 (s, 1H), 8.89 (s, 1H), 8.65 (s, 1H), 8.57 (t, J=6.4 Hz, 1H), 7.87 (d, J=1.6 Hz, 1H), 7.73-7.66 (m, 3H), 7.33 (dd, J=9.2 Hz, 2.0 Hz, 1H), 7.26 (t, J$_{HF}$=74.4 Hz, 1H), 7.11 (d, J=8.4 Hz, 2H), 4.27-4.17 (m, 1H), 4.15-4.01 (m, 2H), 1.37-1.28 (m, 2H), 1.19-1.10 (m, 2H). LC-MS: m/z 543 [M+H]$^+$.

Example 155: 8-(4-(difluoromethoxy)phenyl)-6-(1-methyl-6-oxo-1,6-dihydropyridin-3-yl)-2-((2,2,2-trifluoroethyl)amino)pyrido[4,3-d]pyrimidin-7(6H)-one

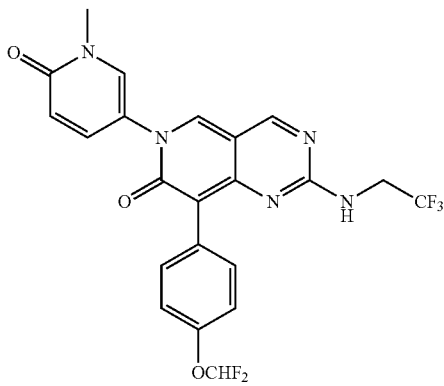 [SMILES: Cn1cc(-n2cc3cnc(NCC(F)(F)F)nc3c(-c3ccc(OC(F)F)cc3)c2=O)ccc1=O]

The title compound was synthesized from intermediate 6c with 5-bromo-1-methylpyridin-2(H)-one via general procedure III method A (CuI, $N^1,N^2$-dimethylcyclohexane-1,2-diamine, CsF, 1,4-dioxane, 100° C.).

$^1$H NMR (400 MHz, DMSO-d$_6$) δ 8.95 (s, 1H), 8.86 (s, 1H), 8.66 (t, J=6.4 Hz, 1H), 8.16 (d, J=2.0 Hz, 1H), 7.67 (d, J=8.8 Hz, 2H), 7.63 (dd, J=10.0 Hz, 2.8 Hz, 1H), 7.28 (t, $J_{HF}$=74.4 Hz, 1H), 7.11 (d, J=8.8 Hz, 2H), 6.48 (d, J=9.2 Hz, 1H), 4.14-4.02 (m, 2H), 3.48 (s, 3H). LC-MS: m/z 494 [M+H]$^+$.

Example 156: 6-(benzo[d]thiazol-6-yl)-8-(4-(difluoromethoxy)phenyl)-2-((2,2,2-trifluoroethyl)amino)pyrido[4,3-d]pyrimidin-7(6H)-one

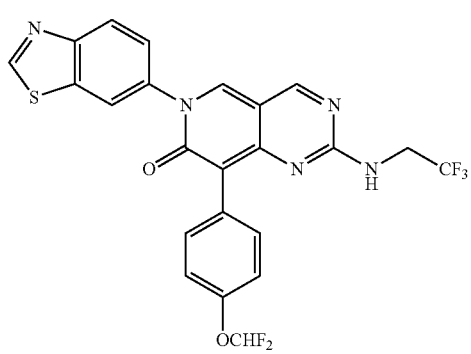 [SMILES: O=c1c(-c2ccc(OC(F)F)cc2)c2nc(NCC(F)(F)F)ncc2cn1-c1ccc2ncsc2c1]

The title compound was synthesized from intermediate 6c with 6-bromobenzo[d]thiazole via general procedure III method A (CuI, $N^1,N^2$-dimethylcyclohexane-1,2-diamine, CsF, 1,4-dioxane, 100° C.).

$^1$H NMR (400 MHz, DMSO-d$_6$) δ 9.55 (s, 1H), 8.98 (s, 1H), 8.96 (s, 1H), 8.64 (t, J=6.0 Hz, 1H), 8.44 (d, J=1.2 Hz, 1H), 8.26 (d, J=8.4 Hz, 1H), 7.78-7.66 (m, 3H), 7.27 (t, $J_{HF}$=74.4 Hz, 1H), 7.13 (d, J=8.4 Hz, 2H), 4.18-4.02 (m, 2H). LC-MS: m/z 520 [M+H]$^+$.

Example 157: 8-(4-(difluoromethoxy)phenyl)-6-(imidazo[1,2-a]pyridin-6-yl)-2-((2,2,2-trifluoroethyl)amino)pyrido[4,3-d]pyrimidin-7(6)-one

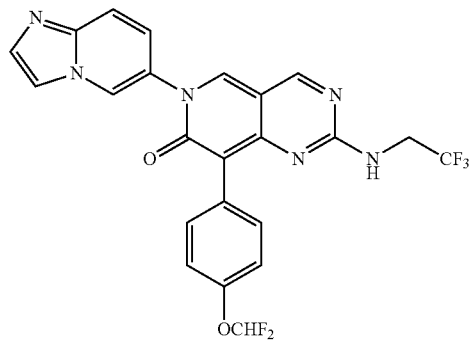 [SMILES: O=c1c(-c2ccc(OC(F)F)cc2)c2nc(NCC(F)(F)F)ncc2cn1-c1ccc2nccn2c1]

The title compound was synthesized from intermediate 6c with 6-bromoimidazo[1,2-a]pyridine via general procedure III method A (CuI, $N^1,N^2$-dimethylcyclohexane-1,2-diamine, CsF, 1,4-dioxane, 100° C.).

$^1$H NMR (400 MHz, DMSO-d$_6$) δ 9.16 (s, 1H), 9.00 (s, 1H), 8.95 (s, 1H), 8.70 (t, J=6.4 Hz, 1H), 8.27 (s, 1H), 7.91 (s, 1H), 7.90 (d, J=9.6 Hz, 1H), 7.77 (d, J=9.2 Hz, 1H), 7.70 (d, J=8.8 Hz, 2H), 7.27 (t, $J_{HF}$=74.4 Hz, 1H), 7.13 (d, J=8.8 Hz, 2H), 4.17-4.03 (m, 2H). LC-MS: m/z 503 [M+H]$^+$.

Example 158: 8-(4-(difluoromethoxy)phenyl)-6-(2,3-dimethyl-2H-indazol-5-yl)-2-((2,2,2-trifluoroethyl)amino)pyrido[4,3-d]pyrimidin-7(6H)-one

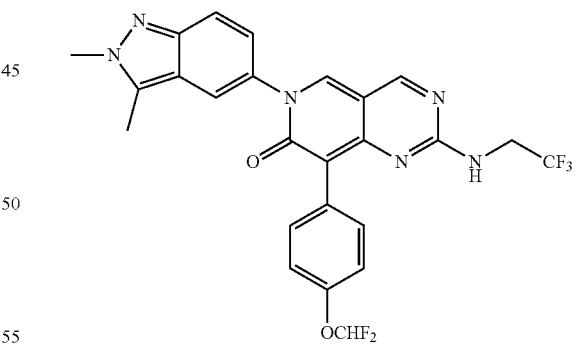

The title compound was synthesized from intermediate 6c with 5-bromo-2,3-dimethyl-2H-indazole via general procedure III method A (CuI, $N^1,N^2$-dimethylcyclohexane-1,2-diamine, CsF, 1,4-dioxane, 100° C.).

$^1$H NMR (400 MHz, DMSO-d$_6$) δ 8.98 (s, 1H), 8.90 (s, 1H), 8.56 (t, J=6.4 Hz, 1H), 7.89 (d, J=1.6 Hz, 1H), 7.70 (d, J=8.8 Hz, 2H), 7.60 (d, J=9.2 Hz, 1H), 7.29 (dd, J=9.2 Hz, 2.0 Hz, 1H), 7.27 (t, $J_{HF}$=74.4 Hz, 1H), 7.11 (d, J=8.8 Hz, 2H), 4.10 (s, 3H), 4.15-4.02 (m, 2H), 2.64 (s, 3H). LC-MS: m/z 531 [M+H]$^+$.

Example 159: 8-(4-(difluoromethoxy)phenyl)-6-(quinolin-6-yl)-2-((2,2,2-trifluoroethyl)amino)pyrido[4,3-d]pyrimidin-7(6H)-one

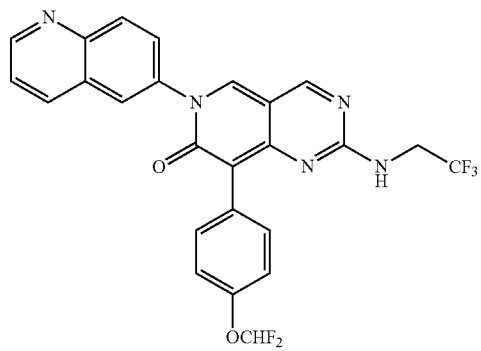 [SMILES: O=c1c(-c2ccc(OC(F)F)cc2)c2nc(NCC(F)(F)F)ncc2cn1-c1ccc2ncccc2c1]

The title compound was synthesized from intermediate 6c with 6-bromoquinoline via general procedure III method A (CuI, $N^1,N^2$-dimethylcyclohexane-1,2-diamine, CsF, 1,4-dioxane, 100° C.).

$^1$H NMR (400 MHz, DMSO-$d_6$) δ 9.03 (s, 1H), 9.01 (s, 1H), 9.00 (s, 1H), 8.85 (t, J=6.4 Hz, 1H), 8.49 (d, J=8.0 Hz, 1H), 8.25 (d, J=2.4 Hz, 1H), 8.17 (d, J=8.8 Hz, 1H), 7.95 (dd, J=8.8 Hz, 2.4 Hz, 1H), 7.73 (d, J=8.8 Hz, 2H), 7.67 (dd, J=8.4 Hz, 4.4 Hz, 1H), 7.27 (t, $J_{HF}$=74.4 Hz, 1H), 7.13 (d, J=8.8 Hz, 2H), 4.17-4.03 (m, 2H). LC-MS: m/z 514 [M+H]$^+$.

Preparation of 2-((2,2,2-trifluoroethyl)amino)-8-(4-(trifluoromethoxy)phenyl)pyrido[4,3-d]pyrimidin-7(6H)-one 6d

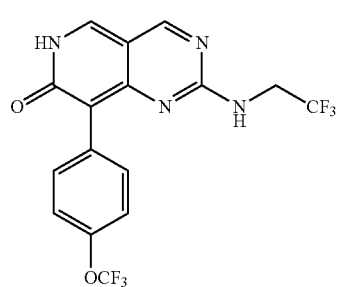

6d 8-(4-(difluoromethoxy)phenyl)-2-((2,2,2-trifluoroethyl)amino)pyrido[4,3-d]pyrimidin-7(6H)-one 6d was synthesized from methyl 2-(4-(trifluoromethoxy)phenyl)acetate via general procedure III (Step B-E). LC-MS: m/z 405 [M+H]$^+$.

Example 160: Preparation of 6-(2-methyl-2H-indazol-5-yl)-2-((2,2,2-trifluoroethyl)amino)-8-(4-(trifluoromethoxy)phenyl)pyrido[4,3-d]pyrimidin-7(6H)-one

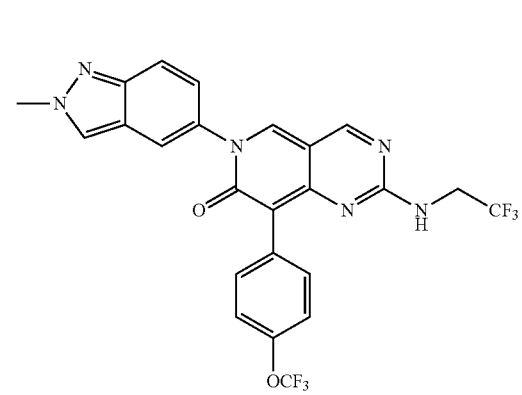 [SMILES: Cn1cc2cc(-n3cc4cnc(NCC(F)(F)F)nc4c(-c4ccc(OC(F)(F)F)cc4)c3=O)ccc2n1]

The title compound was synthesized from intermediate 6d with 5-bromo-2-methyl-2H-indazole via general procedure III method A (CuI, $N^1,N^2$-dimethylcyclohexane-1,2-diamine, CsF, 1,4-dioxane, 100° C.).

$^1$H NMR (400 MHz, DMSO-$d_6$) δ: 8.98 (s, 1H), 8.93 (s, 1H), 8.60 (t, J=6.0 Hz, 1H), 8.51 (s, 1H), 7.91 (d, J=1.2 Hz, 1H), 7.76 (d, J=8.8 Hz, 2H), 7.71 (d, J=9.1 Hz, 1H), 7.34 (dd, J=9.2 Hz, 2.0 Hz, 1H), 7.29 (d, J=8.4 Hz, 2H), 4.22 (s, 3H), 4.14-4.00 (m, 2H). LC-MS: m/z 535 [M+H]$^+$.

Preparation of 2-((2,2,2-trifluoroethyl)amino)-8-(4-(trifluoromethyl)phenyl)pyrido[4,3-d]pyrimidin-7(6H)-one 6e

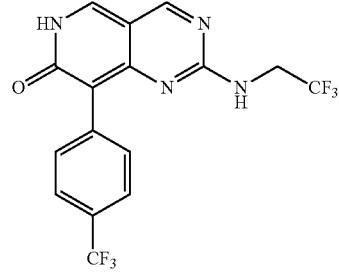

6e 2-((2,2,2-trifluoroethyl)amino)-8-(4-(trifluoromethyl)phenyl)pyrido[4,3-d]pyrimidin-7(6H)-one 6e was synthesized from methyl 2-(4-(trifluoromethyl)phenyl)acetate via general procedure III (Step B-E). LC-MS: m/z 389 [M+H]$^+$.

Example 161: Preparation of 6-(2-methyl-2H-indazol-5-yl)-2-((2,2,2-trifluoroethyl)amino)-8-(4-(trifluoromethyl)phenyl)pyrido[4,3-d]pyrimidin-7(6H)-one

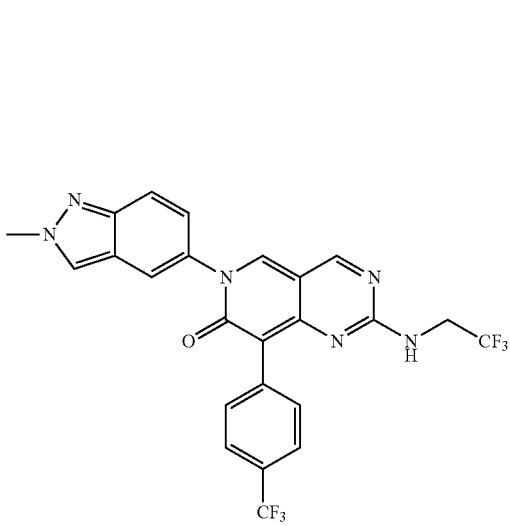 [SMILES: Cn1cc2cc(-n3cc4cnc(NCC(F)(F)F)nc4c(-c4ccc(C(F)(F)F)cc4)c3=O)ccc2n1]

The title compound was synthesized from intermediate 6e with 5-bromo-2-methyl-2H-indazole via general procedure III method A (CuI, $N^1,N^2$-dimethylcyclohexane-1,2-diamine, CsF, 1,4-dioxane, 100° C.).

$^1$H NMR (400 MHz, DMSO-$d_6$) δ: 9.00 (s, 1H), 8.97 (s, 1H), 8.65 (t, J=6.4 Hz, 1H), 8.52 (s, 1H), 7.92 (d, J=1.2 Hz, 1H), 7.88 (d, J=8.4 Hz, 2H), 7.71 (d, J=9.2 Hz, 1H), 7.65 (d, J=8.4 Hz, 2H), 7.35 (dd, J=9.2 Hz, 2.0 Hz, 1H), 4.23 (s, 3H), 4.13-4.00 (m, 2H). LC-MS: m/z 519 [M+H]$^+$.

Preparation of 8-(4-cyclopropylphenyl)-2-((2,2,2-trifluoroethyl)amino)pyrido[4,3-d]pyrimidin-7(6H)-one 6f

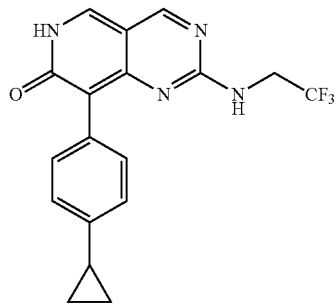

6f 8-(4-cyclopropylphenyl)-2-((2,2,2-trifluoroethyl)amino)pyrido[4,3-d]pyrimidin-7(6H)-one 6f was synthesized from methyl 2-(4-cyclopropylphenyl)acetate via general procedure III (Step B-E). LC-MS: m/z 361 [M+H]$^+$.

Example 162: Preparation of 8-(4-cyclopropylphenyl)-6-(2-methylquinolin-6-yl)-2-((2,2,2-trifluoroethyl)amino)pyrido[4,3-d]pyrimidin-7(6H)-one

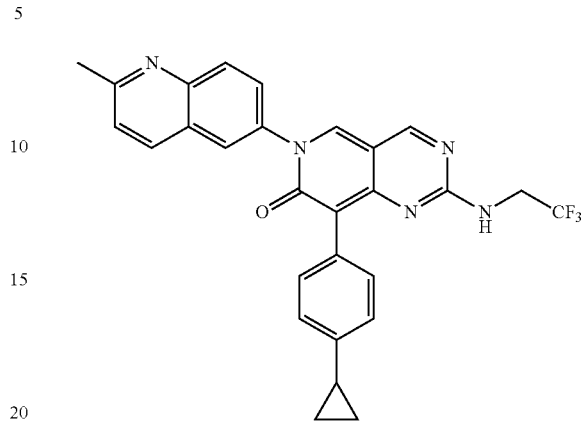

The title compound was synthesized from intermediate 6f with 6-bromo-2-methylquinoline via general procedure III method A (CuI, $N^1,N^2$-dimethylcyclohexane-1,2-diamine, CsF, 1,4-dioxane, 100° C.).

$^1$H NMR (400 MHz, DMSO-$d_6$) δ 8.97 (s, 1H), 8.94 (s, 1H), 8.56 (t, J=6.4 Hz, 1H), 8.34 (d, J=8.4 Hz, 1H), 8.15 (d, J=2.4 Hz, 1H), 8.04 (d, J=9.2 Hz, 1H), 7.86 (dd, J=8.8 Hz, 2.4 Hz, 1H), 7.55 (d, J=8.0 Hz, 2H), 7.54 (d, J=8.4 Hz, 1H), 7.01 (d, J=8.0 Hz, 2H), 4.16-4.03 (m, 2H), 2.71 (s, 3H), 1.98-1.86 (m, 1H), 0.99-0.91 (m, 2H), 0.71-0.63 (m, 2H). LC-MS: m/z 520 [M+H]$^+$.

Example 163: 8-(4-cyclopropylphenyl)-2-((2,2,2-trifluoroethyl)amino)-6-(2-(trifluoromethyl)quinolin-6-yl)pyrido[4,3-d]pyrimidin-7(6H)-one

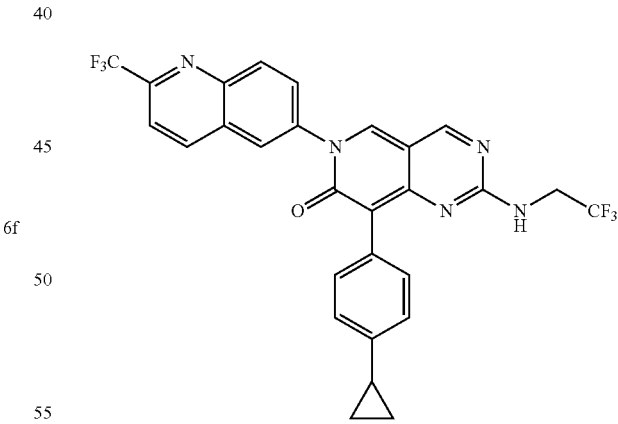

The title compound was synthesized from intermediate 6f with 6-bromo-2-(trifluoromethyl)quinoline via general procedure III method A (CuI, $N^1,N^2$-dimethylcyclohexane-1,2-diamine, CsF, 1,4-dioxane, 100° C.).

$^1$H NMR (400 MHz, DMSO-$d_6$) δ: 8.99 (s, 1H), 8.98 (s, 1H), 8.83 (d, J=8.4 Hz, 1H), 8.60 (t, J=6.4 Hz, 1H), 8.43 (d, J=2.0 Hz, 1H), 8.33 (d, J=9.2 Hz, 1H), 8.14-8.07 (m, 2H), 7.56 (d, J=8.4 Hz, 2H), 7.02 (d, J=8.4 Hz, 2H), 4.17-4.04 (m, 2H), 1.97-1.88 (m, 1H), 0.99-0.92 (m, 2H), 0.70-0.63 (m, 2H). LC-MS: m/z 556 [M+H]$^+$.

Example 164: 8-(4-cyclopropylphenyl)-6-(2,3-dihydrobenzofuran-5-yl)-2-((2,2,2-trifluoroethyl)amino)pyrido[4,3-d]pyrimidin-7(6H)-one

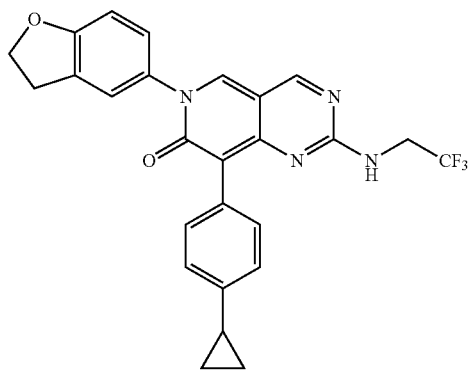 [SMILES: O=c1c(-c2ccc(C3CC3)cc2)c2nc(NCC(F)(F)F)ncc2cn1-c1ccc2c(c1)CCO2]

The title compound was synthesized from intermediate 6f with 5-bromo-2,3-dihydrobenzofuran via general procedure III method A (CuI, $N^1,N^2$-dimethylcyclohexane-1,2-diamine, CsF, 1,4-dioxane, 100° C.).

$^1$H NMR (400 MHz, DMSO-d$_6$) δ: 8.99 (s, 1H), 8.82 (s, 1H), 8.54 (t, J=6.4 Hz, 1H), 7.58 (d, J=8.0 Hz, 2H), 7.45 (s, 1H), 7.28 (dd, J=8.5 Hz, 2.4 Hz, 1H), 7.06 (d, J=8.0 Hz, 2H), 6.96 (d, J=8.4 Hz, 1H), 4.69 (t, J=8.8 Hz, 2H), 4.21-4.06 (m, 2H), 3.31 (t, J=8.8 Hz, 2H), 2.03-1.93 (m, 1H), 1.05-0.97 (m, 2H), 0.77-0.66 (m, 2H). LC-MS: m/z 479 [M+H]$^+$.

Example 165: 8-(4-cyclopropylphenyl)-6-(imidazo[1,2-a]pyridin-6-yl)-2-((2,2,2-trifluoroethyl)amino)pyrido[4,3-d]pyrimidin-7(6H)-one

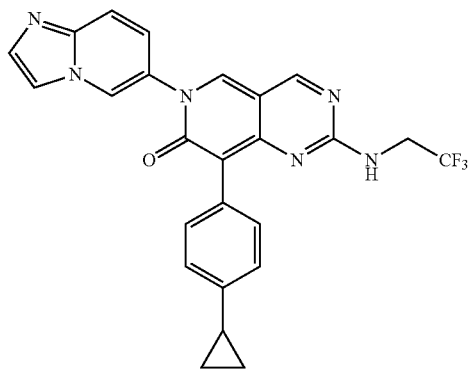 [SMILES: O=c1c(-c2ccc(C3CC3)cc2)c2nc(NCC(F)(F)F)ncc2cn1-c1ccc2nccn2c1]

The title compound was synthesized from intermediate 6f with 6-bromoimidazo[1,2-a]pyridine via general procedure III method A (CuI, $N^1,N^2$-dimethylcyclohexane-1,2-diamine, CsF, 1,4-dioxane, 100° C.).

$^1$H NMR (400 MHz, DMSO-d$_6$) δ: 8.96 (d, J=1.2 Hz, 1H), 8.95 (s, 1H), 8.92 (s, 1H), 8.59 (t, J=6.4 Hz, 1H), 8.06 (s, 1H), 7.71 (s, 1H) 7.69 (d, J=9.2 Hz, 1H), 7.54 (d, J=8.4 Hz, 2H), 7.41 (dd, J=9.6 Hz, 2.0 Hz, 1H), 7.01 (d, J=8.4 Hz, 2H), 4.17-4.03 (m, 2H), 1.98-1.88 (m, 1H), 0.99-0.91 (m, 2H), 0.71-0.62 (m, 2H). LC-MS: m/z 477 [M+H]$^+$.

Example 166: 6-(benzo[d]thiazol-6-yl)-8-(4-cyclopropylphenyl)-2-((2,2,2-trifluoroethyl)amino)pyrido[4,3-d]pyrimidin-7(6)-one

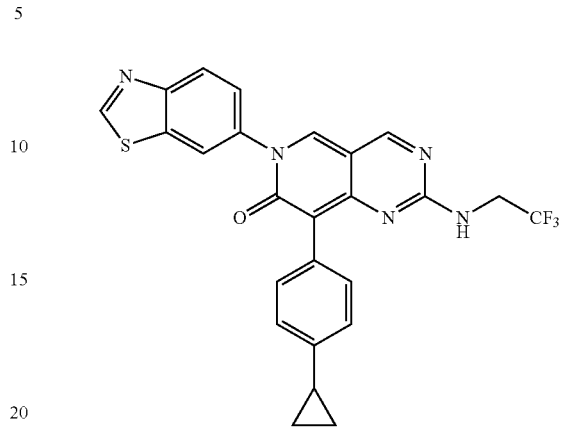

The title compound was synthesized from intermediate 6f with 6-bromobenzo[d]thiazole via general procedure III method A (CuI, $N^1,N^2$-dimethylcyclohexane-1,2-diamine, CsF, 1,4-dioxane, 100° C.).

$^1$H NMR (400 MHz, DMSO-d$_6$) δ 9.54 (s, 1H), 8.95 (s, 1H), 8.90 (s, 1H), 8.56 (t, J=6.4 Hz, 1H), 8.42 (d, J=2.0 Hz, 1H), 8.24 (d, J=8.8 Hz, 1H), 7.71 (dd, J=8.8 Hz, 2.0 Hz, 1H), 7.54 (d, J=8.0 Hz, 2H), 7.01 (d, J=8.0 Hz, 2H), 4.18-4.01 (m, 2H), 1.98-1.86 (m, 1H), 0.99-0.89 (m, 2H), 0.71-0.63 (m, 2H). LC-MS: m/z 494 [M+H]$^+$.

Example 167: 8-(4-cyclopropylphenyl)-6-(4-methoxyphenyl)-2-((2,2,2-trifluoroethyl)amino)pyrido[4,3-d]pyrimidin-7(6)-one

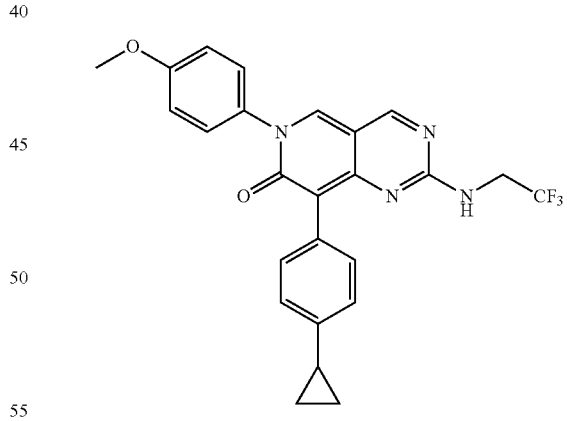

The title compound was synthesized from intermediate 6f with 1-bromo-4-methoxybenzene via general procedure III method A (CuI, $N^1,N^2$-dimethylcyclohexane-1,2-diamine, CsF, 1,4-dioxane, 100° C.).

$^1$H NMR (400 MHz, DMSO-d$_6$) δ 8.94 (s, 1H), 8.77 (s, 1H), 8.49 (t, J=6.4 Hz, 1H), 7.51 (d, J=8.4 Hz, 2H), 7.45 (d, J=8.8 Hz, 2H), 7.08 (d, J=8.8 Hz, 2H), 7.00 (d, J=8.4 Hz, 2H), 4.14-4.00 (m, 2H), 3.83 (s, 3H), 1.97-1.87 (m, 1H), 0.99-0.91 (m, 2H), 0.70-0.63 (m, 2H). LC-MS: m/z 467 [M+H]$^+$.

Example 168: 8-(4-cyclopropylphenyl)-6-(quinolin-6-yl)-2-((2,2,2-trifluoroethyl)amino)pyrido[4,3-d]pyrimidin-7(6)-one

The title compound was synthesized from intermediate 6f with 6-bromoquinoline via general procedure III method A (CuI, N¹,N²-dimethylcyclohexane-1,2-diamine, CsF, 1,4-dioxane, 100° C.).

¹H NMR (400 MHz, DMSO-d₆) δ 9.03 (dd, J=4.4 Hz, 1.6 Hz, 1H), 8.98 (s, 1H), 8.96 (s, 1H), 8.58 (t, J=6.4 Hz, 1H), 8.48 (dd, J=8.4, 1.7 Hz, 1H), 8.24 (d, J=2.0 Hz, 1H), 8.16 (d, J=8.8 Hz, 1H), 7.93 (dd, J=8.8 Hz, 2.4 Hz, 1H), 7.66 (dd, J=8.4 Hz, 4.4 Hz, 1H), 7.56 (d, J=8.4 Hz, 2H), 7.02 (d, J=8.4 Hz, 2H), 4.17-4.04 (m, 2H), 1.98-1.89 (m, 1H), 1.00-0.91 (m, 2H), 0.72-0.63 (m, 2H). LC-MS: m/z 488 [M+H]⁺.

Preparation of 8-(4-chlorophenyl)-2-(ethylamino)pyrido[4,3-d]pyrimidin-7(6H)-one 6g

6g 8-(4-chlorophenyl)-2-(ethylamino)pyrido[4,3-d]pyrimidin-7(6H)-one 6g was synthesized from ethanamine via general procedure III (Step D, E). LC-MS: m/z 301 [M+H]⁺.

Example 169: Preparation of 8-(4-chlorophenyl)-2-(ethylamino)-6-(2-methyl-2H-indazol-5-yl)pyrido[4,3-d]pyrimidin-7(6H)-one

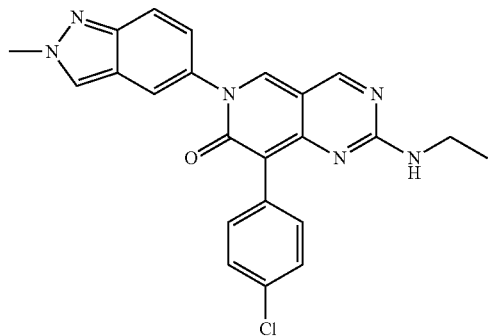

The title compound was synthesized from intermediate 6g with 5-bromo-2-methyl-2H-indazole via general procedure III method A (CuI, N¹,N²-dimethylcyclohexane-1,2-diamine, Cs₂CO₃, 1,4-dioxane, 100° C.).

¹H NMR (400 MHz, DMSO-d₆) δ: 8.86 (s, 1H), 8.77 (s, 1H), 8.49 (s, 1H), 8.07 (t, J=5.6 Hz, 1H), 7.87 (d, J=1.2 Hz, 1H), 7.71 (d, J=8.8 Hz, 2H), 7.69 (d, J=9.2 Hz, 1H), 7.36 (d, J=8.8 Hz, 2H), 7.31 (dd, J=9.2 Hz, 2.0 Hz, 1H), 4.22 (s, 3H), 3.30-3.20 (m, 2H), 1.11 (t, J=7.2 Hz, 1H) LC-MS: m/z 431 [M+H]⁺.

Preparation of 2-(ethylamino)-8-(4-(trifluoromethoxy)phenyl)pyrido[4,3-d]pyrimidin-7(6H)-one 6 h

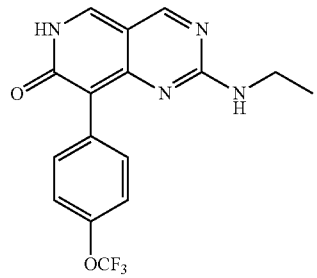

6h 2-(ethylamino)-8-(4-(trifluoromethoxy)phenyl)pyrido[4,3-d]pyrimidin-7(6H)-one 6 h was synthesized from methyl 2-(4-(trifluoromethoxy)phenyl)acetate via general procedure III (Step B-E). LC-MS: m/z 351 [M+H]⁺.

Example 170: Preparation of 2-(ethylamino)-6-(2-methyl-2H-indazol-5-yl)-8-(4-(trifluoromethoxy)phenyl)pyrido[4,3-d]pyrimidin-7(6H)-one

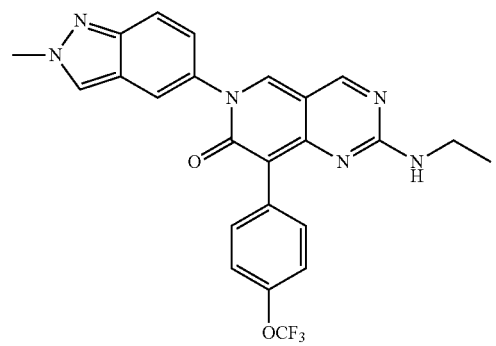

The title compound was synthesized from intermediate 6 h with 5-bromo-2-methyl-2H-indazole via general procedure III method A (CuI, N¹,N²-dimethylcyclohexane-1,2-diamine, CsF, 1,4-dioxane, 100° C.).

¹H NMR (400 MHz, DMSO-d₆) δ 8.86 (s, 1H), 8.78 (s, 1H), 8.50 (s, 1H), 8.09 (t, J=5.6 Hz, 1H), 7.88 (d, J=1.2 Hz, 1H), 7.80 (d, J=8.8 Hz, 2H), 7.69 (d, J=9.2 Hz, 1H), 7.32 (dd, J=9.2 Hz, 1.2 Hz, 1H), 7.29 (d, J=8.8 Hz, 2H), 4.22 (s, 3H), 3.30-3.20 (m, 2H), 1.10 (t, J=6.8 Hz, 3H). LC-MS: m/z 481 [M+H]⁺.

Preparation of 8-(4-(difluoromethoxy)phenyl)-2-(ethylamino)pyrido[4,3-d]pyrimidin-7(6H)-one 6i

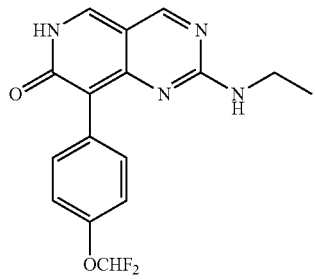

6i 8-(4-(difluoromethoxy)phenyl)-2-(ethylamino)pyrido[4,3-d]pyrimidin-7(6H)-one 6i was synthesized from methyl 2-(4-(difluoromethoxy)phenyl)acetate via general procedure III (Step B-E). LC-MS: m/z 333 [M+H]$^+$.

Preparation of 8-(4-(difluoromethoxy)phenyl)-2-(ethylamino)-6-(2-methyl-2H-indazol-5-yl)pyrido[4,3-d]pyrimidin-7(6H)-one (Example 171)

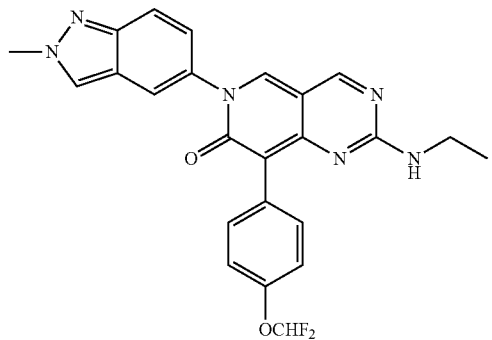

The title compound was synthesized from intermediate 6i with 5-bromo-2-methyl-2H-indazole via general procedure III method A (CuI, N$^1$,N$^2$-dimethylcyclohexane-1,2-diamine, CsF, 1,4-dioxane, 100° C.).

$^1$H NMR (400 MHz, DMSO-d$_6$) δ 8.85 (s, 1H), 8.76 (s, 1H), 8.49 (s, 1H), 8.04 (t, J=5.6 Hz, 1H), 7.87 (d, J=1.2 Hz, 1H), 7.74 (d, J=8.8 Hz, 2H), 7.69 (d, J=9.2 Hz, 1H), 7.31 (dd, J=8.8 Hz, 2.0 Hz, 1H), 7.26 (t, J$_{HF}$=74.4 Hz, 1H), 7.11 (d, J=8.4 Hz, 2H), 4.22 (s, 3H), 3.31-3.15 (m, 2H), 1.11 (t, J=7.2 Hz, 3H). LC-MS: m/z 463 [M+H]$^+$.

Preparation of 2-(cyclopropylamino)-8-(4-(difluoromethoxy)phenyl)pyrido[4,3-d]pyrimidin-7(6H)-one 6j

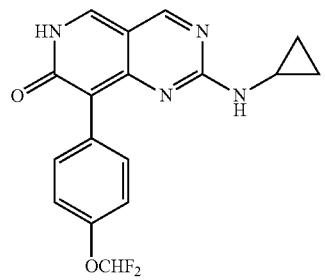

6j 2-(cyclopropylamino)-8-(4-(difluoromethoxy)phenyl)pyrido[4,3-d]pyrimidin-7(6H)-one 6j was synthesized from cyclopropanamine via general procedure III (Step D, E). LC-MS: m/z 345 [M+H]$^+$.

Example 172: Preparation of 2-(cyclopropylamino)-8-(4-(difluoromethoxy)phenyl)-6-(2-methyl-2H-indazol-5-yl)pyrido[4,3-d]pyrimidin-7(6H)-one

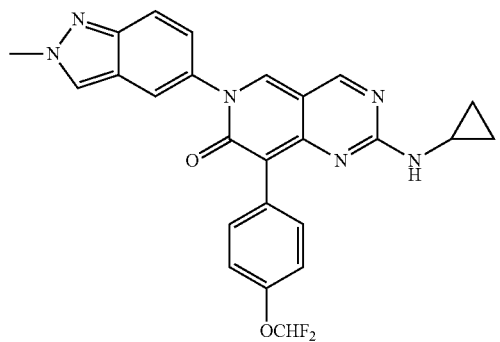 [SMILES: Cn1cc2cc(-n3cc4cnc(NC5CC5)nc4c(-c4ccc(OC(F)F)cc4)c3=O)ccc2n1]

The title compound was synthesized from intermediate 6j with 5-bromo-2-methyl-2H-indazole via general procedure III method A (CuI, N$^1$,N$^2$-dimethylcyclohexane-1,2-diamine, CsF, 1,4-dioxane, 100° C.).

$^1$H NMR (400 MHz, DMSO-d$_6$) δ 8.90 (s, 1H), 8.83 (s, 1H), 8.55 (s, 1H), 8.25 (d, J=4.0 Hz, 1H), 7.97-7.87 (m, 3H), 7.76 (d, J=9.2 Hz, 1H), 7.38 (dd, J=9.2 Hz, 2.0 Hz, 1H), 7.30 (t, J$_{HF}$=74.4 Hz, 1H), 7.17 (d, J=8.4 Hz, 2H), 4.18 (s, 3H), 2.87-2.76 (m, 1H), 0.77-0.70 (m, 2H), 0.66-0.58 (m, 2H). LC-MS: m/z 475 [M+H]$^+$.

Preparation of 8-(4-chlorophenyl)-2-(cyclopropylamino)pyrido[4,3-d]pyrimidin-7(6H)-one 6k

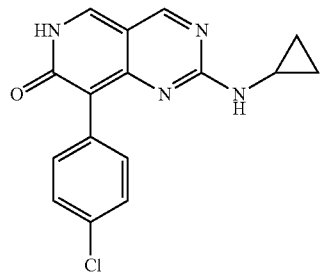

6k 8-(4-chlorophenyl)-2-(cyclopropylamino)pyrido[4,3-d]pyrimidin-7(6H)-one 6k was synthesized from cyclopropanamine via general procedure III (Step D, E). LC-MS: m/z 313 [M+H]$^+$.

Example 173: Preparation of 8-(4-chlorophenyl)-2-(cyclopropylamino)-6-(2-methyl-2H-indazol-5-yl)pyrido[4,3-d]pyrimidin-7(6H)-one

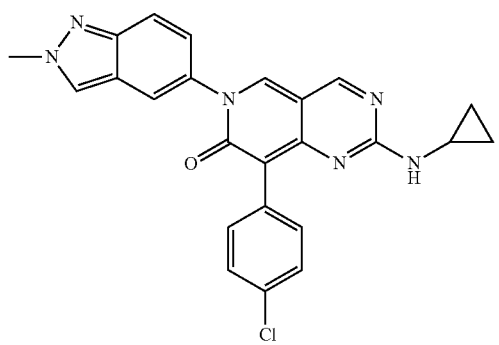 [SMILES: Cn1cc2cc(-n3cc4cnc(NC5CC5)nc4c(-c4ccc(Cl)cc4)c3=O)ccc2n1]

The title compound was synthesized from intermediate 6k with 5-bromo-2-methyl-2H-indazole via general procedure III method A (CuI, $N^1,N^2$-dimethylcyclohexane-1,2-diamine, CsF, 1,4-dioxane, 100° C.).

$^1$H NMR (400 MHz, DMSO-d$_6$) δ 8.85 (s, 1H), 8.79 (s, 1H), 8.50 (s, 1H), 8.22 (d, J=4.0 Hz, 1H), 7.88 (d, J=1.6 Hz, 1H), 7.85 (d, J=8.4 Hz, 2H), 7.70 (d, J=9.2 Hz, 1H), 7.36 (d, J=8.4 Hz, 2H), 7.33 (dd, J=9.2 Hz, 2.0 Hz, 1H), 4.23 (s, 3H), 2.82-2.73 (m, 1H), 0.73-0.64 (m, 2H), 0.59-0.53 (m, 2H). LC-MS: m/z 443 [M+H]$^+$.

Example 174: Preparation of 2-(cyclobutylamino)-8-(4-(difluoromethoxy)phenyl)-6-(2-methyl-2H-indazol-5-yl)pyrido[4,3-d]pyrimidin-7(6H)-one

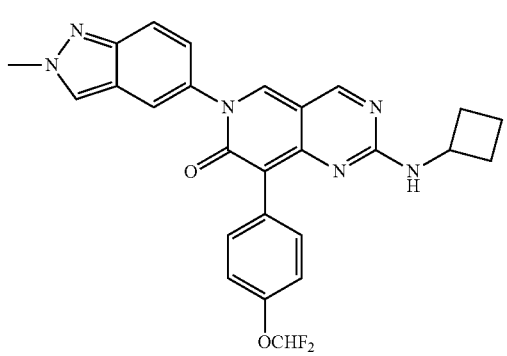 [SMILES: Cn1cc2cc(-n3cc4cnc(NC5CCC5)nc4c(-c4ccc(OC(F)F)cc4)c3=O)ccc2n1]

The title compound was synthesized from intermediate 6l with 5-bromo-2-methyl-2H-indazole via general procedure III method A (CuI, $N^1,N^2$-dimethylcyclohexane-1,2-diamine, CsF, 1,4-dioxane, 100° C.).

$^1$HNMR (400 MHz, DMSO-d$_6$) δ: 8.86 (s, 1H), 8.76 (s, 1H), 8.49 (s, 1H), 8.33 (d, J=6.8 Hz, 1H), 7.82 (d, J=1.2 Hz, 1H), 7.72 (d, J=8.8 Hz, 2H), 7.68 (d, J=9.2 Hz, 1H), 7.31 (dd, J=9.2 Hz, 2.0 Hz, 1H), 7.27 (t, J$_{HF}$=74.4 Hz, 1H), 7.13 (d, J=8.8 Hz, 2H), 4.22 (s, 3H), 4.23-4.11 (m, 1H), 2.23-2.11 (m, 2H), 2.09-1.93 (m, 2H). LC-MS: m/z 489 [M+H]$^+$.

Preparation of 2-(cyclobutylamino)-8-(4-(difluoromethoxy)phenyl)pyrido[4,3-d]pyrimidin-7(6H)-one 6l Preparation of 2-((2,2-difluoroethyl)amino)-8-(4-(difluoromethoxy)phenyl)pyrido[4,3-d]pyrimidin-7(6H)-one 6m 6l

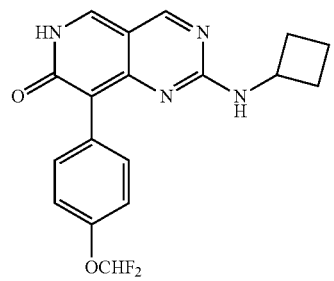

6m

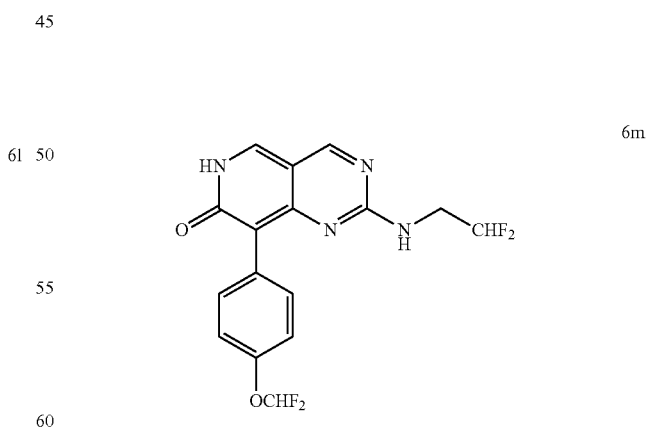

2-(cyclobutylamino)-8-(4-(difluoromethoxy)phenyl)pyrido[4,3-d]pyrimidin-7(6H)-one 6l was synthesized from cyclobutanamine via general procedure III (Step D, E). LC-MS: m/z 359 [M+H]$^+$.

2-((2,2-difluoroethyl)amino)-8-(4-(difluoromethoxy)phenyl)pyrido[4,3-d]pyrimidin-7(6H)-one 6m was synthesized from 2,2-difluoroethanamine via general procedure III (Step D, E). LC-MS: m/z 369 [M+H]$^+$.

Example 175: Preparation of 2-((2,2-difluoroethyl)amino)-8-(4-(difluoromethoxy)phenyl)-6-(2-methyl-2H-indazol-5-yl)pyrido[4,3-d]pyrimidin-7(6H)-one

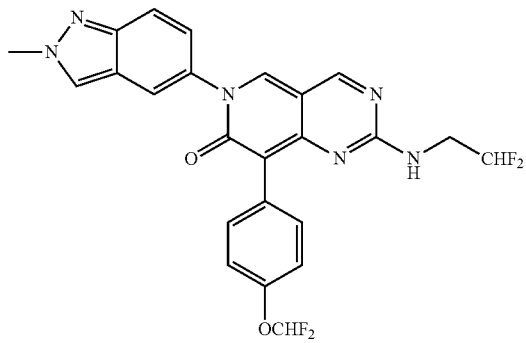 [SMILES: Cn1cc2cc(-n3cc4cnc(NCC(F)F)nc4c(-c4ccc(OC(F)F)cc4)c3=O)ccc2n1]

The title compound was synthesized from intermediate 6m with 5-bromo-2-methyl-2H-indazole via general procedure III method A (CuI, $N^1,N^2$-dimethylcyclohexane-1,2-diamine, CsF, 1,4-dioxane, 100° C.).

$^1$H NMR (400 MHz, DMSO-$d_6$) δ 8.94 (s, 1H), 8.87 (s, 1H), 8.51 (s, 1H), 7.89 (d, J=1.2 Hz, 1H), 7.70 (d, J=9.2 Hz, 3H), 7.32 (dd, J=9.2 Hz, 2.0 Hz, 1H), 7.25 (t, $J_{HF}$=74.4 Hz, 1H), 7.12 (d, J=8.8 Hz, 2H), 6.12 (tt, $J_{HF}$=56.4 Hz, 4.0 Hz, 1H), 4.22 (s, 3H), 3.60 (dt, $J_{HF}$=14.8 Hz, 4.0 Hz, 2H). LC-MS: m/z 499 [M+H]$^+$.

The following compounds were synthesized via general procedure III method A:

| | | |
|---|---|---|
| 101-A | 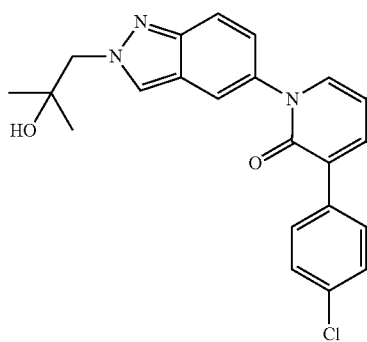<br>8-(4-chlorophenyl)-6-(2-(2-hydroxy-2-methylpropyl)-2H-indazol-5-yl)-2-(2,2,2-trifluoroethylamino)pyrido[4,3-d]pyrimidin-7(6H)-one (synthesized from 8-(4-chlorophenyl)-2-((2,2,2-trifluoroethyl)amino)pyrido[4,3-d]pyrimidin-7(6H)-one & 1-(5-bromo-2H-indazol-2-yl)-2-methylpropan-2-ol (Ref: *Organic Letters*, 16 (11), 3114-3117; 2014)) | LC-MS (ESI): m/z 543 [M + H]$^+$.<br>1H NMR (400 MHz, DMSO-d6) (ratio of tautomers 7:1) δ 9.05 (s, 0.15H), 8.99 (s, 0.15H), 8.97 (s, 0.85H), 8.93 (s, 0.85H), 8.59 (t, J = 6.5 Hz, 1H), 8.46 (d, J = 1.0 Hz, 1H), 7.92 (dd, J = 2.0, 0.8 Hz, 1H), 7.76-7.72 (m, 1H), 7.70-7.66 (m, 1.75H), 7.55 (d, J = 8.3 Hz, 0.25H), 7.40 (d, J = 8.2 Hz, 0.25H), 7.36 (dd, J = 8.2, 1.6 Hz, 1.75H), 7.34-7.31 (m, 1H), 4.89 (s, 1H), 4.39 (s, 2H), 4.23 (s, 0.25H), 4.08 (p, J = 9.3 Hz, 1.75H), 1.13 (s, 6H). |
| 102-A | 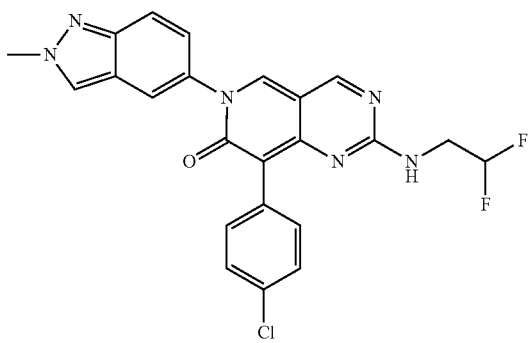<br>8-(4-chlorophenyl)-2-(2,2-difluoroethylamino)-6-(2-methyl-2H-indazol-5-yl)pyrido[4,3-d]pyrimidin-7(6H)-one | LC-MS (ESI): m/z 467 [M + H]$^+$.<br>1H NMR (400 MHz, ) δ 8.94 (s, 1H), 8.88 (s, 1H), 8.50 (s, 1H), 8.38 (t, J = 6.0 Hz, 1H), 7.89 (d, J = 1.9 Hz, 1H), 7.70 (dd, J = 8.8, 6.8 Hz, 3H), 7.41-7.27 (m, 3H), 6.12 (tt, JHF = 56.3, J = 4.1 Hz, 1H), 4.22 (s, 3H), 3.70-3.54 (m, 2H). (Tautomer Ratio 10:1. Only major peaks reported) |

Step F: (Method B: Chan-Lam coupling). 8-(4-methoxyphenyl)-6-(pyridin-4-yl)-2-((2,2,2-trifluoroethyl)amino)pyrido[4,3-d]pyrimidin-7(6H)-one (Example 176)

Method B
Chan-Lam coupling

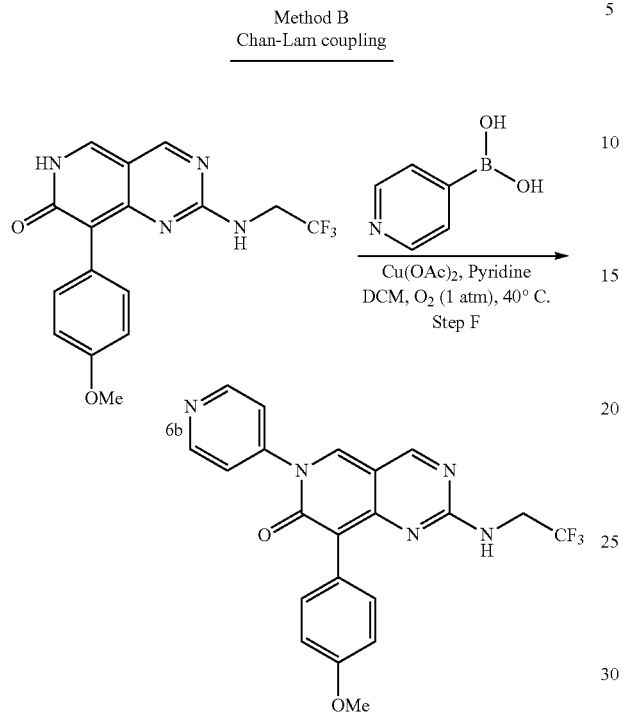

Example 176: A mixture of 8-(4-methoxyphenyl)-2-((2,2,2-trifluoroethyl)amino)pyrido[4,3-d]pyrimidin-7(6H)-one (70.0 mg, 0.2 mmol, 1.0 equiv), pyridin-4-ylboronic acid (50.0 mg, 0.4 mmol, 2.0 equiv), copper acetate (73.0 mg, 0.4 mmol, 2.0 equiv) and pyridine (63.0 mg, 0.8 mmol, 4.0 equiv) in DCM (3.0 mL) was stirred at 40° C. overnight under an atmosphere of O2. After this time, the reaction mixture was diluted with DCM (10.0 mL), washed with H2O (10 mL×3), dried over anhydrous Na2SO4, and concentrated under reduced pressure. The residue was purified by Prep-HPLC to yield 8-(4-methoxyphenyl)-6-(pyridin-4-yl)-2-((2,2,2-trifluoroethyl)amino)pyrido[4,3-d]pyrimidin-7(6)-one $^{1}$H NMR (400 MHz, CDCl$_3$) δ: 8.82 (d, J=6.0 Hz, 2H), 8.75 (s, 1H), 8.08 (s, 1H), 7.68 (d, J=9.2 Hz, 2H), 7.48 (d, J=6.4 Hz, 2H), 6.96 (d, J=8.8 Hz, 2H), 5.81 (t, J=6.8 Hz, 1H), 4.19-4.08 (m, 2H), 3.82 (s, 3H). LC-MS: m/z 428 [M+H]$^+$.

Example 177: Preparation of 6-(2,3-dihydrobenzo[b][1,4]dioxin-6-yl)-8-(4-methoxyphenyl)-2-((2,2,2-trifluoroethyl)amino)pyrido[4,3-d]pyrimidin-7(6H)-one

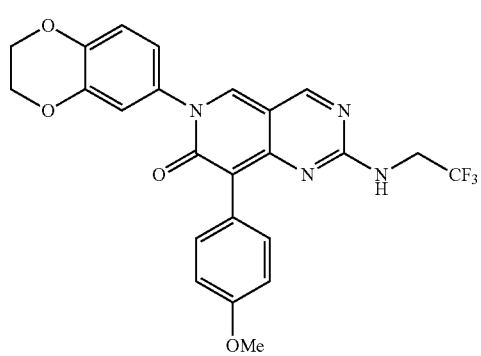

The title compound was synthesized from intermediate 6b with (2,3-dihydrobenzo[b][1,4]dioxin-6-yl)boronic acid via general procedure III method B (Cu(OAc)$_2$, Pyridine, DCM, O$_2$ (1 atm), 40° C.).

$^{1}$H NMR (400 MHz, DMSO-d$_6$) δ 8.93 (s, 1H), 8.74 (s, 1H), 8.49 (t, J=6.4 Hz, 1H), 7.58 (t, J=8.8 Hz, 2H), 7.10 (d, J=2.0 Hz, 1H), 7.01 (s, 1H), 7.00 (d, J=2.4 Hz, 1H), 6.87 (d, J=8.8 Hz, 2H), 4.32 (s, 4H), 4.15-4.01 (m, 2H), 3.78 (s, 3H). LC-MS: m/z 485 [M+H]$^+$.

Example 178: 8-(4-(difluoromethoxy)phenyl)-6-(2,3-dihydrobenzo[b][1,4]dioxin-6-yl)-2-((2,2,2-trifluoroethyl)amino)pyrido[4,3-d]pyrimidin-7(6H)-one

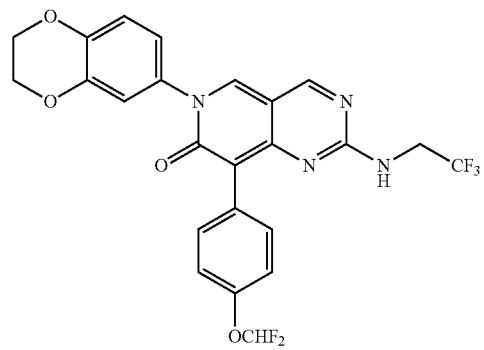 [SMILES: O=c1c(-c2ccc(OC(F)F)cc2)c2nc(NCC(F)(F)F)ncc2cn1-c1ccc2c(c1)OCCO2]

The title compound was synthesized from intermediate 6c with (2,3-dihydrobenzo[b][1,4]dioxin-6-yl)boronic acid via general procedure III method B (Cu(OAc)$_2$, Pyridine, DCM, O$_2$ (1 atm), 40° C.).

$^{1}$H NMR (400 MHz, DMSO-d$_6$) δ 8.94 (s, 1H), 8.79 (s, 1H), 8.56 (t, J=6.4 Hz, 1H), 7.67 (d, J=8.8 Hz, 2H), 7.26 (t, J$_{HF}$=74.4 Hz, 1H), 7.11 (d, J=2.8 Hz, 1H), 7.09 (d, J=8.8 Hz, 2H), 7.12-7.01 (m, 2H), 4.31 (s, 4H), 4.12-4.03 (m, 2H). LC-MS: m/z 521 [M+H]$^+$.

Example 179: 2-(cyclopropylamino)-8-(4-(difluoromethoxy)phenyl)-6-(quinolin-6-yl)pyrido[4,3-d]pyrimidin-7(6)-one

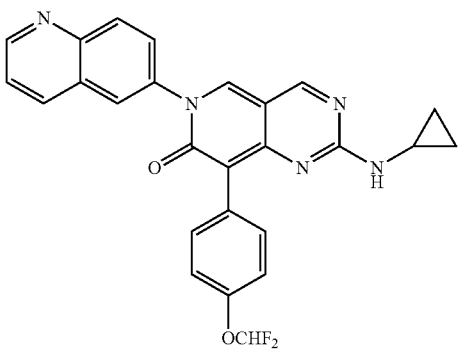 [SMILES: O=c1c(-c2ccc(OC(F)F)cc2)c2nc(NC3CC3)ncc2cn1-c1ccc2ncccc2c1]

The title compound was synthesized from intermediate 6j with quinolin-6-ylboronic acid via general procedure III method B (Cu(OAc)$_2$, Pyridine, DCM, O$_2$ (1 atm), 40° C.).

$^1$H NMR (400 MHz, DMSO-d$_6$) δ 9.02 (dd, J=4.0 Hz, 1.6 Hz, 1H), 8.88 (s, 1H), 8.87 (s, 1H), 8.48 (d, J=8.0 Hz, 1H), 8.27 (d, J=4.4 Hz, 1H), 8.23 (d, J=2.4 Hz, 1H), 8.16 (d, J=8.8 Hz, 1H), 7.93 (dd, J=8.8 Hz, 2.0 Hz, 1H), 7.88 (d, J=8.8 Hz, 2H), 7.66 (dd, J=8.8 Hz, 4.4 Hz, 1H), 7.26 (t, J$_{HF}$=74.4 Hz, 1H), 7.13 (d, J=8.8 Hz, 2H), 2.83-2.74 (m, 1H), 0.74-0.65 (m, 2H), 0.62-0.53 (m, 2H). LC-MS: m/z 472 [M+H]$^+$.

Preparation of 8-(4-bromophenyl)-2-((2,2,2-trifluoroethyl)amino)pyrido[4,3-d]pyrimidin-7(6H)-one 6n

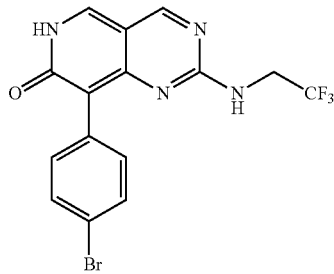

6n 8-(4-bromophenyl)-2-((2,2,2-trifluoroethyl)amino)pyrido [4,3-d]pyrimidin-7(6H)-one 6n was synthesized from methyl 2-(4-bromophenyl)acetate via general procedure III (Step B-E). LC-MS: m/z 399, 401 [M+H]$^+$.

Example 180: Preparation of 8-(4-bromophenyl)-6-(quinolin-6-yl)-2-((2,2,2-trifluoroethyl)amino)pyrido[4,3-d]pyrimidin-7(6)-one

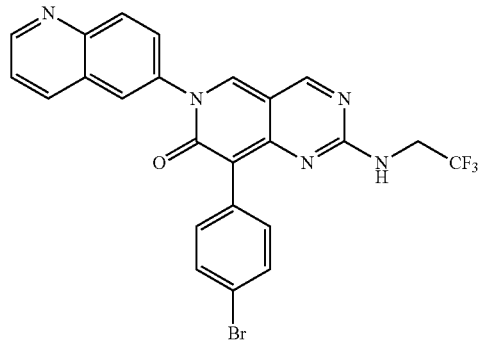 [SMILES: O=c1c(-c2ccc(Br)cc2)c2nc(NCC(F)(F)F)ncc2cn1-c1ccc2ncccc2c1]

The title compound was synthesized from intermediate 6n with quinolin-6-ylboronic acid via general procedure III method B (Cu(OAc)$_2$, Pyridine, DCM, O$_2$ (1 atm), 40° C.).

$^1$H NMR (400 MHz, DMSO-d$_6$) δ 9.03 (d, J=4.0 Hz, 1H), 9.02 (s, 1H), 9.00 (s, 1H), 8.68 (t, J=6.0 Hz, 1H), 8.48 (d, J=8.4 Hz, 1H), 8.24 (d, J=2.0 Hz, 1H), 8.17 (d, J=9.2 Hz, 1H), 7.94 (dd, J=9.2 Hz, 2.0 Hz, 1H), 7.69-7.61 (m, 3H), 7.51 (d, J=8.8 Hz, 2H), 4.17-4.03 (m, 2H). LC-MS: m/z 526, 528 [M+H]$^+$.

The following compound was synthesized via general procedure III (alternate route; steps G-J):

| 103-A | | |
|---|---|---|
| | 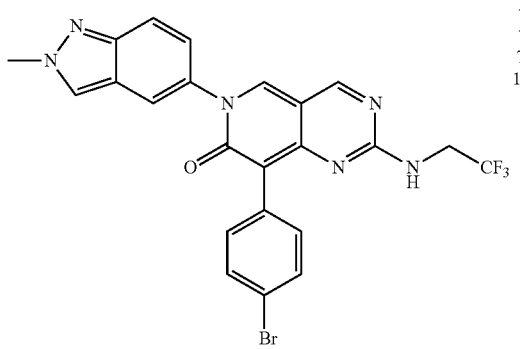 | LC-MS (ESI): m/z 529 [M + H]$^+$. 1H NMR (400 MHz, DMSO-d6) δ 8.96 (s, 1H), 8.82 (d, J = 2.5 Hz, 1H), 8.45 (s, 1H), 7.86 (s, 1H), 7.69 (d, J = 9.1 Hz, 1H), 7.58 (d, J = 8.1 Hz, 2H), 7.48 (d, J = 8.3 Hz, 2H), 7.31 (dd, J = 9.1, 2.0 Hz, 1H), 4.19 (s, 3H), 4.05 (q, J = 9.6 Hz, 2H). (Tautomer Ratio 6:1. Only major peaks reported) |
| | 8-(4-bromophenyl)-6-(2-methyl-2H-indazol-5-yl)-2-(2,2,2-trifluoroethylamino)pyrido[4,3-d]pyrimidin-7(6H)-one | |

Preparation of Example 181

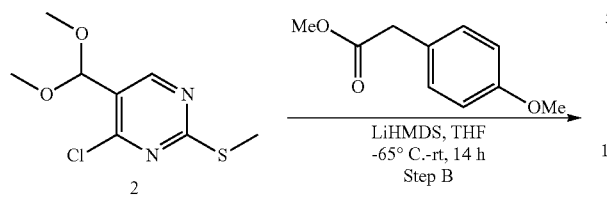

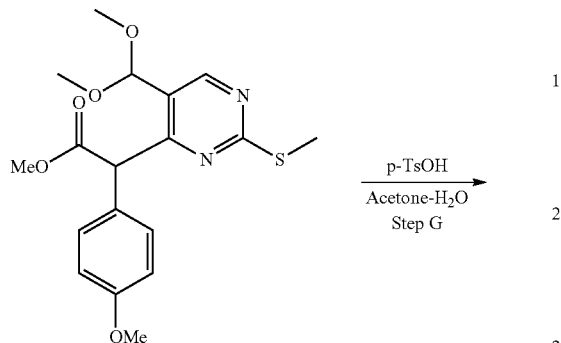

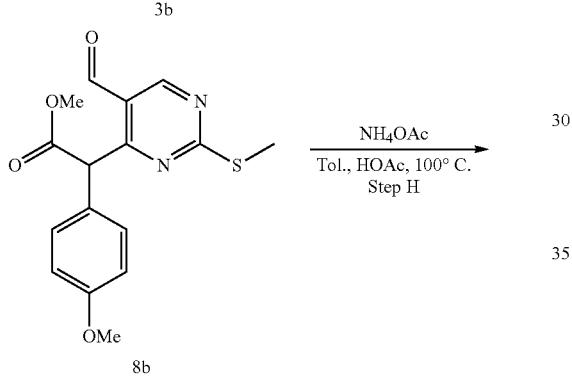

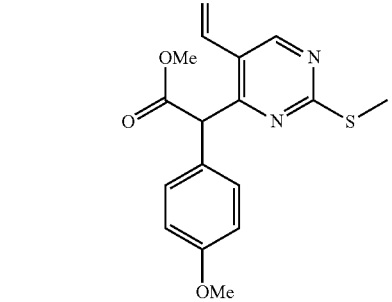

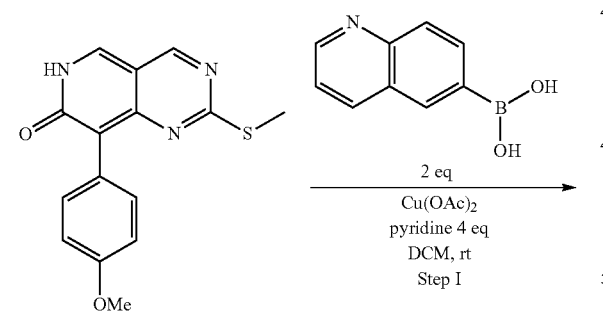

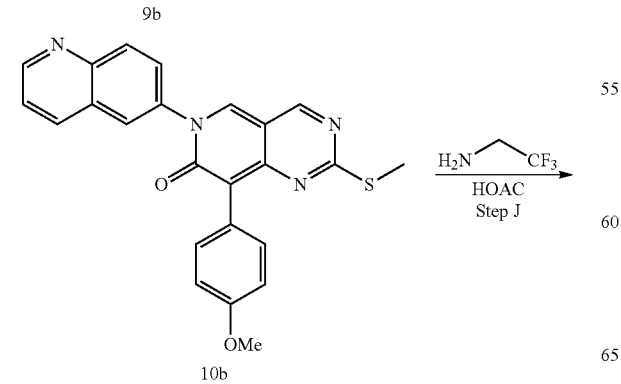

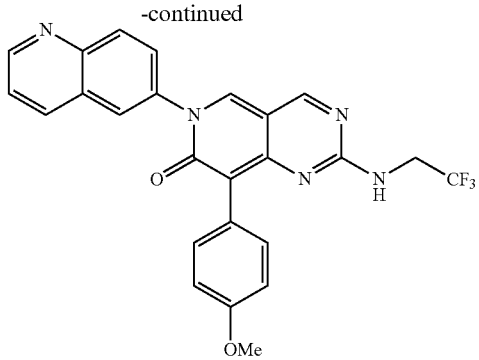

Step G: methyl 2-(5-formyl-2-(methylthio)pyrimidin-4-yl)-2-(4-methoxyphenyl)acetate

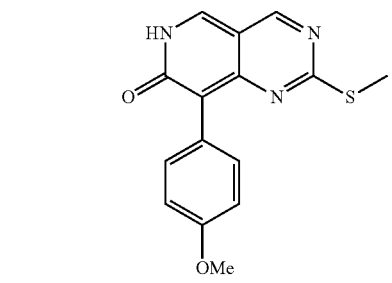 [SMILES: COc1ccc(-c2c(=O)[nH]cc3cnc(SC)nc23)cc1]

To a solution of methyl 2-(5-(dimethoxymethyl)-2-(methylthio)pyrimidin-4-yl)-2-(4-methoxyphenyl)acetate (570 mg, 1.5 mmol 1.0 equiv) in Acetone/H$_2$O (5.0/5.0 mL) was added p-TsOH (77 mg, 0.45 mmol 0.3 equiv). The mixture was then stirred at 70° C. for 2 h. The resulting mixture was extracted with DCM. The organic layer was dried over Na$_2$SO$_4$, filtered and concentrated under vacuum to give the desired product (450 mg, 90% yield) as a yellow oil. LC-MS (ESI): m/z 333 [M+H]$^+$.

Step H: 8-(4-methoxyphenyl)-2-(methylthio)pyrido[4,3-d]pyrimidin-7(6H)-one

To a mixture of 2-(5-formyl-2-(methylthio)pyrimidin-4-yl)-2-(4-methoxyphenyl)acetate (450 mg, 1.35 mmol 1.0 equiv) in toluene/HOAc (5.0/5.0 mL) was added NH$_4$OAc (2.7 g, 350.6 mmol 26.0 equiv). The resulting mixture was stirred at 100° C. for 5 h. At this point, the mixture was concentrated under vacuum and diluted with DCM and H₂O. The aqueous layer was extracted with DCM (10.0 mL×2), and the combined organic layers were dried over Na₂SO₄ and concentrated. The residue was purified by flash chromatography on silica gel eluting with (DCM/MeOH=150:1-50:1) to afford the desired product (180 mg, 44% yield) as a brown solid. LC-MS (ESI): m/z 300 [M+H]⁺.

Step I: 8-(4-methoxyphenyl)-2-(methylthio)-6-(quinolin-6-yl)pyrido[4,3-d]pyrimidin-7(6H)-one

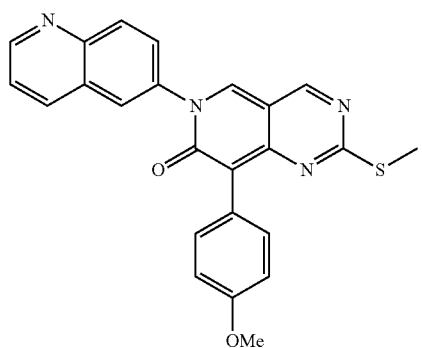

10b

To a solution of 8-(4-methoxyphenyl)-2-(methylthio)pyrido[4,3-d]pyrimidin-7(6H)-one (210.0 mg, 0.7 mmol, 1.0 equiv) in DCM (5.0 mL) was added quinolin-6-ylboronic acid (240 mg, 1.4 mmol, 2.0 equiv), Cu(OAc)₂(250 mg, 1.4 mmol, 2.0 equiv) and pyridine (221 mg, 2.8 mmol 4.0 equiv). The mixture was stirred at 40° C. under O2 (1 atm) overnight. The solvent was removed under vacuum, and the residue was diluted with DCM and H₂O. The aqueous layer was extracted with DCM (10.0 mL×2), and the combined organic layers were dried over Na₂SO₄ and concentrated to give a brown oil. The residue was purified by flash chromatography on silica gel eluting with (DCM/MeOH=200:1-50:1) to afford the desired product (250 mg, 83% yield) as a brown solid. LC-MS (ESI): m/z 427 [M+H]⁺.

Step J: 8-(4-methoxyphenyl)-6-(quinolin-6-yl)-2-((2,2,2-trifluoroethyl)amino)pyrido[4,3-d]pyrimidin-7(6H)-one (Example 181)

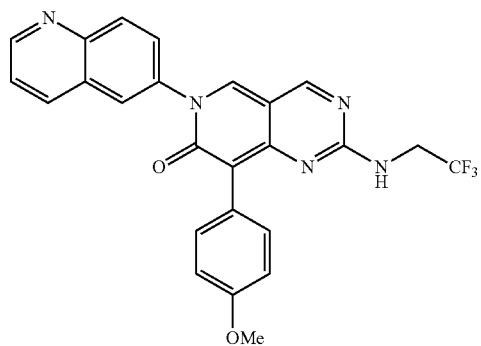 [SMILES: COc1ccc(-c2c(=O)n(-c3ccc4ncccc4c3)cc3cnc(NCC(F)(F)F)nc23)cc1]

To a solution of 8-(4-methoxyphenyl)-2-(methylthio)-6-(quinolin-6-yl)pyrido[4,3-d]pyrimidin-7(6H)-one (63 mg, 0.15 mmol, 1.0 equiv) in HOAc (1.0 mL) was added 2,2,2-trifluoroethanamine (300 mg, 3.0 mmol, 20.0 equiv).

Then the mixture was sealed and stirred at 100° C. overnight. The resulting mixture was concentrated to give a brown oil and purified by flash column chromatography on silica gel to yield 8-(4-methoxyphenyl)-6-(quinolin-6-yl)-2-((2,2,2-trifluoroethyl)amino)pyrido[4,3-d]pyrimidin-7(6H)-one (Example 181)

$^1$H NMR (400 MHz, CDCl₃) δ 9.02 (dd, J=4.3, 1.7 Hz, 1H), 8.76 (s, 1H), 8.28-8.16 (m, 3H), 7.95 (d, J=2.4 Hz, 1H), 7.82 (dd, J=8.9, 2.4 Hz, 1H), 7.73 (d, J=8.5 Hz, 2H), 7.51 (dd, J=8.3, 4.3 Hz, 1H), 6.96 (d, J=8.5 Hz, 2H), 5.74 (t, J=6.4 Hz, 1H), 4.16 (q, J=8.3 Hz, 2H), 3.85 (s, 3H). LC-MS: m/z 478 [M+H]⁺.

Preparation of 8-(4-(difluoromethoxy)phenyl)-2-(methylthio)-6-(quinolin-6-yl)pyrido[4,3-d]pyrimidin-7(6H)-one 10c

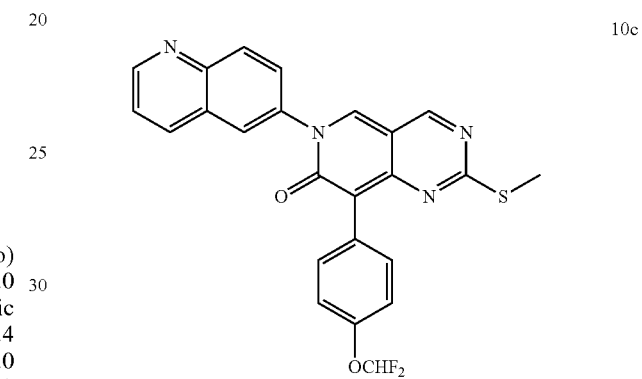

10c 8-(4-(difluoromethoxy)phenyl)-2-(methylthio)-6-(quinolin-6-yl)pyrido[4,3-d]pyrimidin-7(6H)-one 10c was synthesized from methyl 2-(4-(difluoromethoxy)phenyl)acetate via general procedure III (Step B, G-J). LC-MS: m/z 463 [M+H]⁺

Example 182: Preparation of 8-(4-(difluoromethoxy)phenyl)-2-(isopropylamino)-6-(quinolin-6-yl)pyrido[4,3-d]pyrimidin-7(6)-one

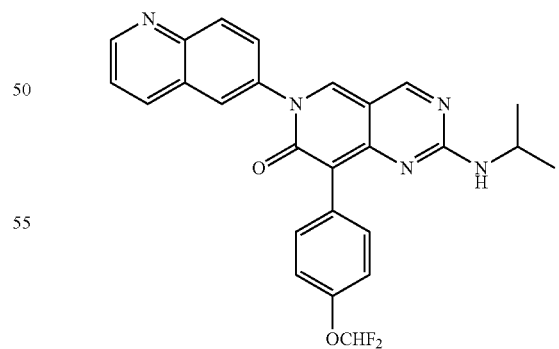

The title compound was synthesized from intermediate 10c with propan-2-amine in the procedure for Example 181 Step J (HOAc, 100° C.).

$^1$H NMR (400 MHz, DMSO-d₆) δ 9.02 (dd, J=4.4 Hz, 2.0 Hz, 1H), 8.88 (s, 1H), 8.86 (s, 1H), 8.48 (d, J=7.6 Hz, 1H), 8.22 (d, J=2.4 Hz, 1H), 8.16 (d, J=8.8 Hz, 1H), 8.04 (d, J=7.6

Hz, 1H), 7.93 (dd, J=8.8 Hz, 2.4 Hz, 1H), 7.75 (d, J=8.8 Hz, 2H), 7.66 (dd, J=8.4 Hz, 4.4 Hz, 1H) 7.27 (t, J$_{HF}$=74.4 Hz, 1H), 7.13 (d, J=8.8 Hz, 2H), 4.00-3.90 (m, 1H), 1.16 (d, J=6.4 Hz, 6H). LC-MS: m/z 474 [M+H]⁺.

Example 183: 2-(cyclobutylamino)-8-(4-(difluoromethoxy)phenyl)-6-(quinolin-6-yl)pyrido[4,3-d]pyrimidin-7(6)-one

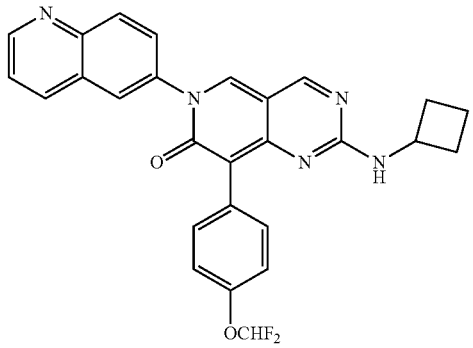 [SMILES: O=c1c(-c2ccc(OC(F)F)cc2)c2nc(NC3CCC3)ncc2cn1-c1ccc2ncccc2c1]

The title compound was synthesized from intermediate 10c with cyclobutanamine in the procedure for Example 181 Step J (HOAc, 100° C.).

¹H NMR (400 MHz, DMSO-d₆) δ: 9.02 (dd, J=4.0 Hz, 1.6 Hz, 1H), 8.88 (s, 1H), 8.86 (s, 1H), 8.47 (d, J=8.4 Hz, 1H), 8.42 (d, J=6.4 Hz, 1H), 8.22 (d, J=2.0 Hz, 1H), 8.15 (d, J=8.4 Hz, 1H), 7.92 (dd, J=9.2 Hz, 2.4 Hz, 1H), 7.74 (d, J=8.8 Hz, 2H), 7.65 (dd, J=8.4 Hz, 4.0 Hz, 1H), 7.27 (t, J$_{HF}$=74.4 Hz, 1H), 7.15 (d, J=8.8 Hz, 2H), 4.25-4.12 (m, 1H), 2.23-2.12 (m, 2H), 2.09-1.92 (m, 2H), 1.71-1.54 (m, 2H). LC-MS: m/z 486 [M+H]⁺.

Example 184: 8-(4-(difluoromethoxy)phenyl)-2-(methylamino)-6-(quinolin-6-yl)pyrido[4,3-d]pyrimidin-7(6H)-one

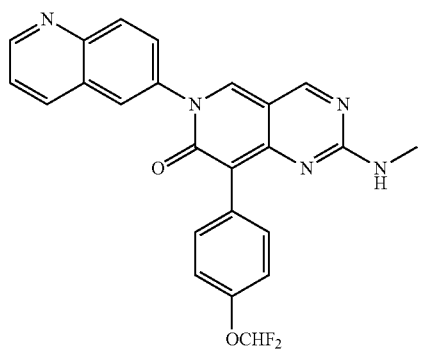 [SMILES: CNc1ncc2cn(-c3ccc4ncccc4c3)c(=O)c(-c3ccc(OC(F)F)cc3)c2n1]

The title compound was synthesized from intermediate 10c with methylamine hydrochloride in the procedure for Example 181 Step J (HOAc, 100° C.).

¹H NMR (400 MHz, DMSO-d₆) δ: 9.02 (dd, J=4.0 Hz, 1.6 Hz, 1H), 8.88 (s, 1H), 8.87 (s, 1H), 8.47 (d, J=8.0 Hz, 1H), 8.23 (d, J=2.0 Hz, 1H), 8.15 (d, J=9.2 Hz, 1H), 8.07-8.02 (m, 1H), 7.93 (dd, J=9.2 Hz, 2.0 Hz, 1H), 7.79 (d, J=8.8 Hz, 2H), 7.66 (dd, J=8.4 Hz, 4.0 Hz, 1H), 7.27 (t, J$_{HF}$=74.6 Hz, 1H), 7.14 (d, J=8.8 Hz, 2H), 2.82 (d, J=5.6 Hz, 3H). LC-MS: m/z 446 [M+H]⁺.

Example 185: 2-(azetidin-1-yl)-8-(4-(difluoromethoxy)phenyl)-6-(quinolin-6-yl)pyrido[4,3-d]pyrimidin-7(6)-one

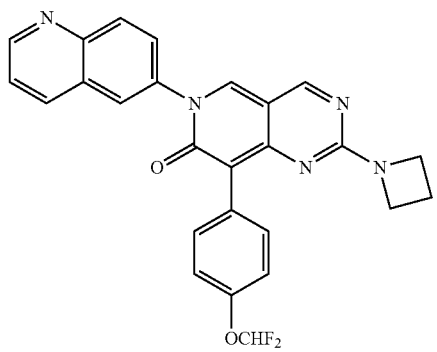 [SMILES: O=c1c(-c2ccc(OC(F)F)cc2)c2nc(N3CCC3)ncc2cn1-c1ccc2ncccc2c1]

The title compound was synthesized from intermediate 10c with azetidine in the procedure for Example 181 Step J (HOAc, 100° C.).

¹H NMR (400 MHz, DMSO-d₆) δ: 9.02 (dd, J=4.4 Hz, 1.6 Hz, 1H), 8.945 (s, 1H), 8.944 (s, 1H), 8.47 (d, J=7.6 Hz, 1H), 8.23 (d, J=2.0 Hz, 1H), 8.14 (d, J=8.8 Hz, 1H), 7.93 (dd, J=8.4 Hz, 2.0 Hz, 1H), 7.76 (d, J=8.8 Hz, 2H), 7.65 (dd, J=8.4 Hz, 4.4 Hz, 1H), 7.26 (t, J$_{HF}$=74.4 Hz, 1H), 7.11 (d, J=8.8 Hz, 2H), 4.24 (t, J=6.4 Hz, 2H), 4.06 (t, J=5.2 Hz, 2H), 2.36-2.25 (m, 2H). LC-MS: m/z 472 [M+H]⁺.

Preparation of 8-(4-bromophenyl)-6-(4-methoxyphenyl)-2-(methylthio)pyrido[4,3-d]pyrimidin-7(6H)-one 10n

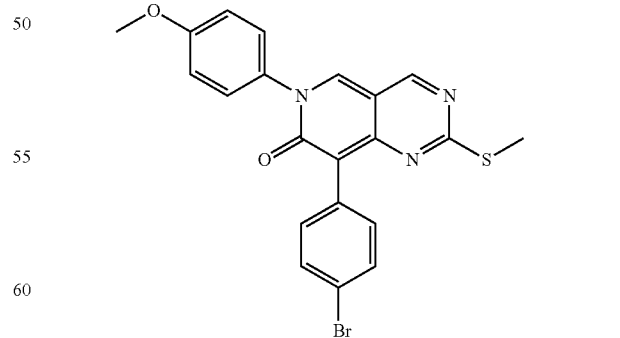

8-(4-bromophenyl)-6-(4-methoxyphenyl)-2-(methylthio)pyrido[4,3-d]pyrimidin-7(6H)-one 10n was synthesized from methyl 2-(4-bromophenyl)acetate via general procedure III (Step B, G-J). LC-MS: m/z 454,456 [M+H]⁺

Example 186: Preparation of 8-(4-bromophenyl)-6-(4-methoxyphenyl)-2-((3,3,3-trifluoropropyl)amino)pyrido[4,3-d]pyrimidin-7(6)-one

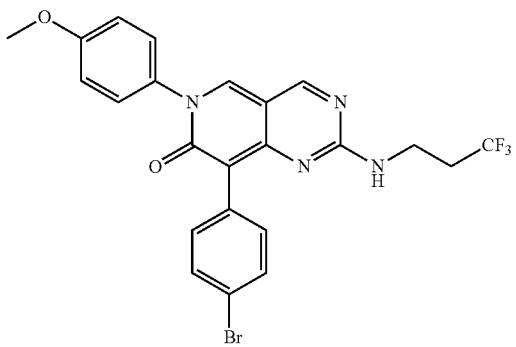 [SMILES: COc1ccc(-n2cc3cnc(NCCC(F)(F)F)nc3c(-c3ccc(Br)cc3)c2=O)cc1]

The title compound was synthesized from intermediate 10n with 3,3,3-Trifluoropropan-1-amine hydrochloride in the procedure for Example 181 Step J (HOAc, 100° C.).

$^1$H NMR (400 MHz, CDCl$_3$) δ 8.66 (s, 1H), 8.11 (s, 1H), 7.61 (d, J=8.4 Hz, 2H), 7.49 (d, J=8.4 Hz, 2H), 7.36 (d, J=8.8 Hz, 2H), 7.01 (d, J=8.8 Hz, 2H), 5.74 (t, J=6.0 Hz, 1H), 3.86 (s, 3H), 3.65 (q, J=6.4 Hz, 2H), 2.50-2.36 (m, 2H). LC-MS: m/z 519, 521 [M+H]$^+$.

Example 187: 8-(4-bromophenyl)-6-(4-methoxyphenyl)-2-(methyl(2,2,2-trifluoroethyl)amino)pyrido[4,3-d]pyrimidin-7(6H)-one

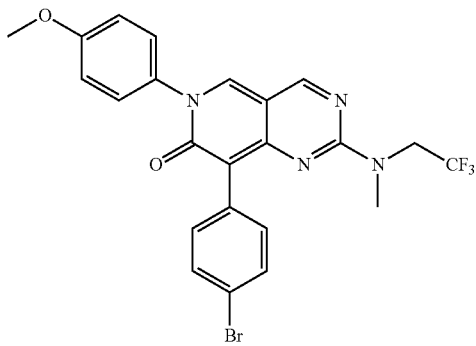 [SMILES: COc1ccc(-n2cc3cnc(N(C)CC(F)(F)F)nc3c(-c3ccc(Br)cc3)c2=O)cc1]

The title compound was synthesized from intermediate 10n with 2,2,2-trifluoro-N-methylethanamine in the procedure for Example 181 Step J (HOAc, 100° C.).

$^1$H NMR (400 MHz, DMSO-d$_6$) δ major isomer: 9.01 (s, 1H), 8.89 (s, 1H), 7.65 (d, J=8.0 Hz, 2H), 7.52 (d, J=8.0 Hz, 2H), 7.48 (d, J=8.8 Hz, 2H), 7.09 (d, J=8.8 Hz, 2H), 4.66 (q, J=9.2 Hz, 2H), 3.83 (s, 3H), 3.15 (s, 3H). minor isomer: 9.07 (s, 1H), 8.92 (s, 1H), 7.59 (d, J=8.4 Hz, 2H), 7.47 (d, J=8.4 Hz, 4H), 7.09 (d, J=8.8 Hz, 2H), 4.46 (q, J=9.2 Hz, 2H), 3.83 (s, 3H), 3.33 (s, 3H). Ratio of two isomers is 2:1. LC-MS: m/z 519, 521 [M+H]$^+$.

Example 188: 8-(4-bromophenyl)-2-(ethylamino)-6-(4-methoxyphenyl)pyrido[4,3-d]pyrimidin-7(6H)-one

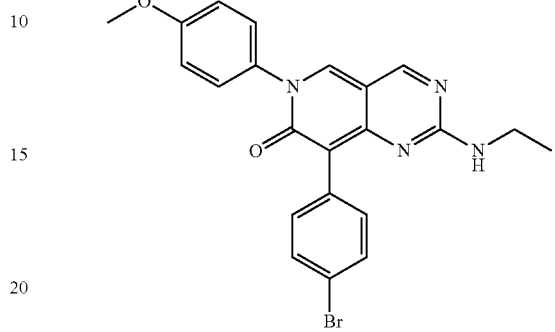

The title compound was synthesized from intermediate 10n with ethylamine hydrochloride in the procedure for Example 181 Step J (HOAc, 100° C.).

$^1$H NMR (400 MHz, DMSO-d$_6$) δ 8.84 (s, 1H), 8.68 (s, 1H), 8.06 (t, J=6.0 Hz, 1H), 7.64 (d, J=8.4 Hz, 2H), 7.48 (d, J=8.4 Hz, 2H), 7.44 (d, J=8.8 Hz, 2H), 7.08 (d, J=8.8 Hz, 2H), 3.83 (s, 3H), 3.29-3.17 (m, 2H), 1.10 (t, J=7.2 Hz, 3H). LC-MS: m/z 451, 453 [M+H]$^+$.

Example 189: 8-(4-bromophenyl)-2-((2,2-difluoroethyl)amino)-6-(4-methoxyphenyl)pyrido[4,3-d]pyrimidin-7(6H)-one

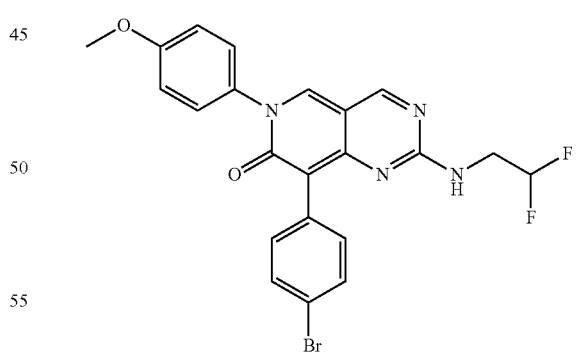

The title compound was synthesized from intermediate 10n with 2,2-difluoroethanamine in the procedure for Example 181 Step J (HOAc, 100° C.).

$^1$H NMR (400 MHz, DMSO-d$_6$) δ 8.92 (s, 1H), 8.79 (s, 1H), 8.37 (t, J=6.0 Hz, 1H), 7.61 (d, J=8.4 Hz, 2H), 7.48 (d, J=8.4 Hz, 2H), 7.46 (d, J=8.8 Hz, 2H), 7.09 (d, J=8.8 Hz, 2H), 6.11 (tt, J$_{HF}$=56.2 Hz, 4.4 Hz, 1H), 3.83 (s, 3H), 3.60 (tt, J=14.4 Hz, 4.4 Hz, 2H). LC-MS: m/z 487, 489 [M+H]$^+$.

Example 190: 8-(4-bromophenyl)-2-((cyclopropylmethyl)amino)-6-(4-methoxyphenyl)pyrido[4,3-d]pyrimidin-7(6H)-one

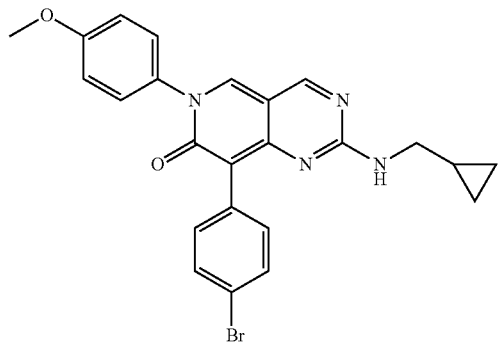 [SMILES: COc1ccc(-n2cc3cnc(NCC4CC4)nc3c(-c3ccc(Br)cc3)c2=O)cc1]

The title compound was synthesized from intermediate 10n with cyclopropylmethanamine in the procedure for Example 181 Step J (HOAc, 100° C.).

$^{1}$H NMR (400 MHz, DMSO-d$_{6}$) δ 8.84 (s, 1H), 8.67 (s, 1H), 8.16 (t, J=6.0 Hz, 1H), 7.60 (d, J=8.4 Hz, 2H), 7.48 (d, J=8.4 Hz, 2H), 7.43 (d, J=8.8 Hz, 2H), 7.07 (d, J=8.4 Hz, 2H), 3.82 (s, 3H), 3.11 (t, J=6.4 Hz, 2H), 1.10-0.95 (m, 1H), 0.44-0.32 (m, 2H), 0.18-0.07 (m, 2H). LC-MS: m/z 477, 479 [M+H]$^{+}$.

Example 191: 8-(4-bromophenyl)-6-(4-methoxyphenyl)-2-(propylamino)pyrido[4,3-d]pyrimidin-7(6H)-one

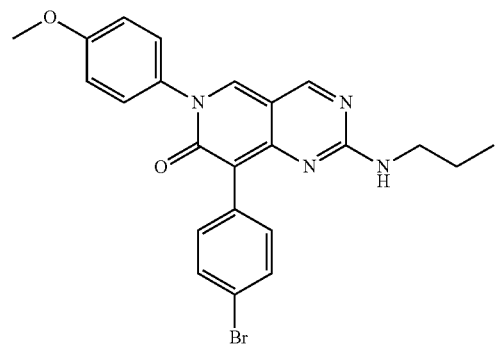 [SMILES: CCCNc1ncc2cn(-c3ccc(OC)cc3)c(=O)c(-c3ccc(Br)cc3)c2n1]

The title compound was synthesized from intermediate 10n with 1-aminopropane Hydrochloride in the procedure for Example 181 Step J (HOAc, 100° C.).

$^{1}$H NMR (400 MHz, DMSO-d$_{6}$) δ 8.84 (s, 1H), 8.68 (s, 1H), 8.11 (t, J=6.4 Hz, 1H), 7.64 (d, J=8.4 Hz, 2H), 7.48 (d, J=8.4 Hz, 2H), 7.45 (d, J=8.8 Hz, 2H), 7.08 (d, J=8.4 Hz, 2H), 3.82 (s, 3H), 3.22-3.12 (m, 2H), 1.59-1.44 (m, 2H), 0.84 (t, J=7.2 Hz, 3H). LC-MS: m/z 465, 467 [M+H]$^{+}$.

Preparation of Example 192

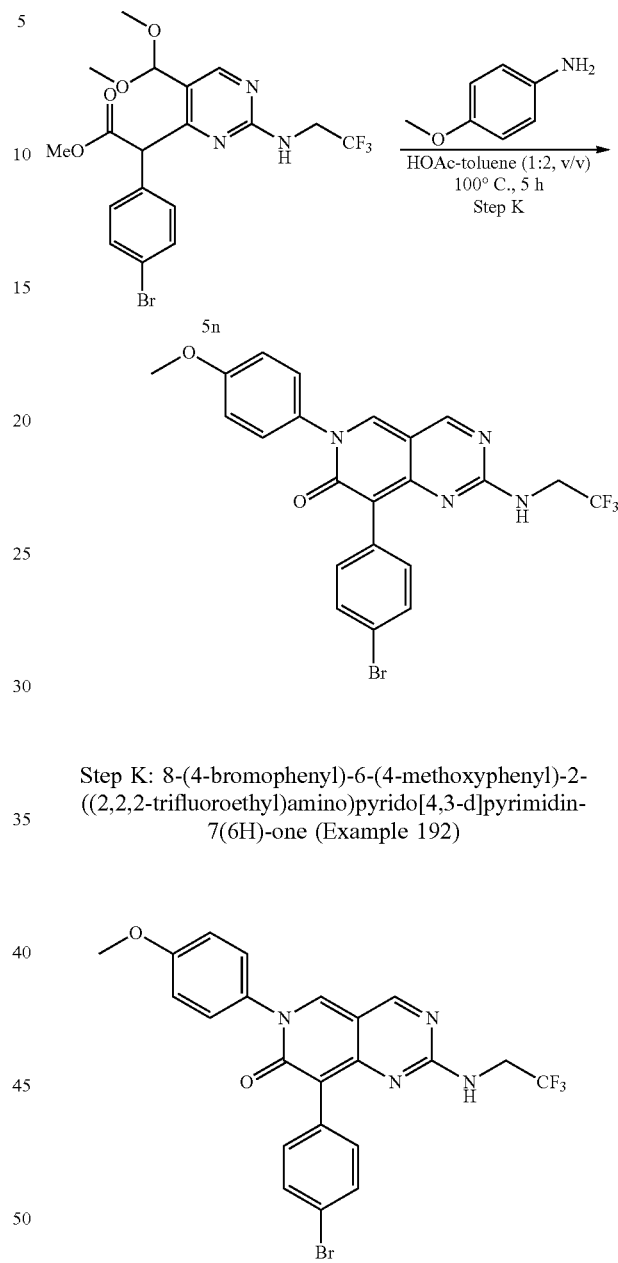

Step K: 8-(4-bromophenyl)-6-(4-methoxyphenyl)-2-((2,2,2-trifluoroethyl)amino)pyrido[4,3-d]pyrimidin-7(6H)-one (Example 192)

A mixture of Methyl 2-(4-bromophenyl)-2-(5-(dimethoxymethyl)-2-((2,2,2-trifluoroethyl)amino)pyrimidin-4-yl)acetate (800 mg, 1.67 mmol, 1.0 equiv.; prepared as in the procedure for Example 123 Step B-D), 4-methoxyaniline (410 mg, 3.34 mmol, 2.0 equiv.), AcOH (4.0 mL), toluene (8.0 mL) and 0.8 ml of water was stirred at 100° C. for 5 h. The mixture was concentrated under reduced pressure, the residue was purified by flash chromatography on silica gel to yield 8-(4-bromophenyl)-6-(4-methoxyphenyl)-2-((2,2,2-trifluoroethyl)amino)pyrido[4,3-d]pyrimidin-7(6H)-one (Example 192)

$^{1}$H NMR (400 MHz, DMSO-d$_{6}$) δ 8.96 (s, 1H), 8.83 (s, 1H), 8.59 (t, J=6.0 Hz, 1H), 7.60 (d, J=8.4 Hz, 2H), 7.51 (d,

J=8.8 Hz, 2H), 7.46 (d, J=8.4 Hz, 2H), 7.09 (d, J=8.8 Hz, 2H), 4.16-4.00 (m, 2H), 3.84 (s, 3H). LC-MS (ESI): m/z 505, 507 [M+H]⁺.

Example 193: 8-(4-chlorophenyl)-6-(4-methoxyphenyl)-2-((2,2,2-trifluoroethyl)amino)pyrido[4,3-d]pyrimidin-7(6H)-one

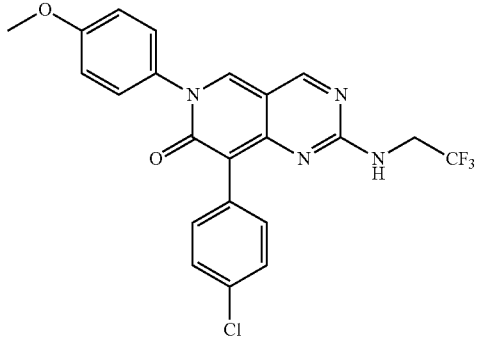 [SMILES: COc1ccc(-n2cc3cnc(NCC(F)(F)F)nc3c(-c3ccc(Cl)cc3)c2=O)cc1]

The title compound was synthesized from intermediate 5a with 4-methoxyaniline in the procedure for Example 192 Step K (HOAc-toulene, 100° C.).

¹H NMR (400 MHz, CDCl₃) δ 8.72 (s, 1H), 8.16 (s, 1H), 7.69 (d, J=8.0 Hz, 2H), 7.41-7.32 (m, 4H), 7.02 (d, J=8.8 Hz, 2H), 5.76 (t, J=6.4 Hz, 1H), 4.18-4.05 (m, 2H), 3.87 (s, 3H). LC-MS: m/z 461 [M+H]⁺.

Example 194: 8-(4-methoxyphenyl)-6-(1-methyl-6-oxo-1,6-dihydropyridin-3-yl)-2-((2,2,2-trifluoroethyl)amino)pyrido[4,3-d]pyrimidin-7(6H)-one

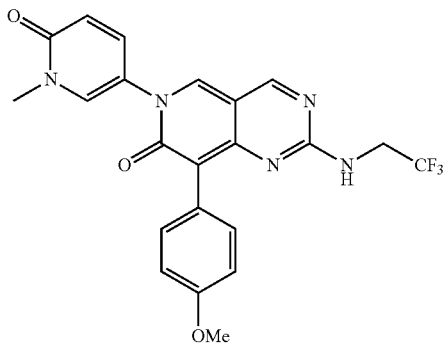 [SMILES: COc1ccc(-c2c(=O)n(-c3ccc(=O)n(C)c3)cc3cnc(NCC(F)(F)F)nc23)cc1]

The title compound was synthesized from intermediate 5b with 5-amino-1-methylpyridin-2(1H)-one in the procedure for Example 192 Step K (HOAc-toluene, 100° C.).

¹H NMR (400 MHz, CDCl₃) δ 8.73 (s, 1H), 8.07 (s, 1H), 7.65 (d, J=8.4 Hz, 2H), 7.61 (d, J=2.0 Hz, 1H), 7.45 (dd, J=9.6 Hz, 2.4 Hz, 1H), 6.95 (dd, J=8.4 Hz, 2H), 6.68 (d, J=10.0 Hz, 1H), 5.75 (t, J=5.6 Hz, 1H), 4.18-4.06 (m, 2H), 3.86 (s, 3H), 3.60 (s, 3H). LC-MS: m/z 458 [M+H]⁺.

Example 195: 8-(4-(difluoromethoxy)phenyl)-6-(4-methoxyphenyl)-2-((2,2,2-trifluoroethyl)amino)pyrido[4,3-d]pyrimidin-7(6H)-one

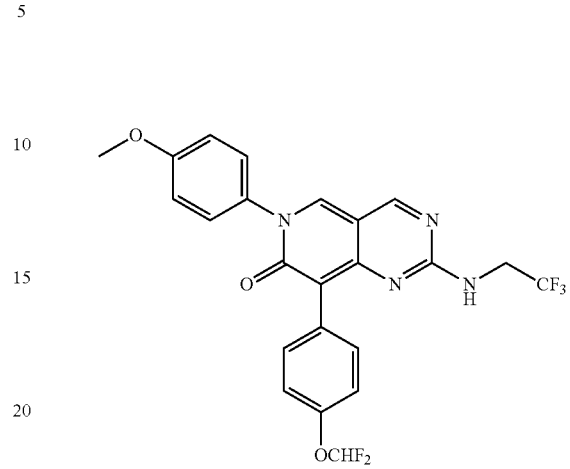

The title compound was synthesized from intermediate 5c with 4-methoxyaniline in the procedure for Example 192 Step K (HOAc-toulene, 100° C.).

¹H NMR (400 MHz, CDCl₃) δ 8.71 (s, 1H), 8.17 (s, 1H), 7.75 (d, J=8.4 Hz, 2H), 7.36 (d, J=8.8 Hz, 2H), 7.13 (d, J=8.4 Hz, 2H), 7.01 (d, J=8.8 Hz, 2H), 6.54 (t, J$_{HF}$=74.6 Hz, 1H), 5.95 (t, J=5.6 Hz, 1H), 4.17-4.02 (m, 2H), 3.86 (s, 3H). LC-MS: m/z 493 [M+H]⁺.

Example 196: 6-(4-methoxyphenyl)-2-((2,2,2-trifluoroethyl)amino)-8-(4-(trifluoromethoxy)phenyl)pyrido[4,3-d]pyrimidin-7(6H)-one

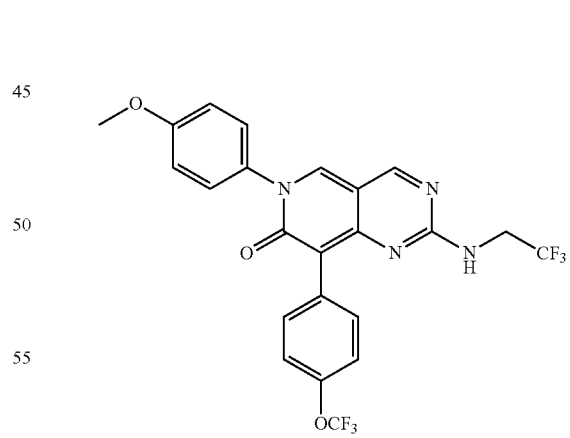

The title compound was synthesized from intermediate 5d with 4-methoxyaniline in the procedure for Example 192 Step K (HOAc-toulene, 100° C.).

1H NMR (400 MHz, CDCl₃) δ 8.73 (s, 1H), 8.18 (s, 1H), 7.78 (d, J=8.0 Hz, 2H), 7.37 (d, J=8.8 Hz, 2H), 7.23 (d, J=8.0 Hz, 2H), 7.02 (d, J=8.8 Hz, 2H), 5.76 (t, J=6.4 Hz, 1H), 4.17-4.05 (m, 2H), 3.87 (s, 3H). LC-MS: m/z 511 [M+H]⁺.

Example 197: 6-(4-methoxyphenyl)-2-((2,2,2-trifluoroethyl)amino)-8-(4-(trifluoromethyl)phenyl)pyrido[4,3-d]pyrimidin-7(6H)-one

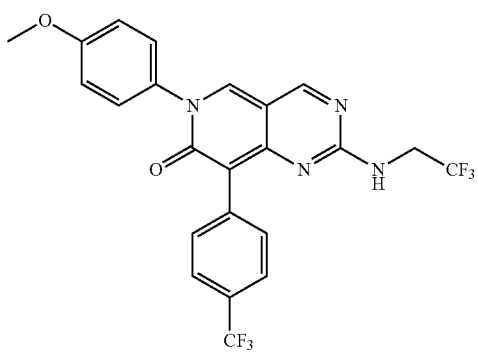 [SMILES: COc1ccc(-n2cc3cnc(NCC(F)(F)F)nc3c(-c3ccc(C(F)(F)F)cc3)c2=O)cc1]

The title compound was synthesized from intermediate 5e with 4-methoxyaniline in the procedure for Example 192 Step K (HOAc-toulene, 100° C.).

$^1$H NMR (400 MHz, CDCl$_3$) δ 8.93 (s, 1H), 8.20 (s, 1H), 7.86 (d, J=8.4 Hz, 2H), 7.63 (d, J=8.4 Hz, 2H), 7.37 (d, J=8.8 Hz, 2H), 7.03 (d, J=8.8 Hz, 2H), 5.76 (t, J=6.0 Hz, 1H), 4.16-4.04 (m, 2H), 3.87 (s, 3H). LC-MS: m/z 495 [M+H]$^+$.

Preparation of methyl 2-(6-cyclopropylpyridin-3-yl)-2-(5-(dimethoxymethyl)-2-((2,2,2-trifluoroethyl)amino)pyrimidin-4-yl)acetate 5o

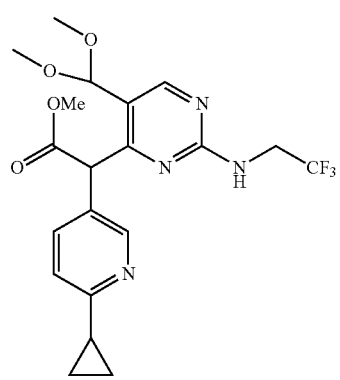

methyl 2-(6-cyclopropylpyridin-3-yl)-2-(5-(dimethoxymethyl)-2-((2,2,2-trifluoroethyl)amino)pyrimidin-4-yl)acetate 5o was synthesized from methyl 2-(6-cyclopropylpyridin-3-yl)acetate via general procedure III (Step B-D). LC-MS: m/z 441 [M+H]$^+$ Example 198: 8-(6-cyclopropylpyridin-3-yl)-6-(4-methoxyphenyl)-2-((2,2,2-trifluoroethyl)amino)pyrido[4,3-d]pyrimidin-7(6)-one

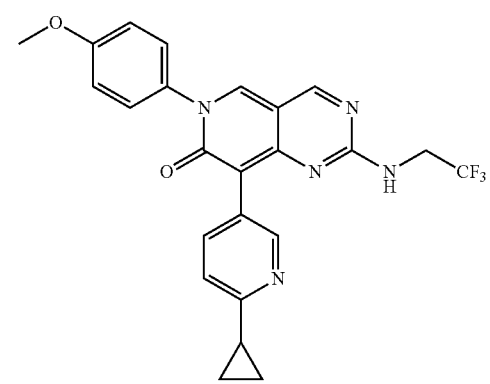

The title compound was synthesized from intermediate 5o with 4-methoxyaniline in the procedure for Example 192 Step K (HOAc-toulene, 100° C.).

$^1$H NMR (400 MHz, DMSO-d$_6$) δ 8.96 (s, 1H), 8.82 (s, 1H), 8.62 (d, J=2.0 Hz, 1H), 8.58 (t, J=6.4 Hz, 1H), 7.84 (dd, J=8.0 Hz, 2.4 Hz, 1H), 7.47 (d, J=8.8 Hz, 2H), 7.23 (d, J=8.0 Hz, 1H), 7.09 (d, J=8.8 Hz, 2H), 4.14-4.00 (m, 2H), 3.83 (s, 3H), 2.14-2.05 (m, 1H), 0.97-0.90 (m, 4H). LC-MS: m/z 468 [M+H]$^+$.

Preparation of methyl 2-(4-cyclobutylphenyl)-2-(5-(dimethoxymethyl)-2-((2,2,2-trifluoroethyl)amino)pyrimidin-4-yl)acetate 5p

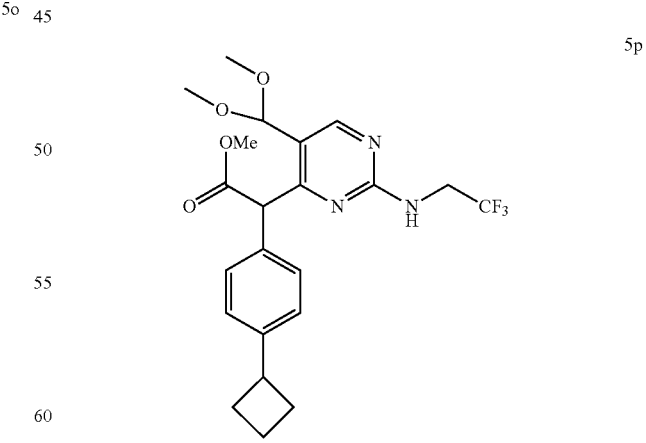

methyl 2-(4-cyclobutylphenyl)-2-(5-(dimethoxymethyl)-2-((2,2,2-trifluoroethyl)amino)pyrimidin-4-yl)acetate 5p was synthesized from methyl 2-(4-cyclobutylphenyl)acetate via general procedure III (Step B-D). LC-MS: m/z 454 [M+H]$^+$ 8-(4-cyclobutylphenyl)-6-(4-methoxyphenyl)-2-((2,2,2-trifluoroethyl)amino)pyrido[4,3-d]pyrimidin-7(6H)-one (Example 199)

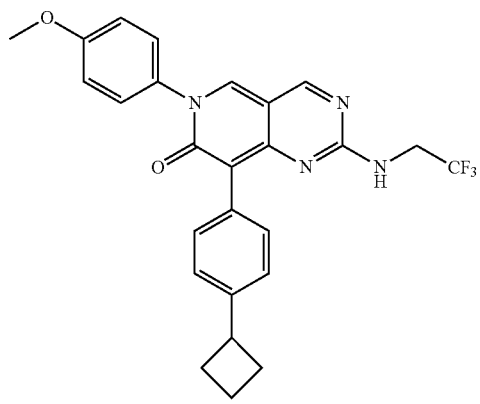 [SMILES: COc1ccc(-n2cc3cnc(NCC(F)(F)F)nc3c(-c3ccc(C4CCC4)cc3)c2=O)cc1]

The title compound was synthesized from intermediate 5p with 4-methoxyaniline in the procedure for Example 192 Step K (HOAc-toulene, 100° C.).

$^1$H NMR (400 MHz, DMSO-d$_6$) δ 8.94 (s, 1H), 8.77 (s, 1H), 8.49 (t, J=6.4 Hz, 1H), 7.57 (d, J=8.4 Hz, 2H), 7.46 (d, J=8.8 Hz, 2H), 7.16 (d, J=8.4 Hz, 2H), 7.09 (d, J=8.8 Hz, 2H), 4.15-4.00 (m, 2H), 3.59-3.48 (m, 1H), 2.37-2.24 (m, 2H), 2.19-2.04 (m, 2H), 2.03-1.90 (m, 1H), 1.88-1.76 (m, 1H). LC-MS: m/z 481 [M+H]$^+$.

Preparation of Example 200

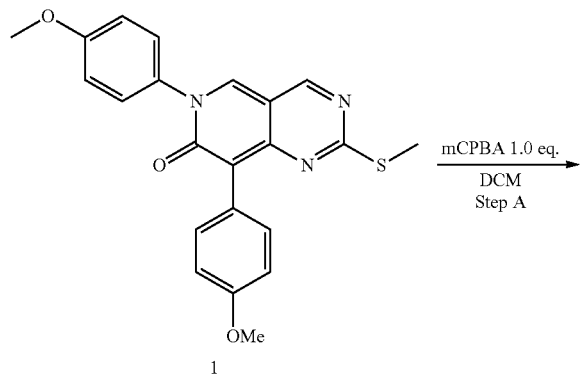

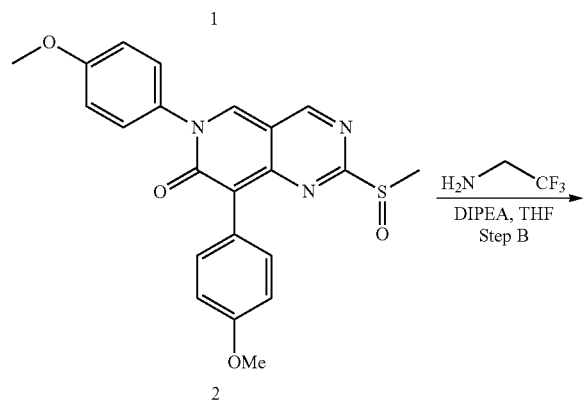

Step A: 6,8-bis(4-methoxyphenyl)-2-(methylsulfinyl)pyrido[4,3-d]pyrimidin-7(6H)-one

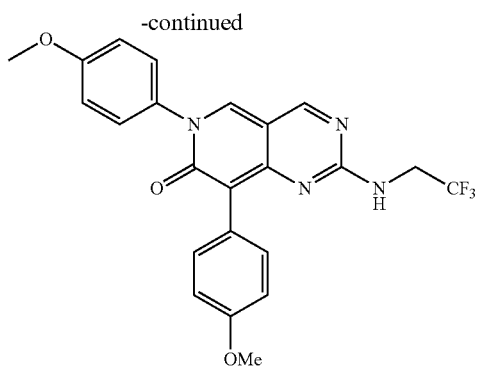

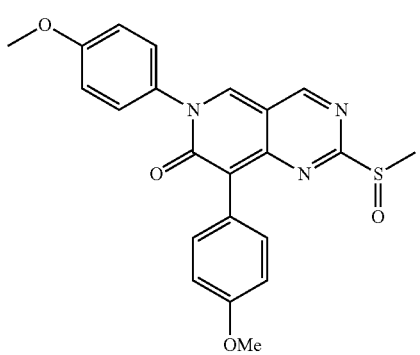

To a solution of 6,8-bis(4-methoxyphenyl)-2-(methylthio)pyrido[4,3-d]pyrimidin-7(6H)-one (180 mg, 0.4 mmol, 1.0 equiv) in DCM (15 mL) was added mCPBA (76 mg, 0.4 mmol, 1.0 equiv) at −5° C. Then the mixture was stirred at −5° C. for 3 h. The solvent was removed under vacuum and the resulting mixture was purified by prep-TLC (PE:EA=1:4) to give 6,8-bis(4-methoxyphenyl)-2-(methylsulfinyl)pyrido[4,3-d]pyrimidin-7(6H)-one (65 mg, 35% yield) as a yellow solid. LC-MS: m/z 422 [M+H]$^+$.

Step B: 6,8-bis(4-methoxyphenyl)-2-(2,2,2-trifluoroethylamino)pyrido[4,3-d]pyrimidin-7(6H)-one (Example 200)

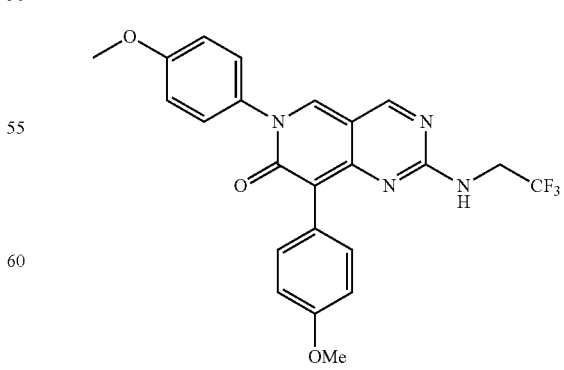

To a solution of 6,8-bis(4-methoxyphenyl)-2-(methylsulfinyl)pyrido[4,3-d]pyrimidin-7(6H)-one (65 mg, 0.15 mmol, 1.0 equiv), DIPEA (10.0 mg, 0.75 mmol, 5 equiv) in THF (3.0 mL) was added 2,2,2-trifluoroethanamine (75 mg, 0.75 mmol, 5 equiv). The mixture was then stirred at 25° C. overnight, and the resulting mixture was concentrated under vacuum before being diluted with DCM (10 mL) and H₂O (10 mL). The aqueous layer was extracted with DCM (10.0 mL×2), and the combined organic layers were concentrated under reduced pressure. The resulting residue was purified by flash column chromatography on silica gel to yield 6,8-bis(4-methoxyphenyl)-2-((2,2,2-trifluoroethyl)amino) pyrido[4,3-d]pyrimidin-7(6H)-one (Example 200).

$^1$H NMR (400 MHz, CDCl$_3$) δ 8.69 (s, 1H), 8.12 (s, 1H), 7.70 (d, J=8.4 Hz, 2H), 7.36 (d, J=9.2 Hz, 2H), 7.02 (d, J=8.8 Hz, 2H), 6.93 (d, J=8.8 Hz, 2H), 5.84 (t, J=6.4 Hz, 1H), 4.19-4.06 (m, 2H), 3.86 (s, 3H), 3.84 (s, 3H). LC-MS: m/z 457 [M+H]$^+$.

Preparation of Example 201

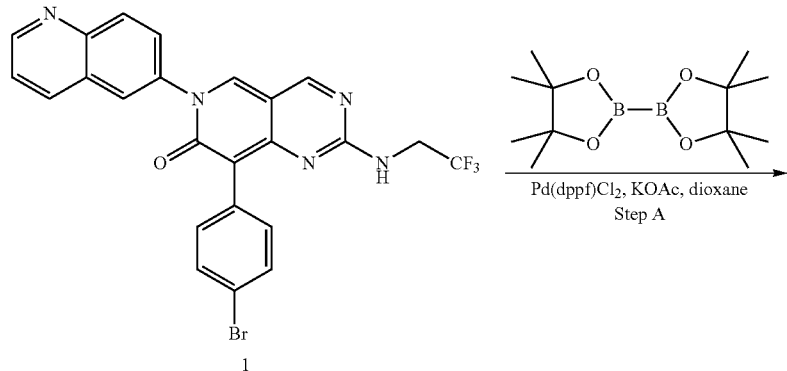

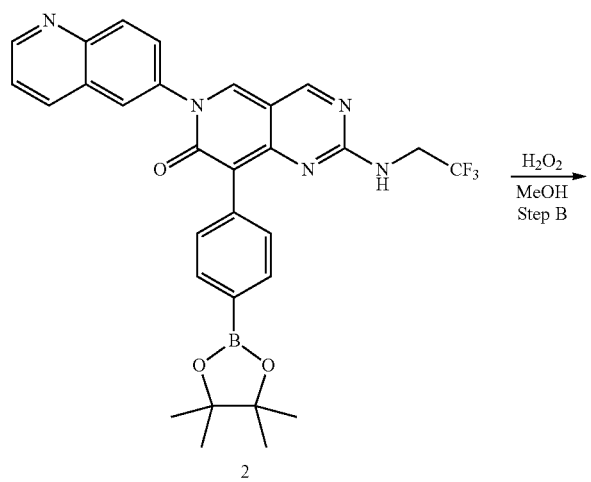

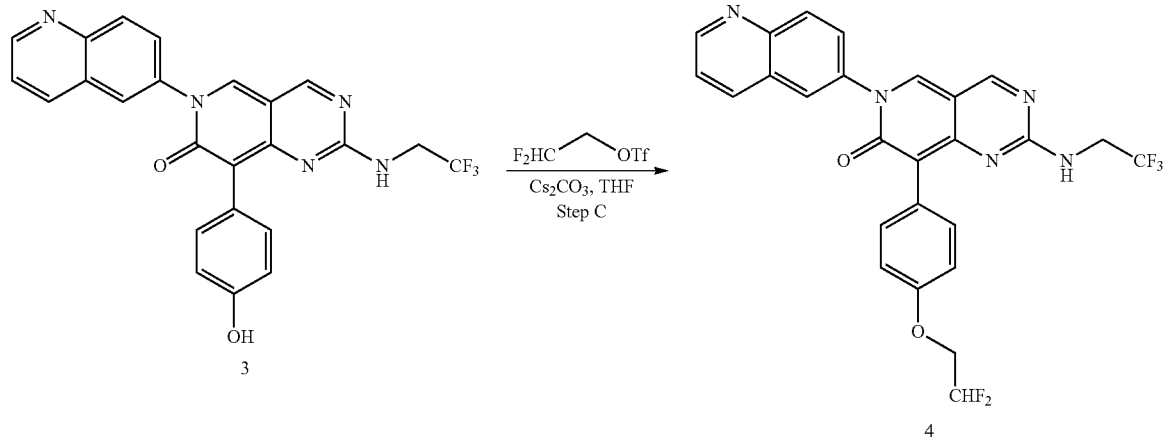

Step A: 6-(quinolin-6-yl)-8-(4-(4,4,5,5-tetramethyl-1,3,2-dioxaborolan-2-yl)phenyl)-2-((2,2,2-trifluoroethyl)amino)pyrido[4,3-d]pyrimidin-7(6H)-one

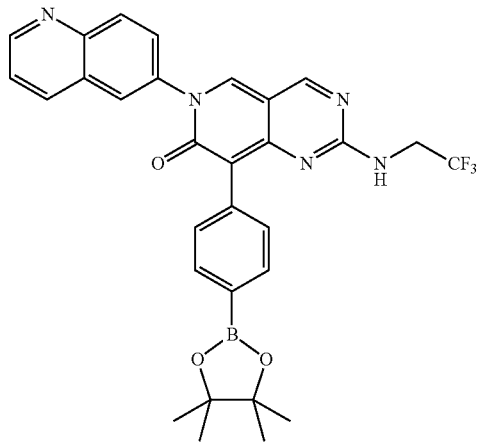 [SMILES: CC1(C)OB(c2ccc(-c3c(=O)n(-c4ccc5ncccc5c4)cc4cnc(NCC(F)(F)F)nc34)cc2)OC1(C)C]

A mixture of 8-(4-bromophenyl)-6-(quinolin-6-yl)-2-((2,2,2-trifluoroethyl)amino)pyrido[4,3-d]pyrimidin-7(6H)-one (Example 180, 160 mg, 0.3 mmol, 1.0 equiv), 4,4,4',4',5,5,5',5'-octamethyl-2,2'-bi(1,3,2-dioxaborolane) (116 mg, 0.46 mmol, 1.5 equiv), Pd(dppf)Cl₂ (22 mg, 0.03 mmol, 0.1 equiv) and KOAc (90 mg, 0.91 mmol, 3.0 equiv) in 1,4-dioxane (5.0 mL) was stirred at 80° C. overnight under an atmosphere of N₂. The mixture was filtered through a short pad of Celite© and the filtrate was concentrated under reduced pressure. Then the residue was further purified by flash column chromatography on silica gel to afford the desired product (110 mg, 63% yield) as a yellow solid. LC-MS (ESI): m/z 574 [M+H]⁺.

Step B: 8-(4-hydroxyphenyl)-6-(quinolin-6-yl)-2-((2,2,2-trifluoroethyl)amino)pyrido[4,3-d]pyrimidin-7(6H)-one

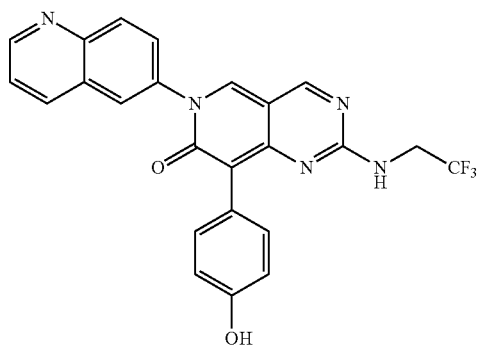

A mixture of 6-(quinolin-6-yl)-8-(4-(4,4,5,5-tetramethyl-1,3,2-dioxaborolan-2-yl) phenyl)-2-((2,2,2-trifluoroethyl) amino)pyrido[4,3-d]pyrimidin-7(6H)-one (100 mg, 0.17 mmol, 1.0 equiv) and H₂O₂ (30% aq., 350 mg, 3.49 mmol, 20.0 equiv) in MeOH (4.0 ml) was stirred at 0° C. for 1 h. The mixture was diluted with EtOAc (10.0 mL), and washed with NaS₂O₃ (sat. aq., 10.0 mL). The organic layer was concentrated under reduced pressure to afford 8-(4-hydroxyphenyl)-6-(quinolin-6-yl)-2-((2,2,2-trifluoroethyl)amino) pyrido[4,3-d]pyrimidin-7(6H)-one (75.0 mg, 95% yield) as a yellow solid, which was taken forward without further purification. LC-MS: m/z 464 [M+H]⁺.

Step C: 8-(4-(2,2-difluoroethoxy)phenyl)-6-(quinolin-6-yl)-2-((2,2,2-trifluoroethyl)amino)pyrido[4,3-d]pyrimidin-7(6H)-one (Example 201)

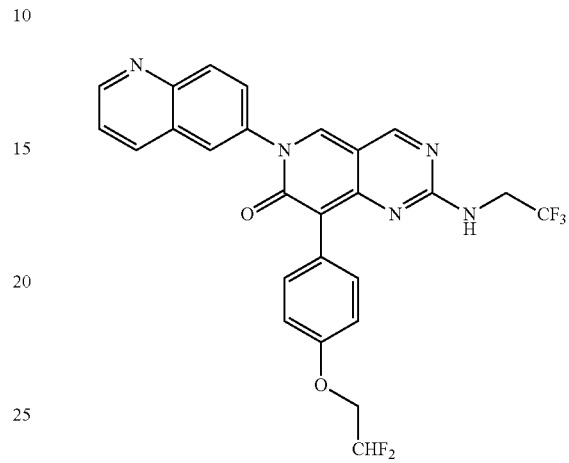

To a mixture of 8-(4-hydroxyphenyl)-6-(quinolin-6-yl)-2-((2,2,2-trifluoroethyl)amino) pyrido[4,3-d]pyrimidin-7(6H)-one (50.0 mg, 0.11 mmol, 1.0 equiv) in THF (3.0 mL), was added 2,2-difluoroethyl trifluoromethanesulfonate (25.0 mg, 0.12 mmol, 1.1 equiv) and Cs₂CO₃ (70.0 mg, 0.22 mmol, 2.0 equiv) at 0° C., after which the resulting mixture was allowed to warm to room temperature and stirred for an additional 3 h. The mixture was concentrated under reduced pressure, and the resulting residue was purified by RP-prep-HPLC to yield 8-(4-(2,2-difluoroethoxy)phenyl)-6-(quinolin-6-yl)-2-((2,2,2-trifluoroethyl)amino)pyrido[4,3-d]pyrimidin-7(6H)-one (Example 201).

¹H NMR (400 MHz, DMSO-d₆) δ 9.03 (dd, J=8.4 Hz, 1.6 Hz, 1H), 8.99 (s, 1H), 8.97 (s, 1H), 8.59 (t, J=6.4 Hz, 1H), 8.48 (d, J=7.6 Hz, 1H), 8.24 (d, J=2.0 Hz, 1H), 8.17 (d, J=9.2 Hz, 1H), 7.94 (dd, J=9.2 Hz, 2.4 Hz, 1H), 7.69-7.61 (m, 3H), 6.97 (d, J=8.8 Hz, 2H), 6.41 (tt, J$_{HF}$=56.2 Hz, 3.6 Hz, 1H), 4.34 (tq, J=14.8 Hz, 3.6 Hz, 2H), 4.18-4.04 (m, 2H). LC-MS (ESI): m/z 528 [M+H]⁺.

Preparation of Example 202

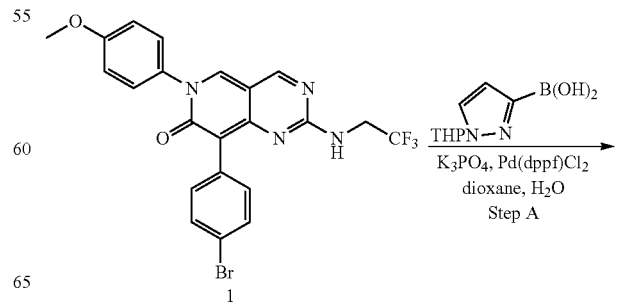

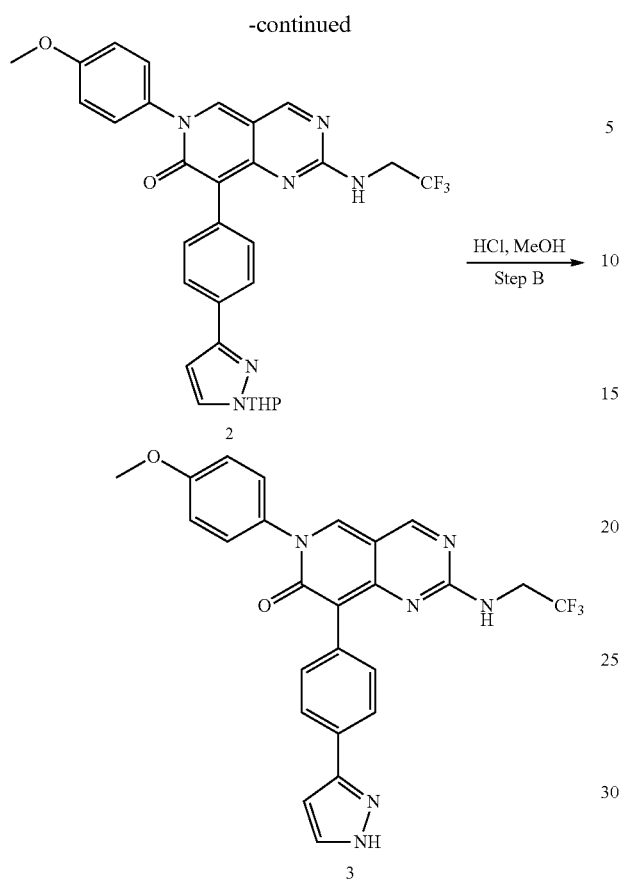

Step A: 6-(4-methoxyphenyl)-8-(4-(1-(tetrahydro-2H-pyran-2-yl)-1H-pyrazol-3-yl)phenyl)-2-((2,2,2-trifluoroethyl)amino)pyrido[4,3-d]pyrimidin-7(6H)-one

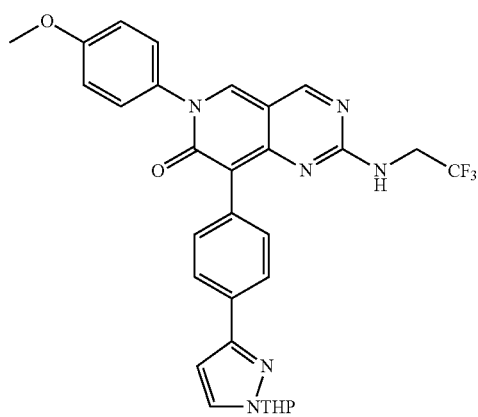

A mixture of 8-(4-bromophenyl)-6-(4-methoxyphenyl)-2-((2,2,2-trifluoroethyl)amino)pyrido[4,3-d]pyrimidin-7(6H)-one (Example 192, 70.0 mg, 0.1 mmol, 1.0 equiv), (1-(tetrahydro-2H-pyran-2-yl)-1H-pyrazol-3-yl)boronic acid (77.0 mg, 0.3 mmol, 3.0 equiv), Pd(dppf)Cl$_2$ (8.0 mg, 0.01 mmol, 0.1 equiv) and K$_3$PO$_4$ (88.0 mg, 0.4 mmol, 4.0 equiv) in dioxane/H$_2$O (4/1, 5.0 mL) was stirred at 100° C. overnight under nitrogen atmosphere. The mixture was cooled to r.t., diluted with water (10.0 mL), extracted with EtOAc (20.0 mL×2), washed with brine (10.0 mL), dried over anhydrous Na$_2$SO$_4$, filtered and concentrated. The residue was purified by column chromatography on silica gel (PE: EA=5:1) to give the desired product (70.0 mg, 88% yield) as a yellow solid. LC-MS: m/z 577 [M+H]$^+$.

Step B: 8-(4-(H-pyrazol-3-yl)phenyl)-6-(4-methoxyphenyl)-2-((2,2,2-trifluoroethyl)amino)pyrido[4,3-d]pyrimidin-7(6H)-one (Example 202)

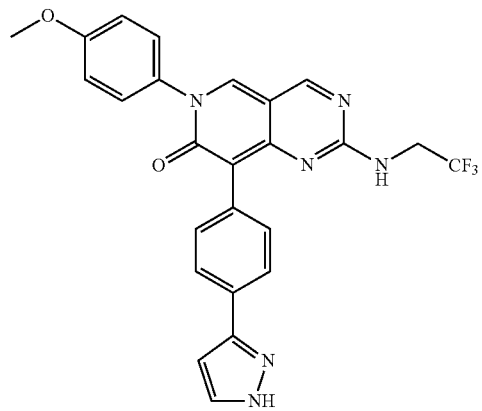 [SMILES: COc1ccc(-n2cc3cnc(NCC(F)(F)F)nc3c(-c3ccc(-c4cc[nH]n4)cc3)c2=O)cc1]

A mixture of 6-(4-methoxyphenyl)-8-(4-(1-(tetrahydro-2H-pyran-2-yl)-1H-pyrazol-3-yl)phenyl)-2-((2,2,2-trifluoroethyl)amino)pyrido[4,3-d]pyrimidin-7(6H)-one (50.0 mg, 0.1 mmol, 1.0 equiv) and HCl (1 M aq., 0.3 mL, 3.0 equiv.) in MeOH (1.0 mL) was stirred at r.t. for 30 minutes. The solution was then concentrated and the resulting residue was purified by RP-prep-HPLC to give 8-(4-(H-pyrazol-3-yl)phenyl)-6-(4-methoxyphenyl)-2-((2,2,2-trifluoroethyl)amino)pyrido[4,3-d]pyrimidin-7(6H)-one (Example 202).
$^1$H NMR (400 MHz, DMSO-d$_6$) δ: 8.97 (s, 1H), 8.81 (s, 1H), 8.55 (t, J=6.4 Hz, 1H), 7.81-7.66 (m, 4H), 7.48 (d, J=9.2 Hz, 2H), 7.40-7.16 (m, 2H), 7.09 (d, J=8.8 Hz, 2H), 6.72 (s, 1H), 4.15-4.03 (m, 2H), 3.83 (s, 3H). LC-MS: m/z 493 [M+H]$^+$.

Example 203: 8-(4-(H-pyrazol-3-yl)phenyl)-6-(quinolin-6-yl)-2-((2,2,2-trifluoroethyl)amino)pyrido[4,3-d]pyrimidin-7(6H)-one

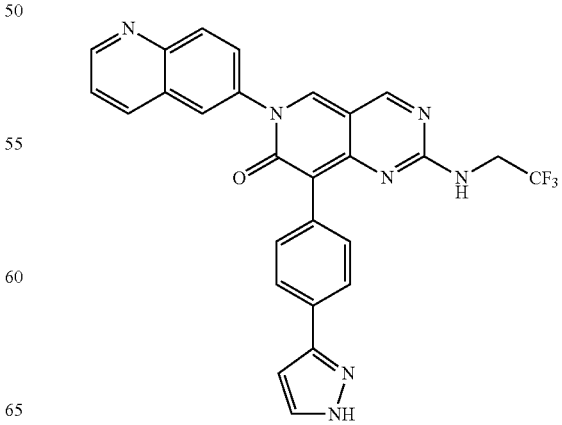

The title compound was synthesized from Example 180 with 1-(tetrahydro-2H-pyran-2-yl)-5-(4,4,5,5-tetramethyl-1,3,2-dioxaborolan-2-yl)-1H-pyrazole as prepared in the procedure for Example 202 (Step A-B).

¹H NMR (400 MHz, DMSO-d₆) δ 9.03 (dd, J=4.4 Hz, 1.6 Hz, 1H), 9.01 (s, 1H), 9.00 (s, 1H), 8.63 (t, J=6.4 Hz, 1H), 8.49 (d, J=7.2 Hz, 1H), 8.26 (d, J=2.0 Hz, 1H), 8.17 (d, J=8.8 Hz, 1H), 8.16 (s, 1H), 7.96 (dd, J=8.4 Hz, 2.0 Hz, 1H), 7.77 (d, J=8.8 Hz, 2H), 7.73 (d, J=8.8 Hz, 2H), 7.71 (br s, 1H), 7.66 (dd, J=8.4 Hz, 4.4 Hz, 1H), 6.73 (d, J=2.0 Hz, 1H), 4.20-4.04 (m, 2H). LC-MS: m/z 514 [M+H]⁺.

Example 204: Preparation of 8-(4-(azetidin-1-yl)phenyl)-6-(4-methoxyphenyl)-2-((2,2,2-trifluoroethyl)amino)pyrido[4,3-d]pyrimidin-7(6H)-one

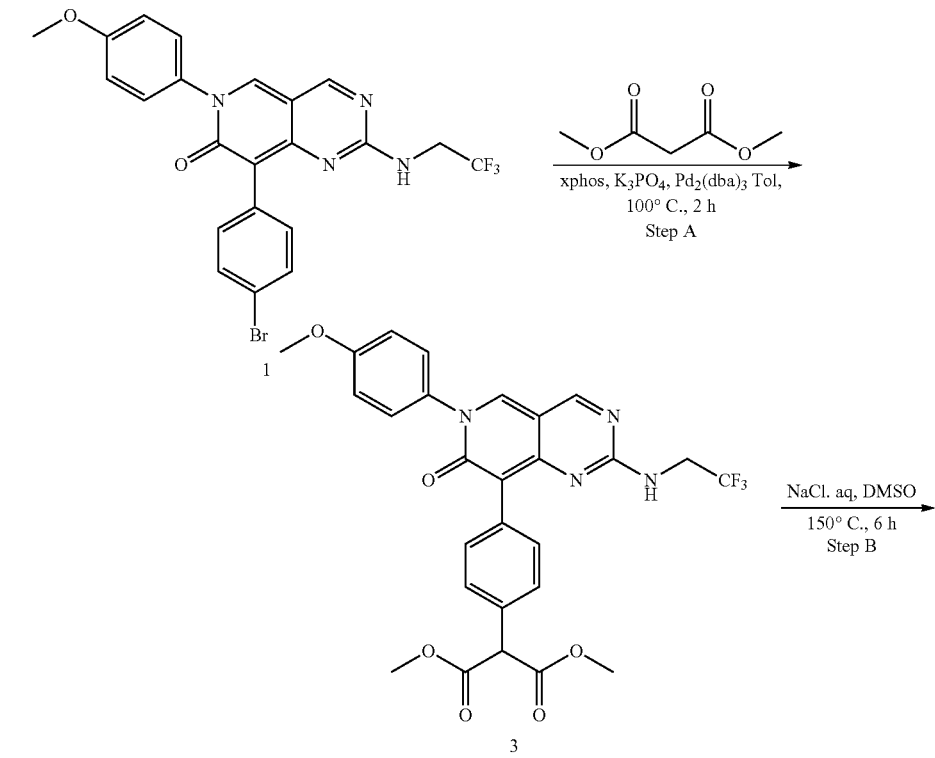

A mixture of 8-(4-bromophenyl)-6-(4-methoxyphenyl)-2-((2,2,2-trifluoroethyl)amino)pyrido[4,3-d]pyrimidin-7(6H)-one (Example 192, 100 mg, 0.2 mmol, 1.0 equiv), azetidine (114.0 mg, 2.0 mmol, 10.0 equiv), Pd₂(dba)₃ (18.0 mg, 0.02 mmol, 0.1 equiv), Ru-Phos (18.0 mg, 0.04 mmol, 0.2 equiv) and K₃PO₄ (127 mg, 0.6 mmol, 3.0 equiv) in toluene (2.0 mL) was stirred at 100° C. in a sealed tube overnight under nitrogen atmosphere. The mixture was concentrated and the residue was purified by RP-prep-HPLC to give 8-(4-(azetidin-1-yl)phenyl)-6-(4-methoxyphenyl)-2-((2,2,2-trifluoroethyl)amino)pyrido[4,3-d]pyrimidin-7(6H)-one (Example 204).

¹H NMR (400 MHz, DMSO-d₆) δ 8.93 (s, 1H), 8.70 (s, 1H), 8.43 (t, J=6.4 Hz, 1H), 7.51 (d, J=8.4 Hz, 2H), 7.45 (d, J=8.8 Hz, 2H), 7.09 (d, J=8.8 Hz, 2H), 6.35 (d, J=8.4 Hz, 2H), 4.18-4.04 (m, 2H), 3.84 (s, 3H), 3.82 (t, J=7.2 Hz, 4H), 2.36-2.26 (m, 2H). LC-MS: m/z 482 [M+H]⁺.

Preparation of Example 205

-continued

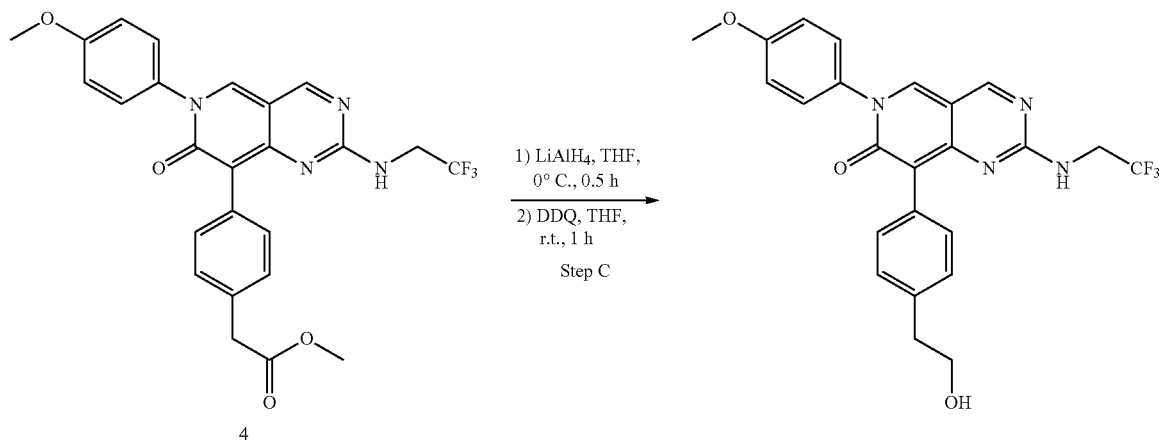

Step A: dimethyl 2-(4-(6-(4-methoxyphenyl)-7-oxo-2-((2,2,2-trifluoroethyl)amino)-6,7-dihydropyrido[4,3-d]pyrimidin-8-yl)phenyl)malonate Step B: methyl 2-(4-(6-(4-methoxyphenyl)-7-oxo-2-((2,2,2-trifluoroethyl)amino)-6,7-dihydropyrido[4,3-d]pyrimidin-8-yl)phenyl)acetate

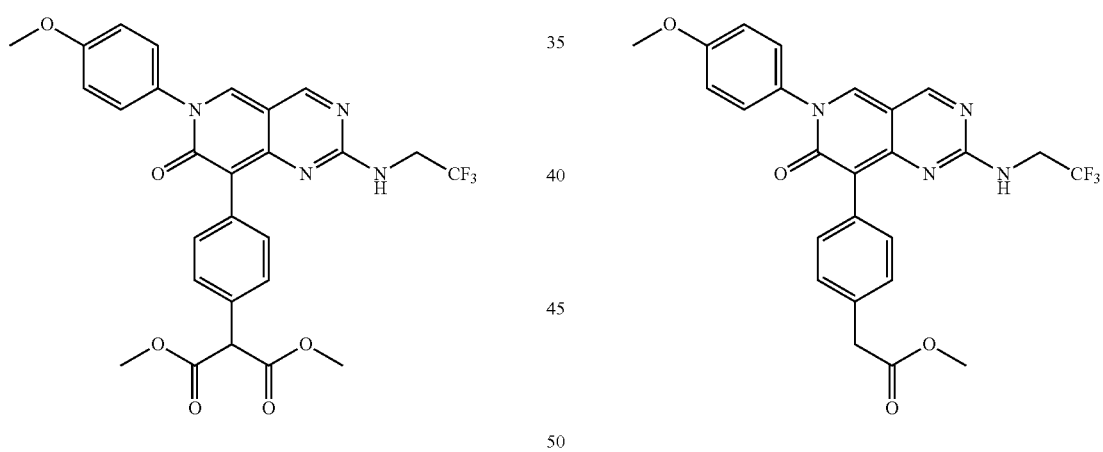

To a solution of 8-(4-bromophenyl)-6-(4-methoxyphenyl)-2-(2,2,2-trifluoroethylamino)pyrido[4,3-d]pyrimidin-7(6H)-one (200.0 mg, 0.396 mmol, 1.0 equiv) in toluene (5.0 mL) was added K$_3$PO$_4$ (168.0 mg, 0.792 mmol, 2.0 equiv), X-Phos (40.0 mg, 0.084 mmol, 0.2 equiv) and Pd$_2$(dba)$_3$ (38.0 mg, 0.045 mmol, 0.1 equiv). Then the resulting mixture was stirred at 100° C. for 2 h under N$_2$. The reaction mixture was diluted with EtOAc (10.0 mL) and washed with H$_2$O (10 mL×3), dried over anhydrous Na$_2$SO$_4$, and concentrated under reduced pressure. The residue was purified by flash column chromatography (PE/EA=3/1-1/1) to afford the desired product (130 mg, 59% yield) as a yellow solid. LC-MS: m/z 557 [M+H]$^+$.

To a solution of 2-(4-(6-(4-methoxyphenyl)-7-oxo-2-(2,2,2-trifluoroethylamino)-6,7-dihydropyrido[4,3-d]pyrimidin-8-yl)phenyl)malonate (130.0 mg, 0.234 mmol, 1.0 equiv) in DMSO (2.0 mL) was added NaCl aq. (0.55 M, 2.0 mL, 5.0 equiv). The resulting mixture was stirred at 150° C. for 6 h. The reaction mixture was then diluted with ethyl acetate (10.0 mL) and washed with H$_2$O (10.0 mL×3), dried over anhydrous Na$_2$SO$_4$, and concentrated under reduced pressure. The residue was purified by flash column chromatography (PE/EA=1/1) to afford 2-(4-(6-(4-methoxyphenyl)-7-oxo-2-((2,2,2-trifluoroethyl) amino)-6,7-dihydropyrido[4,3-d]pyrimidin-8-yl)phenyl)acetate (85.0 mg, 73% yield) as a yellow solid. LC-MS: m/z 499 [M+H]$^+$.

Step C: 8-(4-(2-hydroxyethyl)phenyl)-6-(4-methoxyphenyl)-2-(2,2,2-trifluoroethylamino)pyrido[4,3-d]pyrimidin-7(6H)-one (Example 205)

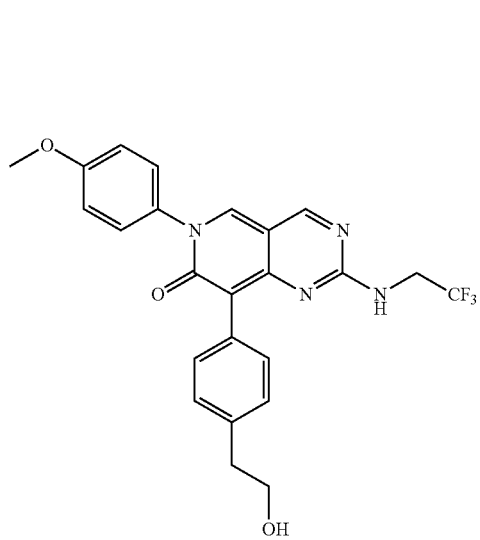 [SMILES: COc1ccc(-n2cc3cnc(NCC(F)(F)F)nc3c(-c3ccc(CCO)cc3)c2=O)cc1]

To a solution of methyl 2-(4-(6-(4-methoxyphenyl)-7-oxo-2-(2,2,2-trifluoroethylamino)-6,7-dihydropyrido[4,3-d]pyrimidin-8-yl)phenyl)acetate (85.0 mg, 0.170 mmol, 1.0 equiv) in THF (3.0 mL) was added LiAlH$_4$ (32.0 mg, 0.842 mmol, 5.0 equiv) at 0° C. The resulting mixture was stirred at 0° C. for 30 minutes. The reaction mixture was then quenched with sodium sulfate decahydrate (100 mg), filtered and concentrated. Then a mixture of the residue and DDQ (57.0 mg, 0.251 mmol, 1.5 equiv) in THF (3.0 mL) was stirred at r.t. for 1 h and then concentrated under reduced pressure. The residue was purified by Prep-HPLC to afford 8-(4-(2-hydroxyethyl)phenyl)-6-(4-methoxyphenyl)-2-(2,2,2-trifluoroethylamino)pyrido[4,3-d]pyrimidin-7(6H)-one (Example 205).

$^1$H NMR (400 MHz, DMSO-d$_6$) δ 8.94 (s, 1H), 8.77 (s, 1H), 8.50 (t, J=6.4 Hz, 1H), 7.55 (d, J=8.0 Hz, 2H), 7.46 (d, J=9.2 Hz, 2H), 7.15 (d, J=8.0 Hz, 2H), 7.09 (d, J=9.2 Hz, 2H), 4.64 (t, J=5.2 Hz, 1H), 4.18-4.04 (m, 2H), 4.15-4.02 (m, 2H), 3.83 (s, 3H), 3.67-3.58 (m, 2H), 2.74 (t, J=7.2 Hz, 2H). LC-MS: m/z 471 [M+H]$^+$.

Preparation of Example 206

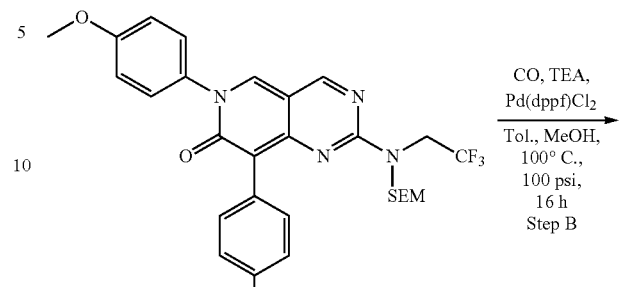

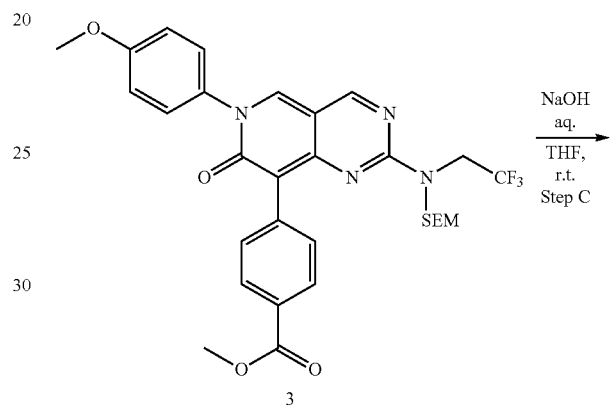

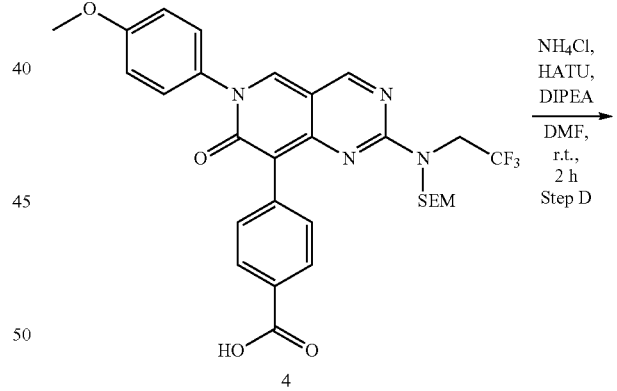

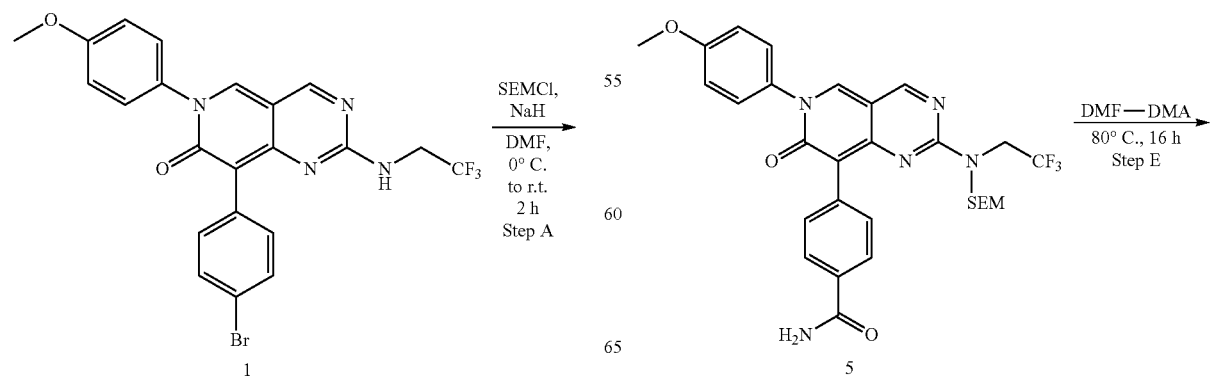

185
-continued

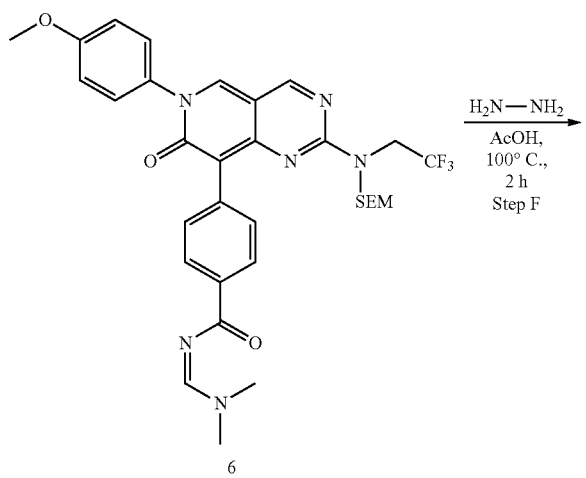

6

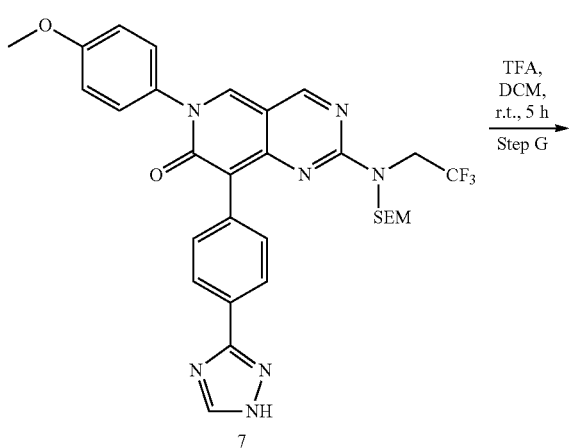

7

Step A: 8-(4-bromophenyl)-6-(4-methoxyphenyl)-2-((2,2,2-trifluoroethyl)((2-(trimethylsilyl)ethoxy)methyl)amino)pyrido[4,3-d]pyrimidin-7(6H)-one

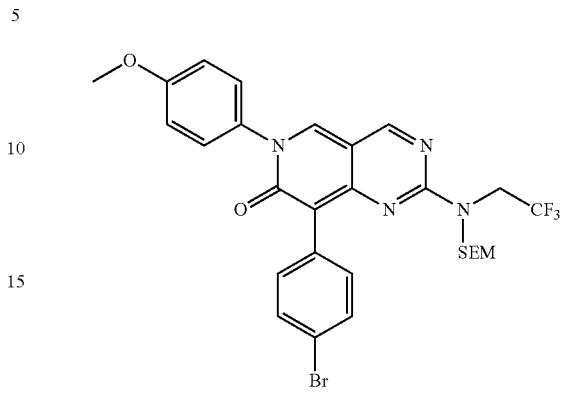

To a solution of 8-(4-bromophenyl)-6-(4-methoxyphenyl)-2-(2,2,2-trifluoroethylamino)pyrido[4,3-d]pyrimidin-7(6H)-one (Example 192, 350.0 mg, 0.7 mmol, 1.0 equiv) in anhydrous DMF (5.0 mL) was added NaH (60% in oil, 57.0 mg, 1.4 mmol, 2.0 equiv) at 0° C. The mixture was stirred at 0° C. for 1 h, and then SEMCl (141.0 mg, 0.86 mmol, 1.2 equiv) was added. The resulting mixture was stirred at r.t. for 1 h. Then the reaction was quenched with ice NH₄Cl aq. (10.0 mL) and extracted with DCM (10.0 mL×2). The combined extracts were washed with brine, dried over anhydrous Na₂SO₄ and concentrated. The residue was purified by flash column chromatography to afford 8-(4-bromophenyl)-6-(4-methoxyphenyl)-2-((2,2,2-trifluoroethyl)((2-(trimethylsilyl)ethoxy)methyl)amino)pyrido[4,3-d]pyrimidin-7(6H)-one (350.0 mg, 77% yield) as a yellow solid. LC-MS: m/z 635 [M+H]⁺.

Step B: methyl 4-(6-(4-methoxyphenyl)-7-oxo-2-((2,2,2-trifluoroethyl)((2-(trimethylsilyl)ethoxy)methyl)amino)-6,7-dihydropyrido[4,3-d]pyrimidin-8-yl)benzoate

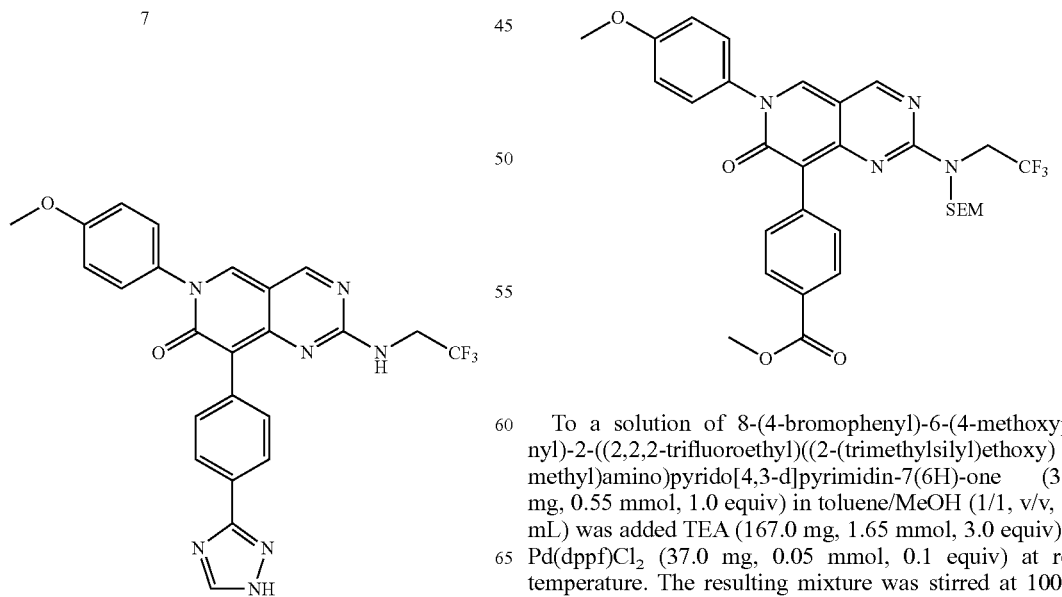

To a solution of 8-(4-bromophenyl)-6-(4-methoxyphenyl)-2-((2,2,2-trifluoroethyl)((2-(trimethylsilyl)ethoxy)methyl)amino)pyrido[4,3-d]pyrimidin-7(6H)-one (350.0 mg, 0.55 mmol, 1.0 equiv) in toluene/MeOH (1/1, v/v, 10.0 mL) was added TEA (167.0 mg, 1.65 mmol, 3.0 equiv) and Pd(dppf)Cl₂ (37.0 mg, 0.05 mmol, 0.1 equiv) at room temperature. The resulting mixture was stirred at 100° C. under CO (1 atm) overnight. The resulting mixture was diluted with water (20.0 mL) and extracted with EtOAc (20.0 mL×3). The organic layers were combined and washed with brine (20 mL), dried over anhydrous Na$_2$SO$_4$ and concentrated. The residue was purified by flash column chromatography (PE/EA=3/1-1/2) to afford methyl 4-(6-(4-methoxyphenyl)-7-oxo-2-((2,2,2-trifluoroethyl)((2-(trimethylsilyl)ethoxy)methyl)amino)-6,7-dihydropyrido[4,3-d]pyrimidin-8-yl)benzoate (280.0 mg, 83% yield) as a yellow solid. LC-MS: m/z 615 [M+H]$^+$.

Step C: 4-(6-(4-methoxyphenyl)-7-oxo-2-((2,2,2-trifluoroethyl)((2-(trimethylsilyl)ethoxy)methyl)amino)-6,7-dihydropyrido[4,3-d]pyrimidin-8-yl)benzoic acid

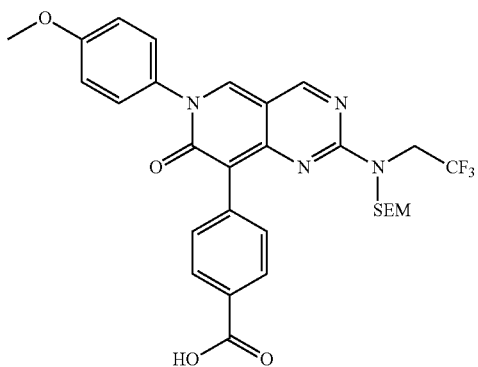 [SMILES: COc1ccc(-n2cc3cnc(N(COCC[Si](C)(C)C)CC(F)(F)F)nc3c(-c3ccc(C(=O)O)cc3)c2=O)cc1]

To a solution of methyl 4-(6-(4-methoxyphenyl)-7-oxo-2-((2,2,2-trifluoroethyl)((2-(trimethylsilyl)ethoxy)methyl)amino)-6,7-dihydropyrido[4,3-d]pyrimidin-8-yl)benzoate (280.0 mg, 0.46 mmol, 1.0 equiv) in THF (5.0 mL) was added LiOH (1N, aq., 4.6 mL, 4.6 mmol, 10.0 equiv) at room temperature. The resulting mixture was stirred overnight. Then the reaction mixture was poured into water (20.0 mL) and adjusted the pH to 6.0 with dilute HCl solution (1N). The mixture was extracted with EtOAc (20.0 mL×3), dried over anhydrous Na$_2$SO$_4$ and concentrated. The residue was purified by flash column chromatography (PE/EA=2:1 to 0:1) to afford 4-(6-(4-methoxyphenyl)-7-oxo-2-((2,2,2-trifluoroethyl)((2-(trimethylsilyl)ethoxy)methyl)amino)-6,7-dihydropyrido[4,3-d]pyrimidin-8-yl)benzoic acid (250.0 mg, 91% yield) as a yellow solid. LC-MS: m/z 601 [M+H]$^+$.

Step D: 4-(6-(4-methoxyphenyl)-7-oxo-2-((2,2,2-trifluoroethyl)((2-(trimethylsilyl)ethoxy)methyl)amino)-6,7-dihydropyrido[4,3-d]pyrimidin-8-yl)benzamide

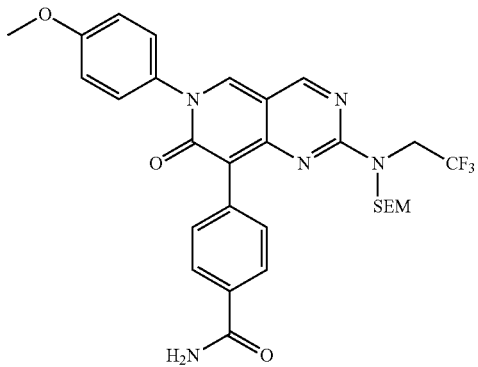 [SMILES: COc1ccc(-n2cc3cnc(N(COCC[Si](C)(C)C)CC(F)(F)F)nc3c(-c3ccc(C(N)=O)cc3)c2=O)cc1]

To a solution of 4-(6-(4-methoxyphenyl)-7-oxo-2-((2,2,2-trifluoroethyl)((2-(trimethylsilyl)ethoxy)methyl)amino)-6,7-dihydropyrido[4,3-d]pyrimidin-8-yl)benzoic acid (250.0 mg, 0.42 mmol, 1.0 equiv) in DMF (5 mL) was added NH$_4$Cl (133.0 mg, 2.08 mmol, 5.0 equiv), DIPEA (268.0 mg, 2.08 mmol, 5.0 equiv) and HATU (316.0 mg, 0.83 mmol, 2.0 equiv). The resulting mixture was stirred at room temperature for 2 h. Then the reaction mixture was diluted with water (20 mL) and extracted with DCM (20 mL×3). The combined extracts were washed with brine, dried over anhydrous Na$_2$SO$_4$ and concentrated. The residue was purified by flash column chromatography (PE/EA=1/1) to afford 4-(6-(4-methoxyphenyl)-7-oxo-2-((2,2,2-trifluoroethyl)((2-(trimethylsilyl)ethoxy)methyl)amino)-6,7-dihydropyrido[4,3-d]pyrimidin-8-yl)benzamide (200. mg, 80% yield) as a yellow solid. LC-MS: m/z 600 [M+H]$^+$.

Step E: (Z)—N-((dimethylamino)methylene)-4-(6-(4-methoxyphenyl)-7-oxo-2-((2,2,2-trifluoroethyl)((2-(trimethylsilyl)ethoxy)methyl)amino)-6,7-dihydropyrido[4,3-d]pyrimidin-8-yl)benzamide

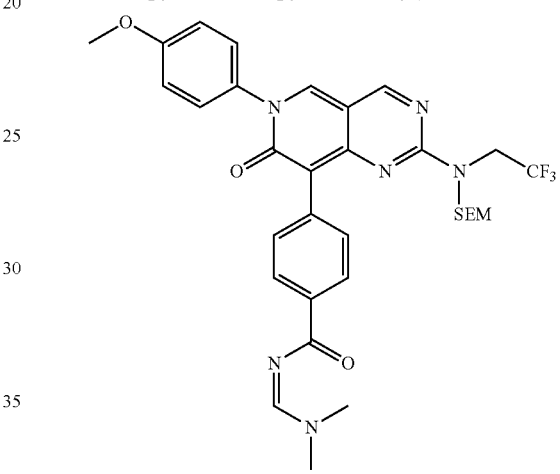

A mixture of 4-(6-(4-methoxyphenyl)-7-oxo-2-((2,2,2-trifluoroethyl)((2-(trimethylsilyl)ethoxy)methyl)amino)-6,7-dihydropyrido[4,3-d]pyrimidin-8-yl)benzamide (100.0 mg, 0.17 mmol, 1.0 equiv) and DMF-DMA (2.0 mL) was stirred at 80° C. for overnight. Then the reaction mixture was concentrated to afford the crude product as a yellow oil. LC-MS: m/z 655 [M+H]$^+$.

Step F: 8-(4-(1H-1,2,4-triazol-3-yl)phenyl)-6-(4-methoxyphenyl)-2-((2,2,2-trifluoroethyl)((2-(trimethylsilyl)ethoxy)methyl)amino)pyrido[4,3-d]pyrimidin-7(6H)-one

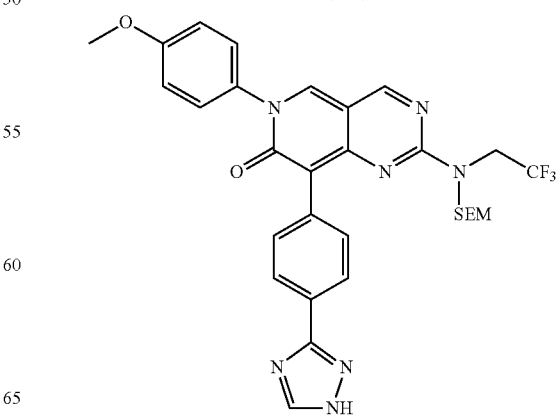

To a solution of (Z)—N-((dimethylamino)methylene)-4-(6-(4-methoxyphenyl)-7-oxo-2-((2,2,2-trifluoroethyl)((2-(trimethylsilyl)ethoxy)methyl)amino)-6,7-dihydropyrido[4,3-d]pyrimidin-8-yl)benzamide (120 mg, 0.17 mmol, 1.0 equiv) in AcOH (2 mL) was added hydrazine monohydrate (27.0 mg, 0.84 mmol, 5.0 equiv) at room temperature. The resulting mixture was stirred at 100° C. for 2 h. Then the reaction was diluted with NaHCO₃(sat. aq., 20 mL) and extracted with EtOAc (20 mL×3). The combined extracts were washed with brine, dried over anhydrous Na₂SO₄ and concentrated. The residue was purified by flash column chromatography (PE/EA=1/1) to afford 8-(4-(1H-1,2,4-triazol-3-yl)phenyl)-6-(4-methoxyphenyl)-2-((2,2,2-trifluoroethyl)((2-(trimethylsilyl)ethoxy)methyl)amino)pyrido[4,3-d]pyrimidin-7(6H)-one (80 mg, 76% yield) as a yellow solid. LC-MS: m/z 624 [M+H]⁺.

Step G: 8-(4-(H-1,2,4-triazol-3-yl)phenyl)-6-(4-methoxyphenyl)-2-(2,2,2-trifluoroethylamino)pyrido[4,3-d]pyrimidin-7(6H)-one

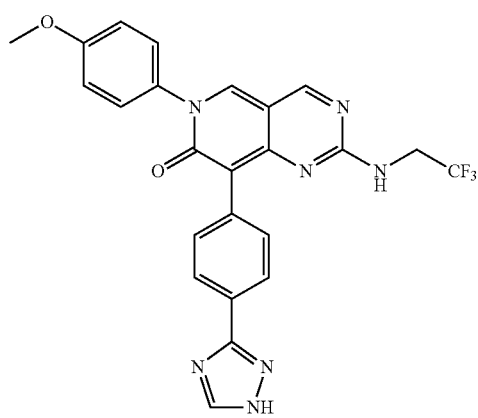

To a solution of 8-(4-(1H-1,2,4-triazol-3-yl)phenyl)-6-(4-methoxyphenyl)-2-((2,2,2-trifluoroethyl)((2-(trimethylsilyl)ethoxy)methyl)amino)pyrido[4,3-d]pyrimidin-7(6H)-one (80 mg, 0.13 mmol, 1.0 equiv) in DCM (3.0 mL) was added trifluoroacetic acid (1.0 mL) at room temperature. The resulting mixture was stirred for 5 h before being concentrated and purified by RP-prep-HPLC to afford 8-(4-(H-1,2,4-triazol-3-yl)phenyl)-6-(4-methoxyphenyl)-2-(2,2,2-trifluoroethylamino)pyrido[4,3-d]pyrimidin-7(6H)-one (Example 206).

¹H NMR (400 MHz, DMSO-d₆) δ 8.97 (s, 1H), 8.84 (s, 1H), 8.58 (t, J=6.4 Hz, 1H), 8.43 (br s, 1H), 7.97 (d, J=8.4 Hz, 2H), 7.78 (d, J=8.4 Hz, 2H), 7.48 (d, J=8.8 Hz, 2H), 7.10 (d, J=8.8 Hz, 2H), 4.16-4.02 (m, 2H), 3.81 (s, 3H). LC-MS: m/z 494 [M+H]⁺.

Preparation of Example 707

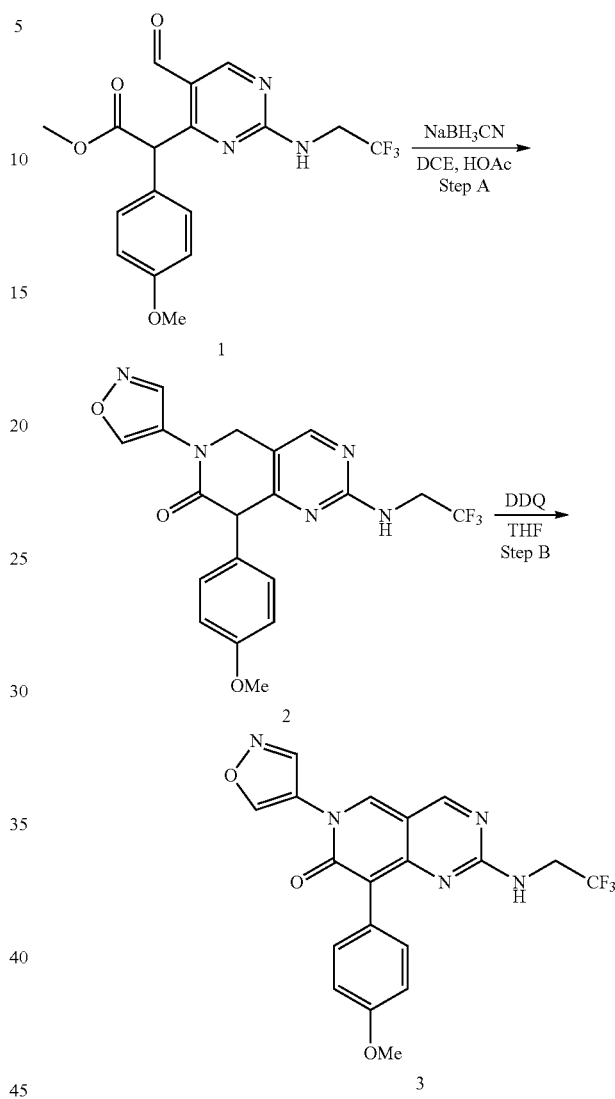

Step A: 6-(isoxazol-4-yl)-8-(4-methoxyphenyl)-2-((2,2,2-trifluoroethyl)amino)-5,6-dihydropyrido[4,3-d]pyrimidin-7(4aH)-one

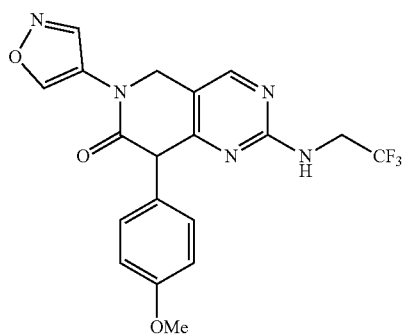 [SMILES: COc1ccc(C2C(=O)N(c3cnoc3)Cc3cnc(NCC(F)(F)F)nc32)cc1]

To a solution of methyl 2-(5-formyl-2-((2,2,2-trifluoroethyl)amino)pyrimidin-4-yl)-2-(4-methoxyphenyl)acetate (as prepared in General procedure III, Step G) (76 mg, 0.2 mmol, 1.0 equiv), isoxazol-4-amine (42 mg, 0.5 mmol, 2.5 equiv) in DCE/MeOH (3/0.5 mL) was added HOAc (42 mg, 0.7 mmol, 3.5 equiv). The mixture was stirred at 45° C. overnight, then the mixture was cooled down to 0° C., NaBH₃CN (12 mg, 0.2 mmol, 1.0 equiv) was added to the reaction mixture in one portion, after which the resulting mixture was allowed to warm to room temperature and stirred for an additional 12 h before being quenched with DCM (10 mL) and H₂O (10 mL). The aqueous layer was extracted with DCM (10 mL×3). The combined organic layers were dried over Na₂SO₄ and concentrated. The residue was purified by Prep-TLC (PE:EA=1/2) to give 6-(isoxazol-4-yl)-8-(4-methoxyphenyl)-2-((2,2,2-trifluoroethyl)amino)-5,6-dihydropyrido[4,3-d]pyrimidin-7(4aH)-one (51 mg, 44% yield) as a white solid. LC-MS: m/z 420 [M+H]⁺.

Step B: 6-(isoxazol-4-yl)-8-(4-methoxyphenyl)-2-((2,2,2-trifluoroethyl)amino)pyrido[4,3-d]pyrimidin-7(6H)-one

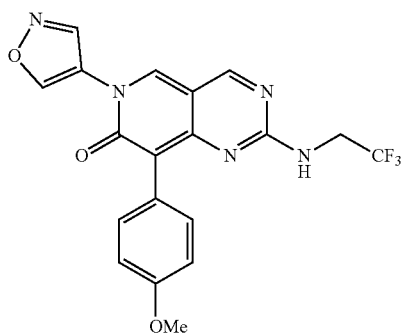 [SMILES: COc1ccc(-c2c(=O)n(-c3cnoc3)cc3cnc(NCC(F)(F)F)nc23)cc1]

A mixture of 6-(isoxazol-4-yl)-8-(4-methoxyphenyl)-2-((2,2,2-trifluoroethyl)amino)-5,6-dihydropyrido[4,3-d]pyrimidin-7(4aH)-one (51.0 mg, 0.12 mmol, 1.0 equiv) and DDQ (40.0 mg, 0.18 mmol, 1.5 equiv) in THF (3.0 mL) was stirred at r.t. for 3 h. The reaction mixture was concentrated under vacuum and the residue was purified by RP-prep-HPLC to give 6-(isoxazol-4-yl)-8-(4-methoxyphenyl)-2-((2,2,2-trifluoroethyl)amino)pyrido[4,3-d]pyrimidin-7(6H)-one (Example 207).

¹H NMR (400 MHz, DMSO-d₆) δ 9.62 (s, 1H), 9.20 (s, 1H), 9.00 (s, 1H), 8.97 (s, 1H), 8.66 (t, J=6.4 Hz, 1H) 7.57 (d, J=8.8 Hz, 2H), 6.89 (d, J=8.8 Hz, 2H), 4.15-4.03 (m, 2H), 3.79 (s, 3H). LC-MS: m/z 418 [M+H]⁺.

Example 208: 8-(4-methoxyphenyl)-6-(H-pyrazol-4-yl)-2-((2,2,2-trifluoroethyl)amino)pyrido[4,3-d]pyrimidin-7(6H)-one

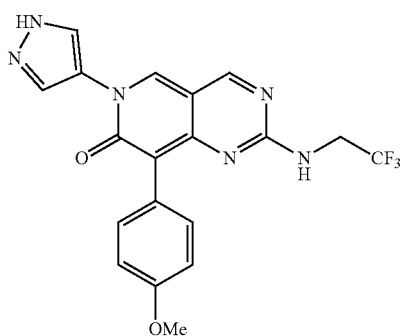 [SMILES: COc1ccc(-c2c(=O)n(-c3cn[nH]c3)cc3cnc(NCC(F)(F)F)nc23)cc1]

The title compound was synthesized from intermediate 1 with 1H-pyrazol-4-amine as prepared in the procedure for Example 207 (Step A-B).

¹HNMR (600 MHz, DMSO-d₆) δ 8.95 (s, 1H), 8.93 (s, 1H), 8.51 (br s, 1H), 8.13 (s, 2H), 7.56 (d, J=8.4 Hz, 2H), 6.88 (d, J=8.4 Hz, 2H), 4.13-4.03 (q, J=9.6 Hz, 2H), 3.78 (s, 3H). LC-MS: m/z 417 [M+H]⁺.

General Procedure V

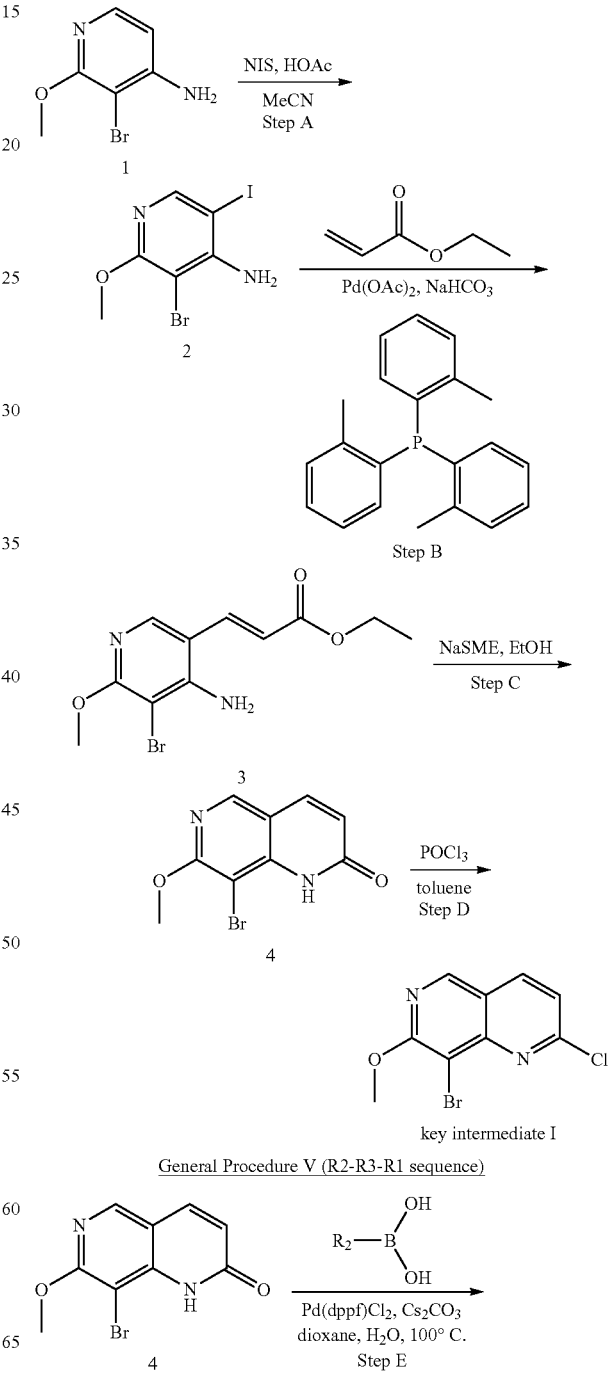

-continued

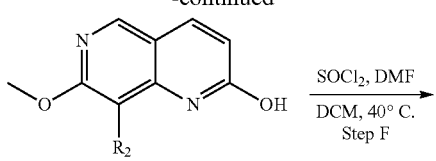
5

SOCl₂, DMF
———————→
DCM, 40° C.
Step F

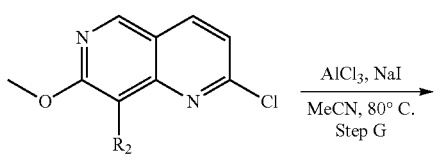
6

AlCl₃, NaI
———————→
MeCN, 80° C.
Step G

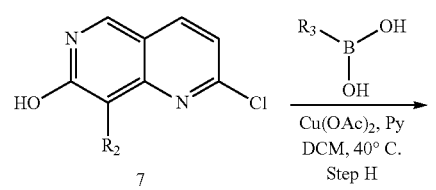
7

R₃B(OH)₂
———————→
Cu(OAc)₂, Py
DCM, 40° C.
Step H

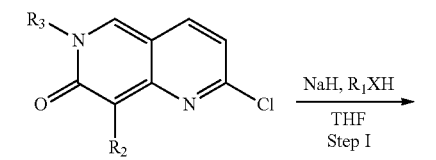
8

NaH, R₁XH
———————→
THF
Step I

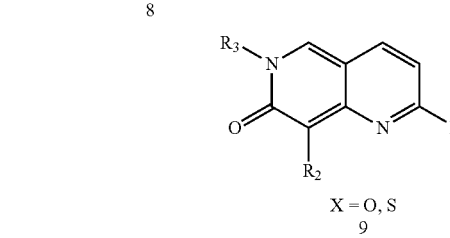
X = O, S
9

General Procedure V (R1-R3-R2 sequence)

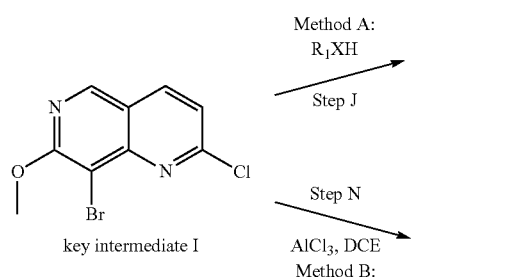
key intermediate I

Method A:
R₁XH
———————→
Step J

Step N
———————→
AlCl₃, DCE
Method B:

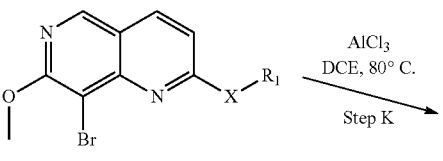
10

AlCl₃
DCE, 80° C.
———————→
Step K

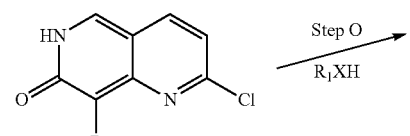
14

Step O
R₁XH
———————→

-continued

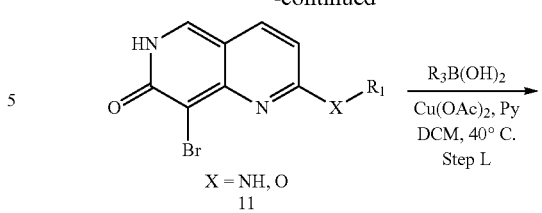
X = NH, O
11

R₃B(OH)₂
———————→
Cu(OAc)₂, Py
DCM, 40° C.
Step L

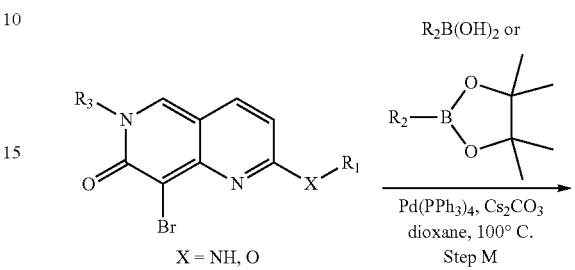
X = NH, O
12

R₂B(OH)₂ or
[pinacol boronate]
———————→
Pd(PPh₃)₄, Cs₂CO₃
dioxane, 100° C.
Step M

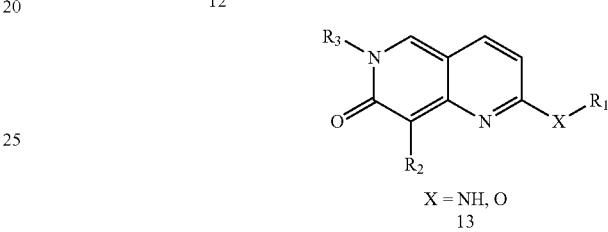
X = NH, O
13

General Procedure V (R1-R2-R3 sequence)

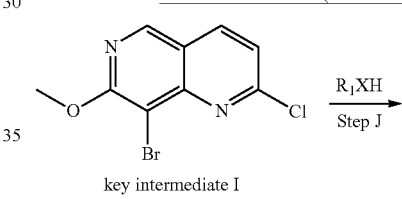
key intermediate I

R₁XH
———————→
Step J

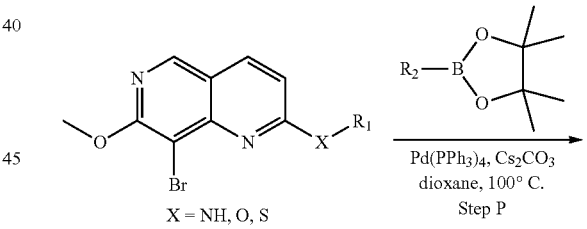
X = NH, O, S
10

R₂B(OH)₂ or
[pinacol boronate]
———————→
Pd(PPh₃)₄, Cs₂CO₃
dioxane, 100° C.
Step P

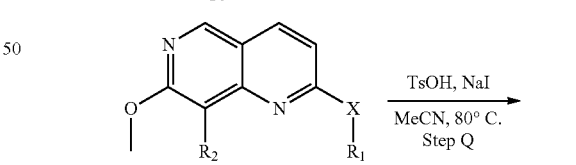
15

TsOH, NaI
———————→
MeCN, 80° C.
Step Q

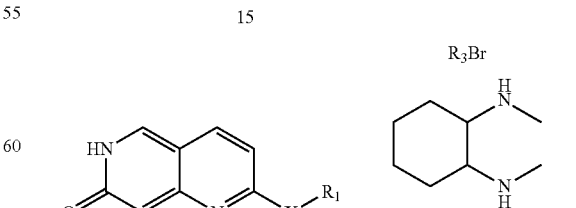
16

R₃Br
[N,N'-dimethylcyclohexane-1,2-diamine]
———————→
CsF, CuI, MeCN, 100° C.
Step R

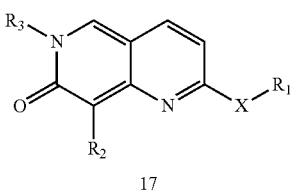

17

Preparation of
8-bromo-2-chloro-7-methoxy-1,6-naphthyridine
(key intermediate I)

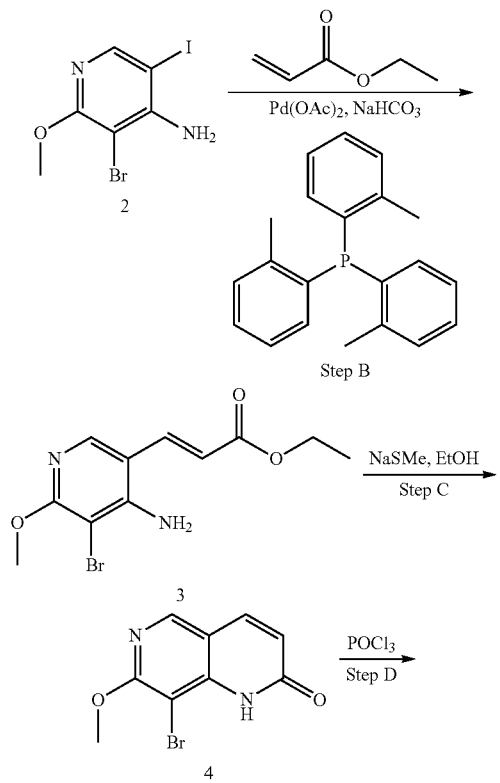

key intermediate I

Step A: 3-bromo-5-iodo-2-methoxypyridin-4-amine

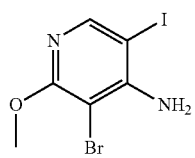

To a solution of 3-bromo-2-methoxypyridin-4-amine (4.0 g, 19.8 mmol, 1.0 equiv.) in acetonitrile (30 mL) and acetic acid (4.1 mL) was added NIS (4.9 g, 21.7 mmol, 1.1 equiv.), and the reaction mixture was stirred at room temperature for 16 h. Then the solvent was removed under reduced pressure. The residue was dissolved in EtOAc (50 mL) and washed with water (50 mL×2). The organic layer was dried over anhydrous $Na_2SO_4$ and concentrated under reduced pressure. The crude product was purified by flash chromatography on silica gel (eluent: PE/EtOAc=4/1) to afford 3-bromo-5-iodo-2-methoxypyridin-4-amine (6.0 g, 92% yield) as a white solid. LC-MS: m/z 329 [M+H]$^+$.

Step B: (E)-ethyl 3-(4-amino-5-bromo-6-methoxy-pyridin-3-yl)acrylate

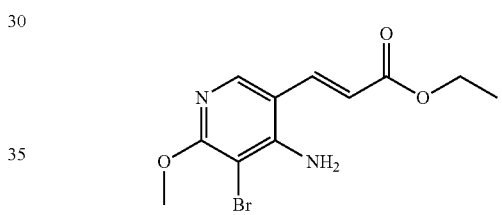

A mixture of 3-bromo-5-iodo-2-methoxypyridin-4-amine (6 g, 18.3 mmol, 1.0 equiv.), trio-tolylphosphine (553 mg, 1.8 mmol, 0.1 equiv.), $NaHCO_3$ (2.7 g, 32.1 mmol, 1.8 equiv.), ethyl acrylate (2 g, 20.1 mmol, 1.1 equiv.) and $Pd(OAc)_2$ (205 mg, 0.9 mmol, 0.05 equiv.) in DMF (30 mL) was stirred at 70° C. under $N_2$ for 16 h. Then the reaction was diluted with 10% aq. LiCl (50 mL) and extracted with EtOAc (50 mL×3). All the organic layers were combined and washed with brine (50 mL), dried over anhydrous $Na_2SO_4$, filtered and concentrated. The residue was purified by flash chromatography on silica gel (eluent: PE/EtOAc=3/1) to afford (E)-ethyl 3-(4-amino-5-bromo-6-methoxypyridin-3-yl)acrylate (4.5 g, 82% yield) as a white solid. LC-MS: m/z 301 [M+H]$^+$.

Step C:
8-bromo-7-methoxy-1,6-naphthyridin-2(1H)-one

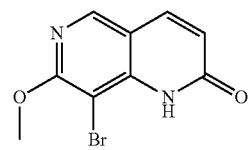

To a solution of (E)-ethyl 3-(4-amino-5-bromo-6-methoxypyridin-3-yl)acrylate (1.5 g, 5.0 mmol, 1.0 equiv.)

in EtOH (10 mL) was added 15% aq. NaSMe (2.6 g, 5.5 mmol, 1.1 equiv.). The resulting mixture was stirred at room temperature overnight. The precipitate was collected by filtration and the filter cake was washed with EtOAc (10 mL) then dried to afford 8-bromo-7-methoxy-1,6-naphthyridin-2(1H)-one (1.0 g, 79% yield) as a yellow solid. LC-MS: m/z 255 [M+H]$^+$.

Step D:
8-bromo-2-chloro-7-methoxy-1,6-naphthyridine (key intermediate I)

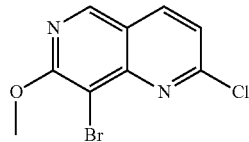

A mixture of 8-bromo-7-methoxy-1,6-naphthyridin-2(1H)-one (2.3 g, 9.0 mmol, 1.0 equiv.) and POCl$_3$ (12.0 mL) was stirred at 80° C. for 2 h. Then the reaction was poured into cooled NaHCO$_3$(Sat. aq., 150 mL) and extracted with EtOAc (50 mL×4). All the organic layers were combined and washed with brine (50 mL), dried over anhydrous Na$_2$SO$_4$, filtered and concentrated. The residue was purified by flash chromatography on silica gel (eluent: PE/EtOAc=3/1) to afford 8-bromo-2-chloro-7-methoxy-1,6-naphthyridine (1.9 g, 77% yield) as an off-white solid. LC-MS: m/z 273 [M+H]$^+$.

Preparation of 8-(4-chlorophenyl)-6-(2-methyl-2H-indazol-5-yl)-2-(2,2,2-trifluoroethylthio)-1,6-naphthyridin-7(6H)-one (Example 209)

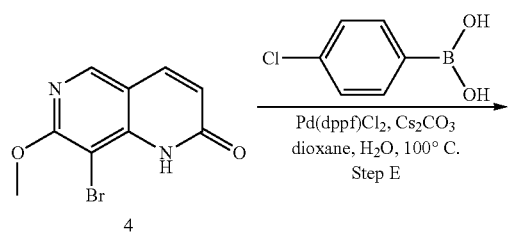

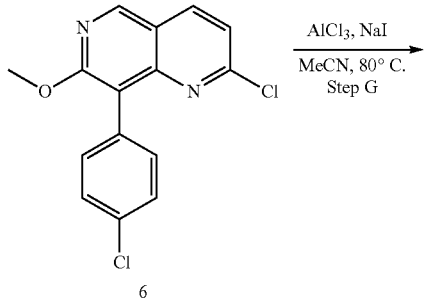

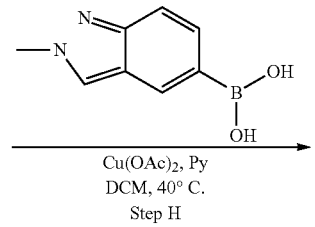

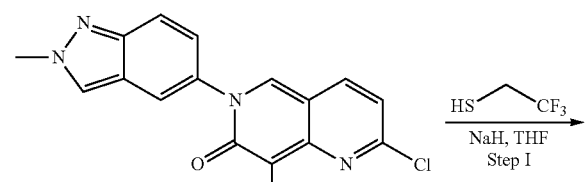

Step E: 8-(4-chlorophenyl)-7-methoxy-1,6-naphthyridin-2(1i)-one

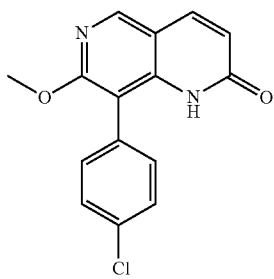 [SMILES: COc1ncc2ccc(=O)[nH]c2c1-c1ccc(Cl)cc1]

A mixture of 8-bromo-7-methoxy-1,6-naphthyridin-2 (1H)-one (10 g, 39.4 mmol, 1.0 equiv.), Pd(dppf)Cl$_2$(1.4 g, 1.9 mmol, 0.05 equiv.), Cs$_2$CO$_3$ (25.6 g, 78.5 mmol, 2.0 equiv.) and 4-chlorophenylboronic acid (9.2 g, 59.0 mmol, 1.5 equiv.) in dioxane/water (200 mL, 9/1, v/v) was stirred at 100° C. under N$_2$ atmosphere for 16 h. Then the reaction mixture was diluted with water (100 mL) and extracted with EtOAc (50 mL×5). All the organic layers were combined and washed with brine (50 mL), dried over anhydrous Na$_2$SO$_4$, filtered and concentrated under reduced pressure. The residue was purified by flash chromatography on silica gel (eluent: PE/EtOAc=2/1) to afford 8-(4-chlorophenyl)-7-methoxy-1,6-naphthyridin-2(1H)-one (10.0 g, 89% yield) as a white solid. LC-MS: m/z 287 [M+H]$^+$.

Step F: 2-chloro-8-(4-chlorophenyl)-7-methoxy-1,6-naphthyridine

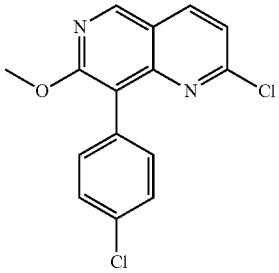 [SMILES: COc1ncc2ccc(Cl)nc2c1-c1ccc(Cl)cc1]

To a solution of 8-(4-chlorophenyl)-7-methoxy-1,6-naphthyridin-2(1H)-one (8 g, 27.9 mmol, 1.0 equiv.) in DCM (100 mL) was added DMF (6.1 g, 83.6 mmol, 3.0 equiv.) and SOCl$_2$ (8.2 g, 83.6 mmol, 3.0 equiv.). Then the reaction was stirred at 80° C. for 16 h. The resulting mixture was cooled to room temperature, concentrated, quenched with ice cooled NaHCO$_3$(Sat. aq., 50 mL) and extracted with EtOAc (50 mL×2). All the organic layers were combined and washed with brine (50 mL), dried over anhydrous Na$_2$SO$_4$, filtered and concentrated under reduced pressure, the residue was purified by flash chromatography on silica gel (eluent: PE/EtOAc=5/1) to afford 2-chloro-8-(4-chlorophenyl)-7-methoxy-1,6-naphthyridine (7.0 g, 83% yield) as a white solid. LC-MS: m/z 305 [M+H]$^+$.

Step G: 2-chloro-8-(4-chlorophenyl)-1,6-naphthyridin-7(6H)-one

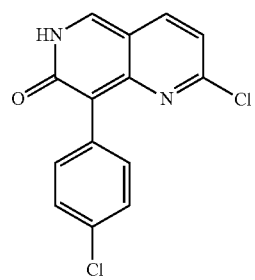 [SMILES: O=c1[nH]cc2ccc(Cl)nc2c1-c1ccc(Cl)cc1]

To a solution of 2-chloro-8-(4-chlorophenyl)-7-methoxy-1,6-naphthyridine (2.0 g, 6.6 mmol, 1.0 equiv.) in MeCN (40.0 mL) was added AlCl$_3$ (1.8 g, 13.5 mmol, 2.0 equiv.) and NaI (2.2 g, 13.3 mmol, 2.0 equiv.). The resulting mixture was stirred at 80° C. for 8 h. Then the reaction mixture was quenched with ice water (20 mL) and extracted with EtOAc (20 mL×3). All the organic layers were combined and washed with brine (50 mL), dried over anhydrous Na$_2$SO$_4$, filtered and concentrated under reduced pressure. The resulting residue was purified by flash chromatography on silica gel (eluent: DCM/acetone=2/1) to afford 2-chloro-8-(4-chlorophenyl)-1,6-naphthyridin-7(6H)-one (1.5 g, 79% yield) as a white solid. LC-MS: m/z 291 [M+H]$^+$.

Step H: 2-chloro-8-(4-chlorophenyl)-6-(2-methyl-2H-indazol-5-yl)-1,6-naphthyridin-7(6H)-one

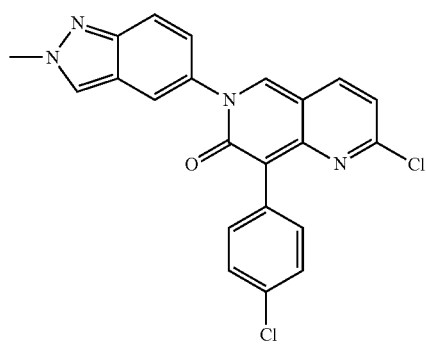

8

To a solution of 2-chloro-8-(4-chlorophenyl)-1,6-naphthyridin-7(6H)-one (1.5 g, 5.2 mmol, 1.0 equiv.) in DCM (20.0 mL) was added Cu(OAc)$_2$ (1.2 g, 5.6 mmol, 1.1 equiv.), pyridine (1.2 g, 15.2 mmol, 3.0 equiv.) and 2-methyl-2H-indazol-5-ylboronic acid (1.4 g, 8.0 mmol, 1.5 equiv.). The reaction mixture was stirred at 40° C. under 02 atmosphere for 16 h, then concentrated under reduced pressure and purified by flash chromatography on silica gel (eluent: PE/EtOAc=1/1) to afford 2-chloro-8-(4-chlorophenyl)-6-(2-methyl-2H-indazol-5-yl)-1,6-naphthyridin-7(6H)-one (1.4 g, 65% yield) as an orange solid. LC-MS: m/z 421 [M+H]$^+$.

Step I: 8-(4-chlorophenyl)-6-(2-methyl-2H-indazol-5-yl)-2-((2,2,2-trifluoroethyl)thio)-1,6-naphthyridin-7(6H)-one (Example 209)

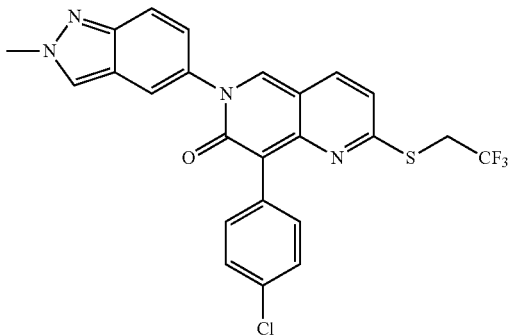

To a solution of 2,2,2-trifluoroethanethiol (124.0 mg, 1.1 mmol, 3.0 equiv.) in 2.0 mL of anhydrous THE was added NaH (60% suspend in mineral oil, 43.0 mg, 1.1 mmol, 3.0 equiv.) in portions at 0° C. The mixture was stirred at 0° C. for 0.5 h. Then a solution of 2-chloro-8-(4-chlorophenyl)-6-(2-methyl-2H-indazol-5-yl)-1,6-naphthyridin-7(6H)-one (150.0 mg, 0.36 mmol, 1.0 equiv.) in THE (1 mL) was added. The reaction mixture was stirred at room temperature for an additional 2 h. The reaction mixture was quenched with NH$_4$Cl (Sat. aq., 10 mL) and extracted with EtOAc (10 mL×3). All the organic layers were combined and washed with brine (50 mL), dried over anhydrous Na$_2$SO$_4$, filtered and concentrated under reduced pressure. The residue was purified by RP-prep-HPLC to afford 8-(4-chlorophenyl)-6-(2-methyl-2H-indazol-5-yl)-2-((2,2,2-trifluoroethyl)thio)-1,6-naphthyridin-7(6H)-one (Example 209).

1H NMR (400 MHz, DMSO-d$_6$) δ: 8.92 (s, 1H), 8.51 (s, 1H), 7.98 (d, J=8.8 Hz, 1H), 7.92 (d, J=2.0 Hz, 1H), 7.72 (d, J=9.2 Hz, 1H), 7.40 (d, J=8.4 Hz, 2H), 7.37 (dd, J=9.2 Hz, 2.0 Hz, 1H), 6.99 (d, J=8.8 Hz, 1H), 4.23 (s, 3H), 4.21-4.08 (m, 2H). LC-MS: m/z 501 (M+H)$^+$.

Example 210: 8-(4-chlorophenyl)-2-cyclopropoxy-6-(2-methyl-2H-indazol-5-yl)-1,6-naphthyridin-7(6H)-one

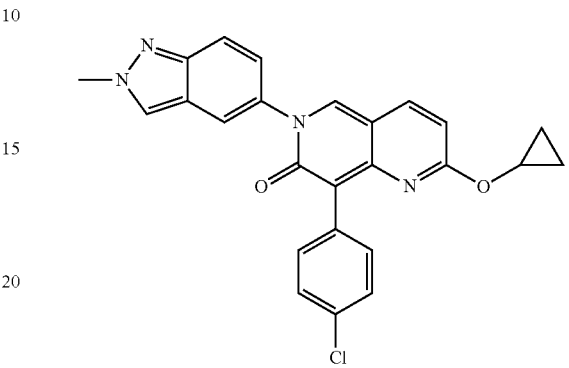

The title compound was synthesized from intermediate 8 with cyclopropanol via general procedure V (Step I) (NaH, anhydrous THF, 0° C. to r.t.).

$^1$H NMR (400 MHz, DMSO-d$_6$) δ: 8.78 (s, 1H), 8.50 (s, 1H), 7.98 (d, J=9.2 Hz, 1H), 7.70 (d, J=2.4 Hz, 1H), 7.77 (d, J=8.8 Hz, 2H), 7.71 (d, J=8.8 Hz, 1H), 7.40 (d, J=8.8 Hz, 2H), 7.34 (dd, J=9.2 Hz, 2.0 Hz, 1H), 6.53 (d, J=9.2 Hz, 1H), 4.23 (s, 3H), 4.21-4.14 (m, 2H), 0.74-0.72 (m, 4H). LC-MS: m/z 443 [M+H]$^+$.

Preparation of 6-(2-methyl-2H-indazol-5-yl)-2-((2,2,2-trifluoroethyl)amino)-8-(4-(trifluoromethoxy)phenyl)-1,6-naphthyridin-7(6H)-one (Example 211)

Method A

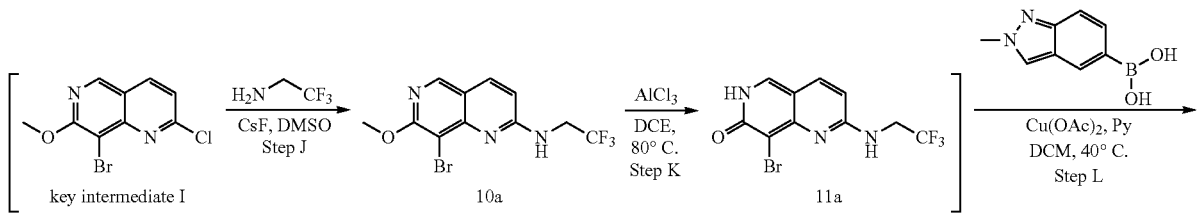

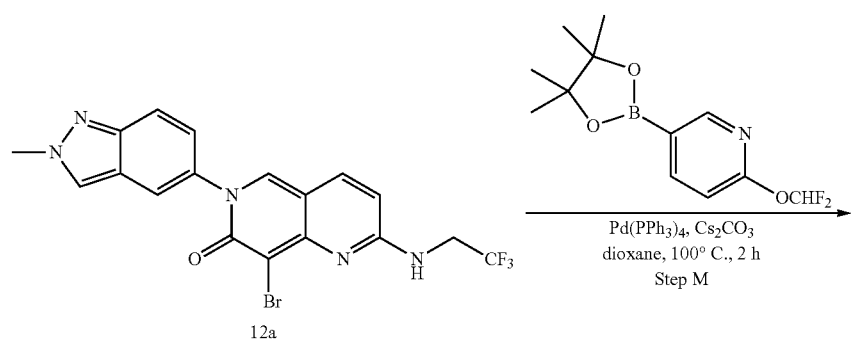

-continued

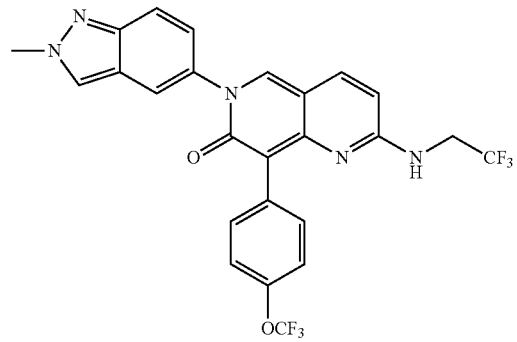

Method A

Step J: 8-bromo-7-methoxy-N-(2,2,2-trifluoroethyl)-1,6-naphthyridin-2-amine 10a

10a

A mixture of 8-bromo-2-chloro-7-methoxy-1,6-naphthyridine (1.0 g, 3.8 mmol, 1.0 equiv.), CsF (860.0 mg, 5.7 mmol, 1.5 equiv.), and 2,2,2-trifluoroethanamine (1.9 g, 18.8 mmol, 5.0 equiv.) in DMSO (10.0 mL) was stirred at 100° C. for 2 h. Then the mixture was poured into ice water (100 mL), and extracted with EtOAc (50 mL×4). All the organic layers were combined, washed with brine (50 mL), dried over anhydrous Na$_2$SO$_4$, filtered and concentrated under reduced pressure. The residue was purified by flash chromatography on silica gel (eluent: PE/EtOAc=2/1) to afford 8-bromo-7-methoxy-N-(2,2,2-trifluoroethyl)-1,6-naphthyridin-2-amine (900 mg, 71% yield) as a white solid. LC-MS: m/z 336 [M+H]$^+$.

Step K: 8-bromo-2-(2,2,2-trifluoroethylamino)-1,6-naphthyridin-7(6H)-one 11a

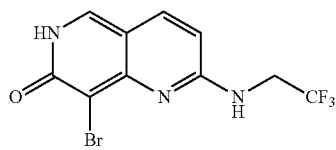

11a

A mixture of 8-bromo-7-methoxy-N-(2,2,2-trifluoroethyl)-1,6-naphthyridin-2-amine (300.0 mg, 0.8 mmol, 1.0 equiv.) and AlCl$_3$ (301.5 mg, 2.2 mmol, 3.0 equiv.) in DCE (10 mL) was stirred at 80° C. for 2 h. The solvent was evaporated under reduced pressure, and the residue was purified by flash chromatography on silica gel (eluent: DCM/MeOH=10/1) to afford 8-bromo-2-(2,2,2-trifluoroethylamino)-1,6-naphthyridin-7(6H)-one (220.0 mg, 92% yield) as a yellow solid. LC-MS: m/z 322 [M+H]$^+$.

Step L: 8-bromo-6-(2-methyl-2H-indazol-5-yl)-2-((2,2,2-trifluoroethyl)amino)-1,6-naphthyridin-7(6H)-one 12a

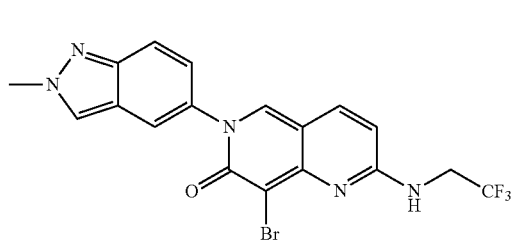

12a 8-bromo-6-(2-methyl-2H-indazol-5-yl)-2-((2,2,2-trifluoroethyl)amino)-1,6-naphthyridin-7(6H)-one 12a was synthesized from intermediate 11a with (2-methyl-2H-indazol-5-yl)boronic acid via general procedure V (Step H). LC-MS: m/z 452 [M+H]$^+$.

Step M: 6-(2-methyl-2H-indazol-5-yl)-2-((2,2,2-trifluoroethyl)amino)-8-(4-(trifluoromethoxy)phenyl)-1,6-naphthyridin-7(6H)-one (Example 211)

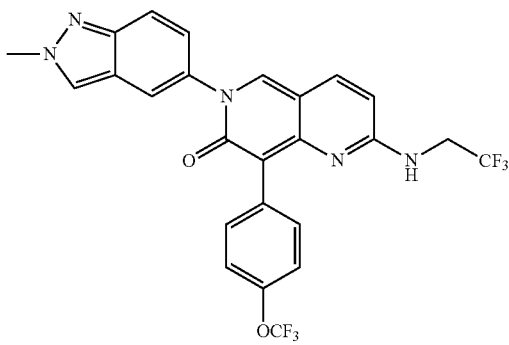

The title compound was synthesized from intermediate 12a with (4-(trifluoromethoxy)phenyl)boronic acid via general procedure V (Step M).

$^1$H NMR (400 MHz, DMSO-d$_6$) δ: 8.52 (s, 1H), 8.48 (s, 1H), 8.34 (t, J=6.4 Hz, 1H), 7.85 (dd, J=2.0 Hz, 0.4 Hz, 1H), 7.76 (d, J=9.2 Hz, 2H), 7.71 (d, J=8.0 Hz, 2H), 7.66 (d, J=9.2

Hz, 1H), 7.31 (dd, J=8.8 Hz, 2.0 Hz, 1H), 7.26 (d, J=8.0 Hz, 2H), 6.49 (d, J=8.8 Hz, 1H), 4.22 (s, 3H), 4.18-4.07 (m, 2H). LC-MS: m/z 534 [M+H]$^+$.

Example 212: 8-(6-cyclopropylpyridin-3-yl)-6-(2-methyl-2H-indazol-5-yl)-2-((2,2,2-trifluoroethyl)amino)-1,6-naphthyridin-7(6H)-one

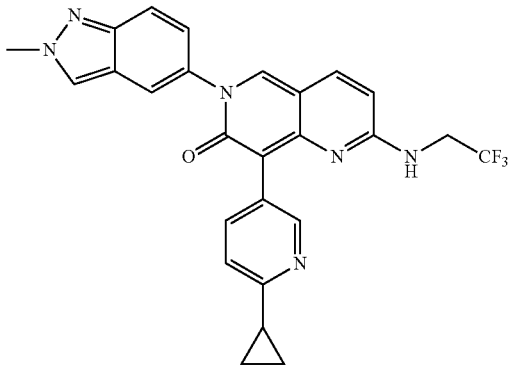 [SMILES: Cn1cc2cc(-n3cc4ccc(NCC(F)(F)F)nc4c(-c4ccc(C5CC5)nc4)c3=O)ccc2n1]

The title compound was synthesized from intermediate 12a with (6-cyclopropylpyridin-3-yl)boronic acid via general procedure V (Step M).

$^1$H NMR (400 MHz, DMSO-d$_6$) δ: 8.61 (d, J=1.2 Hz, 1H), 8.50 (s, 1H), 8.48 (s, 1H), 8.34 (t, J=6.4 Hz, 1H), 7.87-7.80 (m, 2H), 7.75 (d, J=9.2 Hz, 1H), 7.67 (d, J=8.8 Hz, 1H), 7.32 (dd, J=9.2 Hz, 2.0 Hz, 1H), 7.22 (d, J=8.4 Hz, 1H), 6.50 (d, J=8.8 Hz, 1H), 4.22 (s, 3H), 4.21-4.10 (m, 2H), 2.14-2.05 (m, 1H), 0.98-0.88 (m, 4H). LC-MS: m/z 491 [M+H]$^+$.

Example 213: 6-(2-methyl-2H-indazol-5-yl)-2-((2,2,2-trifluoroethyl)amino)-8-(4-(trifluoromethyl)phenyl)-1,6-naphthyridin-7(6H)-one

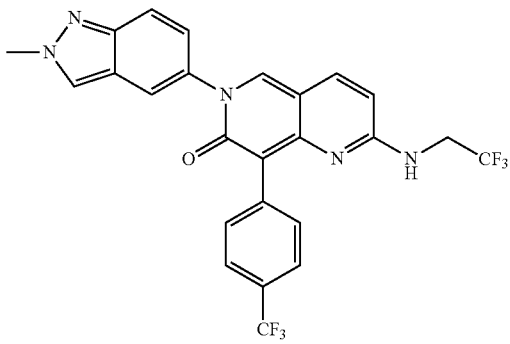

The title compound was synthesized from intermediate 12a with (4-(trifluoromethyl)phenyl)boronic acid via general procedure V (Step M).

$^1$H NMR (400 MHz, DMSO-d$_6$) δ: 8.56 (s, 1H), 8.48 (s, 1H), 8.40 (t, J=6.4 Hz, 1H), 7.89-7.80 (m, 3H), 7.78 (d, J=9.2 Hz, 1H), 7.69 (d, J=9.2 Hz, 1H), 7.63 (d, J=8.4 Hz, 2H), 7.33 (dd, J=9.2 Hz, 2.0 Hz, 1H), 6.52 (d, J=9.2 Hz, 1H), 4.22 (s, 3H), 4.21-4.06 (m, 2H). LC-MS: m/z 518 [M+H]$^+$.

Example 214: 8-(4-(2,2-difluoroethyl)phenyl)-6-(2-methyl-2H-indazol-5-yl)-2-((2,2,2-trifluoroethyl)amino)-1,6-naphthyridin-7(6H)-one

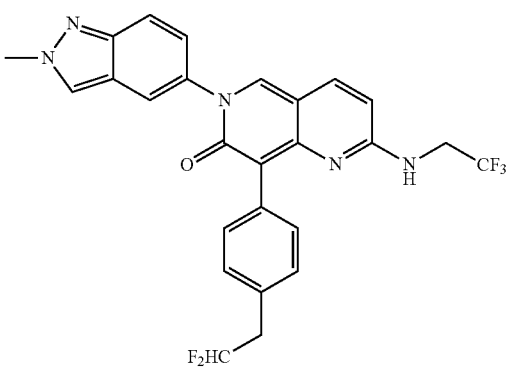 [SMILES: Cn1cc2cc(-n3cc4ccc(NCC(F)(F)F)nc4c(-c4ccc(CC(F)F)cc4)c3=O)ccc2n1]

The title compound was synthesized from intermediate 12a with (4-(2,2-difluoroethyl)phenyl)boronic acid via general procedure V (Step M).

$^1$H NMR (400 MHz, DMSO-d$_6$) δ: 8.47 (s, 2H), 8.31 (br s, 1H), 7.84 (d, J=1.6 Hz, 1H), 7.74 (d, J=9.2 Hz, 1H), 7.67 (d, J=8.8 Hz, 1H), 7.58 (d, J=8.0 Hz, 2H), 7.30 (dd, J=9.2 Hz, 2.0 Hz, 1H), 7.22 (d, J=8.0 Hz, 2H), 6.49 (d, J=8.8 Hz, 1H), 6.24 (tt, J$_{HF}$=56.6 Hz, 4.8 Hz, 1H), 4.22 (s, 3H), 4.23-4.10 (m, 2H), 3.18 (dt, J$_{HF}$=18.2 Hz, 4.8 Hz, 2H). LC-MS: m/z 514 [M+H]$^+$.

Preparation of 2-ethoxy-6-(2-methyl-2H-indazol-5-yl)-8-(4-(trifluoromethyl)phenyl)-1,6-naphthyridin-7(6H)-one (Example 215)

Method B

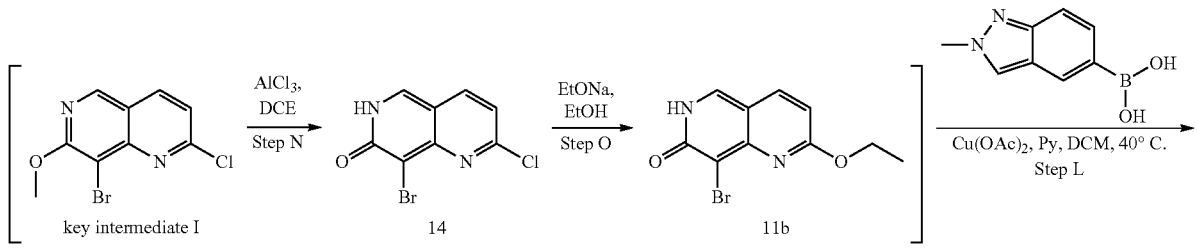

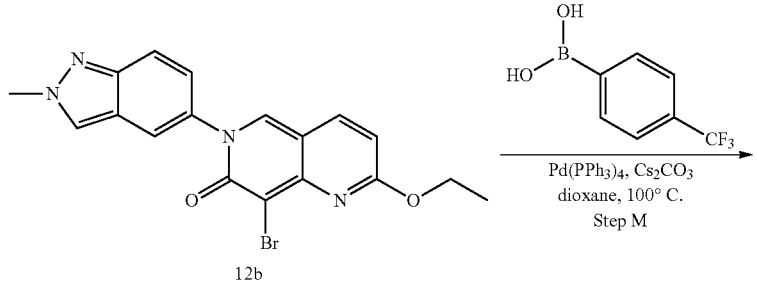

Method B

Step N:
8-bromo-2-chloro-1,6-naphthyridin-7(6H)-one

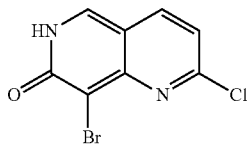

To a solution of 8-bromo-2-chloro-7-methoxy-1,6-naphthyridine (10.1 g, 40.0 mmol 1.0 equiv.) in DCE (180 mL) was added AlCl₃ (15.9 g, 120.0 mmol, 3.0 equiv.) at 10° C. The resulting mixture was then stirred at 80° C. for 2 h and quenched by water (19.4 mL, 1.1 mol, 27.0 equiv.) at 10° C. This quenched mixture was stirred at room temperature for 0.5 h and then filtered. The filter cake was washed with DCM/EtOH (200 mL, 10/1, v/v), and the filtrate was concentrated to give 8-bromo-2-chloro-1,6-naphthyridin-7 (6H)-one (9.8 g, crude) as a yellow solid, which was used directly in the next step. LC-MS: m/z 261 [M+H]⁺.

Step O:
8-bromo-2-ethoxy-1,6-naphthyridin-7(6H)-one

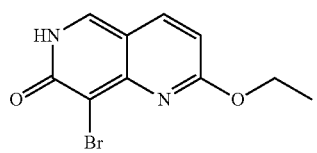

To a solution of 8-bromo-2-chloro-7-methoxy-1,6-naphthyridine (9.5 g, 40.0 mmol, 1.0 equiv.) in EtOH (220.0 mL) was added NaOEt (27.2 g, 400.0 mmol, 10.0 equiv.). The resulting solution was stirred at 100° C. for 5 h. Then the mixture was poured into ice cooled NH₄Cl (Sat. aq., 200 mL) and adjusted to pH=6 with 1N HCl (aq.). The mixture was extracted with EtOAc (100 mL×4) and the organic layers were combined, washed with brine (50 mL), dried over anhydrous Na₂SO₄, filtered and concentrated under reduced pressure. The residue was purified by flash chromatography on silica gel (eluent: DCM/EtOH=50/to 10/1) to give 8-bromo-2-ethoxy-1,6-naphthyridin-7(6H)-one (5.3 g, 49% yield) as a brown solid. LC-MS: m/z 271, 273 [M+H]⁺.

Preparation of 8-bromo-2-ethoxy-6-(2-methyl-2H-indazol-5-yl)-1,6-naphthyridin-7(6H)-one 8-bromo-2-ethoxy-6-(2-methyl-2H-indazol-5-yl)-1,6-naphthyridin-7(6H)-one was synthesized from intermediate 1b with 2-methyl-2H-indazol-5-ylboronic acid as in the procedure for Example 209 (Step H). LC-MS: m/z 399, 401 [M+H]⁺.

Example 215: Preparation of 2-ethoxy-6-(2-methyl-2H-indazol-5-yl)-8-(4-(trifluoromethyl)phenyl)-1,6-naphthyridin-7(6H)-one

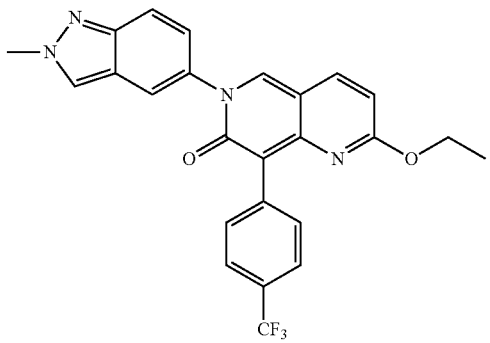

The title compound was synthesized from intermediate 12b with 4-(trifluoromethyl)phenylboronic acid via general procedure V (Step M) (Pd(PPh$_3$)$_4$, Cs$_2$CO$_3$, dioxane, 100° C.).

$^1$H NMR (400 MHz, DMSO-d$_6$) δ: 8.81 (s, 1H), 8.50 (s, 1H), 7.99 (d, J=9.2 Hz, 1H), 7.91 (d, J=1.6 Hz, 1H), 7.88 (d, J=8.0 Hz, 2H), 7.74-7.67 (m, 3H), 7.35 (dd, J=9.2 Hz, 2.0 Hz, 1H), 6.57 (d, J=8.8 Hz, 1H), 4.25 (q, J=7.2 Hz, 2H), 4.23 (s, 3H), 1.26 (t, J=7.2 Hz, 3H). LC-MS: m/z 465 [M+H]$^+$.

Example 216: 8-(6-(difluoromethyl)pyridin-3-yl)-2-ethoxy-6-(2-methyl-2H-indazol-5-yl)-1,6-naphthyridin-7(6H)-one

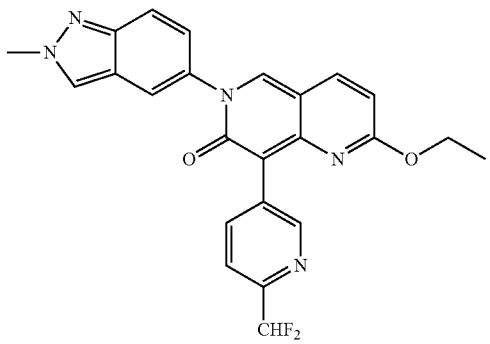 [SMILES: CCOc1ccc2cn(-c3ccc4nn(C)cc4c3)c(=O)c(-c3ccc(C(F)F)nc3)c2n1]

The title compound was synthesized from intermediate 12b with 2-(difluoromethyl)-5-(4,4,5,5-tetramethyl-1,3,2-dioxaborolan-2-yl)pyridine via general procedure V (Step M).

$^1$H NMR (400 MHz, DMSO-d$_6$) δ: 8.95 (d, J=1.2 Hz, 1H), 8.85 (s, 1H), 8.51 (s, 1H), 8.27 (dd, J=8.4 Hz, 2.0 Hz, 1H), 8.02 (d, J=9.2 Hz, 6H), 7.92 (d, J=1.2 Hz, 1H), 7.72 (d, J=3.6 Hz, 1H), 7.70 (d, J=2.8 Hz, 1H), 7.36 (dd, J=9.2 Hz, 2.0 Hz, 1H), 6.98 (t, J$_{HF}$=55.2 Hz, 1H), 6.59 (d, J=9.2 Hz, 1H), 4.25 (q, J=7.2 Hz, 2H), 4.23 (s, 3H), 1.27 (t, J=7.2 Hz, 3H). LC-MS: m/z 448 [M+H]$^+$.

Example 217: 2-ethoxy-6-(2-methyl-2H-indazol-5-yl)-8-(4-(trifluoromethoxy)phenyl)-1,6-naphthyridin-7(6H)-one

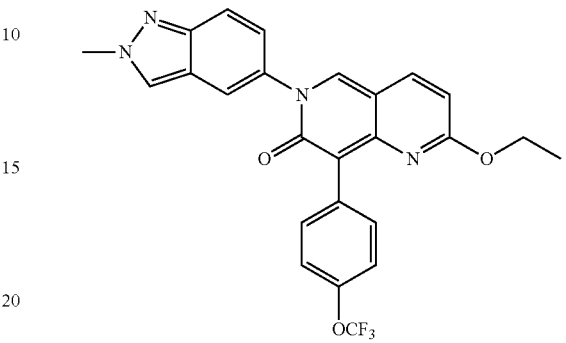

The title compound was synthesized from intermediate 12b with (4-(trifluoromethoxy)phenyl)boronic acid via general procedure V (Step M).

$^1$H NMR (400 MHz, DMSO-d$_6$) δ: 8.77 (s, 1H), 8.50 (s, 1H), 7.98 (d, J=9.0 Hz, 1H), 7.89 (d, J=2.0 Hz, 1H), 7.75 (d, J=8.8 Hz, 2H), 7.70 (d, J=9.0 Hz, 1H), 7.37-7.30 (m, 3H), 6.55 (d, J=9.0 Hz, 1H), 4.25 (q, J=7.2 Hz, 2H), 4.22 (s, 3H), 1.25 (t, J=7.2 Hz, 3H). LC-MS: m/z 481 [M+H]$^+$.

Example 218: 8-(6-(difluoromethoxy)pyridin-3-yl)-2-ethoxy-6-(2-methyl-2H-indazol-5-yl)-1,6-naphthyridin-7(6H)-one

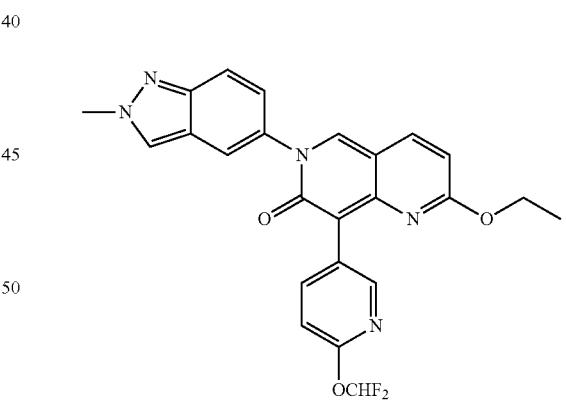

The title compound was synthesized from intermediate 12b with 2-(difluoromethoxy)-5-(4,4,5,5-tetramethyl-1,3,2-dioxaborolan-2-yl)pyridine via general procedure V (Step M).

$^1$H NMR (400 MHz, DMSO-d$_6$) δ: 8.77 (s, 1H), 8.51 (d, J=2.4 Hz, 1H), 8.49 (s, 1H), 8.18 (dd, J=4.4 Hz, 2.0 Hz, 1H), 7.99 (d, J=8.8 Hz, 1H), 7.89 (d, J=2.0 Hz, 1H), 7.74 (t, J$_{HF}$=73.2 Hz, 1H), 7.71 (d, J=9.2 Hz, 1H), 7.35 (dd, J=9.2 Hz, 2.0 Hz, 1H), 7.10 (d, J=8.4 Hz, 1H), 6.57 (d, J=9.2 Hz, 1H), 4.27 (q, J=7.2 Hz, 2H), 4.22 (s, 3H), 1.27 (t, J=7.2 Hz, 3H). LC-MS: m/z 464 [M+H]$^+$.

Example 219: 2-ethoxy-6-(2-methyl-2H-indazol-5-yl)-8-(6-methylpyridin-3-yl)-1,6-naphthyridin-7(6H)-one

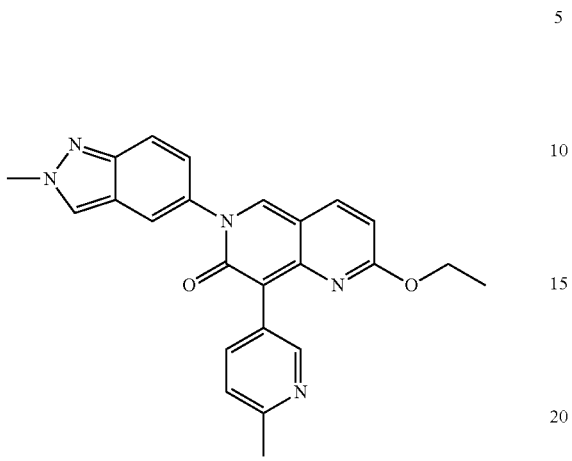

The title compound was synthesized from intermediate 12b with (6-methylpyridin-3-yl)boronic acid via general procedure V (Step M).

$^1$H NMR (400 MHz, DMSO-d$_6$) δ:: 8.75 (s, 1H), 8.70 (br s, 1H), 8.50 (s, 1H), 7.98 (d, J=8.8 Hz, 1H), 7.93 (dd, J=8.4 Hz, 2.0 Hz, 1H), 7.89 (d, J=1.6 Hz, 1H), 7.71 (d, J=9.2 Hz, 1H), 7.35 (dd, J=9.2 Hz, 2.0 Hz, 1H), 7.26 (d, J=8.0 Hz, 1H), 6.55 (d, J=8.8 Hz, 1H), 4.26 (q, J=7.2 Hz, 2H), 4.23 (s, 3H), 1.28 (t, J=7.2 Hz, 3H). LC-MS: m/z 412 [M+H]$^+$.

Example 220: 2-ethoxy-6-(2-methyl-2H-indazol-5-yl)-8-(6-(trifluoromethyl)pyridin-3-yl)-1,6-naphthyridin-7(6H)-one

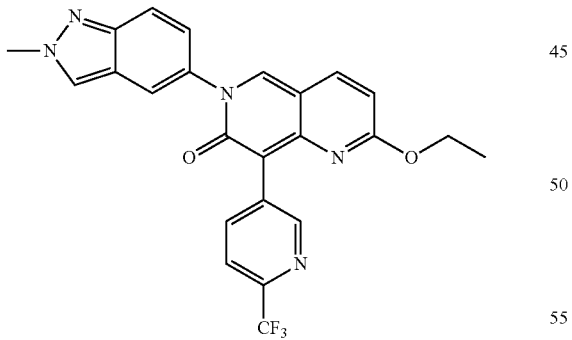

The title compound was synthesized from intermediate 12b with (6-(trifluoromethyl)pyridin-3-yl)boronic acid via general procedure V (Step M).

$^1$H NMR (400 MHz, DMSO-d$_6$) δ: 9.05 (d, J=7.8 Hz, 1H), 8.88 (s, 1H), 8.51 (s, 1H), 8.37 (dd, J=8.0 Hz, 2.0 Hz, 1H), 8.04 (d, J=9.2 Hz, 1H), 7.93 (d, J=2.0 Hz, 1H), 7.92 (d, J=8.4 Hz, 1H), 7.72 (d, J=9.2 Hz, 1H), 7.37 (dd, J=9.6 Hz, 2.0 Hz, 1H), 6.61 (d, J=9.2 Hz, 1H), 4.28 (q, J=7.2 Hz, 2H), 4.23 (s, 3H), 1.28 (t, J=7.2 Hz, 3H). LC-MS: m/z 466 [M+H]$^+$.

Example 221: 8-(6-cyclopropylpyridin-3-yl)-2-ethoxy-6-(2-methyl-2H-indazol-5-yl)-1,6-naphthyridin-7(6H)-one

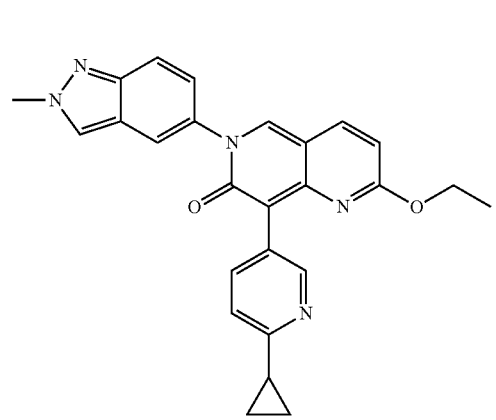 [SMILES: CCOc1ccc2cn(-c3ccc4nn(C)cc4c3)c(=O)c(-c3ccc(C4CC4)nc3)c2n1]

The title compound was synthesized from intermediate 12b with (6-cyclopropylpyridin-3-yl)boronic acid via general procedure V (Step M).

$^1$H NMR (400 MHz, DMSO-d$_6$) δ: 8.93 (s, 1H), 8.89 (s, 1H), 8.51 (s, 1H), 8.04 (d, J=9.2 Hz, 1H), 7.91 (d, J=1.2 Hz, 1H), 7.72 (d, J=9.2 Hz, 1H), 7.56 (d, J=8.0 Hz, 1H), 7.35 (dd, J=9.2 Hz, 2.0 Hz, 1H), 6.63 (d, J=9.2 Hz, 1H), 4.31 (q, J=6.8 Hz, 2H), 4.23 (s, 3H), 2.36-2.25 (m, 1H), 1.31 (t, J=6.8 Hz, 3H), 1.27-1.20 (m, 2H), 1.17-1.09 (m, 2H). LC-MS: m/z 437 [M+H]$^+$.

Example 222: 8-(4-(1H-1,2,4-triazol-3-yl)phenyl)-2-ethoxy-6-(2-methyl-2H-indazol-5-yl)-1,6-naphthyridin-7(6H)-one

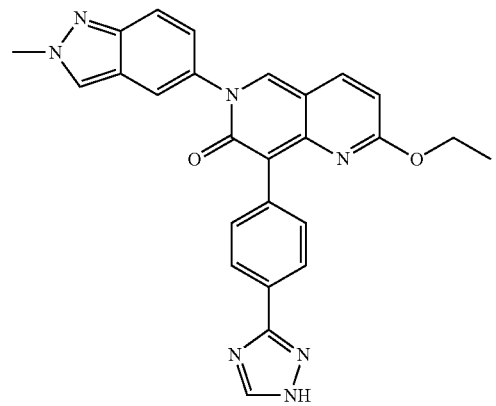

The title compound was synthesized from intermediate 12b with 3-(4-(4,4,5,5-tetramethyl-1,3,2-dioxaborolan-2-yl)phenyl)-1-((2-(trimethylsilyl)ethoxy)methyl)-1H-1,2,4-triazole via general procedure V (Step M) and then deprotection with TFA via general procedure I (Step F).

$^1$H NMR (400 MHz, DMSO-d$_6$) δ: 14.05 (br.s, 1H), 8.75 (s, 1H), 8.50 (s, 1H), 8.39 (br.s, 1H), 8.01 (d, J=8.4 Hz, 2H), 7.98 (d, J=9.2 Hz, 1H), 7.90 (d, J=1.6 Hz, 1H), 7.77 (d, J=8.4 Hz, 2H), 7.71 (d, J=8.8 Hz, 1H), 7.35 (dd, J=8.8 Hz, 2.0 Hz, 1H), 6.55 (d, J=9.2 Hz, 1H), 4.27 (q, J=7.2 Hz, 2H), 4.23 (s, 3H), 1.27 (t, J=7.2 Hz, 3H). LC-MS: m/z 464 [M+H]$^+$.

Example 223: 8-(4-(1H-pyrazol-3-yl)phenyl)-2-ethoxy-6-(2-methyl-2H-indazol-5-yl)-1,6-naphthyridin-7(6H)-one

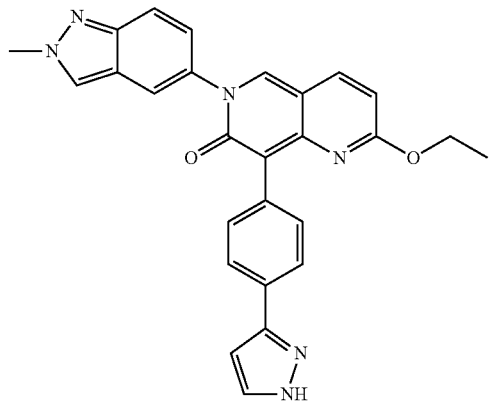

The title compound was synthesized from intermediate 12b with 3-(4-(4,4,5,5-tetramethyl-1,3,2-dioxaborolan-2-yl)phenyl)-1-((2-(trimethylsilyl)ethoxy)methyl)-1H-pyrazole via general procedure V (Step M) and then de-protection with TFA via general procedure I (Step F).

$^1$H NMR (400 MHz, DMSO-d$_6$) δ: 12.87 (br.s, 1H), 8.70 (s, 1H), 8.49 (s, 1H), 7.97 (d, J=9.2 Hz, 1H), 7.89 (d, J=1.2 Hz, 1H), 7.85-7.69 (m, 6H), 7.35 (dd, J=9.2 Hz, 2.0 Hz, 1H), 6.73 (s, 1H), 6.54 (d, J=8.8 Hz, 1H), 4.27 (q, J=7.2 Hz, 2H), 4.22 (s, 3H), 1.27 (t, J=7.2 Hz, 3H). LC-MS: m/z 463 [M+H]$^+$.

Example 224: 8-(4-(1H-imidazol-4-yl)phenyl)-2-ethoxy-6-(2-methyl-2H-indazol-5-yl)-1,6-naphthyridin-7(6H)-one

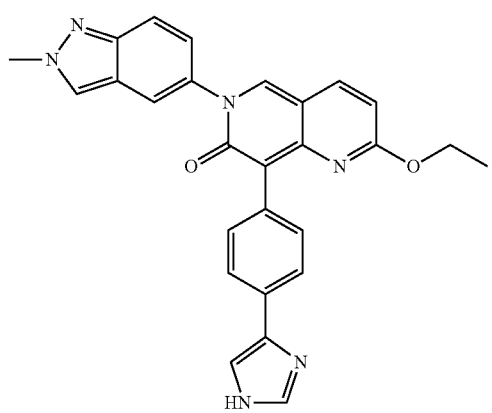 [SMILES: CCOc1ccc2cn(-c3ccc4nn(C)cc4c3)c(=O)c(-c3ccc(-c4c[nH]cn4)cc3)c2n1]

The title compound was synthesized from intermediate 12b with 4-(4-(4,4,5,5-tetramethyl-1,3,2-dioxaborolan-2-yl)phenyl)-1-((2-(trimethylsilyl)ethoxy)methyl)-1H-imidazole via general procedure V (Step M) and then de-protection with TFA via general procedure I (Step F).

$^1$H NMR (400 MHz, DMSO-d$_6$) δ: 12.14 (br s, 1H), 8.70 (s, 1H), 8.50 (s, 1H), 7.96 (d, J=8.8 Hz, 1H), 7.89 (d, J=1.6 Hz, 1H), 7.78-7.58 (m, 7H), 7.35 (dd, J=9.2 Hz, 2.0 Hz, 1H), 6.53 (d, J=9.2 Hz, 1H), 4.27 (q, J=7.2 Hz, 2H), 4.23 (s, 3H), 1.27 (t, J=7.2 Hz, 3H). LC-MS: m/z 463 [M+H]$^+$.

Preparation of 8-bromo-2-ethoxy-6-(2-(2-(methylsulfonyl)ethyl)-2H-indazol-5-yl)-1,6-naphthyridin-7(6H)-one 12c

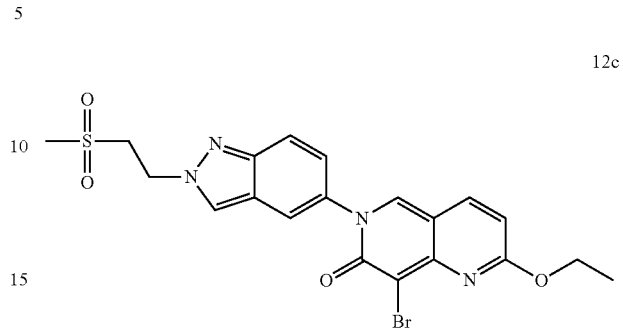

8-bromo-2-ethoxy-6-(2-(2-(methylsulfonyl)ethyl)-2H-indazol-5-yl)-1,6-naphthyridin-7(6H)-one 12c was synthesized from intermediate 1b with 2-(2-(methylsulfonyl)ethyl)-2H-indazol-5-ylboronic acid via general procedure V (Step L). LC-MS: m/z 491, 493 [M+H]$^+$.

Example 225: Preparation of 8-(4-chlorophenyl)-2-ethoxy-6-(2-(2-(methylsulfonyl)ethyl)-2H-indazol-5-yl)-1,6-naphthyridin-7(6H)-one

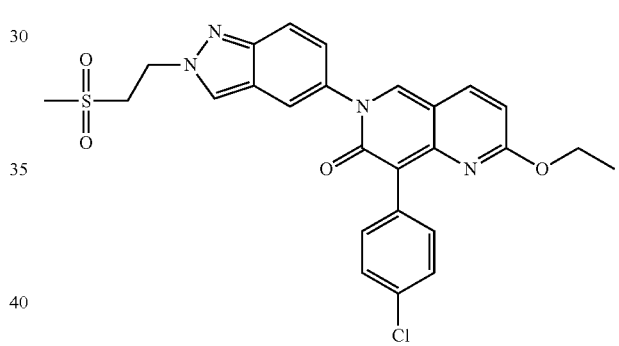

The title compound was synthesized from intermediate 12c with 4-chlorophenylboronic acid via general procedure V (Step M).

$^1$H NMR (400 MHz, DMSO-d$_6$) δ: 8.76 (s, 1H), 8.62 (s, 1H), 8.00-7.93 (m, 2H), 7.87 (d, J=8.8 Hz, 1H), 7.66 (d, J=8.8 Hz, 2H), 7.42-7.36 (m, 3H), 6.54 (d, J=9.2 Hz, 1H), 4.91 (t, J=6.8 Hz, 2H), 4.26 (q, J=6.8 Hz, 2H), 3.80 (t, J=6.8 Hz, 2H), 2.94 (s, 3H), 1.27 (t, J=6.8 Hz, 3H). LC-MS: m/z 523 [M+H]$^+$.

Preparation of 8-bromo-2-ethoxy-6-(1-methyl-1H-benzo[d]imidazol-6-yl)-1,6-naphthyridin-7(6H)-one

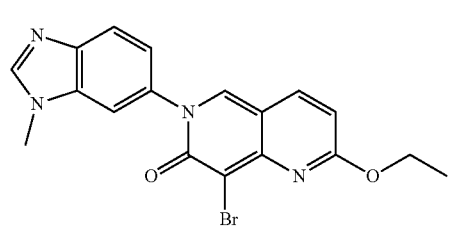

8-bromo-2-ethoxy-6-(1-methyl-1H-benzo[d]imidazol-6-yl)-1,6-naphthyridin-7(6H)-one 12d was synthesized from intermediate 11b with (1-methyl-1H-benzo[d]imidazol-6-yl)boronic acid via general procedure V (Step L). LC-MS: m/z 399 [M+H]$^+$.

Example 226: Preparation of 2-ethoxy-6-(1-methyl-1H-benzo[d]imidazol-6-yl)-8-(6-(trifluoromethyl)pyridin-3-yl)-1,6-naphthyridin-7(6H)-one

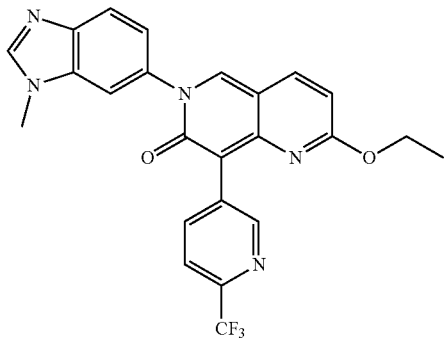 [SMILES: CCOc1ccc2cn(-c3ccc4ncn(C)c4c3)c(=O)c(-c3ccc(C(F)(F)F)nc3)c2n1]

The title compound was synthesized from intermediate 12d with (6-(trifluoromethyl)pyridin-3-yl)boronic acid via general procedure V (Step M).

$^1$H NMR (400 MHz, DMSO-d$_6$) δ: 9.05 (d, J=1.6 Hz, 1H), 8.88 (s, 1H), 8.37 (dd, J=8.4 Hz, 2.0 Hz, 1H), 8.35 (s, 1H), 8.03 (d, J=9.0 Hz, 1H), 7.89 (d, J=2.0 Hz, 1H), 7.80 (d, J=8.4 Hz, 1H), 7.38 (dd, J=8.4 Hz, 2.0 Hz, 1H), 6.62 (d, J=8.8 Hz, 1H), 4.28 (q, J=7.2 Hz, 2H), 3.88 (s, 3H), 1.28 (t, J=7.2 Hz, 3H). LC-MS: m/z 466 [M+H]$^+$.

Example 227: 2-ethoxy-6-(1-methyl-1H-benzo[d]imidazol-6-yl)-8-(4-(trifluoromethyl)phenyl)-1,6-naphthyridin-7(6H)-one

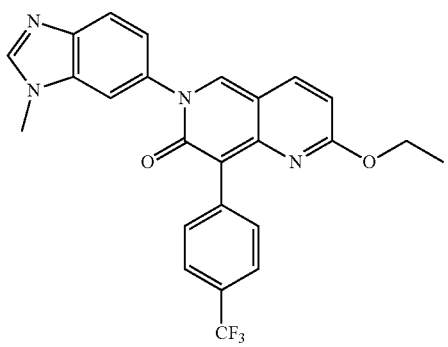 [SMILES: CCOc1ccc2cn(-c3ccc4ncn(C)c4c3)c(=O)c(-c3ccc(C(F)(F)F)cc3)c2n1]

The title compound was synthesized from intermediate 12d with (4-(trifluoromethyl)phenyl)boronic acid via general procedure V (Step M).

$^1$H NMR (400 MHz, DMSO-d$_6$) δ: 8.80 (s, 1H), 8.34 (s, 1H), 8.00 (d, J=8.8 Hz, 1H), 7.90-7.84 (m, 3H), 7.79 (d, J=8.4 Hz, 1H), 7.71 (d, J=8.0 Hz, 2H), 7.36 (dd, J=8.8 Hz, 2.4 Hz, 1H), 6.57 (d, J=8.8 Hz, 1H), 4.25 (q, J=7.2 Hz, 2H), 3.88 (s, 3H), 1.26 (t, J=7.2 Hz, 3H). LC-MS: m/z 465 [M+H]$^+$.

Example 228: 8-(6-cyclopropylpyridin-3-yl)-2-ethoxy-6-(1-methyl-1H-benzo[d]imidazol-6-yl)-1,6-naphthyridin-7(6H)-one

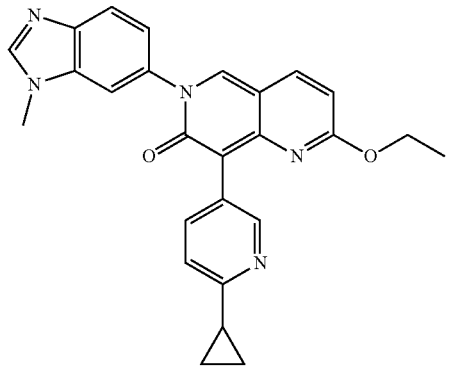 [SMILES: CCOc1ccc2cn(-c3ccc4ncn(C)c4c3)c(=O)c(-c3ccc(C4CC4)nc3)c2n1]

The title compound was synthesized from intermediate 12d with (6-cyclopropylpyridin-3-yl)boronic acid via general procedure V (Step M).

$^1$H NMR (400 MHz, DMSO-d$_6$) δ: 8.74 (s, 1H), 8.64 (d, J=1.6 Hz 1H), 8.34 (s, 1H), 7.97 (d, J=9.2 Hz, 1H), 7.89 (dd, J=8.0 Hz, 2.4 Hz, 1H), 7.85 (d, J=2.4 Hz, 1H), 7.78 (d, J=8.4 Hz, 1H), 7.35 (dd, J=8.8 Hz, 2.0 Hz, 1H), 7.28 (d, J=8.0 Hz, 1H), 6.56 (d, J=9.2 Hz, 1H), 4.26 (q, J=7.2 Hz, 2H), 3.88 (s, 3H), 2.16-2.06 (m, 1H), 1.28 (t, J=7.2 Hz, 3H), 0.99-0.88 (m, 4H). LC-MS: m/z 438 [M+H]$^+$.

Example 229: 8-(6-(difluoromethoxy)pyridin-3-yl)-2-ethoxy-6-(1-methyl-1H-benzo[d]imidazol-6-yl)-1,6-naphthyridin-7(6H)-one

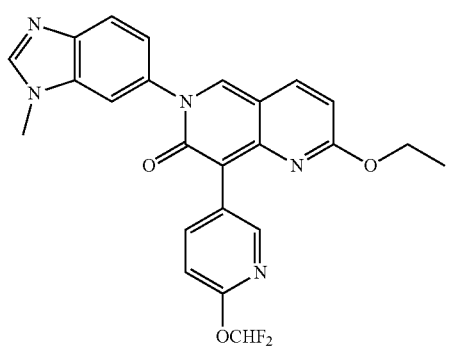

The title compound was synthesized from intermediate 12d with 2-(difluoromethoxy)-5-(4,4,5,5-tetramethyl-1,3,2-dioxaborolan-2-yl)pyridine via general procedure V (Step M).

$^1$H NMR (400 MHz, DMSO-d$_6$) δ: 8.77 (s, 1H), 8.51 (d, J=1.6 Hz, 1H), 8.34 (s, 1H), 8.19 (dd, J=8.8 Hz, 2.0 Hz, 1H), 8.00 (d, J=9.2 Hz, 1H), 7.86 (d, J=2.0 Hz, 1H), 7.79 (d, J=8.4 Hz, 1H), 7.75 (t, J$_{HF}$=73.2 Hz, 1H), 7.36 (dd, J=9.2 Hz, 2.0 Hz, 1H), 7.10 (d, J=9.2 Hz, 1H), 6.58 (d, J=9.2 Hz, 1H), 4.28 (q, J=7.2 Hz, 2H), 3.88 (s, 3H), 1.28 (t, J=7.2 Hz, 3H). LC-MS: m/z 464 [M+H]$^+$.

Preparation of 8-bromo-2-ethoxy-6-(quinolin-6-yl)-1,6-naphthyridin-7(6H)-one 12e

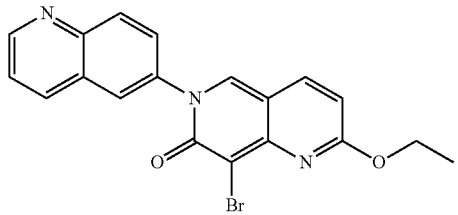

12e 8-bromo-2-ethoxy-6-(quinolin-6-yl)-1,6-naphthyridin-7(6H)-one 12e was synthesized from intermediate 11b with quinolin-6-ylboronic acid via general procedure V (Step L). LC-MS: m/z 396 (M+H)$^+$.

Example 230: Preparation of 8-(4-(difluoromethoxy)phenyl)-2-ethoxy-6-(quinolin-6-yl)-1,6-naphthyridin-7(6H)-one

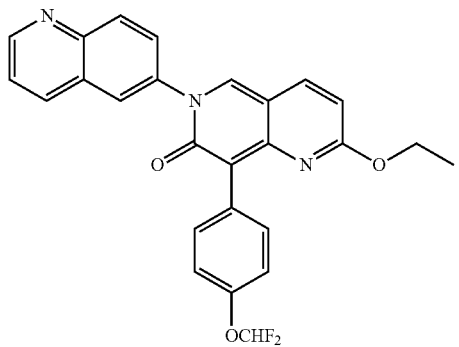 [SMILES: CCOc1ccc2cn(-c3ccc4ncccc4c3)c(=O)c(-c3ccc(OC(F)F)cc3)c2n1]

The title compound was synthesized from intermediate 12e with 2-(4-(difluoromethoxy)phenyl)-4,4,5,5-tetramethyl-1,3,2-dioxaborolane via general procedure V (Step M).

$^1$H NMR (400 MHz, DMSO-d$_6$) δ:: 9.02 (dd, J=4.4 Hz, 2.0 Hz, 1H), 8.83 (s, 1H), 8.48 (dd, J=8.8 Hz, 1.2 Hz, 1H), 8.24 (d, J=2.4 Hz, 1H), 8.16 (d, J=8.8 Hz, 1H), 7.97 (d, J=9.2 Hz, 1H), 7.94 (dd, J=8.8 Hz, 2.0 Hz, 1H), 7.71 (d, J=8.8 Hz, 2H), 7.65 (dd, J=8.4 Hz, 4.0 Hz, 1H), 7.28 (t, J$_{HF}$=74.4 Hz, 1H), 7.16 (d, J=8.8 Hz, 2H), 6.57 (d, J=8.8 Hz, 1H), 4.27 (q, J=7.2 Hz, 2H), 1.28 (t, J=7.2 Hz, 3H). LC-MS: m/z 460 [M+H]$^+$.

Example 231: 8-(6-cyclopropylpyridin-3-yl)-2-ethoxy-6-(quinolin-6-yl)-1,6-naphthyridin-7(6H)-one

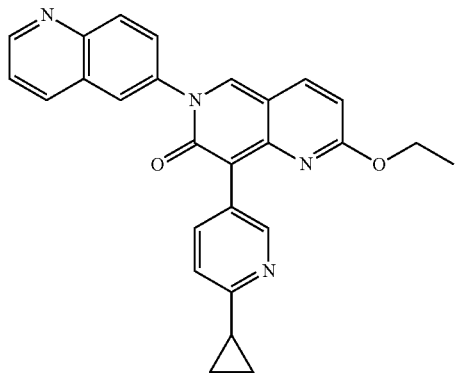 [SMILES: CCOc1ccc2cn(-c3ccc4ncccc4c3)c(=O)c(-c3ccc(C4CC4)nc3)c2n1]

The title compound was synthesized from intermediate 12e with (6-cyclopropylpyridin-3-yl)boronic acid via general procedure V (Step M).

$^1$H NMR (400 MHz, DMSO-d$_6$) δ:: 9.02 (dd, J=4.0 Hz, 2.0 Hz, 1H), 8.84 (s, 1H), 8.65 (d, J=2.0 Hz, 1H), 8.47 (dd, J=8.8 Hz, 2.0 Hz, 1H), 8.24 (d, J=2.4 Hz, 1H), 8.16 (d, J=9.2 Hz, 1H), 7.98 (d, J=9.2 Hz, 1H), 7.94 (dd, J=9.2 Hz, 2.4 Hz, 1H), 7.90 (dd, J=8.0 Hz, 2.0 Hz, 1H), 7.65 (dd, J=8.4 Hz, 4.4 Hz, 1H), 7.28 (d, J=8.0 Hz, 1H), 6.58 (d, J=9.2 Hz, 1H), 4.27 (q, J=7.2 Hz, 2H), 2.16-2.06 (m, 1H), 1.28 (t, J=7.2 Hz, 3H), 0.98-0.91 (m, 4H). LC-MS: m/z 435 [M+H]$^+$.

Example 232: 8-(6-(difluoromethoxy)pyridin-3-yl)-2-ethoxy-6-(quinolin-6-yl)-1,6-naphthyridin-7(6H)-one

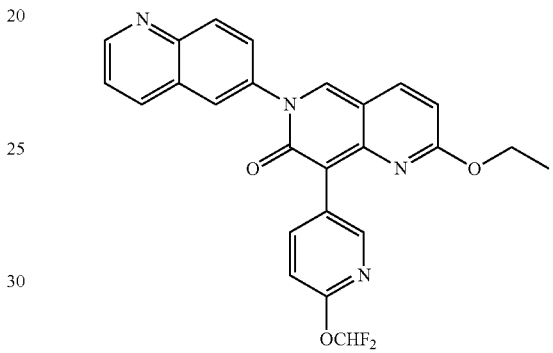

The title compound was synthesized from intermediate 12e with 2-(difluoromethoxy)-5-(4,4,5,5-tetramethyl-1,3,2-dioxaborolan-2-yl)pyridine via general procedure V (Step M).

$^1$H NMR (400 MHz, DMSO-d$_6$) δ: 9.02 (dd, J=4.2 Hz, 2.0 Hz, 1H), 8.89 (s, 1H), 8.53 (d, J=2.0 Hz, 1H), 8.48 (dd, J=8.4 Hz, 1.2 Hz, 1H), 8.25 (d, J=2.4 Hz, 1H), 8.21 (dd, J=8.4 Hz, 2.4 Hz, 1H), 8.17 (d, J=9.0 Hz, 1H), 8.00 (d, J=9.0 Hz, 1H), 7.96 (dd, J=9.0 Hz, 2.0 Hz, 1H), 7.76 (t, J$_{HF}$=73.2 Hz, 1H), 7.66 (dd, J=8.4 Hz, 4.2 Hz, 1H), 7.11 (dd, J=8.4 Hz, 0.4 Hz, 1H), 6.61 (d, J=9.0 Hz, 1H), 4.28 (q, J=7.2 Hz, 2H), 1.28 (t, J=7.2 Hz, 3H). LC-MS: m/z 461 (M+H)$^+$.

Preparation of 8-bromo-2-(cyclopropylmethoxy)-1,6-naphthyridin-7(6H)-one

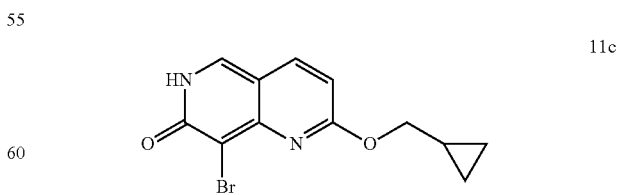

11c 8-bromo-2-(cyclopropylmethoxy)-1,6-naphthyridin-7(6H)-one 11c was synthesized from intermediate 14 with cyclopropylmethanol via general procedure V (Step O). LC-MS: m/z 295 [M+H]$^+$.

Preparation of 8-bromo-2-(cyclopropylmethoxy)-6-(2-methyl-2H-indazol-5-yl)-1,6-naphthyridin-7(6H)-one 12f

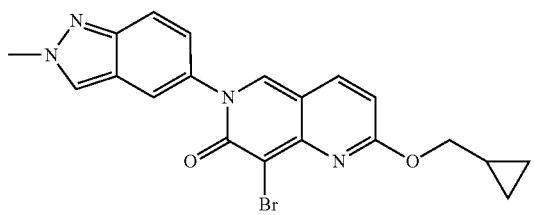

8-bromo-2-(cyclopropylmethoxy)-6-(2-methyl-2H-indazol-5-yl)-1,6-naphthyridin-7(6H)-one 12f was synthesized from intermediate 11c with 2-methyl-2H-indazol-5-ylboronic acid via general procedure V (Step L). LC-MS: m/z 425, 427 [M+H]⁺.

Example 233: Preparation of 8-(4-chlorophenyl)-2-(cyclopropylmethoxy)-6-(2-methyl-2H-indazol-5-yl)-1,6-naphthyridin-7(6H)-one

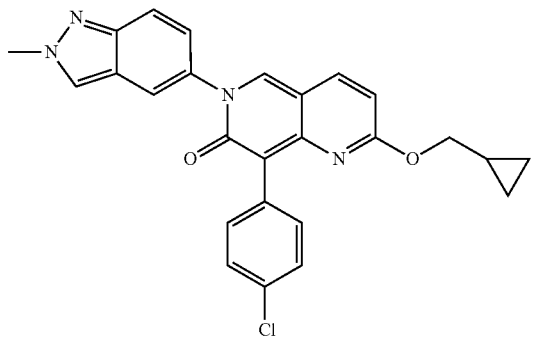 [SMILES: Cn1cc2cc(-n3cc4ccc(OCC5CC5)nc4c(-c4ccc(Cl)cc4)c3=O)ccc2n1]

The title compound was synthesized from intermediate 12f with 4-chlorophenylboronic acid via general procedure V (Step M).

¹H NMR (400 MHz, DMSO-d₆) δ: 8.75 (s, 1H), 8.49 (s, 1H), 7.97 (d, J=9.2 Hz, 1H), 7.89 (dd, J=2.0 Hz, 0.4 Hz, 1H), 7.70 (d, J=9.2 Hz, 1H), 7.65 (d, J=8.8 Hz, 2H), 7.39 (d, J=8.8 Hz, 2H), 7.33 (dd, J=9.2 Hz, 2.0 Hz, 1H), 6.57 (d, J=9.2 Hz, 1H), 4.22 (s, 3H), 4.08 (d, J=7.6 Hz, 2H), 1.23-1.11 (m, 1H), 0.53-0.46 (m, 2H), 0.26-0.20 (m, 2H). LC-MS: m/z 457 [M+H]⁺.

Example 234: Preparation of 8-(4-chlorophenyl)-6-(1-methyl-1H-benzo[d]imidazol-6-yl)-2-(2,2,2-trifluoroethylamino)-1,6-naphthyridin-7(6H)-one

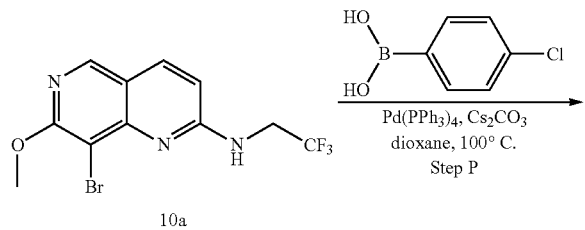

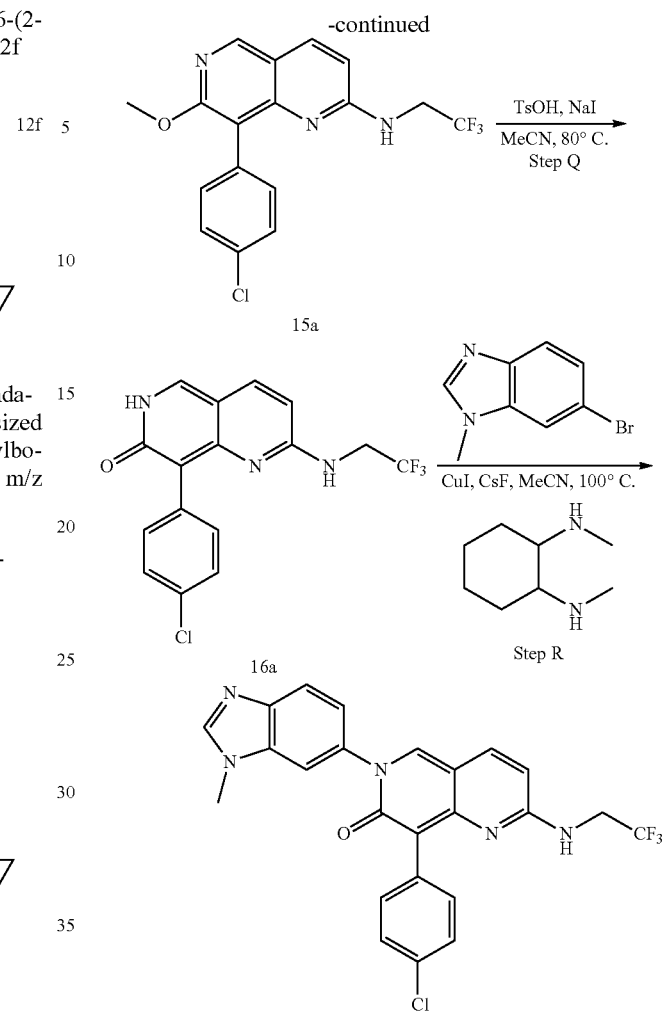

Step P: 8-(4-chlorophenyl)-7-methoxy-N-(2,2,2-trifluoroethyl)-1,6-naphthyridin-2-amine 15a

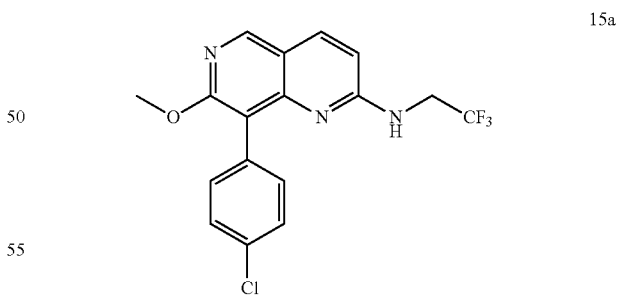

A mixture of 8-bromo-7-methoxy-N-(2,2,2-trifluoroethyl)-1,6-naphthyridin-2-amine (300.0 mg, 0.9 mmol, 1.0 equiv.), Pd(PPh₃)₄ (52.0 mg, 0.05 mmol, 0.05 equiv.), Cs₂CO₃ (580.0 mg, 1.8 mmol, 2.0 equiv.) and 4-chlorophenylboronic acid (208.0 mg, 1.3 mmol, 1.5 equiv.) in dioxane-water (5.0 mL, 9/1, v/v) was stirred at 100° C. under N₂ atmosphere for 16 h. Then the reaction mixture was diluted with water (20 mL) and extracted with EtOAc (20 mL×3). All the organic layers were combined and washed with brine (50 mL), dried over anhydrous Na₂SO₄, filtered and concentrated under reduced pressure. The residue was purified by flash chromatography on silica gel (eluent: PE/EA=2/1) to afford 8-(4-chlorophenyl)-7-methoxy-N-(2,2,2-trifluoroethyl)-1,6-naphthyridin-2-amine (300 mg, 92% yield) as a white solid. LC-MS: m/z 368 [M+H]⁺.

Step Q: 8-(4-chlorophenyl)-2-(2,2,2-trifluoroethyl-amino)-1,6-naphthyridin-7(6H)-one 16a

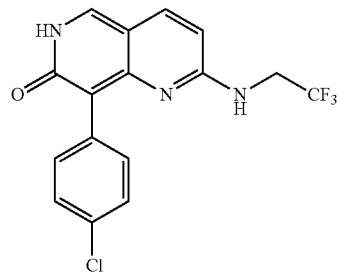

16a

A mixture of 8-(4-chlorophenyl)-7-methoxy-N-(2,2,2-trifluoroethyl)-1,6-naphthyridin-2-amine (300 mg, 0.8 mmol, 1.0 equiv.), TsOH (422 mg, 2.5 mmol, 3.0 equiv.), NaI (407.0 mg, 2.5 mmol, 3.0 equiv.) in MeCN (10 mL) was stirred at 80° C. for 2 h. Then the reaction mixture was quenched with ice water (10 mL) and extracted with EtOAc (10 mL×3). The organic layers were combined, washed with brine (20 mL), dried over anhydrous Na₂SO₄, filtered and concentrated under reduced pressure. The residue was purified by flash chromatography on silica gel (DCM/MeOH=20/1) to afford 8-(4-chlorophenyl)-2-(2,2,2-trifluoroethylamino)-1,6-naphthyridin-7(6H)-one (280 mg, 97% yield) as a white solid. LC-MS: m/z 354 [M+H]⁺.

Example 234, Step R: 8-(4-chlorophenyl)-6-(1-methyl-1H-benzo[d]imidazol-6-yl)-2-(2,2,2-trifluoroethylamino)-1,6-naphthyridin-7(6H)-one

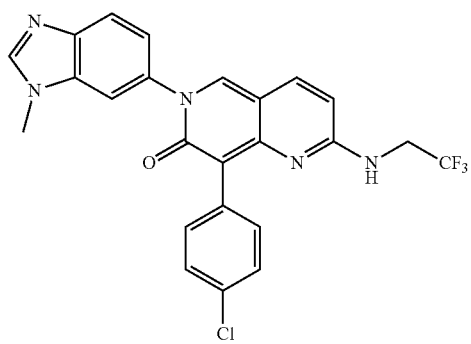

A mixture of 8-(4-chlorophenyl)-2-(2,2,2-trifluoroethyl-amino)-1,6-naphthyridin-7(6H)-one (50.0 mg, 0.14 mmol, 1.0 equiv.), CuI (26.6 mg, 0.14 mmol, 1.0 equiv.), CsF (63.8 mg, 0.4 mmol, 3.0 equiv.), N₁,N₂-dimethylcyclohexane-1,2-diamine (29.8 mg, 0.2 mmol, 1.5 equiv.), and 6-bromo-1-methyl-1H-benzo[d]imidazole (44.3 mg, 0.2 mmol, 1.5 equiv.) in MeCN (3 mL) was stirred at 100° C. under N₂ atmosphere for 3 h. Then the reaction mixture was diluted with water (10 mL) and extracted with EtOAc (10 mL×3). The organic layers were combined, washed with brine (20 mL), dried over anhydrous Na₂SO₄, filtered and concentrated under reduced pressure. The residue was purified by RP-prep-HPLC to afford 8-(4-chlorophenyl)-6-(1-methyl-1H-benzo[d]imidazol-6-yl)-2-(2,2,2-trifluoroethylamino)-1,6-naphthyridin-7(6H)-one (Example 234).
¹H NMR (400 MHz, DMSO-d₆) δ: 8.50 (s, 1H), 8.40-8.28 (m, 2H), 7.82 (s, 1H), 7.75 (d, J=9.2 Hz, 2H), 7.64 (d, J=8.4 Hz, 2H), 7.37-7.28 (m, 3H), 6.51 (d, J=8.8 Hz, 1H), 4.22-4.10 (m, 2H), 3.87 (s, 3H). LC-MS: m/z 484 [M+H]⁺.

Example 235: 8-(4-chlorophenyl)-6-(1-methyl-1H-benzo[d][1,2,3]triazol-6-yl)-2-(2,2,2-trifluoroethyl-amino)-1,6-naphthyridin-7(6H)-one

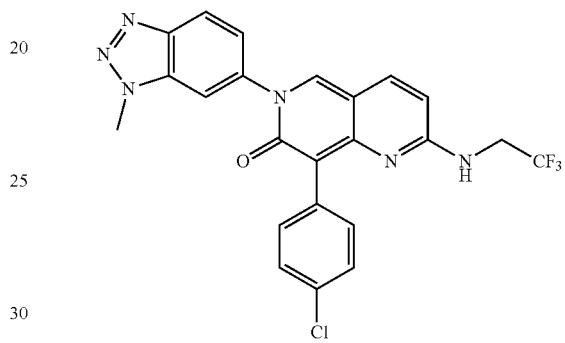

The title compound was synthesized from intermediate 16a with 6-bromo-1-methyl-1H-benzo[d][1,2,3]triazole via general procedure V (Step R).
¹H NMR (400 MHz, DMSO-d₆) δ: 8.53 (s, 1H), 8.41 (t, J=6.0 Hz, 1H), 8.17 (d, J=3.6 Hz, 1H), 8.16 (d, J=2.4 Hz, 1H), 7.75 (d, J=9.2 Hz, 1H), 7.64 (d, J=8.4 Hz, 2H), 7.54 (dd, J=9.2 Hz, 1.6 Hz, 1H), 7.34 (d, J=8.4 Hz, 2H), 6.52 (d, J=9.2 Hz, 1H), 4.35 (s, 3H), 4.23-4.10 (m, 2H). LC-MS: m/z 485 [M+H]⁺.

Example 236: 8-(4-chlorophenyl)-6-(2-methyl-2H-indazol-5-yl)-2-(2,2,2-trifluoroethylamino)-1,6-naphthyridin-7(6H)-one

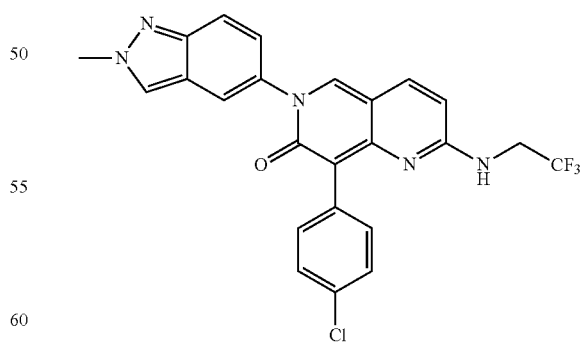

The title compound was synthesized from intermediate 16a with 5-bromo-2-methyl-2H-indazole via general procedure V (Step R).
¹H NMR (400 MHz, DMSO-d₆) δ: 8.51 (s, 1H), 8.47 (s, 1H), 8.36 (t, J=6.4 Hz, 1H), 7.84 (d, J=1.2 Hz, 1H), 7.75 (d, J=8.8 Hz, 1H), 7.68 (d, J=9.2 Hz, 1H), 7.64 (d, J=8.4 Hz, 2H), 7.33 (d, J=8.4 Hz, 2H), 7.31 (dd, J=9.2 Hz, 2.0 Hz, 1H), 6.50 (d, J=9.2 Hz, 1H), 4.22 (s, 3H), 4.09-4.06 (m, 2H). LC-MS: m/z 484 [M+H]⁺.

Example 237: 8-(4-chlorophenyl)-6-(2,3-dimethyl-2H-indazol-5-yl)-2-(2,2,2-trifluoroethylamino)-1,6-naphthyridin-7(6H)-one

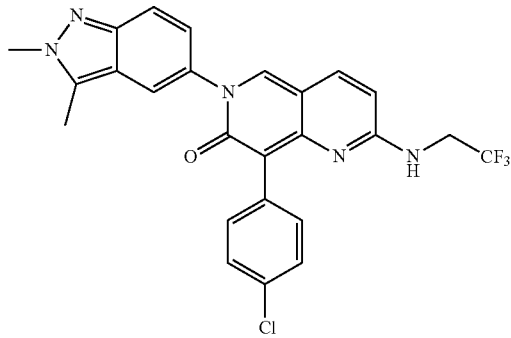 [SMILES: Cc1c2cc(-n3cc4ccc(NCC(F)(F)F)nc4c(-c4ccc(Cl)cc4)c3=O)ccc2nn1C]

The title compound was synthesized from intermediate 16a with 5-bromo-2,3-dimethyl-2H-indazole via general procedure V (Step R).

¹H NMR (400 MHz, DMSO-d₆) δ: 8.50 (s, 1H), 8.34 (br s, 1H), 7.84 (d, J=2.0 Hz, 1H), 7.76 (d, J=8.4 Hz, 1H), 7.65 (d, J=8.8 Hz, 2H), 7.58 (d, J=8.4 Hz, 1H), 7.33 (d, J=8.4 Hz, 2H), 7.27 (d, J=8.8 Hz, 1H), 6.50 (d, J=8.8 Hz, 1H), 4.18-4.03 (m, 2H), 4.10 (s, 3H), 2.64 (s, 3H). LC-MS: m/z 498 [M+H]⁺.

Example 238: 8-(4-chlorophenyl)-6-(4-methoxyphenyl)-2-(2,2,2-trifluoroethylamino)-1,6-naphthyridin-7(6H)-one

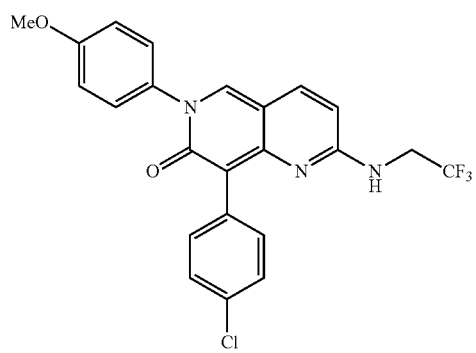 [SMILES: COc1ccc(-n2cc3ccc(NCC(F)(F)F)nc3c(-c3ccc(Cl)cc3)c2=O)cc1]

The title compound was synthesized from intermediate 16a with 1-bromo-4-methoxybenzene via general procedure V (Step R).

¹H NMR (400 MHz, DMSO-d₆) δ:: 8.41 (s, 1H), 8.34 (t, J=6.0 Hz, 1H), 7.74 (d, J=9.2 Hz, 1H), 7.62 (d, J=8.4 Hz, 2H), 7.43 (d, J=8.8 Hz, 2H), 7.33 (d, J=8.4 Hz, 2H), 7.07 (d, J=8.8 Hz, 2H), 6.49 (d, J=9.2 Hz, 1H), 4.20-4.07 (m, 2H), 3.83 (s, 3H). LC-MS: m/z 460 [M+H]⁺.

Preparation of 8-(4-(difluoromethoxy)phenyl)-7-methoxy-N-(2,2,2-trifluoroethyl)-1,6-naphthyridin-2-amine 15b

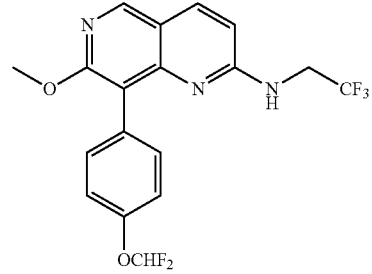

8-(4-(difluoromethoxy)phenyl)-7-methoxy-N-(2,2,2-trifluoroethyl)-1,6-naphthyridin-2-amine 15b was synthesized from intermediate 10a with 2-(4-(difluoromethoxy)phenyl)-4,4,5,5-tetramethyl-1,3,2-dioxaborolane via general procedure V (Step P). LC-MS: m/z 400 [M+H]⁺.

Preparation of 8-(4-(difluoromethoxy)phenyl)-2-(2,2,2-trifluoroethylamino)-1,6-naphthyridin-7(6H)-one 16b

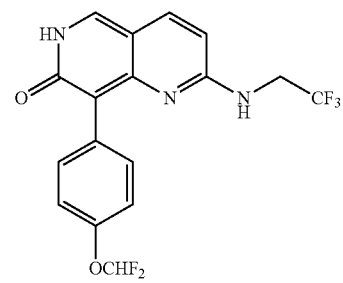

8-(4-(difluoromethoxy)phenyl)-2-(2,2,2-trifluoroethylamino)-1,6-naphthyridin-7(6H)-one 16b was synthesized from intermediate 15b via general procedure V (Step Q). LC-MS: m/z 386 [M+H]⁺.

Example 239: 8-(4-(difluoromethoxy)phenyl)-6-(2-methyl-2H-indazol-5-yl)-2-(2,2,2-trifluoroethylamino)-1,6-naphthyridin-7(6H)-one

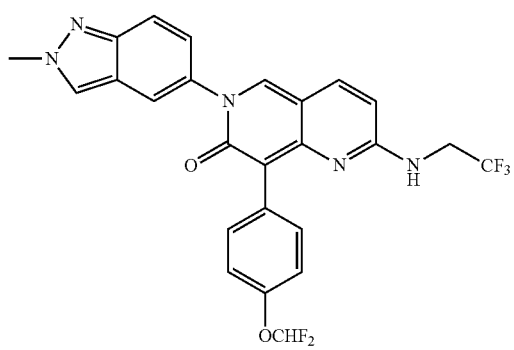

The title compound was synthesized from intermediate 16b with 5-bromo-2-methyl-2H-indazole via general procedure V (Step R).

¹H NMR (400 MHz, DMSO-d₆) δ: 8.49 (s, 1H), 8.48 (s, 1H), 8.31 (t, J=6.0 Hz, 1H), 7.84 (d, J=1.6 Hz, 1H), 7.75 (d, J=9.2 Hz, 1H), 7.71-7.64 (m, 3H), 7.31 (dd, J=9.2 Hz, 1.6 Hz, 1H), 7.25 (t, $J_{HF}$=74.4 Hz, 1H), 7.09 (d, J=8.8 Hz, 2H), 6.49 (d, J=9.2 Hz, 1H), 4.22 (s, 3H), 4.21-4.09 (m, 2H). LC-MS: m/z 516 [M+H]⁺.

Example 240: 8-(4-(difluoromethoxy)phenyl)-6-(1-methyl-1H-benzo[d]imidazol-6-yl)-2-(2,2,2-trifluoroethylamino)-1,6-naphthyridin-7(6H)-one

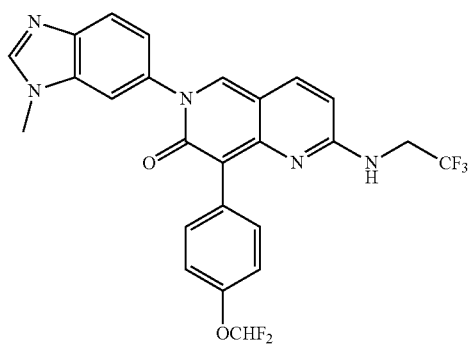 [SMILES: Cn1cnc2ccc(-n3cc4ccc(NCC(F)(F)F)nc4c(-c4ccc(OC(F)F)cc4)c3=O)cc21]

The title compound was synthesized from intermediate 16b with 6-bromo-1-methyl-1H-benzo[d]imidazole via general procedure V (Step R).

¹H NMR (400 MHz, DMSO-d₆) δ: 8.49 (s, 1H), 8.33 (br s, 1H), 8.32 (s, 1H), 7.81 (d, J=1.6 Hz, 1H), 7.78-7.72 (m, 2H), 7.66 (d, J=8.8 Hz, 2H), 7.31 (dd, J=8.4 Hz, 2.0 Hz, 1H), 7.25 (t, $J_{HF}$=74.4 Hz, 1H), 7.09 (d, J=8.8 Hz, 2H), 6.51 (d, J=9.2 Hz, 1H), 4.22-4.10 (m, 2H), 3.87 (s, 3H). LC-MS: m/z 516 [M+H]⁺.

Example 241: 8-(4-(difluoromethoxy)phenyl)-6-(4-methoxyphenyl)-2-(2,2,2-trifluoroethylamino)-1,6-naphthyridin-7(6H)-one

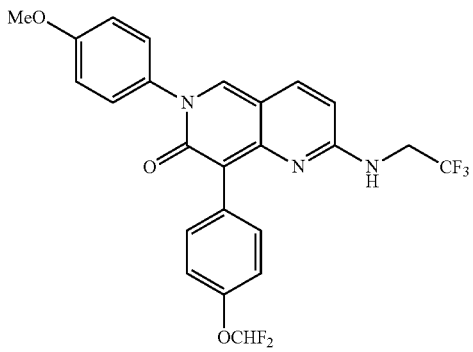 [SMILES: COc1ccc(-n2cc3ccc(NCC(F)(F)F)nc3c(-c3ccc(OC(F)F)cc3)c2=O)cc1]

The title compound was synthesized from intermediate 16b with 1-bromo-4-methoxybenzene via general procedure V (Step R).

¹H NMR (400 MHz, DMSO-d₆) δ: 8.40 (s, 1H), 8.30 (t, J=5.6 Hz, 1H), 7.73 (d, J=9.2 Hz, 1H), 7.63 (d, J=8.8 Hz, 2H), 7.43 (d, J=9.2 Hz, 2H), 7.24 (t, $J_{HF}$=74.4 Hz, 1H), 7.08 (d, J=8.8 Hz, 2H), 7.07 (d, J=9.2 Hz, 2H), 6.48 (d, J=9.2 Hz, 1H), 4.20-4.07 (m, 2H), 3.82 (s, 3H). LC-MS: m/z 492 [M+H]⁺.

Preparation of 8-bromo-N-cyclopropyl-7-methoxy-1,6-naphthyridin-2-amine 10b

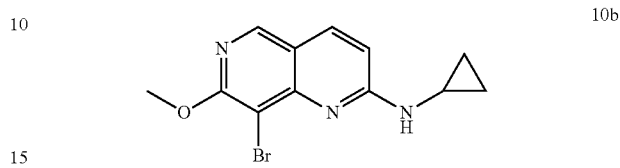

8-bromo-N-cyclopropyl-7-methoxy-1,6-naphthyridin-2-amine 10b was synthesized from key intermediate I with cyclopropanamine via general procedure V (Step J). LC-MS: m/z 294 [M+H]⁺.

Preparation of N-cyclopropyl-8-(4-(difluoromethoxy)phenyl)-7-methoxy-1,6-naphthyridin-2-amine 15c

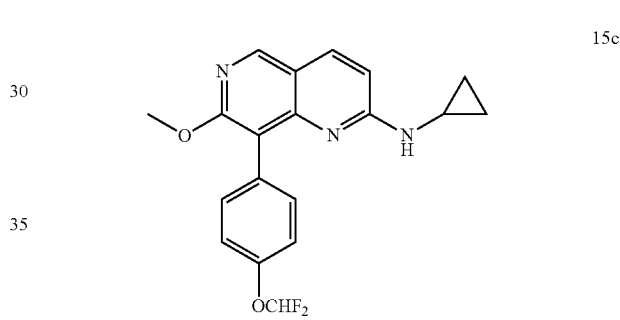

N-cyclopropyl-8-(4-(difluoromethoxy)phenyl)-7-methoxy-1,6-naphthyridin-2-amine 15c was synthesized from intermediate 10b with 2-(4-(difluoromethoxy)phenyl)-4,4,5,5-tetramethyl-1,3,2-dioxaborolane via general procedure V (Step P). LC-MS: m/z 358 [M+H]⁺.

Preparation of 2-(cyclopropylamino)-8-(4-(difluoromethoxy)phenyl)-1,6-naphthyridin-7(6H)-one 16c

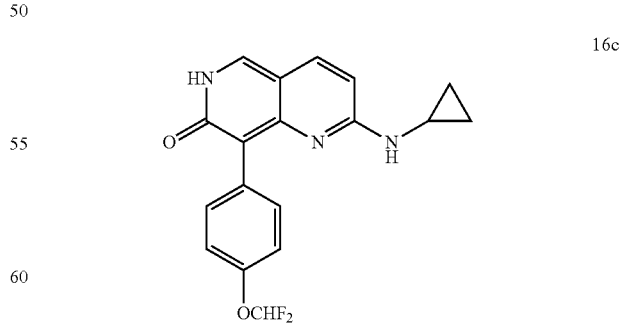

2-(cyclopropylamino)-8-(4-(difluoromethoxy)phenyl)-1,6-naphthyridin-7(6H)-one 16c was synthesized from intermediate 15c via general procedure V (Step Q). LC-MS: m/z 344 [M+H]⁺.

Example 242: Preparation of 2-(cyclopropylamino)-8-(4-(difluoromethoxy)phenyl)-6-(2-methyl-2H-indazol-5-yl)-1,6-naphthyridin-7(6H)-one

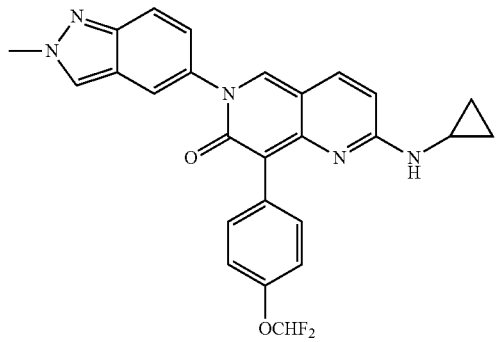

The title compound was synthesized from intermediate 16c with 5-bromo-2-methyl-2H-indazole via general procedure V (Step R).

$^1$H NMR (400 MHz, DMSO-d$_6$) δ: 8.46 (s, 1H), 8.37 (br s, 1H), 7.90 (br s, 1H), 7.84-7.81 (m, 2H), 7.87 (d, J=9.2 Hz, 1H), 7.59 (d, J=8.4 Hz, 1H), 7.29 (dd, J=9.2, 2.0 Hz, 1H), 7.23 (t, J$_{HF}$=74.6 Hz, 1H), 7.08 (d, J=8.4 Hz, 2H), 6.31 (t, J=8.8 Hz, 1H), 4.22 (s, 3H), 2.80-2.70 (m, 1H), 0.80-0.61 (m, 2H), 0.55-0.42 (m, 2H). LC-MS: m/z 474 [M+H]$^+$.

Preparation of 8-bromo-2-ethoxy-7-methoxy-1,6-naphthyridine 10c

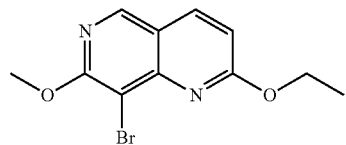

8-bromo-2-ethoxy-7-methoxy-1,6-naphthyridine 10c was synthesized from key intermediate I with EtONa/EtOH via general procedure V (Step J). LC-MS: m/z 283 [M+H]$^+$.

Preparation of 8-(4-chlorophenyl)-2-ethoxy-7-methoxy-1,6-naphthyridine 15d

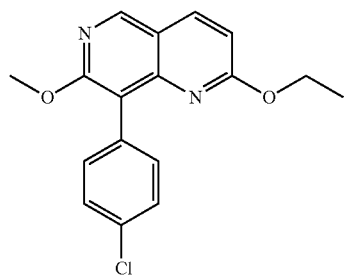

8-(4-chlorophenyl)-2-ethoxy-7-methoxy-1,6-naphthyridine 15d was synthesized from 10c with 4-chlorophenylboronic acid via general procedure V (Step P). LC-MS: m/z 315 [M+H]$^+$.

Preparation of 8-(4-chlorophenyl)-2-ethoxy-1,6-naphthyridin-7(6H)-one 16d

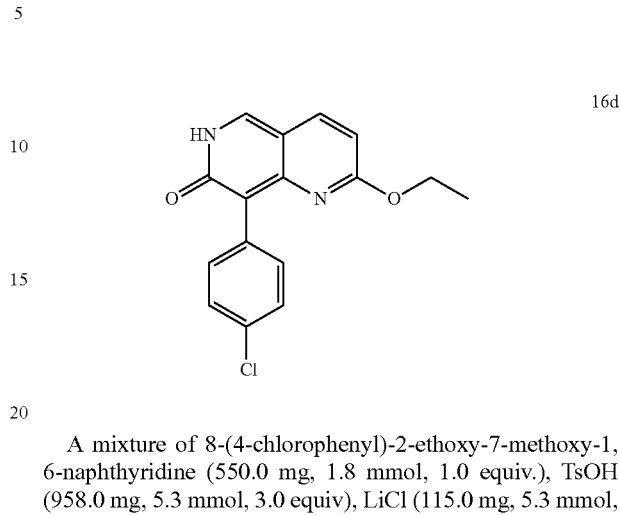

A mixture of 8-(4-chlorophenyl)-2-ethoxy-7-methoxy-1,6-naphthyridine (550.0 mg, 1.8 mmol, 1.0 equiv.), TsOH (958.0 mg, 5.3 mmol, 3.0 equiv), LiCl (115.0 mg, 5.3 mmol, 3.0 equiv) in DMF (12.0 mL) was stirred at 120° C. for 5 h. The mixture was poured into ice NH$_4$Cl aq. (10 mL). The mixture was extracted with EA (10 mL×3), and the combined organic layers were dried over Na$_2$SO$_4$, filtered and concentrated. The residue was purified by flash chromatography on silica gel (PE:EA=4:1 to 0:1) to afford 8-(4-chlorophenyl)-2-ethoxy-1,6-naphthyridin-7(6H)-one (180 mg, 34% yield) as a yellow solid. LC-MS: m/z 301 [M+H]$^+$.

Example 243: Preparation of 8-(4-chlorophenyl)-2-ethoxy-6-(quinolin-6-yl)-1,6-naphthyridin-7(6H)-one

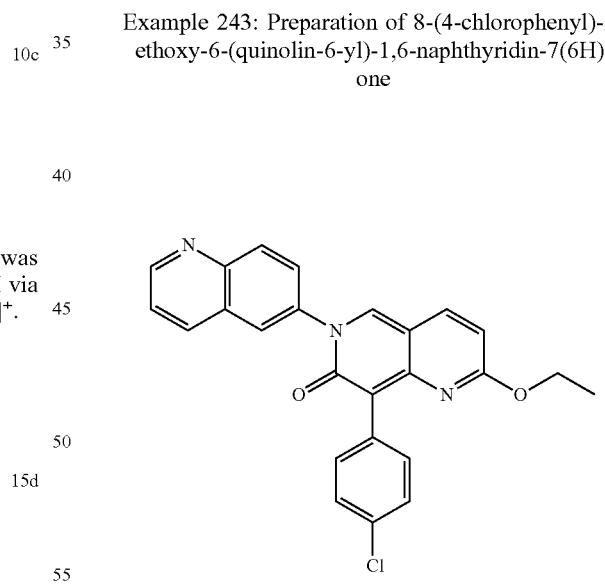

The title compound was synthesized from intermediate 16d with 6-bromoquinoline via general procedure V (Step R).

$^1$H NMR (400 MHz, DMSO-d$_6$) δ: 9.02 (dd, J=8.0, 1.6 Hz, 1H), 8.85 (s, 1H), 8.48 (d, J=7.2 Hz 1H), 8.24 (d, J=2.4 Hz, 1H), 8.16 (d, J=8.8 Hz, 1H), 7.98 (d, J=9.2 Hz, 1H), 7.95 (dd, J=8.8, 2.4 Hz, 1H), 7.68 (d, J=8.4 Hz, 2H), 7.65 (dd, J=8.4, 4.4 Hz, 1H), 7.41 (d, J=8.4 Hz, 2H), 6.57 (d, J=9.2 Hz, 1H), 4.27 (q, J=7.2 Hz, 2H), 1.28 (t, J=7.2 Hz, 3H). LC-MS: m/z 428 [M+H]$^+$.

Example 244: 8-(4-chlorophenyl)-2-ethoxy-6-(quinoxalin-6-yl)-1,6-naphthyridin-7(6H)-one

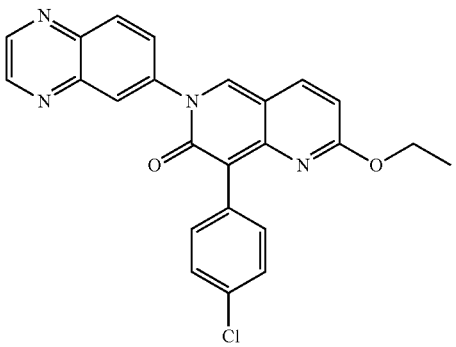

The title compound was synthesized from intermediate 16d with 6-bromoquinoxaline via general procedure V (Step R).

¹H NMR (400 MHz, DMSO-d₆) δ: 9.06 (dd, J=4.4 Hz, 2.0 Hz, 2H), 8.88 (s, 1H), 8.38 (d, J=2.4 Hz, 1H), 8.25 (d, J=8.8 Hz, 1H), 8.09 (dd, J=9.0 Hz, 2.0 Hz, 1H), 7.98 (d, J=9.0 Hz, 1H), 7.69 (d, J=8.8 Hz, 2H), 7.42 (d, J=8.8 Hz, 2H), 6.58 (d, J=9.0 Hz, 1H), 4.27 (q, J=7.2 Hz, 2H), 1.28 (t, J=7.2 Hz, 3H). LC-MS: m/z 429 [M+H]⁺.

Example 245: 8-(4-chlorophenyl)-6-(cinnolin-6-yl)-2-ethoxy-1,6-naphthyridin-7(6H)-one

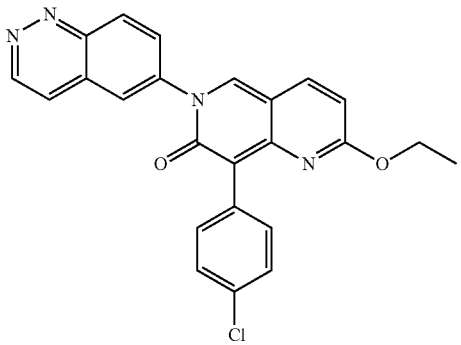 [SMILES: CCOc1ccc2cn(-c3ccc4nnccc4c3)c(=O)c(-c3ccc(Cl)cc3)c2n1]

The title compound was synthesized from intermediate 16d with 6-bromocinnoline via general procedure V (Step R).

¹H NMR (400 MHz, DMSO-d₆) δ:: 9.49 (d, J=6.0 Hz, 1H), 8.87 (s, 1H), 8.62 (d, J=9.2 Hz, 1H), 8.37 (d, J=2.0 Hz, 1H), 8.33 (d, J=6.0 Hz, 1H), 8.18 (d, J=6.4 Hz, 1H), 8.16 (d, J=2.0 Hz, 1H), 7.98 (d, J=9.2 Hz, 1H), 7.69 (d, J=8.6 Hz, 2H), 7.42 (d, J=8.6 Hz, 2H), 6.59 (d, J=9.2 Hz, 1H), 4.28 (q, J=7.2 Hz, 2H), 1.28 (t, J=7.2 Hz, 3H). LC-MS: m/z 429 [M+H]⁺.

Example 246: 8-(4-chlorophenyl)-2-ethoxy-6-(quinazolin-6-yl)-1,6-naphthyridin-7(6H)-one

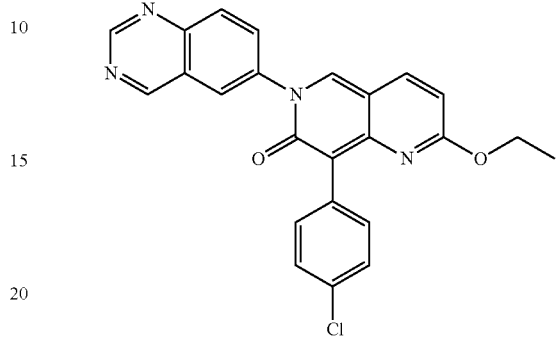

The title compound was synthesized from intermediate 16d with 6-bromoquinazoline via general procedure V (Step R).

¹H NMR (400 MHz, DMSO-d₆) δ:: 9.71 (s, 1H), 9.42 (s, 1H), 8.86 (s, 1H), 8.44 (d, J=2.0 Hz, 1H), 8.24 (dd, J=8.8 Hz, 2.0 Hz, 1H), 8.17 (d, J=8.8 Hz, 1H), 7.97 (d, J=9.2 Hz, 1H), 7.68 (d, J=8.4 Hz, 2H), 7.41 (d, J=8.4 Hz, 2H), 6.59 (d, J=8.8 Hz, 1H), 4.27 (d, J=7.2 Hz, 2H), 1.28 (t, J=7.2 Hz, 3H). LC-MS: m/z 429 [M+H]⁺.

Example 247: 8-(4-chlorophenyl)-2-ethoxy-6-(2-methyl-2H-indazol-5-yl)-1,6-naphthyridin-7(6H)-one

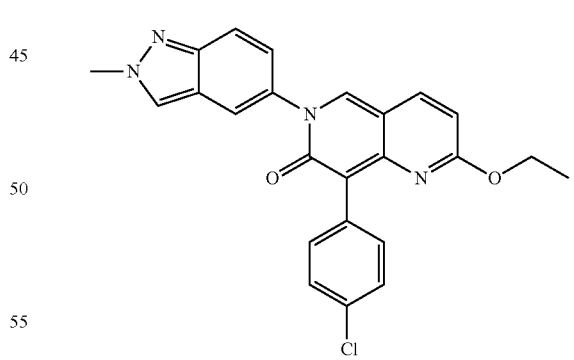

The title compound was synthesized from intermediate 16d with 5-bromo-2-methyl-2H-indazole via general procedure V (Step R).

¹H NMR (400 MHz, DMSO-d₆) δ: 8.75 (s, 1H), 8.50 (s, 1H), 7.97 (d, J=9.1 Hz, 1H), 7.89 (d, J=2.0 Hz, 1H), 7.70 (d, J=9.1 Hz, 1H), 7.66 (d, J=8.6 Hz, 2H), 7.40 (d, J=8.6 Hz, 2H), 7.33 (dd, J=9.2 Hz, 2.4 Hz, 1H), 6.54 (d, J=9.2 Hz, 1H), 4.25 (q, J=6.8 Hz, 2H), 4.22 (s, 3H), 1.27 (t, J=6.8 Hz, 3H). LC-MS: m/z 431 [M+H]⁺.

Example 248: 8-(4-chlorophenyl)-2-ethoxy-6-(1-methyl-1H-benzo[d]imidazol-6-yl)-1,6-naphthyridin-7(6H)-one

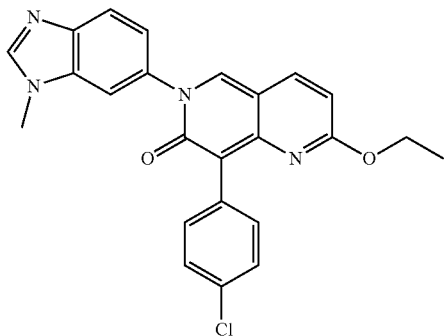 [SMILES: CCOc1ccc2cn(-c3ccc4ncn(C)c4c3)c(=O)c(-c3ccc(Cl)cc3)c2n1]

The title compound was synthesized from intermediate 16d with 6-bromo-1-methyl-1H-benzo[d]imidazole via general procedure V (Step R).

$^1$H NMR (400 MHz, DMSO-d$_6$) δ: 8.74 (s, 1H), 8.34 (s, 1H), 7.97 (d, J=9.0 Hz, 1H), 7.85 (d, J=2.0 Hz, 1H), 7.78 (d, J=8.5 Hz, 1H), 7.67 (d, J=8.4 Hz, 2H), 7.40 (d, J=8.4 Hz, 2H), 7.34 (dd, J=8.5 Hz, 2.0 Hz, 1H), 6.55 (d, J=9.0 Hz, 1H), 4.25 (q, J=7.2 Hz, 2H), 3.87 (s, 3H), 1.27 (t, J=7.2 Hz, 3H). LC-MS: m/z 431 [M+H]$^+$.

Preparation of 8-(4-(difluoromethoxy)phenyl)-2-ethoxy-7-methoxy-1,6-naphthyridine 15e

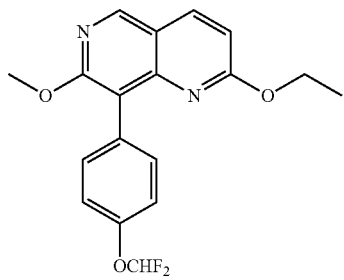

15e 8-(4-(difluoromethoxy)phenyl)-2-ethoxy-7-methoxy-1,6-naphthyridine 15e was synthesized from intermediate 10c with 2-(4-(difluoromethoxy)phenyl)-4,4,5,5-tetramethyl-1,3,2-dioxaborolane via general procedure V (Step P). LC-MS: m/z 347 [M+H]$^+$.

Preparation of 8-(4-(difluoromethoxy)phenyl)-2-ethoxy-1,6-naphthyridin-7(6H)-one 16e

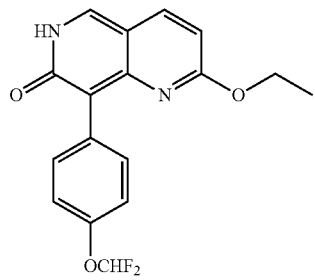

16e 8-(4-(difluoromethoxy)phenyl)-2-ethoxy-1,6-naphthyridin-7(6H)-one 16e was prepared from intermediate 16d via the general procedure V (Step Q). LC-MS: m/z 333 [M+H]$^+$.

Example 249: Preparation of 8-(4-(difluoromethoxy)phenyl)-2-ethoxy-6-(1-(2-(methylsulfonyl)ethyl)-6-oxo-1,6-dihydropyridin-3-yl)-1,6-naphthyridin-7(6H)-one

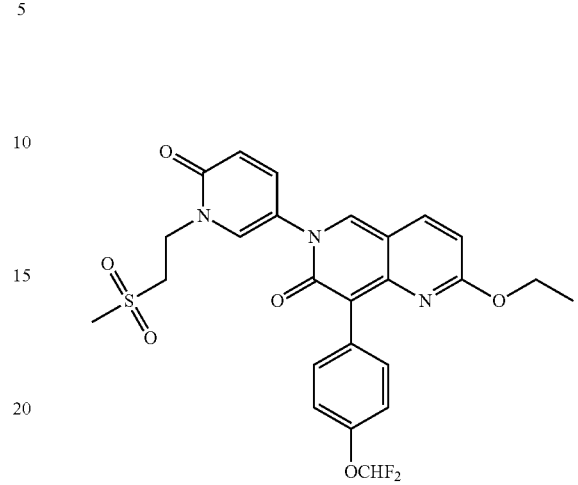

The title compound was synthesized from intermediate 16e with 5-bromo-1-(2-(methylsulfonyl)ethyl)pyridin-2(1H)-one via general procedure V (Step R).

$^1$H NMR (400 MHz, DMSO-d$_6$) δ: 8.61 (s, 1H), 8.17 (d, J=2.8 Hz, 1H), 7.93 (d, J=9.2 Hz, 1H), 7.69 (dd, J=9.6 Hz, 2.8 Hz, 1H), 7.65 (d, J=8.8 Hz, 2H), 7.28 (t, J$_{HF}$=74.4 Hz, 1H), 6.55 (d, J=9.2 Hz, 1H), 6.52 (d, J=9.6 Hz, 1H), 4.34 (t, J=7.2 Hz, 2H), 4.24 (q, J=7.2 Hz, 2H), 3.61 (t, J=7.2 Hz, 2H), 3.08 (s, 3H), 1.26 (t, J=7.2 Hz, 3H). LC-MS: m/z 532 [M+H]$^+$.

Example 250: 8-(4-(difluoromethoxy)phenyl)-2-ethoxy-6-(4-methoxyphenyl)-1,6-naphthyridin-7(6H)-one

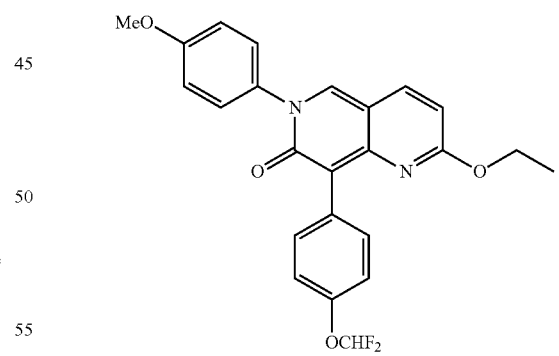

The title compound was synthesized from intermediate 16e with 1-bromo-4-methoxybenzene via general procedure V (Step R).

$^1$H NMR (400 MHz, DMSO-d$_6$) δ: 8.64 (s, 1H), 7.94 (d, J=9.2 Hz, 1H), 7.67 (d, J=8.8 Hz, 2H), 7.46 (d, J=8.8 Hz, 2H), 7.27 (t, J$_{HF}$=74.4 Hz, 1H), 7.15 (d, J=8.8 Hz, 2H), 7.09 (d, J=8.8 Hz, 2H), 6.52 (d, J=9.2 Hz, 1H), 4.24 (q, J=7.2 Hz, 2H), 3.83 (s, 3H), 1.26 (t, J=7.2 Hz, 3H). LC-MS: m/z 439 [M+H]$^+$.

Example 251: 8-(4-(difluoromethoxy)phenyl)-2-ethoxy-6-(2-methyl-2H-indazol-5-yl)-1,6-naphthyridin-7(6H)-one

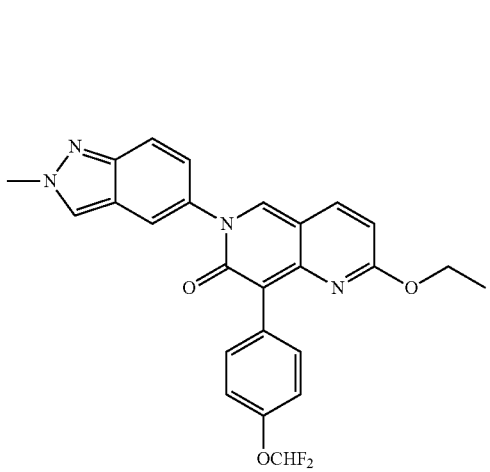

The title compound was synthesized from intermediate 16e with 1-bromo-4-methoxybenzene via general procedure V (Step R).

$^1$H NMR (400 MHz, DMSO-d$_6$) δ: 8.73 (s, 1H), 8.50 (s, 1H), 7.96 (d, J=9.2 Hz, 1H), 7.89 (d, J=1.6 Hz, 1H), 7.73-7.65 (m, 3H), 7.34 (dd, J=9.2 Hz, 2.0 Hz, 1H), 7.28 (t, J$_{HF}$=74.4 Hz, 1H), 7.15 (d, J=8.8 Hz, 2H), 6.54 (d, J=8.8 Hz, 1H), 4.25 (q, J=7.2 Hz, 2H), 4.22 (s, 3H), 1.27 (t, J=7.2 Hz, 3H). LC-MS: m/z 463 [M+H]$^+$.

Example 252: 8-(4-(difluoromethoxy)phenyl)-2-ethoxy-6-(1-methyl-1H-benzo[d][1,2,3]triazol-6-yl)-1,6-naphthyridin-7(6H)-one

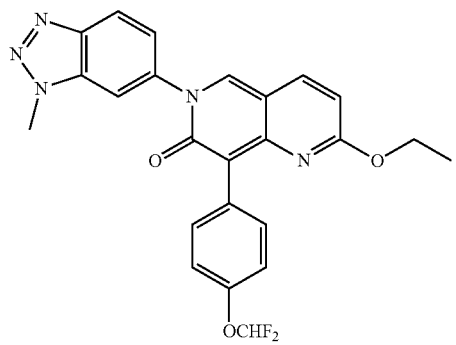 [SMILES: CCOc1ccc2cn(-c3ccc4nnn(C)c4c3)c(=O)c(-c3ccc(OC(F)F)cc3)c2n1]

The title compound was synthesized from intermediate 16e with 6-bromo-1-methyl-1H-benzo[d][1,2,3]triazole via general procedure V (Step R).

$^1$H NMR (400 MHz, DMSO-d$_6$) δ:: 8.76 (s, 1H), 8.22-8.17 (m, 2H), 7.96 (d, J=9.2 Hz, 1H), 7.69 (d, J=8.8 Hz, 2H), 7.58 (dd, J=8.8 Hz, 2.0 Hz, 1H), 8.28 (t, J$_{HF}$=74.4 Hz, 1H), 7.16 (d, J=8.8 Hz, 2H), 6.57 (d, J=9.2 Hz, 1H), 4.35 (s, 3H), 4.26 (q, J=7.2 Hz, 2H), 1.27 (t, J=7.2 Hz, 3H). LC-MS: m/z 464 [M+H]$^+$.

Example 253: 8-(4-(difluoromethoxy)phenyl)-2-ethoxy-6-(1-methyl-1H-benzo[d]imidazol-6-yl)-1,6-naphthyridin-7(6H)-one

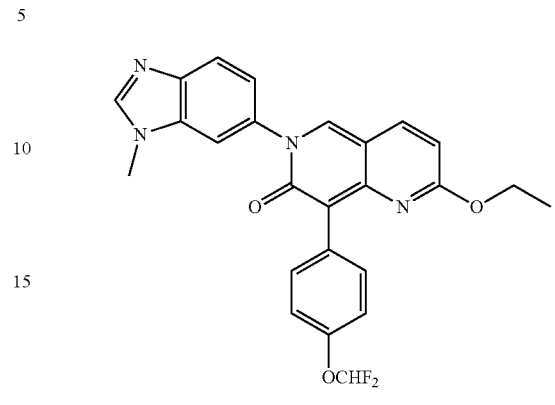

The title compound was synthesized from intermediate 16e with 6-bromo-1-methyl-1H-benzo[d]imidazole via general procedure V (Step R).

$^1$H NMR (400 MHz, DMSO-d$_6$) δ: 8.79 (s, 1H), 8.45 (br s, 1H), 8.03 (d, J=8.8 Hz, 1H), 7.94 (br s, 1H), 7.88 (br s, 1H), 7.65 (d, J=8.6 Hz, 2H), 7.41 (d, J=6.0 Hz, 1H), 7.34 (t, J$_{HF}$=74.4 Hz, 1H), 7.22 (d, J=8.6 Hz, 2H), 6.60 (d, J=8.8 Hz, 1H), 4.32 (q, J=7.2 Hz, 2H), 3.94 (s, 3H), 1.33 (t, J=7.2 Hz, 3H). LC-MS: m/z 463 [M+H]$^+$.

Preparation of 8-bromo-7-methoxy-2-(2,2,2-trifluoroethoxy)-1,6-naphthyridine 10d

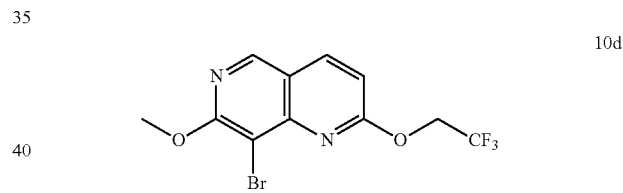

8-bromo-7-methoxy-2-(2,2,2-trifluoroethoxy)-1,6-naphthyridine 10d was synthesized from key intermediate I with 2,2,2-trifluoroethanol via general procedure V (Step J). LC-MS: m/z 337 [M+H]$^+$.

Preparation of 8-(4-chlorophenyl)-7-methoxy-2-(2,2,2-trifluoroethoxy)-1,6-naphthyridine 15f

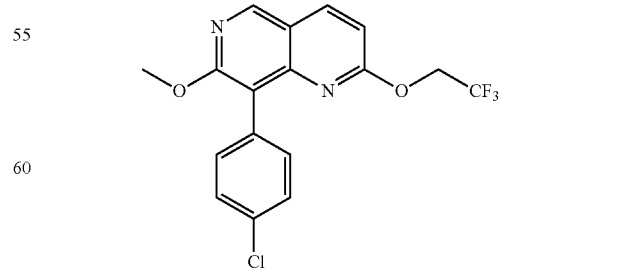

8-(4-chlorophenyl)-7-methoxy-2-(2,2,2-trifluoroethoxy)-1,6-naphthyridine 15f was synthesized from 10d with 4-chlorophenylboronic acid via general procedure V (Step P). LC-MS: m/z 369 [M+H]+.

Preparation of 8-(4-chlorophenyl)-2-(2,2,2-trifluoroethoxy)-1,6-naphthyridin-7(6H)-one 16f

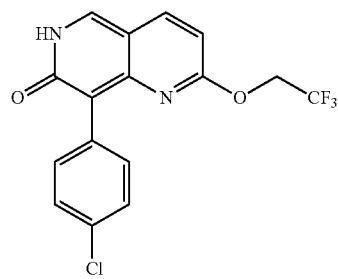

8-(4-chlorophenyl)-2-(2,2,2-trifluoroethoxy)-1,6-naphthyridin-7(6H)-one 16f was synthesized from 15f via general procedure V (Step Q).
LC-MS: m/z 355 [M+H]+.

Example 254: Preparation of 8-(4-chlorophenyl)-6-(2-methyl-2H-indazol-5-yl)-2-(2,2,2-trifluoroethoxy)-1,6-naphthyridin-7(6H)-one

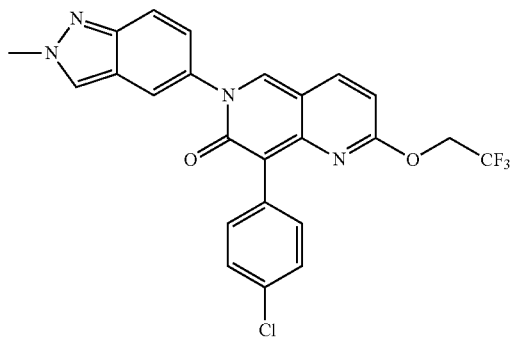

The title compound was synthesized from intermediate 16f with 5-bromo-2-methyl-2H-indazole via general procedure V (Step R).
$^1$H NMR (400 MHz, DMSO-d$_6$) S: 8.86 (s, 1H), 8.50 (s, 1H), 8.10 (d, J=9.2 Hz, 1H), 7.91 (d, J=2.0 Hz, 1H), 7.71 (d, J=9.2 Hz, 1H), 7.68 (d, J=8.8 Hz, 2H), 7.41 (d, J=8.8 Hz, 2H), 7.35 (dd, J=9.2 Hz, 2.0 Hz, 1H), 6.71 (d, J=9.2 Hz, 1H), 4.93 (q, J=9.2 Hz, 2H), 4.23 (s, 3H). LC-MS: m/z 485 [M+H]+.

Example 255: 8-(4-chlorophenyl)-6-(1-methyl-1H-benzo[d]imidazol-6-yl)-2-(2,2,2-trifluoroethoxy)-1,6-naphthyridin-7(6H)-one

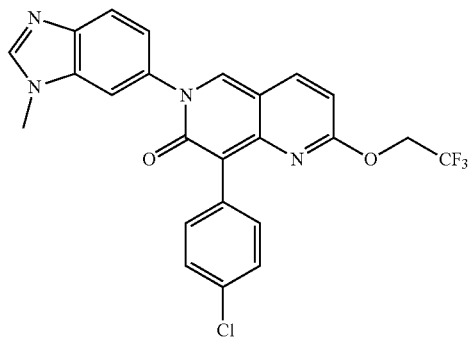 [SMILES: Cn1cnc2ccc(-n3cc4ccc(OCC(F)(F)F)nc4c(-c4ccc(Cl)cc4)c3=O)cc21]

The title compound was synthesized from intermediate 16f with 6-bromo-1-methyl-1H-benzo[d]imidazole via general procedure V (Step R).
$^1$H NMR (400 MHz, DMSO-d$_6$) δ: 8.85 (s, 1H), 8.34 (s, 1H), 8.10 (d, J=9.2 Hz, 1H), 7.87 (d, J=2.0 Hz, 1H), 7.79 (d, J=8.4 Hz, 1H), 7.68 (d, J=8.8 Hz, 2H), 7.42 (d, J=8.8 Hz, 2H), 7.35 (dd, J=8.8 Hz, 2.0 Hz, 1H), 6.71 (d, J=8.8 Hz, 1H), 4.93 (q, J=9.2 Hz, 2H), 3.87 (s, 3H). LC-MS: m/z 485 [M+H]+.

Preparation of 8-(4-(difluoromethoxy)phenyl)-7-methoxy-2-(2,2,2-trifluoroethoxy)-1,6-naphthyridine 15g

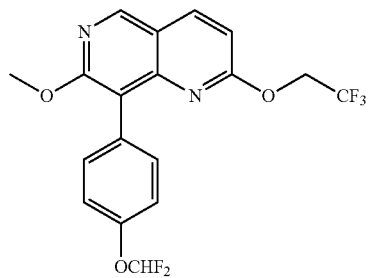

8-(4-(difluoromethoxy)phenyl)-7-methoxy-2-(2,2,2-trifluoroethoxy)-1,6-naphthyridine 15g was synthesized from 10d with 2-(4-(difluoromethoxy)phenyl)-4,4,5,5-tetramethyl-1,3,2-dioxaborolane via general procedure V (Step P). LC-MS: m/z 401 [M+H]+.

Preparation of 8-(4-(difluoromethoxy)phenyl)-2-(2,2,2-trifluoroethoxy)-1,6-naphthyridin-7(6H)-one 16g

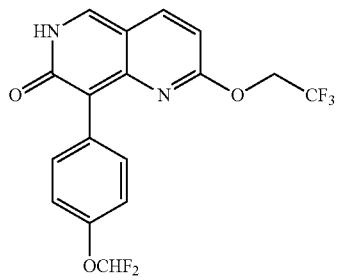

8-(4-(difluoromethoxy)phenyl)-2-(2,2,2-trifluoroethoxy)-1,6-naphthyridin-7(6H)-one 16g was synthesized from 15g via general procedure V (Step Q). LC-MS: m/z 387 [M+H]+.

Example 256: Preparation of 8-(4-(difluoromethoxy)phenyl)-6-(2-methyl-2H-indazol-5-yl)-2-(2,2,2-trifluoroethoxy)-1,6-naphthyridin-7(6H)-one

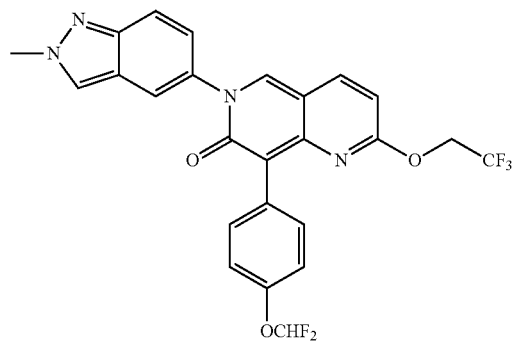

The title compound was synthesized from intermediate 16g with 5-bromo-2-methyl-2H-indazole via general procedure V (Step R).

$^1$H NMR (400 MHz, DMSO-d$_6$) δ: 8.85 (s, 1H), 8.51 (s, 1H), 8.10 (d, J=9.2 Hz, 1H), 7.91 (d, J=2.0 Hz, 1H), 7.73-7.67 (m, 3H), 7.35 (dd, J=9.2 Hz, 2.0 Hz, 1H), 7.28 (t, J$_{HF}$=74.4 Hz, 1H), 7.17 (d, J=8.8 Hz, 2H), 6.70 (d, J=9.2 Hz, 1H), 4.92 (q, J=8.8 Hz, 2H), 4.23 (s, 3H). LC-MS: m/z 517 [M+H]$^+$.

Example 257: 8-(4-(difluoromethoxy)phenyl)-6-(1-methyl-1H-benzo[d]imidazol-6-yl)-2-(2,2,2-trifluoroethoxy)-1,6-naphthyridin-7(6H)-one

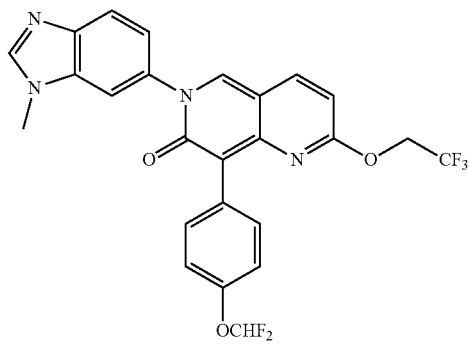

The title compound was synthesized from intermediate 16g with 6-bromo-1-methyl-1H-benzo[d]imidazole via general procedure V (Step R).

$^1$H NMR (400 MHz, DMSO-d$_6$) δ: 8.84 (s, 1H), 8.34 (s, 1H), 8.10 (d, J=9.2 Hz, 1H), 7.87 (d, J=2.0 Hz, 1H), 7.79 (d, J=8.8 Hz, 1H), 7.71 (d, J=8.8 Hz, 2H), 7.36 (dd, J=8.8 Hz, 2.0 Hz, 1H), 7.28 (t, J$_{HF}$=74.4 Hz, 1H), 7.17 (d, J=8.8 Hz, 2H), 6.71 (d, J=9.2 Hz, 1H), 4.93 (q, J=8.8 Hz, 2H), 3.88 (s, 3H). LC-MS: m/z 517 [M+H]$^+$.

Example 258: 8-(4-(difluoromethoxy)phenyl)-6-(4-methoxyphenyl)-2-(2,2,2-trifluoroethoxy)-1,6-naphthyridin-7(6H)-one

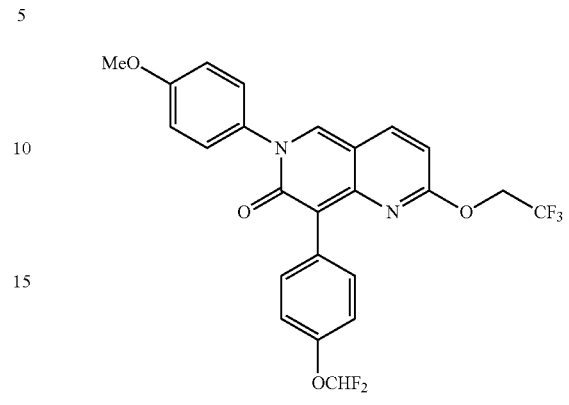

The title compound was synthesized from intermediate 16g with 1-bromo-4-methoxybenzene via general procedure V (Step R).

$^1$H NMR (400 MHz, DMSO-d$_6$) δ: 8.81 (s, 1H), 8.13 (d, J=9.2 Hz, 1H), 7.74 (d, J=8.8 Hz, 2H), 7.54 (d, J=8.8 Hz, 2H), 7.34 (t, J$_{HF}$=74.4 Hz, 1H), 7.22 (d, J=8.8 Hz, 2H), 7.16 (d, J=8.8 Hz, 2H), 6.74 (d, J=8.8 Hz, 1H), 4.97 (q, J=8.8 Hz, 2H), 3.89 (s, 3H). LC-MS: m/z 493 [M+H]$^+$.

Preparation of 8-bromo-2-(ethylthio)-7-methoxy-1,6-naphthyridine 10e

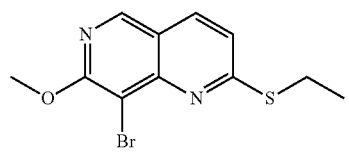

10e 8-bromo-2-(ethylthio)-7-methoxy-1,6-naphthyridine 10e was synthesized from key intermediate I with sodium ethanethiolate via general procedure V (Step J). LC-MS: m/z 299, 301 [M+H]$^+$.

Preparation of 8-(4-chlorophenyl)-2-(ethylthio)-7-methoxy-1,6-naphthyridine 15h

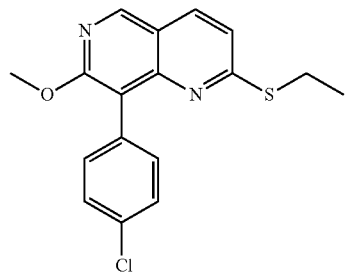

15h 8-(4-chlorophenyl)-2-(ethylthio)-7-methoxy-1,6-naphthyridine 15 h was synthesized from 10e with 4-chlorophenylboronic acid via general procedure V (Step P). LC-MS: m/z 331 [M+H]⁺.

Preparation of 8-(4-chlorophenyl)-2-(ethylthio)-1,6-naphthyridin-7(6H)-one 16 h

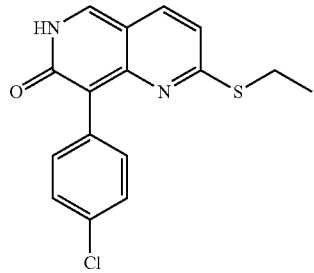

16h 8-(4-chlorophenyl)-2-(ethylthio)-1,6-naphthyridin-7 (6H)-one 16 h was synthesized from 15 h via general procedure V (Step Q). LC-MS: m/z 317 [M+H]⁺.

Example 259: Preparation of 8-(4-chlorophenyl)-2-(ethylthio)-6-(2-methyl-2H-indazol-5-yl)-1,6-naphthyridin-7(6H)-one

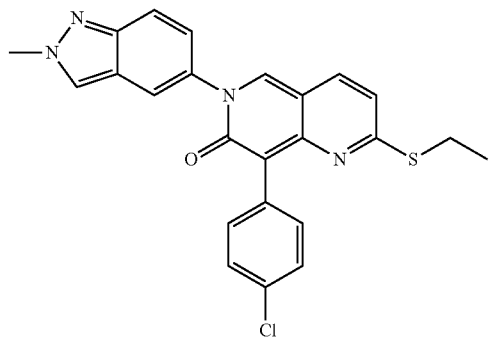

The title compound was synthesized from intermediate 16 h with 5-bromo-2-methyl-2H-indazole via general procedure V (Step R).

¹H NMR (400 MHz, DMSO-d₆) δ: 8.82 (s, 1H), 8.50 (s, 1H), 7.91 (d, J=2.0 Hz, 1H), 7.84 (d, J=8.8 Hz, 1H), 7.71 (d, J=9.2 Hz, 1H), 7.64 (d, J=8.6 Hz, 2H), 7.42 (d, J=8.6 Hz, 2H), 7.35 (dd, J=9.2 Hz, 2.0 Hz, 1H), 6.84 (d, J=8.8 Hz, 1H), 4.23 (s, 3H), 2.99 (q, J=7.2 Hz, 2H), 1.16 (t, J=7.2 Hz, 3H). LC-MS: m/z 447 [M+H]⁺.

Preparation of 8-bromo-7-methoxy-2-propyl-1,6-naphthyridine 10f

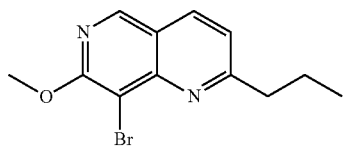

10f

To a mixture of 8-bromo-2-chloro-7-methoxy-1,6-naphthyridine (300.0 mg, 1.1 mmol, 1.0 equiv.) and Fe(acac)₃ (387.0 mg, 1.1 mmol, 1.0 equiv.) in THF/NMP (5.0 mL/0.5 mL) was added 11.0 mL of propylmagnesium bromide (1 M solution in diethyl ether, 11.0 mmol, 10.0 equiv.) slowly at r.t. The mixture was stirred at r.t. for 1 h, and quenched carefully with water. The mixture was diluted with EtOAc, washed with water followed by brine (30 mL), dried over MgSO₄, filtered and concentrated under reduced pressure. The residue was purified by flash chromatography on silica gel (PE/EtOAc=5/1) to give 8-bromo-7-methoxy-2-propyl-1,6-naphthyridine (180 mg, 59% yield) as a yellow solid. LC-MS: m/z 281, 283 [M+H]⁺.

Preparation of 8-(4-(difluoromethoxy)phenyl)-7-methoxy-2-propyl-1,6-naphthyridine 15i

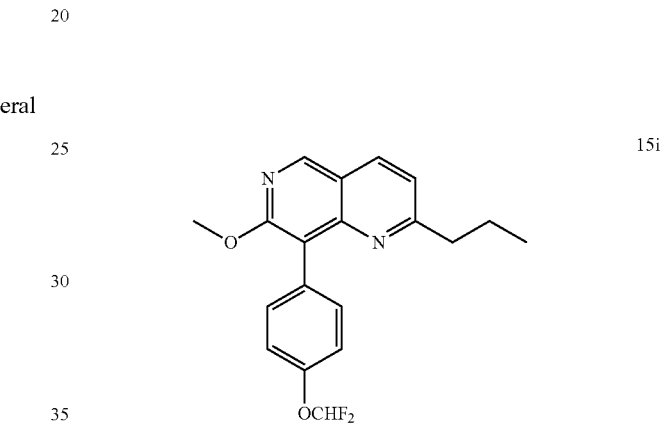

15i 8-(4-(difluoromethoxy)phenyl)-7-methoxy-2-propyl-1,6-naphthyridine 15i was synthesized from 10f with 2-(4-(difluoromethoxy)phenyl)-4,4,5,5-tetramethyl-1,3,2-dioxaborolane via general procedure V (Step P). LC-MS: m/z 345 [M+H]⁺.

Preparation of 8-(4-(difluoromethoxy)phenyl)-2-propyl-1,6-naphthyridin-7(6H)-one 16i

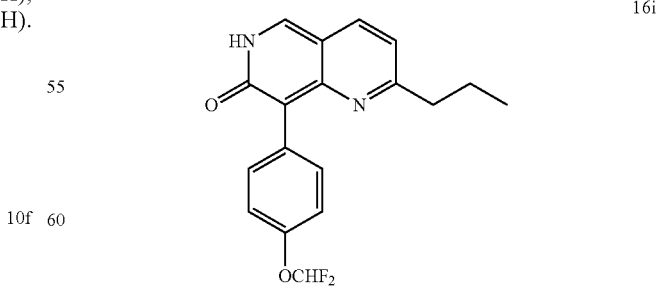

16i 8-(4-(difluoromethoxy)phenyl)-2-propyl-1,6-naphthyridin-7(6H)-one 16i was synthesized from 15i via general procedure V (Step Q). LC-MS: m/z 331 (M+H)⁺.

Example 260: Preparation of 8-(4-(difluoromethoxy)phenyl)-6-(1-methyl-1H-benzo[d]imidazol-6-yl)-2-propyl-1,6-naphthyridin-7(6H)-one

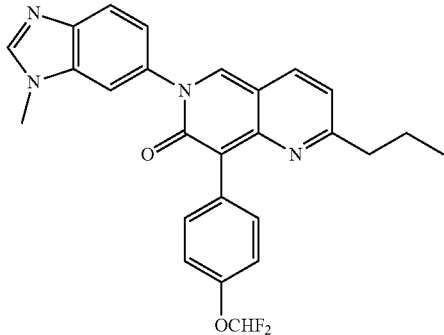 [SMILES: CCCc1ccc2cn(-c3ccc4ncn(C)c4c3)c(=O)c(-c3ccc(OC(F)F)cc3)c2n1]

The title compound was synthesized from intermediate 16i with 6-bromo-1-methyl-1H-benzo[d]imidazole via general procedure V (Step R).

$^1$H NMR (400 MHz, DMSO-d$_6$) δ: 8.87 (s, 1H), 8.34 (s, 1H), 7.99 (d, J=8.8 Hz, 1H), 7.87 (d, J=2.0 Hz, 1H), 7.79 (d, J=8.8 Hz, 1H), 7.65 (d, J=8.6 Hz, 2H), 7.36 (dd, J=8.8 Hz, 2.0 Hz, 1H), 7.29 (t, J$_{HF}$=74.4 Hz, 1H), 7.16 (d, J=8.6 Hz, 2H), 6.93 (d, J=8.8 Hz, 1H), 3.88 (s, 3H), 2.70-2.66 (m, 2H), 1.73-1.62 (m, 2H), 0.92 (t, J=7.2 Hz, 3H). LC-MS: m/z 461 [M+H]$^+$.

The following compounds were synthesized via General Procedure V (steps J, P, Q, and R):

104-A

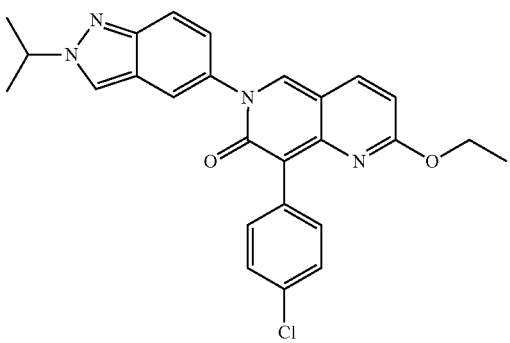

8-(4-chlorophenyl)-2-ethoxy-6-(2-isopropyl-2H-indazol-5-yl)-1,6-naphthyridin-7(6H)-one
(synthesized from 8-(4-chlorophenyl)-2-ethoxy-1,6-naphthyridin-7(6H)-one & 5-bromo-2-isopropyl-2H-indazole (Ref: *Organic Letters*, 16 (11), 3114-3117; 2014))

LC-MS (ESI): m/z 459 [M + H]$^+$.
1H NMR (400 MHz, DMSO-d6) δ 8.73 (s, 1H), 8.57 (d, J = 0.9 Hz, 1H), 7.96 (d, J = 9.1 Hz, 1H), 7.87 (dd, J = 2.1, 0.8 Hz, 1H), 7.72 (dt, J = 9.1, 0.9 Hz, 1H), 7.70-7.64 (m, 2H), 7.43-7.38 (m, 2H), 7.33 (dd, J = 9.1, 2.1 Hz, 1H), 6.54 (d, J = 9.0 Hz, 1H), 4.89 (hept, J = 6.6 Hz, 1H), 4.26 (q, J = 7.0 Hz, 2H), 1.58 (d, J = 6.6 Hz, 6H), 1.27 (t, J = 7.1 Hz, 3H).

105-A

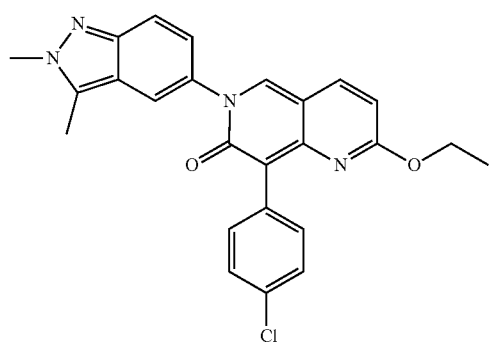

8-(4-chlorophenyl)-6-(2,3-dimethyl-2H-indazol-5-yl)-2-ethoxy-1,6-naphthyridin-7(6H)-one LC-MS (ESI): m/z 445 [M + H]$^+$.
1H NMR (400 MHz, DMSO-d6) δ 8.74 (s, 1H), 7.98 (d, J = 9.0 Hz, 1H), 7.88 (d, J = 1.9 Hz, 1H), 7.70-7.64 (m, 2H), 7.60 (d, J = 9.1 Hz, 1H), 7.44-7.37 (m, 2H), 7.29 (dd, J = 9.1, 2.0 Hz, 1H), 6.54 (d, J = 9.0 Hz, 1H), 4.25 (q, J = 7.0 Hz, 2H), 4.10 (s, 3H), 2.64 (s, 3H), 1.27 (t, J = 7.1 Hz, 3H).

| | | |
|---|---|---|
| 106-A | 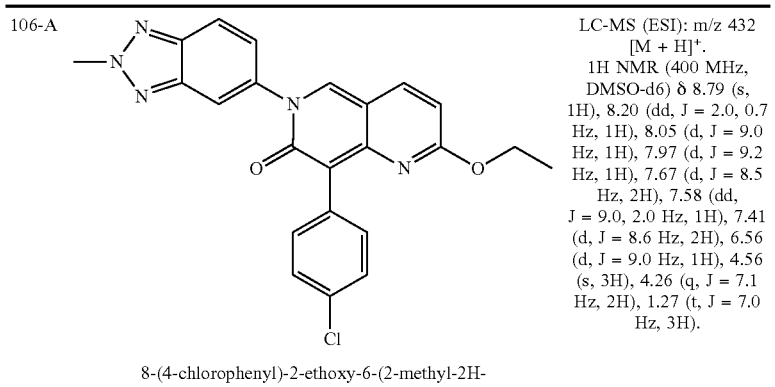<br>8-(4-chlorophenyl)-2-ethoxy-6-(2-methyl-2H-benzo[d][1,2,3]triazol-5-yl)-1,6-naphthyridin-7(6H)-one (synthesized from 8-(4-chlorophenyl)-2-ethoxy-1,6-naphthyridin-7(6H)-one & 5-bromo-2-methyl-2H-benzo[d][1,2,3]triazole (Ref: WO 2007/84451) | LC-MS (ESI): m/z 432 [M + H]⁺.<br>1H NMR (400 MHz, DMSO-d6) δ 8.79 (s, 1H), 8.20 (dd, J = 2.0, 0.7 Hz, 1H), 8.05 (d, J = 9.0 Hz, 1H), 7.97 (d, J = 9.2 Hz, 1H), 7.67 (d, J = 8.5 Hz, 2H), 7.58 (dd, J = 9.0, 2.0 Hz, 1H), 7.41 (d, J = 8.6 Hz, 2H), 6.56 (d, J = 9.0 Hz, 1H), 4.56 (s, 3H), 4.26 (q, J = 7.1 Hz, 2H), 1.27 (t, J = 7.0 Hz, 3H). |
| 107-A | 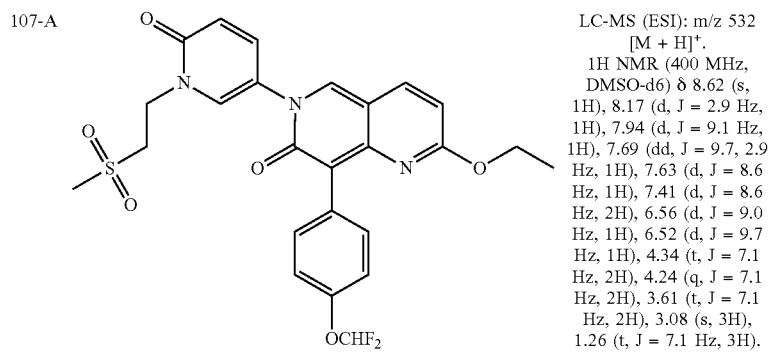<br>8-(4-(difluoromethoxy)phenyl)-2-ethoxy-6-(1-(2-(methylsulfonyl)ethyl)-6-oxo-1,6-dihydropyridin-3-yl)-1,6-naphthyridin-7(6H)-one | LC-MS (ESI): m/z 532 [M + H]⁺.<br>1H NMR (400 MHz, DMSO-d6) δ 8.62 (s, 1H), 8.17 (d, J = 2.9 Hz, 1H), 7.94 (d, J = 9.1 Hz, 1H), 7.69 (dd, J = 9.7, 2.9 Hz, 1H), 7.63 (d, J = 8.6 Hz, 1H), 7.41 (d, J = 8.6 Hz, 2H), 6.56 (d, J = 9.0 Hz, 1H), 6.52 (d, J = 9.7 Hz, 1H), 4.34 (t, J = 7.1 Hz, 2H), 4.24 (q, J = 7.1 Hz, 2H), 3.61 (t, J = 7.1 Hz, 2H), 3.08 (s, 3H), 1.26 (t, J = 7.1 Hz, 3H). |

The following compounds were synthesized via General Procedure V (Method B):

| | | |
|---|---|---|
| 108-A | 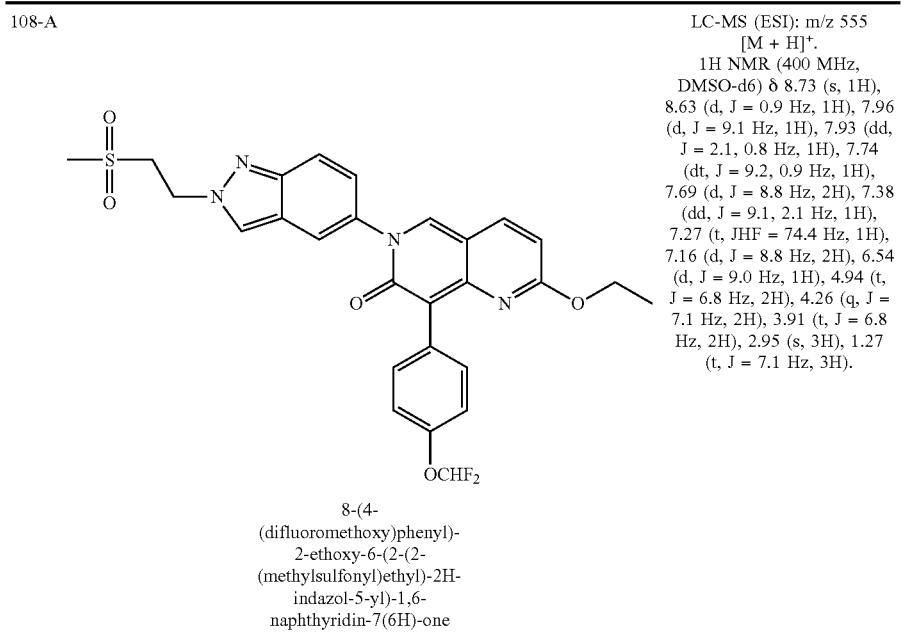<br>8-(4-(difluoromethoxy)phenyl)-2-ethoxy-6-(2-(2-(methylsulfonyl)ethyl)-2H-indazol-5-yl)-1,6-naphthyridin-7(6H)-one | LC-MS (ESI): m/z 555 [M + H]⁺.<br>1H NMR (400 MHz, DMSO-d6) δ 8.73 (s, 1H), 8.63 (d, J = 0.9 Hz, 1H), 7.96 (d, J = 9.1 Hz, 1H), 7.93 (dd, J = 2.1, 0.8 Hz, 1H), 7.74 (dt, J = 9.2, 0.9 Hz, 1H), 7.69 (d, J = 8.8 Hz, 2H), 7.38 (dd, J = 9.1, 2.1 Hz, 1H), 7.27 (t, JHF = 74.4 Hz, 1H), 7.16 (d, J = 8.8 Hz, 2H), 6.54 (d, J = 9.0 Hz, 1H), 4.94 (t, J = 6.8 Hz, 2H), 4.26 (q, J = 7.1 Hz, 2H), 3.91 (t, J = 6.8 Hz, 2H), 2.95 (s, 3H), 1.27 (t, J = 7.1 Hz, 3H). |

| | | |
|---|---|---|
| 109-A | 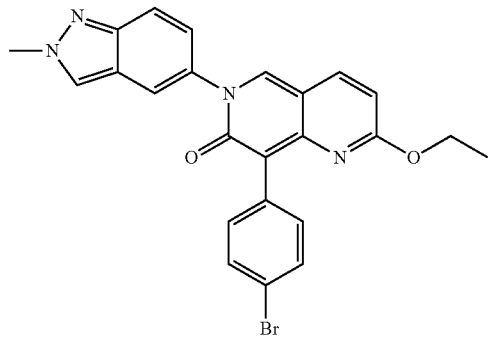<br>8-(4-bromophenyl)-2-ethoxy-6-(2-(methyl-2H-indazol-5-yl)-1,6-naphthyridin-7(6H)-one | LC-MS (ESI): m/z 475 [M + H]⁺.<br>1H NMR (400 MHz, DMSO-d6) δ 8.75 (s, 1H), 8.50 (s, 1H), 7.97 (d, J = 9.1 Hz, 1H), 7.92-7.87 (m, 1H), 7.70 (d, J = 9.1 Hz, 1H), 7.61 (d, J = 8.6 Hz, 2H), 7.53 (d, J = 8.6 Hz, 2H), 7.34 (dd, J = 9.1, 2.0 Hz, 1H), 6.54 (d, J = 8.9 Hz, 1H), 4.30-4.21 (m, 5H), 1.27 (t, J = 7.1 Hz, 3H). |
| 110-A | 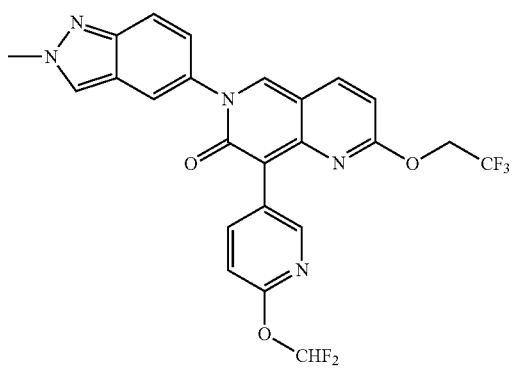<br>8-(6-(difluoromethoxy)pyridin-3-yl)-6-(2-(methyl-2H-indazol-5-yl)-2-(2,2,2-trifluoroethoxy)-1,6-naphthyridin-7(6H)-one | LC-MS (ESI): m/z 518 [M + H]⁺.<br>1H NMR (400 MHz, DMSO-d6) δ 8.91 (s, 1H), 8.57-8.47 (m, 2H), 8.20 (dd, J = 8.6, 2.4 Hz, 1H), 8.13 (d, J = 9.0 Hz, 1H), 7.93 (d, J = 2.0 Hz, 1H), 7.76 (t, JHF = 73.1 Hz, 1H), 7.72 (d, J = 9.1 Hz, 1H), 7.37 (dd, J = 9.1, 2.0 Hz, 1H), 7.11 (d, J = 8.6 Hz, 1H), 6.74 (d, J = 9.0 Hz, 1H), 4.94 (q, J = 9.0 Hz, 2H), 4.23 (s, 3H). |
| 111-A | 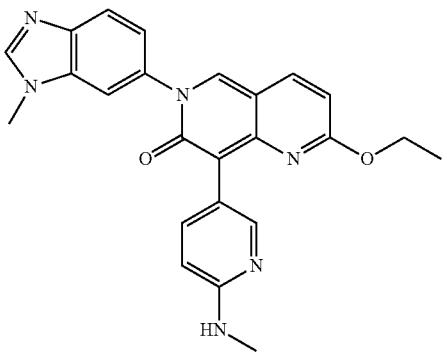<br>2-ethoxy-6-(1-methyl-1H-benzo[d]imidazol-6-yl)-8-(6-(methylamino)pyridin-3-yl)-1,6-naphthyridin-7(6H)-one | LC-MS (ESI): m/z 427 [M + H]⁺.<br>1H NMR (400 MHz, DMSO-d6) δ 8.61 (s, 1H), 8.37-8.29 (m, 2H), 8.19 (s, 1H), 7.93 (d, J = 9.1 Hz, 1H), 7.83 (d, J = 1.9 Hz, 1H), 7.78 (d, J = 8.5 Hz, 1H), 7.71 (dd, J = 8.7, 2.4 Hz, 1H), 7.32 (dd, J = 8.5, 2.0 Hz, 1H), 6.52 (d, J = 8.9 Hz, 1H), 6.44 (d, J = 8.7 Hz, 1H), 6.39 (t, J = 4.9 Hz, 1H), 4.30 (q, J = 7.1 Hz, 2H), 3.87 (s, 3H), 2.79 (d, J = 4.5 Hz, 3H), 1.30 (t, J = 7.0 Hz, 3H). |

| | | |
|---|---|---|
| 112-A | 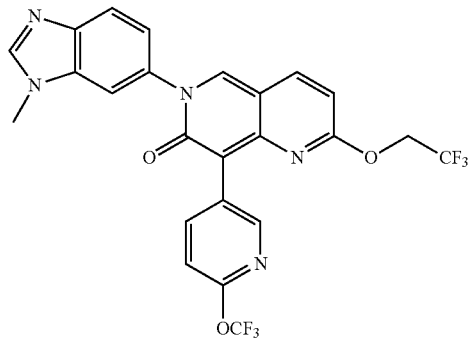<br>6-(1-methyl-1H-benzo[d]imidazol-6-yl)-2-(2,2,2-trifluroethoxy)-8-(6-(trifluoromethoxy)pyridin-3-yl)-1,6-naphthyridin-7(6H)-one | LC-MS (ESI): m/z 536 [M + H]$^+$.<br>1H NMR (400 MHz, DMSO-d6) δ 8.94 (s, 1H), 8.64 (d, J = 2.3 Hz, 1H), 8.36 (s, 1H), 8.29 (dd, J = 8.5, 2.4 Hz, 1H), 8.14 (d, J = 9.0 Hz, 1H), 7.90 (d, J = 2.0 Hz, 1H), 7.80 (d, J = 8.5 Hz, 1H), 7.39 (dd, J = 8.5, 2.1 Hz, 1H), 7.32 (d, J = 8.5 Hz, 1H), 6.76 (d, J = 9.0 Hz, 1H), 4.95 (d, J = 9.0 Hz, 2H), 3.88 (s, 3H). |
| 113-A | 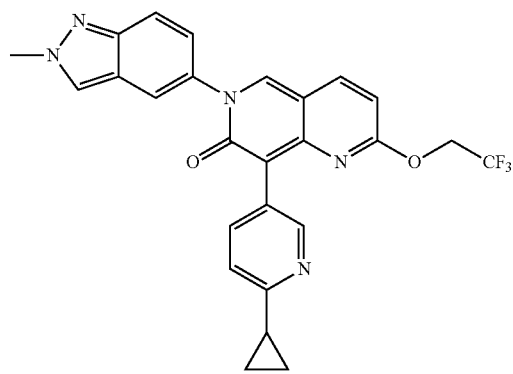<br>8-(6-cyclopropylpyridin-3-yl)-6-(2-methyl-2H-indazol-5-yl)-2-(2,2,2-trifluoroethoxy)-1,6-naphthyridin-7(6H)-one | LC-MS (ESI): m/z 492 [M + H]$^+$.<br>1H NMR (400 MHz, DMSO-d6) δ 8.85 (s, 1H), 8.65 (dd, J = 2.2, 0.8 Hz, 1H), 8.51 (s, 1H), 8.10 (d, J = 9.0 Hz, 1H), 7.93-7.87 (m 2H), 7.72 (dt, J = 9.2, 0.9 Hz, 1H), 7.35 (dd, J = 9.1, 2.0 Hz, 1H), 7.30 (dd, J = 8.1, 0.8 Hz, 1H), 6.71 (d, J = 9.0 Hz, 1H), 4.93 (q, J = 9.1 Hz, 2H), 4.23 (s, 3H), 2.12 (tt, J = 7.6, 5.2 Hz, 1H), 0.95 (ddd, J = 7.3, 5.5, 2.3 Hz, 4H). |
| 114-A | 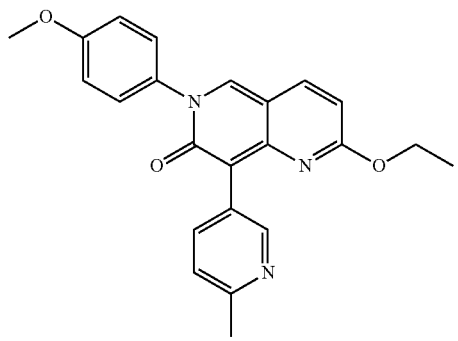<br>2-ethoxy-6-(4-methoxyphenyl)-8-(6-methylpyridin-3-yl)-1,6-naphthyridin-7(6H)-one | LC-MS (ESI): m/z 388 [M + H]$^+$.<br>1H NMR (400 MHz, DMSO-d6) δ 8.68 (dd, J = 2.2, 0.8 Hz, 1H), 8.66 (s, 1H), 7.95 (d, J = 9.1 Hz, 1H), 7.90 (dd, J = 8.0, 2.3 Hz, 1H), 7.47 (d, J = 8.9 Hz, 2H), 7.24 (d, J = 8.1 Hz, 1H), 7.09 (d, J = 9.0 Hz, 2H), 6.54 (d, J = 9.0 Hz, 1H), 4.25 (q, J = 7.0 Hz, 2H), 3.83 (s, 3H), 2.48 (s, 3H), 1.26 (t, J = 7.0 Hz, 3H). |

| | | |
|---|---|---|
| 115-A | 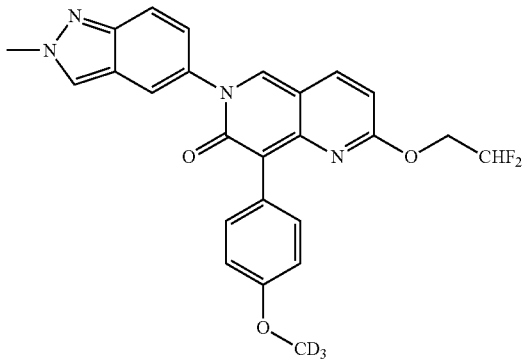<br>2-(2,2-difluoroethoxy)-8-(4-(methoxy-d3)phenyl)-6-(2-methyl-2H-indazol-5-yl)-1,6-naphthyridin-7(6H)-one | LC-MS (ESI): m/z 466 [M + H]⁺.<br>1H NMR (400 MHz, DMSO-d6) δ 8.74 (s, 1H), 8.50 (s, 1H), 8.03 (d, J = 9.0 Hz, 1H), 7.89 (s, 1H), 7.71 (d, J = 9.2 Hz, 1H), 7.58 (d, J = 8.8 Hz, 2H), 7.34 (dd, J = 9.1, 2.1 Hz, 1H), 6.92 (d, J = 8.8 Hz, 2H), 6.63 (d, J = 9.0 Hz, 1H), 6.35 (t, JHF = 54.7 Hz, 1H), 4.50 (td, JHF = 15.0, J = 3.6 Hz, 2H), 4.23 (s, 3H). |
| 116-A | 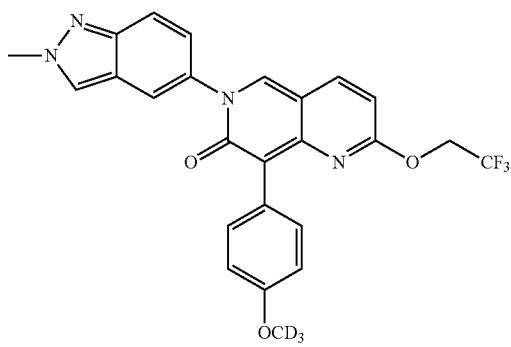<br>8-(4-(methoxy-d3)phenyl)-6-(2-methyl-2H-indazol-5-yl)-2-(2,2,2-trifluoroethoxy)-1,6-naphthyridin-7(6H)-one | LC-MS (ESI): m/z 484 [M + H]⁺.<br>1H NMR (400 MHz, DMSO-d6) δ 8.77 (s, 1H), 8.50 (s, 1H), 8.07 (d, J = 9.0 Hz, 1H), 7.90 (s, 1H), 7.71 (d, J = 9.1 Hz, 1H), 7.59 (d, J = 8.5 Hz, 2H), 7.34 (dd, J = 9.1, 2.1 Hz, 1H), 6.92 (d, J = 8.4 Hz, 2H), 6.67 (d, J = 8.9 Hz, 1H), 4.94 (q, J = 9.1 Hz, 2H), 4.22 (s, 3H). |
| 117-A | 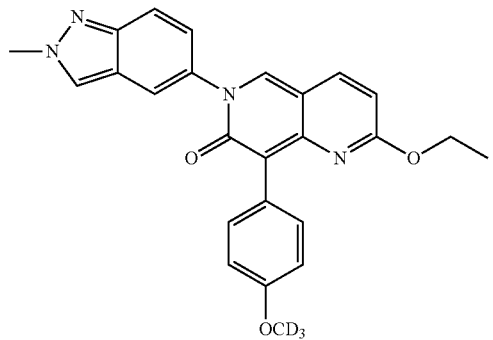<br>2-ethoxy-8-(4-(methoxy-d3)phenyl)-6-(2-methyl-2H-indazol-5-yl)-1,6-naphthyridin-7(6H)-one | LC-MS (ESI): m/z 430 [M + H]⁺.<br>1H NMR (400 MHz, DMSO-d6) δ 8.66 (s, 1H), 8.49 (s, 1H), 7.94 (d, J = 9.1 Hz, 1H), 7.87 (s, 1H), 7.70 (d, J = 9.1 Hz, 1H), 7.58 (d, J = 8.4 Hz, 2H), 7.33 (d, J = 9.3 Hz, 1H), 6.91 (d, J = 8.2 Hz, 2H), 6.51 (d, J = 9.0 Hz, 1H), 4.35-4.08 (m, 5H), 1.26 (q, J = 7.4 Hz, 3H). |

| | | |
|---|---|---|
| 118-A | 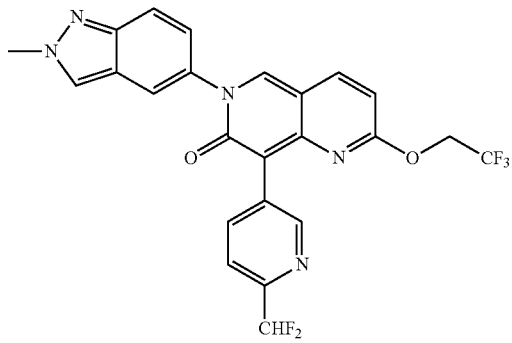<br>8-(6-(difluoromethyl)pyridin-3-yl)-6-(2-methyl-2H-indazol-5-yl)-2-(2,2,2-trifluoroethoxy)-1,6-naphthyridin-7(6H)-one | LC-MS (ESI): m/z 502 [M + H]$^+$.<br>1H NMR (400 MHz, DMSO-d6) δ 8.96 (br s, 2H), 8.52 (s, 1H), 8.29 (dd, J = 8.1, 2.1 Hz, 1H), 8.15 (d, J = 9.0 Hz, 1H), 7.94 (dd, J = 2.1, 0.8 Hz, 1H), 7.75-7.73 (m, 1H), 7.71 (dd, J = 2.2, 1.3 Hz, 1H), 7.38 (dd, J = 9.1, 2.1 Hz, 1H), 6.99 (t, JHF = 55.1 Hz, 1H), 6.76 (d, J = 9.0 Hz, 1H), 4.94 (q, J = 9.0 Hz, 2H), 4.23 (s, 3H). |
| 119-A | 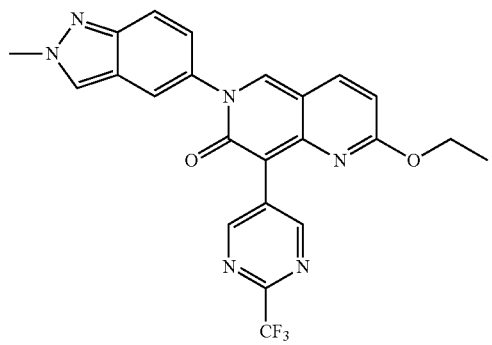<br>2-ethoxy-6-(2-methyl-2H-indazol-5-yl)-8-(2-trifluoromethyl)pyrimidin-5-yl)-1,6-naphthyridin-7(6H)-one | LC-MS (ESI): m/z 467 [M + H]$^+$.<br>1H NMR (400 MHz, DMSO-d6) δ 9.41 (s, 2H), 8.96 (s, 1H), 8.52 (s, 1H), 8.07 (d, J = 9.1 Hz, 1H), 7.94 (dd, J = 2.0, 0.8 Hz, 1H), 7.77-7.69 (m, 1H), 7.38 (dd, J = 9.1, 2.1 Hz, 1H), 6.66 (d, J = 9.0 Hz, 1H), 4.33 (q, J = 7.1 Hz, 2H), 4.23 (s, 3H), 1.30 (t, J = 7.1 Hz, 3H). |
| 120-A | 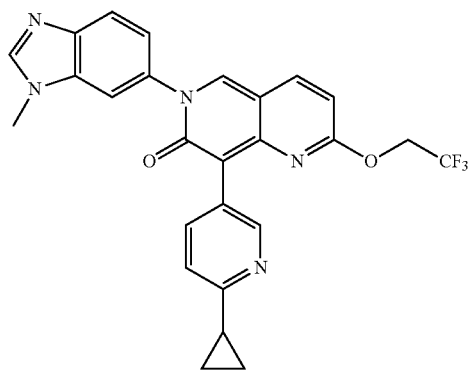<br>8-(6-cyclopropylpyridin-3-yl)-6-(1-methyl-1H-benzo[d]imidazol-6-yl)-2-(2,2,2-trifluoroethoxy)-1,6-naphthyridin-7(6H)-one | LC-MS (ESI): m/z 492 [M + H]$^+$.<br>1H NMR (400 MHz, DMSO-d6) δ 8.85 (s, 1H), 8.65 (d, J = 2.1 Hz, 1H), 8.34 (s, 1H), 8.10 (d, J = 9.0 Hz, 1H), 7.94-7.88 (m, 1H), 7.87 (d, J = 2.0 Hz, 1H), 7.79 (d, J = 8.6 Hz, 1H), 7.36 (dd, J = 8.6, 2.0 Hz, 1H), 7.30 (d, J = 8.0 Hz, 1H), 6.72 (d, J = 9.0 Hz, 1H), 4.94 (q, J = 9.0 Hz, 2H), 3.87 (s, 3H), 2.12 (dq, J = 12.8, 7.9, 6.7 Hz, 1H), 0.96 (dt, J = 10.0, 3.3 Hz, 4H). |

| | | |
|---|---|---|
| 121-A | 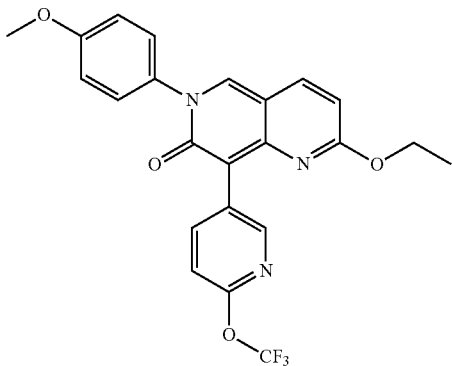<br>2-ethoxy-6-(4-methoxyphenyl)-8-(6-(trifluoromethoxy)pyridin-3-yl)-1,6-naphthyridin-7(6H)-one | LC-MS (ESI): m/z 458 [M + H]$^+$.<br>1H NMR (400 MHz, DMSO-d6) δ 8.74 (s, 1H), 8.60 (dd, J = 2.4, 0.7 Hz, 1H), 8.26 (dd, J = 8.5, 2.4 Hz, 1H), 7.99 (d, J = 9.1 Hz, 1H), 7.49 (d, J = 8.9 Hz, 2H), 7.30 (dd, J = 8.5, 0.7 Hz, 1H), 7.10 (d, J = 9.0 Hz, 2H), 6.57 (d, J = 9.0 Hz, 1H), 4.26 (q, J = 7.0 Hz, 2H), 3.84 (s, 3H), 1.26 (t, J = 7.1 Hz, 3H). |
| 122-A | 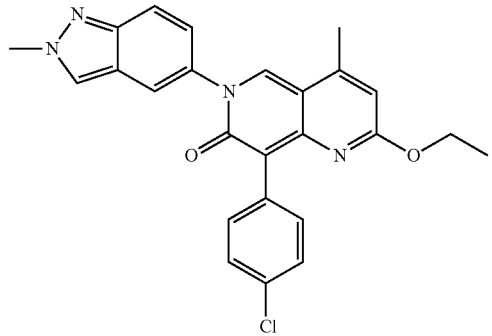<br>8-(4-chlorophenyl)-2-ethoxy-4-methyl-6-(2-methyl-2H-indazol-5-yl)-1,6-naphthyridin-7(6H)-one (synthesized from 3-bromo-5-iodo-2-methoxypyridin-4-amine & ethyl (E)-but-2-enoate via general procedure V (R1-R3-R2 sequence, Method B, Step B-D & L-O)) | LC-MS (ESI): m/z 445 [M + H]$^+$.<br>1H NMR (400 MHz, DMSO-d6) δ 8.56 (s, 1H), 8.49 (s, 1H), 7.89 (d, J = 1.9 Hz, 1H), 7.69 (d, J = 9.1 Hz, 1H), 7.65-7.59 (m, 2H), 7.43-7.37 (m, 2H), 7.34 (dd, J = 9.1, 2.0 Hz, 1H), 6.42 (d, J = 1.3 Hz, 1H), 4.28-4.16 (m, 5H), 2.43 (s, 3H), 1.25 (t, J = 7.0 Hz, 3H). |
| 123-A | 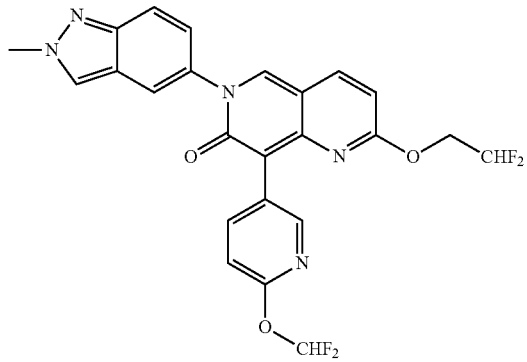<br>2-(2,2-difluoroethoxy)-8-(6-(difluoromethoxy)pyridin-3-yl)-6-(2-methyl-2H-indazol-5-yl)-1,6-naphthyridin-7(6H)-one | LC-MS (ESI): m/z 500 [M + H]$^+$.<br>1H NMR (400 MHz, DMSO-d6) δ 8.87 (s, 1H), 8.55-8.49 (m, 2H), 8.19 (dd, J = 8.5, 2.4 Hz, 1H), 8.08 (d, J = 9.1 Hz, 1H), 7.92 (dd, J = 2.1, 0.8 Hz, 1H), 7.76 (t, JHF = 73.1 Hz, 1H), 7.72 (dt, J = 9.2, 0.9 Hz, 1H), 7.36 (dd, J = 9.1, 2.0 Hz, 1H), 7.10 (dd, J = 8.6, 0.7 Hz, 1H), 6.69 (d, J = 9.0 Hz, 1H), 6.36 (tt, JHF = 54.6, J = 3.4 Hz, 1H), 4.53 (td, JHF = 15.1, J = 3.4 Hz, 2H), 4.23 (s, 3H). |

| | | |
|---|---|---|
| 124-A | 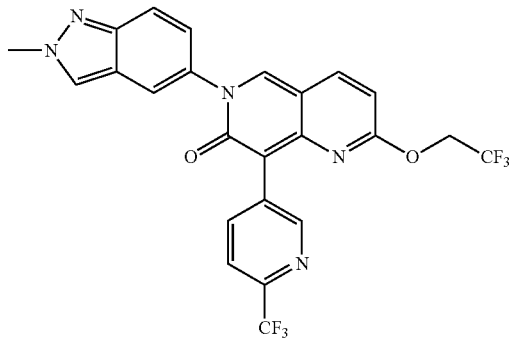<br>6-(2-methyl-2H-indazol-5-yl)-2-(2,2,2-trifluoroethoxy)-8-(6-(trifluoromethyl)pyridin-3-yl)-1,6-naphthyridin-7(6H)-one | LC-MS (ESI): m/z 520 [M + H]+.<br>1H NMR (400 MHz, DMSO-d6) δ 9.06 (d, J = 2.0 Hz, 1H), 9.00 (s, 1H), 8.53 (s, 1H), 8.39 (dd, J = 8.2, 2.0 Hz, 1H), 8.17 (d, J = 9.1 Hz, 1H), 7.96 (dd, J = 2.1, 0.8 Hz, 1H), 7.92 (dd, J = 8.3, 0.8 Hz, 1H), 7.73 (dd, J = 9.2, 0.9 Hz, 1H), 7.39 (dd, J = 9.1, 2.0 Hz, 1H), 6.78 (d, J = 9.0 Hz, 1H), 4.95 (q, J = 9.0 Hz, 2H), 4.24 (s, 3H). |
| 125-A | 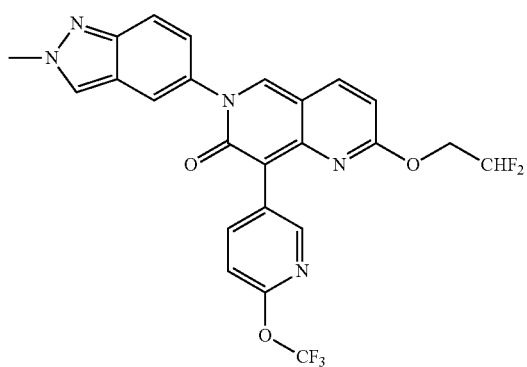<br>2-(2,2-difluoroethoxy)-6-(2-methyl-2H-indazol-5-yl)-8-(6-(trifluoromethoxy)pyridin-3-yl)-1,6-naphthyridin-7(6H)-one | LC-MS (ESI): m/z 518 [M + H]+.<br>1H NMR (400 MHz, DMSO-d6) δ 8.91 (s, 1H), 8.63 (dd, J = 2.4, 0.6 Hz, 1H), 8.52 (s, 1H), 8.29 (dd, J = 8.5, 2.4 Hz, 1H), 8.10 (d, J = 9.1 Hz, 1H), 7.93 (dd, J = 2.0, 0.8 Hz, 1H), 7.72 (dt, J = 9.1, 0.9 Hz, 1H), 7.37 (dd, J = 9.1, 2.1 Hz, 1H), 7.31 (dd, J = 8.4, 0.7 Hz, 1H), 6.70 (d, J = 9.0 Hz, 1H), 6.35 (tt, JHF = 54.6, J = 3.5 Hz, 1H), 4.52 (td, JHF = 15.0, J = 3.6 Hz, 2H), 4.23 (s, 3H). |
| 126-A | 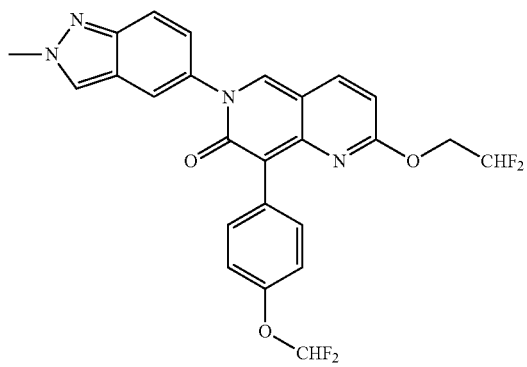<br>2-(2,2-difluoroethoxy)-8-(4-(difluoromethoxy)phenyl)-6-(2-methyl-2H-indazol-5-yl)-1,6-naphthyridin-7(6H)-one | LC-MS (ESI): m/z 499 [M + H]+.<br>1H NMR (400 MHz, DMSO-d6) δ 8.82 (s, 1H), 8.51 (s, 1H), 8.06 (d, J = 9.1 Hz, 1H), 7.91 (dd, J = 2.1, 0.8 Hz, 1H), 7.78-7.63 (m, 3H), 7.35 (dd, J = 9.1, 2.0 Hz, 1H), 7.28 (t, JHF = 74.3 Hz, 1H), 7.17 (d, J = 8.7 Hz, 2H), 6.66 (d, J = 9.0 Hz, 1H), 6.35 (tt, JHF = 54.7, J = 3.5 Hz, 1H), 4.51 (td, J = 15.0, 3.5 Hz, 2H), 4.23 (s, 3H). |

| | | |
|---|---|---|
| 127-A | 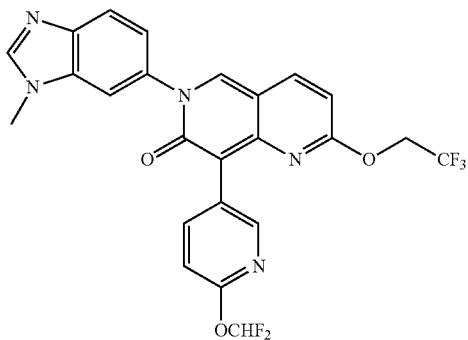

8-(6-(difluoromethoxy)pyridin-3-yl)-6-(1-methyl-1H-benzo[d]imidazol-6-yl)-2-(2,2,2-trifluoroethoxy)-1,6-naphthyridin-7(6H)-one | LC-MS (ESI): m/z 518 [M + H]⁺.
1H NMR (400 MHz, DMSO-d6) δ 8.90 (s, 1H), 8.53 (d, J = 2.4 Hz, 1H), 8.35 (s, 1H), 8.20 (dd, J = 8.5, 2.4 Hz, 1H), 8.13 (d, J = 9.0 Hz, 1H), 7.89 (t, J = 2.0 Hz, 1H), 7.76 (t, JHF = 73.1 Hz, 1H), 7.80 (d, J = 8.5 Hz, 1H), 7.38 (dd, J = 8.5, 2.1 Hz, 1H), 7.11 (d, J = 8.5 Hz, 1H), 6.75 (d, J = 9.0 Hz, 1H), 4.94 (q, J = 9.0 Hz, 2H), 3.88 (s, 3H). |
| 128-A | 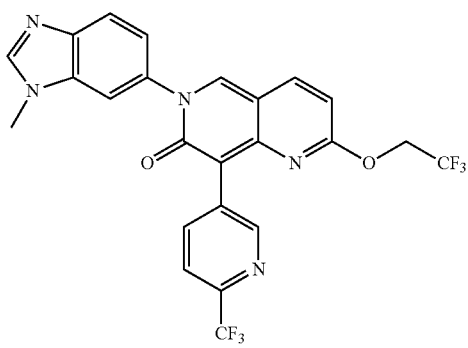

6-(1-methyl-1H-benzo[d]imidazol-6-yl)-2-(2,2,2-trifluoroethoxy)-8-(6-(trifluoromethyl)pyridin-3-yl)-1,6-naphthyridin-7(6H)-one | LC-MS (ESI): m/z 520 [M + H]⁺.
1H NMR (400 MHz, DMSO-d6) δ 9.06 (s, 1H), 8.99 (s, 1H), 8.39 (d, J = 8.7 Hz, 1H), 8.36 (s, 1H), 8.17 (d, J = 9.0 Hz, 1H), 7.96-7.89 (m, 2H), 7.81 (d, J = 8.5 Hz, 1H), 7.40 (dd, J = 8.7, 2.0 Hz, 1H), 6.79 (d, J = 9.0 Hz, 1H), 4.95 (q, J = 9.0 Hz, 2H), 3.88 (s, 3H). |
| 129-A | 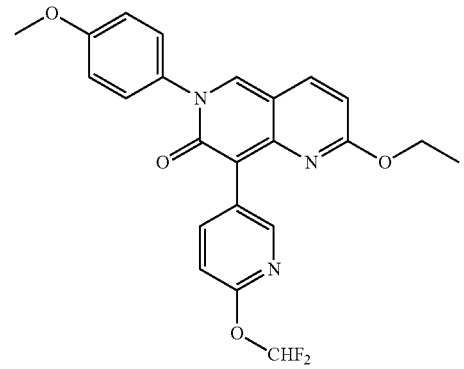

8-(6-(difluoromethoxy)pyridin-3-yl)-2-ethoxy-6-(4-methoxyphenyl)-1,6-naphthyridin-7(6H)-one | LC-MS (ESI): m/z 440 [M + H]⁺.
1H NMR (400 MHz, DMSO-d6) δ 8.70 (s, 1H), 8.50 (dd, J = 2.3, 0.7 Hz, 1H), 8.16 (dd, J = 8.5, 2.4 Hz, 1H), 7.98 (d, J = 9.1 Hz, 1H), 7.76 (t, JHF = 73.1 Hz, 1H), 7.48 (d, J = 8.9 Hz, 2H), 7.13-7.07 (m, 3H), 6.56 (d, J = 9.0 Hz, 1H), 4.26 (q, J = 7.1 Hz, 2H), 3.83 (s, 3H), 1.27 (t, J = 7.1 Hz, 3H). |

130-A

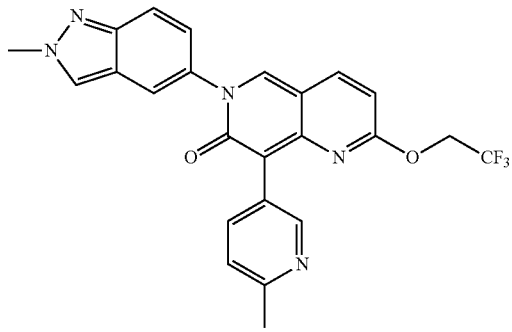

6-(2-methyl-2H-indazol-5-yl)-8-(6-methylpyridin-3-yl)-2-(2,2,2-trifluoroethoxy)-1,6-naphthyridin-7(6H)-one LC-MS (ESI): m/z 466 [M + H]$^+$.
1H NMR (400 MHz, DMSO-d6) δ 8.87 (s, 1H), 8.71 (d, J = 2.2 Hz, 1H), 8.52 (s, 1H), 8.12 (d, J = 9.0 Hz, 1H), 7.98-7.90 (m, 2H), 7.72 (d, J = 9.1 Hz, 1H), 7.37 (dd, J = 9.1, 2.0 Hz, 1H), 7.27 (d, J = 8.0 Hz, 1H), 6.72 (d, J = 9.0 Hz, 1H), 4.94 (d, J = 9.0 Hz, 2H), 4.23 (s, 3H), 2.51 (s, 3H— buried).

131-A

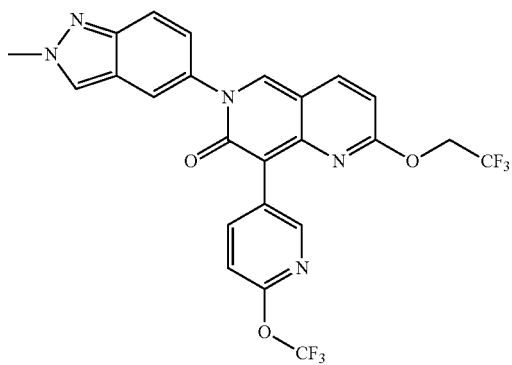

6-(2-methyl-2H-indazol-5-yl)-2-(2,2,2-trifluoroethoxy)-8-(6-(trifluoromethoxy)pyridin-3-yl)-1,6-naphthyridin-7(6H)-one LC-MS (ESI): m/z 536 [M + H]$^+$.
1H NMR (400 MHz, DMSO-d6) δ 8.95 (s, 1H), 8.64 (d, J = 2.4 Hz, 1H), 8.52 (s, 1H), 8.29 (dd, J = 8.5, 2.4 Hz, 1H), 8.14 (d, J = 9.0 Hz, 1H), 7.94 (dd, J = 2.1, 0.8 Hz, 1H), 7.76-7.69 (m, 1H), 7.37 (dd, J = 9.1, 2.0 Hz, 1H), 7.31 (d, J = 8.5 Hz, 1H), 6.75 (d, J = 9.0 Hz, 1H), 4.94 (q, J = 9.1 Hz, 2H), 4.23 (s, 3H).

132-A

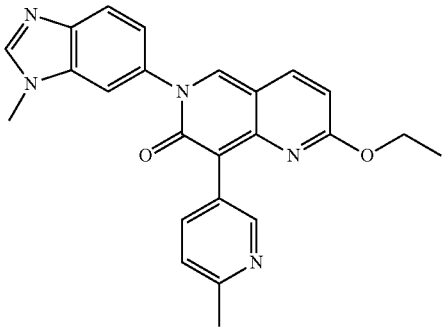

2-ethoxy-6-(1-methyl-1H-benzo[d]imidazol-6-yl)-8-(6-methylpyridin-3-yl)-1,6-naphthyridin-7(6H)-one LC-MS (ESI): m/z 412 [M + H]$^+$.
1H NMR (400 MHz, DMSO-d6) δ 8.75 (s, 1H), 8.70 (d, J = 2.2 Hz, 1H), 8.34 (s, 1H), 7.98 (d, J = 9.1 Hz, 1H), 7.93 (dd, J = 8.0, 2.3 Hz, 1H), 7.86 (d, J = 2.0 Hz, 1H), 7.79 (d, J = 8.5 Hz, 1H), 7.35 (dd, J = 8.5, 2.0 Hz, 1H), 7.25 (d, J = 8.0 Hz, 1H), 6.56 (d, J = 9.0 Hz, 1H), 4.27 (q, J = 7.0 Hz, 2H), 3.88 (s, 3H), 1.28 (t, J = 7.0 Hz, 3H).

| | | |
|---|---|---|
| 133-A | 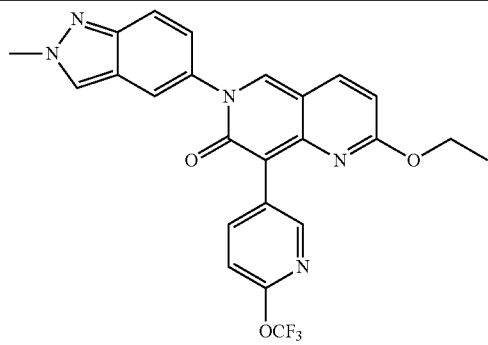<br>2-ethoxy-6-(2-methyl-2H-indazol-5-yl)-8-(6-(trifluoromethoxy)pyridin-3-yl)-1,6-naphthyridin-7(6H)-one | LC-MS (ESI): m/z 482 [M + H]$^+$.<br>1H NMR (400 MHz, DMSO-d6) δ 8.83 (s, 1H), 8.62 (d, J = 2.3 Hz, 1H), 8.51 (s, 1H), 8.28 (dd, J = 8.5, 2.4 Hz, 1H), 8.01 (d, J = 9.0 Hz, 1H), 7.91 (d, J = 2.0 Hz, 1H), 7.72 (d, J = 9.1 Hz, 1H), 7.36 (dd, J = 9.1, 2.0 Hz, 1H), 7.31 (d, J = 8.5 Hz, 1H), 6.59 (d, J = 9.0 Hz, 1H), 4.28 (q, J = 7.1 Hz, 2H), 4.23 (s, 3H), 1.27 (t, J = 7.1 Hz, 3H). |
| 134-A | 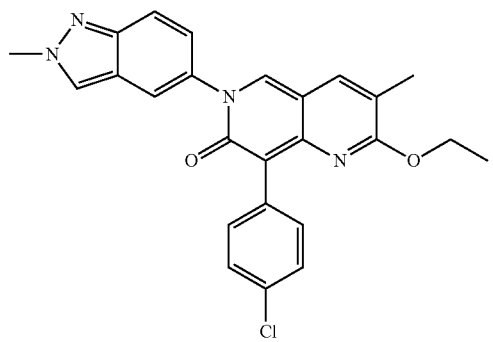<br>8-(4-chlorophenyl)-2-ethoxy-3-methyl-6-(2-methyl-2H-indazol-5-yl)-1,6-naphthyridin-7(6H)-one (syntesized from 3-bromo-5-iodo-2-methoxypyridin-4-amine & ethyl methacrylate via general procedure V (R1-R3-R2 sequence, Method B, Step B-D & L-O)) | LC-MS (ESI): m/z 455 [M + H]$^+$.<br>1H NMR (400 MHz, DMSO-d6) δ 8.62 (s, 1H), 8.49 (s, 1H), 7.86 (dd, J = 2.0, 0.8 Hz, 1H), 7.72 (d, J = 1.4 Hz, 1H), 7.71-7.65 (m, 3H), 7.39 (d, J = 8.5 Hz, 2H), 7.32 (dd, J = 9.1, 2.1 Hz, 1H), 4.28 (q, J = 7.0 Hz, 2H), 4.22 (s, 3H), 2.12 (d, J = 1.2 Hz, 3H), 1.29 (t, J = 7.0 Hz, 3H). |

General Procedure VI

General procedure VI

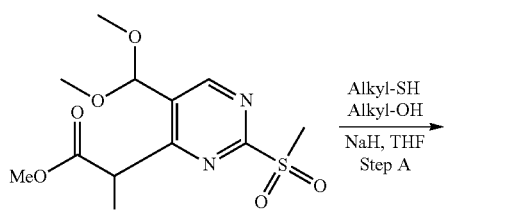

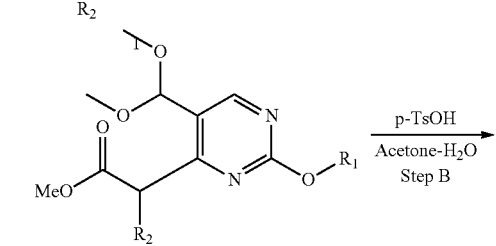

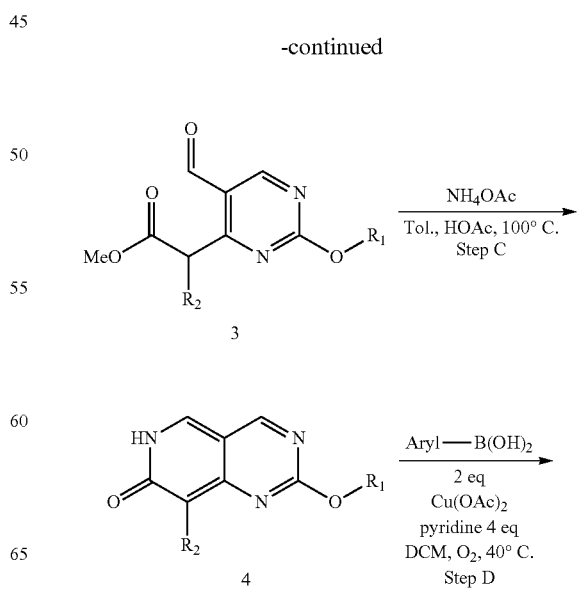

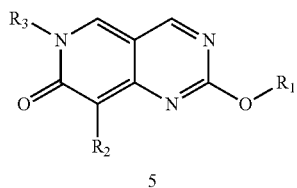

Preparation of Example 261

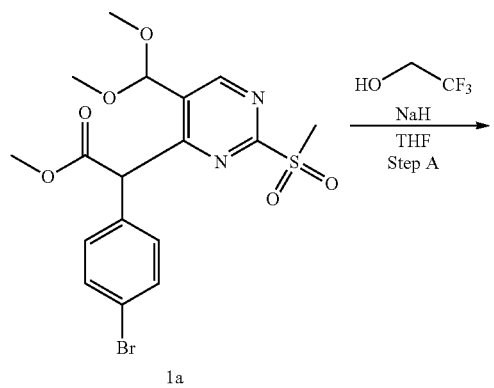

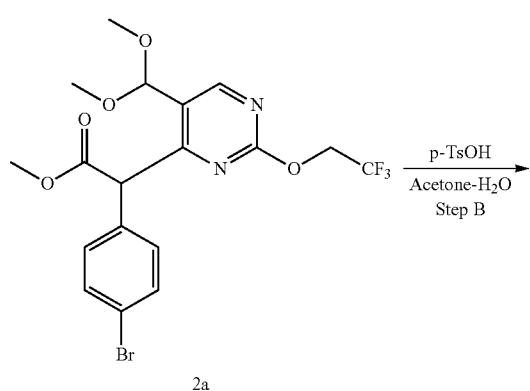

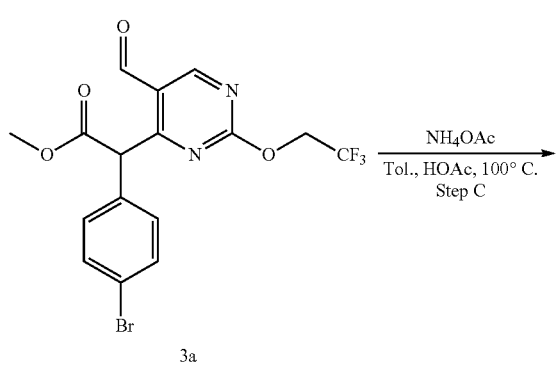

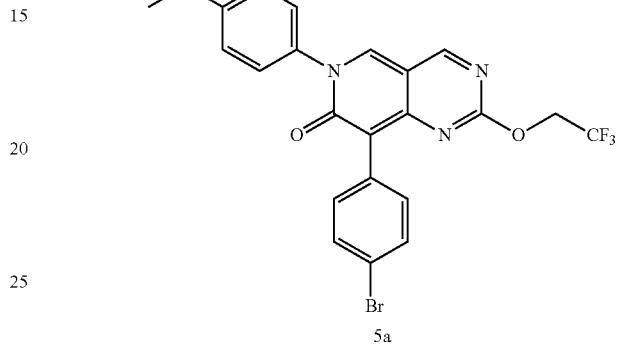

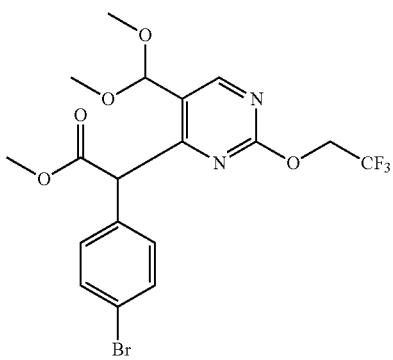 [SMILES: COC(=O)C(c1ccc(Br)cc1)c1nc(OCC(F)(F)F)ncc1C(OC)OC]

Step A: methyl 2-(4-bromophenyl)-2-(5-(dimethoxymethyl)-2-(2,2,2-trifluoroethoxy)pyrimidin-4-yl)acetate To a solution of 2,2,2-trifluoroethanol (150 mg, 1.5 mmol, 3 equiv) in THF (3 mL) was added NaH (60% in mineral oil, 60 mg, 1.5 mmol, 3 equiv) at 0° C. The mixture was stirred at 0° C. for 30 min. Then methyl 2-(4-bromophenyl)-2-(5-(dimethoxymethyl)-2-(methylsulfonyl)pyrimidin-4-yl)acetate (1a) (prepared via General Procedure III using methyl 2-(4-bromophenyl)acetate (Steps A-C)) (230 mg, 0.5 mmol, 1.0 equiv) was added, and then the mixture was stirred at room temperature (25° C.) for an additional 3 h. The reaction mixture was then poured into cooled NH$_4$Cl (Sat. aq.), and the aqueous layer was extracted with EtOAc (10 mL×3). The combined organic layers were dried over Na$_2$SO$_4$ and concentrated to give a brown oil, which was purified by silica gel chromatography (PE:EA=20:1~10:1) to give the methyl 2-(4-bromophenyl)-2-(5-(dimethoxymethyl)-2-(2,2,2-trifluoroethoxy)pyrimidin-4-yl) acetate (150 mg, 62% yield) as a white solid. LC-MS: m/z 479,481 [M+H]$^+$.

Step B: methyl 2-(4-bromophenyl)-2-(5-formyl-2-(2,2,2-trifluoroethoxy)pyrimidin-4-yl)acetate

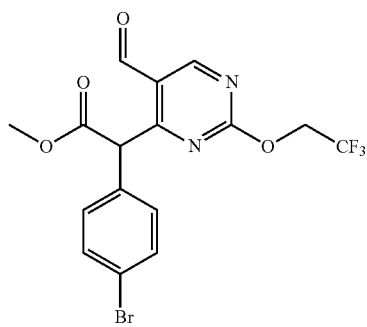 [SMILES: COC(=O)C(c1ccc(Br)cc1)c1nc(OCC(F)(F)F)ncc1C=O]

To a solution of methyl 2-(4-bromophenyl)-2-(5-dimethoxymethyl)-2-(2,2,2-trifluoroethoxy)pyrimidin-4-yl)acetate (120 mg, 0.25 mmol, 1.0 equiv) in acetone (1.5 mL) and H$_2$O (1.5 mL) was added p-TSA (10 mg, 0.075 mmol, 0.3 equiv). The resulting mixture was stirred at 70° C. for 1 h. Then the reaction mixture was extracted with EtOAc (5 mL×3), dried over anhydrous Na$_2$SO$_4$ and concentrated to afford 2-(4-bromophenyl)-2-(5-formyl-2-(2,2,2-trifluoroethoxy)pyrimidin-4-yl)acetate (86 mg, crude) as a white solid. LC-MS: m/z 433, 435 [M+H]$^+$.

Step C: 8-(4-bromophenyl)-2-(2,2,2-trifluoroethoxy)pyrido[4,3-d]pyrimidin-7(6H)-one

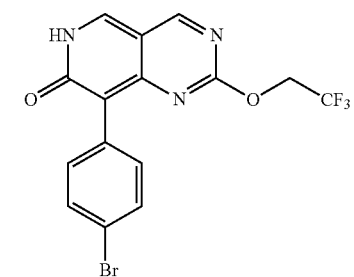 [SMILES: O=c1[nH]cc2cnc(OCC(F)(F)F)nc2c1-c1ccc(Br)cc1]

To a solution of 2-(4-bromophenyl)-2-(5-formyl-2-(2,2,2-trifluoroethoxy)pyrimidin-4-yl)acetate (86 mg, 0.20 mmol, 1.0 equiv) in AcOH (1 mL) and toluene (1 mL) was added NH$_4$OAc (512 mg, 6.4 mmol, 320 equiv). The resulting mixture was stirred at 100° C. for 1.5 h, then the reaction was quenched by adding NaHCO$_3$(aq.). The reaction mixture was extracted with EtOAc (5 mL×3), dried over anhydrous Na$_2$SO$_4$ and concentrated. The resulting crude product was purified by silica gel chromatography to give 8-(4-bromophenyl)-2-(2,2,2-trifluoroethoxy)pyrido[4,3-d]pyrimidin-7(6H)-one (60 mg, 75% yield) as a brown solid. LC-MS: m/z 400, 402 [M+H]$^+$.

Step D: 8-(4-bromophenyl)-6-(4-methoxyphenyl)-2-(2,2,2-trifluoroethoxy)pyrido[4,3-d]pyrimidin-7(6H)-one

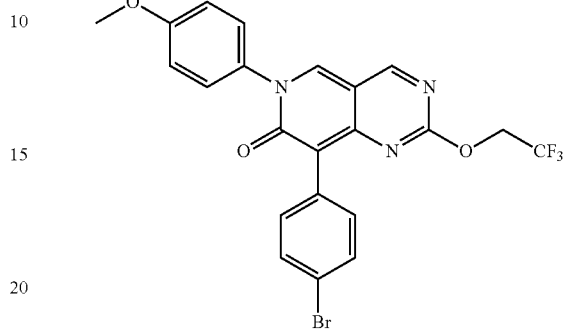

To a solution of 8-(4-bromophenyl)-2-(2,2,2-trifluoroethoxy)pyrido[4,3-d]pyrimidin-7(6H)-one (60 mg, 0.15 mmol, 1.0 equiv) in DCM (3 mL) was added (4-methoxyphenyl) boronic acid (32 mg, 0.3 mmol, 2.0 equiv), Cu(OAc)$_2$(54 mg, 0.3 mmol, 2.0 equiv) and pyridine (48 mg, 0.6 mmol, 4.0 equiv). Then the mixture was stirred at 40° C. under O2 (1 atm) atmosphere overnight. The crude mixture was concentrated under reduced pressure to give a brown oil, then the resulting residue was purified by RP-prep-HPLC to give the 8-(4-bromophenyl)-6-(4-methoxyphenyl)-2-(2,2,2-trifluoroethoxy)pyrido[4,3-d]pyrimidin-7(6H)-one (Example 261).

$^1$H NMR (400 MHz, DMSO-d$_6$) δ: 9.22 (s, 1H), 9.19 (s, 1H), 7.63 (d, J=8.4 Hz, 2H), 7.57 (d, J=8.4 Hz, 2H), 7.52 (d, J=8.8 Hz, 2H), 7.13 (d, J=8.8 Hz, 2H), 4.95 (q, J=8.8 Hz, 2H), 3.84 (s, 3H). LC-MS: m/z 506, 508 [M+H]$^+$.

Preparation of 8-(4-chlorophenyl)-2-(2,2,2-trifluoroethoxy)pyrido[4,3-d]pyrimidin-7(6H)-one 4b

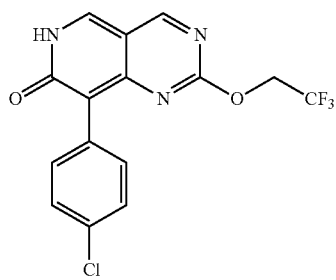

4b 8-(4-chlorophenyl)-2-(2,2,2-trifluoroethoxy)pyrido[4,3-d]pyrimidin-7(6H)-one 4b was synthesized from methyl 2-(4-chlorophenyl)-2-(5-(dimethoxymethyl)-2-(methylsulfonyl)pyrimidin-4-yl)acetate via general procedure VI (Step A-C) LC-MS: m/z 356 [M+H]$^+$.

Example 262: Preparation of 8-(4-chlorophenyl)-6-(2-methyl-2H-indazol-5-yl)-2-(2,2,2-trifluoroethoxy)pyrido[4,3-d]pyrimidin-7(6H)-one

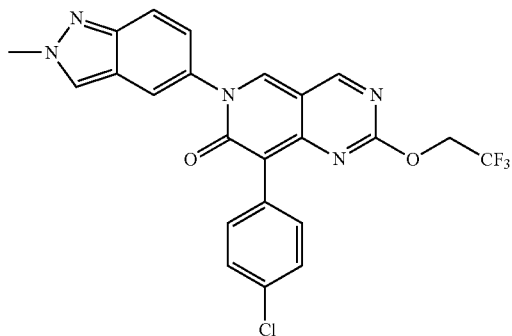 [SMILES: Cn1cc2cc(-n3cc4cnc(OCC(F)(F)F)nc4c(-c4ccc(Cl)cc4)c3=O)ccc2n1]

The title compound was synthesized from intermediate 4b with 2-methyl-2H-indazol-5-ylboronic acid via general procedure VI (Step D) (Cu(OAc)$_2$, pyridine, O$_2$ atmosphere, DCM, 40° C.).
$^1$H NMR (400 MHz, DMSO-d$_6$) δ: 9.28 (s, 1H), 9.23 (s, 1H), 8.54 (s, 1H), 7.96 (d, J=2.0 Hz, 1H), 7.74 (d, J=9.2 Hz, 1H), 7.70 (d, J=8.8 Hz, 2H), 7.44 (d, J=8.8 Hz, 2H), 7.38 (dd, J=9.2 Hz, 2.0 Hz, 1H), 4.95 (q, J=9.2 Hz, 2H), 4.23 (s, 3H). LC-MS: m/z 486 [M+H]$^+$.

Preparation of 8-(4-(difluoromethoxy)phenyl)-2-(2,2,2-trifluoroethoxy)pyrido[4,3-d]pyrimidin-7(6H)-one 4c

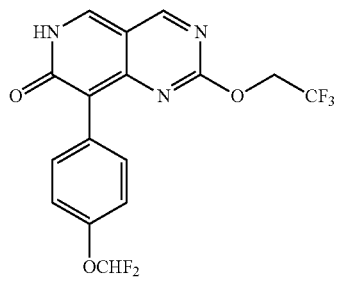

4c 8-(4-(difluoromethoxy)phenyl)-2-(2,2,2-trifluoroethoxy)pyrido[4,3-d]pyrimidin-7(6H)-one 4c was synthesized from methyl 2-(4-(difluoromethoxy)phenyl)-2-(5-(dimethoxymethyl)-2-(methylsulfonyl)pyrimidin-4-yl)acetate via general procedure VI (Step A-C). LC-MS: m/z 388 [M+H]$^+$ Example 263: Preparation of 8-(4-(difluoromethoxy)phenyl)-6-(1-methyl-1H-benzo[d]imidazol-6-yl)-2-(2,2,2-trifluoroethoxy)pyrido[4,3-d]pyrimidin-7(6H)-one

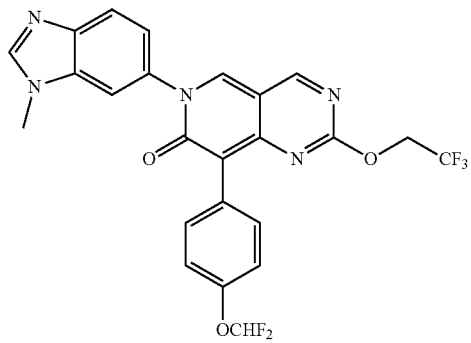 [SMILES: Cn1cnc2ccc(-n3cc4cnc(OCC(F)(F)F)nc4c(-c4ccc(OC(F)F)cc4)c3=O)cc21]

The title compound was synthesized from intermediate 4c with 1-methyl-1H-benzo[d]imidazol-6-ylboronic acid via general procedure VI (Step D) (Cu(OAc)$_2$, pyridine, O$_2$ atmosphere, DCM, 40° C.).
$^1$H NMR (400 MHz, DMSO-d$_6$) δ: 9.26 (s, 1H), 9.24 (s, 1H), 8.37 (s, 1H), 7.91 (d, J=2.0 Hz, 1H), 7.82 (d, J=8.8 Hz, 1H), 7.73 (d, J=8.8 Hz, 2H), 7.40 (dd, J=8.8 Hz, 2.0 Hz, 1H), 7.29 (t, J$_{HF}$=74.2 Hz, 1H), 7.19 (d, J=8.8 Hz, 2H), 4.96 (q, J=7.2 Hz, 2H), 3.88 (s, 3H). LC-MS: m/z 518 [M+H]$^+$.

Example 264: 8-(4-(difluoromethoxy)phenyl)-6-(quinolin-6-yl)-2-(2,2,2-trifluoroethoxy)pyrido[4,3-d]pyrimidin-7(6H)-one

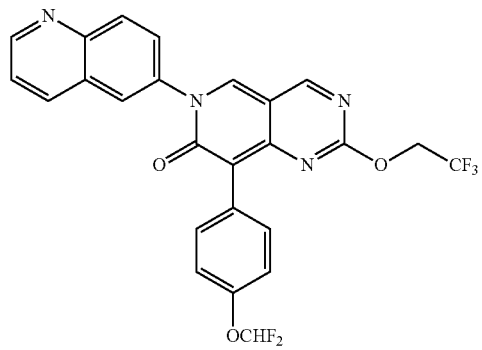 [SMILES: O=c1c(-c2ccc(OC(F)F)cc2)c2nc(OCC(F)(F)F)ncc2cn1-c1ccc2ncccc2c1]

The title compound was synthesized from intermediate 4c with quinolin-6-ylboronic acid via general procedure VI (Step D) (Cu(Ac)$_2$, pyridine, O$_2$ atmosphere, DCM, 40° C.).
$^1$H NMR (400 MHz, DMSO-d$_6$) δ: 9.40 (s, 1H), 9.29 (s, 1H), 9.09 (dd, J=4.2, 1.7 Hz, 1H), 8.55 (d, J=8.3 Hz, 1H), 8.34 (d, J=2.4 Hz, 1H), 8.24 (d, J=9.0 Hz, 1H), 8.02 (dd, J=9.0 Hz, 2.4 Hz, 1H), 7.78 (d, J=8.8 Hz, 2H), 7.72 (dd, J=8.3 Hz, 4.2 Hz, 1H), 7.34 (t, J$_{HF}$=74.2 Hz, 1H), 7.23 (d, J=8.8 Hz, 2H), 5.01 (q, J=8.9 Hz, 2H). LC-MS: m/z 515 [M+H]$^+$.

Example 265: 8-(4-(difluoromethoxy)phenyl)-6-(2-methyl-2H-indazol-5-yl)-2-(2,2,2-trifluoroethoxy)pyrido[4,3-d]pyrimidin-7(6H)-one

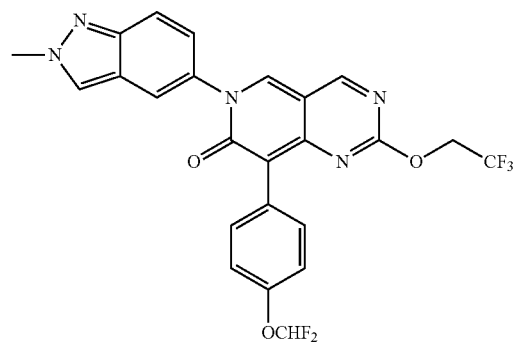

The title compound was synthesized from intermediate 4c with 2-methyl-2H-indazol-5-ylboronic acid via general procedure VI (Step D) (Cu(OAc)$_2$, pyridine, O$_2$ atmosphere, DCM, 40° C.).
$^1$H NMR (400 MHz, DMSO-d$_6$) δ: 9.26 (s, 1H), 9.23 (s, 1H), 8.54 (s, 1H), 7.96 (d, J=2.0 Hz, 1H), 7.75-7.70 (m, 3H), 7.38 (dd, J=9.2 Hz, 2.0 Hz, 1H), 7.29 (t, $J_{HF}$=74.4 Hz, 1H), 7.18 (d, J=8.8 Hz, 2H), 4.96 (q, J=9.0 Hz, 2H), 4.23 (s, 3H). LC-MS: m/z 518 [M+H]⁺.

Example 266: 6-(H-benzo[d]imidazol-6-yl)-8-(4-(difluoromethoxy)phenyl)-2-(2,2,2-trifluoroethoxy)pyrido[4,3-d]pyrimidin-7(6H)-one

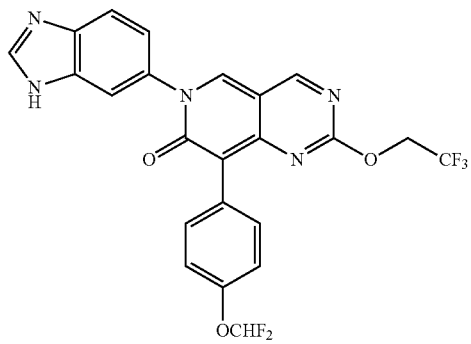 [SMILES: O=c1c(-c2ccc(OC(F)F)cc2)c2nc(OCC(F)(F)F)ncc2cn1-c1ccc2nc[nH]c2c1]

The title compound was synthesized from intermediate 4c with 1-((2-(trimethylsilyl)ethoxy)methyl)-1H-benzo[d]imidazol-6-ylboronic acid via general procedure VI (Step D) (Cu(OAc)₂, pyridine, O₂ atmosphere, DCM, 40° C.), and then de-protection with TFA via general procedure I (Step F).

¹H NMR (400 MHz, DMSO-d₆) δ: 9.26 (s, 1H), 9.23 (s, 1H), 8.45 (br s, 1H), 8.38 (s, 1H), 7.85 (br s, 1H), 7.73 (d, J=8.8 Hz, 2H), 7.37 (br s, 1H), 7.29 (t, $J_{HF}$=74.0 Hz, 1H), 7.18 (d, J=8.8 Hz, 2H), 4.96 (q, J=9.2 Hz, 2H). LC-MS: m/z 504 [M+H]⁺.

Preparation of 8-(4-cyclopropylphenyl)-2-(2,2,2-trifluoroethoxy)pyrido[4,3-d]pyrimidin-7(6H)-one 4d 4d

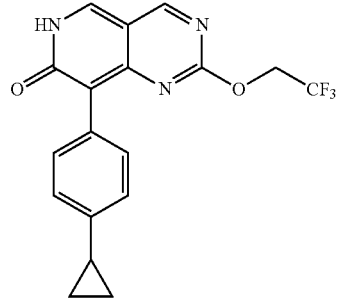

8-(4-cyclopropylphenyl)-2-(2,2,2-trifluoroethoxy)pyrido[4,3-d]pyrimidin-7(6H)-one 4d was synthesized from methyl 2-(4-cyclopropylphenyl)-2-(5-(dimethoxymethyl)-2-(methylsulfonyl)pyrimidin-4-yl)acetate via general procedure VI (Step A-C). LC-MS: m/z 362 [M+H]⁺

Example 267: Preparation of 8-(4-cyclopropylphenyl)-6-(quinolin-6-yl)-2-(2,2,2-trifluoroethoxy)pyrido[4,3-d]pyrimidin-7(6H)-one

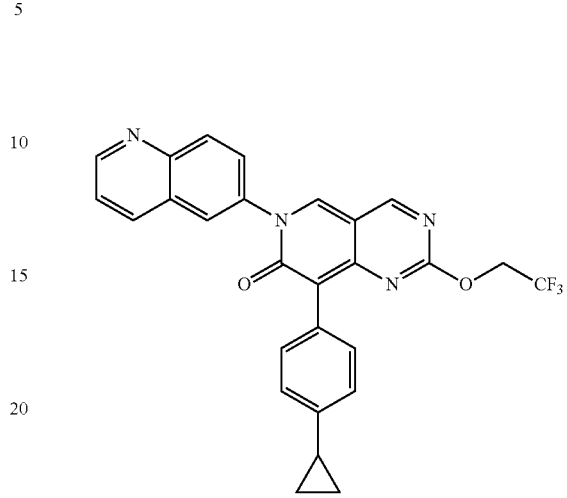

The title compound was synthesized from intermediate 4d with quinolin-6-ylboronic acid via general procedure VI (Step D) (Cu(OAc)₂, pyridine, O₂ atmosphere, DCM, 40° C.).

¹H NMR (400 MHz, DMSO-d₆) δ: 9.31 (s, 1H), 9.23 (s, 1H), 9.04 (dd, J=4.4 Hz, 1.6 Hz, 1H), 8.49 (d, J=7.2 Hz, 1H), 8.28 (d, J=2.4 Hz, 1H), 8.19 (d, J=9.0 Hz, 1H), 7.97 (d, J=9.0 Hz, 2.4 Hz, 1H), 7.66 (dd, J=8.4 Hz, 4.4 Hz, 1H), 7.56 (d, J=8.4 Hz, 2H), 7.09 (d, J=8.4 Hz, 2H), 4.97 (q, J=9.2 Hz, 2H), 1.99-1.90 (m, 1H), 1.01-0.93 (m, 2H), 0.73-0.67 (m, 2H). LC-MS: m/z 489 [M+H]⁺.

Preparation of 2-(2,2,2-trifluoroethoxy)-8-(4-(1-((2-(trimethylsilyl)ethoxy)methyl)-1H-1,2,4-triazol-3-yl)phenyl)pyrido[4,3-d]pyrimidin-7(6H)-one 4e 4e

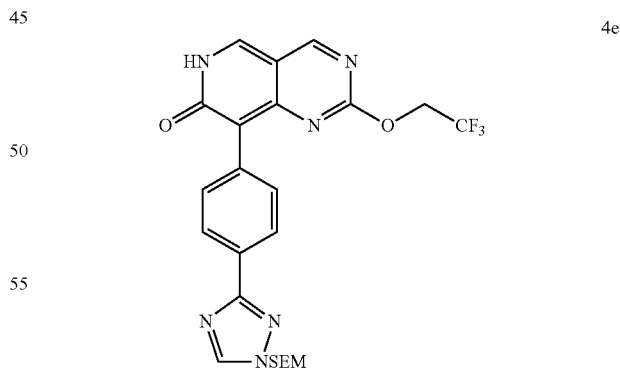

2-(2,2,2-trifluoroethoxy)-8-(4-(1-((2-(trimethylsilyl)ethoxy)methyl)-1H-1,2,4-triazol-3-yl)phenyl)pyrido[4,3-d]pyrimidin-7(6H)-one 4e was synthesized from methyl 2-(5-(dimethoxymethyl)-2-(methylsulfonyl)pyrimidin-4-yl)-2-(4-(1-((2-(trimethylsilyl)ethoxy)methyl)-1H-1,2,4-triazol-3-yl)phenyl)acetate via general procedure VI (Step A-C). LC-MS: m/z 519 [M+H]⁺

Example 268: Preparation of 8-(4-(H-1,2,4-triazol-3-yl)phenyl)-6-(quinolin-6-yl)-2-(2,2,2-trifluoroethoxy)pyrido[4,3-d]pyrimidin-7(6H)-one

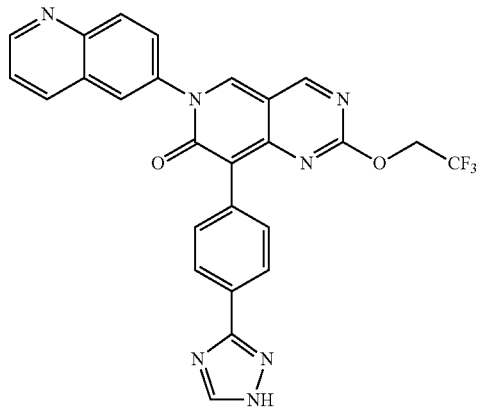 [SMILES: O=c1c(-c2ccc(-c3nc[nH]n3)cc2)c2nc(OCC(F)(F)F)ncc2cn1-c1ccc2ncccc2c1]

The title compound was synthesized from intermediate 4e with quinolin-6-ylboronic acid via general procedure VI (Step D) (Cu(OAc)$_2$, pyridine, O$_2$ atmosphere, DCM, 40° C.), and then de-protection with TFA via general procedure I (Step F).

$^1$H NMR (400 MHz, DMSO-d$_6$) δ:14.20 (br s, 1H), 9.38 (s, 1H), 9.27 (s, 1H), 9.05 (dd, J=8.0 Hz, 1.6 Hz, 1H), 8.51 (d, J=8.0 Hz, 1H), 7.91 (s, 1H), 8.31 (d, J=2.0 Hz, 1H), 8.21 (d, J=8.8 Hz, 1H), 8.05 (d, J=8.4 Hz, 2H), 8.00 (dd, J=9.2 Hz, 2.0 Hz, 1H), 7.83 (d, J=8.4 Hz, 1H), 7.68 (dd, J=8.4 Hz, 4.0 Hz, 1H), 4.99 (q, J=8.8 Hz, 2H). LC-MS: m/z 516 [M+H]$^+$.

Preparation of 8-(4-chlorophenyl)-2-ethoxypyrido[4,3-d]pyrimidin-7(6H)-one 4f

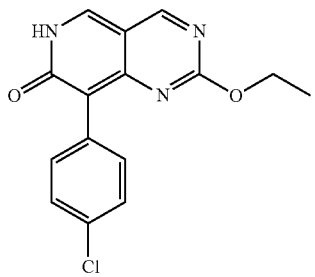

4f 8-(4-chlorophenyl)-2-ethoxypyrido[4,3-d]pyrimidin-7(6H)-one 4f was synthesized from methyl 2-(4-chlorophenyl)-2-(5-(dimethoxymethyl)-2-(methylsulfonyl)pyrimidin-4-yl)acetate with EtOH via general procedure VI (Step A-C). LC-MS: m/z 302 [M+H]$^+$ Preparation of 8-(4-chlorophenyl)-2-ethoxy-6-(1-methyl-1H-benzo[d]imidazol-6-yl)pyrido[4,3-d]pyrimidin-7(6H)-one (Example 269)

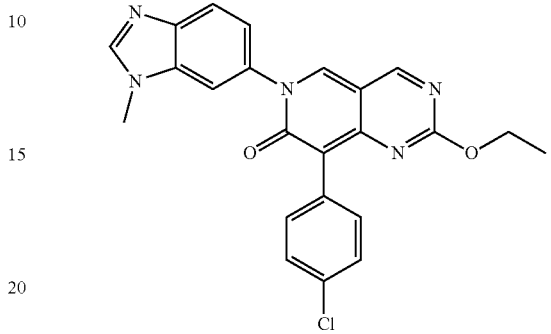

The title compound was synthesized from intermediate 4f with 1-methyl-1H-benzo[d]imidazol-6-ylboronic acid via general procedure VI (Step D) (Cu(OAc)$_2$, pyridine, O$_2$ atmosphere, DCM, 40° C.).

$^1$H NMR (400 MHz, DMSO-d$_6$) δ: 9.17 (s, 2H), 8.36 (s, 1H), 7.89 (d, J=2.0 Hz, 1H), 7.81 (d, J=8.4 Hz, 1H), 7.70 (d, J=8.4 Hz, 2H), 7.43 (d, J=8.4 Hz, 2H), 7.38 (dd, J=8.4 Hz, 2.4 Hz, 1H), 4.30 (q, J=7.2 Hz, 2H), 3.88 (s, 3H), 1.31 (t, J=7.2 Hz, 3H). LC-MS: m/z 432 [M+H]$^+$.

Example 270: 8-(4-chlorophenyl)-2-ethoxy-6-(2-methyl-2H-indazol-5-yl)pyrido[4,3-d]pyrimidin-7(6H)-one

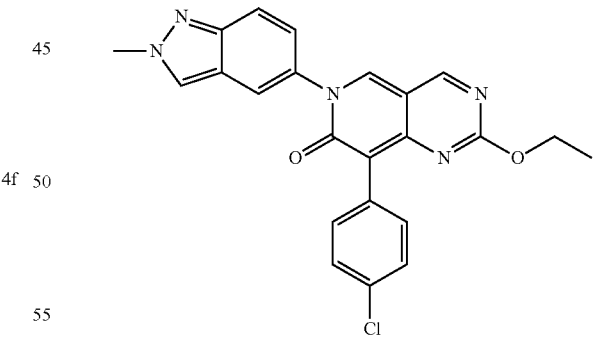

The title compound was synthesized from intermediate 4f with 2-methyl-2H-indazol-5-ylboronic acid via general procedure VI (Step D) (Cu(OAc)$_2$, pyridine, O$_2$ atmosphere, DCM, 40° C.).

$^1$H NMR (400 MHz, DMSO-d$_6$) δ: 9.17 (s, 1H), 9.15 (s, 1H), 8.53 (s, 1H), 7.94 (d, J=2.0 Hz, 1H), 7.73 (d, J=9.2 Hz, 1H), 7.69 (d, J=8.4 Hz, 2H), 7.43 (d, J=8.4 Hz, 2H), 7.36 (dd, J=9.2 Hz, 2.0 Hz, 1H), 4.29 (q, J=7.2 Hz, 2H), 4.23 (s, 3H), 1.30 (t, J=7.2 Hz, 3H). LC-MS: m/z 432 [M+H]$^+$.

Preparation of 8-(4-(difluoromethoxy)phenyl)-2-ethoxypyrido[4,3-d]pyrimidin-7(6H)-one 4g

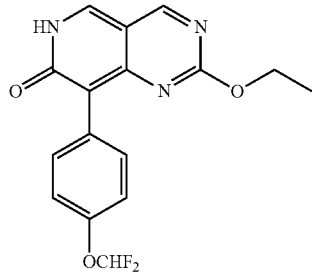

8-(4-(difluoromethoxy)phenyl)-2-ethoxypyrido[4,3-d]pyrimidin-7(6H)-one 4g was synthesized from methyl 2-(4-(difluoromethoxy)phenyl)-2-(5-(dimethoxymethyl)-2-(methylsulfonyl)pyrimidin-4-yl)acetate with EtOH via general procedure VI (Step A-C). LC-MS: m/z 334 [M+H]$^+$ Example 271: Preparation of 8-(4-(difluoromethoxy)phenyl)-2-ethoxy-6-(quinolin-6-yl)pyrido[4,3-d]pyrimidin-7(6H)-one

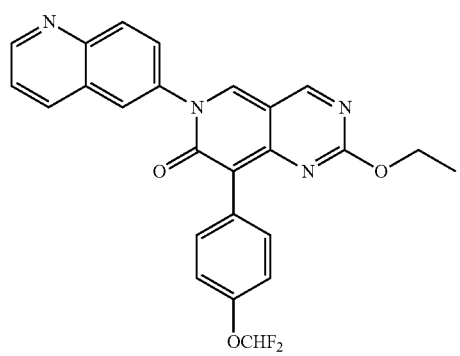 [SMILES: CCOc1ncc2cn(-c3ccc4ncccc4c3)c(=O)c(-c3ccc(OC(F)F)cc3)c2n1]

The title compound was synthesized from intermediate 4g with quinolin-6-ylboronic acid via general procedure VI (Step D) (Cu(OAc)$_2$, pyridine, O$_2$ atmosphere, DCM, 40° C.).

$^1$H NMR (400 MHz, DMSO-d$_6$) δ: 9.30 (s, 1H), 9.22 (s, 1H), 9.08 (dd, J=4.3 Hz, 1.6 Hz, 1H), 8.54 (d, J=8.4 Hz, 1H), 8.32 (d, J=2.4 Hz, 1H), 8.23 (d, J=9.0 Hz, 1H), 8.01 (dd, J=9.0 Hz, 2.4 Hz, 1H), 7.78 (d, J=8.8 Hz, 2H), 7.71 (dd, J=8.8 Hz, 4.3 Hz, 1H), 7.34 (t, J$_{HF}$=74.4 Hz, 1H), 7.23 (d, J=8.8 Hz, 2H), 4.35 (q, J=7.2 Hz, 2H), 1.36 (t, J=7.2 Hz, 3H). LC-MS: m/z 461 [M+H]$^+$.

Example 272: 8-(4-(difluoromethoxy)phenyl)-2-ethoxy-6-(2-methyl-2H-indazol-5-yl)pyrido[4,3-d]pyrimidin-7(6H)-one

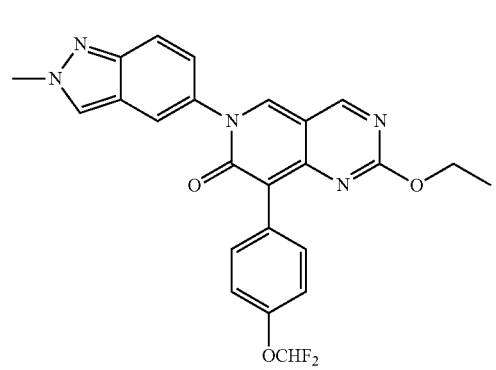

The title compound was synthesized from intermediate 4g with 2-methyl-2H-indazol-5-ylboronic acid via general procedure VI (Step D) (Cu(OAc)$_2$, pyridine, O$_2$ atmosphere, DCM, 40° C.).

$^1$H NMR (400 MHz, DMSO-d$_6$) δ: 9.16 (s, 1H), 9.15 (s, 1H), 8.53 (s, 1H), 7.95 (d, J=2.0 Hz, 1H), 7.75-7.70 (m, 3H), 7.36 (dd, J=9.2 Hz, 2.0 Hz, 1H), 7.29 (t, J$_{HF}$=74.4 Hz, 1H), 7.17 (d, J=8.4 Hz, 2H), 4.30 (q, J=7.2 Hz, 2H), 4.23 (s, 3H), 1.31 (t, J=7.2 Hz, 3H). LC-MS: m/z 464 [M+H]$^+$.

Preparation of 2-cyclopropoxy-8-(4-(difluoromethoxy)phenyl)pyrido[4,3-d]pyrimidin-7(6H)-one 4 h

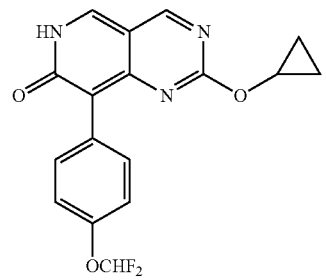

2-cyclopropoxy-8-(4-(difluoromethoxy)phenyl)pyrido[4,3-d]pyrimidin-7(6H)-one 4 h was synthesis from methyl 2-(4-(difluoromethoxy)phenyl)-2-(5-(dimethoxymethyl)-2-(methylsulfonyl)pyrimidin-4-yl)acetate with cyclopropanol via general procedure VI (Step A-C). LC-MS: m/z 346 [M+H]$^+$ Example 273: Preparation of 2-cyclopropoxy-8-(4-(difluoromethoxy)phenyl)-6-(quinolin-6-yl)pyrido[4,3-d]pyrimidin-7(6H)-one

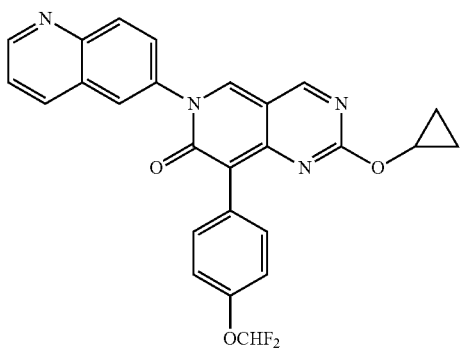 [SMILES: O=c1c(-c2ccc(OC(F)F)cc2)c2nc(OC3CC3)ncc2cn1-c1ccc2ncccc2c1]

The title compound was synthesized from intermediate 4h with quinolin-6-ylboronic acid via general procedure VI (Step D) (Cu(OAc)$_2$, pyridine, O$_2$ atmosphere, DCM, 40° C.).

$^1$H NMR (400 MHz, DMSO-d$_6$) δ: 9.28 (s, 1H), 9.17 (s, 1H), 9.04 (dd, J=4.4 Hz, 1.6 Hz, 1H), 8.49 (d, J=8.4 Hz, 1H), 8.28 (d, J=2.4 Hz, 1H), 8.19 (d, J=9.0 Hz, 1H), 7.97 (dd, J=9.0 Hz, 2.4 Hz, 1H), 7.82 (d, J=8.8 Hz, 2H), 7.67 (dd, J=8.4 Hz, 4.4 Hz, 1H), 7.28 (t, J$_{HF}$=74.4 Hz, 1H), 7.19 (d, J=8.8 Hz, 2H), 4.28-4.19 (m, 1H), 0.80-0.73 (m, 4H). LC-MS: m/z 473 [M+H]$^+$.

Preparation of 8-(4-(difluoromethoxy)phenyl)-2-(2,2,2-trifluoroethylthio)pyrido[4,3-d]pyrimidin-7(6H)-one 4i

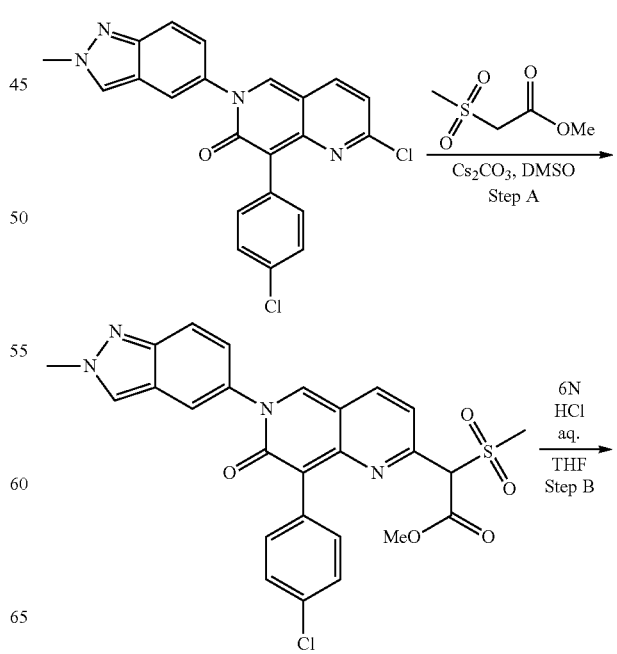

8-(4-(difluoromethoxy)phenyl)-2-(2,2,2-trifluoroethylthio)pyrido[4,3-d]pyrimidin-7(6H)-one 4i was synthesized from methyl 2-(4-(difluoromethoxy)phenyl)-2-(5-(dimethoxymethyl)-2-(methylsulfonyl)pyrimidin-4-yl)acetate with 2,2,2-trifluoroethanethiol via general procedure VI (Step A-C). LC-MS: m/z 404 [M+H]$^+$ Example 274: Preparation of 8-(4-(difluoromethoxy)phenyl)-6-(quinolin-6-yl)-2-(2,2,2-trifluoroethylthio)pyrido[4,3-d]pyrimidin-7(6H)-one

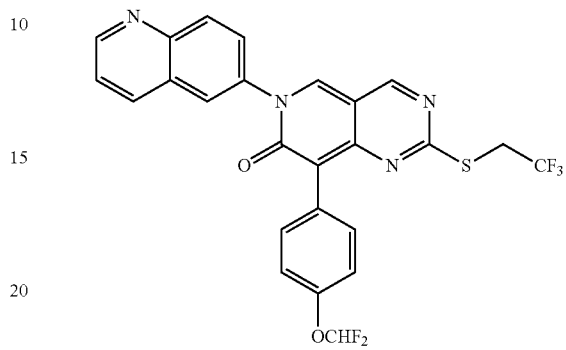

The title compound was synthesized from intermediate 4i with quinolin-6-ylboronic acid via general procedure VI (Step D) (Cu(OAc)$_2$, pyridine, O$_2$ atmosphere, DCM, 40° C.).

$^1$H NMR (400 MHz, DMSO-d$_6$) δ: 9.36 (s, 1H), 9.12 (s, 1H), 9.08 (dd, J=4.3 Hz, 1.6 Hz, 1H), 8.55 (d, J=8.4 Hz, 1H), 8.32 (d, J=2.4 Hz, 1H), 8.22 (d, J=9.0 Hz, 1H), 8.01 (dd, J=9.0 Hz, 2.4 Hz, 1H), 7.71 (dd, J=8.4 Hz, 4.3 Hz, 1H), 7.68 (d, J=8.8 Hz, 2H), 7.29 (t, J$_{HF}$=74.0 Hz, 1H), 7.19 (d, J=8.8 Hz, 2H), 4.11 (q, J=10.4 Hz, 2H). LC-MS: m/z 531 [M+H]$^+$.

Example 135-A: 8-(4-chlorophenyl)-6-(2-methyl-2H-indazol-5-yl)-2-((methylsulfonyl)methyl)-1,6-naphthyridin-7(6H)-one -continued

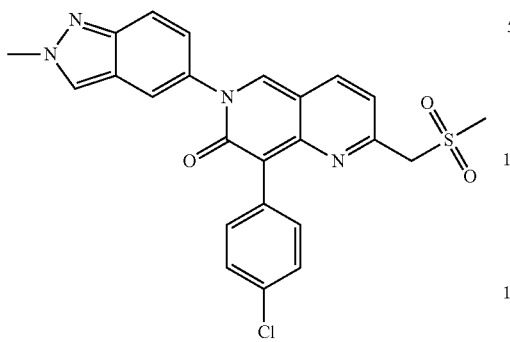

Step A. methyl 2-(8-(4-chlorophenyl)-6-(2-methyl-2H-indazol-5-yl)-7-oxo-6,7-dihydro-1,6-naphthyridin-2-yl)-2-(methylsulfonyl)acetate To a solution of 2-chloro-8-(4-chlorophenyl)-6-(2-methyl-2H-indazol-5-yl)-1,6-naphthyridin-7(6H)-one (200 mg, 0.47 mmol, 1.0 eq., as synthesized in Example 209) in DMSO (3.0 mL) was added $Cs_2CO_3$ (308 mg, 0.95 mmol, 2.0 eq.) and methyl 2-(methylsulfonyl)acetate (144 mg, 0.95 mmol, 2.0 eq.) at room temperature. The reaction mixture was stirred at 100° C. for 14 hrs. The resulting mixture was poured into ice water, the reaction mixture was extracted with EtOAc (20 mL×3), the combined organic layers were washed with brine (20 mL), dried over $Na_2SO_4$ and concentrated under reduced pressure. The residue was purified by flash column chromatography on silica gel to give methyl 2-(8-(4-chlorophenyl)-6-(2-methyl-2H-indazol-5-yl)-7-oxo-6,7-dihydro-1,6-naphthyridin-2-yl)-2-(methylsulfonyl)acetate (70 mg, yield 23%) as a yellow solid. LC-MS (ESI): m/z 537 [M+H]$^+$.

Step B. 8-(4-chlorophenyl)-6-(2-methyl-2H-indazol-5-yl)-2-((methylsulfonyl)methyl)-1,6-naphthyridin-7(6H)-one (135-A)

To a solution of methyl 2-(8-(4-chlorophenyl)-6-(2-methyl-2H-indazol-5-yl)-7-oxo-6,7-dihydro-1,6-naphthyridin-2-yl)-2-(methylsulfonyl)acetate (30 mg, 0.05 mmol, 1.0 eq.) in THF (3 mL) was added 6N HCl aq. (1 mL) at room temperature. The reaction mixture was stirred at 100° C. for 14 hrs. The reaction mixture was extracted with EtOAc (20 mL×3), the combined organic layers were washed with brine (20 mL), dried over $Na_2SO_4$ and concentrated under reduced pressure, the residue was purified by RP-prep-HPLC to give 8-(4-chlorophenyl)-6-(2-methyl-2H-indazol-5-yl)-2-((methylsulfonyl)methyl)-1,6-naphthyridin-7(6H)-one.

$^1$H NMR (400 MHz, DMSO-$d_6$) (ratio of tautomers 5:2) δ (ppm): 9.04 (s, 1H), 8.56 (d, J=8.1 Hz, 0.4H), 8.52 (s, 1H), 8.42 (s, 0.4H), 8.15 (d, J=8.6 Hz, 1H), 7.94 (d, J=2.0 Hz, 1H), 7.75 (d, J=8.1 Hz, 0.4H), 7.72 (d, J=9.1 Hz, 1H), 7.66 (d, J=8.9 Hz, 0.4H), 7.60 (d, J=8.6 Hz, 2H), 7.50 (d, J=8.7 Hz, 0.8H), 7.40 (m, 3H), 7.08 (d, J=8.7 Hz, 1H), 4.77 (s, 0.8H), 4.66 (s, 2H), 4.23 (s, 3H), 4.20 (s, 1.2H), 3.01 (s, 3H), 2.84 (s, 1.2H). LC-MS (ESI): m/z 479 [M+H]$^+$.

Example 136-A: Preparation of: 8-(4-chlorophenyl)-2-(methoxymethyl)-6-(2-methyl-2H-indazol-5-yl)-1,6-naphthyridin-7(6H)-one

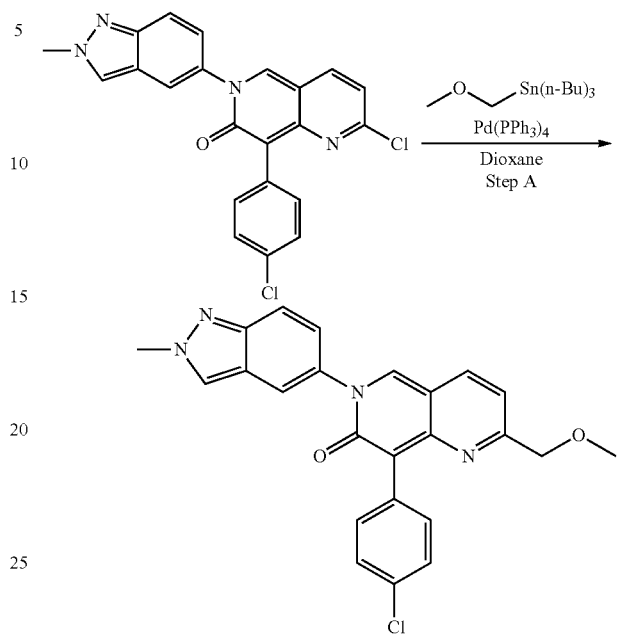

Step A: 8-(4-chlorophenyl)-2-(methoxymethyl)-6-(2-methyl-2H-indazol-5-yl)-1,6-naphthyridin-7(6H)-one A solution of 2-chloro-8-(4-chlorophenyl)-6-(2-methyl-2H-indazol-5-yl)-1,6-naphthyridin-7(6H)-one (100 mg, 0.24 mmol, 1.0 eq., as synthesized in Example 209), tributyl(methoxymethyl)stannane (159 mg, 0.48 mmol, 2.0 eq.) and $Pd(PPh_3)_4$ (24 mg, 0.024 mmol, 0.1 eq.) in dioxane (5 mL) was stirred at 50° C. for 14 hrs under $N_2$ atmosphere. The reaction mixture was dilute with $H_2O$ (10 mL) and extracted with EtOAc (10 mL×3). The combined organic layers were washed with brine (10 mL), dried over $Na_2SO_4$ and concentrated under reduced pressure. The residue was purified by RP-prep-HPLC to give 8-(4-chlorophenyl)-2-(methoxymethyl)-6-(2-methyl-2H-indazol-5-yl)-1,6-naphthyridin-7(6H)-one (136-A). LC-MS (ESI): m/z 431 [M+H]$^+$.

Example 137-A: Preparation of: 2-ethoxy-8-(6-(fluoromethyl)pyridin-3-yl)-6-(2-methyl-2H-indazol-5-yl)-1,6-naphthyridin-7(6H)-one

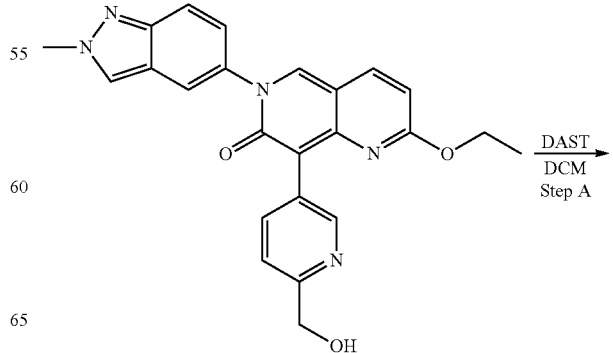

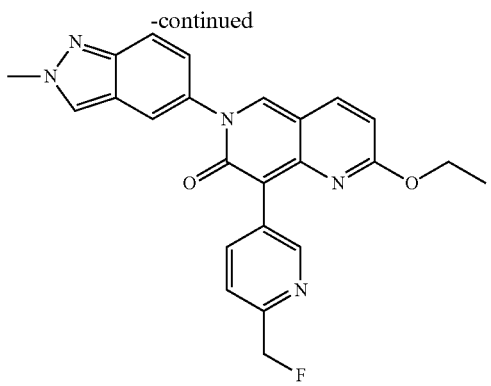

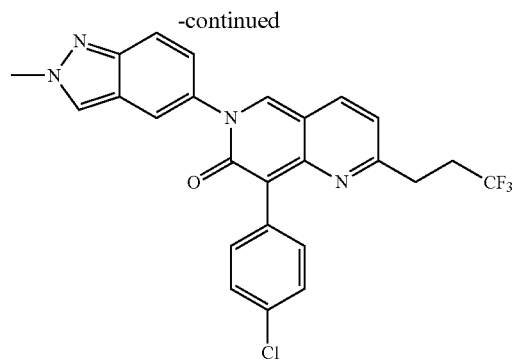

Step A: 2-ethoxy-8-(6-(fluoromethyl)pyridin-3-yl)-6-(2-methyl-2H-indazol-5-yl)-1,6-naphthyridin-7(6H)-one To a solution of 2-ethoxy-8-(6-(hydroxymethyl)pyridin-3-yl)-6-(2-methyl-2H-indazol-5-yl)-1,6-naphthyridin-7(6H)-one (synthesized from 8-bromo-2-ethoxy-6-(2-methyl-2H-indazol-5-yl)-1,6-naphthyridin-7(6H)-one (as synthesized in Example 215) and (6-(hydroxymethyl)pyridin-3-yl)boronic acid via General Procedure V (Step M)) (150 mg, 0.35 mmol, 1.0 eq.) in DCM (4 mL) was added DAST (161 mg, 0.70 mmol, 2.0 eq.) at 0° C. under N$_2$. The resulting mixture was stirred at 0° C. for an additional 1 hr before the reaction was quenched by adding ice water (3 mL). The resulting mixture was extracted with EtOAc (10 mL×3), the combined organic layers were washed with brine (10 mL), dried over Na$_2$SO$_4$ and concentrated under reduced pressure. The residue was purified by RP-prep-HPLC to give 2-ethoxy-8-(6-(fluoromethyl)pyridin-3-yl)-6-(2-methyl-2H-indazol-5-yl)-1,6-naphthyridin-7(6H)-one (137-A).

$^1$H NMR (400 MHz, DMSO-d$_6$) δ (ppm) 8.86 (d, J=2.1 Hz, 1H), 8.81 (s, 1H), 8.51 (s, 1H), 8.15 (dd, J=8.0, 2.1 Hz, 1H), 8.01 (d, J=9.1 Hz, 1H), 7.92 (dd, J=2.1, 0.8 Hz, 1H), 7.72 (dt, J=9.1, 0.9 Hz, 1H), 7.52 (d, J=8.1 Hz, 1H), 7.36 (dd, J=9.1, 2.1 Hz, 1H), 6.58 (d, J=9.0 Hz, 1H), 5.50 (d, J$_{HF}$=47.2 Hz, 2H), 4.27 (q, J=7.2 Hz, 2H), 4.23 (s, 3H), 1.28 (t, J=7.1 Hz, 3H). LC-MS (ESI): m/z 431 [M+H]$^+$.

Example 138-A: Preparation of: 8-(4-chlorophenyl)-6-(2-methyl-2H-indazol-5-yl)-2-(3,3,3-trifluoropropyl)-1,6-naphthyridin-7(6H)-one

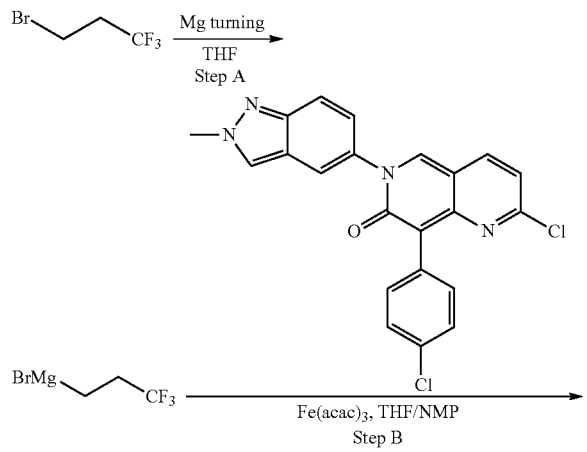

Step A: (3,3,3-trifluoropropyl)magnesium Bromide

Magnesium turnings (136 mg, 5.65 mmol, 1.0 eq.) were suspend in dry THF (4 mL), then 3-bromo-1,1,1-trifluoropropane (1.0 g, 5.65 mmol, 1.0 eq.) was added at room temperature drop-wise. The flask was gently warmed using a heat gun, until bubbling was observed on the surface of the magnesium turnings. The resulting mixture was stirred at 70° C. for an additional 1 h, then the flask was allowed to cool to room temperature resulting in a pale gray solution. The crude Grignard reagent was used in the next step without any further purification or isolation.

Step B: 8-(4-chlorophenyl)-6-(2-methyl-2H-indazol-5-yl)-2-(3,3,3-trifluoropropyl)-1,6-naphthyridin-7(6H)-one To a solution of 2-chloro-8-(4-chlorophenyl)-6-(2-methyl-2H-indazol-5-yl)-1,6-naphthyridin-7(6H)-one (100 mg, 0.24 mmol, 1.0 eq., as synthesized in Example 209) and Fe(acac)$_3$ (85 mg, 0.24 mmol, 1.0 eq.) in THF/NMP mixture (4.4 mL, 10/1, v/v) was added the crude (3,3,3-trifluoropropyl)magnesium bromide (2 mL, 2.4 mmol, 10 eq.) solution drop-wise at room temperature. The resulting mixture was stirred at room temperature for 14 hrs, then the reaction was quenched by adding NH$_4$Cl (Sat. aq.) (5 mL) at 0° C. The mixture was extracted with EtOAc (10 mL×3), the combined organic layers were washed with brine (10 mL), dried over Na$_2$SO$_4$ and concentrated under reduced pressure. The residue was purified by RP-prep-HPLC to give 8-(4-chlorophenyl)-6-(2-methyl-2H-indazol-5-yl)-2-(3,3,3-trifluoropropyl)-1,6-naphthyridin-7(6H)-one (138-A).

$^1$H NMR (400 MHz, DMSO-d$_6$) δ (ppm) 8.94 (s, 1H), 8.51 (s, 1H), 8.04 (d, J=8.7 Hz, 1H), 7.93 (dd, J=2.1, 0.8 Hz, 1H), 7.72 (dt, J=9.0, 0.9 Hz, 1H), 7.67-7.60 (m, 2H), 7.41 (d, J=8.6 Hz, 2H), 7.37 (dd, J=9.1, 2.0 Hz, 1H), 7.00 (d, J=8.7 Hz, 1H), 4.23 (s, 3H), 3.03 (t, J=7.6 Hz, 2H), 2.77-2.60 (m, 2H). LC-MS (ESI): m/z 483 [M+H]$^+$.

General Procedure VII

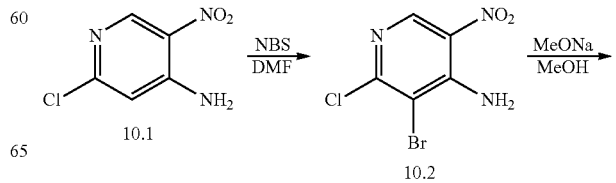

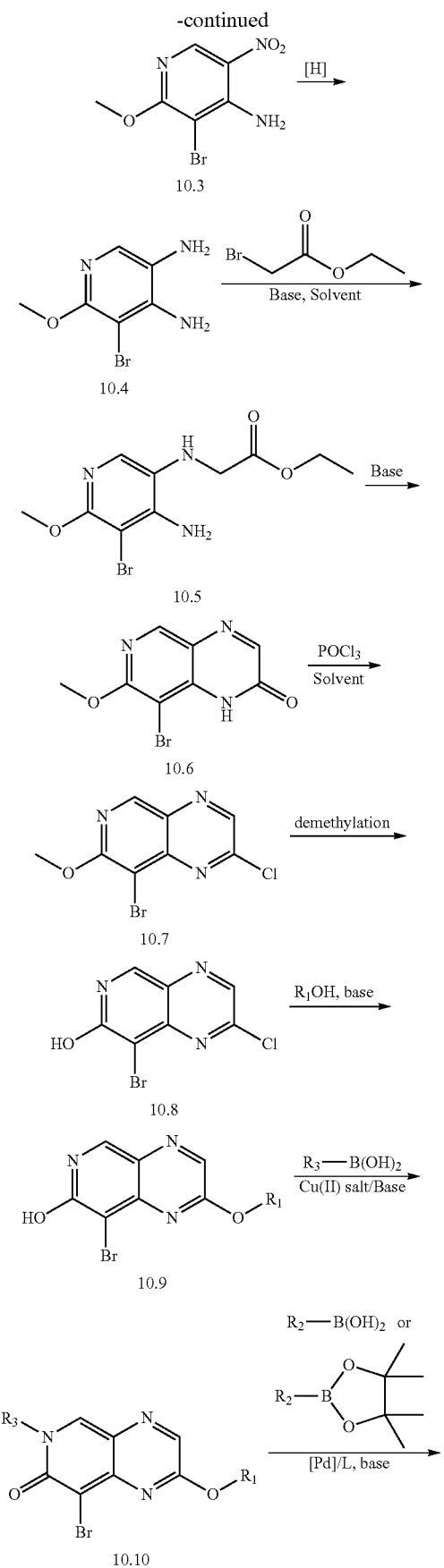

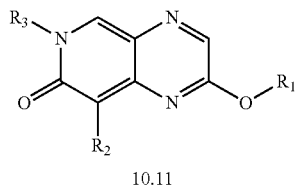

Compounds of structure 10.11 were obtained by General Procedure VII. Substituted pyridine 10.1 was treated with NBS to generate bromo-pyridine 10.2, reacted with NaOMe to generate methoxy-pyridine 10.3, and then reduced to give diamino-pyridine 10.4. Compound 10.4 was reacted with ethyl bromoacetate to give compound 10.5 and then treated with base to generate bicyclic structure 10.6. Following treatment with POCl₃ to generate compound 10.7 and demethylation to generate compound 10.8, the desired R groups could be installed sequentially. The desired $R_1$ group was introduced through a nucleophilic aromatic substitution reaction to afford compounds of structure 10.9. The desired $R_3$ group was introduced through a copper mediated Chan-Lam coupling to afford compounds of structure 10.10. The desired $R_2$ group was introduced through a palladium mediated Suzuki coupling to afford final compounds of structure 10.11.

Example 139-A: Preparation of 139-A Via General Procedure VII

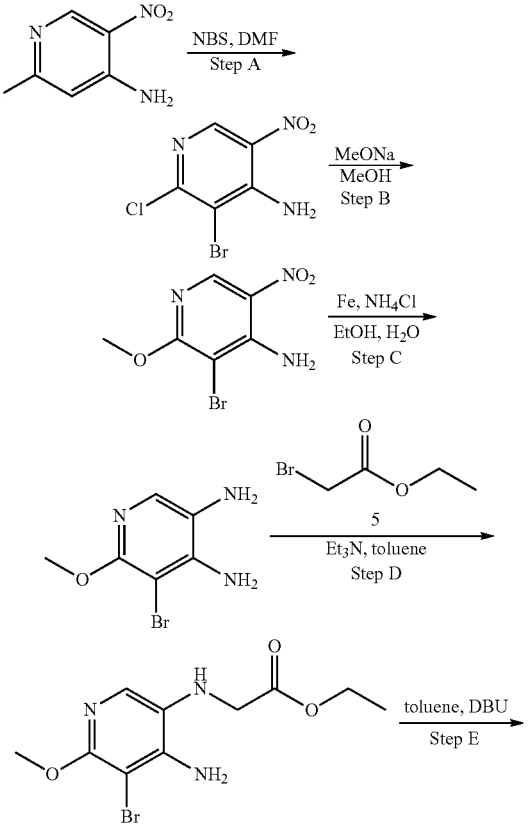

-continued

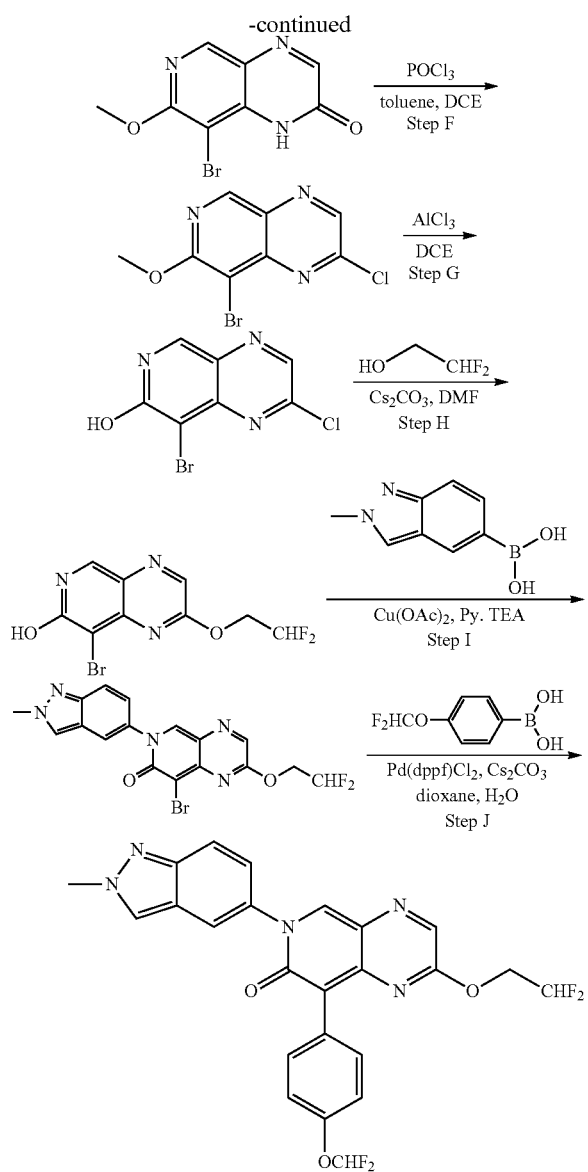

Step A: 3-bromo-2-chloro-5-nitropyridin-4-amine

To a solution of 2-chloro-5-nitropyridin-4-amine (5.0 g, 28.8 mmol, 1.0 eq.) in DMF (20 mL) was added NBS (6.16 g, 34.6 mmol, 1.2 eq.) in several portions. After stirring at room temperature for 4 hrs, most of the solvent was removed under reduced pressure, the residue was suspended in cool water (30 mL), and the solid was filtered and dried under reduced pressure to give 3-bromo-2-chloro-5-nitropyridin-4-amine (6.2 g, 85% yield) as an off-white solid. LC-MS (ESI): m/z 252,254 [M+H]$^+$.

Step B: 3-bromo-2-methoxy-5-nitropyridin-4-amine

To a suspension of 3-bromo-2-chloro-5-nitropyridin-4-amine (6.0 g, 23.8 mmol, 1.0 eq.) in methanol (50 mL) was added a solution of NaOMe (freshly prepared from Na (658 mg, 28.6 mmol, 1.2 eq.) in 5 mL anhydrous MeOH). The reaction mixture was refluxed for 12 hrs. The methanol was removed under reduced pressure, the residue was suspended in cool water (50 mL), and the resulting precipitate was filtered, washed with ice water and dried under vacuum to give 3-bromo-2-methoxy-5-nitropyridin-4-amine (5.8 g, 98% yield) as an off-white solid. LC-MS (ESI): m/z 248, 250 [M+H]$^+$ Step C: 5-bromo-6-methoxypyridine-3,4-diamine To a solution of 3-bromo-2-methoxy-5-nitropyridin-4-amine (5.8 g, 23.3 mmol, 1.0 eq.) and NH$_4$Cl (6.35 g, 116.5 mmol, 5.0 eq.) in EtOH/H$_2$O (40 mL, 3/1, v/v) was added iron powder (5.22 g, 93.2 mmol, 4.0 eq.), and the resulting mixture was heated to 80° C. for 4 hrs. The mixture was allowed to cool to room temperature, filtered through a short pad of Celite®, and extracted with EtOAc (30 mL×3). The combined organic layers were dried over Na$_2$SO$_4$, concentrated under reduced pressure, and the residue was purified by flash column chromatography on silica gel to give 5-bromo-6-methoxypyridine-3,4-diamine (4.0 g, 79% yield) as a brown solid, which should be used as soon as possible in next step. LC-MS (ESI): m/z 218, 220 [M+H]$^+$ Step D: ethyl (4-amino-5-bromo-6-methoxypyridin-3-yl)glycinate To a mixture of 5-bromo-6-methoxypyridine-3,4-diamine (3.6 g, 16.4 mmol, 1.0 eq.) and TEA (2.5 mL, 18.0 mmol, 1.1 eq.) in dry toluene (30 mL) was added ethyl 2-bromoacetate (3.0 g, 18.0 mmol, 1,1 eq.) drop-wise at 0° C. After addition, the reaction mixture was allowed to warm to room temperature and stirred for another 4 hrs. The reaction was then quenched by adding NH$_4$Cl (Sat. aq.) (20 mL), the resulting mixture was extracted with EtOAc (30 mL×3), the combined organic layers were dried over Na$_2$SO$_4$ and then concentrated under reduced pressure to give a crude mixture (5.2 g, crude oil), which was used in next step without further purification.

Step E: 8-bromo-7-methoxypyrido[3,4-b]pyrazin-2(1H)-one

A mixture containing crude ethyl (4-amino-5-bromo-6-methoxypyridin-3-yl)glycinate (5.2 g) and DBU (2.74 g, 18.0 mmol, 1.1 eq) in toluene (20 mL) was refluxed for 14 hrs. The resulting mixture was concentrated under reduced pressure and purified by flash column chromatography on silica gel to give 8-bromo-7-methoxypyrido[3,4-b]pyrazin-2(1H)-one (2.1 g, two step overall 50% yield) as an off-white solid. LC-MS (ESI): m/z 256, 258 [M+H]$^+$.

Step F: 8-bromo-2-chloro-7-methoxypyrido[3,4-b]pyrazine

To a solution of 8-bromo-7-methoxy-1H,2H-pyrido[3,4-b]pyrazin-2-one (1.5 g, 5.85 mmol, 1.0 eq.) in toluene/DCE (40 mL, 1/1, v/v) was added POCl$_3$ (2.70 g, 17.6 mmol, 3.0 eq.) and the reaction mixture was stirred at 90° C. for 15 hrs. The reaction mixture was then concentrated under reduced pressure, the residue was diluted with ice water (50 mL), basified to pH=7-8 with Na$_2$CO$_3$ (sat. aq.), and extracted with EtOAc (50 mL×3). The combined organic layers were washed with brine (50 mL), dried over Na$_2$SO$_4$, concentrated under reduced pressure, and purified by flash column chromatography on silica gel to afford 8-bromo-2-chloro-7-methoxypyrido[3,4-b]pyrazine (1 g, 3.64 mmol, 62%) as a pale yellow oil. LC-MS (ESI): m/z 274, 276 [M+H]$^+$.

Step G: 8-bromo-2-chloropyrido[3,4-b]pyrazin-7-ol

To a solution of 8-bromo-2-chloro-7-methoxypyrido[3,4-b]pyrazine (1 g, 3.64 mmol, 1.0 eq.) in DCE (15 mL) was added anhydrous AlCl$_3$ (0.73 g, 5.46 mmol, 1.5 eq.) and the reaction mixture was stirred at 70° C. for 2 hrs. The reaction mixture was cooled to 0° C., quenched with ice water (50 mL) and extracted with EtOAc (50 mL×3). The combined organic layers were washed with brine (50 mL), dried over Na$_2$SO$_4$, concentrated under reduced pressure, and the residue was purified by flash column chromatography on silica gel to afford 8-bromo-2-chloropyrido[3,4-b]pyrazin-7-ol (700 mg, 74% yield) as a pale yellow solid. LC-MS (ESI): m/z 260, 262 [M+H]$^+$.

Step H: 8-bromo-2-(2,2-difluoroethoxy)pyrido[3,4-b]pyrazin-7-ol

To a solution of 8-bromo-2-chloropyrido[3,4-b]pyrazin-7-ol (390 mg, 1.5 mmol, 1.0 eq.) in 2,2-difluoroethan-1-ol (5 mL) was added Cs$_2$CO$_3$ (978 mg, 3.0 mmol, 2.0 eq.) and the reaction mixture was stirred at 90° C. for 3 hrs. The reaction mixture was cooled to 0° C., quenched with ice water (30 mL), adjusted to pH=6 with dilute HCl (1N, aq.), and extracted with DCM (50 mL×3). The combined organic layers were washed with brine (50 mL), dried over Na$_2$SO$_4$, concentrated under reduced pressure, and the residue was purified by flash column chromatography on silica gel to afford 8-bromo-2-(2,2-difluoroethoxy)pyrido[3,4-b]pyrazin-7-ol (30 mg, 7%) as a pale yellow solid. LC-MS (ESI): m/z 306,308 [M+H]$^+$.

Step I: 8-bromo-2-(2,2-difluoroethoxy)-6-(2-methyl-2H-indazol-5-yl)pyrido[3,4-b]pyrazin-7(6H)-one A mixture of 8-bromo-2-(2,2-difluoroethoxy)pyrido[3,4-b]pyrazin-7-ol (30 mg, 0.1 mmol), (2-methyl-2H-indazol-5-yl)boronic acid (35 mg, 0.2 mmol), Cu(OAc)$_2$ (29 mg, 0.15 mmol, 1.5 eq.), pyridine (24 μL, 0.3 mmol, 0.3 eq.) and TEA (42 μL, 0.3 mmol, 0.3 eq.) in DCM (0.5 mL) was stirred under O2 atmosphere at 40° C. for 15 hrs. The reaction mixture was diluted with H$_2$O (5 mL) and extracted with DCM (5 mL×3). The combined organic layers were washed with brine (5 mL), dried over Na$_2$SO$_4$, and the residue was purified by flash column chromatography on silica gel to afford 8-bromo-2-(2,2-difluoroethoxy)-6-(2-methyl-2H-indazol-5-yl)pyrido[3,4-b]pyrazin-7(6H)-one (20 mg, 46%) as a yellow solid. LC-MS (ESI): m/z 436, 438 [M+H]$^+$.

Step J: 2-(2,2-difluoroethoxy)-8-(4-(difluoromethoxy)phenyl)-6-(2-methyl-2H-indazol-5-yl)pyrido[3,4-b]pyrazin-7(6H)-one A mixture of 8-bromo-2-(2,2-difluoroethoxy)-6-(2-methyl-2H-indazol-5-yl)pyrido[3,4-b]pyrazin-7(6H)-one (20 mg, 0.046 mmol, 1.0 eq.), (4-(difluoromethoxy)phenyl)boronic acid (17 mg, 0.092 mmol, 2.0 eq.), Pd(dppf)Cl$_2$ (6.8 mg, 0.009 mmol, 0.2 eq.) and Cs$_2$CO$_3$ (50 mg, 0.138 mmol, 3.0 eq.) in a dioxane/H$_2$O mixture (0.5 mL, 9/1, v/v) was stirred at 100° C. under N$_2$ atmosphere for 15 hours. The reaction mixture was concentrated under reduced pressure, and the residue was purified by RP-prep-HPLC to afford 2-(2,2-difluoroethoxy)-8-(4-(difluoromethoxy)phenyl)-6-(2-methyl-2H-indazol-5-yl)pyrido[3,4-b]pyrazin-7(6H)-one (139-A).

$^1$H NMR (400 MHz, DMSO-d$_6$) δ: 8.85 (s, 1H), 8.51 (s, 1H), 8.26 (s, 1H), 7.93 (d, J=1.2 Hz, 1H), 7.73-7.67 (i, 3H), 7.35 (dd, J=9.2 Hz, 2.0 Hz, 1H), 7.29 (t, J$_{HF}$=Hz, 1H), 7.18 (d, J=8.8 Hz, 2H), 6.41(tt, J$_{HF}$=54.2 Hz, J=3.2 Hz, 1H), 4.57(td, J$_{HF}$=14.8 Hz, J=3.2 Hz, 2H), 4.23 (s, 3H). LC-MS (ESI): m/z 500 [M+H]$^+$.

The procedure set forth above for General Procedure VII was used to synthesize the following compounds by using appropriate starting materials:

| Example | Structure | Characterization |
| --- | --- | --- |
| 140-A | 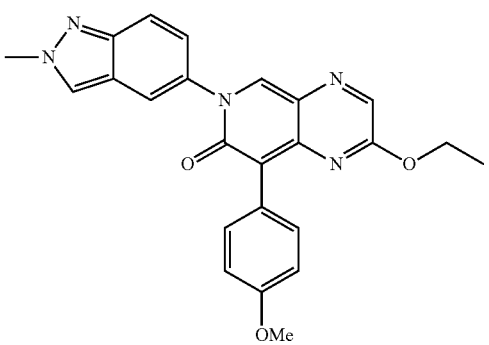 2-ethoxy-8-(4-(methoxyphenyl)-6-(2-methyl-2H-indazol-5-yl)pyrido[3,4-b]pyrazin-7(6H)-one | LC-MS (ESI): m/z 428 [M + H]+. $^1$H NMR (400 MHz, DMSO-d$_6$) δ 8.71 (s, 1H), 8.50 (s, 1H), 8.11 (s, 1H), 7.91 (d, J = 2.0 Hz, 1H), 7.70 (d, J = 9.1 Hz, 1H), 7.60-7.54 (m, 2H), 7.34 (dd, J = 9.1, 2.1 Hz, 1H), 6.94 (d, J = 8.8 Hz, 2H), 4.32 (q, J = 7.1 Hz, 2H), 4.23 (s, 3H), 3.79 (s, 3H), 1.33 (t, J = 7.0 Hz, 3H). |

| Example | Structure | Characterization |
|---|---|---|
| 141-A | 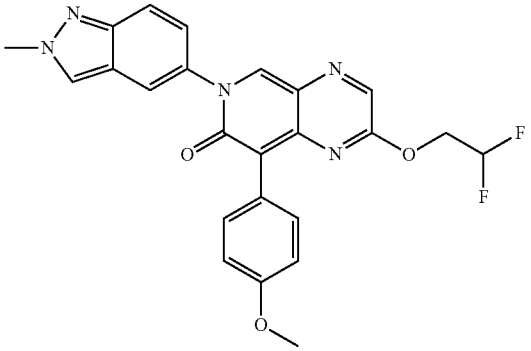<br>2-(2,2-difluoroethoxy)-8-(4-methoxyphenyl)-6-(2-methyl-2H-indazol-5-yl)pyrido[3,4-b]pyrazin-7(6H)-one | LC-MS (ESI): m/z 464 [M + H]+.<br>$^1$H NMR (400 MHz, DMSO-$d_6$) δ 8.78 (s, 1H), 8.50 (s, 1H), 8.23 (s, 1H), 7.92 (d, J = 2.1 Hz, 1H), 7.70 (d, J = 9.0 Hz, 1H), 7.58 (d, J = 8.8 Hz, 2H), 7.34 (dd, J = 9.1, 2.0 Hz, 1H), 6.94 (d, J = 8.9 Hz, 2H), 6.41 (tt, $J_{HF}$ = 54.3, J = 3.3 Hz, 1H), 4.57 (td, $J_{HF}$ = 15.1, J = 3.3 Hz, 2H), 4.23 (s, 3H), 3.79 (s, 3H). |
| 142-A | 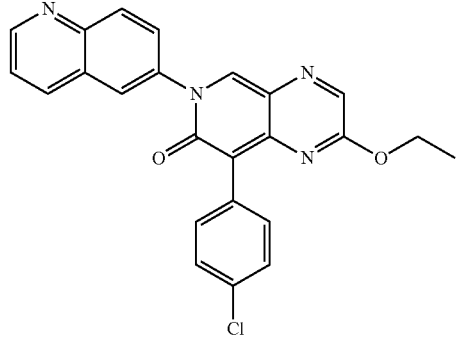<br>8-(4-chlorophenyl)-2-ethoxy-6-(quinolin-6-yl)pyrido[3,4-b]pyrazin-7(6H)-one | LC-MS (ESI): m/z 429 [M + H]+.<br>$^1$H NMR (400 MHz, DMSO-$d_6$) δ 9.03 (dd, J = 4.2, 1.7 Hz, 1H), 8.94 (s, 1H), 8.49 (d, J = 8.2 Hz, 1H), 8.27 (d, J = 2.4 Hz, 1H), 8.20-8.14 (m, 2H), 7.96 (dd, J = 9.0, 2.4 Hz, 1H), 7.72-7.62 (m, 3H), 7.49-7.40 (m, 2H), 4.33 (q, J = 7.0 Hz, 2H), 1.34 (t, J = 7.1 Hz, 3H). |
| 143-A | 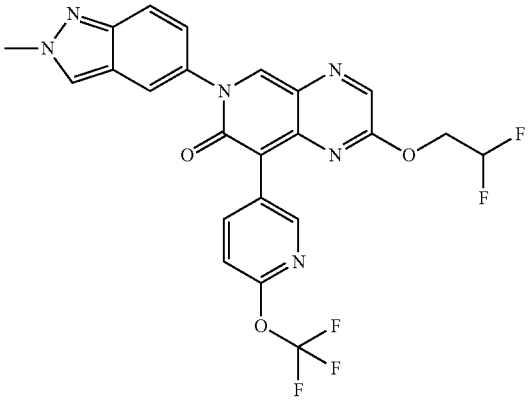<br>2-(2,2-difluoroethoxy)-6-(2-methyl-2H-indazol-5-yl)-8-(6-(trifluoromethoxy)pyridin-3-yl)pyrido[3,4-b]pyrazin-7(6H)-one | LC-MS (ESI): m/z 519 [M + H]+.<br>$^1$H NMR (400 MHz, DMSO-$d_6$) δ 8.97 (s, 1H), 8.64 (d, J = 2.3 Hz, 1H), 8.52 (s, 1H), 8.31 (s, 1H), 8.30 (dd, J = 8.6, 2.5 Hz, 1H), 7.96 (dd, J = 2.1, 0.8 Hz, 1H), 7.73 (dd, J = 9.1, 0.9 Hz, 1H), 7.38 (dd, J = 9.1, 2.1 Hz, 1H), 7.34 (d, J = 8.5 Hz, 1H), 6.42 (tt, $J_{HF}$ = 54.2, J = 3.3 Hz, 1H), 4.60 (td, $J_{HF}$ = 15.1, J = 3.3 Hz, 2H), 4.24 (s, 3H). |

| Example | Structure | Characterization |
|---|---|---|
| 144-A | 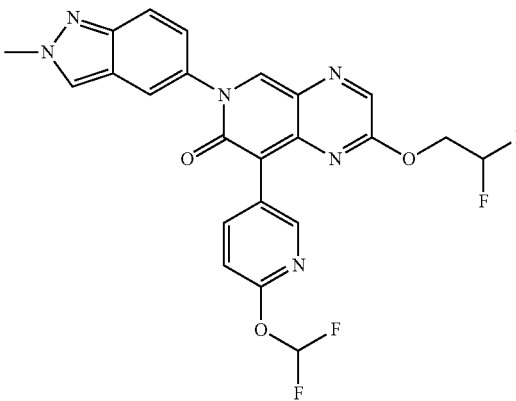<br>2-(2,2-difluoroethoxy)-8-(6-(difluoromethoxy)pyridin-3-yl)-6-(2-methyl-2H-indazol-5-yl)pyrido[3,4-b]pyrazin-7(6H)-one | LC-MS (ESI): m/z 501 [M + H]+.<br>$^1$H NMR (400 MHz, DMSO-d$_6$) δ 8.92 (s, 1H), 8.56-8.49 (m, 2H), 8.29 (s, 1H), 8.19 (dd, J = 8.6, 2.3 Hz, 1H), 7.94 (s, 1H), 7.72 (d, J = 9.1 Hz, 1H), 7.67 (t, $J_{HF}$ = 73.1 Hz, 1H), 7.37 (dd, J = 9.2, 2.0 Hz, 1H), 7.13 (d, J = 8.5 Hz, 1H), 6.42 (t, $J_{HF}$ = 54.2 Hz, 1H), 4.59 (td, $J_{HF}$ = 15.2, J = 3.2 Hz, 2H), 4.23 (s, 3H). |
| 145-A | 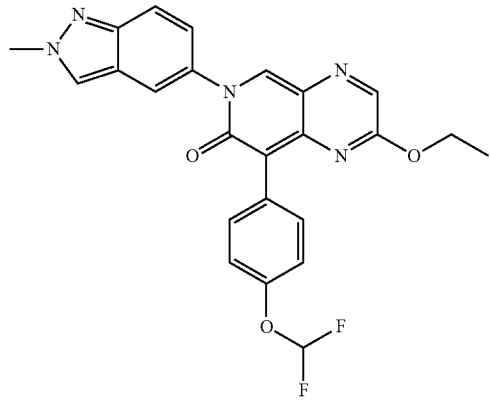<br>8-(4-(difluoromethoxy)phenyl)-2-ethoxy-6-(2-methyl-2H-indazol-5-yl)pyrido[3,4-b]pyrazin-7(6H)-one | LC-MS (ESI): m/z 464 [M + H]+.<br>$^1$H NMR (400 MHz, DMSO-d$_6$) δ 8.78 (s, 1H), 8.50 (s, 1H), 8.14 (s, 1H), 7.92 (dd, J = 2.0, 0.8 Hz, 1H), 7.74-7.66 (m, 3H), 7.35 (dd, J = 9.1, 2.1 Hz, 1H), 7.30 (t, $J_{HF}$ = 74.3 Hz, 1H), 7.18 (d, J = 8.7 Hz, 2H), 4.32 (q, J = 7.0 Hz, 2H), 4.23 (s, 3H), 1.33 (t, J = 7.0 Hz, 3H). |
| 146-A | 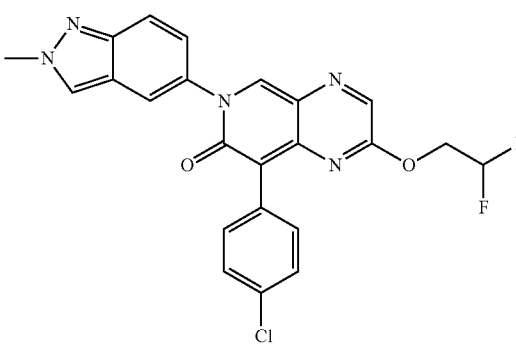<br>8-(4-chlorophenyl)-2-(2,2-difluoroethoxy)-6-(2-methyl-2H-indazol-5-yl)pyrido[3,4-b]pyrazin-7(6H)-one | LC-MS (ESI): m/z 468 [M + H]+.<br>$^1$H NMR (400 MHz, DMSO-d$_6$) δ 8.89 (s, 1H), 8.51 (s, 1H), 8.27 (s, 1H), 7.94 (d, J = 2.0 Hz, 1H), 7.71 (d, J = 9.1 Hz, 1H), 7.68 (d, J = 8.6 Hz, 2H), 7.44 (d, J = 8.6 Hz, 2H), 7.36 (dd, J = 9.1, 2.1 Hz, 1H), 6.42 (tt, $J_{HF}$ = 54.2, J = 3.2 Hz, 1H), 4.58 (td, $J_{HF}$ = 15.2, J = 3.2 Hz, 2H), 4.23 (s, 3H). |

| Example | Structure | Characterization |
|---|---|---|
| 147-A | 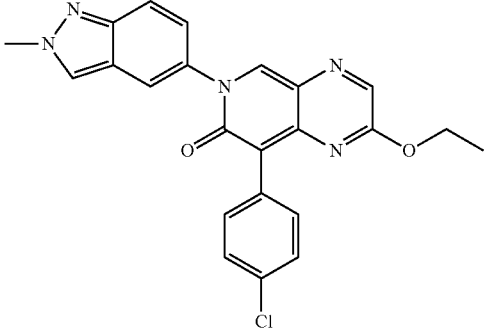<br>8-(4-chlorophenyl)-2-ethoxy-6-(2-methyl-2H-indazol-5-yl)pyrido[3,4-b]pyrazin-7(6H)-one | LC-MS (ESI): m/z 432 [M + H]+.<br>$^1$H NMR (400 MHz, Chloroform-d) δ 8.38 (s, 1H), 7.99 (d, J = 11.4 Hz, 2H), 7.81 (d, J = 9.1 Hz, 1H), 7.75 (d, J = 1.9 Hz, 1H), 7.66 (d, J = 8.5 Hz, 2H), 7.37 (dd, J = 8.7, 1.9 Hz, 3H), 4.37 (q, J = 7.1 Hz, 2H), 4.27 (s, 3H), 1.39 (t, J = 7.1 Hz, 3H). |
| 148-A | 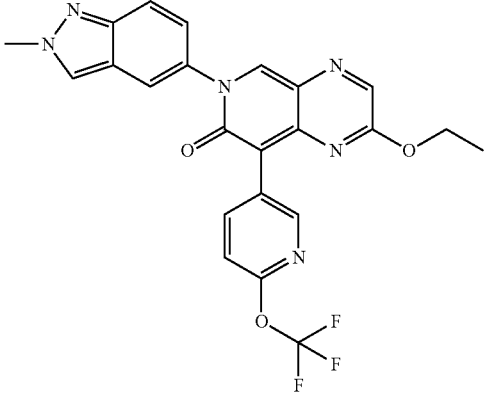<br>2-ethoxy-6-(2-methyl-2H-indazol-5-yl)-8-(6-(trifluoromethoxy)pyridin-3-yl)pyrido[3,4-b]pyrazin-7(6H)-one | LC-MS (ESI): m/z 483 [M + H]+.<br>$^1$H NMR (400 MHz, DMSO-d$_6$) δ 8.89 (d, J = 0.5 Hz, 1H), 8.63 (d, J = 2.3 Hz, 1H), 8.52 (s, 1H), 8.29 (dd, J = 8.5, 2.4 Hz, 1H), 8.19 (s, 1H), 7.94 (dd, J = 2.1, 0.8 Hz, 1H), 7.72 (dt, J = 9.1, 0.9 Hz, 1H), 7.40-7.30 (m, 2H), 4.35 (q, J = 7.0 Hz, 2H), 4.23 (s, 3H), 1.33 (t, J = 7.1 Hz, 3H). |
| 149-A | 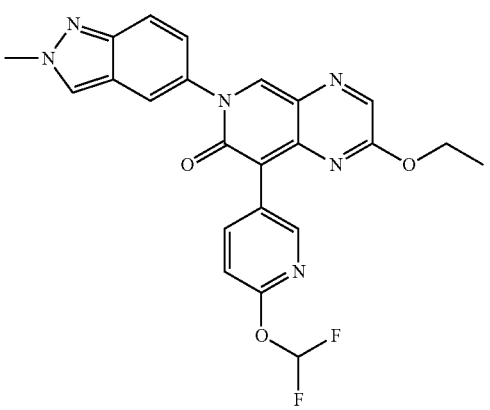<br>8-(6-(difluoromethoxy)pyridin-3-yl)-2-ethoxy-6-(2-methyl-2H-indazol-5-yl)pyrido[3,4-b]pyrazin-7(6H)-one | LC-MS (ESI): m/z 465 [M + H]+.<br>$^1$H NMR (400 MHz, DMSO-d$_6$) δ 8.84 (d, J = 0.6 Hz, 1H), 8.54-8.48 (m, 2H), 8.22-8.14 (m, 2H), 7.93 (dd, J = 2.0, 0.8 Hz, 1H), 7.77 (t, J$_{HF}$ = 73.0 Hz, 1H), 7.71 (dt, J = 9.2, 0.9 Hz, 1H), 7.36 (dd, J = 9.1, 2.0 Hz, 1H), 7.12 (dd, J = 8.6, 0.7 Hz, 1H), 4.33 (q, J = 7.1 Hz, 2H), 4.23 (s, 3H), 1.33 (t, J = 7.1 Hz, 3H). |

-continued

| Example | Structure | Characterization |
|---|---|---|
| 150-A | 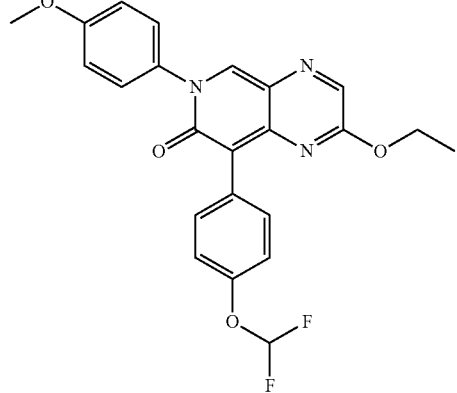<br>8-(4-(difluoromethoxy)phenyl)-2-ethoxy-6-(4-methoxyphenyl)pyrido[3,4-b]pyrazin-7(6H)-one | LC-MS (ESI): m/z 440 [M + H]+.<br>$^1$H NMR (400 MHz, DMSO-$d_6$)<br>δ 8.69 (s, 1H), 8.13 (s, 1H), 7.67 (d, J = 8.6 Hz, 2H), 7.53-7.45 (m, 2H), 7.39 (t, $J_{HF}$ = 73.5 Hz, 1H), 7.18 (d, J = 8.5 Hz, 2H), 7.10 (d, J = 8.9 Hz, 2H), 4.30 (q, J = 7.0 Hz, 2H), 3.84 (s, 3H), 1.32 (t, J = 7.1 Hz, 3H). |

Example 275: Biochemical Assay

Mat2A protein was expressed by recombinant baculovirus in SF9 infected cells using the Bac to Bac system cloned into the pFASTBAC1 vector (Invitrogen, Carlsbad, Calif.). Recombinant MAT2A was isolated from the cell lysate of 150 g of infected cells using HP Ni sepharose column chromatography. Recombinant MAT2A homodimer was eluted with 250 and 500 mM imidazole, and fractions containing MAT2A were identified by sodium dodecyl sulfate polyacrylamide gel electrophoresis and pooled.

For determination of the inhibitory potency of compounds against the MAT2A homodimer, protein was diluted to 4 g/mL in assay buffer (50 mM Tris, pH 8.0, 50 mM KCl, 15 mM MgCl2, 0.3 mM EDTA, 0.005% [w/v] bovine serum albumin [BSA]). Test compound was prepared in 100% dimethyl sulfoxide (DMSO) at 50× the desired final concentration. A 1 L volume of compound dilution was added to 40 μL of enzyme dilution and the mixture was allowed to equilibrate for 60 minutes at 25° C. The enzymatic assay was initiated by the addition of 10 μL of substrate mix (500 μM ATP, pH 7.0, 400 μM L-methionine in 1× assay buffer), and the mixture was incubated for a further 60 minutes at 25° C. The reaction was halted and the liberated phosphate released by the enzyme in stoichiometric amounts by the production of S-adenosyl methionine (SAM) was measured using the PiColorLock Gold kit (Innova Biosciences, UK). Absolute product amounts were determined by comparison to a standard curve of potassium phosphate buffer, pH 8.0.

Specific compounds disclosed herein were tested in the foregoing assay and they were determined to inhibit MAT2A with an $IC_{50}$ according to the following scores: (A) less than 100 nM, (B) between 100 nM and 1 μM, and (C) between 1 μM and 10 μM, as shown in Table 4 below.

Example 276: Cellular Assay of Target Engagement (SAM)

Measurement of MAT2A activity in cells was made by direct quantitation of the abundance of the product of its enzymatic activity, SAM. Cancer cells were treated with candidate MAT2A inhibitors for a suitable incubation period, and the cells were then lysed using a reagent which quenched any further enzyme activity. Soluble metabolites including SAM were collected and SAM itself was directly measured from the lysate using quantitative LC-MS/MS.

A typical assay was performed using an HCT116 human colon carcinoma cell line which was genetically engineered to delete the MTAP gene (commercially available from Horizon Discovery). This cell line was utilized because it was determined that loss of the MTAP gene predicts sensitivity to MAT2A inhibitors. Cells were plated in 96-well dishes at appropriate cell density. Following 24 hours, cells were then treated with the candidate MAT2A inhibitor. Prior to addition to cells, the compound was first serially diluted in 100% DMSO, typically as a 3-fold serial dilution starting at 500× top dose with 10 dose points including DMSO only control. Compound was then transferred to a working stock plate in cell culture media by adding 5 μl of compound in DMSO to 495 μl of cell culture media. This working stock was then added to cells via a further 5-fold dilution, by adding 25 μl of working stock to 100 μl of cells in culture media. Following compound addition, cells were incubated at 37° C./5% $CO_2$ for 72 hrs.

To quantitate SAM levels following compound treatment, cells were gently washed once in Ammonium Carbonate buffer (75 mM at pH 7.4), placed on dry ice, and lysed with metabolite extraction buffer (80% cold methanol and 20% water (v/v) with acetic acid at 1 M final concentration with 200 ng/mL deuterated d3-SAM as internal control). Following centrifugation at 4° C. at 3,200 rpm for 30 minutes, the supernatant was collected and stored at −80° C. until analysis by Liquid Chromatography with tandem Mass Spectrometry (LC-MS/MS). LC-MS/MS analysis was performed using an API6500 Mass Spectrometer (Sciex, Framingham, Mass., USA) operating in positive ion spray mode and equipped with a Waters UPLC Acquity (Waters, Milford, Mass., USA) BEH Amide column. Multiple Reaction Monitoring data was acquired for SAM and the d3-SAM standard, using a mass transition pair at m/z 399.2→250.1 and 402.2→250.1, respectively. In a typical LC-MS/MS analysis, the initial flow rate was 0.5 ml/min of 25% mobile phase A (acetonitrile and water at 5:95 (v/v) with 1% formic acid and 10 mM ammonium acetate) and 75% mobile phase B (acetonitrile and water at 95:5 (v/v) with 1% formic acid and 10 mM ammonium acetate), 0.2-0.5 minutes with 75%-35% mobile phase B, 25%-65% mobile phase A, at 0.5 min 65% mobile phase A and 35% mobile phase B, 1.0-1.1 minutes with 35%-75% mobile phase B, 65%-25% mobile phase A, at 1.1 min 25% mobile phase A and 75% mobile phase B with a total run time of 1.5 minutes.

Specific compounds disclosed herein were tested in the foregoing assay and they were determined to inhibit SAM with an $IC_{50}$ according to the following scores: (A) less than 100 nM (>60% maximum inhibition), (B) between 100 nM and 1 μM (>60% maximum inhibition), and (NT) not tested, as shown in Table 4 below.

Example 277: Assay for Inhibition of Cellular Proliferation

Test compound impact on cancer cell growth was assessed by treating cancer cells with compound for 4 days and then measuring proliferation using an ATP-based cell proliferation readout (Cell Titer Glo, Promega Corporation). In a typical assay an isogenic pair of HCT116 human colon carcinoma cell lines which vary only in MTAP deletion status (HCT116 MTAP+/+ and HCT116 MTAP-/-) were plated in 96-well dishes at appropriate cell density. Following 24 hours, cells were then treated with the candidate MAT2A inhibitor. Prior to addition to cells, the compound was first serially diluted in 100% DMSO, typically as a 3-fold serial dilution starting at 500× top dose with 10 dose points including DMSO only control. Compound was then transferred to a working stock plate in cell culture media by adding 5 μl of compound in DMSO to 495 μl of cell culture media. This working stock was then added to cells via a further 5-fold dilution, by adding 25 μl of working stock to 100 μl of cells in culture media. Following compound addition, cells were incubated at 37° C./5% $C_{O2}$ for 4 days.

To measure inhibition of cellular proliferation, cells were allowed to equilibrate to room temperature for 30 minutes, and were then treated with 125 μl of Cell Titer Glo reagent. The plate was then covered with aluminum foil and shaken for 15 minutes to ensure complete mixing and full cell lysis. Luminescent signal was then measured using a plate-based luminometer Veritas version 1.9.2 using ATP standard curve to confirm assay reproducibility from run to run. This luminescence measure was converted to a proliferation index by subtracting from each data point the ATP luminescence signal measured from a bank (no cells) well and dividing by the ATP luminescence signal measured in 0.2% DMSO control well adjusted for signal in blank well. Compound activity was then represented as a percentage change in proliferation relative to a within-plate DMSO control against $\log_{10}$ of compound concentration in molar (M) units.

Specific compounds disclosed herein were tested in the foregoing assay and they were determined to inhibit cellular proliferation with an $IC_{50}$ according to the following scores: (A) less than 100 nM (>30% maximum inhibition for MTAP -/-; >10% maximum inhibition for MTAP +/+), (B) between 100 nM and 10 M (>30% maximum inhibition for MTAP -/-; >10% maximum inhibition for MTAP +/+), (C) greater than 10 M, and (NT) not tested, as shown in Table 4 below.

TABLE 4

| Compound No. | Enzyme Inhibition (Example 275) | Cell 72 h SAM Inhibition (MTAP -/-; Example 276) | 4 Day Relative Growth Inhibition (MTAP -/-; Example 277) | 4 Day Relative Growth Inhibition (MTAP +/+; Example 277) |
|---|---|---|---|---|
| 101 | B | NT | NT | NT |
| 102 | C | NT | NT | NT |
| 103 | B | NT | NT | NT |
| 104 | C | NT | NT | NT |
| 105 | C | NT | NT | NT |
| 106 | C | NT | NT | NT |
| 107 | C | NT | NT | NT |
| 108 | C | NT | NT | NT |
| 109 | B | NT | NT | NT |
| 110 | B | NT | NT | NT |
| 111 | C | NT | NT | NT |
| 112 | B | NT | NT | NT |
| 113 | B | NT | NT | NT |
| 114 | B | NT | NT | NT |
| 115 | B | NT | NT | NT |
| 116 | C | NT | NT | NT |
| 117 | C | NT | NT | NT |
| 118 | C | NT | NT | NT |
| 119 | C | NT | NT | NT |
| 120 | C | NT | NT | NT |
| 121 | B | NT | NT | NT |
| 122 | B | NT | NT | NT |
| 123 | A | A | A | B |
| 124 | A | A | A | C |
| 125 | A | NT | NT | NT |
| 126 | C | NT | NT | NT |
| 127 | A | A | A | C |
| 128 | A | NT | NT | NT |
| 129 | A | B | B | C |
| 130 | A | NT | NT | NT |
| 131 | A | NT | NT | NT |
| 132 | A | A | A | C |
| 133 | A | A | A | C |
| 134 | A | NT | NT | NT |
| 135 | A | A | A | B |
| 136 | B | NT | NT | NT |
| 137 | A | B | B | C |
| 138 | B | NT | NT | NT |
| 139 | A | A | B | C |
| 140 | B | NT | NT | NT |
| 141 | A | A | A | C |
| 142 | B | NT | NT | NT |
| 143 | A | B | B | C |
| 144 | A | B | B | C |
| 145 | A | A | A | C |
| 146 | B | NT | NT | NT |
| 147 | A | B | B | C |
| 148 | A | A | A | B |
| 149 | A | NT | NT | NT |
| 150 | A | A | B | B |
| 151 | A | A | A | B |
| 152 | A | A | A | C |
| 153 | A | A | A | C |
| 154 | A | NT | NT | NT |
| 155 | A | B | B | B |
| 156 | A | A | A | C |
| 157 | A | A | B | C |
| 158 | A | A | A | C |
| 159 | A | A | A | B |
| 160 | A | A | A | C |
| 161 | A | A | A | C |
| 162 | A | NT | NT | NT |
| 163 | C | NT | NT | NT |
| 164 | A | NT | NT | NT |
| 165 | A | NT | NT | NT |
| 166 | A | A | A | C |
| 167 | A | B | B | C |
| 168 | A | A | A | C |
| 169 | A | A | A | C |
| 170 | A | NT | NT | NT |
| 171 | A | A | A | C |
| 172 | A | A | A | C |
| 173 | A | NT | NT | NT |

TABLE 4-continued

| Compound No. | Enzyme Inhibition (Example 275) | Cell 72 h SAM Inhibition (MTAP −/−; Example 276) | 4 Day Relative Growth Inhibition (MTAP −/−; Example 277) | 4 Day Relative Growth Inhibition (MTAP +/+; Example 277) |
|---|---|---|---|---|
| 174 | A | NT | NT | NT |
| 175 | A | NT | NT | NT |
| 176 | B | NT | NT | NT |
| 177 | A | A | B | C |
| 178 | A | A | B | B |
| 179 | A | B | B | C |
| 180 | A | A | A | C |
| 181 | A | A | B | C |
| 182 | A | A | B | C |
| 183 | A | B | B | C |
| 184 | A | NT | NT | NT |
| 185 | C | NT | NT | NT |
| 186 | B | NT | NT | NT |
| 187 | C | NT | NT | NT |
| 188 | A | A | B | C |
| 189 | A | A | B | B |
| 190 | A | NT | NT | NT |
| 191 | A | NT | NT | NT |
| 192 | A | A | B | C |
| 193 | A | B | B | C |
| 194 | B | NT | NT | NT |
| 195 | A | A | A | C |
| 196 | A | NT | NT | NT |
| 197 | B | NT | NT | NT |
| 198 | A | B | B | C |
| 199 | C | NT | NT | NT |
| 200 | A | B | B | B |
| 201 | B | NT | NT | NT |
| 202 | A | B | B | C |
| 203 | A | B | C | C |
| 204 | B | NT | NT | NT |
| 205 | A | A | B | C |
| 206 | A | B | B | B |
| 207 | B | NT | NT | NT |
| 208 | A | NT | NT | NT |
| 209 | A | A | A | C |
| 210 | A | A | A | C |
| 211 | A | A | A | C |
| 212 | A | A | A | C |
| 213 | A | A | A | C |
| 214 | A | NT | NT | NT |
| 215 | A | A | A | B |
| 216 | A | A | A | B |
| 217 | A | A | B | C |
| 218 | A | A | A | B |
| 219 | A | A | A | B |
| 220 | A | A | A | B |
| 221 | A | A | B | C |
| 222 | A | A | B | C |
| 223 | A | B | B | C |
| 224 | A | B | C | C |
| 225 | B | A | B | B |
| 226 | A | A | A | B |
| 227 | A | A | A | B |
| 228 | A | A | A | B |
| 229 | A | A | A | B |
| 230 | A | A | A | B |
| 231 | A | A | B | C |
| 232 | A | A | A | C |
| 233 | A | A | A | C |
| 234 | A | A | A | C |
| 235 | A | A | A | C |
| 236 | A | A | A | C |
| 237 | A | A | A | C |
| 238 | A | NT | NT | NT |
| 239 | A | A | A | B |
| 240 | A | A | A | C |
| 241 | A | A | A | B |
| 242 | A | A | A | C |
| 243 | A | A | A | C |
| 244 | A | A | A | B |
| 245 | A | A | B | C |
| 246 | A | B | B | B |
| 247 | A | A | A | B |
| 248 | A | A | A | B |
| 249 | A | A | B | B |
| 250 | A | A | A | B |
| 251 | A | A | A | B |
| 252 | A | A | B | B |
| 253 | A | A | A | B |
| 254 | A | A | A | C |
| 255 | A | A | A | C |
| 256 | A | A | B | B |
| 257 | A | A | B | B |
| 258 | A | A | B | B |
| 259 | A | A | A | C |
| 260 | A | A | A | C |
| 261 | A | NT | NT | NT |
| 262 | A | A | B | C |
| 263 | A | NT | NT | NT |
| 264 | A | A | B | B |
| 265 | A | A | A | C |
| 266 | B | NT | NT | NT |
| 267 | A | NT | NT | NT |
| 268 | A | B | B | C |
| 269 | A | A | B | C |
| 270 | A | A | A | C |
| 271 | A | NT | NT | NT |
| 272 | A | A | B | C |
| 273 | A | NT | NT | NT |
| 274 | A | NT | NT | NT |
| 101-A | A | A | A | C |
| 102-A | A | A | A | B |
| 103-A | A | A | A | C |
| 104-A | A | A | B | B |
| 105-A | A | A | A | B |
| 106-A | A | A | B | C |
| 107-A | A | A | A | B |
| 108-A | A | A | A | B |
| 109-A | A | A | A | B |
| 110-A | A | A | A | B |
| 111-A | A | A | A | B |
| 112-A | A | A | A | B |
| 113-A | A | A | A | B |
| 114-A | A | A | A | B |
| 115-A | A | A | A | B |
| 116-A | A | A | A | C |
| 117-A | A | A | A | B |
| 118-A | A | A | A | B |
| 119-A | A | A | A | B |
| 120-A | A | A | A | B |
| 121-A | A | A | B | B |
| 122-A | A | A | A | B |
| 123-A | A | A | A | B |
| 124-A | A | A | B | B |
| 125-A | A | A | A | B |
| 126-A | A | A | A | B |
| 127-A | A | B | A | B |
| 128-A | A | A | A | B |
| 129-A | A | A | B | B |
| 130-A | A | A | A | B |
| 131-A | A | A | B | B |
| 132-A | A | A | A | B |
| 133-A | A | A | A | P |
| 134-A | A | A | A | C |
| 135-A | B | NT | NT | NT |
| 136-A | A | NT | NT | NT |
| 137-A | A | A | A | B |
| 138-A | A | B | B | B |
| 139-A | A | A | A | B |
| 140-A | A | A | A | C |
| 141-A | A | A | A | B |
| 142-A | A | B | B | C |
| 143-A | A | A | A | B |
| 144-A | A | A | B | B |
| 145-A | A | A | A | B |

TABLE 4-continued

| Compound No. | Enzyme Inhibition (Example 275) | Cell 72 h SAM Inhibition (MTAP −/−; Example 276) | 4 Day Relative Growth Inhibition (MTAP −/−; Example 277) | 4 Day Relative Growth Inhibition (MTAP +/+; Example 277) |
|---|---|---|---|---|
| 146-A | A | A | A | B |
| 147-A | A | A | A | C |
| 148-A | A | A | B | B |
| 149-A | A | A | B | B |
| 150-A | A | A | B | B |

Additional compounds as set forth in Table 5 below exhibit enzyme inhibition greater than 10 μm (Example 275) or less than 50% inhibition at maximum concentration.

TABLE 5

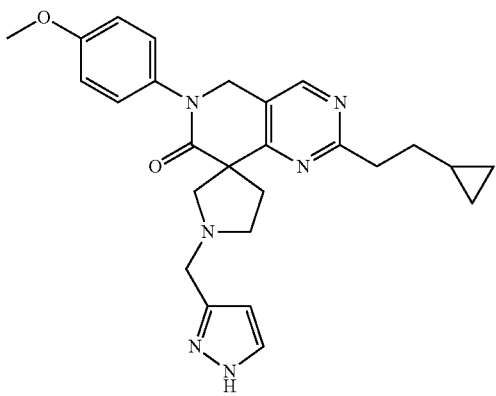 [SMILES: COc1ccc(N2Cc3cnc(CCC4CC4)nc3C3(CCN(Cc4cc[nH]n4)C3)C2=O)cc1]

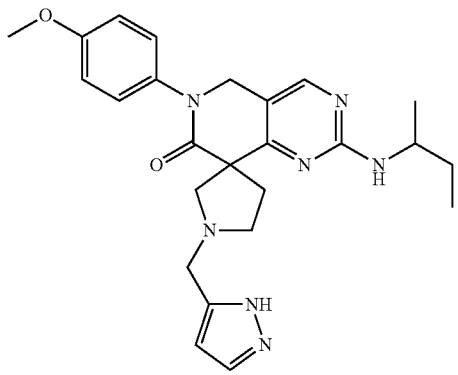 [SMILES: CCC(C)Nc1ncc2c(n1)C1(CCN(Cc3ccn[nH]3)C1)C(=O)N(c1ccc(OC)cc1)C2]

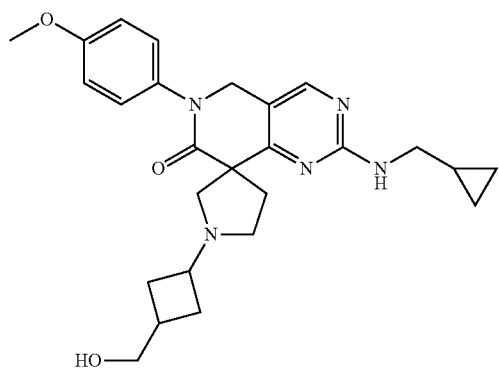 [SMILES: COc1ccc(N2Cc3cnc(NCC4CC4)nc3C3(CCN(C4CC(CO)C4)C3)C2=O)cc1]

TABLE 5-continued
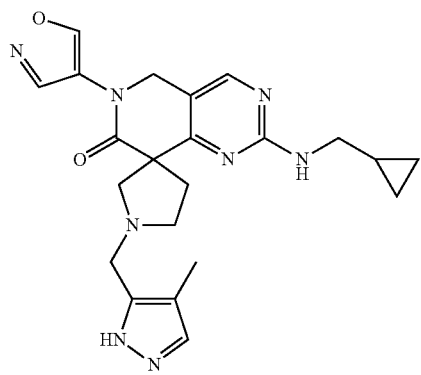 [SMILES: Cc1cn[nH]c1CN1CCC2(C1)C(=O)N(/C(C=N)=C/O)Cc1cnc(NCC3CC3)nc12]
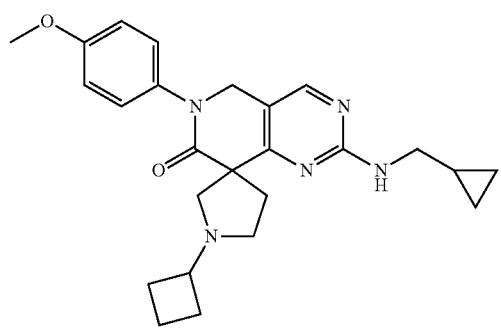 [SMILES: COc1ccc(N2Cc3cnc(NCC4CC4)nc3C3(CCN(C4CCC4)C3)C2=O)cc1]
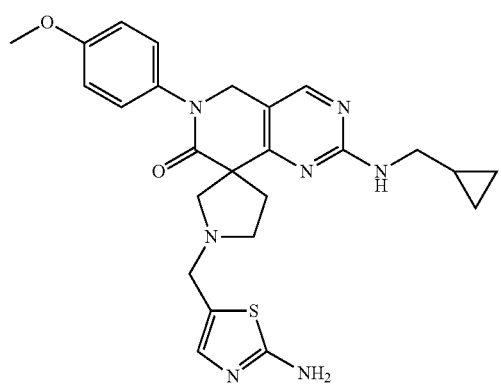 [SMILES: COc1ccc(N2Cc3cnc(NCC4CC4)nc3C3(CCN(Cc4cnc(N)s4)C3)C2=O)cc1]
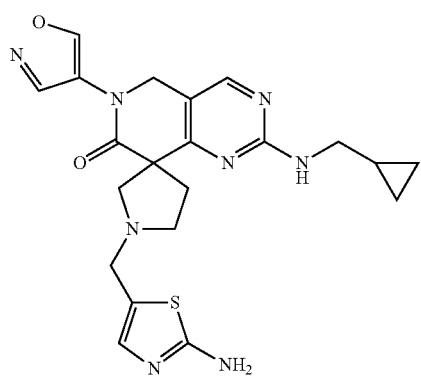 [SMILES: N=C/C(=C\O)N1Cc2cnc(NCC3CC3)nc2C2(CCN(Cc3cnc(N)s3)C2)C1=O]

TABLE 5-continued
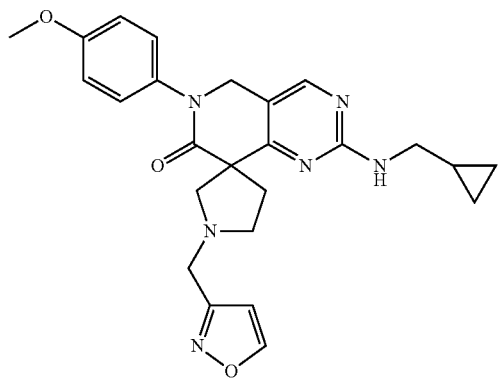 [SMILES: COc1ccc(N2Cc3cnc(NCC4CC4)nc3C3(CCN(Cc4ccon4)C3)C2=O)cc1]
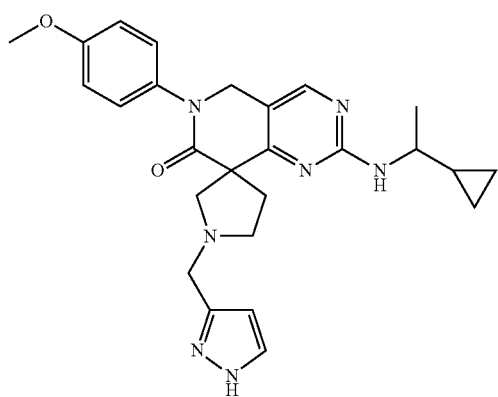 [SMILES: COc1ccc(N2Cc3cnc(NC(C)C4CC4)nc3C3(CCN(Cc4cc[nH]n4)C3)C2=O)cc1]
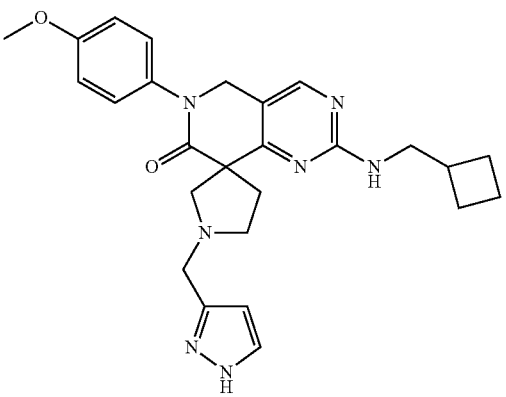 [SMILES: COc1ccc(N2Cc3cnc(NCC4CCC4)nc3C3(CCN(Cc4cc[nH]n4)C3)C2=O)cc1]
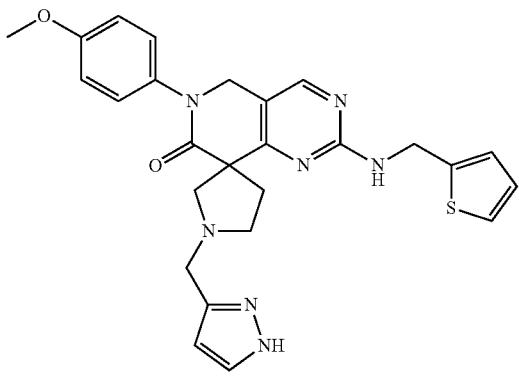 [SMILES: COc1ccc(N2Cc3cnc(NCc4cccs4)nc3C3(CCN(Cc4cc[nH]n4)C3)C2=O)cc1]

TABLE 5-continued
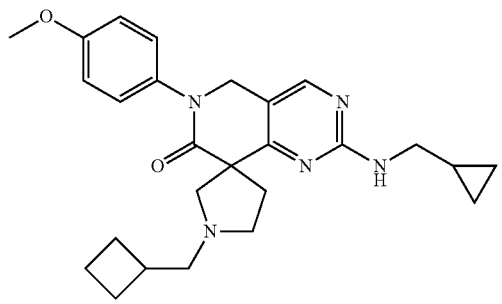 [SMILES: COc1ccc(N2Cc3cnc(NCC4CC4)nc3C3(CCN(CC4CCC4)C3)C2=O)cc1]
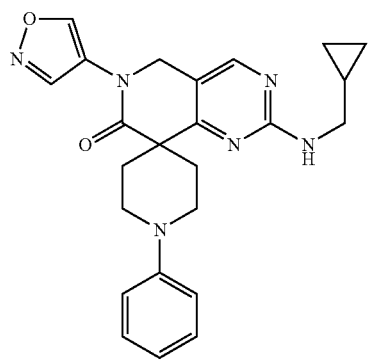 [SMILES: O=C1N(c2cnoc2)Cc2cnc(NCC3CC3)nc2C12CCN(c1ccccc1)CC2]
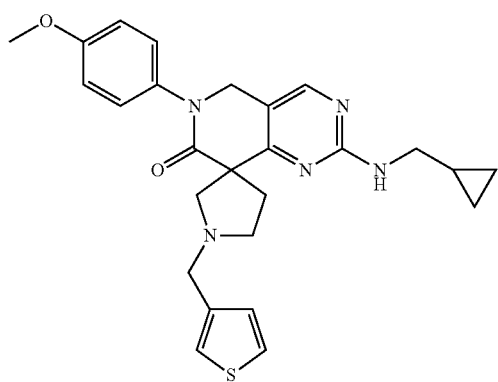 [SMILES: COc1ccc(N2Cc3cnc(NCC4CC4)nc3C3(CCN(Cc4ccsc4)C3)C2=O)cc1]
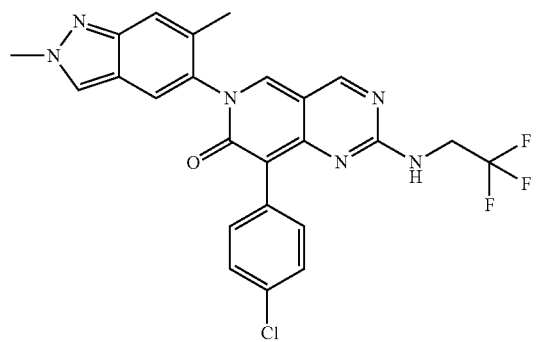 [SMILES: Cc1cc2nn(C)cc2cc1-n1cc2cnc(NCC(F)(F)F)nc2c(-c2ccc(Cl)cc2)c1=O]

TABLE 5-continued
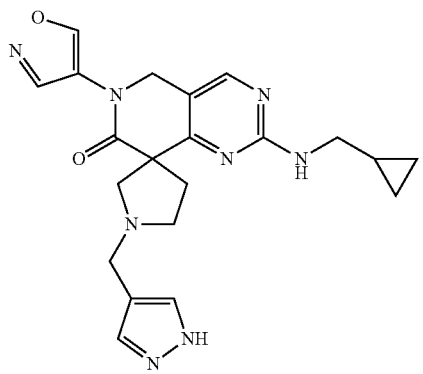 [SMILES: N=C/C(=C\O)N1Cc2cnc(NCC3CC3)nc2C2(CCN(Cc3cn[nH]c3)C2)C1=O]
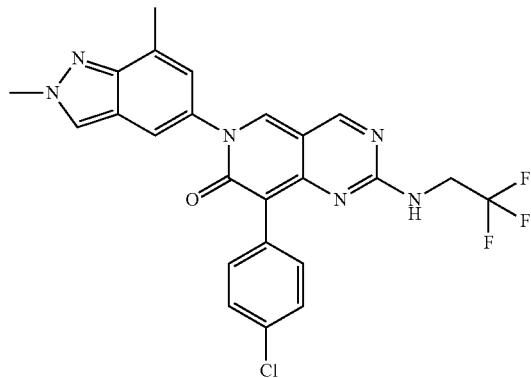 [SMILES: Cc1cc(-n2cc3cnc(NCC(F)(F)F)nc3c(-c3ccc(Cl)cc3)c2=O)cc2cn(C)nc12]
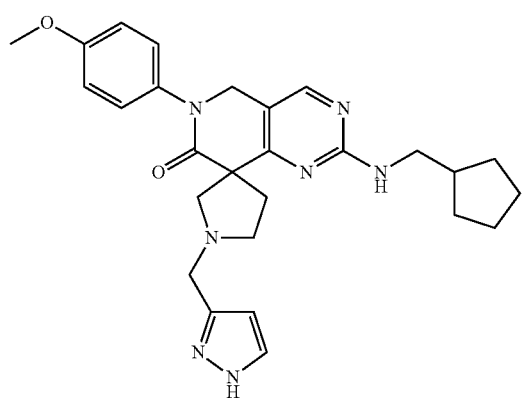 [SMILES: COc1ccc(N2Cc3cnc(NCC4CCCC4)nc3C3(CCN(Cc4cc[nH]n4)C3)C2=O)cc1]
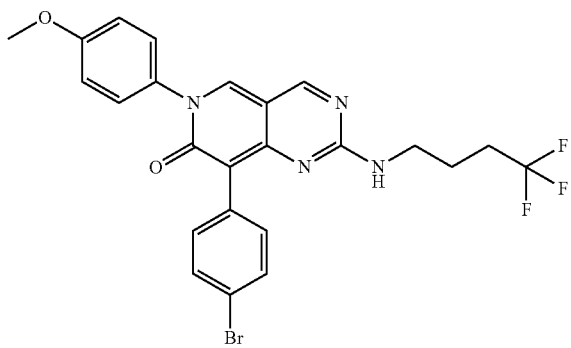 [SMILES: COc1ccc(-n2cc3cnc(NCCCC(F)(F)F)nc3c(-c3ccc(Br)cc3)c2=O)cc1]

TABLE 5-continued
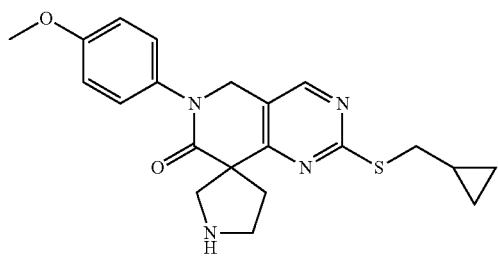 [SMILES: COc1ccc(N2Cc3cnc(SCC4CC4)nc3C3(CCNC3)C2=O)cc1]
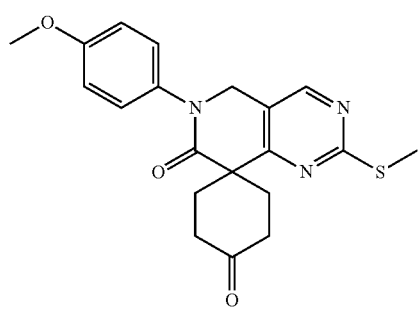
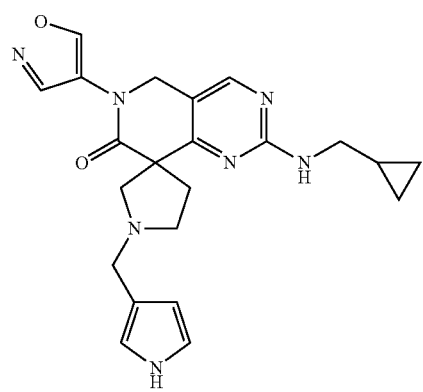
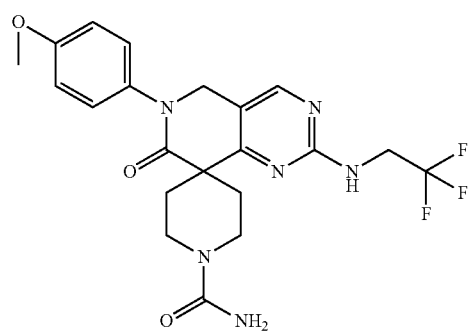 [SMILES: COc1ccc(N2Cc3cnc(NCC(F)(F)F)nc3C3(CCN(C(N)=O)CC3)C2=O)cc1]

TABLE 5-continued
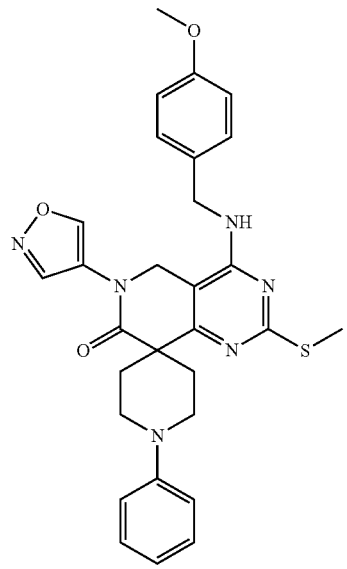 [SMILES: COc1ccc(CNc2nc(SC)nc3c2CN(c2cnoc2)C(=O)C32CCN(c3ccccc3)CC2)cc1]
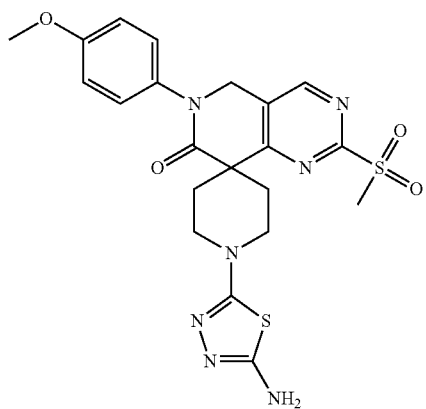 [SMILES: COc1ccc(N2Cc3cnc(S(C)(=O)=O)nc3C3(CCN(c4nnc(N)s4)CC3)C2=O)cc1]
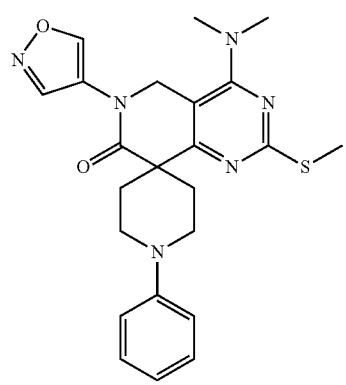 [SMILES: CSc1nc(N(C)C)c2c(n1)C1(CCN(c3ccccc3)CC1)C(=O)N(c1cnoc1)C2]

TABLE 5-continued
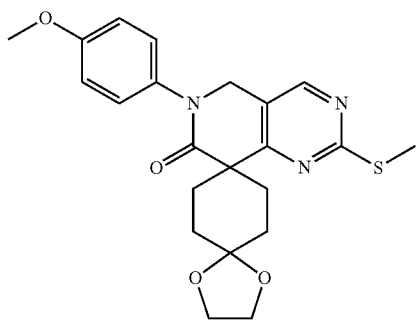
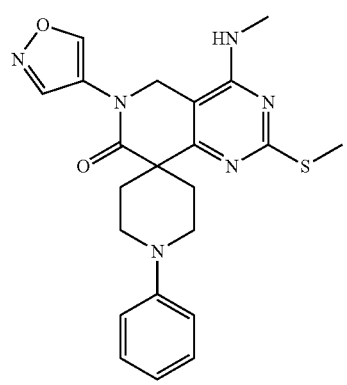 [SMILES: CNc1nc(SC)nc2c1CN(c1cnoc1)C(=O)C21CCN(c2ccccc2)CC1]
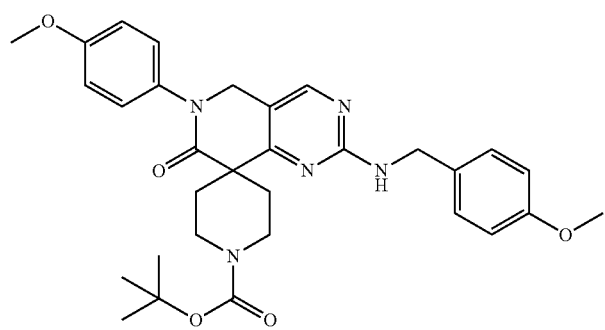
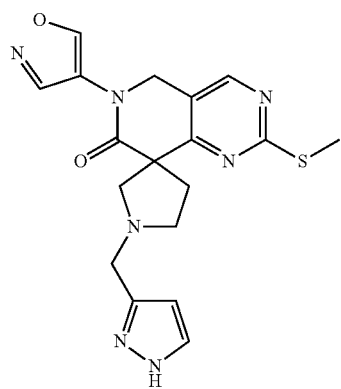 [SMILES: CSc1ncc2c(n1)C1(CCN(Cc3cc[nH]n3)C1)C(=O)N(/C(C=N)=C/O)C2]

TABLE 5-continued
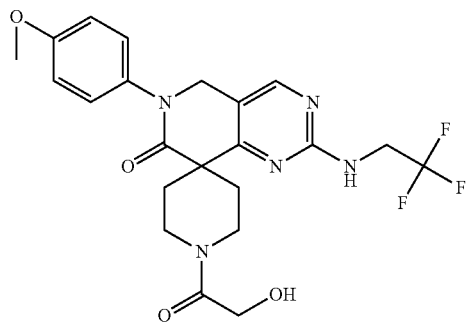 [SMILES: COc1ccc(N2Cc3cnc(NCC(F)(F)F)nc3C3(CCN(C(=O)CO)CC3)C2=O)cc1]
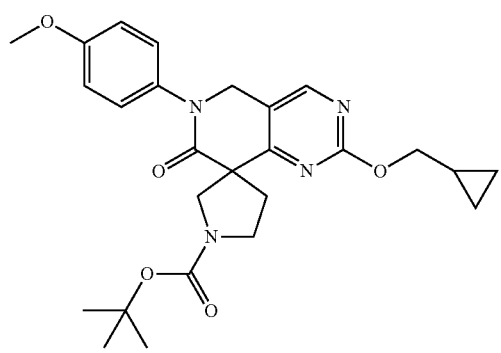 [SMILES: COc1ccc(N2Cc3cnc(OCC4CC4)nc3C3(CCN(C(=O)OC(C)(C)C)C3)C2=O)cc1]
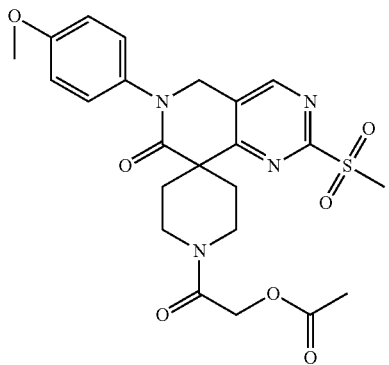 [SMILES: COc1ccc(N2Cc3cnc(S(C)(=O)=O)nc3C3(CCN(C(=O)COC(C)=O)CC3)C2=O)cc1]
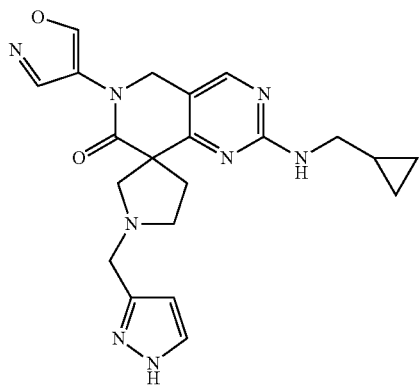 [SMILES: N=C/C(=C\O)N1Cc2cnc(NCC3CC3)nc2C2(CCN(Cc3cc[nH]n3)C2)C1=O]

TABLE 5-continued
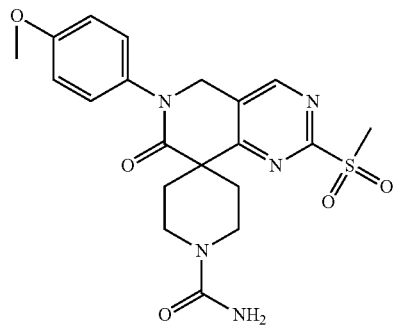 [SMILES: COc1ccc(N2Cc3cnc(S(C)(=O)=O)nc3C3(CCN(C(N)=O)CC3)C2=O)cc1]
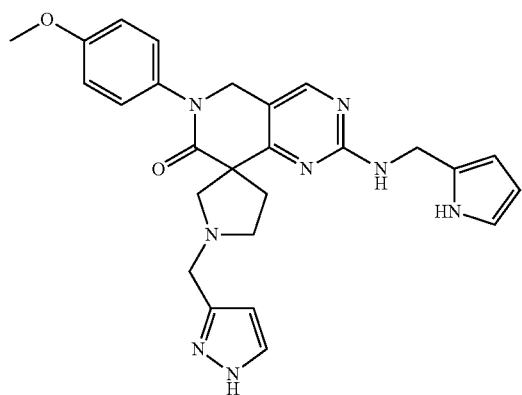 [SMILES: COc1ccc(N2Cc3cnc(NCc4ccc[nH]4)nc3C3(CCN(Cc4cc[nH]n4)C3)C2=O)cc1]
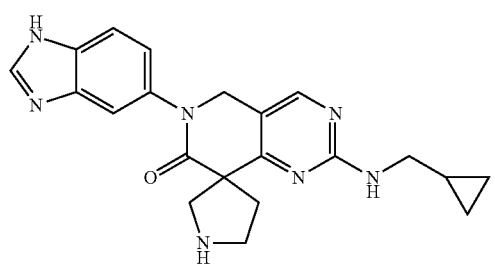 [SMILES: O=C1N(c2ccc3[nH]cnc3c2)Cc2cnc(NCC3CC3)nc2C12CCNC2]
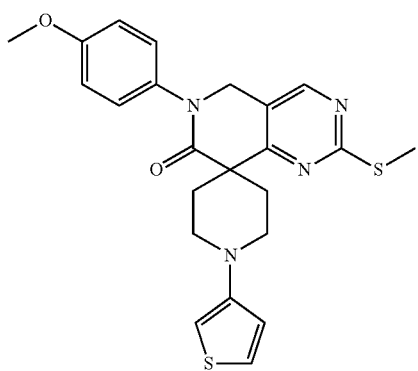

TABLE 5-continued
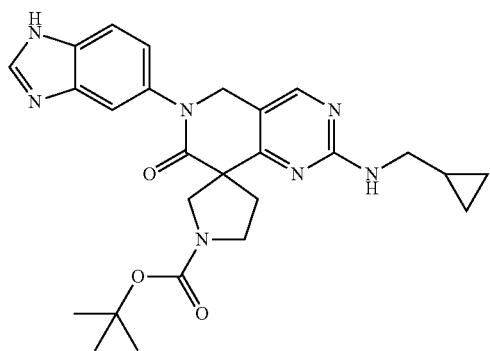 [SMILES: CC(C)(C)OC(=O)N1CCC2(C1)C(=O)N(c1ccc3[nH]cnc3c1)Cc1cnc(NCC3CC3)nc12]
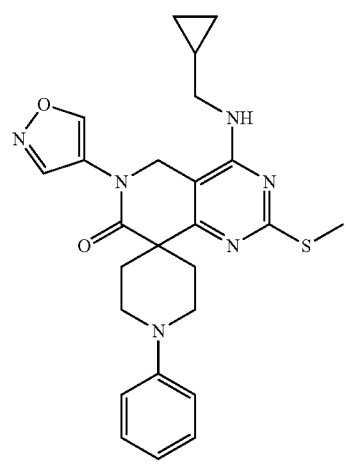 [SMILES: CSc1nc(NCC2CC2)c2c(n1)C1(CCN(c3ccccc3)CC1)C(=O)N(c1cnoc1)C2]
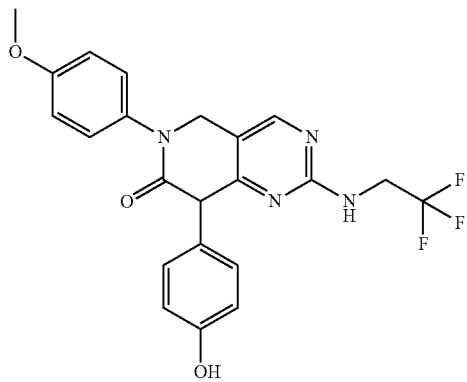 [SMILES: COc1ccc(N2Cc3cnc(NCC(F)(F)F)nc3C(c3ccc(O)cc3)C2=O)cc1]
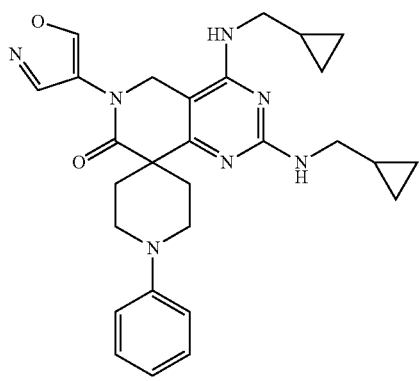 [SMILES: N=C/C(=C\O)N1Cc2c(NCC3CC3)nc(NCC3CC3)nc2C2(CCN(c3ccccc3)CC2)C1=O]

TABLE 5-continued
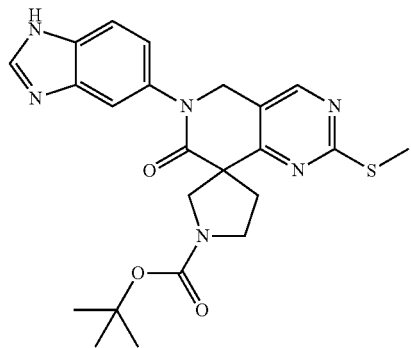 [SMILES: CSc1ncc2c(n1)C1(CCN(C(=O)OC(C)(C)C)C1)C(=O)N(c1ccc3[nH]cnc3c1)C2]
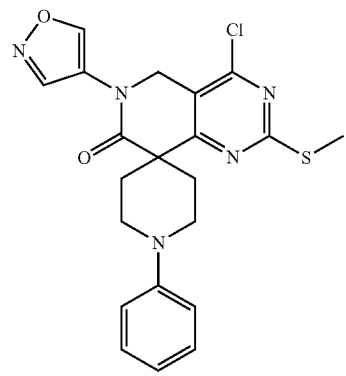 [SMILES: CSc1nc(Cl)c2c(n1)C1(CCN(c3ccccc3)CC1)C(=O)N(c1cnoc1)C2]
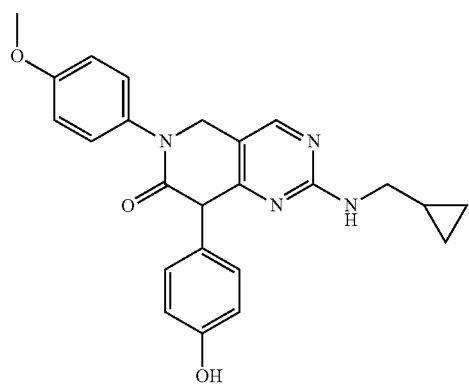 [SMILES: COc1ccc(N2Cc3cnc(NCC4CC4)nc3C(c3ccc(O)cc3)C2=O)cc1]
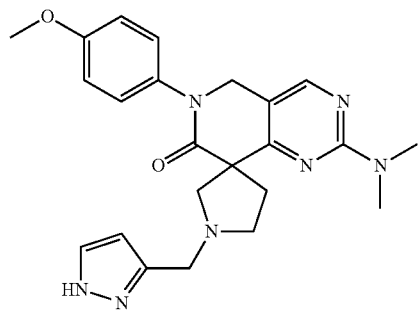

TABLE 5-continued
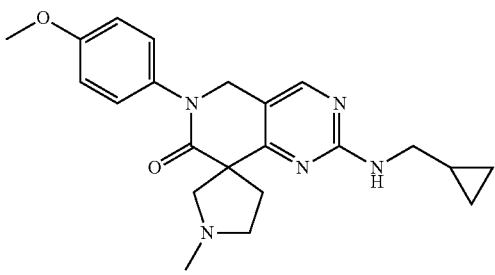 [SMILES: COc1ccc(N2Cc3cnc(NCC4CC4)nc3C3(CCN(C)C3)C2=O)cc1]
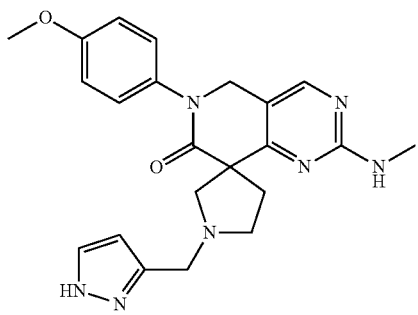
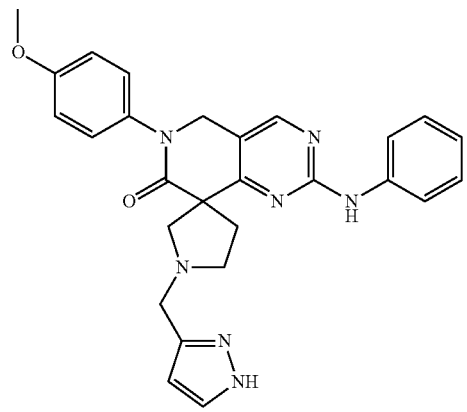 [SMILES: COc1ccc(N2Cc3cnc(Nc4ccccc4)nc3C3(CCN(Cc4cc[nH]n4)C3)C2=O)cc1]
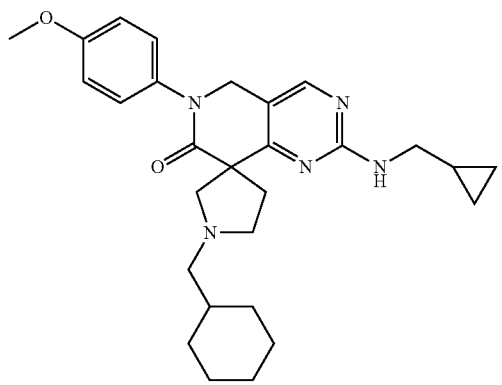 [SMILES: COc1ccc(N2Cc3cnc(NCC4CC4)nc3C3(CCN(CC4CCCCC4)C3)C2=O)cc1]
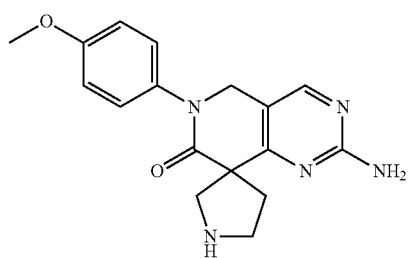 [SMILES: COc1ccc(N2Cc3cnc(N)nc3C3(CCNC3)C2=O)cc1]

TABLE 5-continued
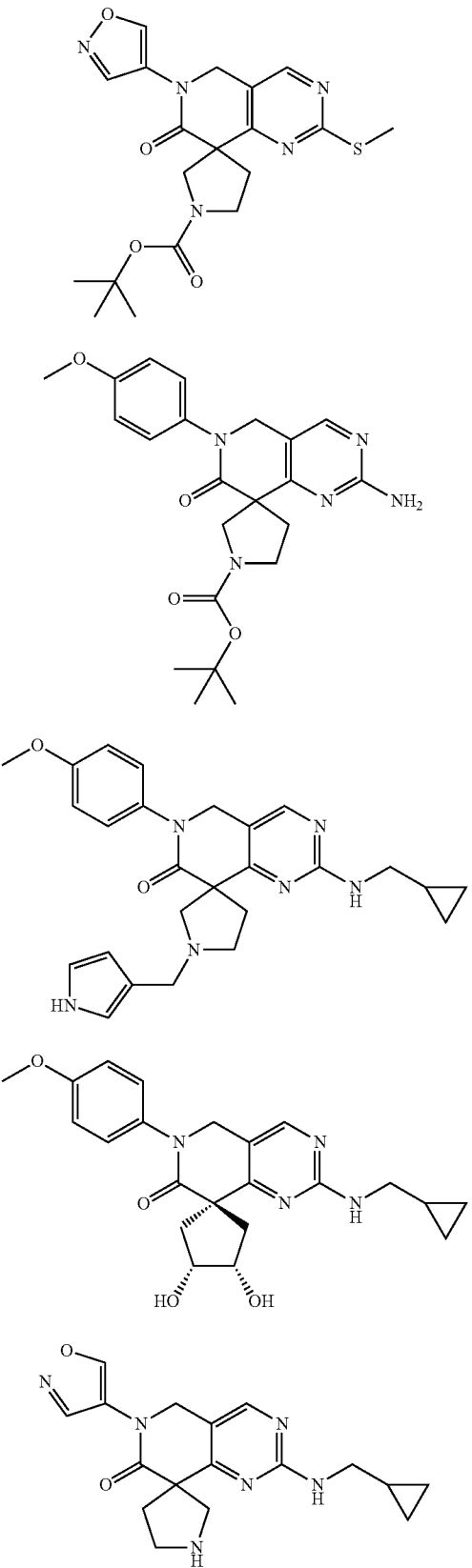

TABLE 5-continued

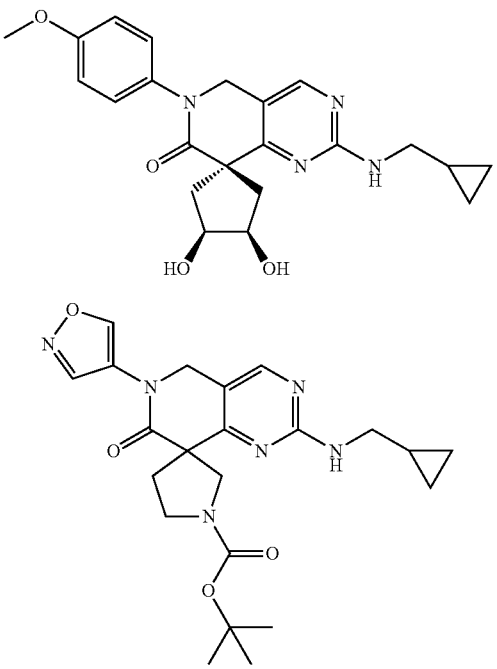

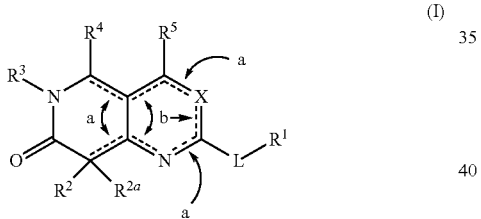

We claim:
1. A compound of Formula I:

$$\text{(I)}$$

[Structure with $R^4$, $R^5$, $R^3$, $R^2$, $R^{2a}$, $R^1$, X, L, a, b positions]

wherein:
X is N or $CR^6$;
L is O, S, NR, or a bond;
R is H or $C_1$-$C_6$-alkyl;
$R^1$ is selected from the group consisting of $C_1$-$C_6$-alkyl, $C_2$-$C_6$-alkenyl, $C_3$-$C_6$-carbocyclyl, —($C_1$-$C_6$-alkyl)($C_3$-$C_6$-carbocyclyl), and —($C_1$-$C_6$-alkyl)($C_3$-$C_6$-cycloalkenyl), wherein
  any alkyl in $R^1$ is straight or branched, and
  $R^1$ is optionally substituted by 1-6 halo;
  or when L is NR, then R and $R^1$ in combination with L is a 3- to 6 membered heterocycloalkyl (wherein 1-4 ring members are independently N, O, or S) optionally substituted by one or more $R^A$;
$R^2$ and $R^3$ are independently selected from the group consisting of $C_6$-$C_{10}$-aryl, 5- to 10-membered heteroaryl (wherein 1-4 heteroaryl members are independently N, O, or S), and 3- to 14-membered heterocycloalkyl (wherein 1-4 heterocycloalkyl members are independently N, O, or S),
  wherein $R^2$ and $R^3$ are independently and optionally substituted by one or more substituents that are selected from the group consisting of $R^A$, $OR^A$, halo, —N=N—$R^A$, $NR^AR^B$, —($C_1$-$C_6$-alkyl)$NR^AR^B$, —C(O)O$R^A$, —C(O)$NR^AR^B$, —OC(O)$R^A$, and —CN;
$R^{2a}$ is absent or present and, if present, it is taken together with $R^2$ and the carbon atom to which they are attached to form a spiro-fused 5- to 6-membered carbocyclyl or heterocycloalkyl (wherein 1-4 carbocyclyl or heterocycloalkyl members are independently N, O, or S), and each bond ≈ (a) is a single bond and each bond ≈ (b) is a double bond;
  wherein the spiro-fused 5- to 6-membered carbocyclyl or heterocycloalkyl is optionally substituted by one or more $R^A$;
  and if $R^{2a}$ is absent, then each bond ≈ (a) is a double bond and each bond ≈ (b) is a single bond;
$R^4$, $R^5$, and $R^6$ are independently selected from the group consisting of $R^A$, $OR^A$, halo, $NR^AR^B$, —($C_1$-$C_6$-alkyl)$NR^AR^B$, —C(O)O$R^A$, —C(O)$NR^AR^B$, and —OC(O)$R^A$;
$R^A$ and $R^B$ are independently selected from the group consisting of H, —CN, -hydroxy, oxo, $C_1$-$C_6$-alkyl, $C_1$-$C_6$-alkoxy, $C_2$-$C_6$-alkenyl, $C_2$-$C_6$-alkynyl, $NH_2$, —S(O)$_{0-2}$—($C_1$-$C_6$-alkyl), —S(O)$_{0-2}$—($C_6$-$C_{10}$-aryl), —C(O)($C_1$-$C_6$-alkyl), —C(O)($C_3$-$C_{14}$-carbocyclyl), —$C_3$-$C_{14}$-carbocyclyl, —($C_1$-$C_6$-alkyl)($C_3$-$C_{14}$-carbocyclyl), $C_6$-$C_{10}$-aryl, 3- to 14-membered heterocycloalkyl, —($C_1$-$C_6$-alkyl)-(3- to 14-membered heterocycloalkyl) (wherein 1-4 heterocycloalkyl members are independently N, O, or S), and 5- to 10 membered heteroaryl (wherein 1-4 heteroaryl members are independently N, O, or S);
  wherein each alkyl, alkoxy, alkenyl, alkynyl, aryl, carbocyclyl, heterocycloalkyl, and heteroaryl moiety of $R^A$ and $R^B$ is optionally substituted with one or more substituents selected from the group consisting of hydroxy, halo, —NR'$_2$ (wherein each R' is independently selected from the group consisting of $C_1$-$C_6$-alkyl, $C_2$-$C_6$-alkenyl, $C_2$-$C_6$-alkynyl, $C_6$-$C_{10}$-aryl, 3- to 14-membered heterocycloalkyl, —($C_1$-$C_6$-alkyl)-(3- to 14-membered heterocycloalkyl) (wherein 1-4 ring members are independently N, O, or S), and 5- to 10 membered heteroaryl (wherein 1-4 heteroaryl members are independently N, O, or S)), —NHC(O)(O$C_1$-$C_6$-alkyl), —$NO_2$, —CN, oxo, —C(O)OH, —C(O)O($C_1$-$C_6$-alkyl), —$C_1$-$C_6$-alkyl($C_1$-$C_6$-alkoxy), —C(O)$NH_2$, $C_1$-$C_6$-alkyl, —C(O)$C_1$-$C_6$-alkyl, —O$C_1$-$C_6$-alkyl, —Si($C_1$-$C_6$-alkyl)$_3$, —S(O)$_{0-2}$—($C_1$-$C_6$-alkyl), $C_6$-$C_{10}$-aryl, —($C_1$-$C_6$-alkyl)($C_6$-$C_{10}$-aryl), 3-to 14-membered heterocycloalkyl, —($C_1$-$C_6$-alkyl)-(3- to 14-membered heterocycle) (wherein 1-4 heterocycle members are independently N, O, or S), and —O($C_6$-$C_{14}$-aryl), wherein each alkyl, alkenyl, aryl, and heterocycloalkyl in $R^A$ and $R^B$ is optionally substituted with one or more substituents selected from the group consisting of hydroxy, —O$C_1$-$C_6$-alkyl, halo, —$NH_2$, —($C_1$-$C_6$-alkyl)$NH_2$, —C(O)OH, CN, and oxo, or a pharmaceutically acceptable salt thereof.

2. The compound or pharmaceutically acceptable salt thereof according to claim 1, wherein $R^{2a}$ is absent; and each bond ⁓ (a) is a double bond and each bond ⁓ (b) is a single bond.

3. The compound or pharmaceutically acceptable salt thereof according to claim 2, wherein the compound has a structure according to Formula (IA):

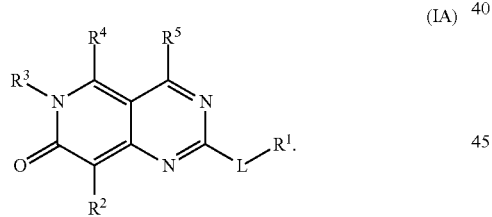

(IA)

4. The compound or pharmaceutically acceptable salt thereof according to claim 2, wherein the compound has a structure according to Formula (IB):

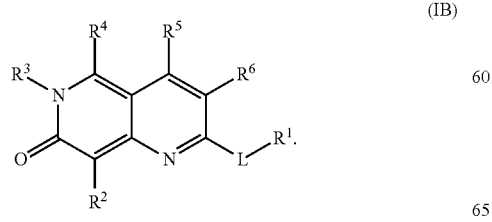

(IB)

5. A compound of Formula (II):

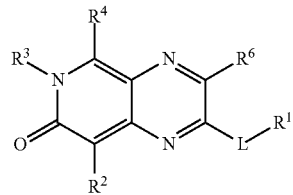

(II)

wherein:
L is O, S, NR, or a bond;
R is H or $C_1$-$C_6$-alkyl;
$R^1$ is selected from the group consisting of $C_1$-$C_6$-alkyl, $C_2$-$C_6$-alkenyl, $C_3$-$C_6$-carbocyclyl, —($C_1$-$C_6$-alkyl)($C_3$-$C_6$-carbocyclyl), and —($C_1$-$C_6$-alkyl)($C_3$-$C_6$-cycloalkenyl), wherein:
any alkyl in $R^1$ is straight or branched, and
$R^1$ is optionally substituted by 1-6 halo;
or when L is NR, then R and $R^1$ in combination with L is a 3- to 6-membered heterocycloalkyl (wherein 1-4 ring members are independently N, O, or S) optionally substituted by one or more $R^A$;
$R^2$ and $R^3$ are independently selected from the group consisting of $C_6$-$C_{10}$-aryl, 5- to 10-membered heteroaryl (wherein 1-4 heteroaryl members are independently N, O, or S), and 3- to 14-membered heterocycloalkyl (wherein 1-4 heterocycloalkyl members are independently N, O, or S),
wherein $R^2$ and $R^3$ are independently and optionally substituted by one or more substituents that are selected from the group consisting of $R^A$, $OR^A$, halo, —N=N—$R^A$, $NR^AR^B$, —($C_1$-$C_6$-alkyl)$NR^AR^B$, —C(O)$OR^A$, —C(O)$NR^AR^B$, —OC(O)$R^A$, and —CN;
$R^4$ and $R^6$ are independently selected from the group consisting of $R^A$, $OR^A$, halo, $NR^AR^B$, —($C_1$-$C_6$-alkyl)$NR^AR^B$, —C(O)$OR^A$—C(O)$NR^AR^B$, and —OC(O)$R^A$;
$R^A$ and $R^B$ are independently selected from the group consisting of H, —CN, -hydroxy, oxo, $C_1$-$C_6$-alkyl, $C_1$-$C_6$-alkoxy, $C_2$-$C_6$-alkenyl, $C_2$-$C_6$-alkynyl, $NH_2$, —S(O)$_{0-2}$—($C_1$-$C_6$-alkyl), —S(O)$_{0-2}$—($C_6$-$C_{10}$-aryl), —C(O)($C_1$-$C_6$-alkyl), —C(O)($C_3$-$C_{14}$-carbocyclyl), —$C_3$-$C_{14}$-carbocyclyl, —($C_1$-$C_6$-alkyl)($C_3$-$C_{14}$-carbocyclyl), $C_6$-$C_{10}$-aryl, 3- to 14-membered heterocycloalkyl, —($C_1$-$C_6$-alkyl)-(3- to 14-membered heterocycloalkyl) (wherein 1-4 heterocycloalkyl members are independently N, O, or S), and 5- to 10-membered heteroaryl (wherein 1-4 heteroaryl members are independently N, O, or S);
wherein each alkyl, alkoxy, alkenyl, alkynyl, aryl, carbocyclyl, heterocycloalkyl, and heteroaryl moiety of $R^A$ and $R^B$ is optionally substituted with one or more substituents selected from the group consisting of hydroxy, halo, —NR'$_2$ (wherein each R' is independently selected from the group consisting of $C_1$-$C_6$-alkyl, $C_2$-$C_6$-alkenyl, $C_2$-$C_6$-alkynyl, $C_6$-$C_{10}$-aryl, 3- to 14-membered heterocycloalkyl, —($C_1$-$C_6$-alkyl)-(3- to 14-membered heterocycloalkyl) (wherein 1-4 ring members are independently N, O, or S), and 5- to 10 membered heteroaryl (wherein 1-4 heteroaryl members are independently N, O, or S)), —NHC(O)(O$C_1$-$C_6$- alkyl), —NO$_2$, —CN, oxo, —C(O)OH, —C(O)O(C$_1$-C$_6$-alkyl), —C$_1$-C$_6$-alkyl(C$_1$-C$_6$-alkoxy), —C(O)NH$_2$, C$_1$-C$_6$-alkyl, —C(O)C$_1$-C$_6$-alkyl, —OC$_1$-C$_6$-alkyl, —Si(C$_1$-C$_6$-alkyl)$_3$, —S(O)$_{0-2}$—(C$_1$-C$_6$-alkyl), C$_6$-C$_{10}$-aryl, —(C$_1$-C$_6$-alkyl)(C$_6$-C$_{10}$-aryl), 3- to 14-membered heterocycloalkyl, —(C$_1$-C$_6$-alkyl)-(3- to 14 membered heterocycle) (wherein 1-4 heterocycle members are independently N, O, or S), and —O(C$_6$-C$_{14}$-aryl), wherein each alkyl, alkenyl, aryl, and heterocycloalkyl in R$^A$ and R$^B$ is optionally substituted with one or more substituents selected from the group consisting of hydroxy, —OC$_1$-C$_6$-alkyl, halo, —NH$_2$, —(C$_1$-C$_6$-alkyl)NH$_2$, —C(O)OH, CN, and oxo, or a pharmaceutically acceptable salt thereof.

6. The compound or pharmaceutically acceptable salt thereof according to claim 1, wherein each of R$^4$, R$^5$, and R$^6$ (if present) is independently selected from the group consisting of H, C$_1$-C$_6$-alkyl, and C$_1$-C$_6$-alkoxy.

7. The compound or pharmaceutically acceptable salt thereof according to of claim 1, wherein at least one of R$^4$, R$^5$, and R$^6$ (if present) is H.

8. The compound or pharmaceutically acceptable salt thereof according to claim 1, wherein R$^4$ is H.

9. The compound or pharmaceutically acceptable salt thereof according to claim 1, wherein R$^5$ is H.

10. The compound or pharmaceutically acceptable salt thereof according to claim 1, wherein R$^6$ is H.

11. The compound or pharmaceutically acceptable salt thereof according to claim 1, wherein each of R$^4$, R$^5$, and R$^6$ (if present) is H.

12. The compound according to claim 1, wherein R$^2$ is C$_6$-C$_{10}$-aryl or 5- to 10-membered heteroaryl.

13. The compound or pharmaceutically acceptable salt thereof according to claim 12, wherein R$^2$ is C$_6$-C$_{10}$-aryl.

14. The compound or pharmaceutically acceptable salt thereof according to claim 13, wherein R$^2$ is phenyl.

15. The compound or pharmaceutically acceptable salt thereof according to claim 12, wherein R$^2$ is 5- to 10-membered heteroaryl, and wherein 1 ring member is N.

16. The compound or pharmaceutically acceptable salt thereof according to claim 15, wherein R$^2$ is pyridyl.

17. The compound or pharmaceutically acceptable salt thereof according to of claim 1, wherein R$^3$ is 3- to 14-membered heterocycloalkyl or 5- to 10-membered heteroaryl.

18. The compound or pharmaceutically acceptable salt thereof according to claim 17, wherein R$^3$ is selected from the group consisting of benzothiazolyl, benzoisothiazolyl, benzoxazolyl, pyridinyl, pyridinonyl, benzimidazolyl, benzotriazolyl, indazolyl, quinoxalinyl, quinolinyl, quinazolinyl, imidazopyridinyl, pyrazolopyridinyl, cinnolinyl, isoxazolyl, pyrazolyl, benzofuranyl, dihydrobenzofuranyl, and tetrahydrobenzodioxinyl.

19. The compound or pharmaceutically acceptable salt thereof according to claim 1, wherein R$^3$ is C$_6$-C$_{10}$-aryl.

20. The compound or pharmaceutically acceptable salt thereof according to claim 1, wherein L is O or NR.

21. The compound or pharmaceutically acceptable salt thereof according to claim 20, wherein R$^1$ is C$_1$-C$_6$-alkyl or C$_3$-C$_6$-carbocyclyl.

22. The compound or pharmaceutically acceptable salt thereof according to claim 20, wherein R$^1$ is C$_1$-C$_3$-alkyl that is optionally substituted by 1-3 F.

23. The compound or pharmaceutically acceptable salt thereof according to claim 2, wherein:

L is O or NR and R is H;

R$^1$ is C$_1$-C$_3$-alkyl that is optionally substituted by 1-3 F;

R$^2$ is 3- to 14-membered heterocycloalkyl or 5- to 10-membered heteroaryl (wherein 1 heterocycloalkyl or heteroaryl member is N) or C$_6$-C$_{10}$-aryl;

R$^3$ is 3- to 14-membered heterocycloalkyl or 5- to 10-membered heteroaryl wherein 1 to 3 heterocycloalkyl or heteroaryl members are independently N, O, or S; and each of R$^4$, R$^5$, and R$^6$ (if present) is H.

24. The compound or pharmaceutically acceptable salt thereof according to claim 23, wherein L is NR.

25. The compound or pharmaceutically acceptable salt thereof according to claim 1, wherein R$^{2a}$ is present and it is taken together with R$^2$ and the carbon atom to which they are attached to form a spiro-fused 5- to 6-membered carbocyclyl or heterocycloalkyl (wherein 1-4 heterocycloalkyl members are independently selected from N, O, or S), each bond ⋍ (a) is a single bond and each bond ⋍ (b) is a double bond; and wherein the spiro-fused 5- to 6-membered carbocyclyl or heterocycloalkyl is optionally substituted by one or more R$^A$.

26. The compound or pharmaceutically acceptable salt thereof according to claim 24, wherein R$^{2a}$, R$^2$, and the carbon atom to which they are attached form a spiro-fused 5-membered heterocycloalkyl, wherein 1 heterocycloalkyl member is N.

27. The compound or pharmaceutically acceptable salt thereof according to claim 24, wherein R$^{2a}$, R$^2$, and the carbon atom to which they are attached are taken together to form a spiro-fused 6-membered heterocycloalkyl, wherein 1 heterocycloalkyl member is N.

28. The compound or pharmaceutically acceptable salt thereof according to claim 24, wherein R$^{2a}$, R$^2$, and the carbon atom to which they are attached are taken together to form a spiro-fused 6-membered carbocyclyl.

29. The compound or pharmaceutically acceptable salt thereof according to claim 24, wherein X is N.

30. The compound or pharmaceutically acceptable salt thereof according to claim 24, wherein each of R$^4$ and R$^5$ is independently selected from the group consisting of H, C$_1$-C$_6$-alkyl, and C$_1$-C$_6$-alkoxy.

31. The compound or pharmaceutically acceptable salt thereof according to claim 24, wherein each of R$^4$ and R$^5$ is H.

32. The compound or pharmaceutically acceptable salt thereof according to claim 24, wherein R$^3$ is 5- to 10 membered heteroaryl wherein 2 heteroaryl members are independently N, O, or S.

33. The compound or pharmaceutically acceptable salt thereof according to claim 24, wherein R$^3$ is C$_6$-C$_{10}$-aryl.

34. The compound according to claim 1, wherein the compound is:

| 101 | 105 |
|---|---|
| 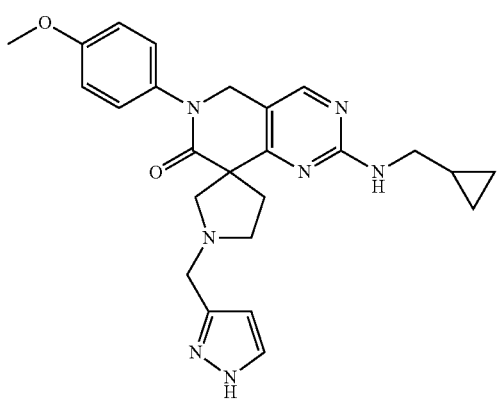 [SMILES: COc1ccc(N2Cc3cnc(NCC4CC4)nc3C3(CCN(Cc4cc[nH]n4)C3)C2=O)cc1] | 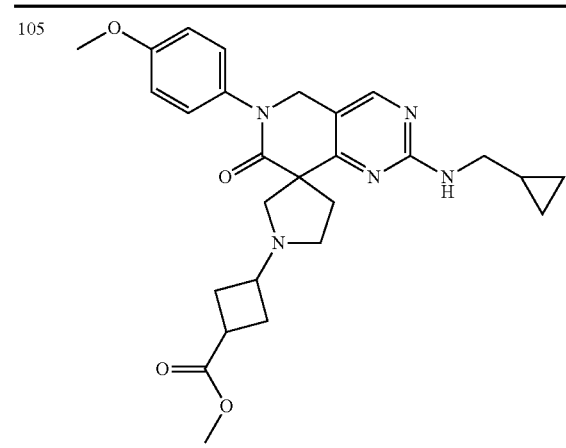 |
| 102 | 106 |
| 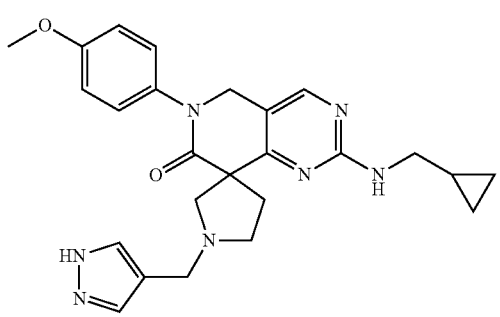 [SMILES: COc1ccc(N2Cc3cnc(NCC4CC4)nc3C3(CCN(Cc4cn[nH]c4)C3)C2=O)cc1] | 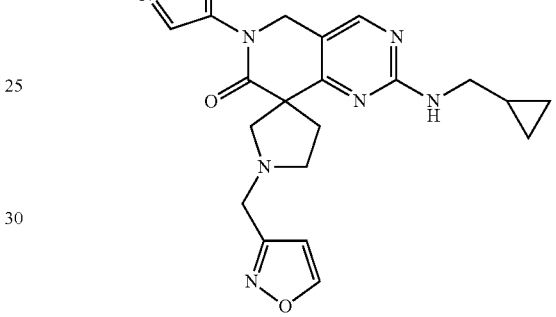 |
| 103 | 107 |
| 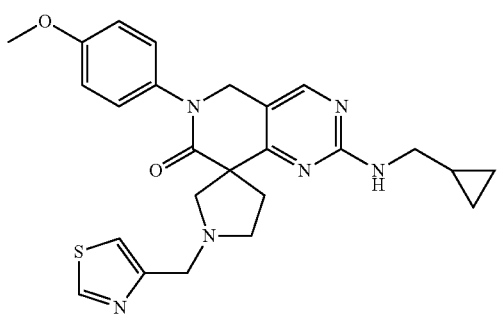 [SMILES: COc1ccc(N2Cc3cnc(NCC4CC4)nc3C3(CCN(Cc4cscn4)C3)C2=O)cc1] | 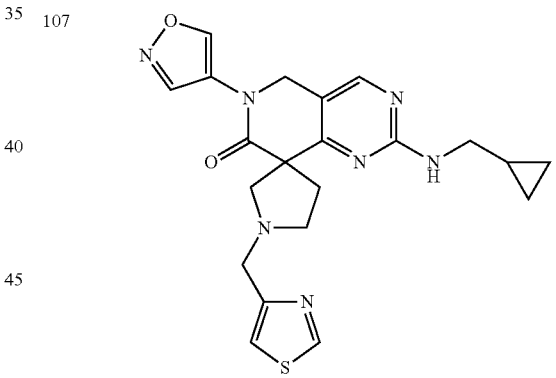 |
| 104 | 108 |
| 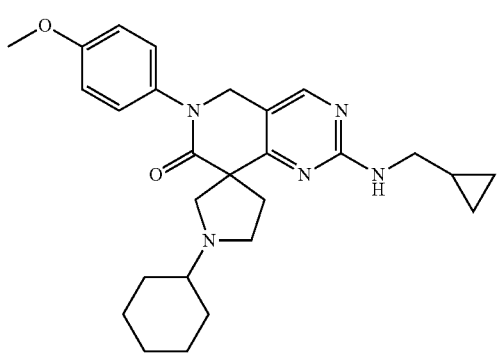 [SMILES: COc1ccc(N2Cc3cnc(NCC4CC4)nc3C3(CCN(C4CCCCC4)C3)C2=O)cc1] | 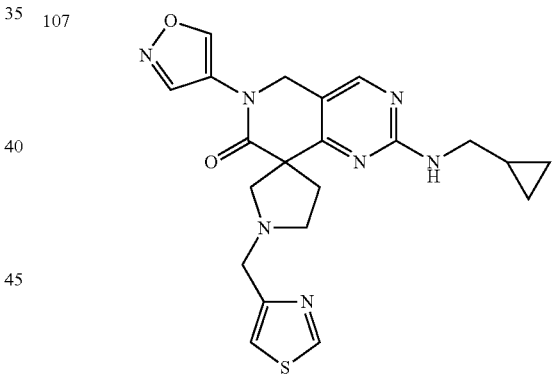 |

335
-continued
109 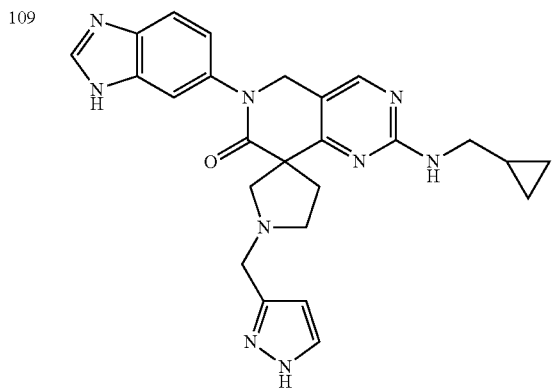
110 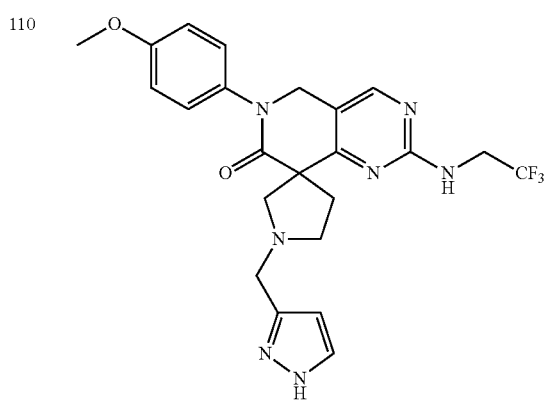
111 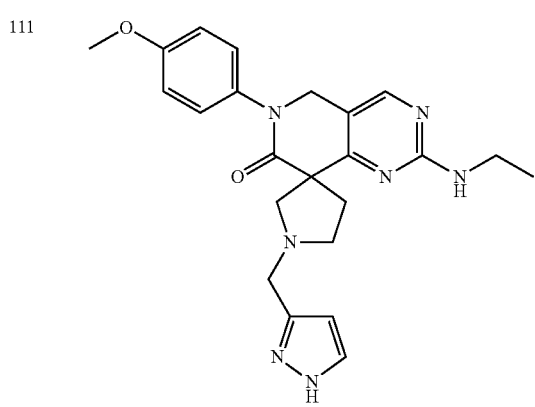
112 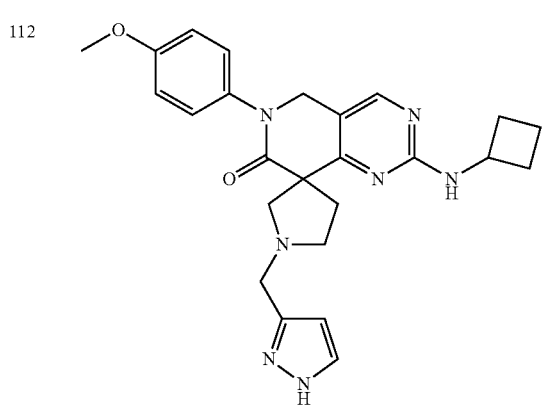
336
-continued
113 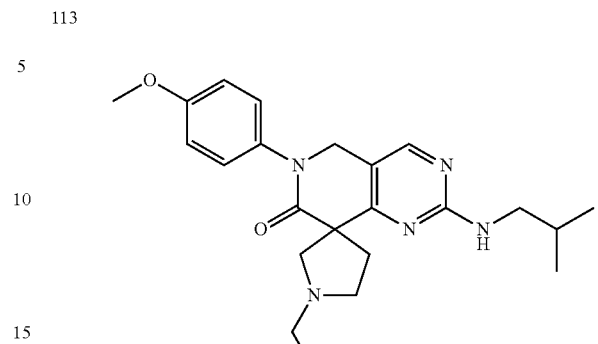
114 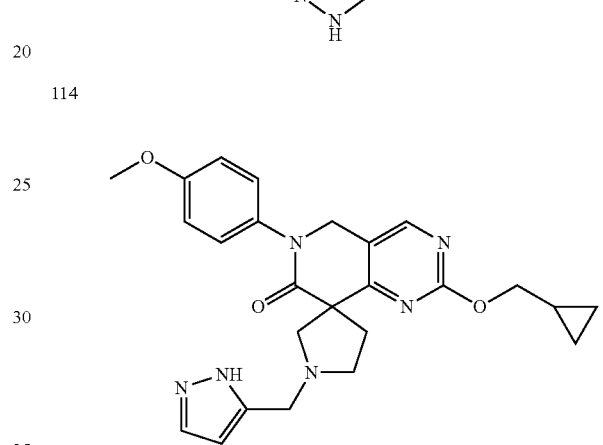
115 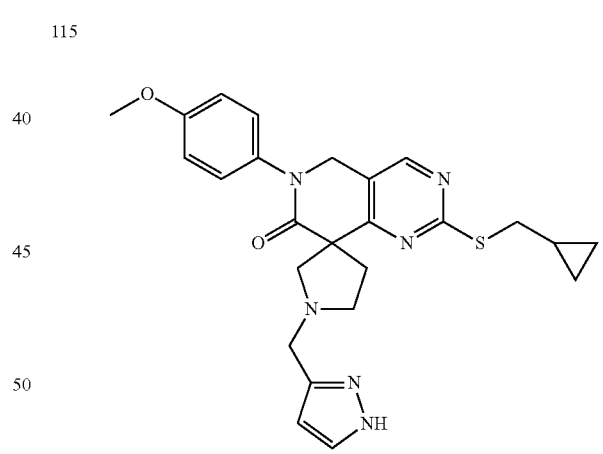
116 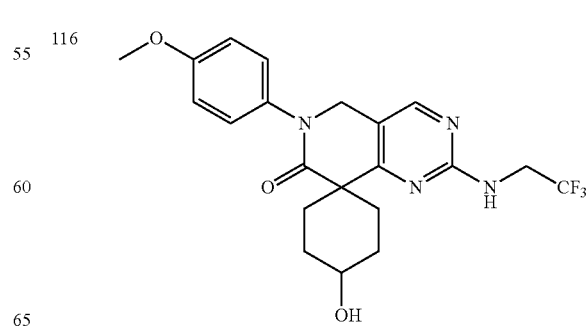

117
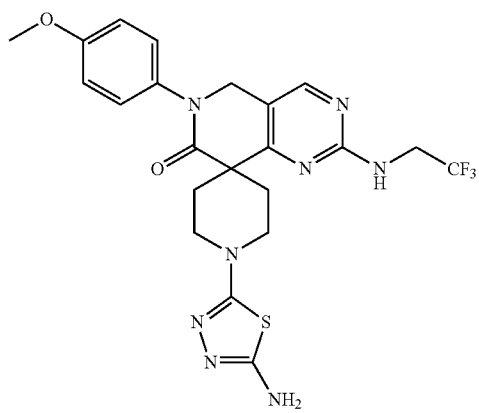 [SMILES: COc1ccc(N2Cc3cnc(NCC(F)(F)F)nc3C3(CCN(c4nnc(N)s4)CC3)C2=O)cc1]
118
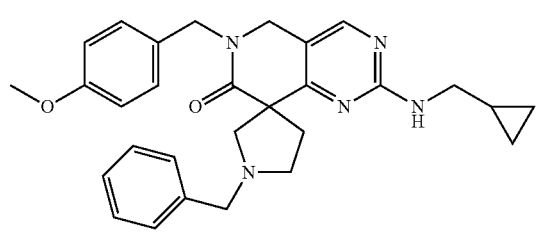 [SMILES: COc1ccc(CN2Cc3cnc(NCC4CC4)nc3C3(CCN(Cc4ccccc4)C3)C2=O)cc1]
119
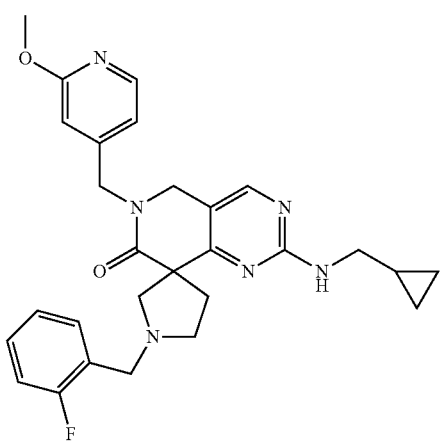 [SMILES: COc1cc(CN2Cc3cnc(NCC4CC4)nc3C3(CCN(Cc4ccccc4F)C3)C2=O)ccn1]
120
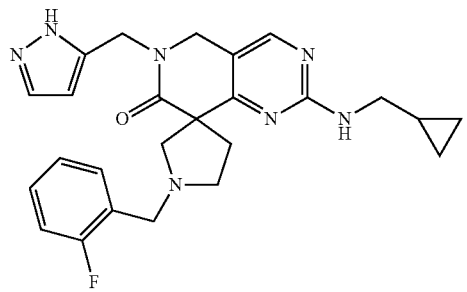 [SMILES: O=C1N(Cc2ccn[nH]2)Cc2cnc(NCC3CC3)nc2C12CCN(Cc1ccccc1F)C2]
121
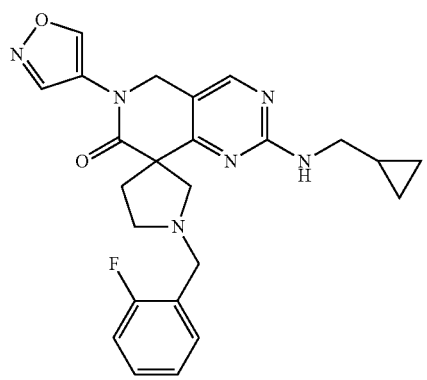 [SMILES: O=C1N(c2cnoc2)Cc2cnc(NCC3CC3)nc2C12CCN(Cc1ccccc1F)C2]
122
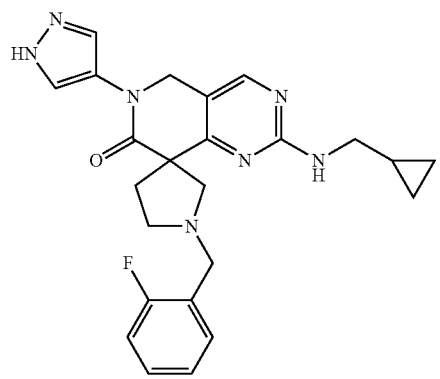 [SMILES: O=C1N(c2cn[nH]c2)Cc2cnc(NCC3CC3)nc2C12CCN(Cc1ccccc1F)C2]
or a pharmaceutically acceptable salt thereof.
35. The compound according to claim 1, wherein the compound is:
123
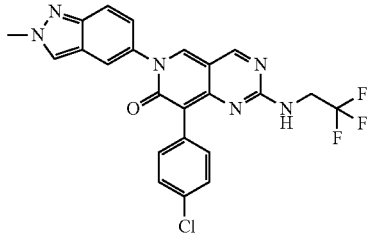 [SMILES: Cn1cc2cc(-n3cc4cnc(NCC(F)(F)F)nc4c(-c4ccc(Cl)cc4)c3=O)ccc2n1]
124
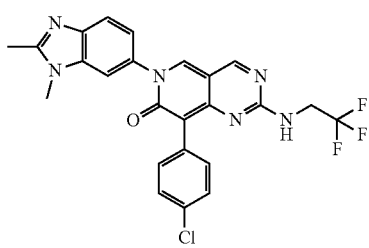 [SMILES: Cc1nc2ccc(-n3cc4cnc(NCC(F)(F)F)nc4c(-c4ccc(Cl)cc4)c3=O)cc2n1C]

| 339 -continued | 340 -continued |
|---|---|
| 125 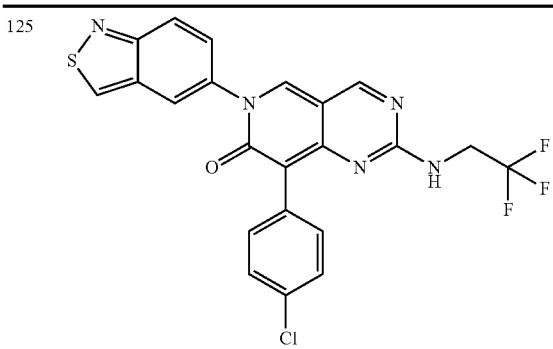 | 130 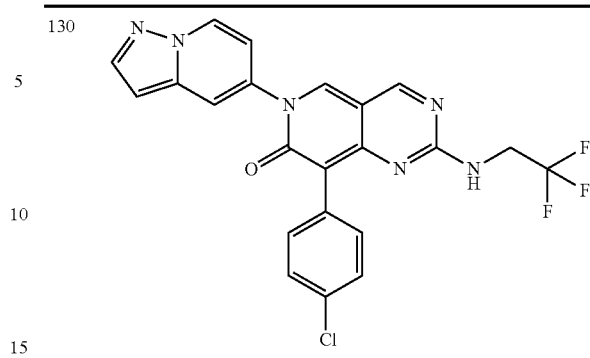 |
| 126 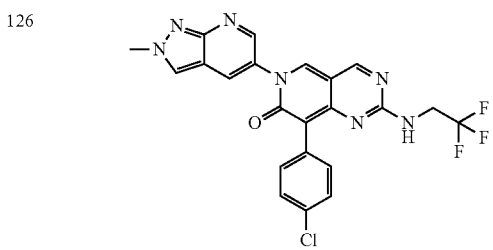 | 131 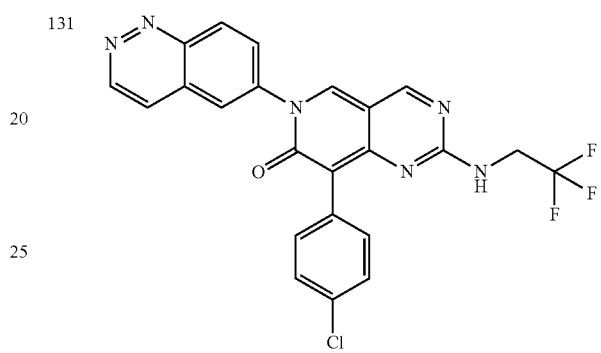 |
| 127 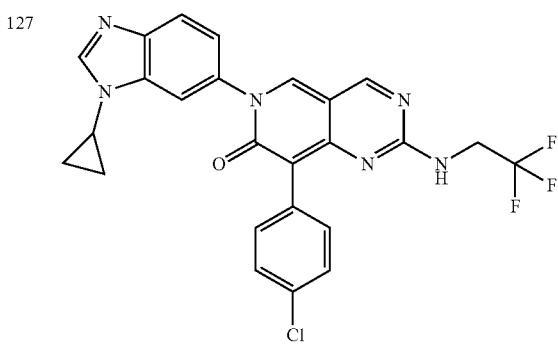 | 132 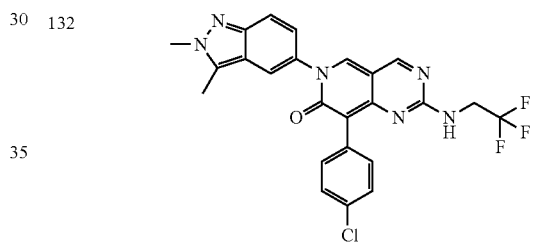 |
| 128 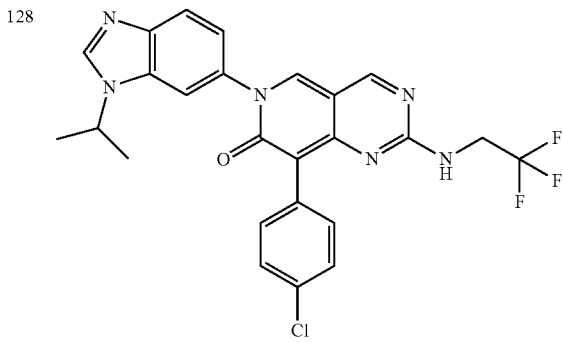 | 133 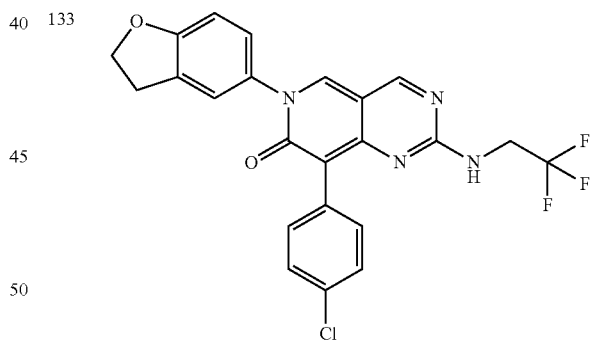 |
| 129 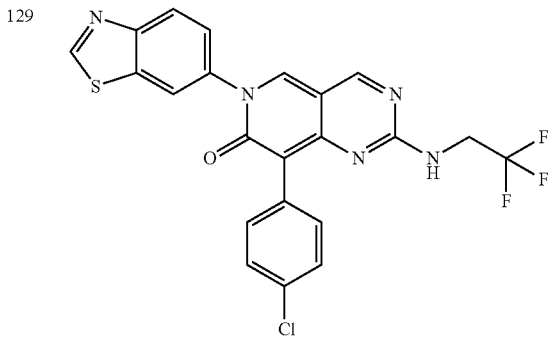 | 134 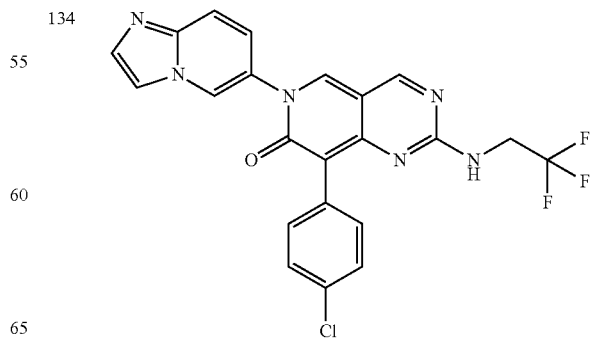 |

| 135 | 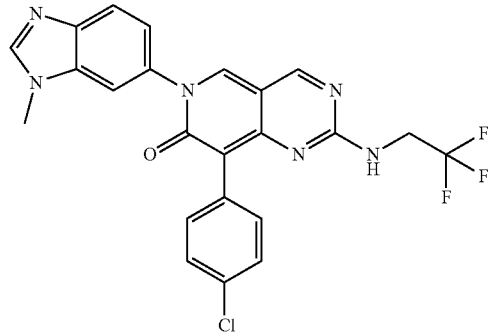 [SMILES: Cn1cnc2ccc(-n3cc4cnc(NCC(F)(F)F)nc4c(-c4ccc(Cl)cc4)c3=O)cc21] | 140 | 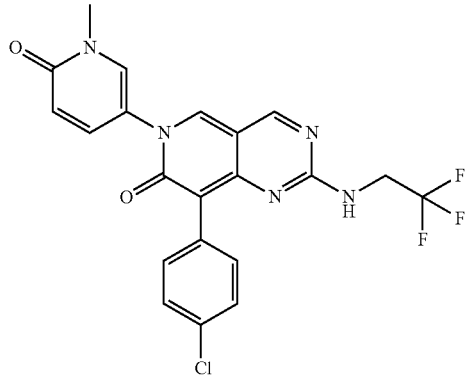 |
| --- | --- | --- | --- |
| 136 | | 141 | 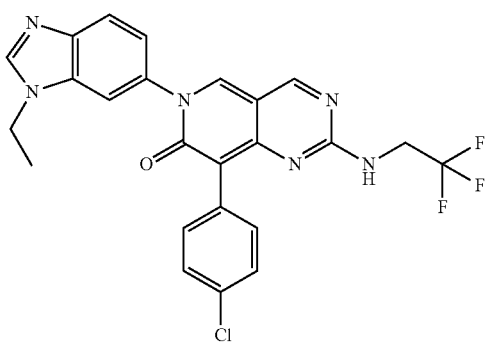 |
| 137 | 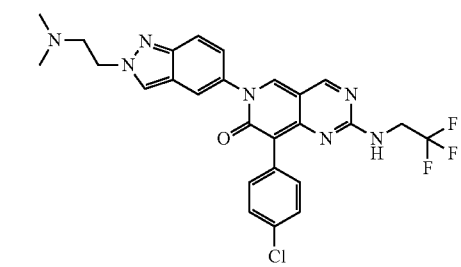 [SMILES: CN(C)CCn1cc2cc(-n3cc4cnc(NCC(F)(F)F)nc4c(-c4ccc(Cl)cc4)c3=O)ccc2n1] | | |
| 138 | 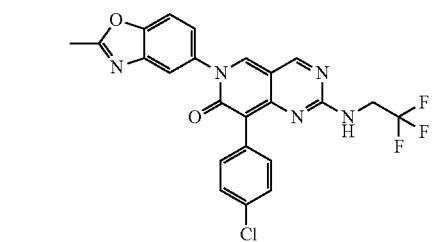 [SMILES: Cc1nc2cc(-n3cc4cnc(NCC(F)(F)F)nc4c(-c4ccc(Cl)cc4)c3=O)ccc2o1] | 142 | |
| 139 | 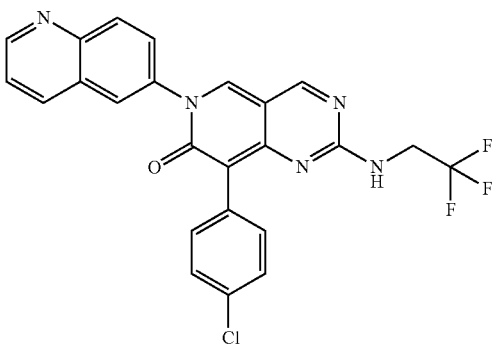 [SMILES: O=c1c(-c2ccc(Cl)cc2)c2nc(NCC(F)(F)F)ncc2cn1-c1ccc2ncccc2c1] | 143 | 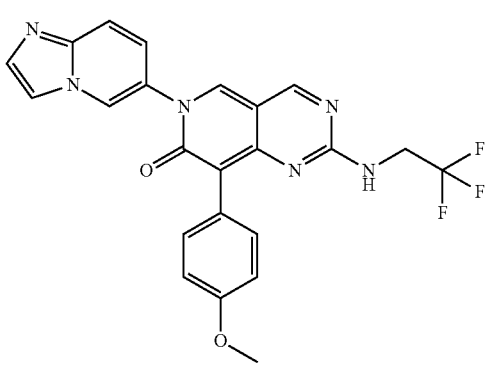 [SMILES: COc1ccc(-c2c(=O)n(-c3ccc4nccn4c3)cc3cnc(NCC(F)(F)F)nc23)cc1] |

| 343 -continued | 344 -continued |
|---|---|
| 144 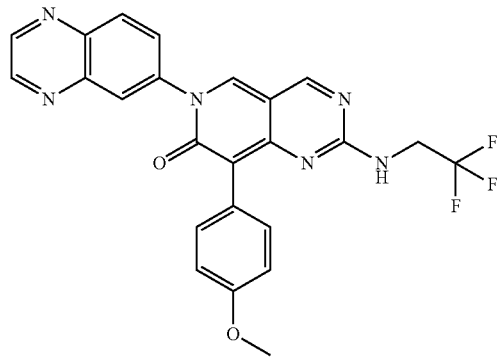 [SMILES: COc1ccc(-c2c(=O)n(-c3ccc4nccnc4c3)cc3cnc(NCC(F)(F)F)nc23)cc1] | 148 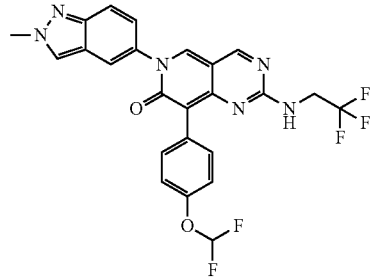 |
| 145 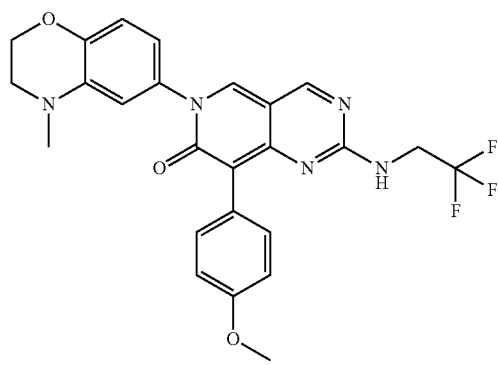 [SMILES: COc1ccc(-c2c(=O)n(-c3ccc4c(c3)N(C)CCO4)cc3cnc(NCC(F)(F)F)nc23)cc1] | 149 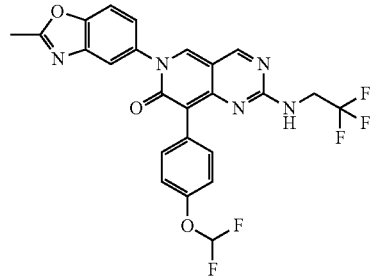 |
|  | 150 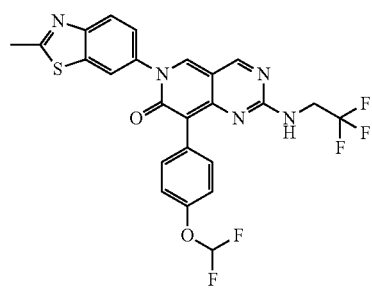 |
| 146 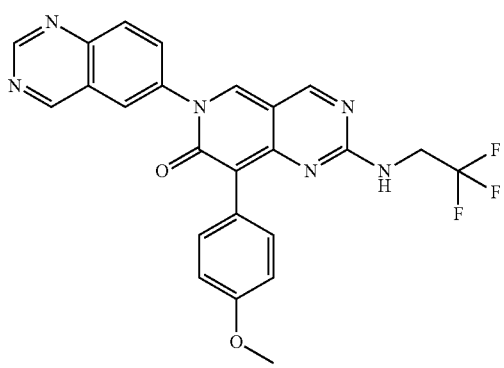 [SMILES: COc1ccc(-c2c(=O)n(-c3ccc4ncncc4c3)cc3cnc(NCC(F)(F)F)nc23)cc1] | 151 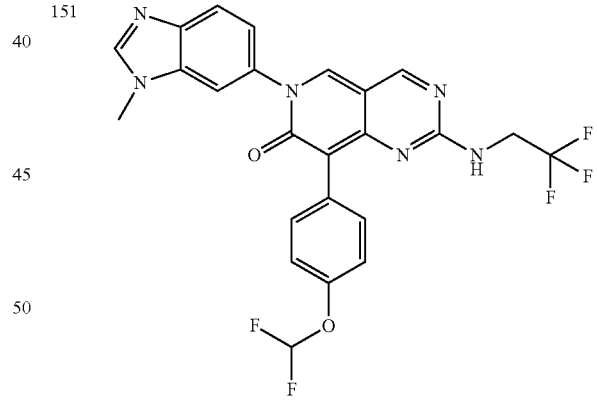 |
| 147 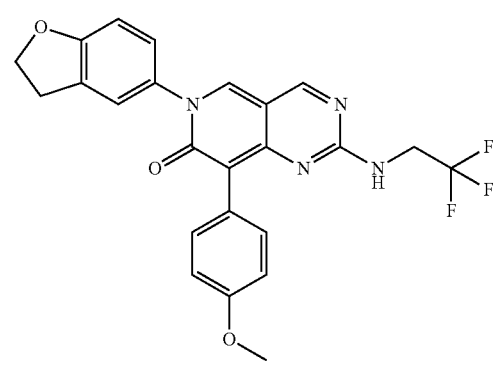 [SMILES: COc1ccc(-c2c(=O)n(-c3ccc4c(c3)CCO4)cc3cnc(NCC(F)(F)F)nc23)cc1] | 152 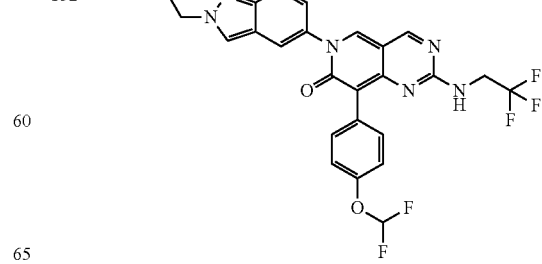 |

153 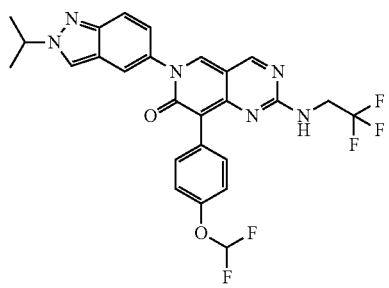 [SMILES: CC(C)n1cc2cc(-n3cc4cnc(NCC(F)(F)F)nc4c(-c4ccc(OC(F)F)cc4)c3=O)ccc2n1]
154 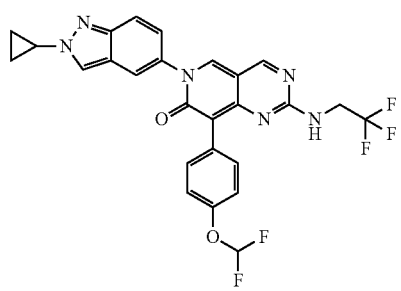 [SMILES: O=c1c(-c2ccc(OC(F)F)cc2)c2nc(NCC(F)(F)F)ncc2cn1-c1ccc2nn(C3CC3)cc2c1]
155 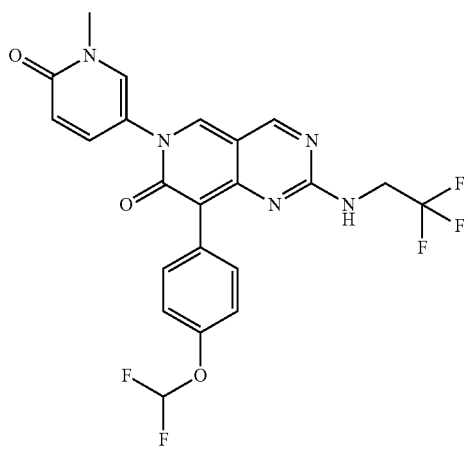 [SMILES: Cn1cc(-n2cc3cnc(NCC(F)(F)F)nc3c(-c3ccc(OC(F)F)cc3)c2=O)ccc1=O]
156 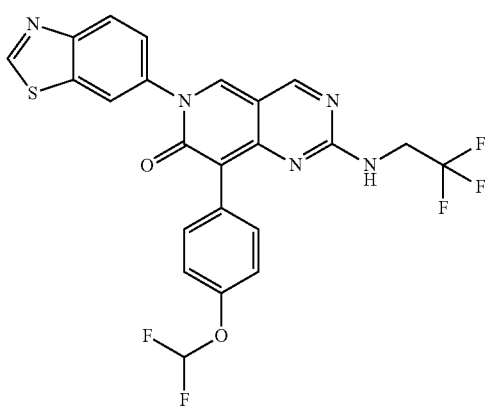 [SMILES: O=c1c(-c2ccc(OC(F)F)cc2)c2nc(NCC(F)(F)F)ncc2cn1-c1ccc2ncsc2c1]
157 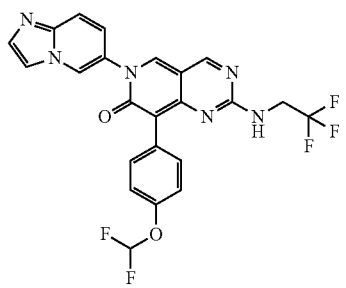 [SMILES: O=c1c(-c2ccc(OC(F)F)cc2)c2nc(NCC(F)(F)F)ncc2cn1-c1ccc2nccn2c1]
158 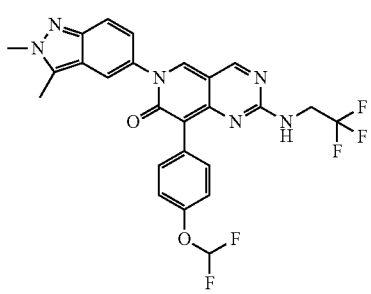 [SMILES: Cc1c2cc(-n3cc4cnc(NCC(F)(F)F)nc4c(-c4ccc(OC(F)F)cc4)c3=O)ccc2nn1C]
159 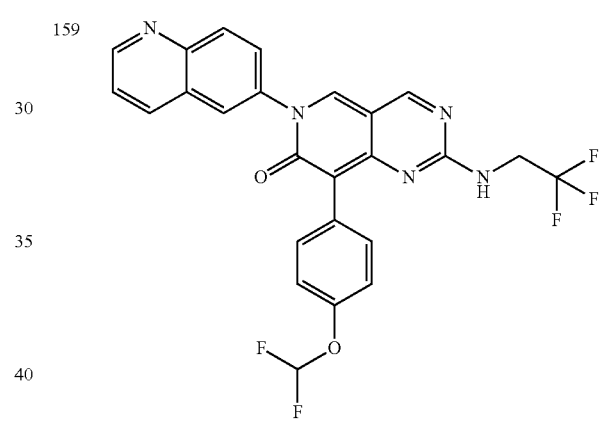
160 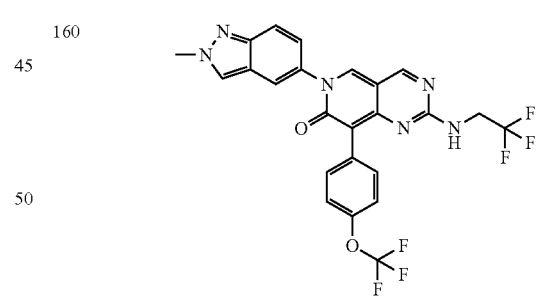
161 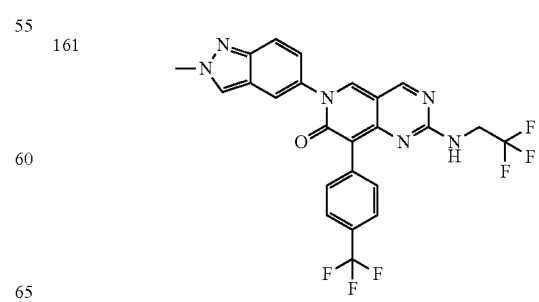

| 162 | 166 |
|---|---|
| 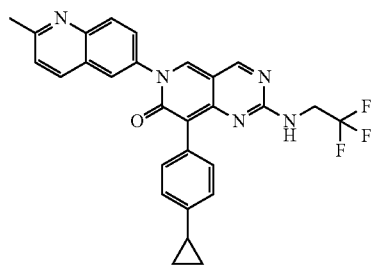 [SMILES: Cc1ccc2cc(-n3cc4cnc(NCC(F)(F)F)nc4c(-c4ccc(C5CC5)cc4)c3=O)ccc2n1] | 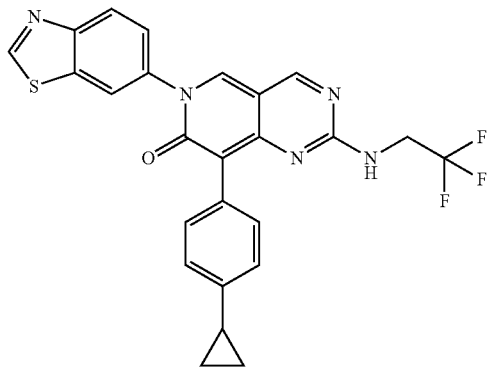 |
| 163 | 167 |
| 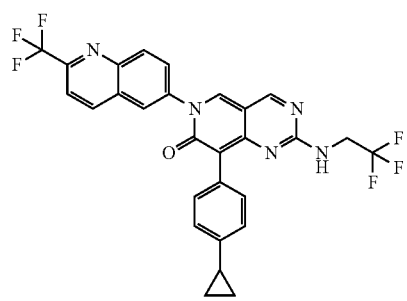 [SMILES: O=c1c(-c2ccc(C3CC3)cc2)c2nc(NCC(F)(F)F)ncc2cn1-c1ccc2nc(C(F)(F)F)ccc2c1] | 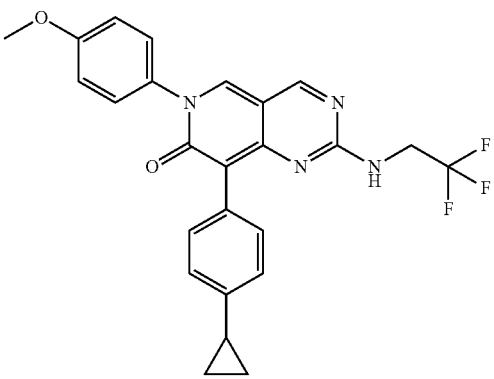 |
| 164 | 168 |
| 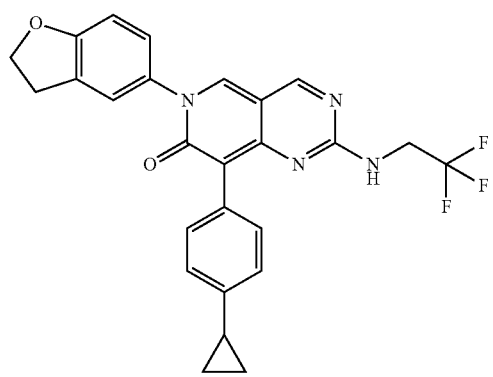 [SMILES: O=c1c(-c2ccc(C3CC3)cc2)c2nc(NCC(F)(F)F)ncc2cn1-c1ccc2c(c1)CCO2] | 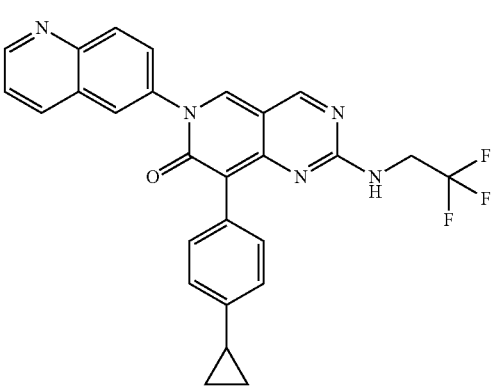 |
| 165 | 169 |
| 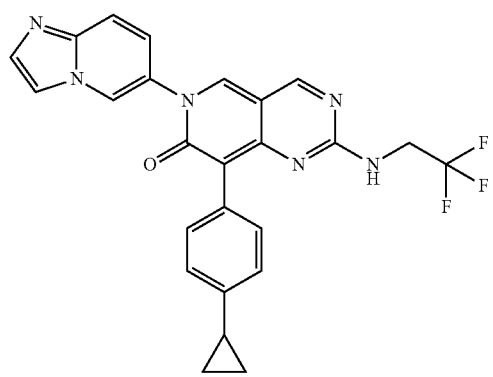 [SMILES: O=c1c(-c2ccc(C3CC3)cc2)c2nc(NCC(F)(F)F)ncc2cn1-c1ccc2nccn2c1] | 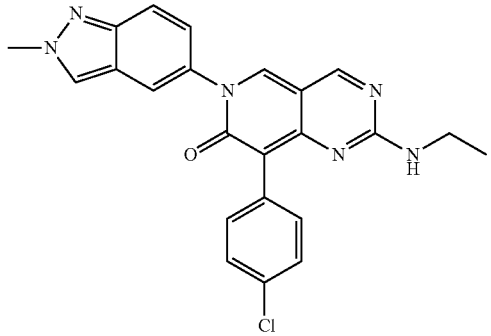 [SMILES: CCNc1ncc2cn(-c3ccc4nn(C)cc4c3)c(=O)c(-c3ccc(Cl)cc3)c2n1] |

| 170 | 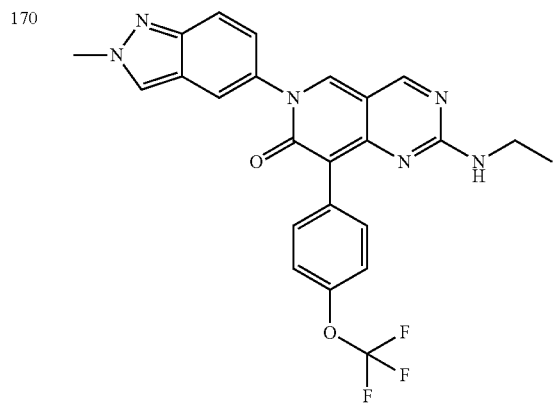 |
| 171 | 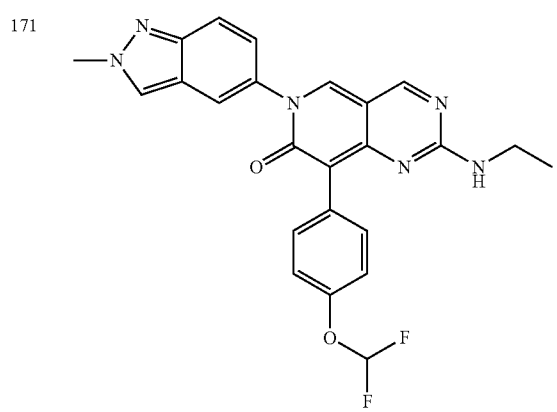 |
| 172 | 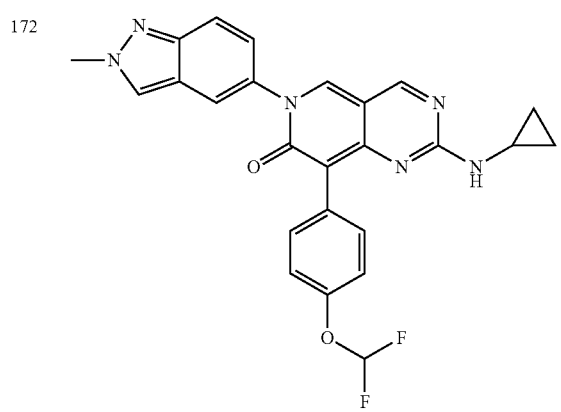 |
| 173 | 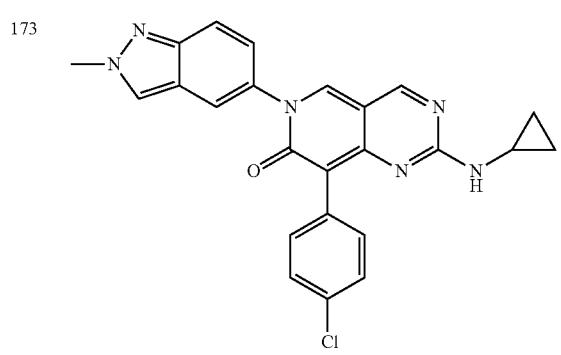 |
| 174 | 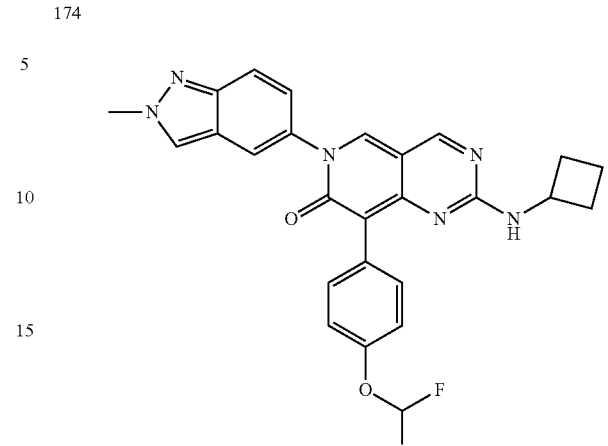 |
| 175 | 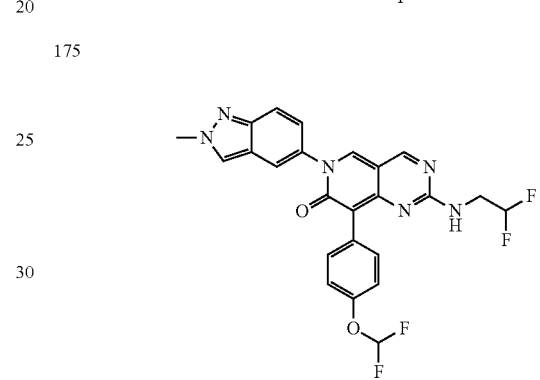 |
| 176 | 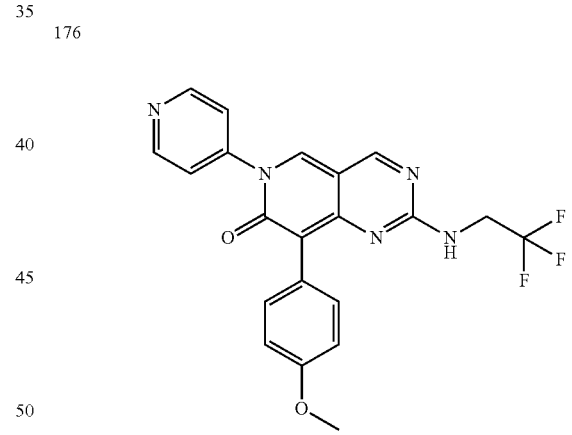 |
| 177 | 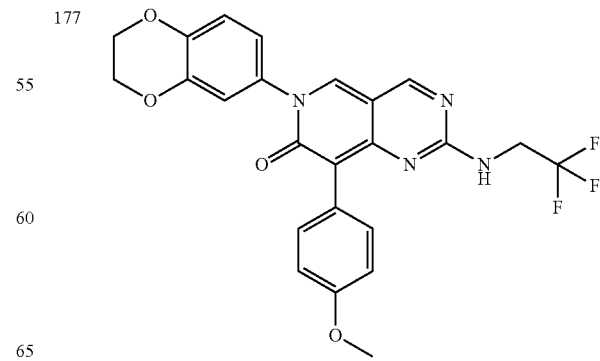 |

| 351 -continued | 352 -continued |
|---|---|
| 178 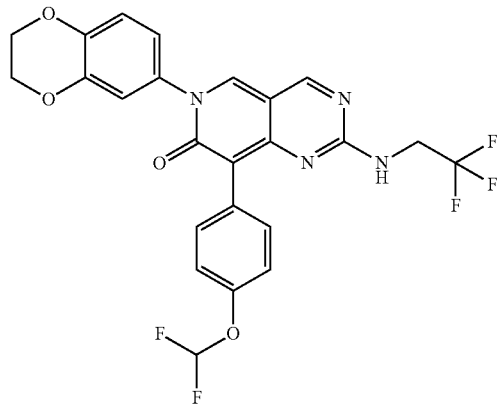 [SMILES: O=c1c(-c2ccc(OC(F)F)cc2)c2nc(NCC(F)(F)F)ncc2cn1-c1ccc2c(c1)OCCO2] | 182 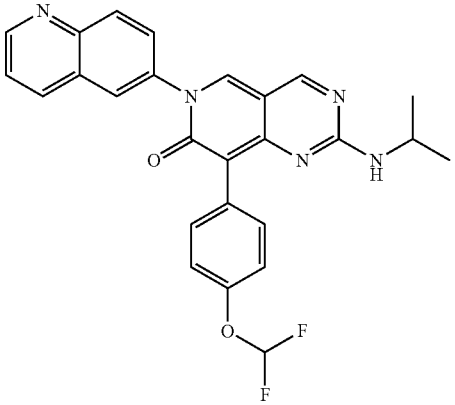 [SMILES: CC(C)Nc1ncc2cn(-c3ccc4ncccc4c3)c(=O)c(-c3ccc(OC(F)F)cc3)c2n1] |
| 179 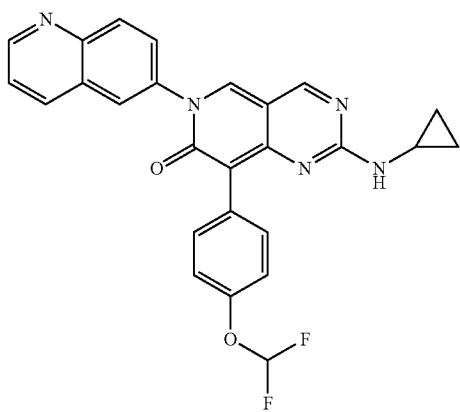 | 183 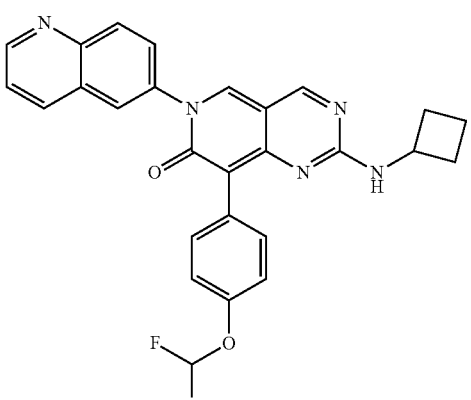 |
| 180 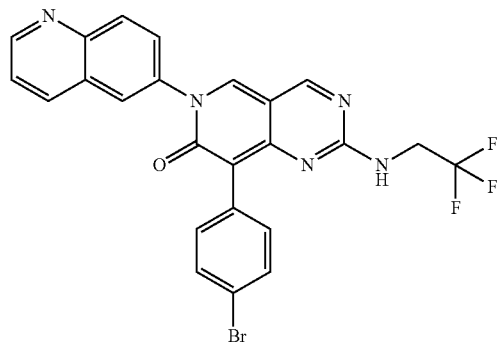 | 184 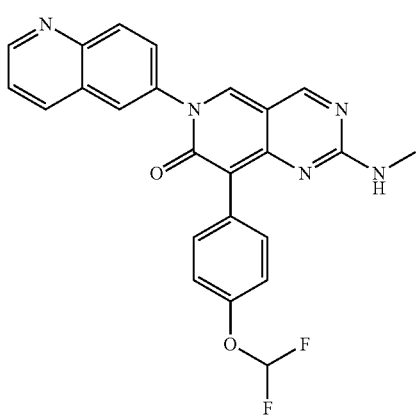 [SMILES: CNc1ncc2cn(-c3ccc4ncccc4c3)c(=O)c(-c3ccc(OC(F)F)cc3)c2n1] |
| 181 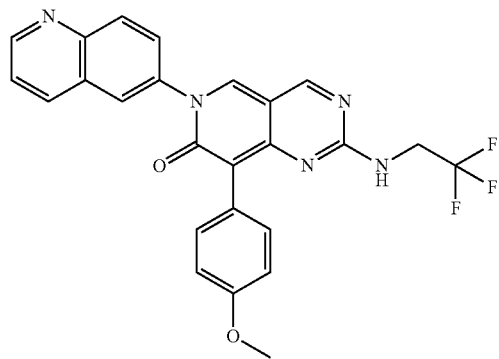 | 185 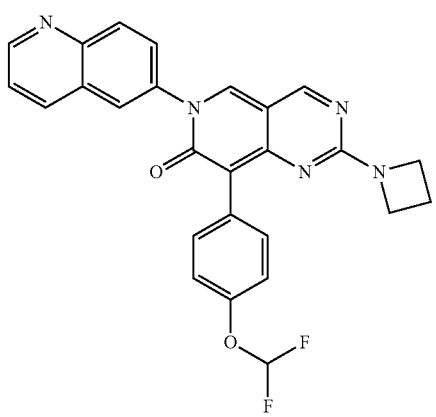 [SMILES: O=c1c(-c2ccc(OC(F)F)cc2)c2nc(N3CCC3)ncc2cn1-c1ccc2ncccc2c1] |

186 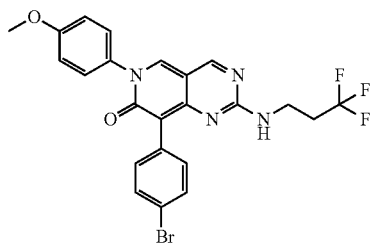 [SMILES: COc1ccc(-n2cc3cnc(NCCC(F)(F)F)nc3c(-c3ccc(Br)cc3)c2=O)cc1]
187 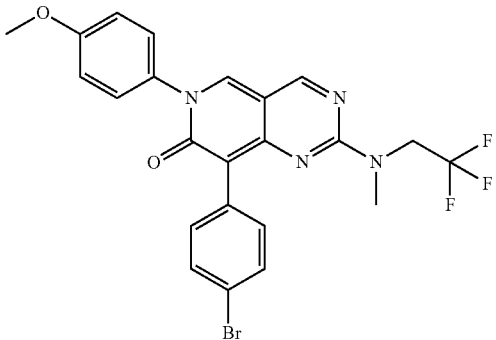 [SMILES: COc1ccc(-n2cc3cnc(N(C)CC(F)(F)F)nc3c(-c3ccc(Br)cc3)c2=O)cc1]
188 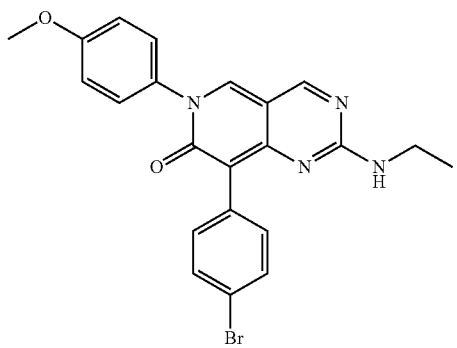 [SMILES: CCNc1ncc2cn(-c3ccc(OC)cc3)c(=O)c(-c3ccc(Br)cc3)c2n1]
189 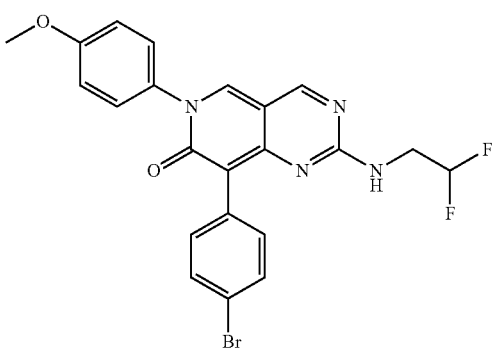 [SMILES: COc1ccc(-n2cc3cnc(NCC(F)F)nc3c(-c3ccc(Br)cc3)c2=O)cc1]
190 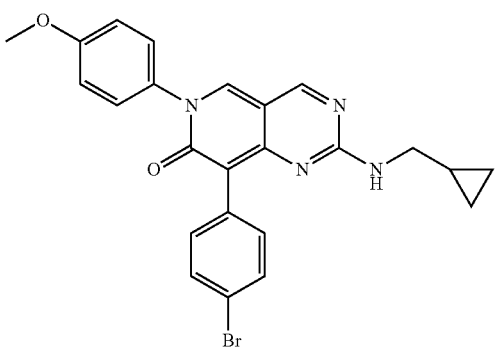 [SMILES: COc1ccc(-n2cc3cnc(NCC4CC4)nc3c(-c3ccc(Br)cc3)c2=O)cc1]
191 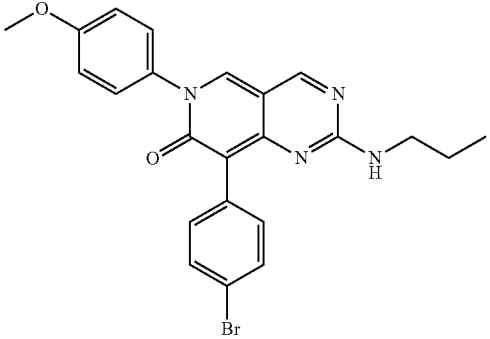 [SMILES: CCCNc1ncc2cn(-c3ccc(OC)cc3)c(=O)c(-c3ccc(Br)cc3)c2n1]
192 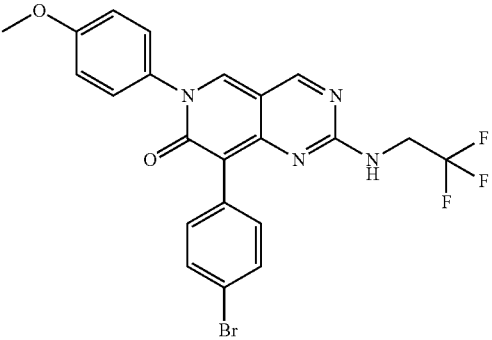 [SMILES: COc1ccc(-n2cc3cnc(NCC(F)(F)F)nc3c(-c3ccc(Br)cc3)c2=O)cc1]
193 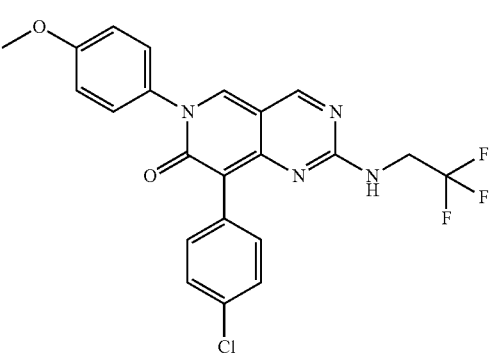 [SMILES: COc1ccc(-n2cc3cnc(NCC(F)(F)F)nc3c(-c3ccc(Cl)cc3)c2=O)cc1]
194 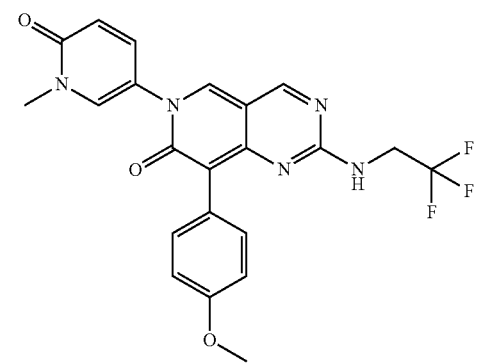 [SMILES: COc1ccc(-c2c(=O)n(-c3ccc(=O)n(C)c3)cc3cnc(NCC(F)(F)F)nc23)cc1]

| 355 -continued | 356 -continued |
|---|---|
| 195 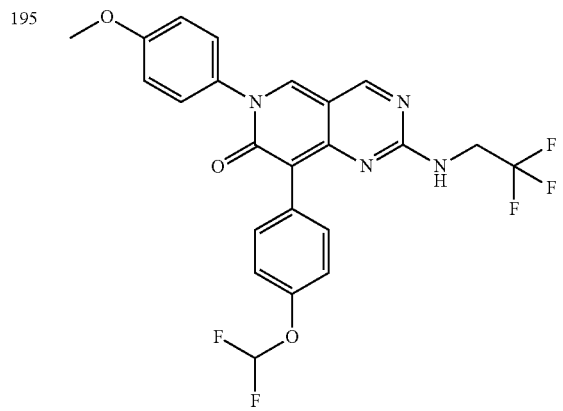 | 199 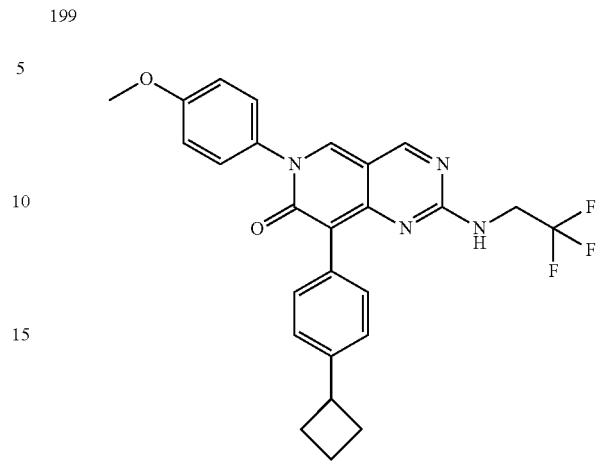 |
| 196 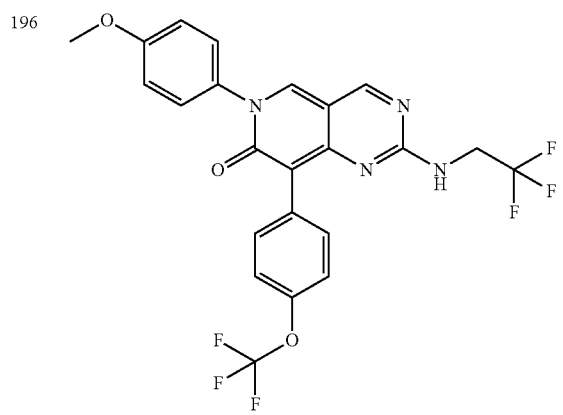 | 200 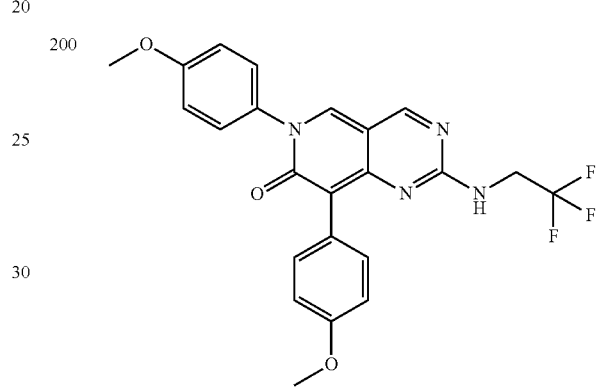 |
| 197 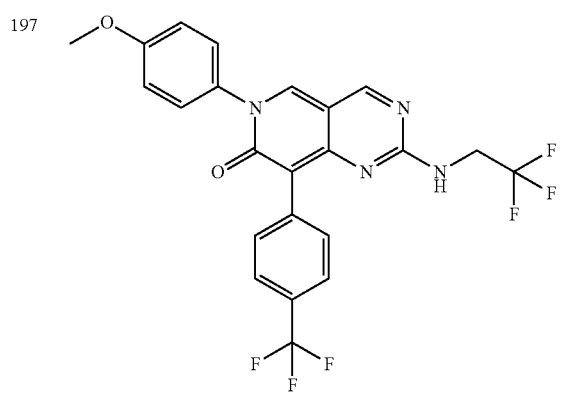 | 201 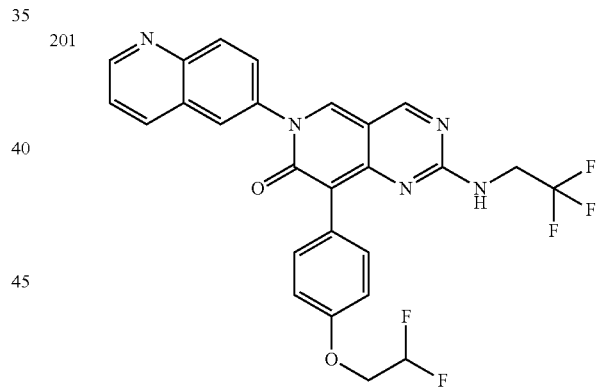 |
| 198 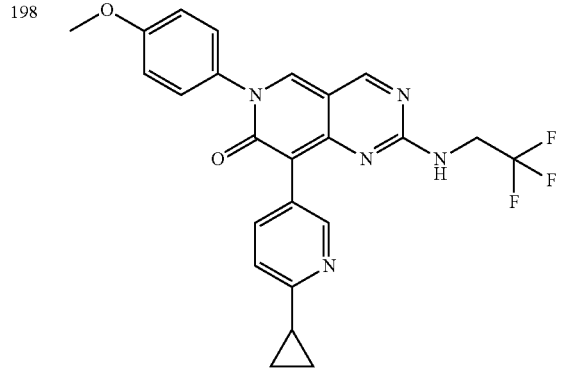 | 202 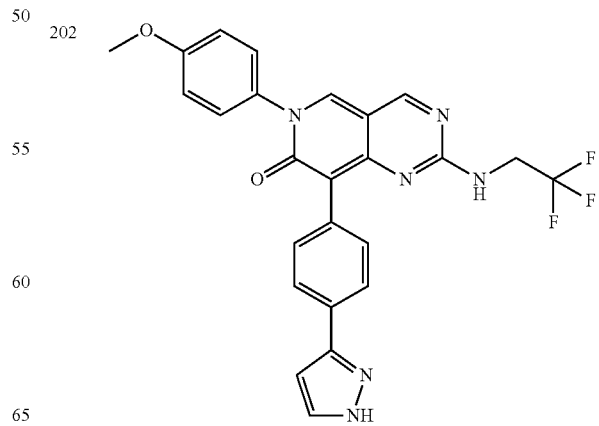 |

203 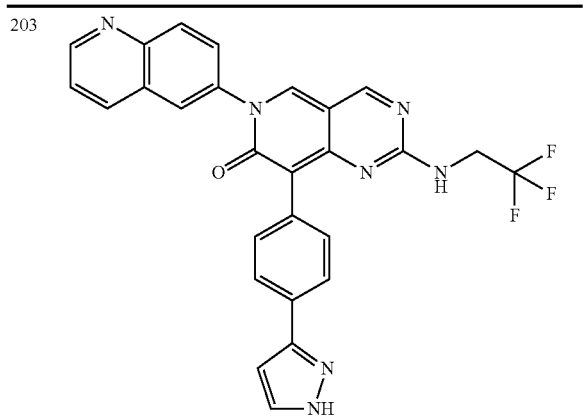
204 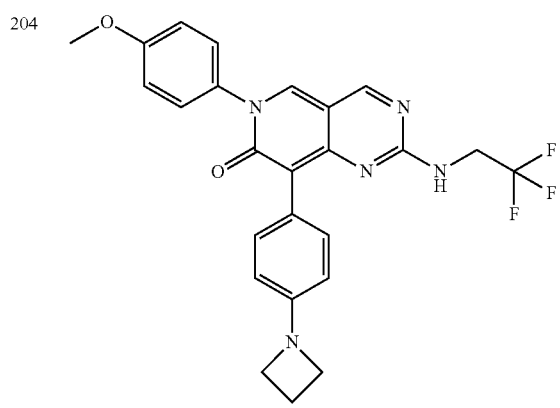
205 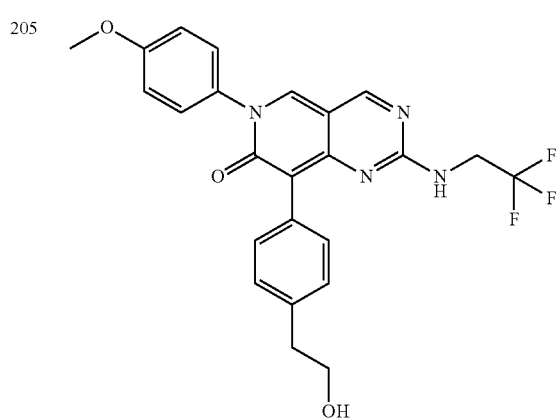
206 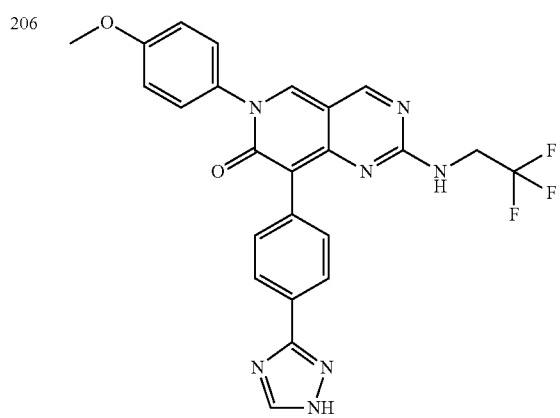
207 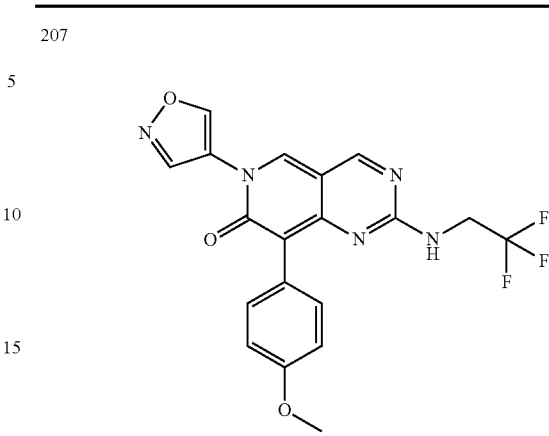
208 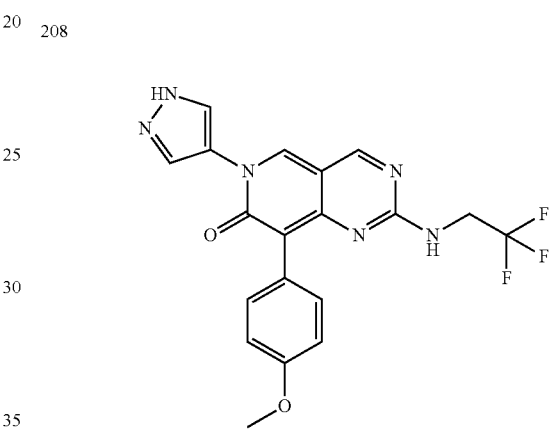
or a pharmaceutically acceptable salt thereof.
36. The compound according to claim 1, wherein the compound is:
209
210
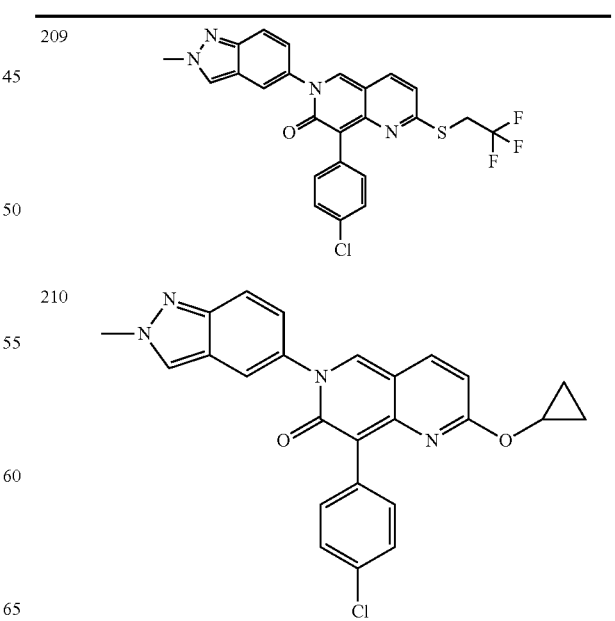

| 211 | 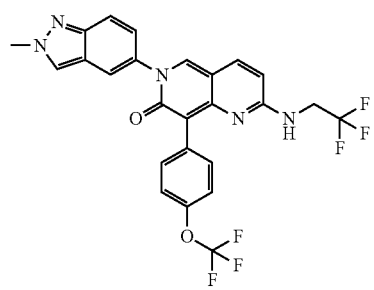 [SMILES: Cn1cc2cc(-n3cc4ccc(NCC(F)(F)F)nc4c(-c4ccc(OC(F)(F)F)cc4)c3=O)ccc2n1] | 216 | 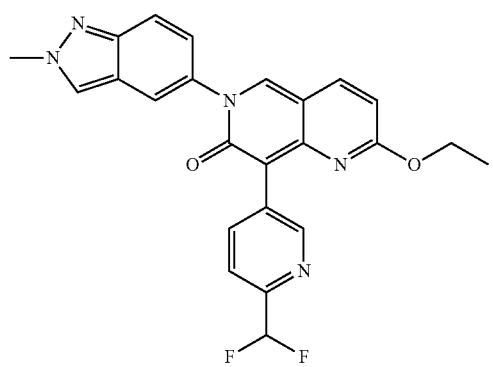 |
| 212 | 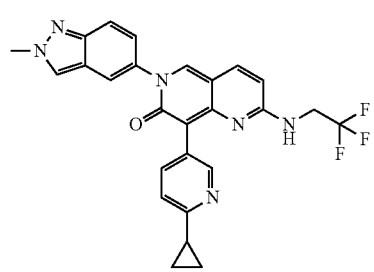 [SMILES: Cn1cc2cc(-n3cc4ccc(NCC(F)(F)F)nc4c(-c4ccc(C5CC5)nc4)c3=O)ccc2n1] | 217 | 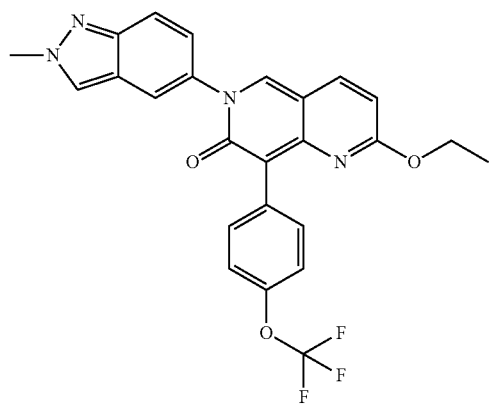 [SMILES: CCOc1ccc2cn(-c3ccc4nn(C)cc4c3)c(=O)c(-c3ccc(OC(F)(F)F)cc3)c2n1] |
| 213 | 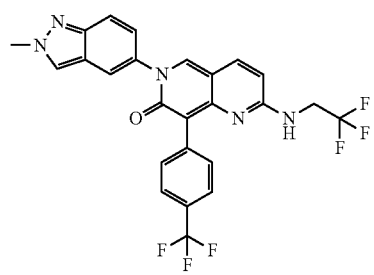 | 218 | 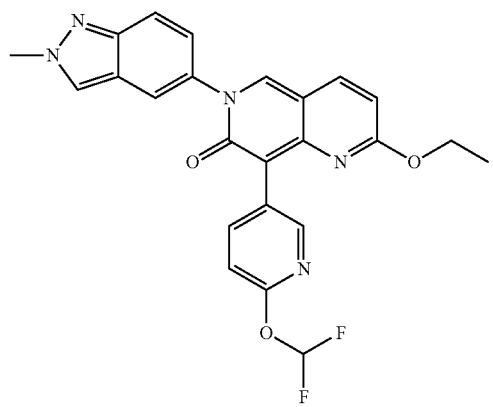 |
| 214 | 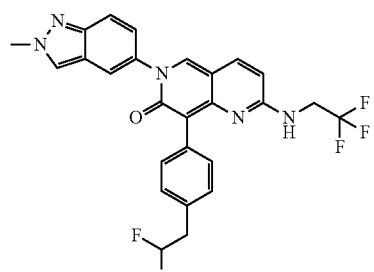 | 219 | 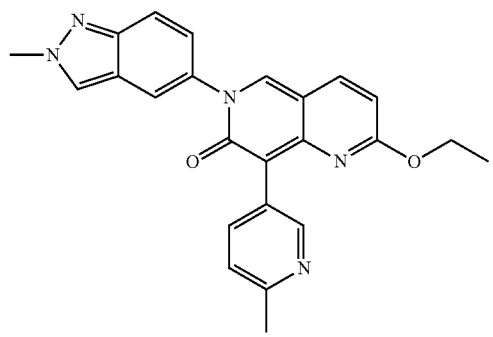 [SMILES: CCOc1ccc2cn(-c3ccc4nn(C)cc4c3)c(=O)c(-c3ccc(C)nc3)c2n1] |
| 215 | 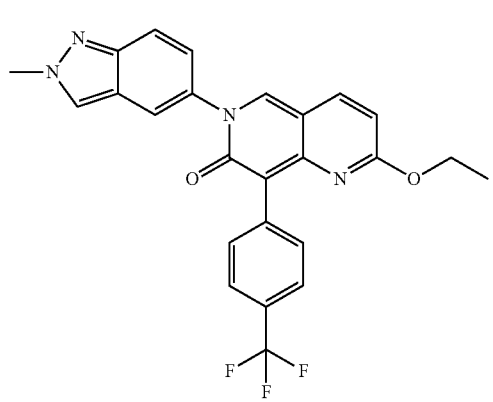 | | |

| 361 -continued | 362 -continued |
|---|---|
| 220 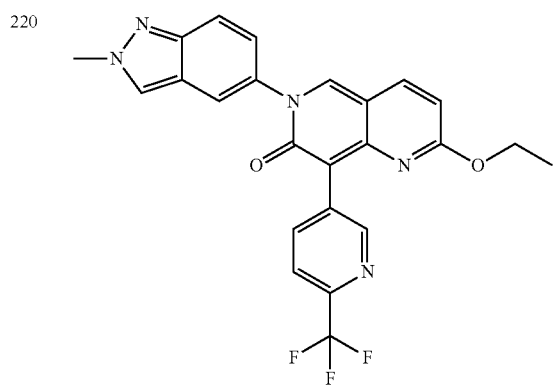 | 224 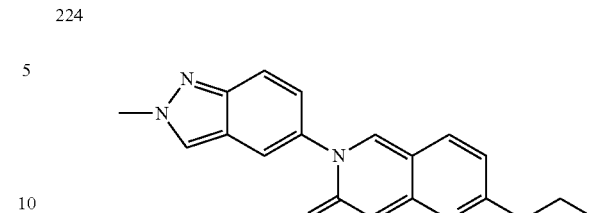 |
| 221 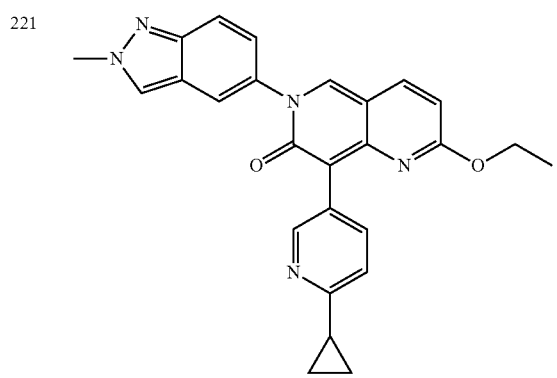 | 225 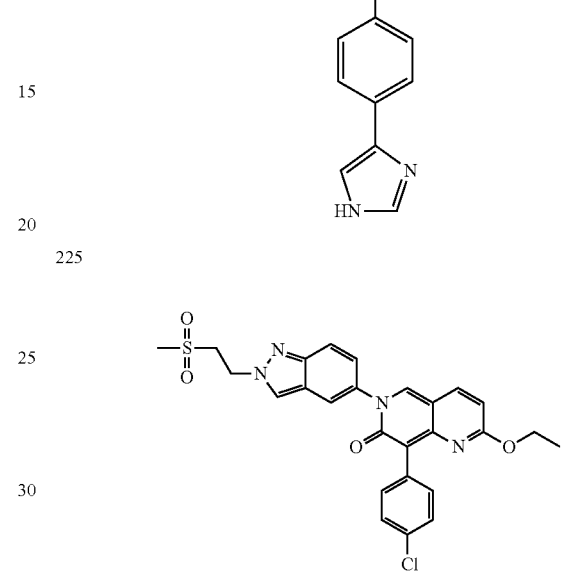 |
| 222 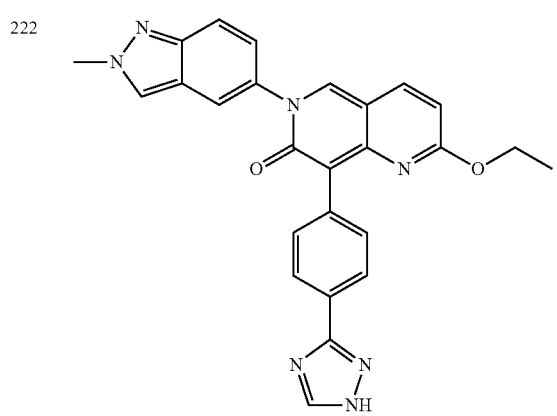 | 226 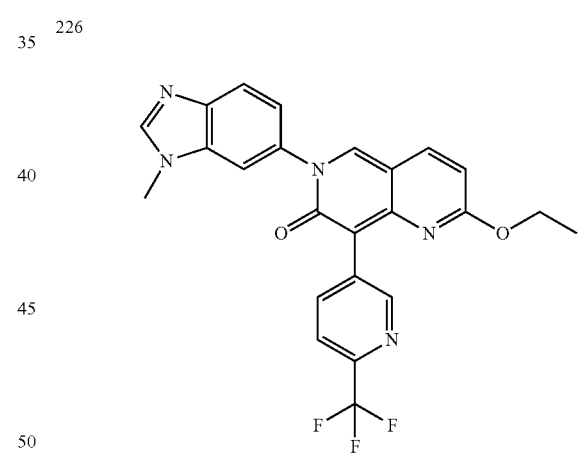 |
| 223 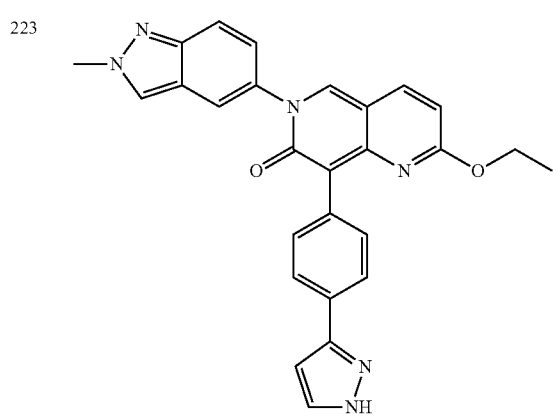 | 227 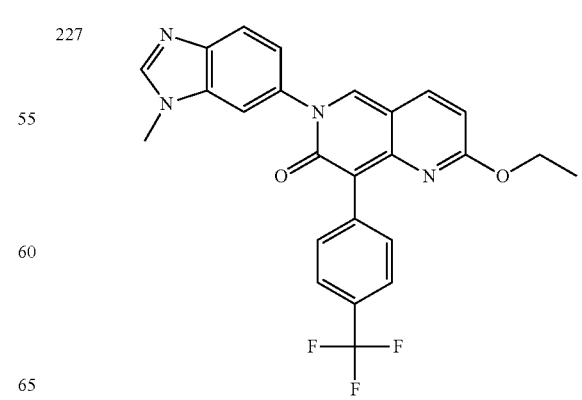 |

| 363 -continued | 364 -continued |
|---|---|
| 228 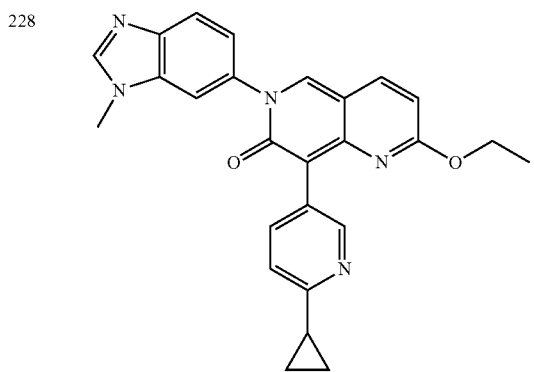 | 232 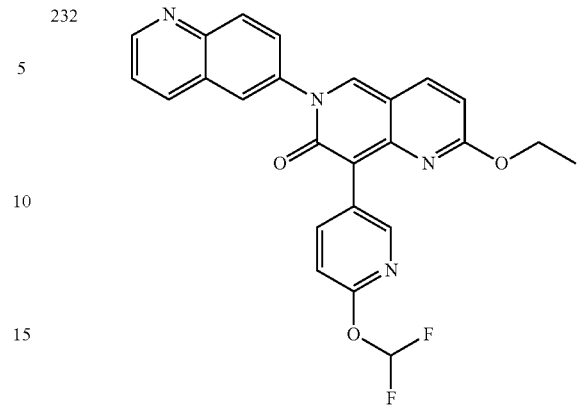 |
| 229 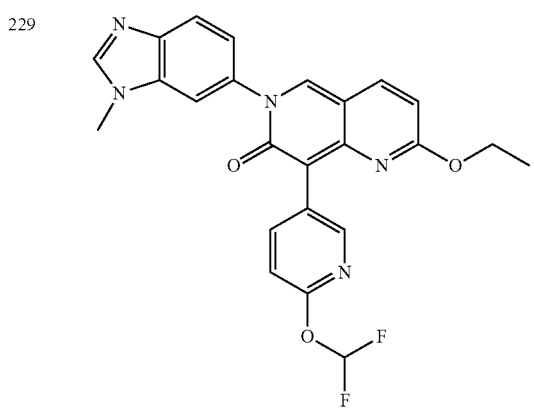 | 233 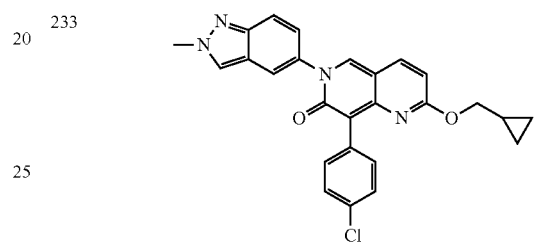 |
| 230 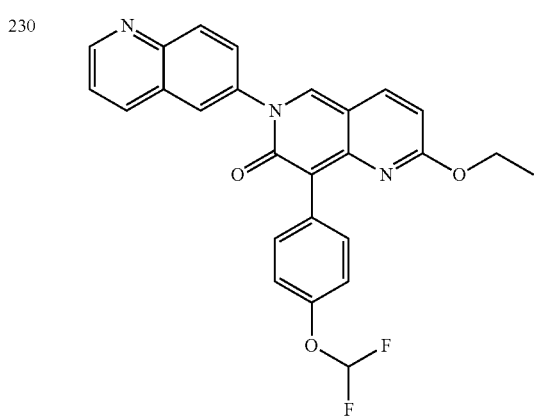 | 234 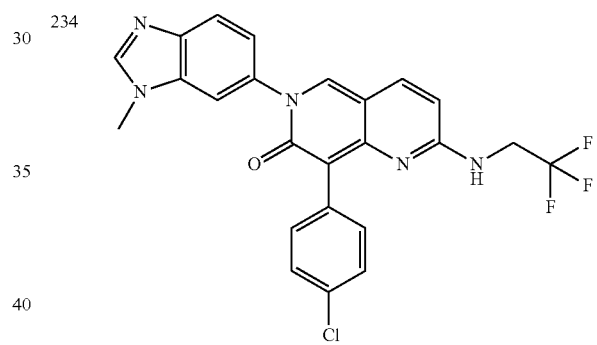 |
| 231 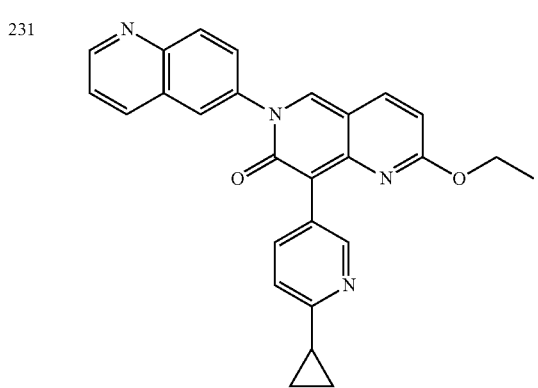 | 235 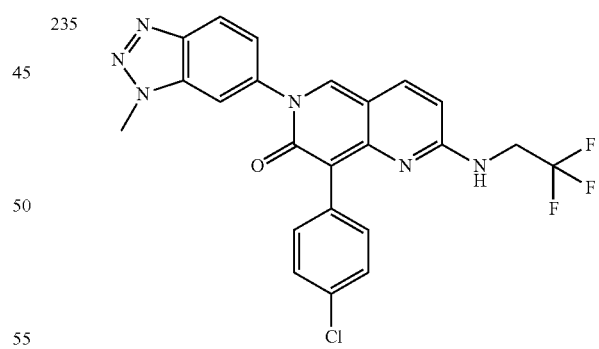 |
| | 236 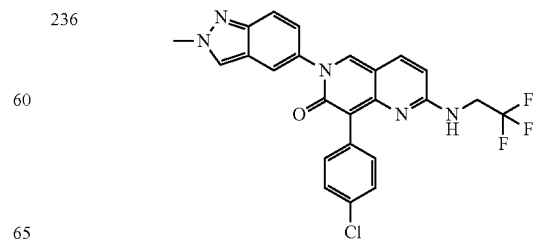 |

237
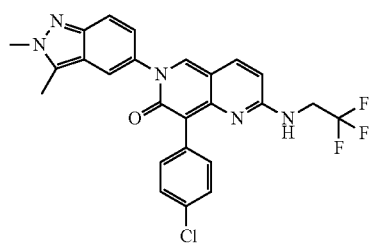 [SMILES: Cc1c2cc(-n3cc4ccc(NCC(F)(F)F)nc4c(-c4ccc(Cl)cc4)c3=O)ccc2nn1C]
238
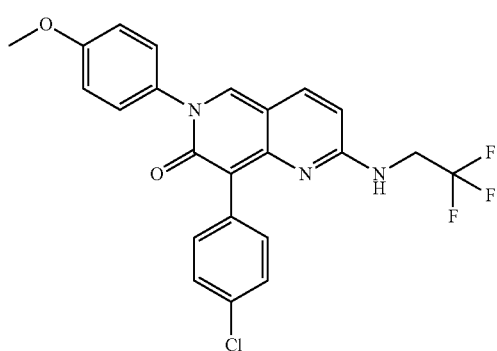 [SMILES: COc1ccc(-n2cc3ccc(NCC(F)(F)F)nc3c(-c3ccc(Cl)cc3)c2=O)cc1]
239
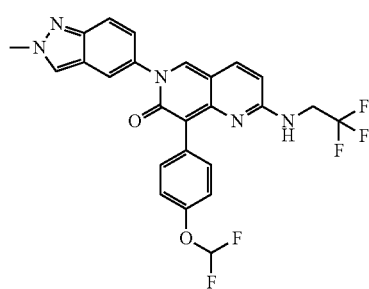 [SMILES: Cn1cc2cc(-n3cc4ccc(NCC(F)(F)F)nc4c(-c4ccc(OC(F)F)cc4)c3=O)ccc2n1]
240
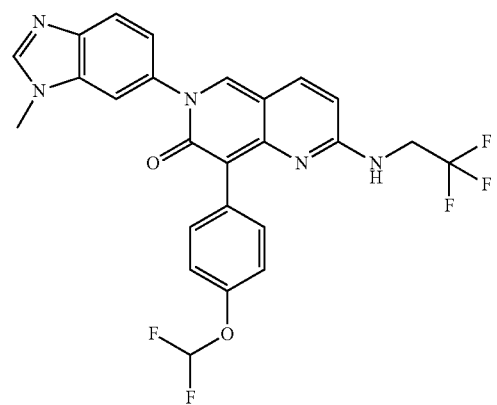 [SMILES: Cn1cnc2ccc(-n3cc4ccc(NCC(F)(F)F)nc4c(-c4ccc(OC(F)F)cc4)c3=O)cc21]
241
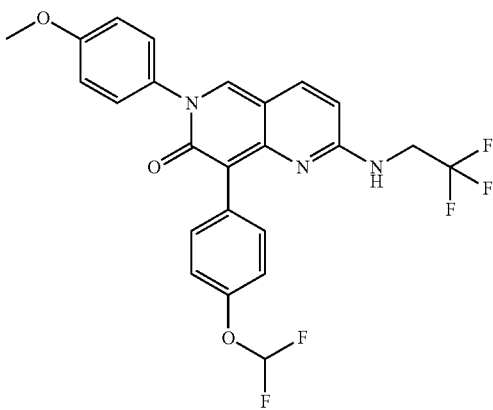 [SMILES: COc1ccc(-n2cc3ccc(NCC(F)(F)F)nc3c(-c3ccc(OC(F)F)cc3)c2=O)cc1]
242
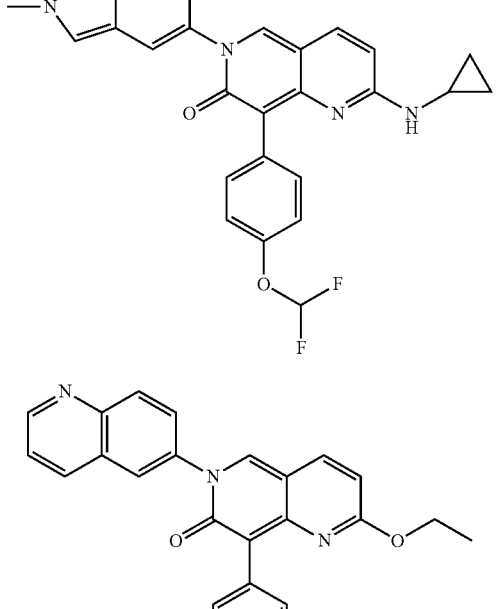
243
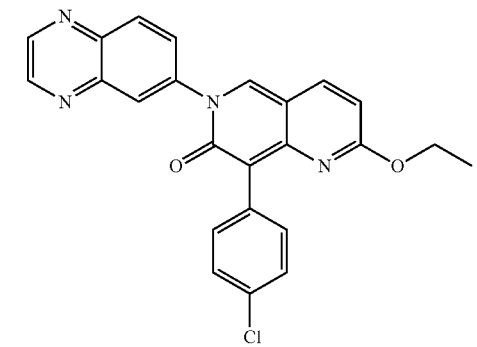 [SMILES: CCOc1ccc2cn(-c3ccc4nccnc4c3)c(=O)c(-c3ccc(Cl)cc3)c2n1]
244

| 367 -continued | 368 -continued |
|---|---|
| 245 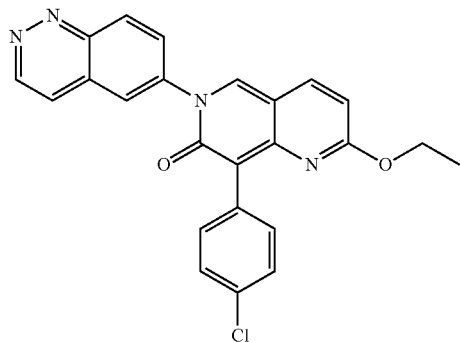 [SMILES: CCOc1ccc2cn(-c3ccc4nnccc4c3)c(=O)c(-c3ccc(Cl)cc3)c2n1] | 249 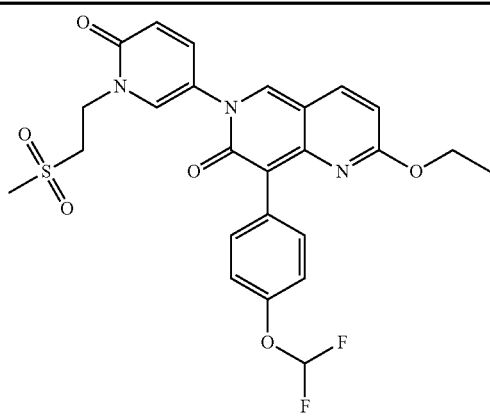 |
| 246 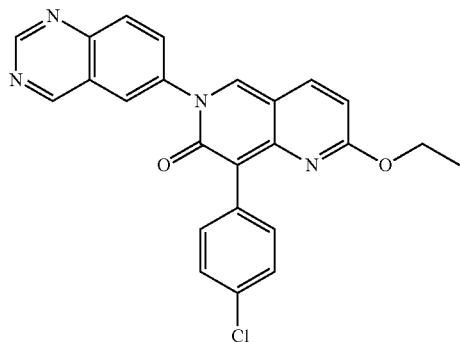 [SMILES: CCOc1ccc2cn(-c3ccc4ncncc4c3)c(=O)c(-c3ccc(Cl)cc3)c2n1] | 250 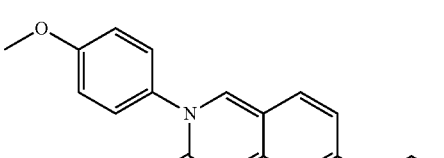<br>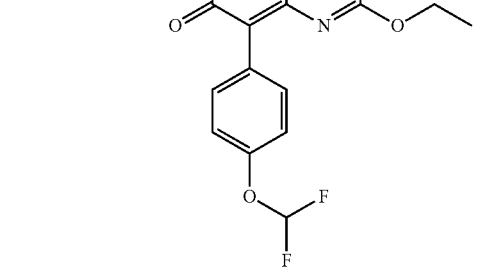 |
| 247 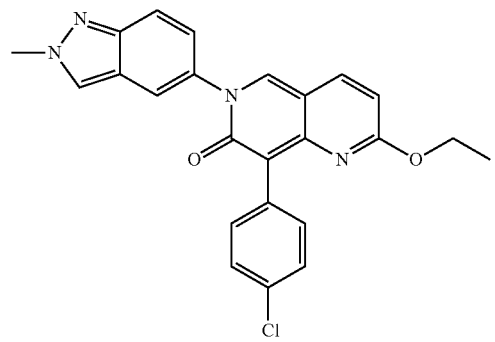 | 251 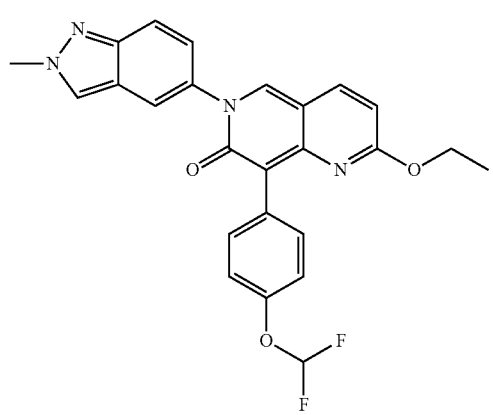 |
| 248 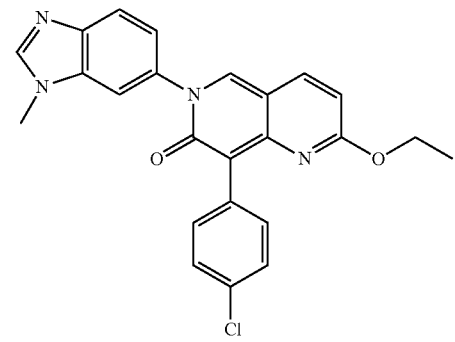 [SMILES: CCOc1ccc2cn(-c3ccc4ncn(C)c4c3)c(=O)c(-c3ccc(Cl)cc3)c2n1] | 252 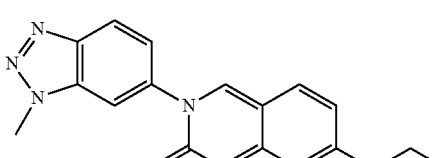 |

| 253 | 257 |
|---|---|
| 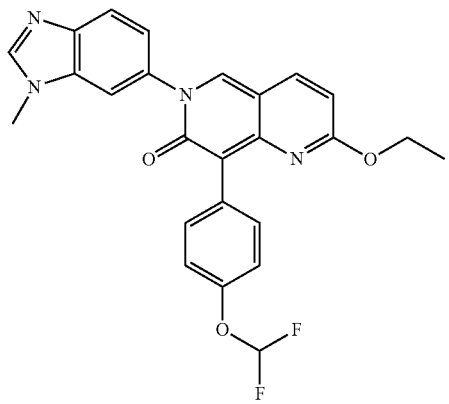 [SMILES: CCOc1ccc2cn(-c3ccc4ncn(C)c4c3)c(=O)c(-c3ccc(OC(F)F)cc3)c2n1] | 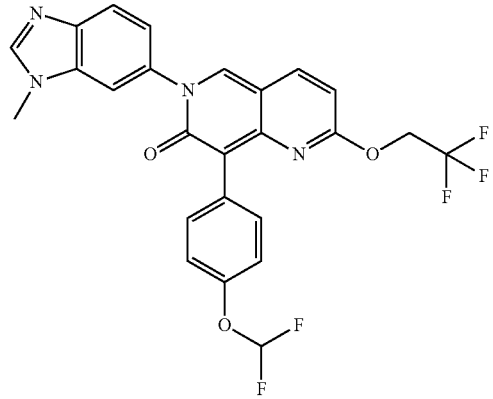 [SMILES: Cn1cnc2ccc(-n3cc4ccc(OCC(F)(F)F)nc4c(-c4ccc(OC(F)F)cc4)c3=O)cc21] |
| 254 | 258 |
| 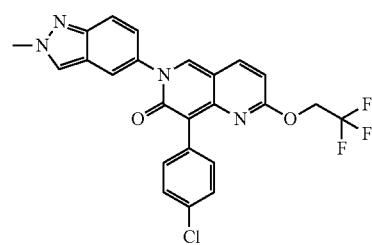 | 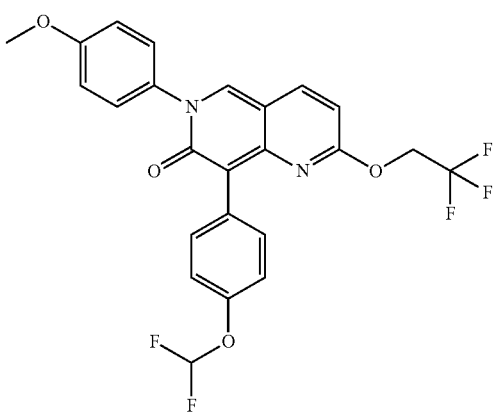 [SMILES: COc1ccc(-n2cc3ccc(OCC(F)(F)F)nc3c(-c3ccc(OC(F)F)cc3)c2=O)cc1] |
| 255 | 259 |
| 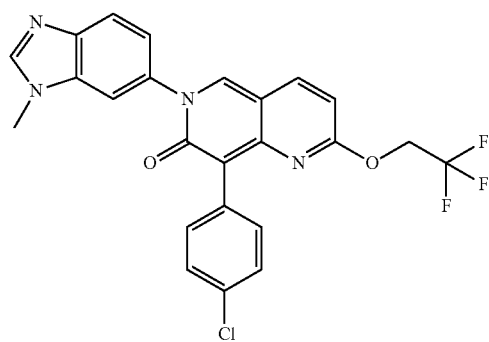 | 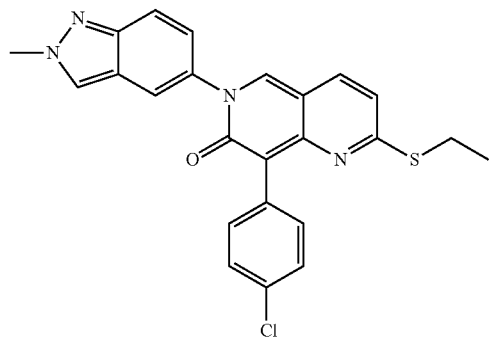 |
| 256 | 260 |
| 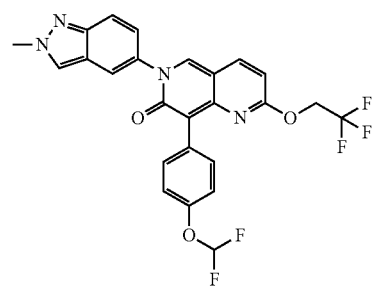 | 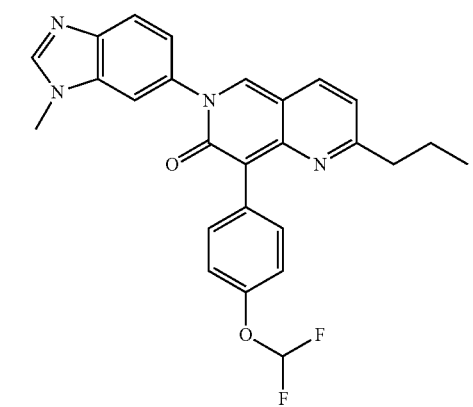 |

261 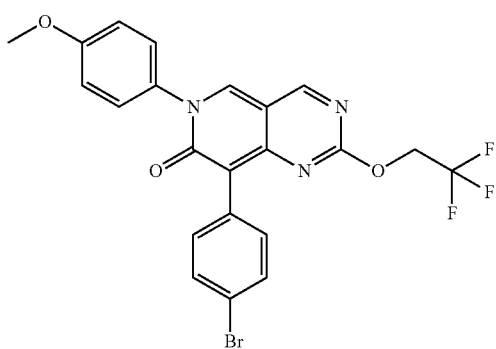 [SMILES: COc1ccc(-n2cc3cnc(OCC(F)(F)F)nc3c(-c3ccc(Br)cc3)c2=O)cc1]
262 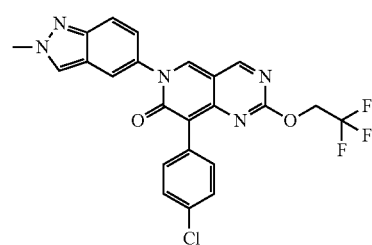 [SMILES: Cn1cc2cc(-n3cc4cnc(OCC(F)(F)F)nc4c(-c4ccc(Cl)cc4)c3=O)ccc2n1]
263 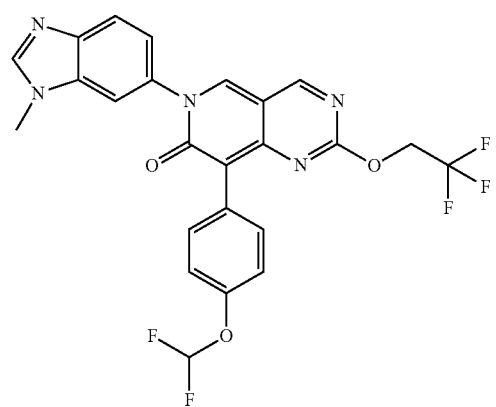 [SMILES: Cn1cnc2ccc(-n3cc4cnc(OCC(F)(F)F)nc4c(-c4ccc(OC(F)F)cc4)c3=O)cc21]
264 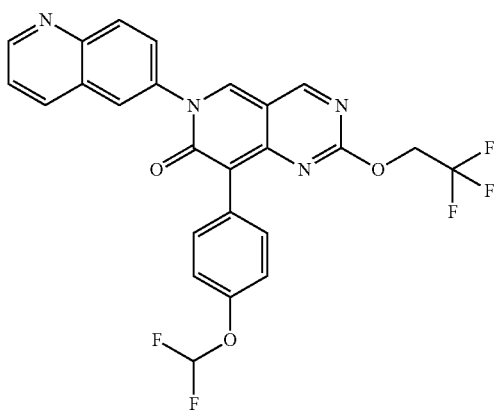 [SMILES: O=c1c(-c2ccc(OC(F)F)cc2)c2nc(OCC(F)(F)F)ncc2cn1-c1ccc2ncccc2c1]
265 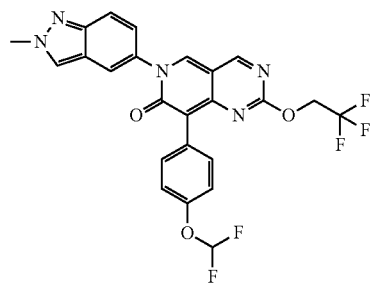
266 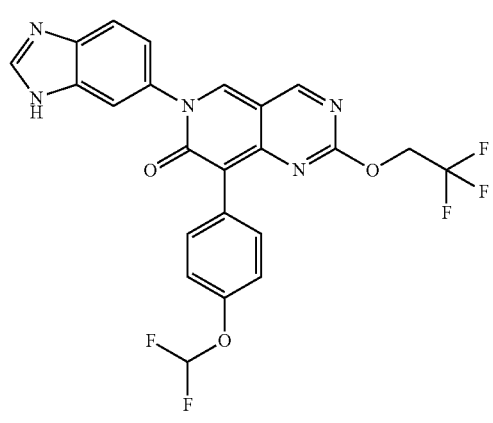 [SMILES: O=c1c(-c2ccc(OC(F)F)cc2)c2nc(OCC(F)(F)F)ncc2cn1-c1ccc2nc[nH]c2c1]
267 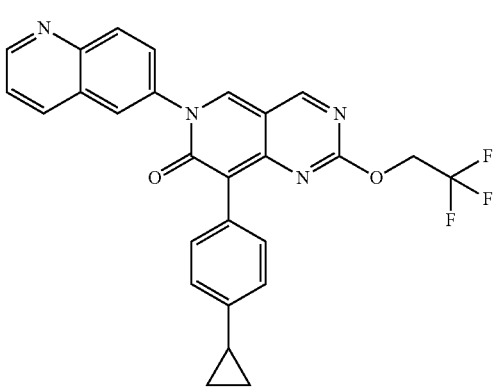 [SMILES: O=c1c(-c2ccc(C3CC3)cc2)c2nc(OCC(F)(F)F)ncc2cn1-c1ccc2ncccc2c1]
268 

269 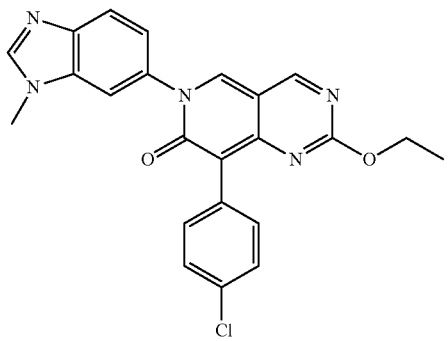 [SMILES: CCOc1ncc2cn(-c3ccc4ncn(C)c4c3)c(=O)c(-c3ccc(Cl)cc3)c2n1]
270 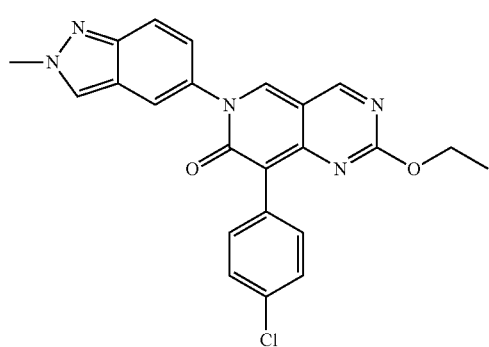
271 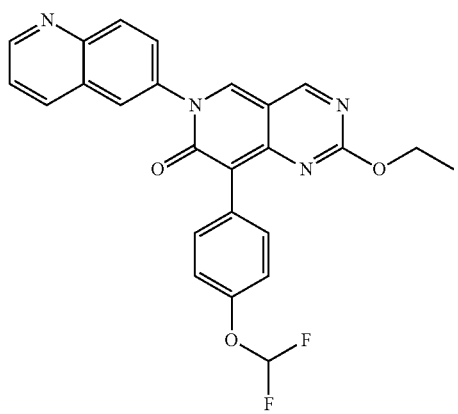 [SMILES: CCOc1ncc2cn(-c3ccc4ncccc4c3)c(=O)c(-c3ccc(OC(F)F)cc3)c2n1]
272 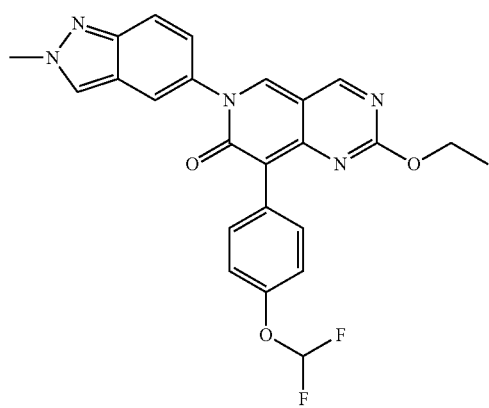 [SMILES: CCOc1ncc2cn(-c3ccc4nn(C)cc4c3)c(=O)c(-c3ccc(OC(F)F)cc3)c2n1]
273 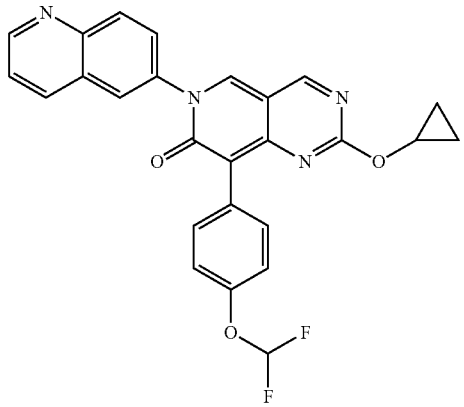 [SMILES: O=c1c(-c2ccc(OC(F)F)cc2)c2nc(OC3CC3)ncc2cn1-c1ccc2ncccc2c1]
274 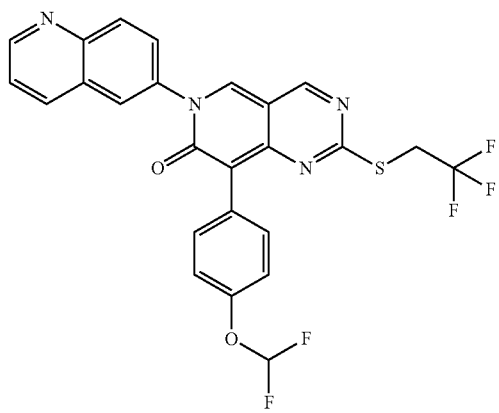 [SMILES: O=c1c(-c2ccc(OC(F)F)cc2)c2nc(SCC(F)(F)F)ncc2cn1-c1ccc2ncccc2c1]
or a pharmaceutically acceptable salt thereof.
37. The compound according to claim 1, wherein the compound is:
101-A 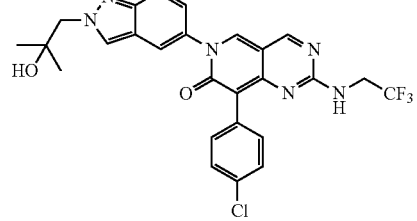
102-A 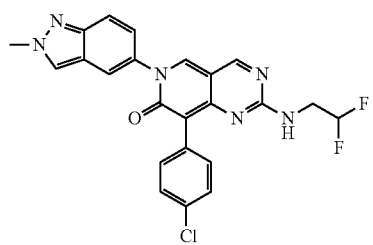 [SMILES: Cn1cc2cc(-n3cc4cnc(NCC(F)F)nc4c(-c4ccc(Cl)cc4)c3=O)ccc2n1]

103-A
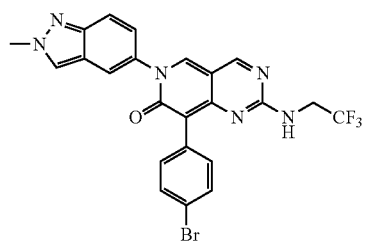 [SMILES: Cn1cc2cc(-n3cc4cnc(NCC(F)(F)F)nc4c(-c4ccc(Br)cc4)c3=O)ccc2n1]
104-A
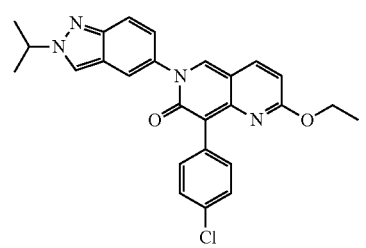 [SMILES: CCOc1ccc2cn(-c3ccc4nn(C(C)C)cc4c3)c(=O)c(-c3ccc(Cl)cc3)c2n1]
105-A
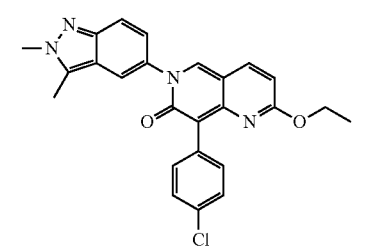 [SMILES: CCOc1ccc2cn(-c3ccc4nn(C)c(C)c4c3)c(=O)c(-c3ccc(Cl)cc3)c2n1]
106-A
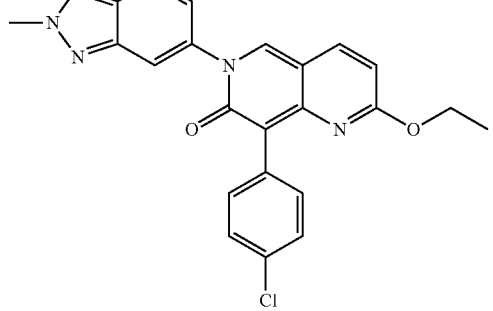
107-A
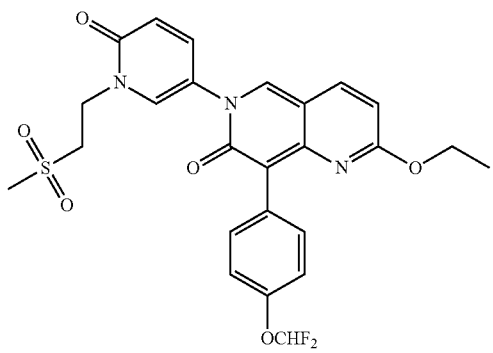 [SMILES: CCOc1ccc2cn(-c3ccc(=O)n(CCS(C)(=O)=O)c3)c(=O)c(-c3ccc(OC(F)F)cc3)c2n1]
108-A
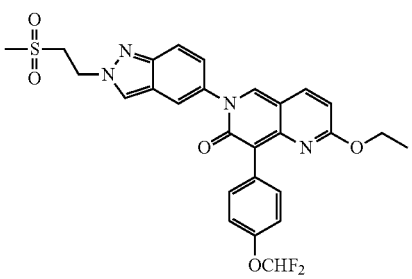 [SMILES: CCOc1ccc2cn(-c3ccc4nn(CCS(C)(=O)=O)cc4c3)c(=O)c(-c3ccc(OC(F)F)cc3)c2n1]
109-A
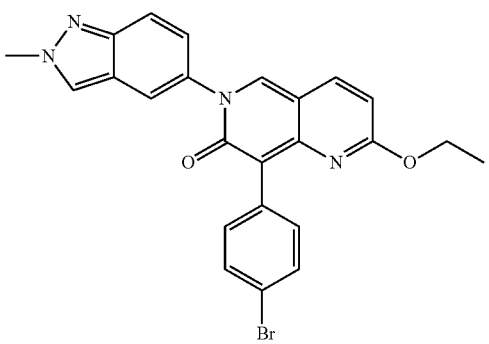
110-A
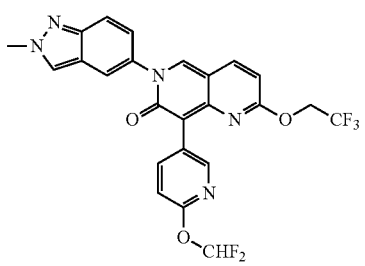 [SMILES: Cn1cc2cc(-n3cc4ccc(OCC(F)(F)F)nc4c(-c4ccc(OC(F)F)nc4)c3=O)ccc2n1]
111-A
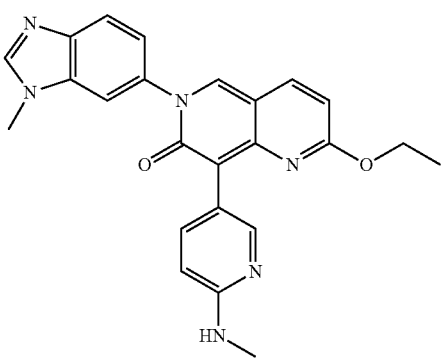 [SMILES: CCOc1ccc2cn(-c3ccc4ncn(C)c4c3)c(=O)c(-c3ccc(NC)nc3)c2n1]
112-A
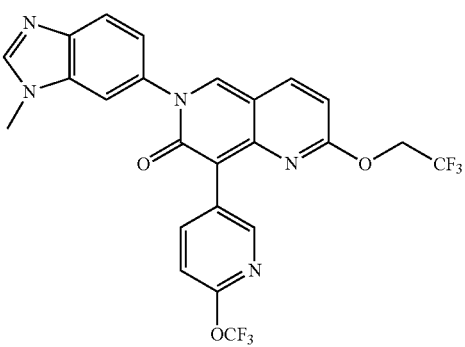 [SMILES: Cn1cnc2ccc(-n3cc4ccc(OCC(F)(F)F)nc4c(-c4ccc(OC(F)(F)F)nc4)c3=O)cc21]

113-A
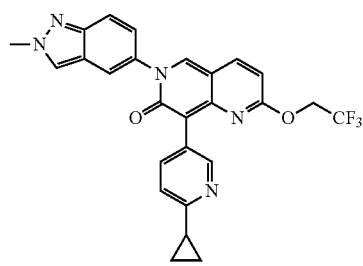 [SMILES: Cn1cc2cc(-n3cc4ccc(OCC(F)(F)F)nc4c(-c4ccc(C5CC5)nc4)c3=O)ccc2n1]
114-A
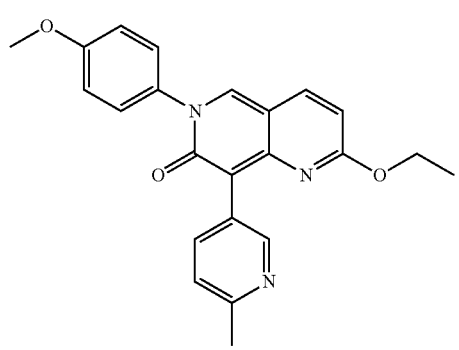 [SMILES: CCOc1ccc2cn(-c3ccc(OC)cc3)c(=O)c(-c3ccc(C)nc3)c2n1]
115-A
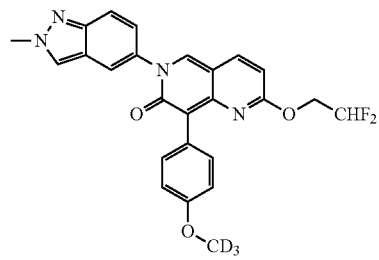
116-A
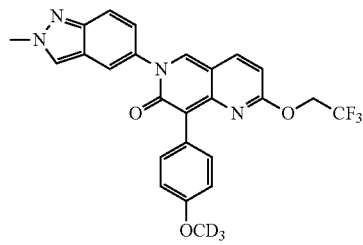
117-A
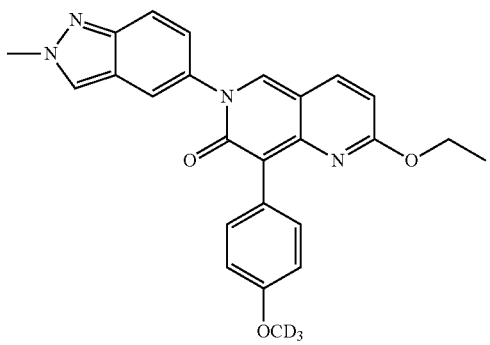
118-A
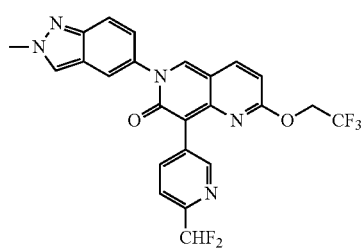 [SMILES: Cn1cc2cc(-n3cc4ccc(OCC(F)(F)F)nc4c(-c4ccc(C(F)F)nc4)c3=O)ccc2n1]
119-A
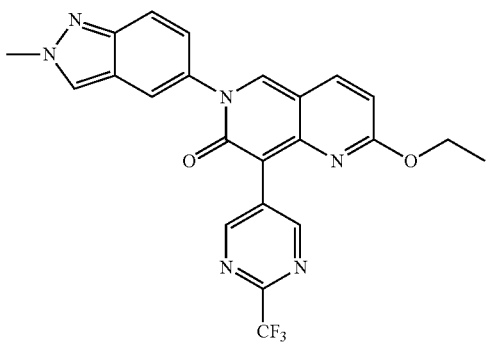
120-A
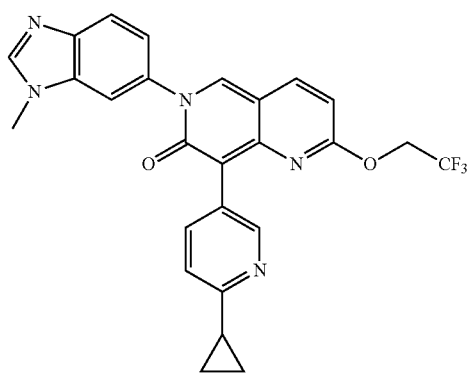 [SMILES: Cn1cnc2ccc(-n3cc4ccc(OCC(F)(F)F)nc4c(-c4ccc(C5CC5)nc4)c3=O)cc21]
121-A
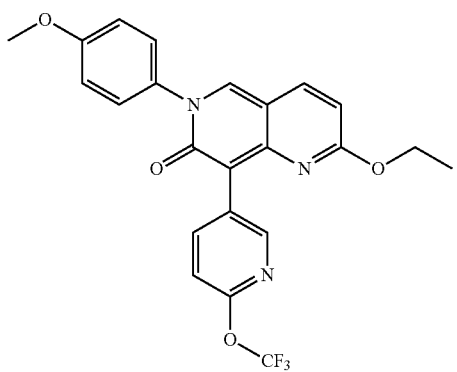 [SMILES: CCOc1ccc2cn(-c3ccc(OC)cc3)c(=O)c(-c3ccc(OC(F)(F)F)nc3)c2n1]

-continued
122-A
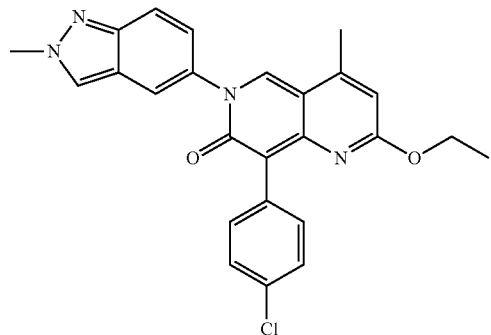
123-A
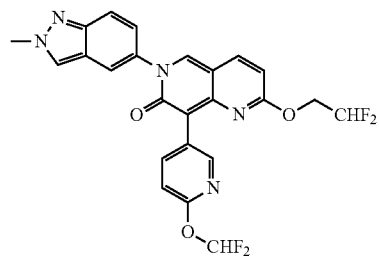 [SMILES: Cn1cc2cc(-n3cc4ccc(OCC(F)F)nc4c(-c4ccc(OC(F)F)nc4)c3=O)ccc2n1]
124-A
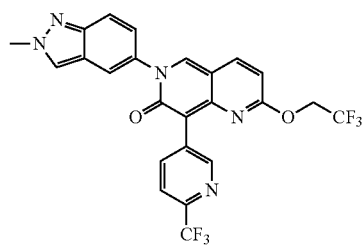 [SMILES: Cn1cc2cc(-n3cc4ccc(OCC(F)(F)F)nc4c(-c4ccc(C(F)(F)F)nc4)c3=O)ccc2n1]
125-A
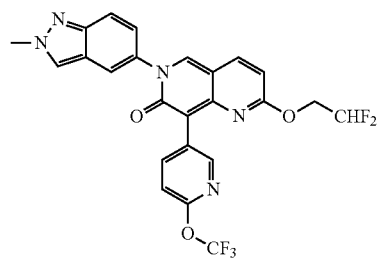
126-A
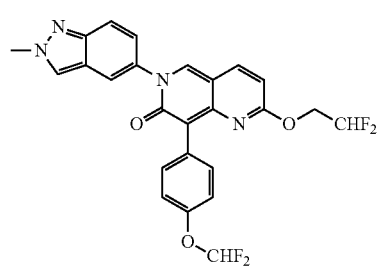
-continued
127-A
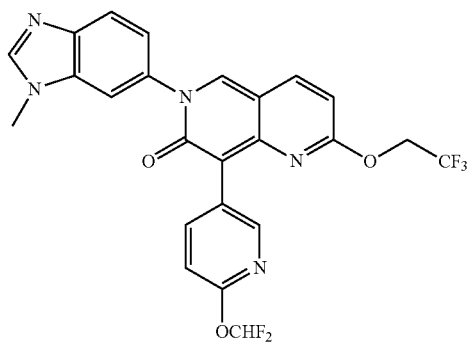 [SMILES: Cn1cnc2ccc(-n3cc4ccc(OCC(F)(F)F)nc4c(-c4ccc(OC(F)F)nc4)c3=O)cc21]
128-A
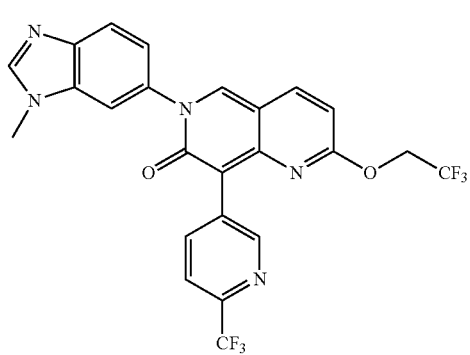 [SMILES: Cn1cnc2ccc(-n3cc4ccc(OCC(F)(F)F)nc4c(-c4ccc(C(F)(F)F)nc4)c3=O)cc21]
129-A
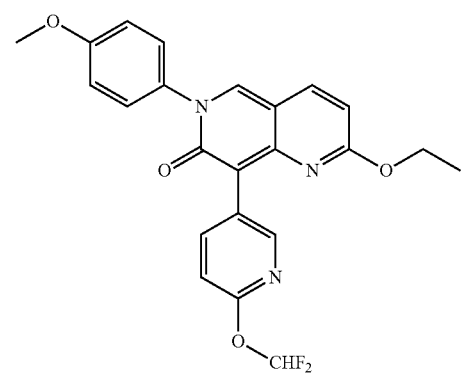 [SMILES: CCOc1ccc2cn(-c3ccc(OC)cc3)c(=O)c(-c3ccc(OC(F)F)nc3)c2n1]
130-A
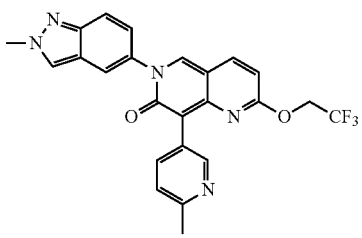 [SMILES: Cc1ccc(-c2c(=O)n(-c3ccc4nn(C)cc4c3)cc3ccc(OCC(F)(F)F)nc23)cn1]
131-A
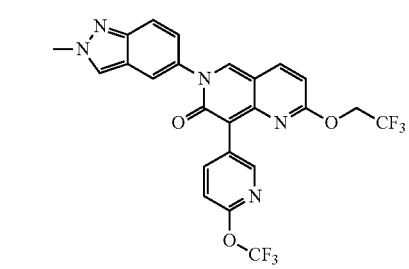 [SMILES: Cn1cc2cc(-n3cc4ccc(OCC(F)(F)F)nc4c(-c4ccc(OC(F)(F)F)nc4)c3=O)ccc2n1]

132-A
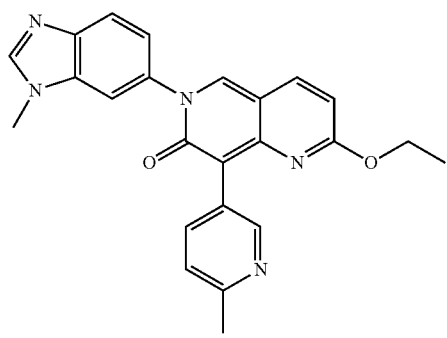 [SMILES: CCOc1ccc2cn(-c3ccc4ncn(C)c4c3)c(=O)c(-c3ccc(C)nc3)c2n1]
133-A
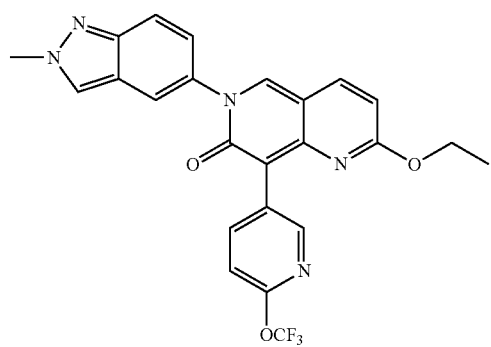
134-A
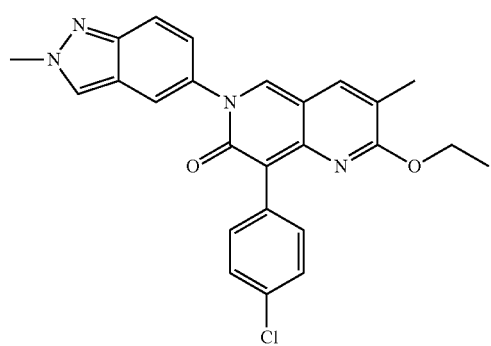 [SMILES: CCOc1nc2c(-c3ccc(Cl)cc3)c(=O)n(-c3ccc4nn(C)cc4c3)cc2cc1C]
135-A
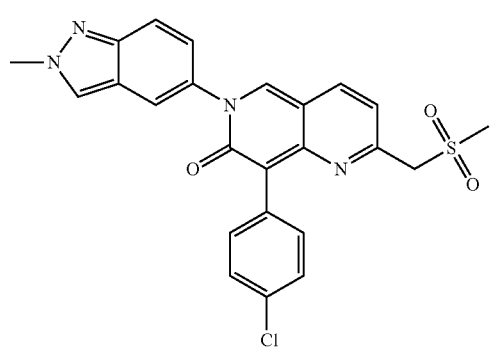
136-A
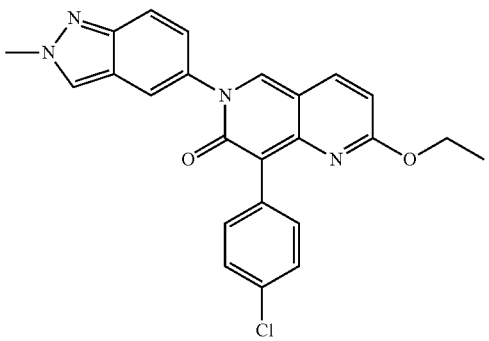
137-A
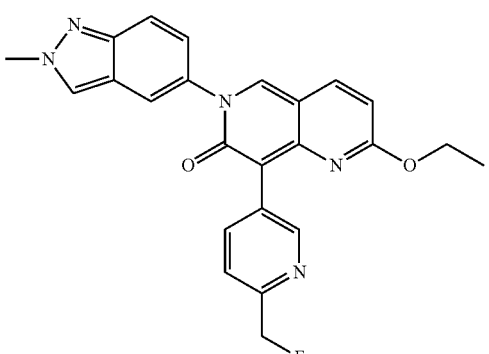
138-A
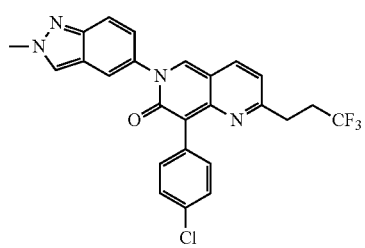 [SMILES: Cn1cc2cc(-n3cc4ccc(CCC(F)(F)F)nc4c(-c4ccc(Cl)cc4)c3=O)ccc2n1]
or a pharmaceutically acceptable salt thereof.
38. The compound according to claim 5, wherein the compound is:
139-A
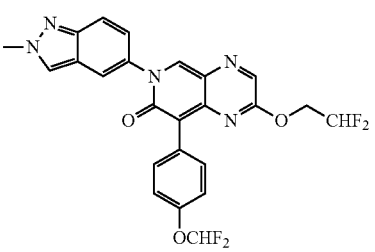 [SMILES: Cn1cc2cc(-n3cc4ncc(OCC(F)F)nc4c(-c4ccc(OC(F)F)cc4)c3=O)ccc2n1]

140-A
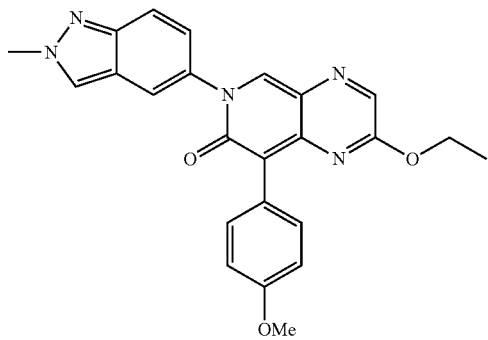 [SMILES: CCOc1cnc2cn(-c3ccc4nn(C)cc4c3)c(=O)c(-c3ccc(OC)cc3)c2n1]
141-A
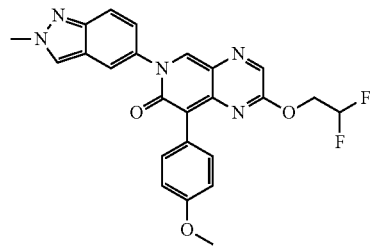 [SMILES: COc1ccc(-c2c(=O)n(-c3ccc4nn(C)cc4c3)cc3ncc(OCC(F)F)nc23)cc1]
142-A
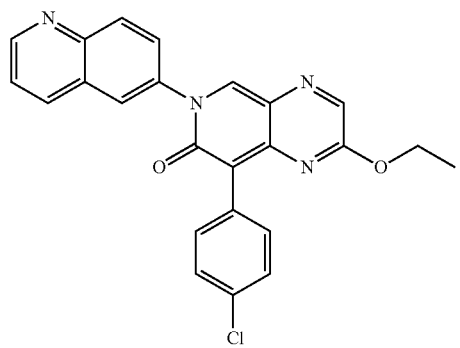 [SMILES: CCOc1cnc2cn(-c3ccc4ncccc4c3)c(=O)c(-c3ccc(Cl)cc3)c2n1]
143-A
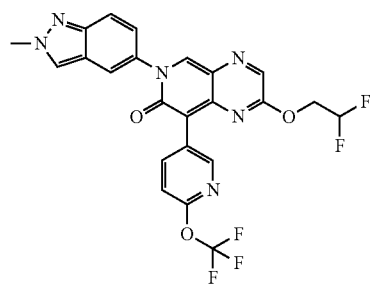 [SMILES: Cn1cc2cc(-n3cc4ncc(OCC(F)F)nc4c(-c4ccc(OC(F)(F)F)nc4)c3=O)ccc2n1]
144-A
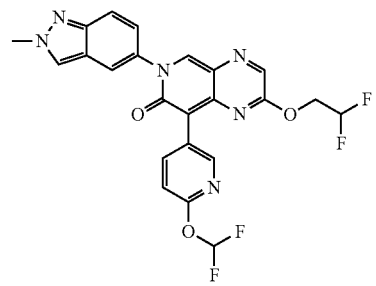 [SMILES: Cn1cc2cc(-n3cc4ncc(OCC(F)F)nc4c(-c4ccc(OC(F)F)nc4)c3=O)ccc2n1]
145-A
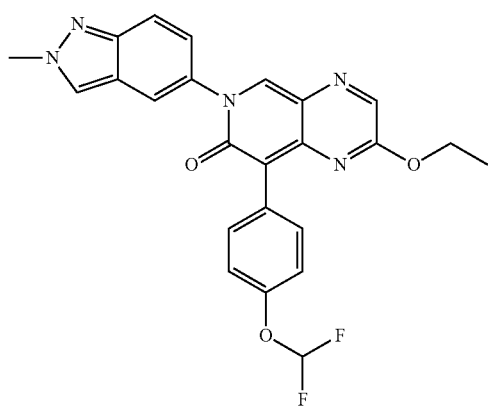 [SMILES: CCOc1cnc2cn(-c3ccc4nn(C)cc4c3)c(=O)c(-c3ccc(OC(F)F)cc3)c2n1]
146-A
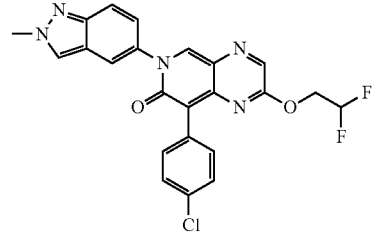 [SMILES: Cn1cc2cc(-n3cc4ncc(OCC(F)F)nc4c(-c4ccc(Cl)cc4)c3=O)ccc2n1]
147-A
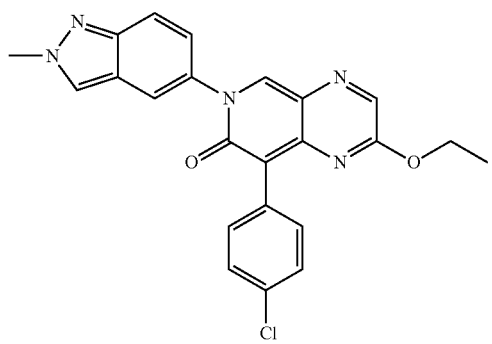 [SMILES: CCOc1cnc2cn(-c3ccc4nn(C)cc4c3)c(=O)c(-c3ccc(Cl)cc3)c2n1]

148-A

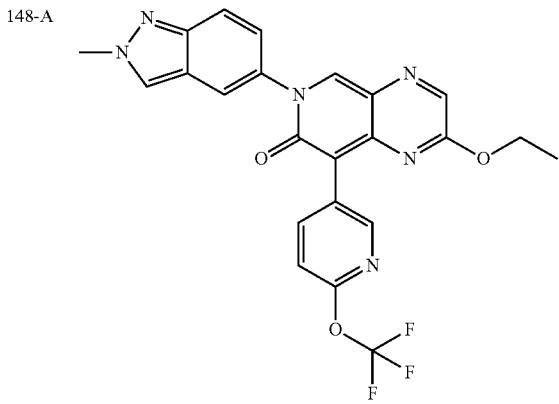

150-A

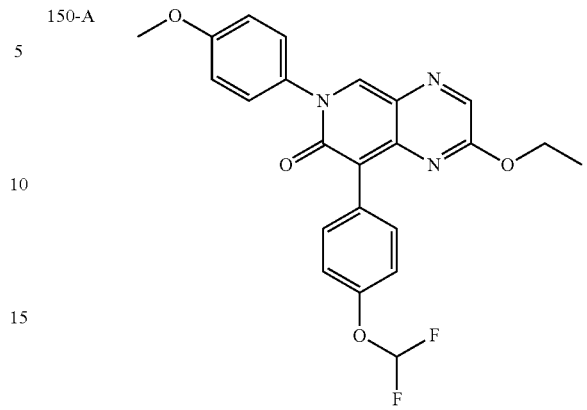

149-A

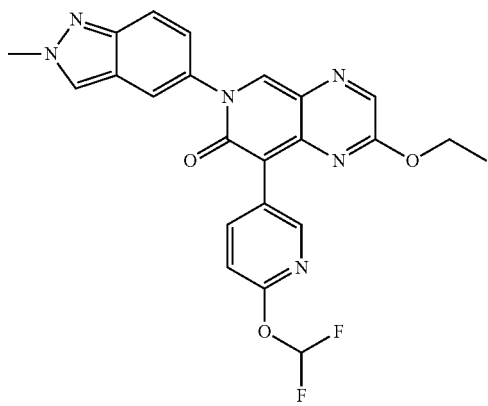 [SMILES: CCOc1cnc2cn(-c3ccc4nn(C)cc4c3)c(=O)c(-c3ccc(OC(F)F)nc3)c2n1]

or a pharmaceutically acceptable salt thereof.

39. A pharmaceutical composition comprising a therapeutically effective amount of a compound according to claim 1 or a pharmaceutically acceptable salt thereof, and a pharmaceutically acceptable carrier.

40. A method for treating a liver or colon cancer in a subject suffering therefrom, comprising administering to the subject an effective amount of the compound of claim 1; wherein the subject's liver or colon cancer is an MTAP null cancer.

41. The method according to claim 40, wherein the liver or colon cancer is an MTAP-deleted cancer.

42. The method of claim 40, wherein the MTAP gene in the cancer is deleted, lost, or deactivated.

43. The method of claim 40, wherein the MTAP protein in the cancer has a reduced or impaired function.

44. A method of inhibiting MAT2A in a cancer comprising contacting the cancer with a compound according to claim 1.

* * * * *